United States Patent
Bonazzi et al.

(10) Patent No.: US 12,172,984 B2
(45) Date of Patent: Dec. 24, 2024

(54) PYRAZOLOPYRIDINE DERIVATIVES AND USES THEREOF

(71) Applicant: Novartis AG, Basel (CH)

(72) Inventors: Simone Bonazzi, Cambridge, MA (US); Artiom Cernijenko, Cambridge, MA (US); Jennifer Stroka Cobb, Stow, MA (US); Natalie Alysia Dales, Arlington, MA (US); Janetta Dewhurst, Framingham, MA (US); Matthew James Hesse, Oakland, CA (US); Rama Jain, Danville, CA (US); John Ryan Kerrigan, Wakefield, MA (US); Hasnain Ahmed Malik, Boston, MA (US); James R. Manning, Emeryville, CA (US); Gary O'Brien, Maynard, MA (US); Andrew W. Patterson, Somerville, MA (US); Noel Marie-France Thomsen, Chelmsford, MA (US); Pamela Yf Ting, Somerville, MA (US)

(73) Assignee: NOVARTIS AG, Basel (CH)

(*) Notice: Subject to any disclaimer, the term of this patent is extended or adjusted under 35 U.S.C. 154(b) by 0 days.

(21) Appl. No.: 18/460,428

(22) Filed: Sep. 1, 2023

(65) Prior Publication Data
US 2024/0158374 A1     May 16, 2024

Related U.S. Application Data

(62) Division of application No. 17/693,759, filed on Mar. 14, 2022, now Pat. No. 11,787,785.

(60) Provisional application No. 63/164,130, filed on Mar. 22, 2021, provisional application No. 63/161,139, filed on Mar. 15, 2021.

(51) Int. Cl.
*C07D 403/14*     (2006.01)
*A61P 7/00*     (2006.01)
*C07D 405/14*     (2006.01)
*C07D 417/14*     (2006.01)

(52) U.S. Cl.
CPC ........... *C07D 403/14* (2013.01); *A61P 7/00* (2018.01); *C07D 405/14* (2013.01); *C07D 417/14* (2013.01)

(58) Field of Classification Search
None
See application file for complete search history.

(56) References Cited

U.S. PATENT DOCUMENTS

| | | | |
|---|---|---|---|
| 10,414,755 B2 * | 9/2019 | Beckwith | C07D 417/14 |
| 10,640,489 B2 * | 5/2020 | Beckwith | C07D 417/14 |
| 10,647,701 B2 * | 5/2020 | Beckwith | C07D 487/04 |
| 2020/0016143 A1 * | 1/2020 | Beckwith | A61K 31/498 |
| 2020/0019461 A1 * | 1/2020 | Sugiyama | G06F 11/1048 |
| 2023/0108325 A1 | 4/2023 | Bonazzi et al. | |

FOREIGN PATENT DOCUMENTS

| | | | |
|---|---|---|---|
| EP | 2165707 A1 | 3/2010 | |
| EP | 3202461 A1 | 8/2017 | |
| WO | 2005055929 A2 | 6/2005 | |
| WO | 2005111018 A1 | 11/2005 | |
| WO | 2014009295 A1 | 1/2014 | |
| WO | 2019140387 A1 | 7/2019 | |
| WO | 2020132561 A1 | 6/2020 | |
| WO | 2020206424 A1 | 10/2020 | |

* cited by examiner

*Primary Examiner* — Samantha L Shterengarts
*Assistant Examiner* — Jed A Kucharczk
(74) *Attorney, Agent, or Firm* — Emily T. Wu

(57) ABSTRACT

The present disclosure relates to compounds of formula (I) and pharmaceutical compositions and their use in reducing Widely Interspaced Zinc Finger Motifs (WIZ) expression levels, or inducing fetal hemoglobin (HbF) expression, and in the treatment of inherited blood disorders (e.g., hemoglobinopathies, e.g., beta-hemoglobinopathies), such as sickle cell disease and beta-thalassemia.

30 Claims, 1 Drawing Sheet
Specification includes a Sequence Listing.

PYRAZOLOPYRIDINE DERIVATIVES AND USES THEREOF

CLAIM OF PRIORITY

This application is a divisional application which claims priority to U.S. patent application Ser. No. 17/693,759, filed on Mar. 14, 2022, which claims the benefit of U.S. Provisional Application No. 63/161,139 filed on Mar. 15, 2021, and U.S. Provisional Application No. 63/164,130 filed on Mar. 22, 2021, the disclosures of which are incorporated by reference herein in their entirety.

SEQUENCE LISTING

The instant application contains a Sequence Listing which has been submitted electronically in XML format and is hereby incorporated by reference in its entirety. Said XML copy, created on Aug. 30, 2023 is named PAT059039-US-DIV_ST26 SQL.txt and is 20,480 bytes in size.

FIELD OF THE DISCLOSURE

The present disclosure relates to pyrazolopyridine derivatives compounds and pharmaceutical compositions and their use in reducing Widely Interspaced Zinc Finger Motifs (WIZ) protein expression levels and/or inducing fetal hemoglobin (HbF) protein expression levels, and in the treatment of inherited blood disorders (hemoglobinopathies, e.g., beta-hemoglobinopathies), such as sickle cell disease and beta-thalassemia.

BACKGROUND OF THE DISCLOSURE

Sickle cell disease (SCD) is a group of severe inherited blood disorders that cause red blood cells to contort into a sickle shape. These cells can cause blockages in blood flow, leading to intense pain, organ damage and premature death. Beta thalassemias are a group of inherited blood disorders that are caused by reduced or absent synthesis of beta globin, causing anemia.

Fetal hemoglobin (HbF) induction is known to ameliorate symptoms in SCD and beta-thalassemia patients, with both genetic (single nucleotide polymorphisms in the globin control locus & BCL11A) and pharmacologic (hydroxyurea) validation in the clinic (Vinjamur, D. S., et al. (2018), *The British Journal of Haematology*, 180(5), 630-643). Hydroxyurea is the current standard of care for SCD and is thought to provide benefit via induction of HbF, but is genotoxic, causes dose-limiting neutropenia and has a response rate of less than 40%. Other mechanisms being targeted clinically and preclinically include inhibition of HDAC1/2 (Shearstone et al., 2016, *PLoS One*, 11(4), e0153767), LSD1 (Rivers et al., 2018, *Experimental Hematology*, 67, 60-64), DNMT1, PDE9a (McArthur et al., 2019, *Haematologica.* doi:10.3324/haematol.2018.213462), HRI kinase (Grevet et al., 2018, *Science*, 361(6399), 285-290) and G9a/GLP (Krivega et al., 2015, *Blood*, 126(5), 665-672; Renneville et al., 2015, *Blood*, 126(16), 1930-1939). Additionally, the immunomodulators pomalidomide and lenalidomide induce HbF ex vivo in human primary erythroid cells (Moutouh-de Parseval, L. A. et al. (2008), *The Journal of Clinical Investigation*, 118(1), 248-258) and in vivo (Meiler, S. E. et al. (2011), Blood, 118(4), 1109-1112). WIZ is ubiquitously expressed and plays a role in targeting the G9a/GLP histone methyltransferases to genomic loci to regulate chromatin structure and transcription (Bian, Chen, et al. (2015), *eLife* 2015; 4:e05606.

SUMMARY OF THE DISCLOSURE

The disclosure relates to a therapeutic agent, which is effective in reducing WIZ protein expression levels and/or inducing fetal hemoglobin (HbF) expression. The disclosure further relates to pyrazolopyridine compounds, which are effective in reducing WIZ protein expression levels and/or inducing fetal hemoglobin (HbF) expression, pharmaceutically acceptable salts thereof, compositions thereof, and their use in therapies for the conditions and purposes detailed above.

The disclosure provides, in a first aspect, a compound of formula (I″) or a pharmaceutically acceptable salt, hydrate, solvate, prodrug, stereoisomer, or tautomer thereof, wherein:

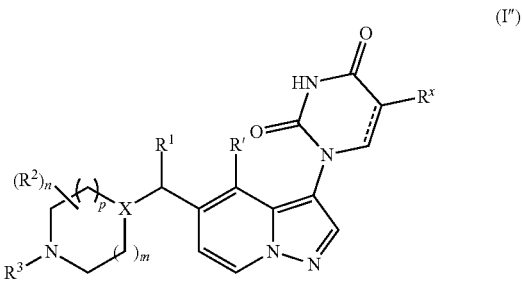

(I″)

≡ is a single bond or a double bond;
X is selected from CH, CF, and N;
$R^x$ is selected from hydrogen, $C_1$-$C_6$alkyl, halo (e.g., F, Cl), $C_1$-$C_6$alkoxyl, and $C_3$-$C_8$cycloalkyl;
R' is selected from hydrogen and $C_1$-$C_6$alkyl;
$R^1$ is selected from hydrogen and $C_1$-$C_6$alkyl;
each $R^2$ is independently selected from $C_1$-$C_6$alkyl, $C_1$-$C_6$haloalkyl, halo, and oxo, wherein the $C_1$-$C_6$alkyl is substituted with 0-1 occurrence of $R^{2a}$; or 2 $R^2$ on non-adjacent carbon atoms together with the non-adjacent carbon atoms to which they are attached form a bridging ring;
$R^{2a}$ is selected from $C_1$-$C_6$alkoxyl and hydroxyl;
$R^3$ is selected from hydrogen, $C_1$-$C_8$alkyl, $CN_2$—$C_6$alkenyl, —$SO_2R^4$, $C_1$-$C_6$haloalkyl, —C(=O)—O—($R^5$), —C(=O)—($R^6$), $C_3$-$C_{10}$cycloalkyl, and a 4- to 10-membered heterocyclyl comprising 1-2 heteroatoms independently selected from N, O and S, wherein the $C_1$-$C_8$alkyl and $C_1$-$C_6$haloalkyl are each independently substituted with 0-3 occurrences of $R^{3a}$, and wherein the $C_3$-$C_{10}$cycloalkyl and 4- to 10-membered heterocyclyl are each independently substituted with 0-3 occurrences of $R^{3b}$;
or
$R^3$ together with the nitrogen atom to which it is attached and $R^2$ together with the carbon atom to which it is attached form a 5- or 6-membered heterocyclyl comprising 0-1 additional heteroatom selected from N, O and S, which 5- or 6-membered heterocyclyl is substituted with 0-2 occurrences of an oxo group;
each $R^{3a}$ is independently selected from $C_3$-$C_{10}$cycloalkyl, a 4- to 10-membered heterocyclyl comprising 1-2 heteroatoms independently selected from N, O and S, a 5- to 10-membered heteroaryl comprising 1-4 heteroatoms independently selected from N, O, and S, $C_6$-$C_{10}$aryl, $C_1$-$C_6$alkoxyl, hydroxyl, and —C(=O)—NR⁷R⁸, wherein the C₃-C₁₀cycloalkyl, 4- to 6-membered heterocyclyl, 5- to 10-membered heteroaryl and C₆-C₁₀aryl are substituted with 0-4 occurrences of $R^{3b}$;

each $R^{3b}$ is independently selected from $C_1$-$C_6$alkoxyl, halo, $C_1$-$C_6$haloalkyl, $C_1$-$C_6$haloalkoxyl, $C_1$-$C_6$alkyl, —CN, —SO₂NR⁷R⁸, —SO₂R⁴, and hydroxyl;

$R^4$ is selected from $C_3$-$C_8$cycloalkyl, $C_1$-$C_6$alkyl, a 4- to 6-membered heterocyclyl comprising 1-2 heteroatoms independently selected from N, O and S, $C_6$-$C_{10}$aryl, and —NR$^{4b}$R$^{4c}$, wherein the $C_1$-$C_6$alkyl is substituted with 0-1 occurrence of $R^{4a}$;

$R^{4a}$ is selected from $C_3$-$C_8$cycloalkyl, $C_6$-$C_{10}$aryl, and $C_1$-$C_6$alkoxyl;

$R^{4b}$ is selected from hydrogen, and $C_1$-$C_6$alkyl;

$R^{4c}$ is selected from hydrogen, $C_1$-$C_6$alkyl, and $C_3$-$C_8$cycloalkyl;

$R^5$ is selected from $C_1$-$C_6$alkyl, $C_3$-$C_8$cycloalkyl, and $C_6$-$C_{10}$aryl;

$R^6$ is selected from $C_1$-$C_6$alkyl, $C_3$-$C_8$cycloalkyl, $C_6$-$C_{10}$aryl, a 4- to 10-membered heterocyclyl comprising 1-2 heteroatoms independently selected from N, O and S, and —NR$^{4b}$R$^{4c}$, wherein the $C_1$-$C_6$alkyl is substituted with 0-1 occurrence of $R^{6a}$, the $C_3$-$C_8$cycloalkyl is substituted with 0-1 occurrence of $R^{6b}$, and the 4- to 10-membered heterocyclyl is substituted with 0-1 occurrence of $C_1$-$C_6$alkyl;

$R^{6a}$ is selected from $C_6$-$C_{10}$aryl and $C_3$-$C_8$cycloalkyl;

$R^{6b}$ is selected from halo, $C_1$-$C_6$haloalkyl, $C_1$-$C_6$haloalkoxyl, and $C_1$-$C_6$alkyl;

$R^7$ is selected from hydrogen and $C_1$-$C_6$alkyl;

$R^8$ is selected from hydrogen and $C_1$-$C_6$alkyl;

or $R^7$ and $R^8$ together with the nitrogen atom to which they are attached form a 5- or 6-membered heterocyclyl comprising 0-1 additional heteroatom selected from N, O, and S;

n is 0, 1, 2, 3 or 4;

m is 0, 1 or 2; and p is 0 or 1.

The disclosure provides, in a further aspect, a compound of formula (I') or a pharmaceutically acceptable salt, hydrate, solvate, prodrug, stereoisomer, or tautomer thereof, wherein:

(I')

=== is a single bond or a double bond;

X is selected from CH, CF, and N;

R' is selected from hydrogen and $C_1$-$C_6$alkyl;

$R^1$ is selected from hydrogen and $C_1$-$C_6$alkyl;

each $R^2$ is independently selected from $C_1$-$C_6$alkyl, $C_1$-$C_6$haloalkyl, halo, and oxo, wherein the $C_1$-$C_6$alkyl is substituted with 0-1 occurrence of $R^{2a}$; or 2 $R^2$ on non-adjacent carbon atoms together with the non-adjacent carbon atoms to which they are attached form a bridging ring;

$R^{2a}$ is selected from $C_1$-$C_6$alkoxyl and hydroxyl;

$R^3$ is selected from hydrogen, $C_1$-$C_8$alkyl, $C_2$-$C_6$alkenyl, —SO₂R⁴, $C_1$-$C_6$haloalkyl, —C(=O)—O—(R⁵) and —C(=O)—(R⁶), wherein the $C_1$-$C_8$alkyl and $C_1$-$C_6$haloalkyl are independently substituted with 0-3 occurrences of $R^{3a}$;

or $R^3$ together with the nitrogen atom to which it is attached and $R^2$ together with the carbon atom to which it is attached form a 5- or 6-membered heterocyclyl comprising 0-1 additional heteroatom selected from N, O and S;

each $R^{3a}$ is independently selected from $C_3$-$C_{10}$cycloalkyl, a 4- to 6-membered heterocyclyl comprising 1-2 heteroatoms independently selected from N, O and S, a 5- to 10-membered heteroaryl comprising 1-4 heteroatoms independently selected from N, O, and S, $C_6$-$C_{10}$aryl, $C_1$-$C_6$alkoxyl, hydroxyl, and —C(=O)—NR⁷R⁸, wherein the $C_3$-$C_{10}$cycloalkyl, 4- to 6-membered heterocyclyl, 5- to 10-membered heteroaryl and $C_6$-$C_{10}$aryl are substituted with 0-4 occurrences of $R^{3b}$;

each $R^{3b}$ is independently selected from $C_1$-$C_6$alkoxyl, halo, $C_1$-$C_6$haloalkyl, $C_1$-$C_6$haloalkoxyl, $C_1$-$C_6$alkyl, —CN, —SO₂NR⁷R⁸, —SO₂R⁴, and hydroxyl;

$R^4$ is selected from $C_3$-$C_8$cycloalkyl, $C_1$-$C_6$alkyl, a 4- to 6-membered heterocyclyl comprising 1-2 heteroatoms independently selected from N, O and S, and $C_6$-$C_{10}$aryl, wherein the $C_1$-$C_6$alkyl is substituted with 0-1 occurrence of $R^{4a}$;

$R^{4a}$ is selected from $C_3$-$C_8$cycloalkyl, $C_6$-$C_{10}$aryl, and $C_1$-$C_6$alkoxyl;

$R^5$ is selected from $C_1$-$C_6$alkyl, $C_3$-$C_8$cycloalkyl, and $C_6$-$C_{10}$aryl;

$R^6$ is selected from $C_1$-$C_6$alkyl, $C_3$-$C_8$cycloalkyl, and $C_6$-$C_{10}$aryl, wherein the $C_1$-$C_6$alkyl is substituted with 0-1 occurrence of $R^{6a}$ and the $C_3$-$C_8$cycloalkyl is substituted with 0-1 occurrence of $R^{6b}$;

$R^{6a}$ is selected from $C_6$-$C_{10}$aryl and $C_3$-$C_8$cycloalkyl;

$R^{6b}$ is selected from halo, $C_1$-$C_6$haloalkyl, $C_1$-$C_6$haloalkoxyl, and $C_1$-$C_6$alkyl;

$R^7$ is selected from hydrogen and $C_1$-$C_6$alkyl;

$R^8$ is selected from hydrogen and $C_1$-$C_6$alkyl;

or $R^7$ and $R^8$ together with the nitrogen atom to which they are attached form a 5- or 6-membered heterocyclyl comprising 0-1 additional heteroatom selected from N, O, and S;

n is 0, 1, 2, 3 or 4;

m is 0, 1 or 2; and p is 0 or 1.

The disclosure provides, in a further aspect, a compound of formula (I) or a pharmaceutically acceptable salt, hydrate, solvate, prodrug, stereoisomer, or tautomer thereof, wherein:

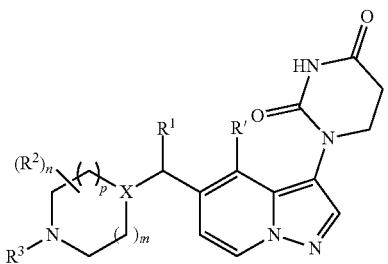
(I)

X is selected from CH, CF, and N;

R' is selected from hydrogen and $C_1$-$C_6$alkyl;

$R^1$ is selected from hydrogen and $C_1$-$C_6$alkyl;

each $R^2$ is independently selected from $C_1$-$C_6$alkyl, $C_1$-$C_6$haloalkyl, halo, and oxo, wherein the $C_1$-$C_6$alkyl is substituted with 0-1 occurrence of $R^{2a}$; or 2 $R^2$ on non-adjacent carbon atoms together with the non-adjacent carbon atoms to which they are attached form a bridging ring;

$R^{2a}$ is selected from $C_1$-$C_6$alkoxyl and hydroxyl;

$R^3$ is selected from hydrogen, $C_1$-$C_8$alkyl, $C_2$-$C_6$alkenyl, —$SO_2R^4$, $C_1$-$C_6$haloalkyl, —C(=O)—O—($R^5$) and —C(=O)—($R^6$), wherein the $C_1$-$C_8$alkyl and $C_1$-$C_6$haloalkyl are independently substituted with 0-3 occurrences of $R^{3a}$;

or $R^3$ together with the nitrogen atom to which it is attached and $R^2$ together with the carbon atom to which it is attached form a 5- or 6-membered heterocyclyl comprising 0-1 additional heteroatom selected from N, O and S;

each $R^{3a}$ is independently selected from $C_3$-$C_{10}$cycloalkyl, a 4- to 6-membered heterocyclyl comprising 1-2 heteroatoms independently selected from N, O and S, a 5- to 10-membered heteroaryl comprising 1-4 heteroatoms independently selected from N, O, and S, $C_6$-$C_{10}$aryl, $C_1$-$C_6$alkoxyl, hydroxyl, and —C(=O)—$NR^7R^8$, wherein the $C_3$-$C_{10}$cycloalkyl, 4- to 6-membered heterocyclyl, 5- to 10-membered heteroaryl and $C_6$-$C_{10}$aryl are substituted with 0-4 occurrences of $R^{3b}$;

each $R^{3b}$ is independently selected from $C_1$-$C_6$alkoxyl, halo, $C_1$-$C_6$haloalkyl, $C_1$-$C_6$haloalkoxyl, $C_1$-$C_6$alkyl, —CN, —$SO_2NR^7R^8$, —$SO_2R^4$, and hydroxyl;

$R^4$ is selected from $C_3$-$C_8$cycloalkyl, $C_1$-$C_6$alkyl, a 4- to 6-membered heterocyclyl comprising 1-2 heteroatoms independently selected from N, O and S, and $C_6$-$C_{10}$aryl, wherein the $C_1$-$C_6$alkyl is substituted with 0-1 occurrence of $R^{4a}$;

$R^{4a}$ is selected from $C_3$-$C_8$cycloalkyl, $C_6$-$C_{10}$aryl, and $C_1$-$C_6$alkoxyl;

$R^5$ is selected from $C_1$-$C_6$alkyl, $C_3$-$C_8$cycloalkyl, and $C_6$-$C_{10}$aryl;

$R^6$ is selected from $C_1$-$C_6$alkyl, $C_3$-$C_8$cycloalkyl, and $C_6$-$C_{10}$aryl, wherein the $C_1$-$C_6$alkyl is substituted with 0-1 occurrence of $R^{6a}$ and the $C_3$-$C_8$cycloalkyl is substituted with 0-1 occurrence of $R^{6b}$;

$R^{6a}$ is selected from $C_6$-$C_{10}$aryl and $C_3$-$C_8$cycloalkyl;

$R^{6b}$ is selected from halo, $C_1$-$C_6$haloalkyl, $C_1$-$C_6$haloalkoxyl, and $C_1$-$C_6$alkyl;

$R^7$ is selected from hydrogen and $C_1$-$C_6$alkyl;

$R^8$ is selected from hydrogen and $C_1$-$C_6$alkyl;

or $R^7$ and $R^8$ together with the nitrogen atom to which they are attached form a 5- or 6-membered heterocyclyl comprising 0-1 additional heteroatom selected from N, O, and S;

n is 0, 1, 2, 3 or 4;

m is 0, 1 or 2; and p is 0 or 1.

In a further aspect, the disclosure provides a pharmaceutical composition comprising a therapeutically effective amount of a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof, and a pharmaceutically acceptable carrier or excipient.

In a further aspect, the disclosure provides a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof, for use as a medicament.

In a further aspect, the disclosure provides a method of treating or preventing a disease or disorder in a subject in need thereof, the method comprising administering to the subject a therapeutically effective amount of a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof.

In a further aspect, the disclosure provides a method of treating or preventing a disorder that is affected by the reduction or modulation of WIZ protein levels, in a subject in need thereof, the method comprising administering to the subject a therapeutically effective amount of a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof.

In a further aspect, the disclosure provides a method of inhibiting WIZ protein expression in a subject in need thereof, the method comprising administering to the subject a therapeutically effective amount of a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof.

In a further aspect, the disclosure provides a method of degrading WIZ protein in a subject in need thereof, the method comprising administering to the subject a therapeutically effective amount of a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof.

In an further aspect, the disclosure provides a method of inhibiting, reducing, or eliminating the activity of WIZ protein or WIZ protein expression, the method comprising administering to the subject a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof.

In a further aspect, the disclosure provides a method of inducing or promoting fetal hemoglobin in a subject in need thereof, the method comprising administering to the subject a therapeutically effective amount of a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof.

In a further aspect, the disclosure provides a method of reactivating fetal hemoglobin production or expression in a subject in need thereof, the method comprising administering to the subject a therapeutically effective amount of a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof.

In an further aspect, the disclosure provides a method of increasing fetal hemoglobin expression in a subject in need thereof, the method comprising administering to the subject a therapeutically effective amount of a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof.

In a further aspect, the disclosure provides a method of treating a hemoglobinopathy, e.g., a beta-hemoglobinopathy, in a subject in need thereof, the method comprising administering to the subject a therapeutically effective amount of a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof.

In a further aspect, the disclosure provides a method of treating a sickle cell disease in a subject in need thereof, the method comprising administering to the subject a therapeutically effective amount of a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof.

In a further aspect, the disclosure provides a method of treating beta-thalassemia in a subject in need thereof, the method comprising administering to the subject a therapeutically effective amount of a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof.

In a further aspect, the disclosure provides a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof, for use in the treatment of a disease or disorder.

In a further aspect, the disclosure provides a compound of (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof, for use in the treatment of a disease or disorder selected from sickle cell disease and beta-thalassemia.

In a further aspect, the disclosure provides a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof, for use in the treatment or prevention of a disease or disorder that is affected by the reduction of WIZ protein levels.

In a further aspect, the disclosure provides a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof, for use in the treatment or prevention of a disease or disorder that is affected by the inhibition or reduction of WIZ protein expression.

In a further aspect, the disclosure provides a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof, for use in the treatment or prevention of a disease or disorder that is affected by the degradation of WIZ protein.

In a further aspect, the disclosure provides a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof, for use in inhibiting, reducing, or eliminating the activity of WIZ protein or WIZ protein expression.

In a further aspect, the disclosure provides a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof, for use in inducing or promoting fetal hemoglobin.

In a further aspect, the disclosure provides a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof, for use in reactivating fetal hemoglobin production or expression.

In a further aspect, the disclosure provides a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof, for use in increasing fetal hemoglobin expression.

In a further aspect, the disclosure provides a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof, for use in the treatment of a hemoglobinopathy.

In a further aspect, the disclosure provides a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof, for use in the treatment of a sickle cell disease.

In a further aspect, the disclosure provides a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof, for use in the treatment of beta-thalassemia.

In a further aspect, the disclosure provides a compound of (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof, for use in the treatment of a disease or disorder affected by an increase in fetal hemoglobin expression.

In a further aspect, the disclosure provides a compound of (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof, for use in the treatment of a disease or disorder affected by the inhibition, reduction, or elimination of the activity of WIZ protein or WIZ protein expression.

In a further aspect, the disclosure provides a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof, for use in the treatment of a disease or disorder affected by the induction or promotion of fetal hemoglobin.

In a further aspect, the disclosure provides a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof, for use in the treatment of a disease or disorder affected by the reactivation of fetal hemoglobin production or expression.

Various other aspects of the disclosure are described herein and in the claims.

Unless otherwise defined, all technical and scientific terms used herein have the same meaning as commonly understood by one of ordinary skill in the art to which this disclosure belongs. In the specification and claims, the singular forms also include the plural unless the context clearly dictates otherwise. Although methods and materials similar or equivalent to those described herein can be used in the practice or testing of the disclosure, suitable methods and materials are described below. All publications, patent applications, patents, and other references mentioned herein are incorporated by reference in their entireties for all purposes. The references cited herein are not admitted to be prior art to the claimed disclosure. In the case of conflict, the present specification, including definitions, will control. In addition, the materials, methods, and examples are illustrative only and are not intended to be limiting.

Other features and advantages of compounds, compositions, and methods disclosed herein will be apparent from the following detailed description and claims.

DETAILED DESCRIPTION OF THE DISCLOSURE

Figure 1A:
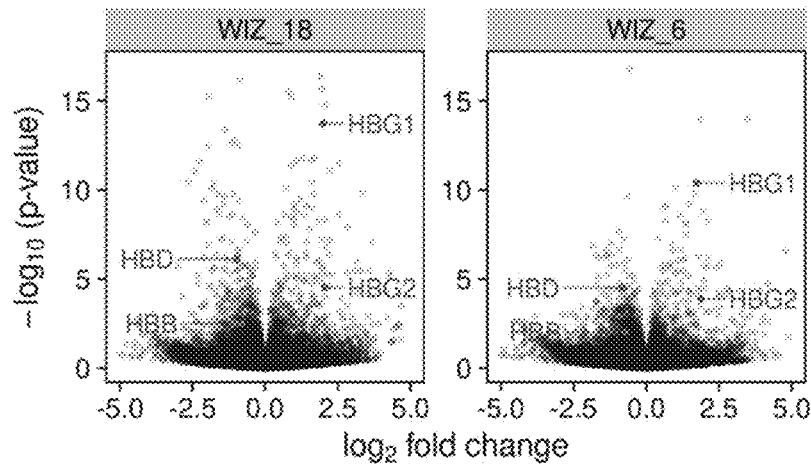
FIG. 1A depicts a volcano plot of differentially expressed genes from WIZ KO cells as compared to a scrambled gRNA control. Each dot represents a gene. HBG1/2 genes are differentially upregulated with WIZ_6 and WIZ_18 gRNA targeting WIZ KO.

The compounds disclosed herein are effective in reducing WIZ protein expression levels, or inducing fetal hemoglobin (HbF) expression. Without wishing to be bound by any theory, it is believed that the disclosed compounds may treat blood disorders, such as inherited blood disorders, e.g., sickle cell disease, and beta-thalassemia by inducing fetal hemoglobin HbF expression.

Definitions

Unless specified otherwise, the terms "compounds of the present disclosure," "compounds of the disclosure," or "compound of the disclosure" refer to compounds of formulae (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), and (Ie), exemplified compounds, salts thereof, particularly pharmaceutically acceptable salts thereof, hydrates, solvates, prodrugs, as well as all stereoisomers (including diastereoisomers and enantiomers), rotamers, tautomers, and isotopically labeled compounds (including deuterium substitutions), as well as inherently formed moieties.

In the groups, radicals, or moieties defined below, the number of carbon atoms is often specified preceding the group, for example, $C_1$-$C_8$alkyl means an alkyl group or radical having 1 to 8 carbon atoms. In general, for groups comprising two or more subgroups, the last named group is the radical attachment point, for example, "alkylaryl" means a monovalent radical of the formula alkyl-aryl-, while "arylalkyl" means a monovalent radical of the formula aryl-alkyl-.

Furthermore, the use of a term designating a monovalent radical where a divalent radical is appropriate shall be construed to designate the respective divalent radical and vice versa. Unless otherwise specified, conventional definitions of terms control and conventional stable atom valences are presumed and achieved in all formulas and groups. The articles "a" and "an" refer to one or more than one (e.g., to at least one) of the grammatical object of the article. By way of example, "an element" means one element or more than one element.

The term "and/or" means either "and" or "or" unless indicated otherwise.

The term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

As used herein the term "$C_1$-$C_8$alkyl" refers to a straight or branched hydrocarbon chain radical consisting solely of carbon and hydrogen atoms, containing no unsaturation, having from one to eight carbon atoms, and which is attached to the rest of the molecule by a single bond. The terms "$C_1$-$C_3$alkyl", "$C_1$-$C_4$alkyl", "$C_1$-$C_6$alkyl", are to be construed accordingly. Examples of $C_1$-$C_8$alkyl include, but are not limited to, methyl, ethyl, n-propyl, 1-methylethyl (iso-propyl), n-butyl, 1-methylpropyl (sec-butyl), 2-methylpropyl (iso-butyl or i-butyl), 1,1-dimethylethyl (t-butyl), n-pentyl, 3-pentyl, n-hexyl, n-heptyl, 4-heptyl, n-octyl, 2-isopropyl-3-methylbutyl.

As used herein, the term "$C_1$-$C_6$alkoxyl" refers to a radical of the formula —OR, where $R_a$ is a $C_1$-$C_6$alkyl radical as generally defined above. Examples of $C_1$-$C_6$alkoxyl include, but are not limited to, methoxy, ethoxy, propoxy, iso-propoxy, butoxy, iso-butoxy, tert-butoxy, sec-butoxy, pentoxy, and hexoxy.

As used herein, the term "$C_1$-$C_6$haloalkyl" refers to $C_1$-$C_6$alkyl radical, as defined above, substituted by one or more halo radicals, as defined herein. Examples of $C_1$-$C_6$haloalkyl include, but are not limited to, trifluoromethyl, difluoromethyl, fluoromethyl, trichloromethyl, 1,1-difluoroethyl, 2,2-difluoroethyl, 2,2,2-trifluoroethyl, 2-fluoropropyl, 1,1,1-trifluoropropyl, 2,2-difluoropropyl, 3,3-difluoropropyl and 1-fluoromethyl-2-fluoroethyl, 1,3-dibromopropan-2-yl, 3-bromo-2-fluoropropyl, 1,1,2,2-tetrafluoropropyl, and 1,4,4-trifluorobutan-2-yl.

As used herein, the term "$C_1$-$C_6$haloalkoxyl" means a $C_1$-$C_6$alkoxyl group as defined herein substituted with one or more halo radicals. Examples of $C_1$-$C_6$haloalkoxyl groups include, but are not limited to, trifluoromethoxy, difluoromethoxy, fluoromethoxy, trichloromethoxy, 1,1-difluoroethoxy, 2,2-difluoroethoxy, 2,2,2-trifluoroethoxy, 1-fluoromethyl-2-fluoroethoxy, pentafluoroethoxy, 2-fluoropropoxy, 3,3-difluoropropoxy and 3-dibromopropoxy. Preferably, the one or more halo radicals of $C_1$-$C_6$haloalkoxyl is fluoro. Preferably, $C_1$-$C_6$haloalkoxyl is selected from trifluoromethoxy, difluoromethoxy, fluoromethoxy, 1,1-difluoroethoxy, 2,2-difluoroethoxy, 2,2,2-trifluoroethoxy, 1-fluoromethyl-2-fluoroethoxy, and pentafluoroethoxy.

The term "halogen" or "halo" means fluoro, chloro, bromo or iodo.

As used herein, the term "cycloalkyl" means a monocyclic or polycyclic saturated or partially unsaturated carbon ring containing 3-18 carbon atoms wherein there are no delocalized pi electrons (aromaticity) shared among the ring carbon. The terms "$C_3$-$C_{10}$cycloalkyl", "$C_3$-$C_8$cycloalkyl", "$C_4$-$C_{10}$cycloalkyl" and "$C_4$-$C_7$cycloalkyl" are to be construed accordingly. The term polycyclic encompasses bridged (e.g., norbonane), fused (e.g., decalin) and spirocyclic cycloalkyl. Preferably, cycloalkyl, e.g., $C_3$-$C_{10}$cycloalkyl, is a monocyclic, bridged or spirocyclic hydrocarbon group of 3 to 10 carbon atoms.

Examples of cycloalkyl groups include, without limitations, cyclopropenyl, cyclopropyl cyclobutyl, cyclobutenyl, cyclopentyl, cyclohexyl, cycloheptenyl, cyclooctanyl, norboranyl, norborenyl, spiro[3.3]heptanyl (e.g., spiro[3.3]heptan-6-yl), bicyclo[2.2.2]octanyl, bicyclo[2.2.2]octenyl, adamantyl and derivatives thereof. Preferably, the cycloalkyl group is saturated.

Preferred examples of $C_3$-$C_{10}$cycloalkyl include, but are not limited to, cyclopropyl, cyclobutyl, cyclopentyl, cyclohexyl, spiro[3.3]heptanyl (e.g., spiro[3.3]heptan-6-yl), bicyclo[1.1.1]pentyl, bicyclo[2.1.1]hexyl, bicyclo[2.1.1]heptyl, bicyclo[2.2.2]octyl and adamantyl.

"Heterocyclyl" means a saturated or partially saturated monocyclic or polycyclic ring containing carbon and at least one heteroatom selected from oxygen, nitrogen, and sulfur (O, N, and S) and wherein there are no delocalized pi electrons (aromaticity) shared among the ring carbon or heteroatoms. The terms "4- to 10-membered heterocyclyl", "4- to 6-membered heterocyclyl" and "5- or 6-membered heterocyclyl" are to be construed accordingly. The heterocyclyl ring structure may be substituted by one or more substituents. The substituents can themselves be optionally substituted. The heterocyclyl may be bonded via a carbon atom or heteroatom. The term polycyclic encompasses bridged, fused and spirocyclic heterocyclyl.

Examples of heterocyclyl rings include, but are not limited to, oxetanyl, azetidinyl, tetrahydrofuranyl, tetrahydropyranyl, pyrrolidinyl, oxazolinyl, isoxazolinyl, oxazolidinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, 1,4-dioxanyl, dihydrofuranyl, 1,3-dioxolanyl, imidazolidinyl, dihydroisoxazolinyl, pyrrolinyl, pyrazolinyl, oxazepinyl, dithiolanyl, homotropanyl, dihydropyranyl (e.g., 3,6-dihydro-2H-pyranyl), oxaspiroheptanyl (e.g., 2-oxaspiro[3.3]heptan-6-yl), diazabicyclo[3.2.1]octan-3-yl), 2-azaspiro[3.3]heptanyl (e.g., 2-azaspiro[3.3]heptan-6-yl), and the like.

Preferred examples of heterocyclyl include, without limitations, oxetanyl, azetidinyl, pyrrolidinyl, tetrahydrofuranyl, tetrahydrothienyl, piperidinyl, piperazinyl, dihydroisoxazolinyl, tetrahydropyranyl, morpholinyl, dihydropyranyl (e.g., 3,6-dihydro-2H-pyranyl) 2-azaspiro[3.3]heptanyl (e.g., 2-azaspiro[3.3]heptan-6-yl) and oxaspiroheptanyl (e.g., 2-oxaspiro[3.3]heptan-6-yl).

As used herein, the term "aryl" as used herein means monocyclic, bicyclic or polycyclic carbocyclic aromatic rings. Examples of aryl include, but are not limited to, phenyl, naphthyl (e.g., naphth-1-yl, naphth-2-yl), anthryl (e.g., anthr-1-yl, anthr-9-yl), phenanthryl (e.g., phenanthr-1-yl, phenanthr-9-yl), and the like. Aryl is also intended to include monocyclic, bicyclic or polycyclic carbocyclic aromatic rings substituted with carbocyclic aromatic rings. Representative examples are biphenyl (e.g., biphenyl-2-yl, biphenyl-3-yl, biphenyl-4-yl), phenylnaphthyl (e.g., 1-phenylnaphth-2-yl, 2-phenylnaphth-1-yl), and the like. Aryl is also intended to include partially saturated bicyclic or polycyclic carbocyclic rings with at least one unsaturated moiety (e.g., a benzo moiety). Representative examples are, indanyl (e.g., indan-1-yl, indan-5-yl), indenyl (e.g., inden-1-yl, inden-5-yl), 1,2,3,4-tetrahydronaphthyl (e.g., 1,2,3,4-tetrahydronaphth-1-yl, 1,2,3,4-tetrahydronaphth-2-yl, 1,2,3,4-tetrahydronaphth-6-yl), 1,2-dihydronaphthyl (e.g., 1,2-dihydronaphth-1-yl, 1,2-dihydronaphth-4-yl, 1,2-dihydronaphth-6-yl), fluorenyl (e.g., fluoren-1-yl, fluoren-4-yl, fluoren-9-yl), and the like. Aryl is also intended to include partially saturated bicyclic or polycyclic carbocyclic aromatic rings containing one or two bridges. Representative examples are, benzonorbornyl (e.g., benzonorborn-3-yl, benzonorborn-6-yl), 1,4-ethano-1,2,3,4-tetrahydronapthyl (e.g., 1,4-ethano-1,2,3,4-tetrahydronapth-2-yl, 1,4-ethano-1,2,3,4-tetrahydronapth-10-yl), and the like. The term "$C_6$-$C_{10}$aryl" is to be construed accordingly.

Preferred examples of aryl include, but are not limited to, indenyl, (e.g., inden-1-yl, inden-5-yl) phenyl ($C_6H_5$), naphthyl ($C_{10}H_7$) (e.g., naphth-1-yl, naphth-2-yl), indanyl (e.g., indan-1-yl, indan-5-yl), and tetrahydronaphthalenyl (e.g., 1,2,3,4-tetrahydronaphthalenyl).

Preferably, $C_6$-$C_{10}$aryl refers to a monocyclic or bicyclic carbocyclic aromatic ring.

Preferred examples of $C_6$-$C_{10}$aryl include, but are not limited to, phenyl and naphthyl. In an embodiment, $C_6$-$C_{10}$aryl is phenyl.

As used herein, the term "heteroaryl" as used herein is intended to include monocyclic heterocyclic aromatic rings containing one or more heteroatoms selected from oxygen, nitrogen, and sulfur (O, N, and S). Representative examples are pyrrolyl, furanyl, thienyl, oxazolyl, thiazolyl, imidazolyl, pyrazolyl, isothiazolyl, isooxazolyl, triazolyl, (e.g., 1,2,4-triazolyl), oxadiazolyl, (e.g., 1,2,3-oxadiazolyl, 1,2,4-oxadiazolyl, 1,2,5-oxadiazolyl, 1,3,4-oxadiazolyl), thiadiazolyl (e.g., 1,2,3-thiadiazolyl, 1,2,4-thiadiazolyl, 1,2,5-thiadiazolyl, 1,3,4-thiadiazolyl), tetrazolyl, pyranyl, pyridinyl, pyridazinyl, pyrimidinyl, pyrazinyl, 1,2,3-triazinyl, 1,2,4-triazinyl, 1,3,5-triazinyl, thiadiazinyl, azepinyl, azecinyl, and the like.

Heteroaryl is also intended to include bicyclic heterocyclic aromatic rings containing one or more heteroatoms selected from oxygen, nitrogen, and sulfur (O, N, and S). Representative examples are indolyl, isoindolyl, benzofuranyl, benzothiophenyl, indazolyl, benzopyranyl, benzimidazolyl, benzothiazolyl, benzisothiazolyl, benzoxazolyl, benzisoxazolyl, benzoxazinyl, benzotriazolyl, naphthyridinyl, phthalazinyl, pteridinyl, purinyl, quinazolinyl, cinnolinyl, quinolinyl, isoquinolinyl, quinoxalinyl, oxazolopyridinyl, isooxazolopyridinyl, pyrrolopyridinyl, furopyridinyl, thienopyridinyl, imidazopyridinyl, imidazopyrimidinyl, pyrazolopyridinyl, pyrazolopyrimidinyl, pyrazolotriazinyl, thiazolopyridinyl, thiazolopyrimidinyl, imdazothiazolyl, triazolopyridinyl, triazolopyrimidinyl, and the like.

Heteroaryl is also intended to include polycyclic heterocyclic aromatic rings containing one or more heteroatoms selected from oxygen, nitrogen, and sulfur (O, N, and S). Representative examples are carbazolyl, phenoxazinyl, phenazinyl, acridinyl, phenothiazinyl, carbolinyl, phenanthrolinyl, and the like.

Heteroaryl is also intended to include partially saturated monocyclic, bicyclic or polycyclic heterocyclyls containing one or more heteroatoms selected oxygen, nitrogen, and sulfur (O, N, and S). Representative examples are imidazolinyl, indolinyl, dihydrobenzofuranyl, dihydrobenzothienyl, dihydrobenzopyranyl, dihydropyridooxazinyl, dihydrobenzodioxinyl (e.g., 2,3-dihydrobenzo[b][1,4]dioxinyl), benzodioxolyl (e.g., benzo[d][1,3]dioxole), dihydrobenzooxazinyl (e.g., 3,4-dihydro-2H-benzo[b][1,4]oxazine), tetrahydroindazolyl, tetrahydrobenzimidazolyl, tetrahydroimidazo[4,5-c]pyridyl, tetrahydroquinolinyl, tetrahydroisoquinolinyl, tetrahydroquinoxalinyl, and the like.

The heteroaryl ring structure may be substituted by one or more substituents. The substituents can themselves be optionally substituted. The heteroaryl ring may be bonded via a carbon atom or heteroatom.

The term "5-10 membered heteroaryl" is to be construed accordingly.

Examples of 5-10 membered heteroaryl include, but are not limited to, indolyl, imidazopyridyl, isoquinolinyl, benzooxazolonyl, pyridinyl, pyrimidinyl, pyridinonyl, benzotriazolyl, pyridazinyl, pyrazolotriazinyl, indazolyl, benzimidazolyl, quinolinyl, triazolyl, (e.g., 1,2,4-triazolyl), pyrazolyl, thiazolyl, oxazolyl, isooxazolyl, pyrrolyl, oxadiazolyl, (e.g., 1,2,3-oxadiazolyl, 1,2,4-oxadiazolyl, 1,2,5-oxadiazolyl, 1,3,4-oxadiazolyl), imidazolyl, pyrrolopyridinyl, tetrahydroindazolyl, quinoxalinyl, thiadiazolyl (e.g., 1,2,3-thiadiazolyl, 1,2,4-thiadiazolyl, 1,2,5-thiadiazolyl, 1,3,4-thiadiazolyl), pyrazinyl, oxazolopyridinyl, pyrazolopyrimidinyl, benzoxazolyl, indolinyl, isooxazolopyridinyl, dihydropyridooxazinyl, tetrazolyl, dihydrobenzodioxinyl (e.g., 2,3-dihydrobenzo[b][1,4]dioxinyl), benzodioxolyl (e.g., benzo[d][1,3]dioxole) and dihydrobenzooxazinyl (e.g., 3,4-dihydro-2H-benzo[b][1,4]oxazine).

As used herein, the term "oxo" refers to the radical =O.

"Cyano" or "—CN" means a substituent having a carbon atom joined to a nitrogen atom by a triple bond, e.g., C≡N.

The term "$C_2$-$C_6$alkenyl" as used herein represents a branched or straight hydrocarbon group having from 2 to 6 carbon atoms and at least one double bond. Representative examples are ethenyl (or vinyl), propenyl (e.g., prop-1-enyl, prop-2-enyl), 2-methylprop-1-enyl, 2-methylprop-2-enyl, 1,1-(dimethyl)prop-2-enyl, butadienyl (e.g., buta-1,3-dienyl), butenyl (e.g., but-1-en-1-yl, but-2-en-1-yl), 2-methylbut-1-enyl, pentenyl (e.g., pent-1-enyl, pent-2-enyl), hexenyl (e.g., hex-1-enyl, hex-2-enyl, hex-3-enyl), 2-methylpent-3-enyl, and the like.

As used herein, the term "bridging ring" refers to a ring formed at two non-adjacent carbon atoms of the heterocycloalkyl moiety of formula (I), linked to form a $C_1$-$C_3$ alkylene linker, wherein one of the carbon atoms of said linker is optionally replaced by a heteroatom selected from nitrogen, oxygen and sulfur. In a preferred embodiment, the alkylene linker comprises carbon atoms only.

As used herein, the term "$C_1$-$C_3$alkylene" refers to a straight hydrocarbon chain bivalent radical consisting solely of carbon and hydrogen atoms, containing no unsaturation, having from one to three carbon atoms.

As used herein, the term "optionally substituted" includes unsubstituted or substituted.

As used herein, "╱*" denotes the point of attachment to the other part of the molecule.

As used herein, the term nitrogen protecting group (PG) in a compound of Formula (X) or any intermediates in any of the general schemes 1 to 5 and subformulae thereof refers to a group that should protect the functional groups concerned against unwanted secondary reactions, such as acylations, etherifications, esterifications, oxidations, solvolysis and similar reactions. It may be removed under deprotection conditions. Depending on the protecting group employed, the skilled person would know how to remove the protecting group to obtain the free amine $NH_2$ group by reference to known procedures. These include reference to organic chemistry textbooks and literature procedures such as J. F. W. McOmie, "Protective Groups in Organic Chemistry", Plenum Press, London and New York 1973; T. W. Greene and P. G. M. Wuts, "Greene's Protective Groups in Organic Synthesis", Fourth Edition, Wiley, New York 2007; in "The Peptides"; Volume 3 (editors: E. Gross and J. Meienhofer), Academic Press, London and New York 1981; P. J. Kocienski, "Protecting Groups", Third Edition, Georg Thieme Verlag, Stuttgart and New York 2005; and in "Methoden der organischen Chemie" (Methods of Organic Chemistry), Houben Weyl, 4th edition, Volume 15/I, Georg Thieme Verlag, Stuttgart 1974.

Preferred nitrogen protecting groups generally comprise: $C_1$-$C_6$alkyl (e.g., tert-butyl), preferably $C_1$-$C_4$alkyl, more preferably $C_1$-$C_2$alkyl, most preferably $C_1$alkyl which is mono-, di- or tri-substituted by trialkylsilyl-$C_1$-$C_7$alkoxy (e.g., trimethylsilyethoxy), aryl, preferably phenyl, or a heterocyclic group (e.g., benzyl, cumyl, benzhydryl, pyrrolidinyl, trityl, pyrrolidinylmethyl, 1-methyl-1,1-dimethylbenzyl, (phenyl)methylbenzene) wherein the aryl ring or the heterocyclic group is unsubstituted or substituted by one or more, e.g., two or three, residues, e.g., selected from the group consisting of $C_1$-$C_7$alkyl, hydroxy, $C_1$-$C_7$alkoxy (e.g., para-methoxy benzyl (PMB), $C_2$-$C_8$-alkanoyl-oxy, halogen, nitro, cyano, and $CF_3$, aryl-$C_1$-$C_2$-alkoxycarbonyl (preferably phenyl-$C_1$-$C_2$-alkoxycarbonyl (e.g., benzyloxycarbonyl (Cbz), benzyloxymethyl (BOM), pivaloyloxymethyl (POM)), $C_1$-$C_{10}$-alkenyloxycarbonyl, $C_1$-$C_6$alkylcarbonyl (e.g., acetyl or pivaloyl), $C_6$-$C_{10}$-arylcarbonyl; $C_1$-$C_6$-alkoxycarbonyl (e.g., tertbutoxycarbonyl (Boc), methylcarbonyl, trichloroethoxycarbonyl (Troc), pivaloyl (Piv), allyloxycarbonyl), $C_6$-$C_{10}$-aryl$C_1$-$C_6$-alkoxycarbonyl (e.g., 9-fluorenylmethyloxycarbonyl (Fmoc)), allyl or cinnamyl, sulfonyl or sulfenyl, succinimidyl group, silyl groups (e.g., triarylsilyl, trialkylsilyl, triethylsilyl (TES), trimethylsilylethoxymethyl (SEM), trimethylsilyl (TMS), triisopropylsilyl or tertbutyldimethylsilyl).

According to the disclosure, the preferred nitrogen protecting group (PG) can be selected from the group comprising tert-butyloxycarbonyl (Boc), benzyloxycarbonyl (Cbz), para-methoxy benzyl (PMB), 2,4-dimethoxybenzyl (DMB), methyloxycarbonyl, trimethylsilylethoxymethyl (SEM) and benzyl. The nitrogen protecting group (PG) is preferably an acid labile protecting group, e.g., tert-butyloxycarbonyl (Boc), 2,4-dimethoxybenzyl (DMB).

In some embodiments, the compounds of the disclosure are selective over other proteins.

As used herein, the term "therapeutic agent" in connection with methods of reducing WIZ protein expression levels and/or inducing fetal hemoglobin (HbF) expression, refers to a substance that results in a detectably lower expression of WIZ gene or WIZ protein or lower activity level of WIZ proteins as compared to those levels without such substance.

As used herein "modulator" or "degrader", means, for example, a compound of the disclosure, that effectively modulates, decreases, or reduces the levels of a specific protein (e.g., WIZ) or degrades a specific protein (e.g., WIZ). The amount of a specific protein (e.g., WIZ) degraded can be measured by comparing the amount of the specific protein (e.g., WIZ) remaining after treatment with a compound of the disclosure as compared to the initial amount or level of the specific protein (e.g., WIZ) present as measured prior to treatment with a compound of the disclosure.

As used herein "selective modulator", "selective degrader", or "selective compound" means, for example, a compound of the disclosure, that effectively modulates, decreases, or reduces the levels of a specific protein (e.g., WIZ) or degrades a specific protein (e.g., WIZ) to a greater extent than any other protein. A "selective modulator", "selective degrader", or "selective compound" can be identified, for example, by comparing the ability of a compound to modulate, decrease, or reduce the levels of or to degrade a specific protein (e.g., WIZ) to its ability to modulate, decrease, or reduce the levels of or to degrade other proteins. In some embodiments, the selectivity can be identified by measuring the $EC_{50}$ or $IC_{50}$ of the compounds. Degradation may be achieved through mediation of an E3 ligase, e.g., E3-ligase complexes comprising the protein Cereblon.

In one embodiment, the specific protein degraded is WIZ protein. In an embodiment, at least about 30% of WIZ is degraded compared to initial levels. In an embodiment, at least about 40% of WIZ is degraded compared to initial levels. In an embodiment, at least about 50% of WIZ is degraded compared to initial levels. In an embodiment, at least about 60% of WIZ is degraded compared to initial levels. In an embodiment, at least about 70% of WIZ is degraded compared to initial levels. In an embodiment, at least about 75% of WIZ is degraded compared to initial levels. In an embodiment, at least about 80% of WIZ is degraded compared to initial levels. In an embodiment, at least about 85% of WIZ is degraded compared to initial levels. In an embodiment, at least about 90% of WIZ is degraded compared to initial levels. In an embodiment, at least about 95% of WIZ is degraded compared to initial levels. In an embodiment, over 95% of WIZ is degraded compared to initial levels. In an embodiment, at least about 99% of WIZ is degraded compared to initial levels.

In an embodiment, the WIZ is degraded in an amount of from about 30% to about 99% compared to initial levels. In an embodiment, the WIZ is degraded in an amount of from about 40% to about 99% compared to initial levels. In an embodiment, the WIZ is degraded in an amount of from about 50% to about 99% compared to initial levels. In an embodiment, the WIZ is degraded in an amount of from about 60% to about 99% compared to initial levels. In an embodiment, the WIZ is degraded in an amount of from about 70% to about 99% compared to initial levels. In an embodiment, the WIZ is degraded in an amount of from about 80% to about 99% compared to initial levels. In an embodiment, the WIZ is degraded in an amount of from about 90% to about 99% compared to initial levels. In an embodiment, the WIZ is degraded in an amount of from about 95% to about 99% compared to initial levels. In an embodiment, the WIZ is degraded in an amount of from about 90% to about 95% compared to initial levels.

As used herein, the terms "inducing fetal hemoglobin", "fetal hemoglobin induction", or "increasing fetal hemoglobin expression" refer to increasing the percentage of HbF in the blood of a subject. In an embodiment, the amount of total HbF in the blood of the subject increases. In an embodiment, the amount of total hemoglobin in the blood of the subject increases. In an embodiment, the amount of HbF is increased by at least about 10%, or at least about 20%, or at least about 30%, or at least about 40%, or at least about 50%, or at least about 60%, or at least about 70%, or at least about 80%, or at least about 90%, or at least about 100%, or more than 100%, for example, at least about 2-fold, or at least about 3-fold, or at least about 4-fold, or at least about 5-fold, or at least about 6-fold, or at least about 7-fold, or at least about 8-fold, or at least about 9-fold, or at least about 10-fold, or more than 10-fold as compared to either in the absence of a compound disclosed herein.

In an embodiment, the total hemoglobin in the blood, e.g., the blood in a subject, is increased by at least about 10%, or at least about 20%, or at least about 30%, or at least about 40%, or at least about 50%, or at least about 60%, or at least about 70%, or at least about 80%, or at least about 90%, or at least about 100%, or more than 100%, for example, at least about 2-fold, or at least about 3-fold, or at least about 4-fold, or at least about 5-fold, or at least about 6-fold, or at least about 7-fold, or at least about 8-fold, or at least about 9-fold, or at least about 10-fold, or more than 10-fold as compared to either in the absence of a compound disclosed herein.

The term "a therapeutically effective amount" of a compound of the disclosure refers to an amount of the compound of the disclosure that will elicit the biological or medical response of a subject, for example, reduction or inhibition of an enzyme or a protein activity, or ameliorate symptoms, alleviate conditions, slow or delay disease progression, or prevent a disease, etc. In one embodiment, the term "a therapeutically effective amount" refers to the amount of the compound of the disclosure that, when administered to a subject, is effective to (1) at least partially alleviate, prevent and/or ameliorate a condition, or a disorder or a disease (i) mediated by WIZ, or (ii) associated with WIZ activity, or (iii) characterized by activity (normal or abnormal) of WIZ: (2) reduce or inhibit the activity of WIZ; or (3) reduce or inhibit the expression of WIZ. In another embodiment, the term "a therapeutically effective amount" refers to the amount of the compound of the disclosure that, when administered to a cell, or a tissue, or a non-cellular biological material, or a medium, is effective to at least partially reducing or inhibiting the activity of WIZ; or at least partially reducing or inhibiting the expression of WIZ.

"HbF-dependent disease or disorder" means any disease or disorder which is directly or indirectly affected by the modulation of HbF protein levels.

As used herein, the term "subject" refers to primates (e.g., humans, male or female), dogs, rabbits, guinea pigs, pigs, rats and mice. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers to alleviating or ameliorating the disease or disorder (i.e., slowing or arresting the development of the disease or at least one of the clinical symptoms thereof); or alleviating or ameliorating at least one physical parameter or biomarker associated with the disease or disorder, including those which may not be discernible to the patient.

As used herein, the term "prevent", "preventing" or "prevention" of any disease or disorder refers to the prophylactic treatment of the disease or disorder; or delaying the onset or progression of the disease or disorder As used herein, a subject is "in need of" a treatment if such subject would benefit biologically, medically or in quality of life from such treatment.

As used herein, the term "a," "an," "the" and similar terms used in the context of the disclosure (especially in the context of the claims) are to be construed to cover both the singular and plural unless otherwise indicated herein or clearly contradicted by the context.

Various enumerated embodiments of the disclosure are described herein. It will be recognized that features specified in each embodiment may be combined with other specified features to provide further embodiments of the disclosure.

Enumerated Embodiments

Embodiment 1. A compound of Formula (I″) or a pharmaceutically acceptable salt, hydrate, solvate, prodrug, stereoisomer, or tautomer thereof, wherein:

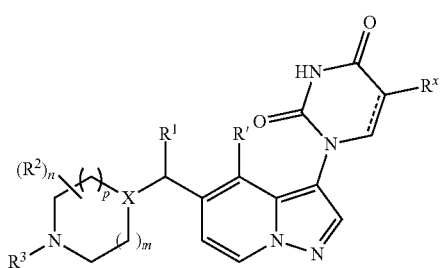

(I″)

=== is a single bond or a double bond;
X is selected from CH, CF, and N;
$R^x$ is selected from hydrogen, $C_1$-$C_6$alkyl, halo (e.g., F, Cl), $C_1$-$C_6$alkoxyl, and $C_3$-$C_8$cycloalkyl;
R' is selected from hydrogen and $C_1$-$C_6$alkyl;
$R^1$ is selected from hydrogen and $C_1$-$C_6$alkyl;
each $R^2$ is independently selected from $C_1$-$C_6$alkyl, $C_1$-$C_6$haloalkyl, halo, and oxo, wherein the $C_1$-$C_6$alkyl is substituted with 0-1 occurrence of $R^{2a}$; or $2R^2$ on non-adjacent carbon atoms together with the non-adjacent carbon atoms to which they are attached form a bridging ring;
$R^{2a}$ is selected from $C_1$-$C_6$alkoxyl and hydroxyl;
$R^3$ is selected from hydrogen, $C_1$-$C_8$alkyl, $C_2$-$C_6$alkenyl, —$SO_2R^4$, $C_1$-$C_6$haloalkyl, —C(=O)—O—($R^5$), —C(=O)—($R^6$), $C_3$-$C_{10}$cycloalkyl, and a 4- to 10-membered heterocyclyl comprising 1-2 heteroatoms independently selected from N, O and S, wherein the $C_1$-$C_8$alkyl and $C_1$-$C_6$haloalkyl are each independently substituted with 0-3 occurrences of $R^{3a}$, and wherein the $C_3$-$C_{10}$cycloalkyl and 4- to 10-membered heterocyclyl are each independently substituted with 0-3 occurrences of $R^{3b}$;
or
$R^3$ together with the nitrogen atom to which it is attached and $R^2$ together with the carbon atom to which it is attached form a 5- or 6-membered heterocyclyl comprising 0-1 additional heteroatom selected from N, O and S, which 5- or 6-membered heterocyclyl is substituted with 0-2 occurrences of an oxo group;

each $R^{3a}$ is independently selected from $C_3$-$C_{10}$cycloalkyl, a 4- to 10-membered heterocyclyl comprising 1-2 heteroatoms independently selected from N, O and S, a 5- to 10-membered heteroaryl comprising 1-4 heteroatoms independently selected from N, O, and S, $C_6$-$C_{10}$aryl, $C_1$-$C_6$alkoxyl, hydroxyl, and —C(=O)—$NR^7R^8$, wherein the $C_3$-$C_{10}$cycloalkyl, 4- to 6-membered heterocyclyl, 5- to 10-membered heteroaryl and $C_6$-$C_{10}$aryl are substituted with 0-4 occurrences of $R^{3b}$;
each $R^{3b}$ is independently selected from $C_1$-$C_6$alkoxyl, halo, $C_1$-$C_6$haloalkyl, $C_1$-$C_6$haloalkoxyl, $C_1$-$C_6$alkyl, —CN, —$SO_2NR^7R^8$, —$SO_2R^4$, and hydroxyl;
$R^4$ is selected from $C_3$-$C_8$cycloalkyl, $C_1$-$C_6$alkyl, a 4- to 6-membered heterocyclyl comprising 1-2 heteroatoms independently selected from N, O and S, $C_6$-$C_{10}$aryl, and —$NR^{4b}R^{4c}$, wherein the $C_1$-$C_6$alkyl is substituted with 0-1 occurrence of $R^{4a}$;
$R^{4a}$ is selected from $C_3$-$C_8$cycloalkyl, $C_6$-$C_{10}$aryl, and $C_1$-$C_6$alkoxyl;
$R^{4b}$ is selected from hydrogen, and $C_1$-$C_6$alkyl;
$R^{4c}$ is selected from hydrogen, $C_1$-$C_6$alkyl, and $C_3$-$C_8$cycloalkyl;
$R^5$ is selected from $C_1$-$C_6$alkyl, $C_3$-$C_8$cycloalkyl, and $C_6$-$C_{10}$aryl;
$R^6$ is selected from $C_1$-$C_6$alkyl, $C_3$-$C_8$cycloalkyl, $C_6$-$C_{10}$aryl, a 4- to 10-membered heterocyclyl comprising 1-2 heteroatoms independently selected from N, O and S, and —$NR^{4b}R^{4c}$, wherein the $C_1$-$C_6$alkyl is substituted with 0-1 occurrence of $R^{6a}$, the $C_3$-$C_8$cycloalkyl is substituted with 0-1 occurrence of $R^{6b}$, and the 4- to 10-membered heterocyclyl is substituted with 0-1 occurrence of $C_1$-$C_6$alkyl;
$R^{6a}$ is selected from $C_6$-$C_{10}$aryl and $C_3$-$C_8$cycloalkyl;
$R^{6b}$ is selected from halo, $C_1$-$C_6$haloalkyl, $C_1$-$C_6$haloalkoxyl, and $C_1$-$C_6$alkyl;
$R^7$ is selected from hydrogen and $C_1$-$C_6$alkyl;
$R^8$ is selected from hydrogen and $C_1$-$C_6$alkyl;
or
$R^7$ and $R^8$ together with the nitrogen atom to which they are attached form a 5- or 6-membered heterocyclyl comprising 0-1 additional heteroatom selected from N, O, and S;
n is 0, 1, 2, 3 or 4;
m is 0, 1 or 2; and
p is 0 or 1.
Embodiment 2. A compound of Formula (I′) or a pharmaceutically acceptable salt, hydrate, solvate, prodrug, stereoisomer, or tautomer thereof, wherein:

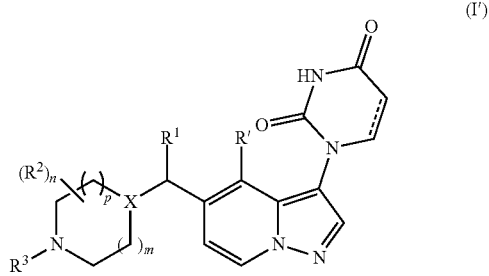

(I′)

=== is a single bond or a double bond;
X is selected from CH, CF, and N;
R' is selected from hydrogen and $C_1$-$C_6$alkyl;
$R^1$ is selected from hydrogen and $C_1$-$C_6$alkyl;

each $R^2$ is independently selected from $C_1$-$C_6$alkyl, $C_1$-$C_6$haloalkyl, halo, and oxo, wherein the $C_1$-$C_6$alkyl is substituted with 0-1 occurrence of $R^{2a}$; or 2 $R^2$ on non-adjacent carbon atoms together with the non-adjacent carbon atoms to which they are attached form a bridging ring;

$R^{2a}$ is selected from $C_1$-$C_6$alkoxyl and hydroxyl;

$R^3$ is selected from hydrogen, $C_1$-$C_8$alkyl, $C_2$-$C_6$alkenyl, —$SO_2R^4$, $C_1$-$C_6$haloalkyl, —C(=O)—O—($R^5$) and —C(=O)—($R^6$), wherein the $C_1$-$C_8$alkyl and $C_1$-$C_6$haloalkyl are independently substituted with 0-3 occurrences of $R^{3a}$;

or $R^3$ together with the nitrogen atom to which it is attached and $R^2$ together with the carbon atom to which it is attached form a 5- or 6-membered heterocyclyl comprising 0-1 additional heteroatom selected from N, O and S;

each $R^{3a}$ is independently selected from $C_3$-$C_{10}$cycloalkyl, a 4- to 6-membered heterocyclyl comprising 1-2 heteroatoms independently selected from N, O and S, a 5- to 10-membered heteroaryl comprising 1-4 heteroatoms independently selected from N, O, and S, $C_6$-$C_{10}$aryl, $C_1$-$C_6$alkoxyl, hydroxyl, and —C(=O)—$NR^7R^8$, wherein the $C_3$-$C_{10}$cycloalkyl, 4- to 6-membered heterocyclyl, 5- to 10-membered heteroaryl and $C_6$-$C_{10}$aryl are substituted with 0-4 occurrences of $R^{3b}$;

each $R^{3b}$ is independently selected from $C_1$-$C_6$alkoxyl, halo, $C_1$-$C_6$haloalkyl, $C_1$-$C_6$haloalkoxyl, $C_1$-$C_6$alkyl, —CN, —$SO_2NR^7R^8$, —$SO_2R^4$, and hydroxyl;

$R^4$ is selected from $C_3$-$C_8$cycloalkyl, $C_1$-$C_6$alkyl, a 4- to 6-membered heterocyclyl comprising 1-2 heteroatoms independently selected from N, O and S, and $C_6$-$C_{10}$aryl, wherein the $C_1$-$C_6$alkyl is substituted with 0-1 occurrence of $R^{4a}$;

$R^{4a}$ is selected from $C_3$-$C_8$cycloalkyl, $C_6$-$C_{10}$aryl, and $C_1$-$C_6$alkoxyl;

$R^5$ is selected from $C_1$-$C_6$alkyl, $C_3$-$C_8$cycloalkyl, and $C_6$-$C_{10}$aryl;

$R^6$ is selected from $C_1$-$C_6$alkyl, $C_3$-$C_8$cycloalkyl, and $C_6$-$C_{10}$aryl, wherein the $C_1$-$C_6$alkyl is substituted with 0-1 occurrence of $R^{6a}$ and the $C_3$-$C_8$cycloalkyl is substituted with 0-1 occurrence of $R^{6b}$;

$R^{6a}$ is selected from $C_6$-$C_{10}$aryl and $C_3$-$C_8$cycloalkyl;

$R^{6b}$ is selected from halo, $C_1$-$C_6$haloalkyl, $C_1$-$C_6$haloalkoxyl, and $C_1$-$C_6$alkyl;

$R^7$ is selected from hydrogen and $C_1$-$C_6$alkyl;

$R^8$ is selected from hydrogen and $C_1$-$C_6$alkyl;

or $R^7$ and $R^8$ together with the nitrogen atom to which they are attached form a 5- or 6-membered heterocyclyl comprising 0-1 additional heteroatom selected from N, O, and S;

n is 0, 1, 2, 3 or 4;

m is 0, 1 or 2; and p is 0 or 1.

Embodiment 3. A compound of Formula (I) or a pharmaceutically acceptable salt, hydrate, solvate, prodrug, stereoisomer, or tautomer thereof, wherein:

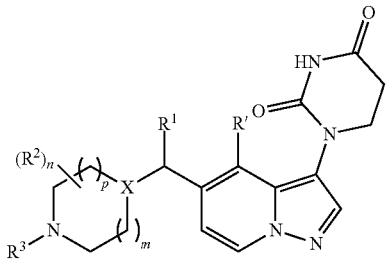

X is selected from X is selected from CH, CF, and N;

R' is selected from hydrogen and $C_1$-$C_6$alkyl;

$R^1$ is selected from hydrogen and $C_1$-$C_6$alkyl;

each $R^2$ is independently selected from $C_1$-$C_6$alkyl, $C_1$-$C_6$haloalkyl, halo, and oxo, wherein the $C_1$-$C_6$alkyl is substituted with 0-1 occurrence of $R^{2a}$; or 2 $R^2$ on non-adjacent carbon atoms together with the non-adjacent carbon atoms to which they are attached form a bridging ring;

$R^{2a}$ is selected from $C_1$-$C_6$alkoxyl and hydroxyl;

$R^3$ is selected from hydrogen, $C_1$-$C_8$alkyl, $C_2$-$C_6$alkenyl, —$SO_2R^4$, $C_1$-$C_6$haloalkyl, —C(=O)—O—($R^5$) and —C(=O)—($R^6$), wherein the $C_1$-$C_8$alkyl and $C_1$-$C_6$haloalkyl are independently substituted with 0-3 occurrences of $R^{3a}$;

or $R^3$ together with the nitrogen atom to which it is attached and $R^2$ together with the carbon atom to which it is attached form a 5- or 6-membered heterocyclyl comprising 0-1 additional heteroatom selected from N, O and S;

each $R^{3a}$ is independently selected from $C_3$-$C_{10}$cycloalkyl, a 4- to 6-membered heterocyclyl comprising 1-2 heteroatoms independently selected from N, O and S, a 5- to 10-membered heteroaryl comprising 1-4 heteroatoms independently selected from N, O, and S, $C_6$-$C_{10}$aryl, $C_1$-$C_6$alkoxyl, hydroxyl, and —C(=O)—$NR^7R^8$, wherein the $C_3$-$C_{10}$cycloalkyl, 4- to 6-membered heterocyclyl, 5- to 10-membered heteroaryl and $C_6$-$C_{10}$aryl are substituted with 0-4 occurrences of $R^{3b}$;

each $R^{3b}$ is independently selected from $C_1$-$C_6$alkoxyl, halo, $C_1$-$C_6$haloalkyl, $C_1$-$C_6$haloalkoxyl, $C_1$-$C_6$alkyl, —CN, —$SO_2NR^7R^8$, —$SO_2R^4$, and hydroxyl;

$R^4$ is selected from $C_3$-$C_8$cycloalkyl, $C_1$-$C_6$alkyl, a 4- to 6-membered heterocyclyl comprising 1-2 heteroatoms independently selected from N, O and S, and $C_6$-$C_{10}$aryl, wherein the $C_1$-$C_6$alkyl is substituted with 0-1 occurrence of $R^{4a}$;

$R^{4a}$ is selected from $C_3$-$C_8$cycloalkyl, $C_6$-$C_{10}$aryl, and $C_1$-$C_6$alkoxyl;

$R^5$ is selected from $C_1$-$C_6$alkyl, $C_3$-$C_8$cycloalkyl, and $C_6$-$C_{10}$aryl;

$R^6$ is selected from $C_1$-$C_6$alkyl, $C_3$-$C_8$cycloalkyl, and $C_6$-$C_{10}$aryl, wherein the $C_1$-$C_6$alkyl is substituted with 0-1 occurrence of $R^{6a}$ and the $C_3$-$C_8$cycloalkyl is substituted with 0-1 occurrence of $R^{6b}$;

$R^{6a}$ is selected from $C_6$-$C_{10}$aryl and $C_3$-$C_8$cycloalkyl;

$R^{6b}$ is selected from halo, $C_1$-$C_6$haloalkyl, $C_1$-$C_6$haloalkoxyl, and $C_1$-$C_6$alkyl;

$R^7$ is selected from hydrogen and $C_1$-$C_6$alkyl;

$R^8$ is selected from hydrogen and $C_1$-$C_6$alkyl;

or

R$^7$ and R$^8$ together with the nitrogen atom to which they are attached form a 5- or 6-membered heterocyclyl comprising 0-1 additional heteroatom selected from N, O, and S;

n is 0, 1, 2, 3 or 4;

m is 0, 1 or 2; and p is 0 or 1.

Embodiment 4. The compound of any one of Embodiments 1 to 3, or a pharmaceutically acceptable salt, hydrate, solvate, prodrug, stereoisomer, or tautomer thereof, wherein X is selected from CH, CF, and N;

R' is selected from hydrogen and C$_1$-C$_3$alkyl;

R$^1$ is selected from hydrogen and C$_1$-C$_3$alkyl;

each R$^2$ is independently selected from unsubstituted C$_1$-C$_6$alkyl, C$_1$-C$_6$haloalkyl and halo; or 2 R$^2$ on non-adjacent carbon atoms together with the non-adjacent carbon atoms to which they are attached form a bridging ring;

R$^3$ is selected from hydrogen, C$_1$-C$_8$alkyl, C$_2$-C$_6$alkenyl, —SO$_2$R$^4$, C$_1$-C$_6$haloalkyl, —C(=O)—O—(R$^5$) and —C(=O)—(R$^6$), wherein the C$_1$-C$_8$alkyl and C$_1$-C$_6$haloalkyl are independently substituted with 0-3 occurrences of R$^{3a}$;

or

R$^3$ together with the nitrogen atom to which it is attached and R$^2$ together with the carbon atom to which it is attached form a 5- or 6-membered heterocyclyl comprising 0-1 additional heteroatom selected from N and O;

each R$^{3a}$ is independently selected from C$_3$-C$_{10}$cycloalkyl, a 4- to 6-membered heterocyclyl comprising 1-2 heteroatoms independently selected from N, O and S, a 5- to 10-membered heteroaryl comprising 1-4 heteroatoms independently selected from N, O, and S, C$_6$-C$_{10}$aryl, C$_1$-C$_6$alkoxyl, hydroxyl, and —C(=O)—NR$^7$R$^8$, wherein the C$_3$-C$_{10}$cycloalkyl, 4- to 6-membered heterocyclyl, 5- to 10-membered heteroaryl and C$_6$-C$_{10}$aryl are substituted with 0-4 occurrences of R$^{3b}$;

each R$^{3b}$ is independently selected from C$_1$-C$_6$alkoxyl, halo, C$_1$-C$_6$haloalkyl, C$_1$-C$_6$haloalkoxyl, C$_1$-C$_6$alkyl, —CN, —SO$_2$NR$^7$R$^8$, —SO$_2$R$^4$, and hydroxyl;

R$^4$ is selected from C$_3$-C$_8$cycloalkyl, C$_1$-C$_6$alkyl, a 4- to 6-membered heterocyclyl comprising 1-2 heteroatoms independently selected from N, O and S, and C$_6$-C$_{10}$aryl, wherein the C$_1$-C$_6$alkyl is substituted with 0-1 occurrence of R$^{4a}$;

R$^{4a}$ is selected from C$_3$-C$_8$cycloalkyl, C$_6$-C$_{10}$aryl, and C$_1$-C$_6$alkoxyl;

R$^5$ is selected from C$_1$-C$_6$alkyl, C$_3$-C$_8$cycloalkyl, and C$_6$-C$_{10}$aryl;

R$^6$ is selected from C$_1$-C$_6$alkyl, C$_3$-C$_8$cycloalkyl, and C$_6$-C$_{10}$aryl, wherein the C$_1$-C$_6$alkyl is substituted with 0-1 occurrence of R$^{6a}$ and the C$_3$-C$_8$cycloalkyl is substituted with 0-1 occurrence of R$^{6b}$;

R$^{6a}$ is selected from C$_6$-C$_{10}$aryl and C$_3$-C$_8$cycloalkyl;

R$^{6b}$ is selected from chloro, fluoro, C$_1$-C$_6$haloalkyl, C$_1$-C$_6$haloalkoxyl, and C$_1$-C$_6$alkyl;

R$^7$ is selected from hydrogen and C$_1$-C$_6$alkyl;

R$^8$ is selected from hydrogen and C$_1$-C$_6$alkyl;

or

R$^7$ and R$^8$ together with the nitrogen atom to which they are attached form a 5- or 6-membered heterocyclyl comprising 0-1 additional heteroatom selected from N, O, and S;

n is 0, 1, 2 or 3;

m is 0, 1 or 2; and p is 0 or 1.

Embodiment 5. The compound of any one of the preceding Embodiments, or a pharmaceutically acceptable salt, hydrate, solvate, prodrug, stereoisomer, or tautomer thereof, wherein X is selected from CH and N;

R' is selected from hydrogen and methyl;

R$^1$ is selected from hydrogen and methyl;

each R$^2$ is independently selected from unsubstituted C$_1$-C$_6$alkyl and halo; or 2 R$^2$ on non-adjacent carbon atoms together with the non-adjacent carbon atoms to which they are attached form a C$_1$-C$_3$alkylene bridging ring;

R$^3$ is selected from hydrogen, C$_1$-C$_8$alkyl, C$_2$-C$_6$alkenyl, —SO$_2$R$^4$, C$_1$-C$_6$haloalkyl, —C(=O)—O—(R$^5$) and —C(=O)—(R$^6$), wherein the C$_1$-C$_8$alkyl and C$_1$-C$_6$haloalkyl are independently substituted with 0-3 occurrences of R$^{3a}$;

or

R$^3$ together with the nitrogen atom to which it is attached and R$^2$ together with the carbon atom to which it is attached form a 5- or 6-membered heterocyclyl comprising 0-1 additional 0 heteroatom;

each R$^{3a}$ is independently selected from C$_3$-C$_{10}$cycloalkyl, a 4- to 6-membered heterocyclyl comprising 1-2 heteroatoms independently selected from N, O and S, a 5- to 10-membered heteroaryl comprising 1-4 heteroatoms independently selected from N, O, and S and phenyl, wherein the C$_3$-C$_{10}$cycloalkyl, 4- to 6-membered heterocyclyl, 5- to 10-membered heteroaryl and phenyl are substituted with 0-4 occurrences of R$^{3b}$;

each R$^{3b}$ is independently selected from C$_1$-C$_6$alkoxyl, halo, C$_1$-C$_6$haloalkyl, C$_1$-C$_6$haloalkoxyl, C$_1$-C$_6$alkyl, —CN, —SO$_2$NR$^7$R$^8$, —SO$_2$R$^4$, and hydroxyl;

R$^4$ is selected from C$_3$-C$_8$cycloalkyl, C$_1$-C$_6$alkyl, a 4- to 6-membered heterocyclyl comprising 1-2 heteroatoms independently selected from N, O and S, and C$_6$-C$_{10}$aryl, wherein the C$_1$-C$_6$alkyl is substituted with 0-1 occurrence of R$^{4a}$;

R$^{4a}$ is selected from C$_3$-C$_8$cycloalkyl, C$_6$-C$_{10}$aryl, and C$_1$-C$_6$alkoxyl;

R$^5$ is selected from C$_1$-C$_6$alkyl, C$_3$-C$_6$cycloalkyl, and C$_6$-C$_{10}$aryl;

R$^6$ is selected from C$_1$-C$_6$alkyl, C$_3$-C$_8$cycloalkyl, and C$_6$-C$_{10}$aryl, wherein the C$_1$-C$_6$alkyl is substituted with 0-1 occurrence of R$^{6a}$ and the C$_3$-C$_8$cycloalkyl is substituted with 0-1 occurrence of R$^{6b}$;

R$^{6a}$ is selected from C$_6$-C$_{10}$aryl and C$_3$-C$_8$cycloalkyl;

R$^{6b}$ is selected from chloro, fluoro, C$_1$-C$_6$haloalkyl, C$_1$-C$_6$haloalkoxyl, and C$_1$-C$_6$alkyl;

R$^7$ is selected from hydrogen and C$_1$-C$_6$alkyl;

R$^8$ is selected from hydrogen and C$_1$-C$_6$alkyl;

or

R$^7$ and R$^8$ together with the nitrogen atom to which they are attached form a 5- or 6-membered heterocyclyl comprising 0-1 additional heteroatom selected from N, O, and S;

n is 0, 1, 2 or 3;

m is 0, 1 or 2; and p is 0 or 1.

Embodiment 6. The compound of any one of the preceding Embodiments, or a pharmaceutically acceptable salt, hydrate, solvate, prodrug, stereoisomer, or tautomer thereof, wherein X is selected from CH and N;

R' is hydrogen;

R¹ is hydrogen;
each R² is independently selected from unsubstituted C₁-C₆alkyl and fluoro; or 2 R² on non-adjacent carbon atoms together with the non-adjacent carbon atoms to which they are attached form a C₁-C₃alkylene bridging ring;
R³ is selected from C₁-C₈alkyl, C₂-C₆alkenyl, —SO₂R⁴ and C₁-C₆haloalkyl, wherein the C₁-C₈alkyl is substituted with 0-2 occurrences of R³ᵃ and the C₁-C₆haloalkyl is substituted with 0-1 occurrence of R³ᵃ;
each R³ᵃ is independently selected from C₃-C₁₀cycloalkyl, a 4- to 6-membered heterocyclyl comprising 1-2 heteroatoms independently selected from N and O, a 5- to 6-membered heteroaryl comprising 1-3 heteroatoms independently selected from N, O, and S and phenyl, wherein the C₃-C₁₀cycloalkyl, 4- to 6-membered heterocyclyl, 5- to 6-membered heteroaryl and phenyl are substituted with 0-4 occurrences of R³ᵇ;
each R³ᵇ is independently selected from halo, C₁-C₆haloalkyl, C₁-C₆haloalkoxyl, C₁-C₆alkyl, and hydroxyl;
R⁴ is selected from C₃-C₈cycloalkyl, C₁-C₆alkyl, a 4- to 6-membered heterocyclyl comprising 1-2 heteroatoms independently selected from N, O and S, and C₆-C₁₀aryl, wherein the C₁-C₆alkyl is substituted with 0-1 occurrence of R⁴ᵃ;
R⁴ᵃ is selected from C₃-C₈cycloalkyl, C₆-C₁₀aryl, and C₁-C₆alkoxyl;
n is 0, 1, 2 or 3;
m is 1 or 2; and
p is 0 or 1.

Embodiment 7. The compound of any one of the preceding Embodiments, or a pharmaceutically acceptable salt, hydrate, solvate, prodrug, stereoisomer, or tautomer thereof, wherein
X is selected from CH and N;
R' is hydrogen;
R¹ is hydrogen;
each R² is independently selected from unsubstituted C₁-C₆alkyl; or 2 R² on non-adjacent carbon atoms together with the non-adjacent carbon atoms to which they are attached form a C₁-C₃alkylene bridging ring;
R³ is selected from C₁-C₈alkyl, C₂-C₆alkenyl, —SO₂R⁴ and unsubstituted C₁-C₆haloalkyl, wherein the C₁-C₈alkyl is substituted with 0-2 occurrences of R³ᵃ;
each R³ᵃ is independently selected from C₃-C₁₀cycloalkyl, a 4- to 6-membered heterocyclyl comprising 1-2 heteroatoms independently selected from N and O, a 5- to 6-membered heteroaryl comprising 1-3 heteroatoms independently selected from N, O, and S and phenyl, wherein the C₃-C₁₀cycloalkyl, 4- to 6-membered heterocyclyl, 5- to 6-membered heteroaryl and phenyl are substituted with 0-3 occurrences of R³ᵇ;
each R³ᵇ is independently selected from halo, C₁-C₆haloalkyl, C₁-C₆haloalkoxyl, C₁-C₆alkyl, and hydroxyl;
R⁴ is selected from C₃-C₈cycloalkyl, C₁-C₆alkyl, a 4- to 6-membered heterocyclyl comprising 1-2 heteroatoms independently selected from N, O and S, and C₆-C₁₀aryl, wherein the C₁-C₆alkyl is substituted with 1 occurrence of R⁴ᵃ;
R⁴ᵃ is selected from C₃-C₈cycloalkyl, C₆-C₁₀aryl, and C₁-C₆alkoxyl;
n is 0, 1 or 2;
m is 1 or 2; and
p is 1.

Embodiment 8. The compound of any one of the preceding Embodiments, or a pharmaceutically acceptable salt, hydrate, solvate, prodrug, stereoisomer, or tautomer thereof, wherein
X is selected from CH and N;
R' is hydrogen;
R¹ is hydrogen;
each R² is independently selected from unsubstituted C₁-C₃alkyl;
R³ is selected from C₁-C₆alkyl, C₂-C₆alkenyl, —SO₂R⁴ and unsubstituted C₁-C₆haloalkyl, wherein the C₁-C₆alkyl is substituted with 0-2 occurrences of R³ᵃ;
each R³ᵃ is independently selected from C₃-C₁₀cycloalkyl, a 4- to 6-membered heterocyclyl comprising 1 O heteroatom, a 6-membered heteroaryl comprising 1-2 N heteroatoms and phenyl, wherein the C₃-C₁₀cycloalkyl, 4- to 6-membered heterocyclyl, 6-membered heteroaryl and phenyl are substituted with 0-2 occurrences of R³ᵇ;
each R³ᵇ is independently selected from chloro, fluoro, C₁-C₆haloalkyl, C₁-C₆haloalkoxyl and C₁-C₆alkyl;
R⁴ is selected from C₃-C₈cycloalkyl, C₁-C₆alkyl, a 4- to 6-membered heterocyclyl comprising 1 O heteroatom and phenyl, wherein the C₁-C₆alkyl is substituted with 1 occurrence of R⁴ᵃ;
R⁴ᵃ is selected from C₃-C₈cycloalkyl and phenyl;
n is 0, 1 or 2;
m is 1 or 2; and
p is 1.

Embodiment 9. The compound of Embodiment 1, or a pharmaceutically acceptable salt, hydrate, solvate, prodrug, stereoisomer, or tautomer thereof, of Formula (Ia"):

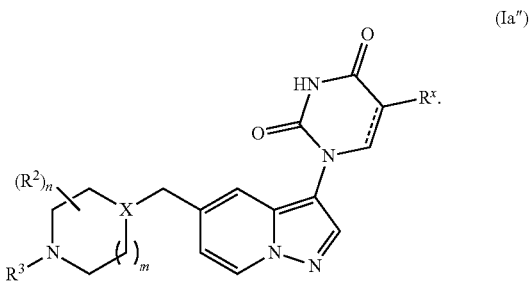

(Ia")

Embodiment 10. The compound of any one of Embodiments 1 and 2, or a pharmaceutically acceptable salt, hydrate, solvate, prodrug, stereoisomer, or tautomer thereof, of Formula (Ia'):

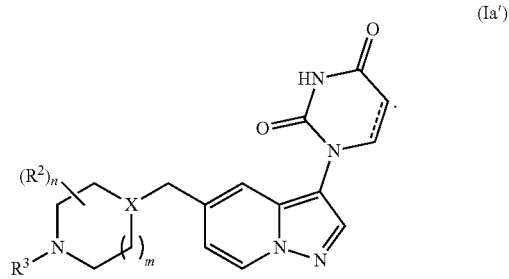

(Ia')

Embodiment 11. The compound of any one of the preceding Embodiments, or a pharmaceutically acceptable salt, hydrate, solvate, prodrug, stereoisomer, or tautomer thereof, of Formula (Ia):

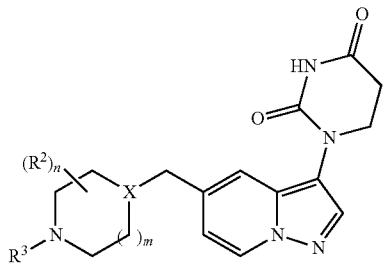

(Ia)

Embodiment 12. The compound of any one of the preceding Embodiments, or a pharmaceutically acceptable salt, hydrate, solvate, prodrug, stereoisomer, or tautomer thereof, wherein $R^3$ is selected from $C_1$-$C_6$alkyl and —$CH_2$—$R^{3a}$.

Embodiment 13. The compound of any one of Embodiments 1 and 9, or a pharmaceutically acceptable salt, hydrate, solvate, prodrug, stereoisomer, or tautomer thereof, of Formula (Ib"):

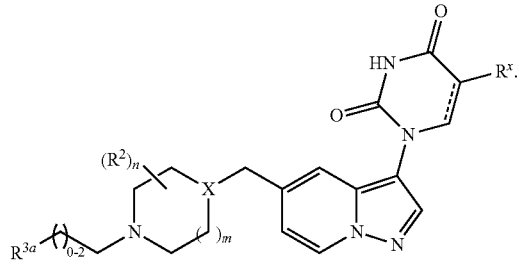

(Ib")

Embodiment 14. The compound of any one Embodiments 1, 2, 9 and 10, or a pharmaceutically acceptable salt, hydrate, solvate, prodrug, stereoisomer, or tautomer thereof, of Formula (Ib'):

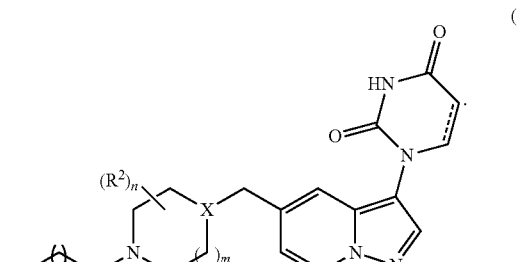

(Ib')

Embodiment 15. The compound of any one of the preceding Embodiments, or a pharmaceutically acceptable salt, hydrate, solvate, prodrug, stereoisomer, or tautomer thereof, of Formula (Ib):

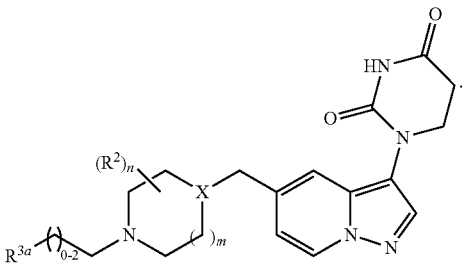

(Ib)

Embodiment 16. The compound of any one of Embodiments 1 and 9, or a pharmaceutically acceptable salt, hydrate, solvate, prodrug, stereoisomer, or tautomer thereof, of Formula (Ic"), wherein:

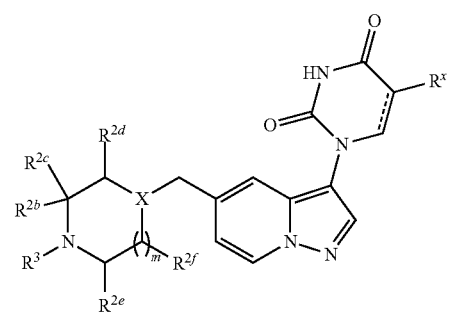

(Ic")

- $\rlap{=}{-}$ is a single bond or a double bond;
- X is selected from CH, CF and N;
- $R^x$ is selected from hydrogen, $C_1$-$C_6$alkyl, halo (e.g., F, Cl), $C_1$-$C_6$alkoxyl, and $C_3$-$C_8$cycloalkyl;
- $R^{2b}$ is selected from hydrogen, $C_1$-$C_6$alkyl, $C_1$-$C_6$haloalkyl, and halo, wherein the $C_1$-$C_6$alkyl is substituted with 0-1 occurrence of $R^{2a}$;
- $R^{2c}$ is selected from hydrogen and $C_1$-$C_6$alkyl, wherein the $C_1$-$C_6$alkyl is substituted with 0-1 occurrence of $R^{2a}$;
- or $R^{2b}$ and $R^{2c}$ together with the carbon atoms to which they are attached form an oxo group;
- each of $R^{2d}$ and $R^{2e}$ is independently selected from hydrogen, $C_1$-$C_6$alkyl, $C_1$-$C_6$haloalkyl, halo, and oxo, wherein the $C_1$-$C_6$alkyl is substituted with 0-1 occurrence of $R^{2a}$;
- $R^{2f}$ is hydrogen;
- or $R^{2b}$ and $R^{2e}$ or $R^{2b}$ and $R^{2f}$ together with the carbon atoms to which they are attached form a bridging ring;
- $R^{2a}$ is selected from $C_1$-$C_6$alkoxyl and hydroxyl; and
- $R^3$ is defined according to any one of the preceding Embodiments.

Embodiment 17. The compound of any one of Embodiments 1, 2, 9 and 10, or a pharmaceutically acceptable salt, hydrate, solvate, prodrug, stereoisomer, or tautomer thereof, of Formula (Ic'), wherein:

(Ic')

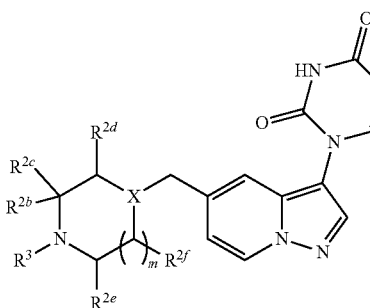

=== is a single bond or a double bond;
X is selected from CH, CF and N;
$R^{2b}$ is selected from hydrogen, $C_1$-$C_6$alkyl, $C_1$-$C_6$haloalkyl, and halo, wherein the $C_1$-$C_6$alkyl is substituted with 0-1 occurrence of $R^{2a}$;
$R^{2c}$ is selected from hydrogen and $C_1$-$C_6$alkyl, wherein the $C_1$-$C_6$alkyl is substituted with 0-1 occurrence of $R^{2a}$;
or $R^{2b}$ and $R^{2c}$ together with the carbon atoms to which they are attached form an oxo group;
each of $R^{2d}$ and $R^{2e}$ is independently selected from hydrogen, $C_1$-$C_6$alkyl, $C_1$-$C_6$haloalkyl, halo, and oxo, wherein the $C_1$-$C_6$alkyl is substituted with 0-1 occurrence of $R^{2a}$;
$R^{2f}$ is hydrogen;
or $R^{2b}$ and $R^{2e}$ or $R^{2b}$ and $R^{2f}$ together with the carbon atoms to which they are attached form a bridging ring;
$R^{2a}$ is selected from $C_1$-$C_6$alkoxyl and hydroxyl; and
$R^3$ is defined according to any one of the preceding Embodiments.

Embodiment 18. The compound of any one of Embodiments 1 to 12, 16 and 17, or a pharmaceutically acceptable salt, hydrate, solvate, prodrug, stereoisomer, or tautomer thereof, of Formula (Ic), wherein:

(Ic)

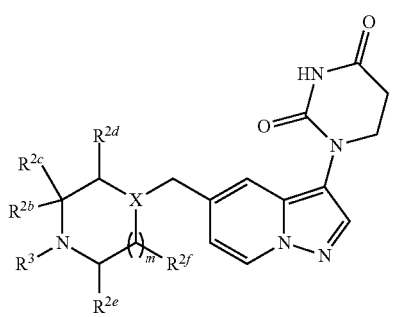

X is selected from CH, CF and N;
$R^{2b}$ is selected from hydrogen, $C_1$-$C_6$alkyl, $C_1$-$C_6$haloalkyl, and halo, wherein the $C_1$-$C_6$alkyl is substituted with 0-1 occurrence of $R^{2a}$;
$R^{2c}$ is selected from hydrogen and $C_1$-$C_6$alkyl, wherein the $C_1$-$C_6$alkyl is substituted with 0-1 occurrence of $R^{2a}$;
or $R^{2b}$ and $R^{2c}$ together with the carbon atoms to which they are attached form an oxo group;
each of $R^{2d}$ and $R^{2e}$ is independently selected from hydrogen, $C_1$-$C_6$alkyl, $C_1$-$C_6$haloalkyl, halo, and oxo, wherein the $C_1$-$C_6$alkyl is substituted with 0-1 occurrence of $R^{2a}$;
$R^{2f}$ is hydrogen;
or $R^{2b}$ and $R^{2e}$ or $R^{2b}$ and $R^{2f}$ together with the carbon atoms to which they are attached form a bridging ring;
$R^{2a}$ is selected from $C_1$-$C_6$alkoxyl and hydroxyl; and
$R^3$ is defined according to any one of the preceding Embodiments.

Embodiment 19. The compound of any one of Embodiments 16 to 18, or a pharmaceutically acceptable salt, hydrate, solvate, prodrug, stereoisomer, or tautomer thereof, wherein
X is selected from CH and N;
$R^{2b}$ is selected from hydrogen, $C_1$-$C_3$alkyl, $C_1$-$C_3$haloalkyl, and halo, wherein the $C_1$-$C_3$alkyl is substituted with 0-1 occurrence of $R^{2a}$;
$R^{2c}$ is selected from hydrogen and $C_1$-$C_3$alkyl, wherein the $C_1$-$C_3$alkyl is substituted with 0-1 occurrence of $R^{2a}$;
or $R^{2b}$ and $R^{2c}$ together with the carbon atoms to which they are attached form an oxo group;
each of $R^{2d}$ and $R^{2e}$ is independently selected from hydrogen, $C_1$-$C_3$alkyl, $C_1$-$C_3$haloalkyl, halo, and oxo, wherein the $C_1$-$C_3$alkyl is substituted with 0-1 occurrence of $R^{2a}$; $R^{2f}$ is hydrogen;
or $R^{2b}$ and $R^{2e}$ or $R^{2b}$ and $R^{2f}$ together with the carbon atoms to which they are attached form a bridging ring;
$R^{2a}$ is selected from $C_1$-$C_6$alkoxyl and hydroxyl;
$R^3$ is selected from $C_1$-$C_8$alkyl, $C_2$-$C_6$alkenyl, —$SO_2R^4$, $C_1$-$C_6$haloalkyl, —C(=O)—O—($R^5$) and —C(=O)—($R^6$), wherein the $C_1$-$C_8$alkyl and $C_1$-$C_6$haloalkyl are independently substituted with 0-3 occurrences of $R^{3a}$;
each $R^{3a}$ is independently selected from $C_3$-$C_{10}$cycloalkyl, a 4- to 6-membered heterocyclyl comprising 1-2 heteroatoms independently selected from N, O and S, a 5- to 10-membered heteroaryl comprising 1-4 heteroatoms independently selected from N, O, and S, $C_6$-$C_{10}$aryl, $C_1$-$C_6$alkoxyl, hydroxyl, and —C(=O)—$NR^7R^8$, wherein the $C_3$-$C_{10}$cycloalkyl, 4- to 6-membered heterocyclyl, 5- to 10-membered heteroaryl and $C_6$-$C_{10}$aryl are substituted with 0-4 occurrences of $R^{3b}$;
each $R^{3b}$ is independently selected from $C_1$-$C_6$alkoxyl, halo, $C_1$-$C_6$haloalkyl, $C_1$-$C_6$haloalkoxyl, $C_1$-$C_6$alkyl, —CN, —$SO_2NR^7R^8$, —$SO_2R^4$, and hydroxyl;
$R^4$ is selected from $C_3$-$C_8$cycloalkyl, $C_1$-$C_6$alkyl, a 4- to 6-membered heterocyclyl comprising 1-2 heteroatoms independently selected from N, O and S, and $C_6$-$C_{10}$aryl, wherein the $C_1$-$C_6$alkyl is substituted with 0-1 occurrence of $R^{4a}$;
$R^{4a}$ is selected from $C_3$-$C_8$cycloalkyl, $C_6$-$C_{10}$aryl, and $C_1$-$C_6$alkoxyl;
$R^5$ is selected from $C_1$-$C_6$alkyl and $C_6$-$C_{10}$aryl;
$R^6$ is selected from $C_1$-$C_6$alkyl, $C_3$-$C_8$cycloalkyl, and $C_6$-$C_{10}$aryl, wherein the $C_1$-$C_6$alkyl is substituted with 0-1 occurrence of $R^{6a}$ and the $C_3$-$C_8$cycloalkyl is substituted with 0-1 occurrence of $R^{6b}$;
$R^{6a}$ is selected from $C_6$-$C_{10}$aryl and $C_3$-$C_8$cycloalkyl;
$R^{6b}$ is selected from halo, $C_1$-$C_6$haloalkyl, $C_1$-$C_6$haloalkoxyl, and $C_1$-$C_6$alkyl;
$R^7$ is selected from hydrogen and $C_1$-$C_6$alkyl;
$R^8$ is selected from hydrogen and $C_1$-$C_6$alkyl;
or
$R^7$ and $R^8$ together with the nitrogen atom to which they are attached form a 5- or 6-membered heterocyclyl comprising 0-1 additional heteroatom selected from N, O, and S; and
m is 1 or 2.

Embodiment 20. The compound of any one of Embodiments 16 to 19, or a pharmaceutically acceptable salt, hydrate, solvate, prodrug, stereoisomer, or tautomer thereof, wherein X is selected from CH and N;
each of $R^{2b}$, $R^{2c}$, $R^{2d}$ and $R^{2e}$ is independently selected from hydrogen and unsubstituted $C_1$-$C_3$alkyl;
$R^{2f}$ is hydrogen;
or $R^{2b}$ and $R^{2e}$ or $R^{2b}$ and $R^{2f}$ together with the carbon atoms to which they are attached form a $C_1$-$C_3$alkylene bridging ring;
$R^3$ is selected from $C_1$-$C_8$alkyl, $C_2$-$C_6$alkenyl, —$SO_2R^4$, and $C_1$-$C_6$haloalkyl, wherein the $C_1$-$C_8$alkyl and $C_1$-$C_6$haloalkyl are independently substituted with 0-3 occurrences of $R^{3a}$;
each $R^{3a}$ is independently selected from $C_3$-$C_{10}$cycloalkyl, a 4- to 6-membered heterocyclyl comprising 1-2 heteroatoms independently selected from N, O and S, a 5- to 10-membered heteroaryl comprising 1-4 heteroatoms independently selected from N, O, and S, $C_6$-$C_{10}$aryl, $C_1$-$C_6$alkoxyl, hydroxyl, and —C(=O)—$NR^7R^8$, wherein the $C_3$-$C_{10}$cycloalkyl, 4- to 6-membered heterocyclyl, 5- to 10-membered heteroaryl and $C_6$-$C_{10}$aryl are substituted with 0-4 occurrences of $R^{3b}$;
each $R^{3b}$ is independently selected from $C_1$-$C_6$alkoxyl, halo, $C_1$-$C_6$haloalkyl, $C_1$-$C_6$haloalkoxyl, $C_1$-$C_6$alkyl, —CN, —$SO_2NR^7R^8$, —$SO_2R^4$, and hydroxyl;
$R^4$ is selected from $C_3$-$C_8$cycloalkyl, $C_1$-$C_6$alkyl, a 4- to 6-membered heterocyclyl comprising 1-2 heteroatoms independently selected from N, O and S, and $C_6$-$C_{10}$aryl, wherein the $C_1$-$C_6$alkyl is substituted with 0-1 occurrence of $R^{4a}$;
$R^{4a}$ is selected from $C_3$-$C_8$cycloalkyl, $C_6$-$C_{10}$aryl, and $C_1$-$C_6$alkoxyl;
$R^7$ is selected from hydrogen and $C_1$-$C_6$alkyl;
$R^8$ is selected from hydrogen and $C_1$-$C_6$alkyl;
or
$R^7$ and $R^8$ together with the nitrogen atom to which they are attached form a 5- or 6-membered heterocyclyl comprising 0-1 additional heteroatom selected from N, O, and S; and
m is 1 or 2.

Embodiment 21. The compound according to any of Embodiments 16 to 20, or a pharmaceutically acceptable salt, hydrate, solvate, prodrug, stereoisomer, or tautomer thereof, wherein X is selected from CH and N;
each of $R^{2b}$, $R^{2c}$, $R^{2d}$ and $R^{2e}$ is independently selected from hydrogen and unsubstituted $C_1$-$C_3$alkyl;
$R^{2f}$ is hydrogen;
$R^3$ is selected from $C_1$-$C_8$alkyl, $C_2$-$C_6$alkenyl, —$SO_2R^4$, and $C_1$-$C_6$haloalkyl, wherein the $C_1$-$C_8$alkyl and $C_1$-$C_6$haloalkyl are independently substituted with 0-3 occurrences of $R^{3a}$;
each $R^{3a}$ is independently selected from $C_3$-$C_{10}$cycloalkyl, a 4- to 6-membered heterocyclyl comprising 1-2 heteroatoms independently selected from N, O and S, a 5- to 10-membered heteroaryl comprising 1-4 heteroatoms independently selected from N, O, and S and phenyl, wherein the $C_3$-$C_{10}$cycloalkyl, 4- to 6-membered heterocyclyl, 5- to 10-membered heteroaryl and phenyl are substituted with 0-4 occurrences of $R^{3b}$;
each $R^{3b}$ is independently selected from $C_1$-$C_6$alkoxyl, halo, $C_1$-$C_6$haloalkyl, $C_1$-$C_6$haloalkoxyl, $C_1$-$C_6$alkyl, and hydroxyl;

$R^4$ is selected from $C_3$-$C_8$cycloalkyl, $C_1$-$C_6$alkyl, a 4- to 6-membered heterocyclyl comprising 1-2 heteroatoms independently selected from N, O and S, and $C_6$-$C_{10}$aryl, wherein the $C_1$-$C_6$alkyl is substituted with 1 occurrence of $R^{4a}$;
$R^{4a}$ is selected from $C_3$-$C_8$cycloalkyl, $C_6$-$C_{10}$aryl, and $C_1$-$C_6$alkoxyl; and
m is 1.

Embodiment 22. The compound of any one of Embodiments 1, 9 and 16, or a pharmaceutically acceptable salt, hydrate, solvate, prodrug, stereoisomer, or tautomer thereof, of Formula (Id″), wherein:

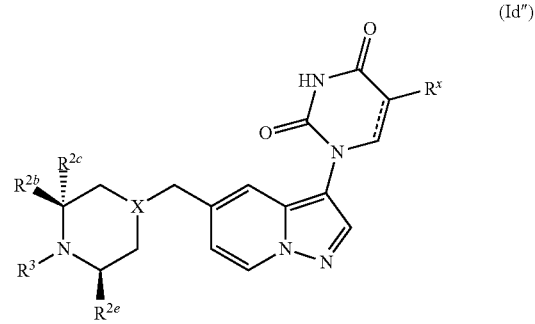

(Id″)

$R^{2b}$, $R^{2c}$ and $R^{2e}$ are defined according to any of Embodiments 16 to 21.

Embodiment 23. The compound of any one of Embodiments 1, 2, 9, 10, 16, 17 and 22, or a pharmaceutically acceptable salt, hydrate, solvate, prodrug, stereoisomer, or tautomer thereof, of Formula (Id′), wherein:

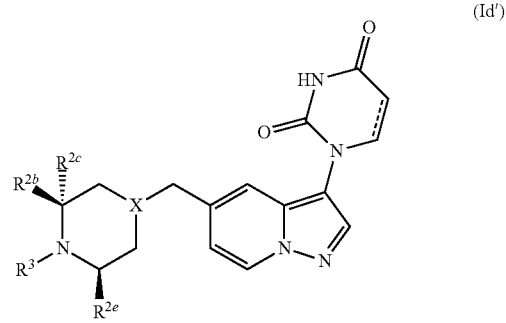

(Id′)

$R^{2b}$, $R^{2c}$ and $R^{2e}$ are defined according to any of Embodiments 16 to 21.

Embodiment 24. The compound of any one of Embodiments 1 to 12 and 16 to 23, or a pharmaceutically acceptable salt, hydrate, solvate, prodrug, stereoisomer, or tautomer thereof, of Formula (Id), wherein:

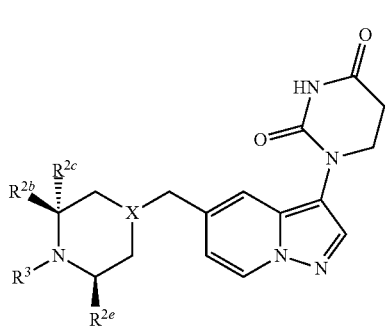

(Id)

R[2b], R[2c] and R[2e] are defined according to any of Embodiments 16 to 21.

Embodiment 25. The compound of any one of Embodiments 1 to 12 and 16 to 24, or a pharmaceutically acceptable salt, hydrate, solvate, prodrug, stereoisomer, or tautomer thereof, of Formula (Id-1), wherein:

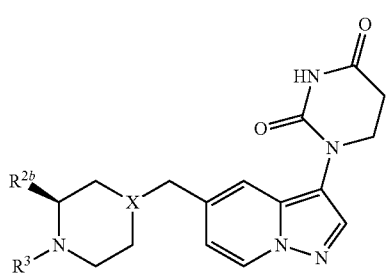

(Id-1)

$R^{2b}$ is selected from hydrogen and $C_1$-$C_4$alkyl; and

X and $R^3$ are defined according to any one of the preceding Embodiments.

Embodiment 26. The compound Embodiment 25, or a pharmaceutically acceptable salt, hydrate, solvate, prodrug, stereoisomer, or tautomer thereof, wherein:

X is CH or N;

$R^{2b}$ is selected from hydrogen and $C_1$-$C_4$alkyl;

$R^3$ is selected from $C_1$-$C_8$alkyl, —$SO_2R^4$, and —C(=O)—($R^6$), wherein the $C_1$-$C_8$alkyl is independently substituted with 0-3 occurrences of $R^{3a}$;

each $R^{3a}$ is independently selected from $C_3$-$C_{10}$cycloalkyl, a 4- to 6-membered heterocyclyl comprising 1-2 heteroatoms independently selected from N, O and S, $C_1$-$C_6$alkoxyl, and hydroxyl, wherein the $C_3$-$C_{10}$cycloalkyl and 4- to 6-membered heterocyclyl are substituted with 0-2 occurrences of $R^{3b}$;

each $R^{3b}$ is independently selected from $C_1$-$C_6$alkoxyl, halo, $C_1$-$C_6$haloalkyl, $C_1$-$C_6$haloalkoxyl, $C_1$-$C_6$alkyl, —CN, —$SO_2R^4$, and hydroxyl.

Embodiment 27. The compound of any one of Embodiments 25 and 26, or a pharmaceutically acceptable salt, hydrate, solvate, prodrug, stereoisomer, or tautomer thereof, of Formula (Id-2) or (Id-3):

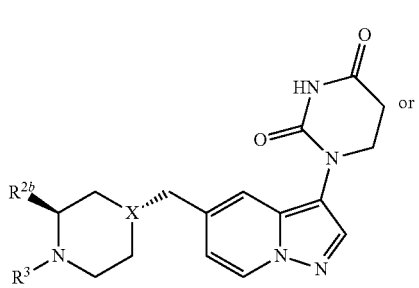

(Id-2)

or

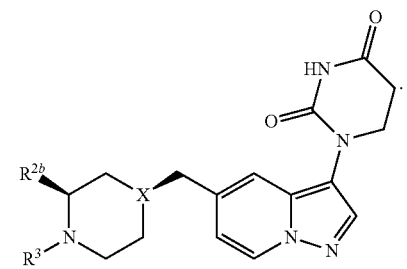

(Id-3)

Embodiment 28. The compound of any one of Embodiments 1, 9, 13, 16 and 22, or a pharmaceutically acceptable salt, hydrate, solvate, prodrug, stereoisomer, or tautomer thereof, of Formula (Ie″), wherein:

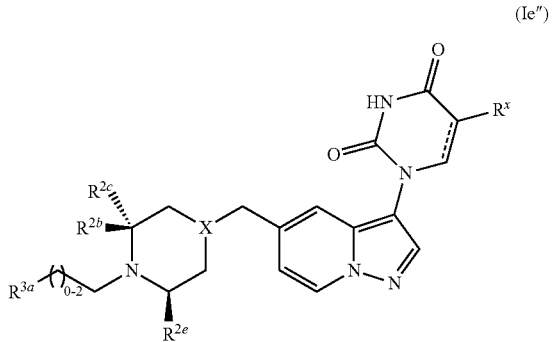

(Ie″)

R[2b], R[2c] and R[2e] are defined according to any of Embodiments 16 to 21.

Embodiment 29. The compound of any one Embodiments 1, 2, 9, 10, 13, 14, 16, 17, 22, 23 and 28, or a pharmaceutically acceptable salt, hydrate, solvate, prodrug, stereoisomer, or tautomer thereof, of Formula (Ie′), wherein:

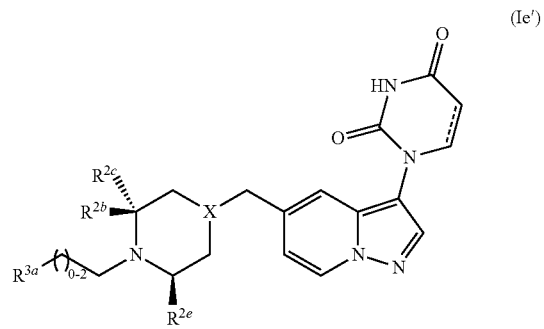

(Ie′)

$R^{2b}$, $R^{2c}$ and $R^{2e}$ are defined according to any of Embodiments 16 to 21.

Embodiment 30. The compound of any one of the preceding Embodiments, or a pharmaceutically acceptable salt, hydrate, solvate, prodrug, stereoisomer, or tautomer thereof, of Formula (Ie), wherein:

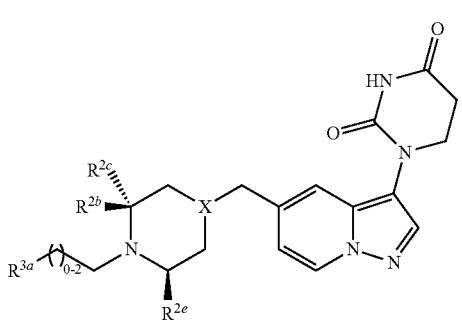

(Ie)

$R^{2b}$, $R^{2c}$ and $R^{2e}$ are defined according to any of Embodiments 16 to 21.

Embodiment 31. The compound of any one of the preceding Embodiments, or a pharmaceutically acceptable salt, hydrate, solvate, prodrug, stereoisomer, or tautomer thereof, wherein X is CH.

Embodiment 32. The compound of any one of the preceding Embodiments, or a pharmaceutically acceptable salt, hydrate, solvate, prodrug, stereoisomer, or tautomer thereof, wherein X is N.

Embodiment 33. The compound of any one of Embodiments 1 to 15, or a pharmaceutically acceptable salt, hydrate, solvate, prodrug, stereoisomer, or tautomer thereof, wherein n is selected from 0 and 1, and m is selected from 1 and 2.

Embodiment 34. The compound of any one of Embodiments 1 to 15, or a pharmaceutically acceptable salt, hydrate, solvate, prodrug, stereoisomer, or tautomer thereof, wherein $R^2$ is unsubstituted $C_1$-$C_6$alkyl, e.g., methyl, and n is 1.

Embodiment 35. The compound of any one of Embodiments 1 to 20 and 33, or a pharmaceutically acceptable salt, hydrate, solvate, prodrug, stereoisomer, or tautomer thereof, wherein m is 1.

Embodiment 36. The compound of any one of Embodiments 1 to 12, 16 to 27, and 31 to 35, or a pharmaceutically acceptable salt, hydrate, solvate, prodrug, stereoisomer, or tautomer thereof, wherein $R^3$ is $C_1$-$C_6$alkyl, wherein the $C_1$-$C_6$alkyl is substituted with 1 occurrence of $R^{3a}$.

Embodiment 37. The compound of any one of Embodiments 1 to 12, 16 to 27, and 31 to 36, or a pharmaceutically acceptable salt, hydrate, solvate, prodrug, stereoisomer, or tautomer thereof, wherein $R^3$ is selected from methyl, ethyl, n-propyl, i-propyl, 2-propanyl, butyl, i-butyl, 2-butanyl, 3-methyl-2-butanyl, i-pentyl, 3-pentanyl, neopentyl, 2,4-dimethylpentanyl, and —$CH_2$—$(CH_2)_{0-1}$—$R^{3a}$.

Embodiment 38. The compound of any one of the preceding Embodiments, or a pharmaceutically acceptable salt, hydrate, solvate, prodrug, stereoisomer, or tautomer thereof, wherein $R^{3a}$ is $C_3$-$C_{10}$cycloalkyl, wherein the $C_3$-$C_{10}$cycloalkyl is substituted with 0-4 occurrences of $R^{3b}$, wherein each $R^{3b}$ is independently selected from $C_1$-$C_6$alkoxyl, chloro, fluoro, $C_1$-$C_6$haloalkyl, $C_1$-$C_6$haloalkoxyl and $C_1$-$C_6$alkyl.

Embodiment 39. The compound of any one of the preceding Embodiments, or a pharmaceutically acceptable salt, hydrate, solvate, prodrug, stereoisomer, or tautomer thereof, wherein $R^{3a}$ is selected from cyclopropyl, cyclobutyl, cyclopentyl, cyclohexyl, cycloheptyl,

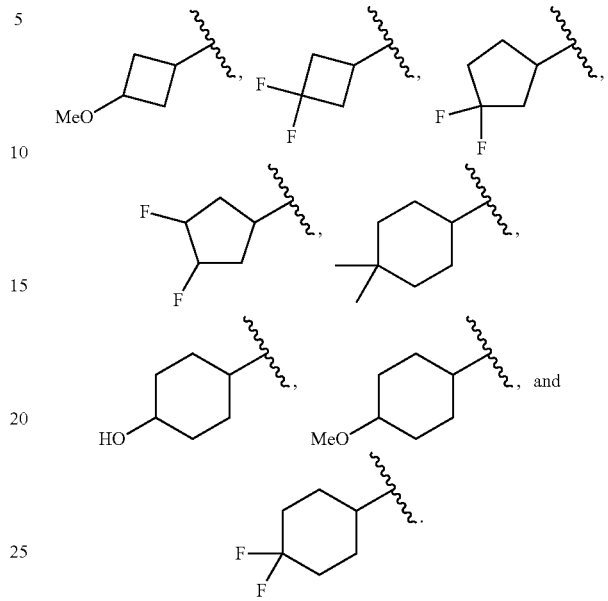

Embodiment 40. The compound of any one of the preceding Embodiments, or a pharmaceutically acceptable salt, hydrate, solvate, prodrug, stereoisomer, or tautomer thereof, wherein $R^{3a}$ is $C_3$-$C_7$cycloalkyl, wherein the $C_3$-$C_7$cycloalkyl is substituted with 0-2 occurrences of fluoro.

Embodiment 41. The compound of any one of Embodiments 16 to 40, or a pharmaceutically acceptable salt, hydrate, solvate, prodrug, stereoisomer, or tautomer thereof, wherein each of $R^{2b}$ and $R^{2e}$ is independently selected from hydrogen and unsubstituted $C_1$-$C_3$alkyl; and $R^{2c}$ is hydrogen.

Embodiment 42. The compound of any one of Embodiments 16 to 41, or a pharmaceutically acceptable salt, hydrate, solvate, prodrug, stereoisomer, or tautomer thereof, wherein each of $R^{2b}$ and $R^{2e}$ is independently selected from hydrogen and methyl; and $R^{2c}$ is hydrogen.

Embodiment 43. The compound of any one of Embodiments 16 to 42, or a pharmaceutically acceptable salt, hydrate, solvate, prodrug, stereoisomer, or tautomer thereof, wherein $R^{2b}$ is unsubstituted $C_1$-$C_3$alkyl (e.g., methyl); $R^{2c}$ is hydrogen; and $R^{2e}$ is selected from hydrogen and unsubstituted $C_1$-$C_3$alkyl.

Embodiment 44. The compound of any one of Embodiments 16 to 43, or a pharmaceutically acceptable salt, hydrate, solvate, prodrug, stereoisomer, or tautomer thereof, wherein $R^{2b}$ is methyl and $R^{2c}$, $R^{2d}$, $R^{2e}$ and $R^{2f}$ are all hydrogen.

Embodiment 45. The compound of any one of Embodiments 1 to 15 and 31 to 44, or a pharmaceutically acceptable salt, hydrate, solvate, prodrug, stereoisomer, or tautomer thereof, wherein $R^2$ is unsubstituted $C_1$-$C_3$alkyl, and n is 1.

Embodiment 46. The compound of any one of Embodiments 1, 2, 4 to 10, 12 to 14, 16, 17, 19 to 23, 28, 29 and 31 to 45, wherein ═ is a double bond.

Embodiment 47. The compound of any one of the preceding Embodiments ═ is a single bond.

Embodiment 48. The compound of Embodiment 1 or a pharmaceutically acceptable salt, hydrate, solvate, prodrug, stereoisomer, or tautomer thereof, selected from:

35

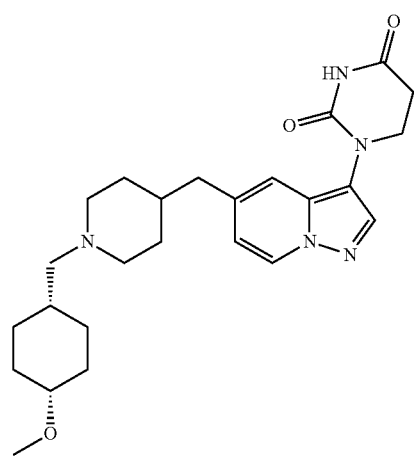

1-(5-(((1-(((1s,4s)-4-methoxycyclohexyl)methyl)piperidin-4-yl)methyl)pyrazolo[1,5-a]pyridin-3-yl)dihydropyrimidine-2,4(1H,3H)-dione

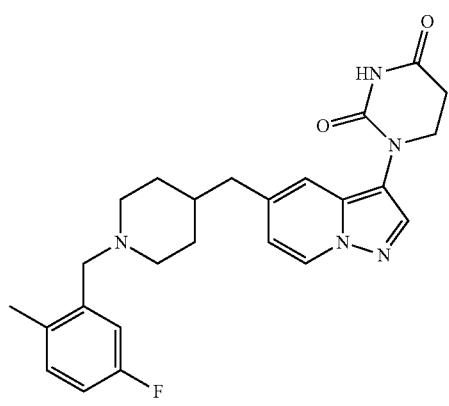

1-(5-((1-(5-fluoro-2-methylbenzyl)piperidin-4-yl)methyl)pyrazolo[1,5-a]pyridin-3-yl)dihydropyrimidine-2,4(1H,3H)-dione

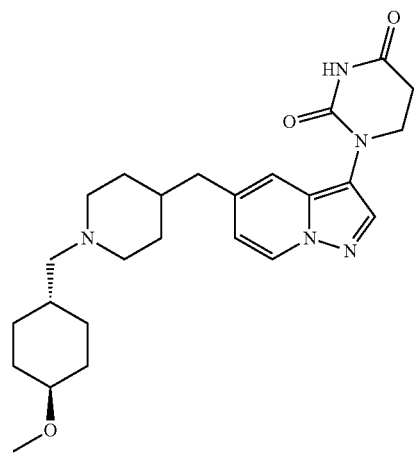

1-(5-(((1-(((1r,4r)-4-methoxycyclohexyl)methyl)piperidin-4-yl)methyl)pyrazolo[1,5-a]pyridin-3-yl)dihydropyrimidine-2,4(1H,3H)-dione 36
-continued

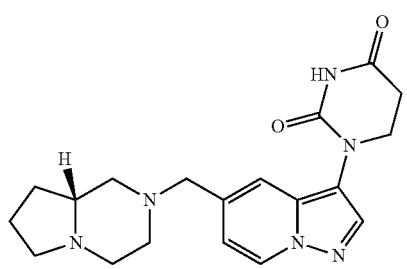

(R)-1-(5-((hexahydropyrrolo[1,2-a]pyrazin-2(1H)-yl)methyl)pyrazolo[1,5-a]pyridin-3-yl)dihydropyrimidine-2,4(1H,3H)-dione

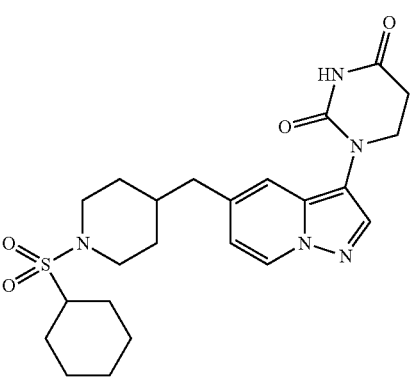

1-(5-(((1-(cyclohexylsulfonyl)piperidin-4-yl)methyl)pyrazolo[1,5-a]pyridin-3-yl)dihydropyrimidine-2,4(1H,3H)-dione

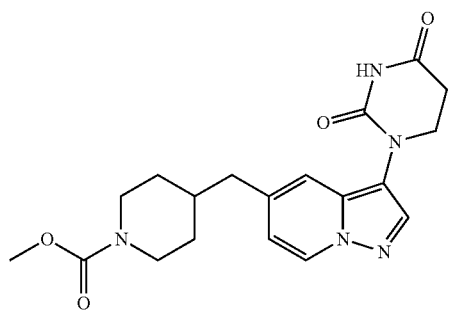

methyl 4-((3-(2,4-dioxotetrahydropyrimidin-1(2H)-yl)pyrazolo[1,5-a]pyridin-5-yl)methyl)piperidine-1-carboxylate

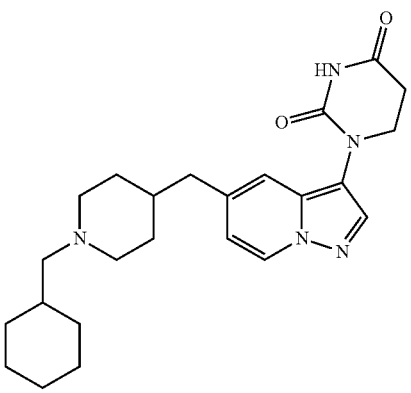

1-(5-(((1-(cyclohexylmethyl)piperidin-4-yl)methyl)pyrazolo[1,5-a]pyridin-3-yl)dihydropyrimidine-2,4(1H,3H)-dione

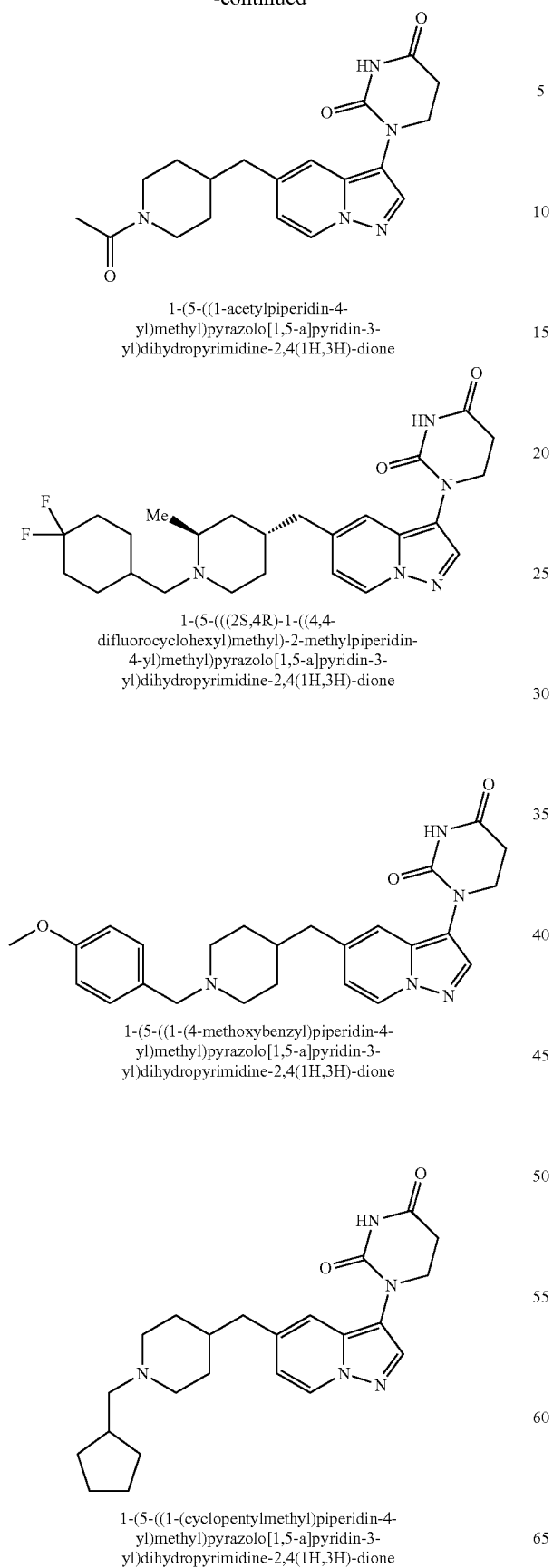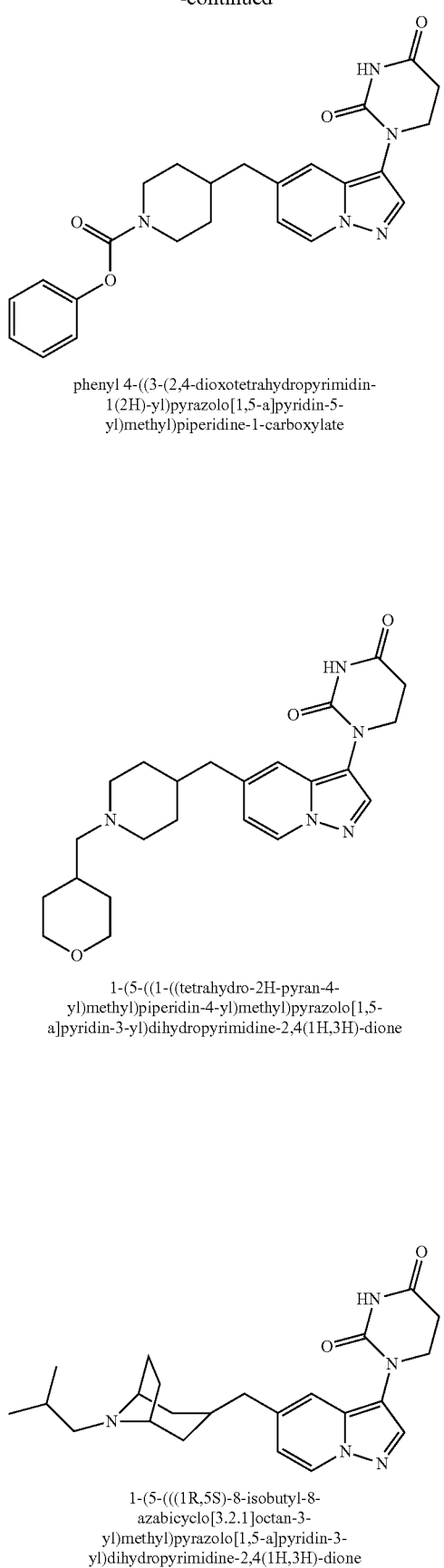

1-(5-((1-acetylpiperidin-4-yl)methyl)pyrazolo[1,5-a]pyridin-3-yl)dihydropyrimidine-2,4(1H,3H)-dione 1-(5-(((2S,4R)-1-((4,4-difluorocyclohexyl)methyl)-2-methylpiperidin-4-yl)methyl)pyrazolo[1,5-a]pyridin-3-yl)dihydropyrimidine-2,4(1H,3H)-dione 1-(5-((1-(4-methoxybenzyl)piperidin-4-yl)methyl)pyrazolo[1,5-a]pyridin-3-yl)dihydropyrimidine-2,4(1H,3H)-dione 1-(5-((1-(cyclopentylmethyl)piperidin-4-yl)methyl)pyrazolo[1,5-a]pyridin-3-yl)dihydropyrimidine-2,4(1H,3H)-dione phenyl 4-((3-(2,4-dioxotetrahydropyrimidin-1(2H)-yl)pyrazolo[1,5-a]pyridin-5-yl)methyl)piperidine-1-carboxylate 1-(5-((1-((tetrahydro-2H-pyran-4-yl)methyl)piperidin-4-yl)methyl)pyrazolo[1,5-a]pyridin-3-yl)dihydropyrimidine-2,4(1H,3H)-dione 1-(5-(((1R,5S)-8-isobutyl-8-azabicyclo[3.2.1]octan-3-yl)methyl)pyrazolo[1,5-a]pyridin-3-yl)dihydropyrimidine-2,4(1H,3H)-dione

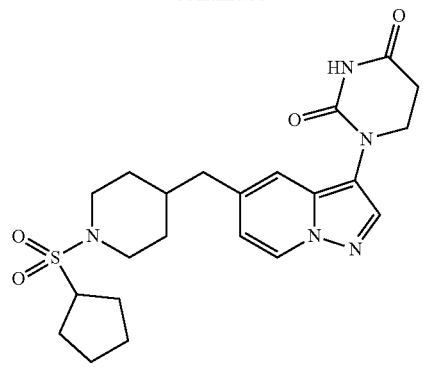

1-(5-((1-(cyclopentylsulfonyl)piperidin-4-
yl)methyl)pyrazolo[1,5-a]pyridin-3-
yl)dihydropyrimidine-2,4(1H,3H)-dione

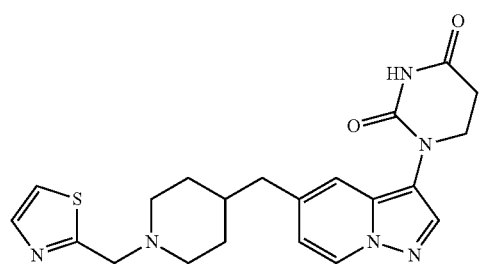

1-(5-((1-(thiazol-2-ylmethyl)piperidin-4-
yl)methyl)pyrazolo[1,5-a]pyridin-3-
yl)dihydropyrimidine-2,4(1H,3H)-dione

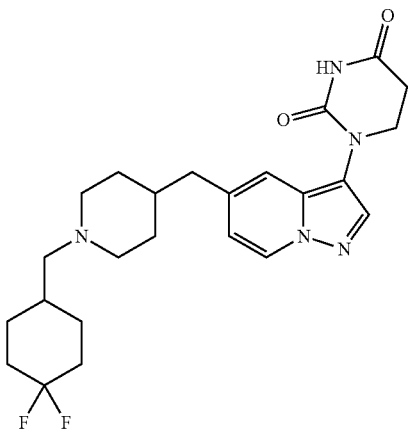

1-(5-((1-((4,4-
difluorocyclohexyl)methyl)piperidin-4-
yl)methyl)pyrazolo[1,5-a]pyridin-3-
yl)dihydropyrimidine-2,4(1H,3H)-dione

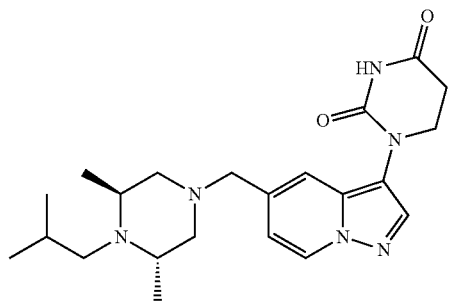

1-(5-(((3S,5S)-4-isobutyl-3,5-
dimethylpiperazin-1-yl)methyl)pyrazolo[1,5-
a]pyridin-3-yl)dihydropyrimidine-2,4(1H,3H)-dione

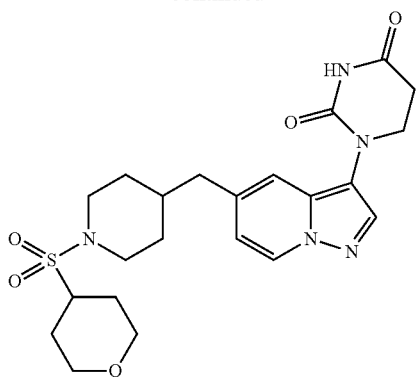

1-(5-((1-((tetrahydro-2H-pyran-4-
yl)sulfonyl)piperidin-4-yl)methyl)pyrazolo[1,5-
a]pyridin-3-yl)dihydropyrimidine-2,4(1H,3H)-dione

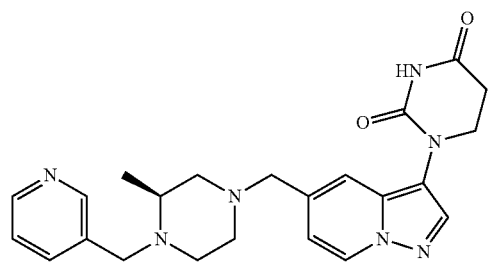

(S)-1-(5-((3-methyl-4-(pyridin-3-
ylmethyl)piperazin-1-yl)methyl)pyrazolo[1,5-
a]pyridin-3-yl)dihydropyrimidine-2,4(1H,3H)-dione

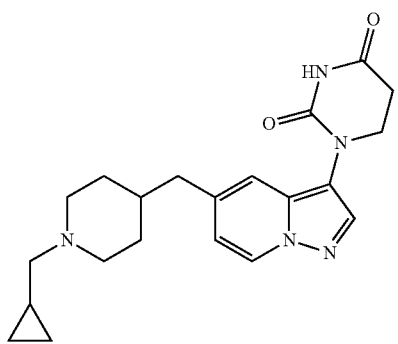

1-(5-((1-(cyclopropylmethyl)piperidin-4-
yl)methyl)pyrazolo[1,5-a]pyridin-3-
yl)dihydropyrimidine-2,4(1H,3H)-dione

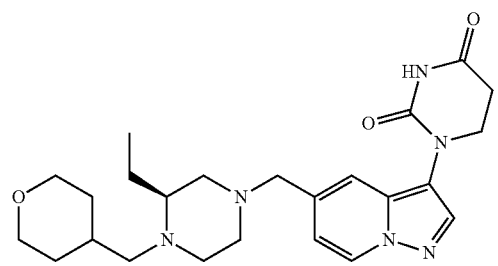

(S)-1-(5-((3-ethyl-4-((tetrahydro-2H-pyran-4-
yl)methyl)piperazin-1-yl)methyl)pyrazolo[1,5-
a]pyridin-3-yl)dihydropyrimidine-2,4(1H,3H)-dione

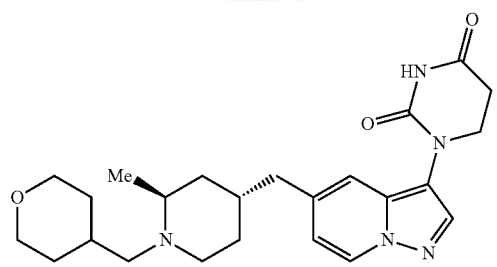

1-(5-(((2S,4R)-2-methyl-1-((tetrahydro-2H-pyran-4-yl)methyl)piperidin-4-yl)methyl)pyrazolo[1,5-a]pyridin-3-yl)dihydropyrimidine-2,4(1H,3H)-dione

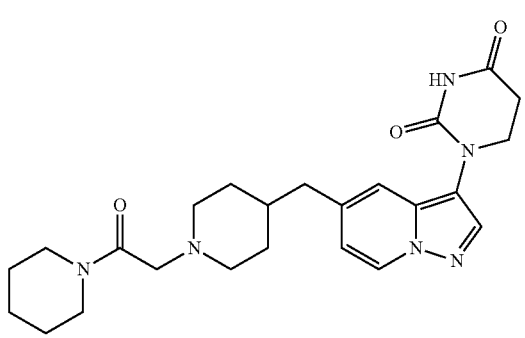

1-(5-((1-(2-oxo-2-(piperidin-1-yl)ethyl)piperidin-4-yl)methyl)pyrazolo[1,5-a]pyridin-3-yl)dihydropyrimidine-2,4(1H,3H)-dione

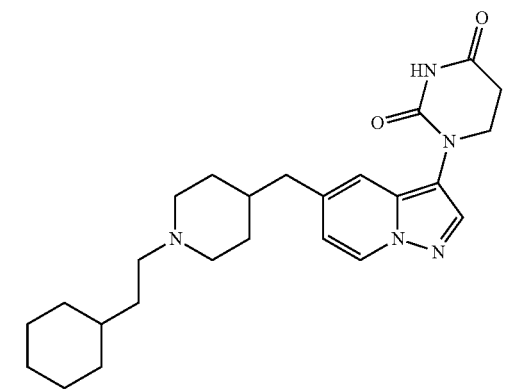

1-(5-((1-(2-cyclohexylethyl)piperidin-4-yl)methyl)pyrazolo[1,5-a]pyridin-3-yl)dihydropyrimidine-2,4(1H,3H)-dione

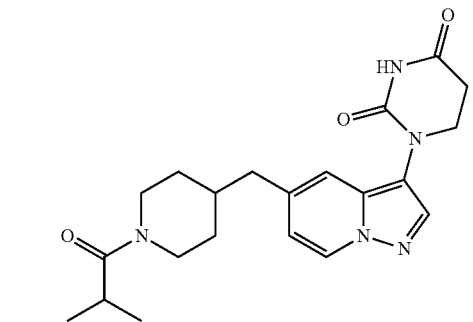

1-(5-((1-isobutyrylpiperidin-4-yl)methyl)pyrazolo[1,5-a]pyridin-3-yl)dihydropyrimidine-2,4(1H,3H)-dione

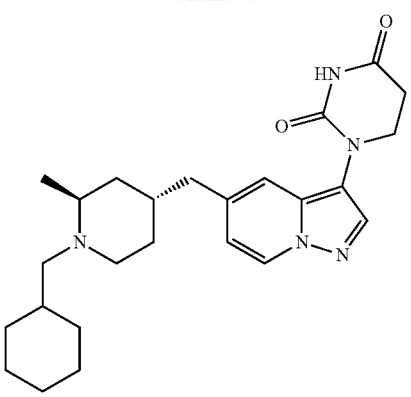

1-(5-(((2S,4R)-1-(cyclohexylmethyl)-2-methylpiperidin-4-yl)methyl)pyrazolo[1,5-a]pyridin-3-yl)dihydropyrimidine-2,4(1H,3H)-dione

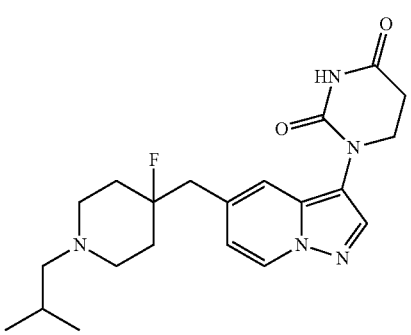

1-(5-((4-fluoro-1-isobutylpiperidin-4-yl)methyl)pyrazolo[1,5-a]pyridin-3-yl)dihydropyrimidine-2,4(1H,3H)-dione

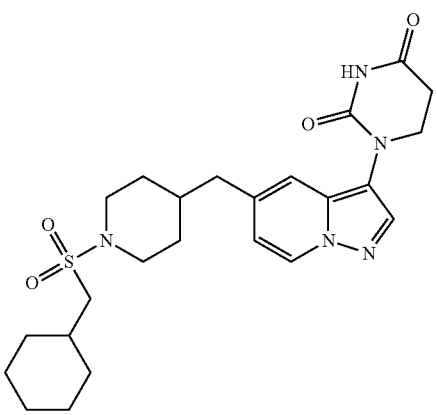

1-(5-((1-((cyclohexylmethyl)sulfonyl)piperidin-4-yl)methyl)pyrazolo[1,5-a]pyridin-3-yl)dihydropyrimidine-2,4(1H,3H)-dione -continued

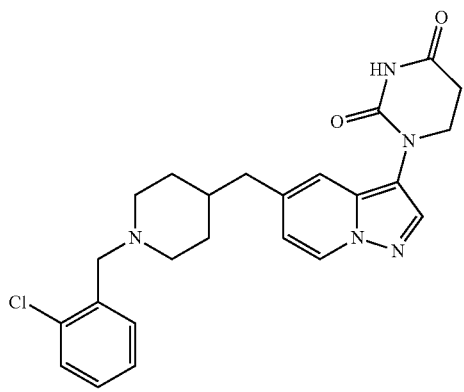

1-(5-((1-(2-chlorobenzyl)piperidin-4-
yl)methyl)pyrazolo[1,5-a]pyridin-3-
yl)dihydropyrimidine-2,4(1H,3H)-dione

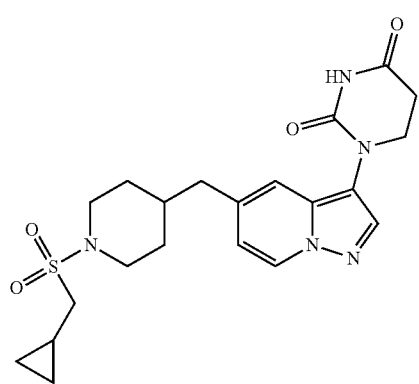

1-(5-((1-((cyclopropylmethyl)sulfonyl)piperidin-4-
yl)methyl)pyrazolo[1,5-a]pyridin-3-
yl)dihydropyrimidine-2,4(1H,3H)-dione

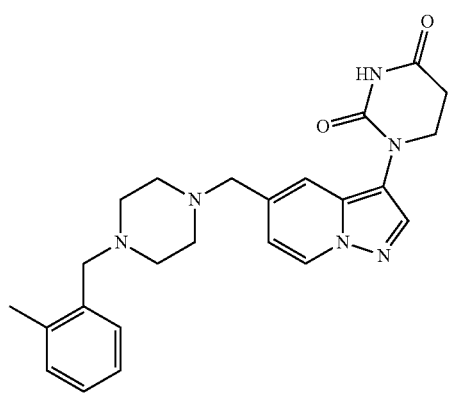

1-(5-((4-(2-methylbenzyl)piperazin-1-
yl)methyl)pyrazolo[1,5-a]pyridin-3-
yl)dihydropyrimidine-2,4(1H,3H)-dione -continued

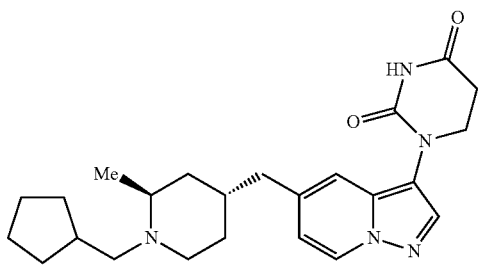

1-(5-(((2S,4R)-1-(cyclopentylmethyl)-2-
methylpiperidin-4-yl)methyl)pyrazolo[1,5-
a]pyridin-3-yl)dihydropyrimidine-2,4(1H,3H)-dione

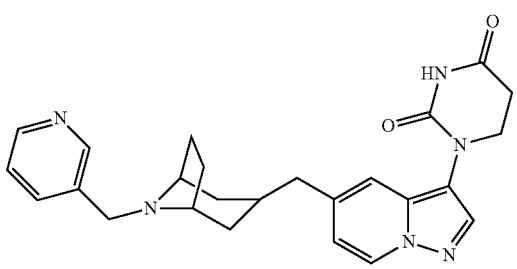

1-(5-((((1R,5S)-8-(pyridin-3-ylmethyl)-8-
azabicyclo[3.2.1]octan-3-
yl)methyl)pyrazolo[1,5-a]pyridin-3-
yl)dihydropyrimidine-2,4(1H,3H)-dione

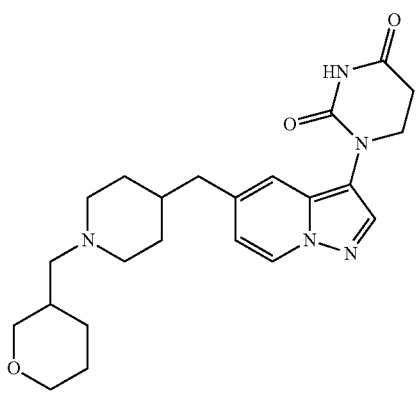

1-(5-((1-((tetrahydro-2H-pyran-3-
yl)methyl)piperidin-4-yl)methyl)pyrazolo[1,5-
a]pyridin-3-yl)dihydropyrimidine-2,4(1H,3H)-dione

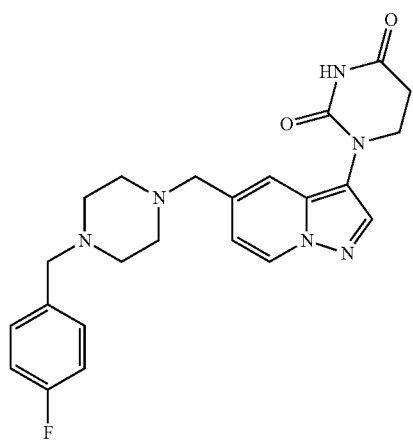

1-(5-((4-(4-fluorobenzyl)piperazin-1-
yl)methyl)pyrazolo[1,5-a]pyridin-3-
yl)dihydropyrimidine-2,4(1H,3H)-dione

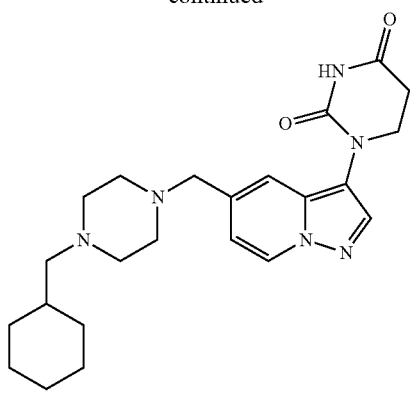

1-(5-((4-(cyclohexylmethyl)piperazin-1-
yl)methyl)pyrazolo[1,5-a]pyridin-3-
yl)dihydropyrimidine-2,4(1H,3H)-dione

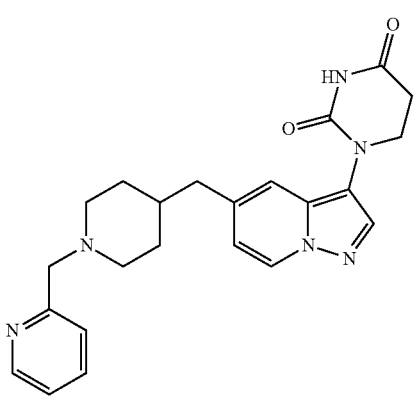

1-(5-((1-(pyridin-2-ylmethyl)piperidin-4-
yl)methyl)pyrazolo[1,5-a]pyridin-3-
yl)dihydropyrimidine-2,4(1H,3H)-dione

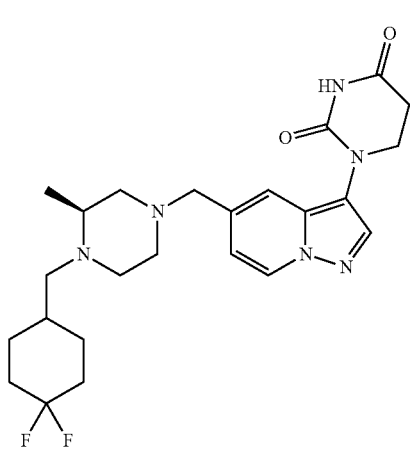

(S)-1-(5-((4-((4,4-difluorocyclohexyl)methyl)-
3-methylpiperazin-1-yl)methyl)pyrazolo[1,5-
a]pyridin-3-yl)dihydropyrimidine-2,4(1H,3H)-dione

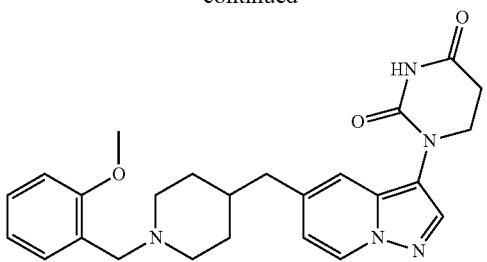

1-(5-((1-(2-methoxybenzyl)piperidin-4-
yl)methyl)pyrazolo[1,5-a]pyridin-3-
yl)dihydropyrimidine-2,4(1H,3H)-dione

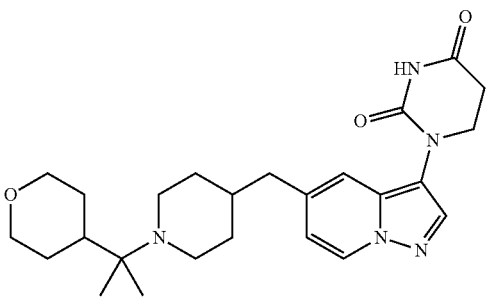

1-(5-((1-(2-(tetrahydro-2H-pyran-4-yl)propan-
2-yl)piperidin-4-yl)methyl)pyrazolo[1,5-
a]pyridin-3-yl)dihydropyrimidine-2,4(1H,3H)-dione

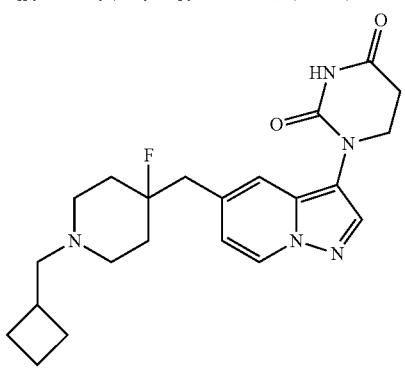

1-(5-((1-(cyclobutylmethyl)-4-fluoropiperidin-
4-yl)methyl)pyrazolo[1,5-a]pyridin-3-
yl)dihydropyrimidine-2,4(1H,3H)-dione

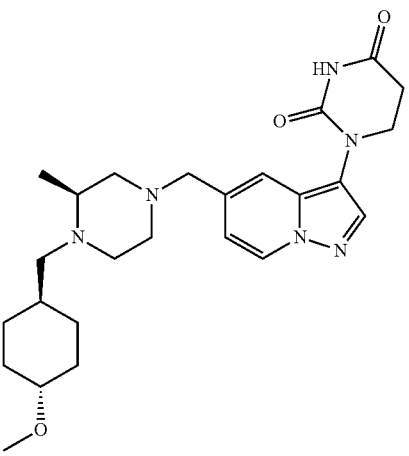

1-(5-(((S)-4-(((1r,4S)-4-
methoxycyclohexyl)methyl)-3-
methylpiperazin-1-yl)methyl)pyrazolo[1,5-
a]pyridin-3-yl)dihydropyrimidine-2,4(1H,3H)-dione -continued

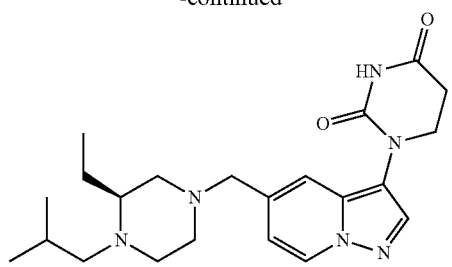

(S)-1-(5-((3-ethyl-4-isobutylpiperazin-1-yl)methyl)pyrazolo[1,5-a]pyridin-3-yl)dihydropyrimidine-2,4(1H,3H)-dione

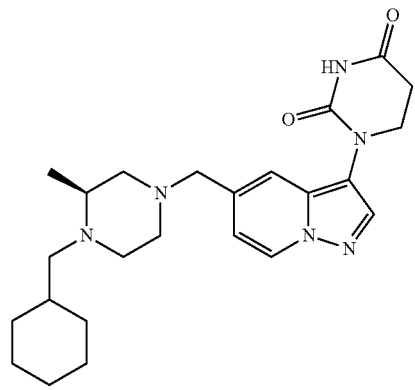

(S)-1-(5-((4-(cyclohexylmethyl)-3-methylpiperazin-1-yl)methyl)pyrazolo[1,5-a]pyridin-3-yl)dihydropyrimidine-2,4(1H,3H)-dione

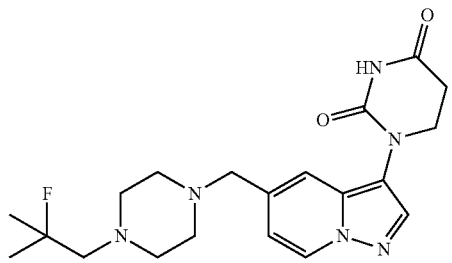

1-(5-((4-(2-fluoro-2-methylpropyl)piperazin-1-yl)methyl)pyrazolo[1,5-a]pyridin-3-yl)dihydropyrimidine-2,4(1H,3H)-dione

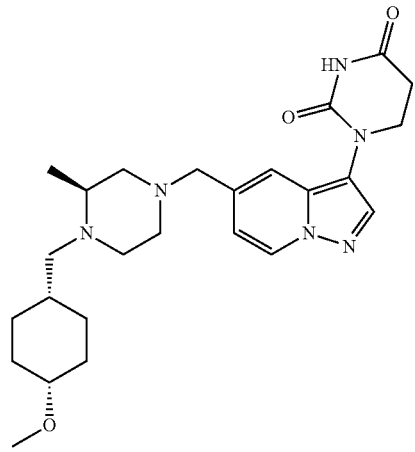

1-(5-(((S)-4-(((1s,4R)-4-methoxycyclohexyl)methyl)-3-methylpiperazin-1-yl)methyl)pyrazolo[1,5-a]pyridin-3-yl)dihydropyrimidine-2,4(1H,3H)-dione -continued

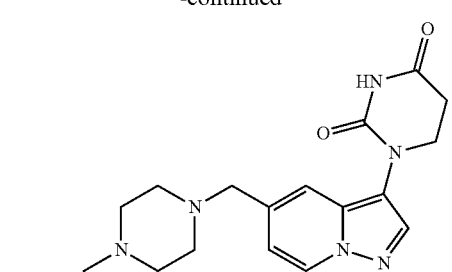

1-(5-((4-(3-methylbenzyl)piperazin-1-yl)methyl)pyrazolo[1,5-a]pyridin-3-yl)dihydropyrimidine-2,4(1H,3H)-dione

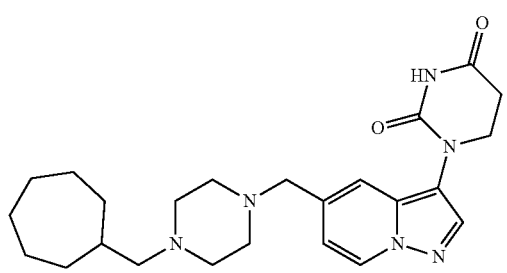

1-(5-((1-(cycloheptylmethyl)piperidin-4-yl)methyl)pyrazolo[1,5-a]pyridin-3-yl)dihydropyrimidine-2,4(1H,3H)-dione

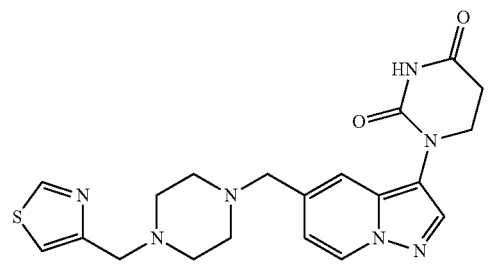

1-(5-((1-(thiazol-4-ylmethyl)piperidin-4-yl)methyl)pyrazolo[1,5-a]pyridin-3-yl)dihydropyrimidine-2,4(1H,3H)-dione

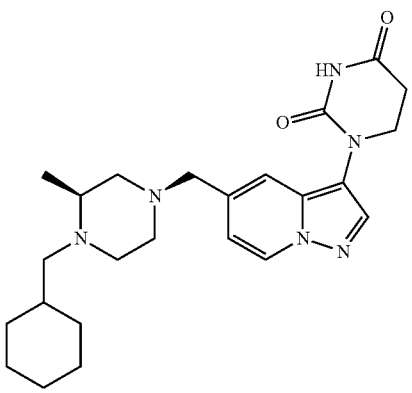

1-(5-(((2S,4S)-1-(cyclohexylmethyl)-2-methylpiperidin-4-yl)methyl)pyrazolo[1,5-a]pyridin-3-yl)dihydropyrimidine-2,4(1H,3H)-dione

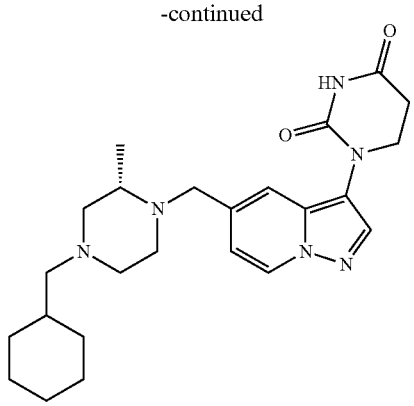

(S)-1-(5-((4-(cyclohexylmethyl)-2-
methylpiperazin-1-yl)methyl)pyrazolo[1,5-
a]pyridin-3-yl)dihydropyrimidine-2,4(1H,3H)-dione

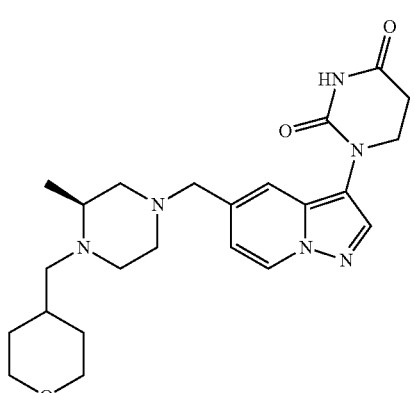

(S)-1-(5-((3-methyl-4-((tetrahydro-2H-pyran-
4-yl)methyl)piperazin-1-
yl)methyl)pyrazolo[1,5-a]pyridin-3-
yl)dihydropyrimidine-2,4(1H,3H)-dione

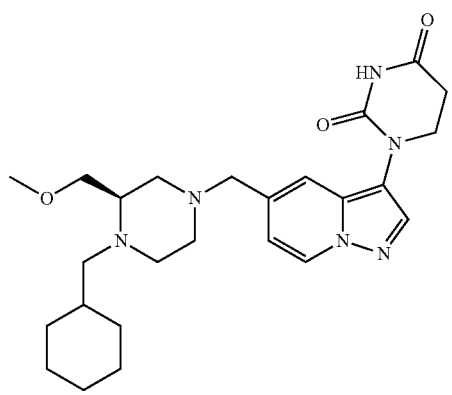

(R)-1-(5-((4-(cyclohexylmethyl)-3-
(methoxymethyl)piperazin-1-
yl)methyl)pyrazolo[1,5-a]pyridin-3-
yl)dihydropyrimidine-2,4(1H,3H)-dione

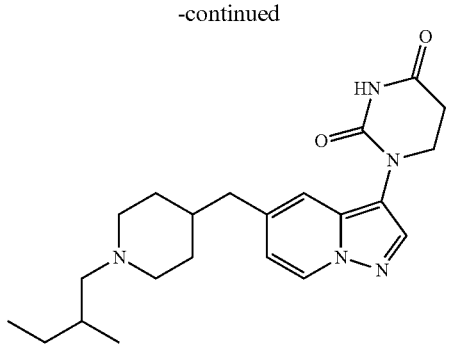

1-(5-((1-(2-methylbutyl)piperidin-4-
yl)methyl)pyrazolo[1,5-a]pyridin-3-
yl)dihydropyrimidine-2,4(1H,3H)-dione

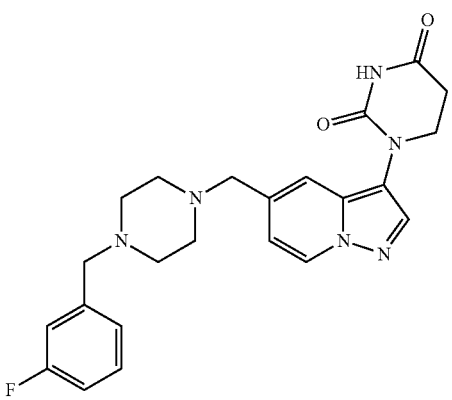

1-(5-((4-(3-fluorobenzyl)piperazin-1-
yl)methyl)pyrazolo[1,5-a]pyridin-3-
yl)dihydropyrimidine-2,4(1H,3H)-dione

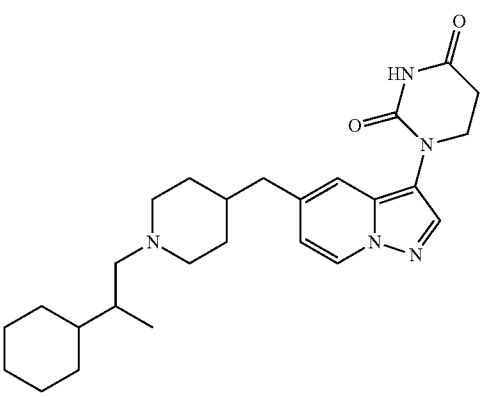

1-(5-((1-(2-cyclohexylpropyl)piperidin-4-
yl)methyl)pyrazolo[1,5-a]pyridin-3-
yl)dihydropyrimidine-2,4(1H,3H)-dione 51
-continued

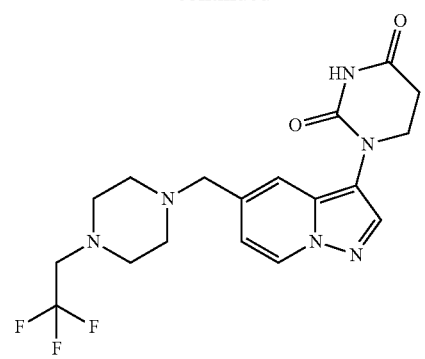

1-(5-((4-(2,2,2-trifluoroethyl)piperazin-1-
yl)methyl)pyrazolo[1,5-a]pyridin-3-
yl)dihydropyrimidine-2,4(1H,3H)-dione

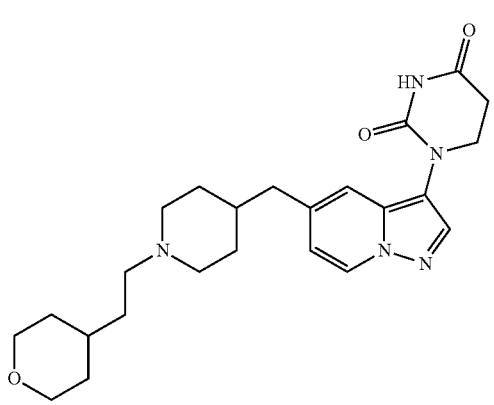

1-(5-((1-(2-(tetrahydro-2H-pyran-4-
yl)ethyl)piperidin-4-yl)methyl)pyrazolo[1,5-
a]pyridin-3-yl)dihydropyrimidine-2,4(1H,3H)-dione

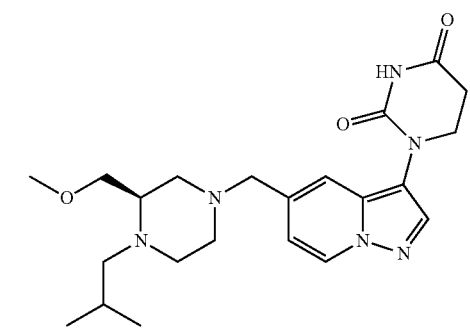

(R)-1-(5-((4-isobutyl-3-
(methoxymethyl)piperazin-1-
yl)methyl)pyrazolo[1,5-a]pyridin-3-
yl)dihydropyrimidine-2,4(1H,3H)-dione 52
-continued

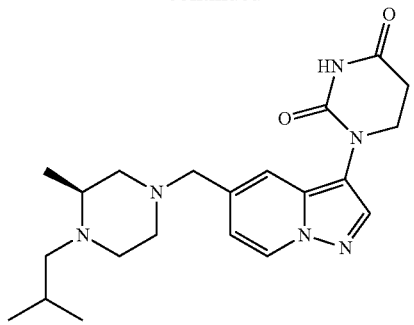

(S)-1-(5-((4-isobutyl-3-methylpiperazin-1-
yl)methyl)pyrazolo[1,5-a]pyridin-3-
yl)dihydropyrimidine-2,4(1H,3H)-dione

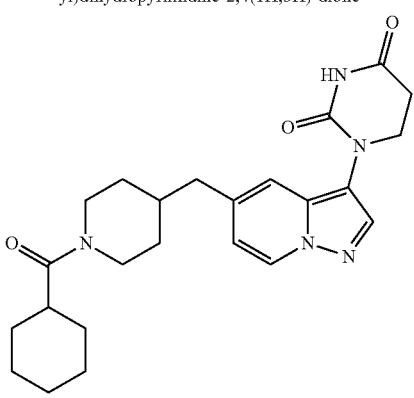

1-(5-((1-(cyclohexanecarbonyl)piperidin-4-
yl)methyl)pyrazolo[1,5-a]pyridin-3-
yl)dihydropyrimidine-2,4(1H,3H)-dione

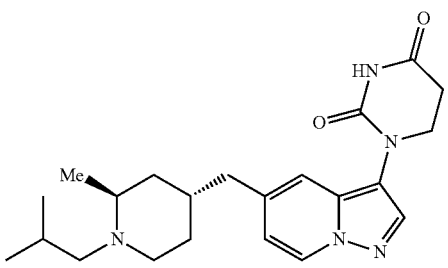

1-(5-(((2S,4R)-1-isobutyl-2-methylpiperidin-4-
yl)methyl)pyrazolo[1,5-a]pyridin-3-
yl)dihydropyrimidine-2,4(1H,3H)-dione

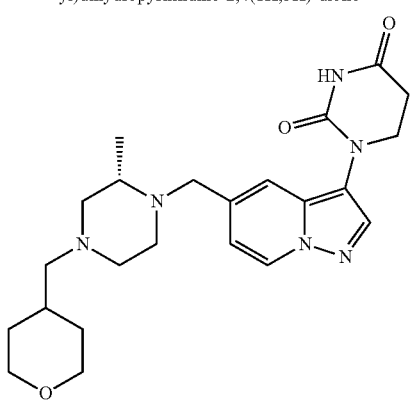

(S)-1-(5-((2-methyl-4-((tetrahydro-2H-pyran-
4-yl)methyl)piperazin-1-
yl)methyl)pyrazolo[1,5-a]pyridin-3-
yl)dihydropyrimidine-2,4(1H,3H)-dione 53
-continued

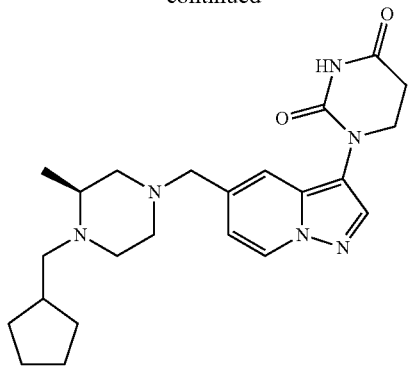

(S)-1-(5-((4-cyclopentylmethyl)-3-
methylpiperazin-1-yl)methyl)pyrazolo[1,5-
a]pyridin-3-yl)dihydropyrimidine-2,4(1H,3H)-dione

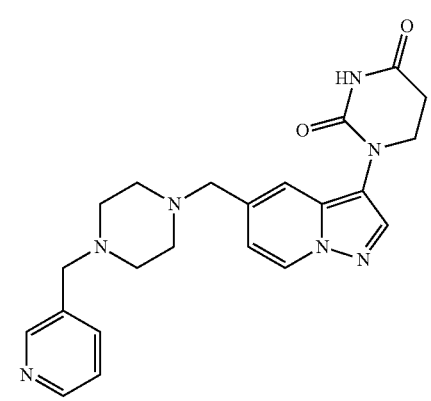

1-(5-((4-(pyridin-3-ylmethyl)piperazin-1-
yl)methyl)pyrazolo[1,5-a]pyridin-3-
yl)dihydropyrimidine-2,4(1H,3H)-dione

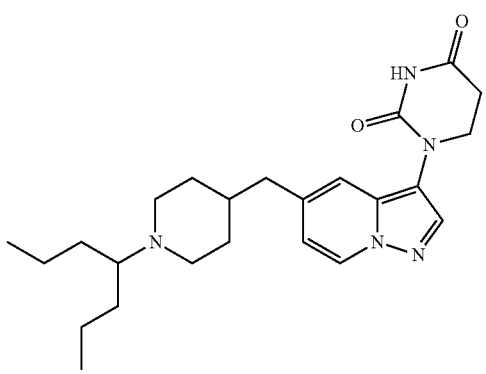

1-(5-((1-(heptan-4-yl)piperidin-4-
yl)methyl)pyrazolo[1,5-a]pyridin-3-
yl)dihydropyrimidine-2,4(1H,3H)-dione 54
-continued

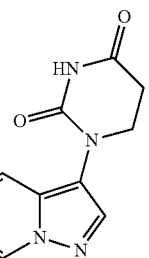

1-(5-((1-(3-hydroxy-2-
(hydroxymethyl)propyl)piperidin-4-
yl)methyl)pyrazolo[1,5-a]pyridin-3-
yl)dihydropyrimidine-2,4(1H,3H)-dione

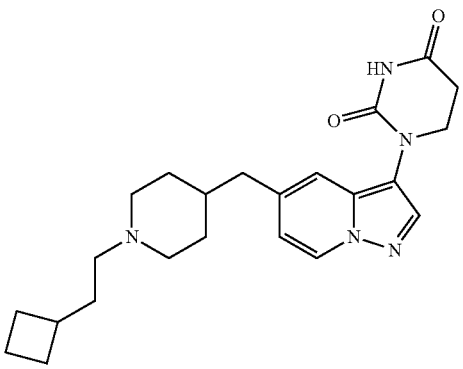

1-(5-((1-(2-cyclobutylethyl)piperidin-4-
yl)methyl)pyrazolo[1,5-a]pyridin-3-
yl)dihydropyrimidine-2,4(1H,3H)-dione

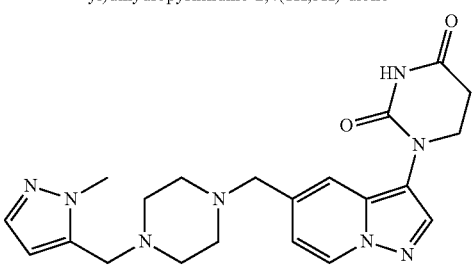 
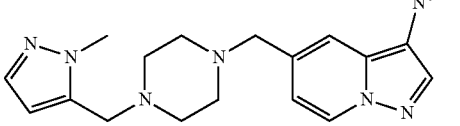

1-(5-((4-((1-methyl-1H-pyrazol-5-
yl)methyl)piperazin-1-yl)methyl)pyrazolo[1,5-
a]pyridin-3-yl)dihydropyrimidine-2,4(1H,3H)-dione

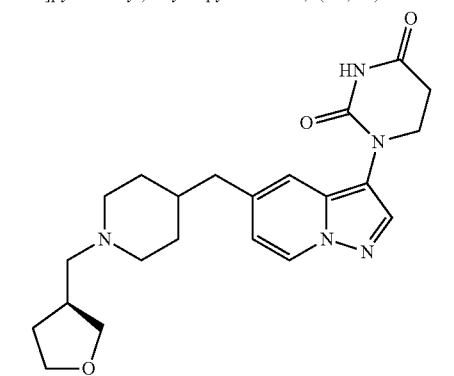

(S)-1-(5-((1-((tetrahydrofuran-3-
yl)methyl)piperidin-4-yl)methyl)pyrazolo[1,5-
a]pyridin-3-yl)dihydropyrimidine-2,4(1H,3H)-dione

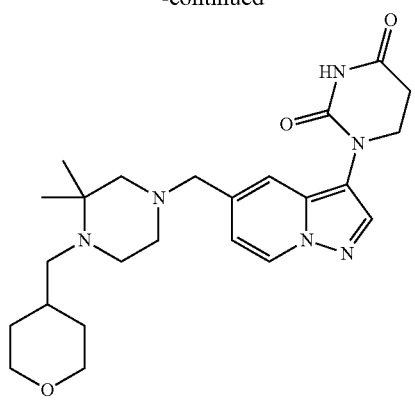

1-(5-((3,3-dimethyl-4-((tetrahydro-2H-pyran-4-yl)methyl)piperazin-1-yl)methyl)pyrazolo[1,5-a]pyridin-3-yl)dihydropyrimidine-2,4(1H,3H)-dione

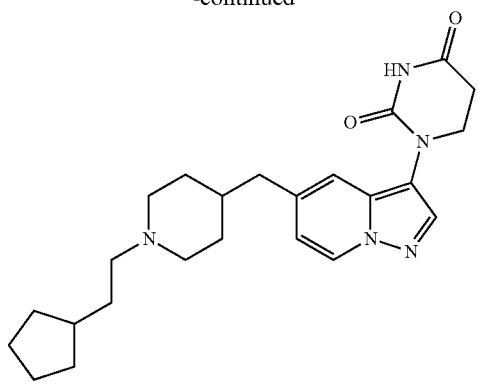

1-(5-((1-(2-cyclopentylethyl)piperidin-4-yl)methyl)pyrazolo[1,5-a]pyridin-3-yl)dihydropyrimidine-2,4(1H,3H)-dione

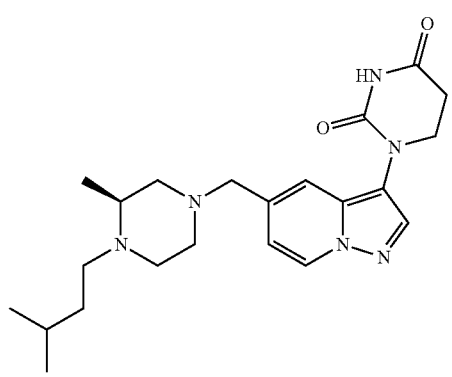

(S)-1-(5-((4-isopentyl-3-methylpiperazin-1-yl)methyl)pyrazolo[1,5-a]pyridin-3-yl)dihydropyrimidine-2,4(1H,3H)-dione

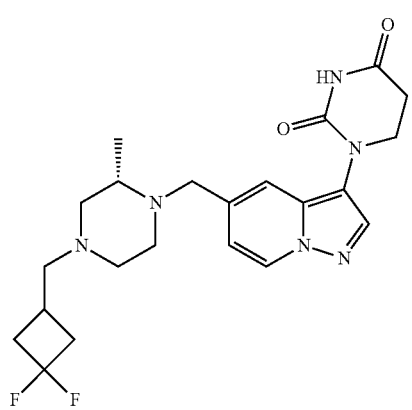

(S)-1-(5-((4-((3,3-difluorocyclobutyl)methyl)-2-methylpiperazin-1-yl)methyl)pyrazolo[1,5-a]pyridin-3-yl)dihydropyrimidine-2,4(1H,3H)-dione

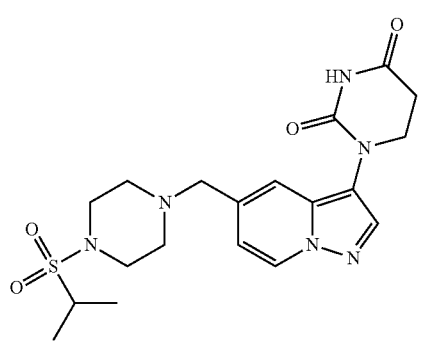

1-(5-((4-(isopropylsulfonyl)piperazin-1-yl)methyl)pyrazolo[1,5-a]pyridin-3-yl)dihydropyrimidine-2,4(1H,3H)-dione

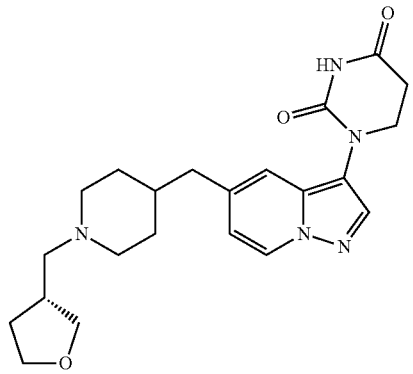

(R)-1-(5-((1-((tetrahydrofuran-3-yl)methyl)piperidin-4-yl)methyl)pyrazolo[1,5-a]pyridin-3-yl)dihydropyrimidine-2,4(1H,3H)-dione 57
-continued

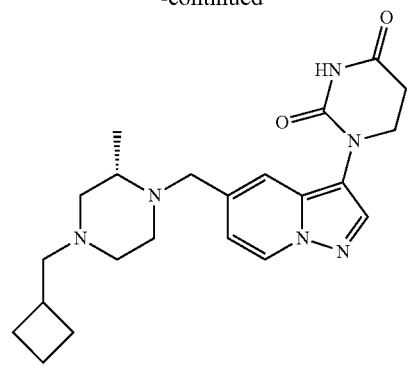

(S)-1-(5-((4-(cyclobutylmethyl)-2-methylpiperazin-1-yl)methyl)pyrazolo[1,5-a]pyridin-3-yl)dihydropyrimidine-2,4(1H,3H)-dione

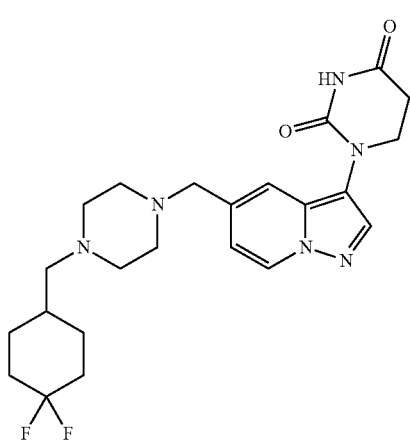

1-(5-((4-((4,4-difluorocyclohexyl)methyl)piperazin-1-yl)methyl)pyrazolo[1,5-a]pyridin-3-yl)dihydropyrimidine-2,4(1H,3H)-dione

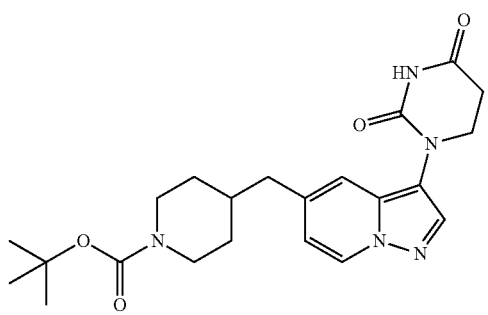

tert-butyl 4-((3-(2,4-dioxotetrahydropyrimidin-1(2H)-yl)pyrazolo[1,5-a]pyridin-5-yl)methyl)piperidine-1-carboxylate 58
-continued

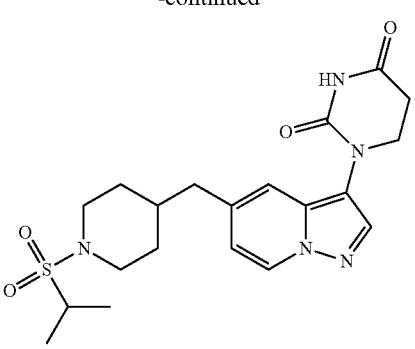

1-(5-((1-(isopropylsulfonyl)piperidin-4-yl)methyl)pyrazolo[1,5-a]pyridin-3-yl)dihydropyrimidine-2,4(1H,3H)-dione

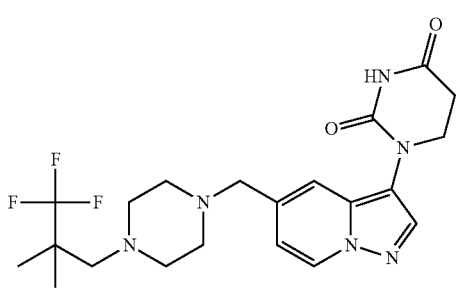

1-(5-((4-(3,3,3-trifluoro-2,2-dimethylpropyl)piperazin-1-yl)methyl)pyrazolo[1,5-a]pyridin-3-yl)dihydropyrimidine-2,4(1H,3H)-dione

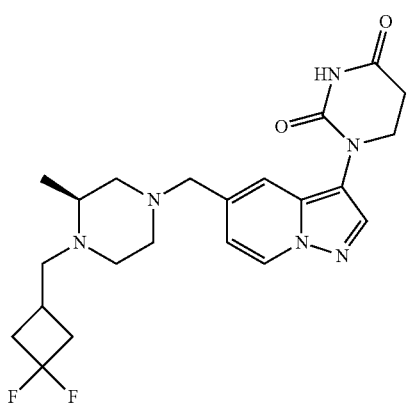

(S)-1-(5-((4-((3,3-difluorocyclobutyl)methyl)-3-methylpiperazin-1-yl)methyl)pyrazolo[1,5-a]pyridin-3-yl)dihydropyrimidine-2,4(1H,3H)-dione

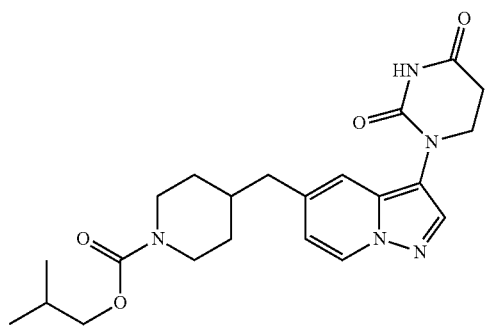

isobutyl 4-((3-(2,4-dioxotetrahydropyrimidin-1(2H)-yl)pyrazolo[1,5-a]pyridin-5-yl)methyl)piperidine-1-carboxylate

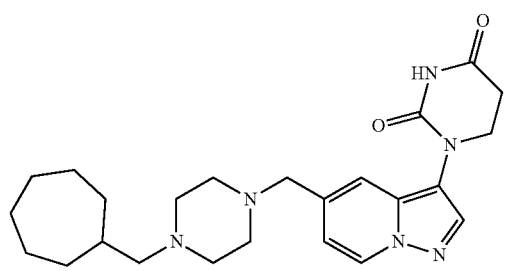

1-(5-((4-(cycloheptylmethyl)piperazin-1-
yl)methyl)pyrazolo[1,5-a]pyridin-3-
yl)dihydropyrimidine-2,4(1H,3H)-dione

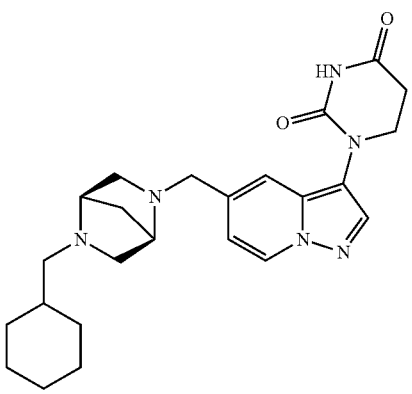

1-(5-(((1R,4R)-5-(cyclohexylmethyl)-2,5-
diazabicyclo[2.2.1]heptan-2-
yl)methyl)pyrazolo[1,5-a]pyridin-3-
yl)dihydropyrimidine-2,4(1H,3H)-dione

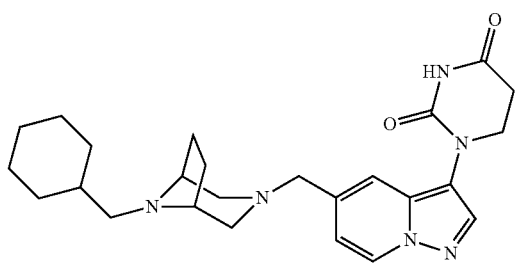

1-(5-(((1R,5S)-8-(cyclohexylmethyl)-3,8-
diazabicyclo[3.2.1]octan-3-
yl)methyl)pyrazolo[1,5-a]pyridin-3-
yl)dihydropyrimidine-2,4(1H,3H)-dione

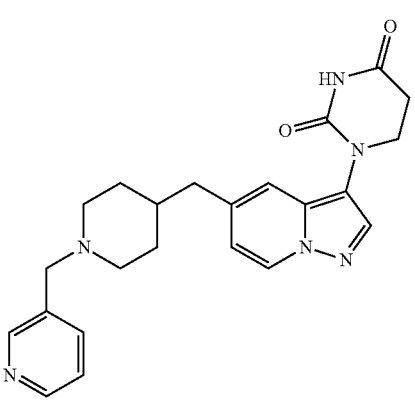

1-(5-((1-(pyridin-3-ylmethyl)piperidin-4-
yl)methyl)pyrazolo[1,5-a]pyridin-3-
yl)dihydropyrimidine-2,4(1H,3H)-dione

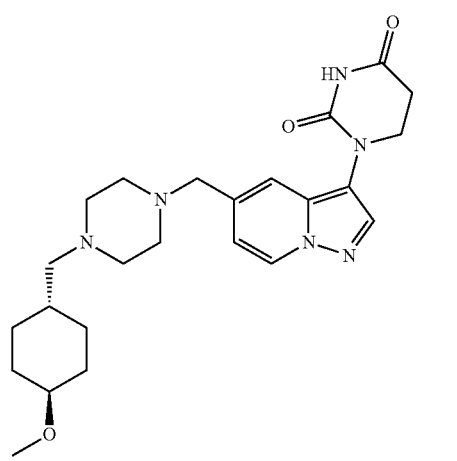

1-(5-((4-(((1r,4r)-4-
methoxycyclohexyl)methyl)piperazin-1-
yl)methyl)pyrazolo[1,5-a]pyridin-3-
yl)dihydropyrimidine-2,4(1H,3H)-dione

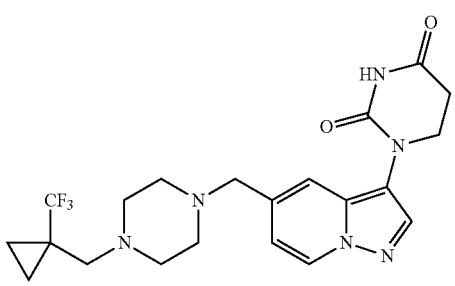

1-(5-((4-((1-
(trifluoromethyl)cyclopropyl)methyl)piperazin-
1-yl)methyl)pyrazolo[1,5-a]pyridin-3-
yl)dihydropyrimidine-2,4(1H,3H)-dione

61

-continued

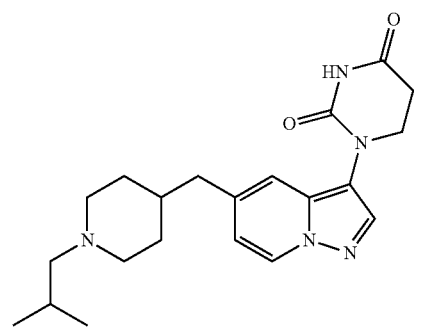

1-(5-((1-isobutylpiperidin-4-
yl)methyl)pyrazolo[1,5-a]pyridin-3-
yl)dihydropyrimidine-2,4(1H,3H)-dione

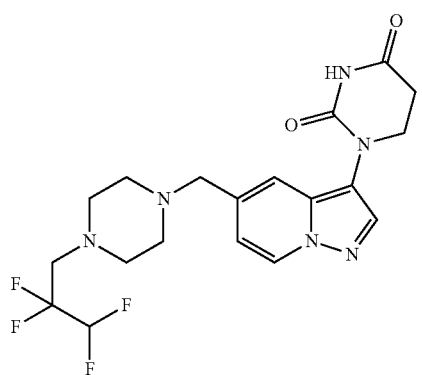

1-(5-((4-(2,2,3,3-tetrafluoropropyl)piperazin-1-
yl)methyl)pyrazolo[1,5-a]pyridin-3-
yl)dihydropyrimidine-2,4(1H,3H)-dione

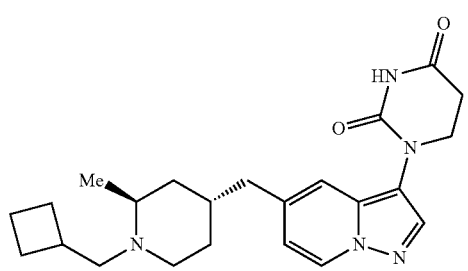

1-(5-(((2S,4R)-1-(cyclobutylmethyl)-2-
methylpiperidin-4-yl)methyl)pyrazolo[1,5-
a]pyridin-3-yl)dihydropyrimidine-2,4(1H,3H)-dione

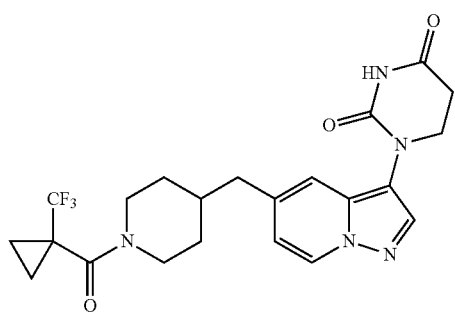

1-(5-((1-(1-(trifluoromethyl)cyclopropane-1-
carbonyl)piperidin-4-yl)methyl)pyrazolo[1,5-
a]pyridin-3-yl)dihydropyrimidine-2,4(1H,3H)-dione

62

-continued

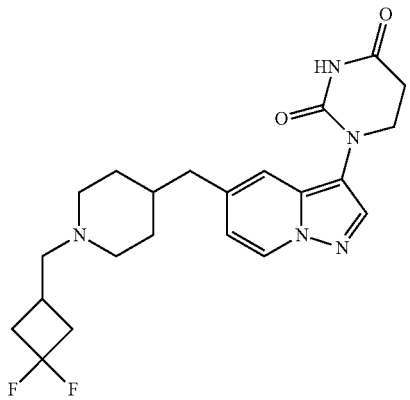

1-(5-((1-((3,3-
difluorocyclobutyl)methyl)piperidin-4-
yl)methyl)pyrazolo[1,5-a]pyridin-3-
yl)dihydropyrimidine-2,4(1H,3H)-dione

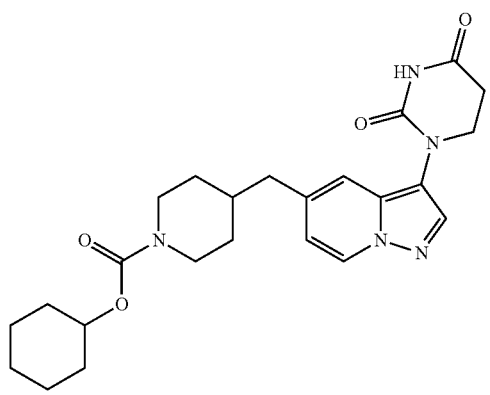

cyclohexyl 4-((3-(2,4-
dioxotetrahydropyrimidin-1(2H-
yl)pyrazolo[1,5-a]pyridin-5-
yl)methyl)piperidine-1-carboxylate

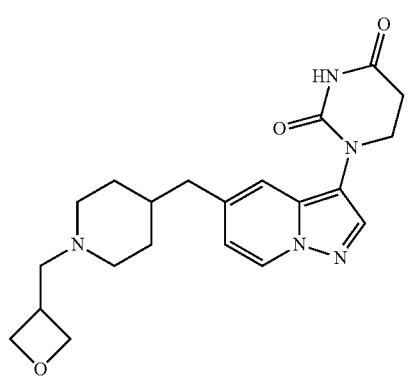

1-(5-((1-(oxetan-3-ylmethyl)piperidin-4-
yl)methyl)pyrazolo[1,5-a]pyridin-3-
yl)dihydropyrimidine-2,4(1H,3H)-dione

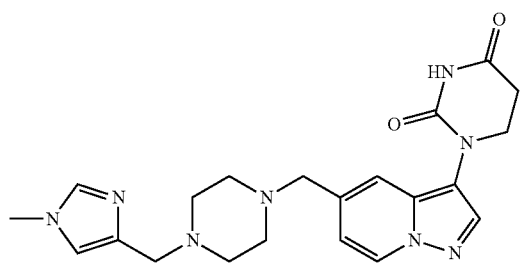

1-(5-((4-((1-methyl-1H-imidazol-4-
yl)methyl)piperazin-1-yl)methyl)pyrazolo[1,5-
a]pyridin-3-yl)dihydropyrimidine-2,4(1H,3H)-dione

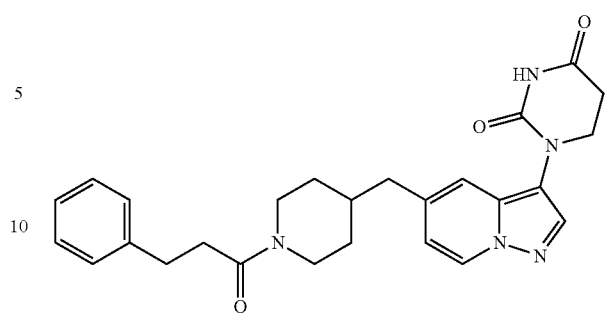

1-(5-((1-(3-phenylpropanoyl)piperidin-4-
yl)methyl)pyrazolo[1,5-a]pyridin-3-
yl)dihydropyrimidine-2,4(1H,3H)-dione

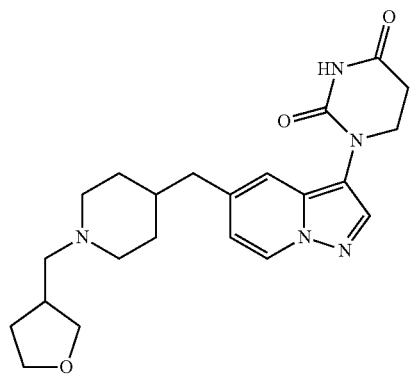

1-(5-((1-((tetrahydrofuran-3-
yl)methyl)piperidin-4-yl)methyl)pyrazolo[1,5-
a]pyridin-3-yl)dihydropyrimidine-2,4(1H,3H)-dione

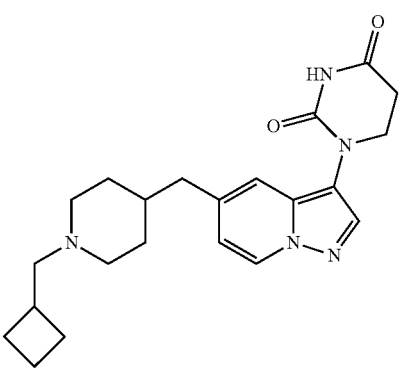

1-(5-((1-(cyclobutylmethyl)piperidin-4-
yl)methyl)pyrazolo[1,5-a]pyridin-3-
yl)dihydropyrimidine-2,4(1H,3H)-dione

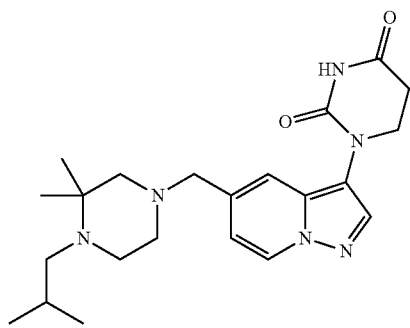

1-(5-((4-isobutyl-3,3-dimethylpiperazin-1-
yl)methyl)pyrazolo[1,5-a]pyridin-3-
yl)dihydropyrimidine-2,4(1H,3H)-dione

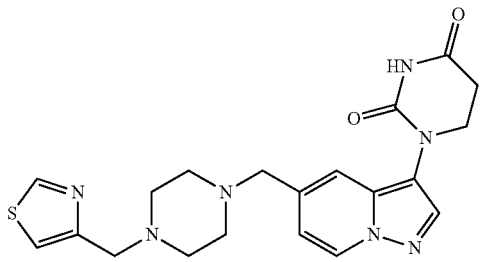

1-(5-((4-(thiazol-4-ylmethyl)piperazin-1-
yl)methyl)pyrazolo[1,5-a]pyridin-3-
yl)dihydropyrimidine-2,4(1H,3H)-dione

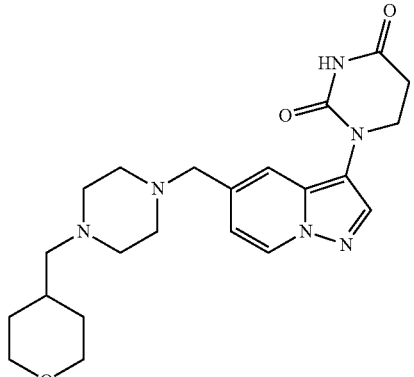

1-(5-((4-((tetrahydro-2H-pyran-4-
yl)methyl)piperazin-1-yl)methyl)pyrazolo[1,5-
a]pyridin-3-yl)dihydropyrimidine-2,4(1H,3H)-dione

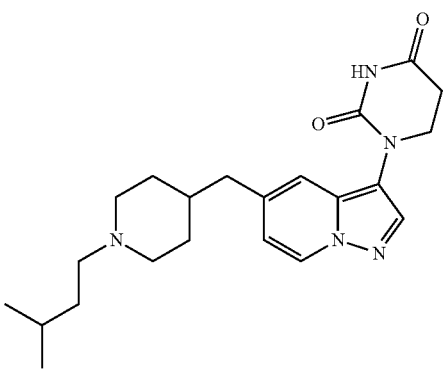

1-(5-((1-isopentylpiperidin-4-
yl)methyl)pyrazolo[1,5-a]pyridin-3-
yl)dihydropyrimidine-2,4(1H,3H)-dione

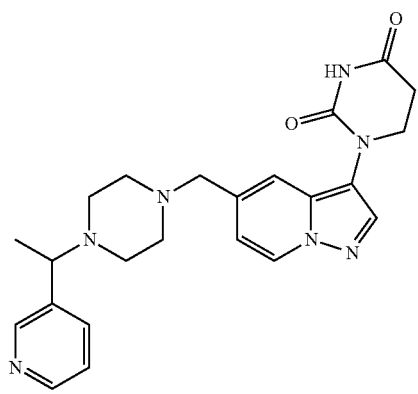

1-(5-((4-(1-(pyridin-3-yl)ethyl)piperazin-1-yl)methyl)pyrazolo[1,5-a]pyridin-3-yl)dihydropyrimidine-2,4(1H,3H)-dione

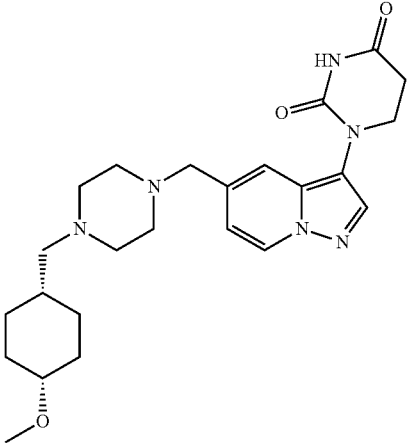

1-(5-((4-(((1s,4s)-4-methoxycyclohexyl)methyl)piperazin-1-yl)methyl)pyrazolo[1,5-a]pyridin-3-yl)dihydropyrimidine-2,4(1H,3H)-dione

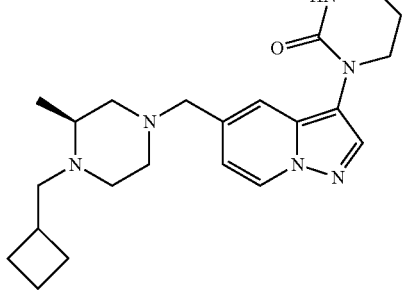

(S)-1-(5-((4-(cyclobutylmethyl)-3-methylpiperazin-1-yl)methyl)pyrazolo[1,5-a]pyridin-3-yl)dihydropyrimidine-2,4(1H,3H)-dione

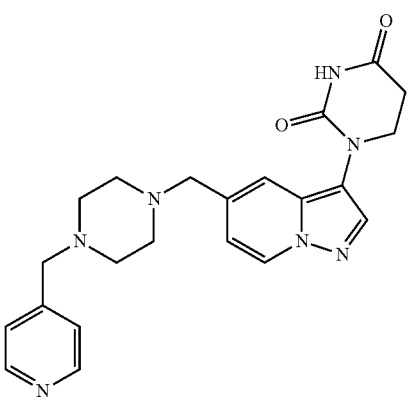

1-(5-((4-(pyridin-4-ylmethyl)piperazin-1-yl)methyl)pyrazolo[1,5-a]pyridin-3-yl)dihydropyrimidine-2,4(1H,3H)-dione

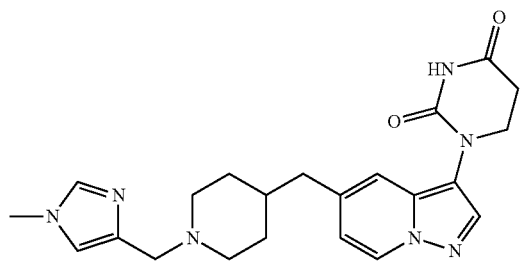

1-(5-((1-((1-methyl-1H-imidazol-4-yl)methyl)piperidin-4-yl)methyl)pyrazolo[1,5-a]pyridin-3-yl)dihydropyrimidine-2,4(1H,3H)-dione

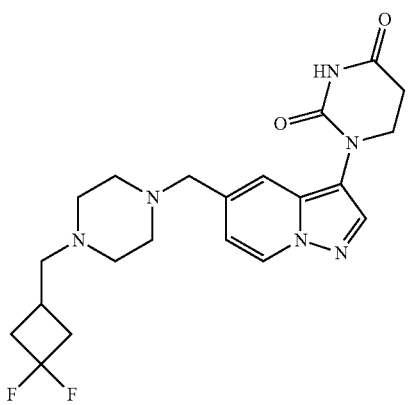

1-(5-((4-((3,3-difluorocyclobutyl)methyl)piperazin-1-yl)methyl)pyrazolo[1,5-a]pyridin-3-yl)dihydropyrimidine-2,4(1H,3H)-dione

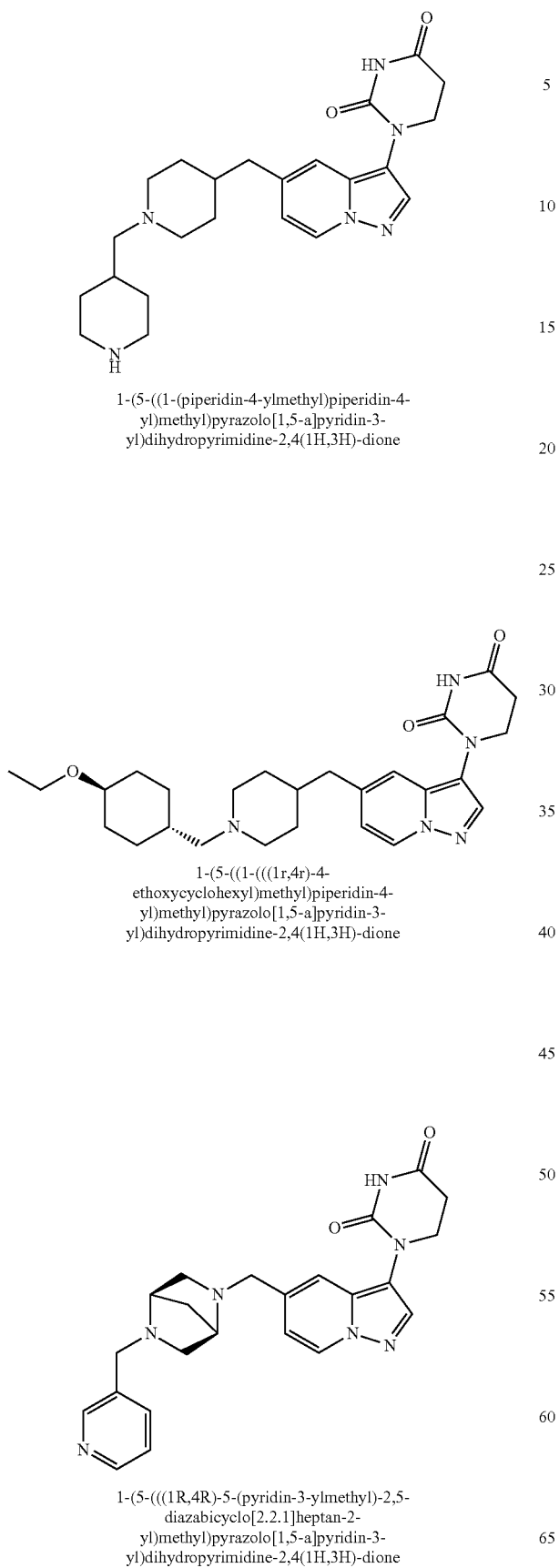

1-(5-((1-(piperidin-4-ylmethyl)piperidin-4-
yl)methyl)pyrazolo[1,5-a]pyridin-3-
yl)dihydropyrimidine-2,4(1H,3H)-dione 1-(5-((1-(((1r,4r)-4-
ethoxycyclohexyl)methyl)piperidin-4-
yl)methyl)pyrazolo[1,5-a]pyridin-3-
yl)dihydropyrimidine-2,4(1H,3H)-dione 1-(5-(((1R,4R)-5-(pyridin-3-ylmethyl)-2,5-
diazabicyclo[2.2.1]heptan-2-
yl)methyl)pyrazolo[1,5-a]pyridin-3-
yl)dihydropyrimidine-2,4(1H,3H)-dione

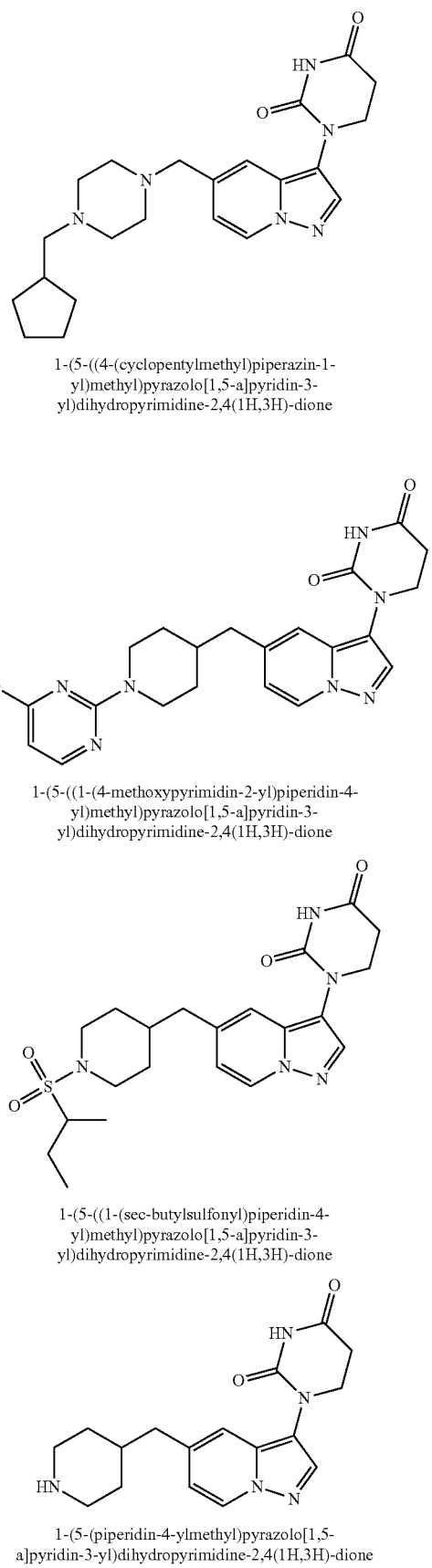

1-(5-((4-(cyclopentylmethyl)piperazin-1-
yl)methyl)pyrazolo[1,5-a]pyridin-3-
yl)dihydropyrimidine-2,4(1H,3H)-dione 1-(5-((1-(4-methoxypyrimidin-2-yl)piperidin-4-
yl)methyl)pyrazolo[1,5-a]pyridin-3-
yl)dihydropyrimidine-2,4(1H,3H)-dione 1-(5-((1-(sec-butylsulfonyl)piperidin-4-
yl)methyl)pyrazolo[1,5-a]pyridin-3-
yl)dihydropyrimidine-2,4(1H,3H)-dione 1-(5-(piperidin-4-ylmethyl)pyrazolo[1,5-
a]pyridin-3-yl)dihydropyrimidine-2,4(1H,3H)-dione 69
-continued

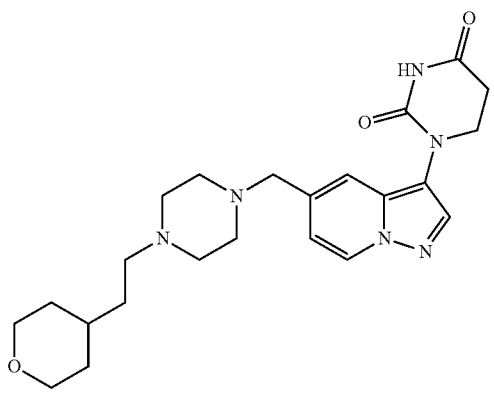

1-(5-((4-(2-(tetrahydro-2H-pyran-4-yl)ethyl)piperazin-1-yl)methyl)pyrazolo[1,5-a]pyridin-3-yl)dihydropyrimidine-2,4(1H,3H)-dione

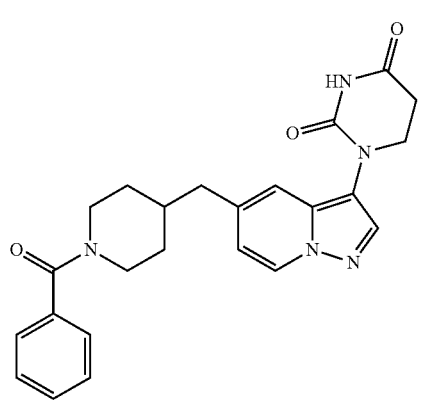

1-(5-((1-benzoylpiperidin-4-yl)methyl)pyrazolo[1,5-a]pyridin-3-yl)dihydropyrimidine-2,4(1H,3H)-dione

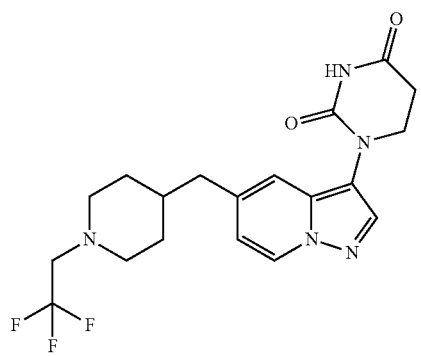

1-(5-((1-(2,2,2-trifluoroethyl)piperidin-4-yl)methyl)pyrazolo[1,5-a]pyridin-3-yl)dihydropyrimidine-2,4(1H,3H)-dione 70
-continued

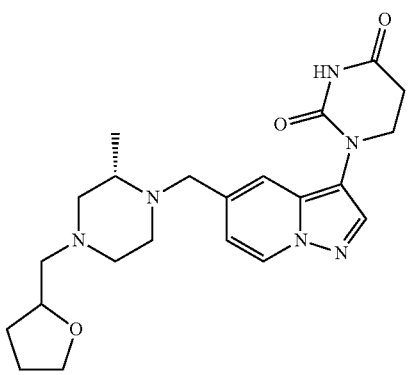

1-(5-(((2S)-2-methyl-4-((tetrahydrofuran-2-yl)methyl)piperazin-1-yl)methyl)pyrazolo[1,5-a]pyridin-3-yl)dihydropyrimidine-2,4(1H,3H)-dione

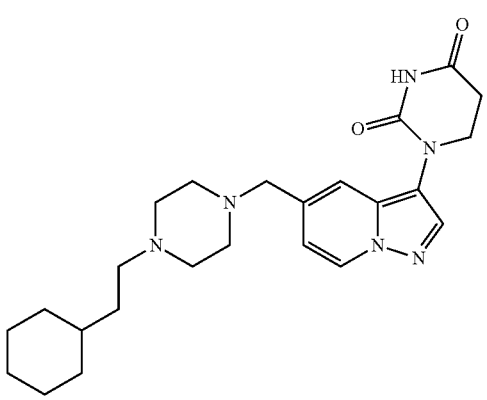

1-(5-((4-(2-cyclohexylethyl)piperazin-1-yl)methyl)pyrazolo[1,5-a]pyridin-3-yl)dihydropyrimidine-2,4(1H,3H)-dione

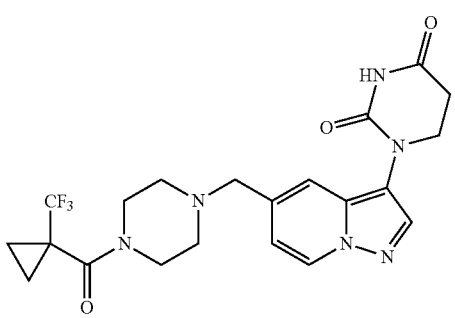

1-(5-((4-(1-(trifluoromethyl)cyclopropane-1-carbonyl)piperazin-1-yl)methyl)pyrazolo[1,5-a]pyridin-3-yl)dihydropyrimidine-2,4(1H,3H)-dione

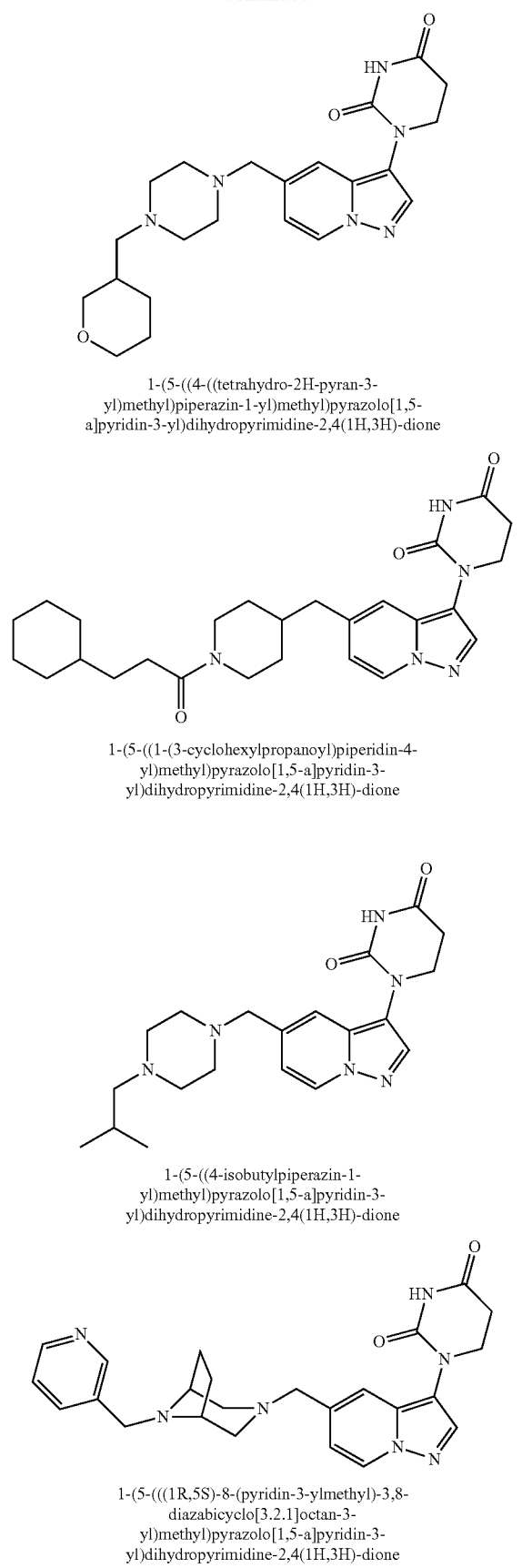

1-(5-((4-((tetrahydro-2H-pyran-3-yl)methyl)piperazin-1-yl)methyl)pyrazolo[1,5-a]pyridin-3-yl)dihydropyrimidine-2,4(1H,3H)-dione 1-(5-((1-(3-cyclohexylpropanoyl)piperidin-4-yl)methyl)pyrazolo[1,5-a]pyridin-3-yl)dihydropyrimidine-2,4(1H,3H)-dione 1-(5-((4-isobutylpiperazin-1-yl)methyl)pyrazolo[1,5-a]pyridin-3-yl)dihydropyrimidine-2,4(1H,3H)-dione 1-(5-(((1R,5S)-8-(pyridin-3-ylmethyl)-3,8-diazabicyclo[3.2.1]octan-3-yl)methyl)pyrazolo[1,5-a]pyridin-3-yl)dihydropyrimidine-2,4(1H,3H)-dione

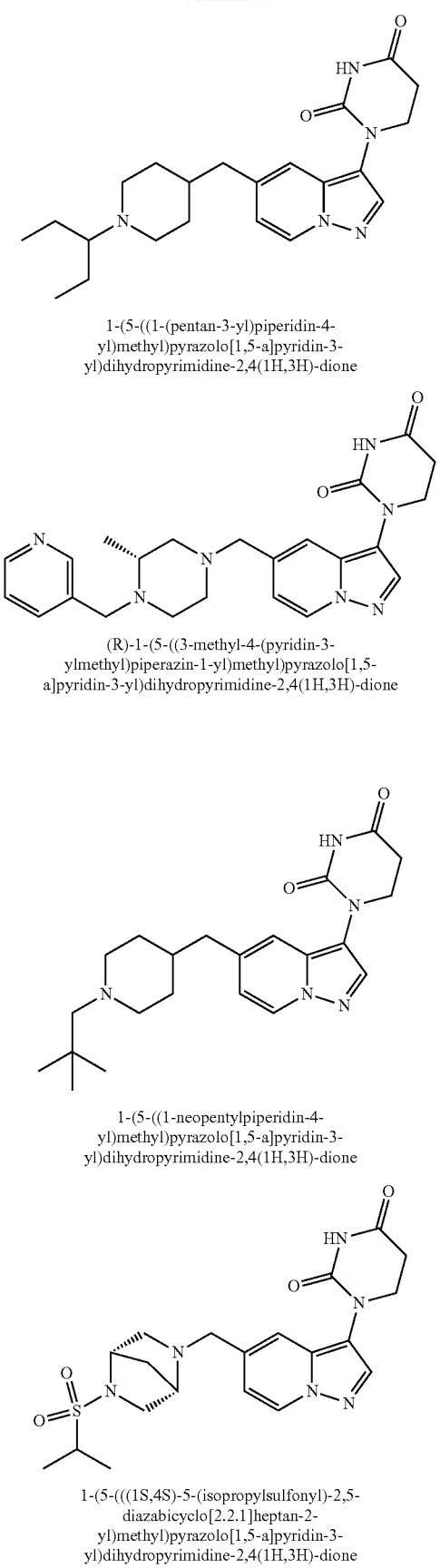

1-(5-((1-(pentan-3-yl)piperidin-4-yl)methyl)pyrazolo[1,5-a]pyridin-3-yl)dihydropyrimidine-2,4(1H,3H)-dione (R)-1-(5-((3-methyl-4-(pyridin-3-ylmethyl)piperazin-1-yl)methyl)pyrazolo[1,5-a]pyridin-3-yl)dihydropyrimidine-2,4(1H,3H)-dione 1-(5-((1-neopentylpiperidin-4-yl)methyl)pyrazolo[1,5-a]pyridin-3-yl)dihydropyrimidine-2,4(1H,3H)-dione 1-(5-(((1S,4S)-5-(isopropylsulfonyl)-2,5-diazabicyclo[2.2.1]heptan-2-yl)methyl)pyrazolo[1,5-a]pyridin-3-yl)dihydropyrimidine-2,4(1H,3H)-dione

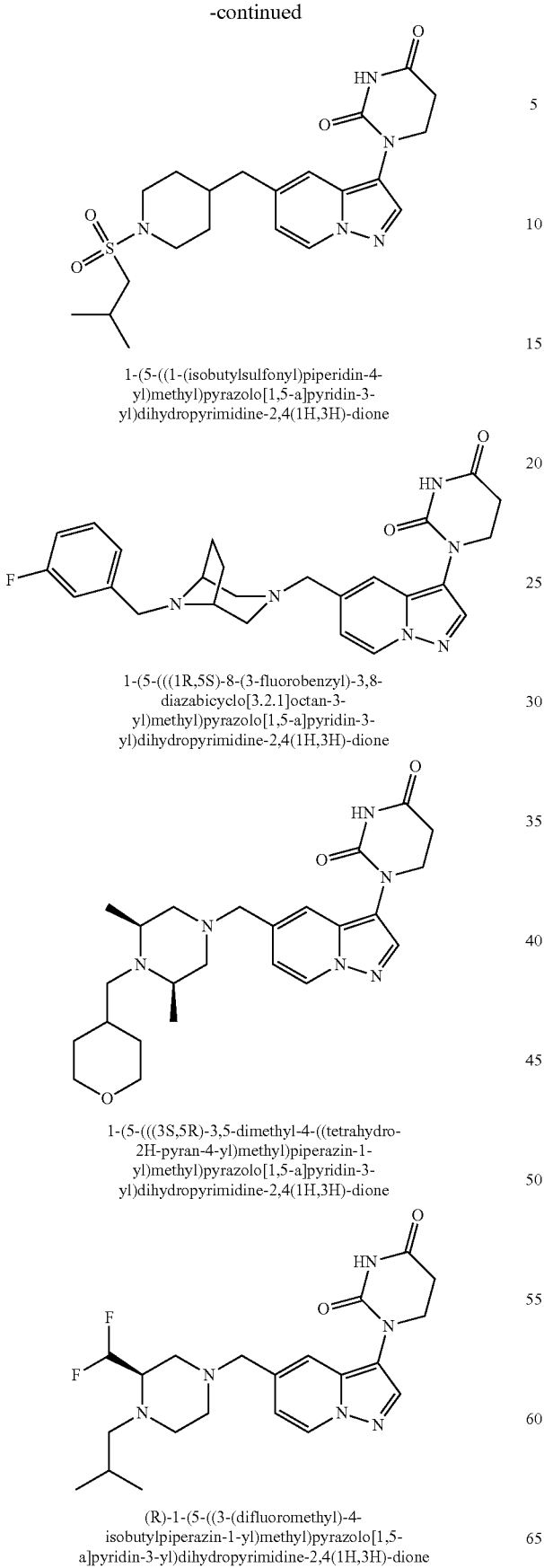

1-(5-((1-(isobutylsulfonyl)piperidin-4-
yl)methyl)pyrazolo[1,5-a]pyridin-3-
yl)dihydropyrimidine-2,4(1H,3H)-dione 1-(5-(((1R,5S)-8-(3-fluorobenzyl)-3,8-
diazabicyclo[3.2.1]octan-3-
yl)methyl)pyrazolo[1,5-a]pyridin-3-
yl)dihydropyrimidine-2,4(1H,3H)-dione 1-(5-(((3S,5R)-3,5-dimethyl-4-((tetrahydro-
2H-pyran-4-yl)methyl)piperazin-1-
yl)methyl)pyrazolo[1,5-a]pyridin-3-
yl)dihydropyrimidine-2,4(1H,3H)-dione (R)-1-(5-((3-(difluoromethyl)-4-
isobutylpiperazin-1-yl)methyl)pyrazolo[1,5-
a]pyridin-3-yl)dihydropyrimidine-2,4(1H,3H)-dione

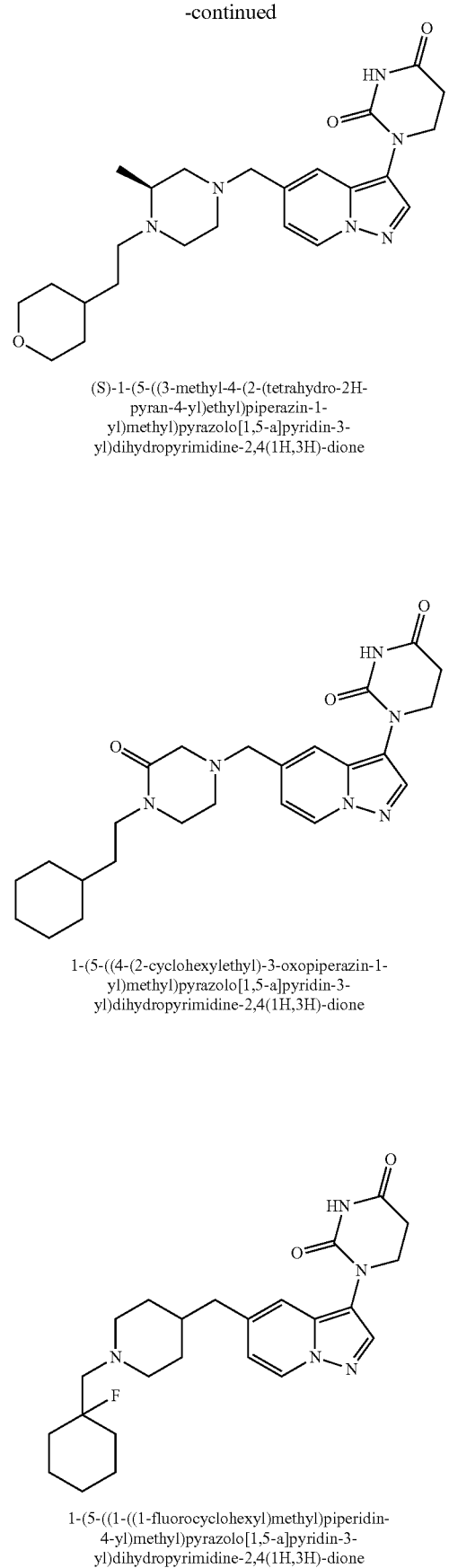

(S)-1-(5-((3-methyl-4-(2-(tetrahydro-2H-
pyran-4-yl)ethyl)piperazin-1-
yl)methyl)pyrazolo[1,5-a]pyridin-3-
yl)dihydropyrimidine-2,4(1H,3H)-dione 1-(5-((4-(2-cyclohexylethyl)-3-oxopiperazin-1-
yl)methyl)pyrazolo[1,5-a]pyridin-3-
yl)dihydropyrimidine-2,4(1H,3H)-dione 1-(5-((1-((1-fluorocyclohexyl)methyl)piperidin-
4-yl)methyl)pyrazolo[1,5-a]pyridin-3-
yl)dihydropyrimidine-2,4(1H,3H)-dione 75
-continued

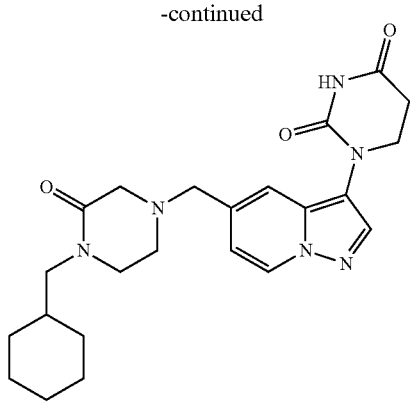

1-(5-((4-(cyclohexylmethyl)-3-oxopiperazin-1-
yl)methyl)pyrazolo[1,5-a]pyridin-3-
yl)dihydropyrimidine-2,4(1H,3H)-dione

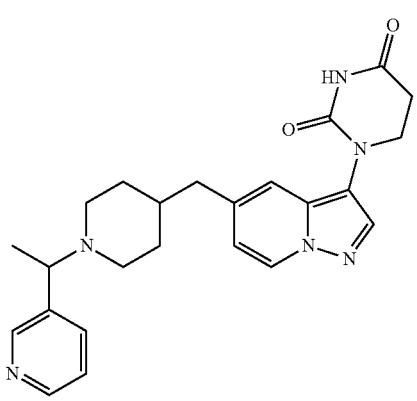

1-(5-((1-(1-(pyridin-3-yl)ethyl)piperidin-4-
yl)methyl)pyrazolo[1,5-a]pyridin-3-
yl)dihydropyrimidine-2,4(1H,3H)-dione

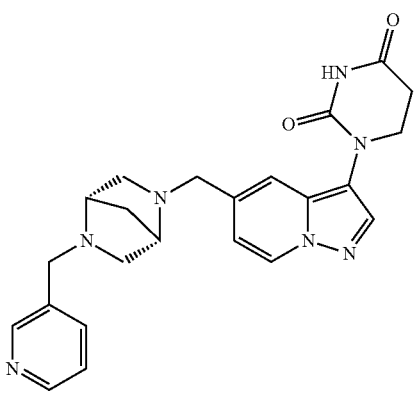

1-(5-(((1S,4S)-5-(pyridin-3-ylmethyl)-2,5-
diazabicyclo[2.2.1]heptan-2-
yl)methyl)pyrazolo[1,5-a]pyridin-3-
yl)dihydropyrimidine-2,4(1H,3H)-dione 76
-continued

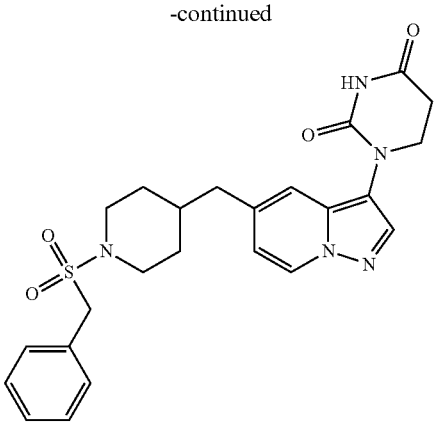

1-(5-((1-(benzylsulfonyl)piperidin-4-
yl)methyl)pyrazolo[1,5-a]pyridin-3-
yl)dihydropyrimidine-2,4(1H,3H)-dione

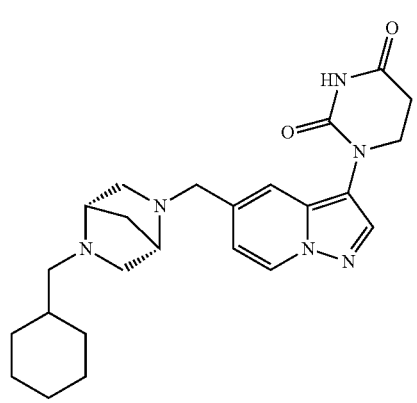

1-(5-(((1S,4S)-5-(cyclohexylmethyl)-2,5-
diazabicyclo[2.2.1]heptan-2-
yl)methyl)pyrazolo[1,5-a]pyridin-3-
yl)dihydropyrimidine-2,4(1H,3H)-dione

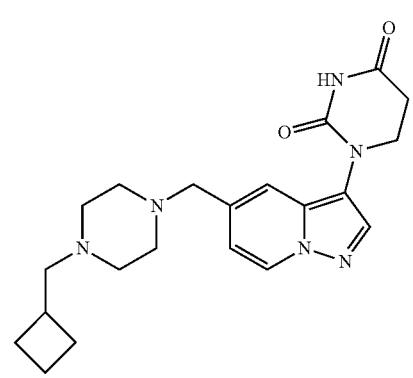

1-(5-((4-(cyclobutylmethyl)piperazin-1-
yl)methyl)pyrazolo[1,5-a]pyridin-3-
yl)dihydropyrimidine-2,4(1H,3H)-dione

77

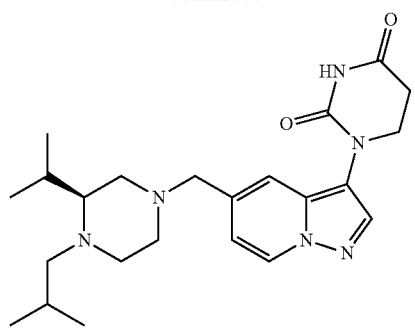

(S)-1-(5-((4-isobutyl-3-isopropylpiperazin-1-
yl)methyl)pyrazolo[1,5-a]pyridin-3-
yl)dihydropyrimidine-2,4(1H,3H)-dione

78

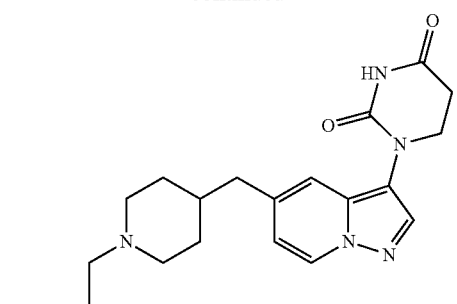

1-(5-((1-(3-fluorobenzyl)piperidin-4-
yl)methyl)pyrazolo[1,5-a]pyridin-3-
yl)dihydropyrimidine-2,4(1H,3H)-dione

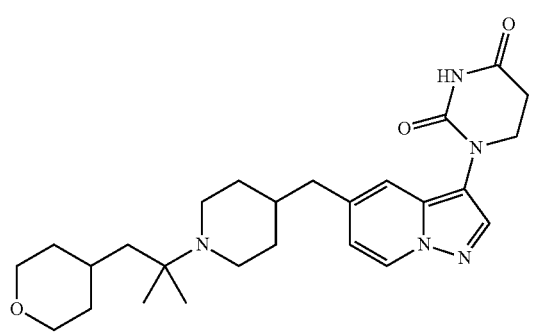

1-(5-((1-(2-methyl-1-(tetrahydro-2H-pyran-4-
yl)propan-2-yl)piperidin-4-
yl)methyl)pyrazolo[1,5-a]pyridin-3-
yl)dihydropyrimidine-2,4(1H,3H)-dione

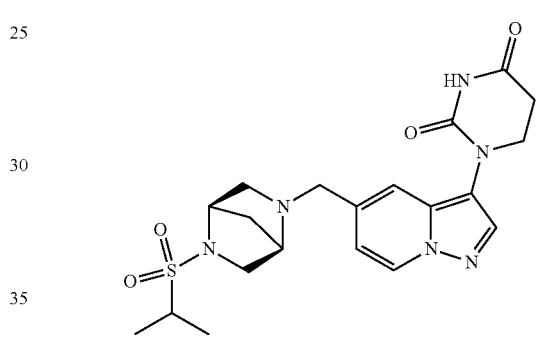

1-(5-((((1R,4R)-5-(isopropylsulfonyl)-2,5-
diazabicyclo[2.2.1]heptan-2-
yl)methyl)pyrazolo[1,5-a]pyridin-3-
yl)dihydropyrimidine-2,4(1H,3H)-dione

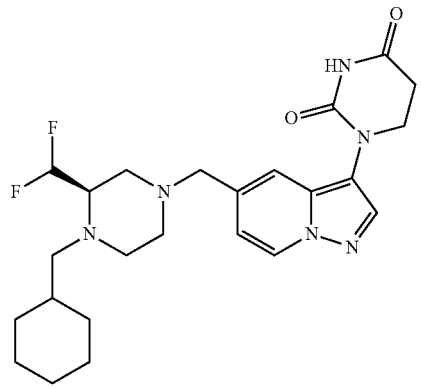

(R)-1-(5-((4-(cyclohexylmethyl)-3-
(difluoromethyl)piperazin-1-
yl)methyl)pyrazolo[1,5-a]pyridin-3-
yl)dihydropyrimidine-2,4(1H,3H)-dione

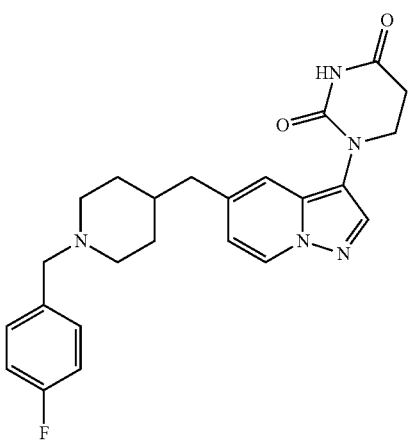

1-(5-((1-(4-fluorobenzyl)piperidin-4-
yl)methyl)pyrazolo[1,5-a]pyridin-3-
yl)dihydropyrimidine-2,4(1H,3H)-dione

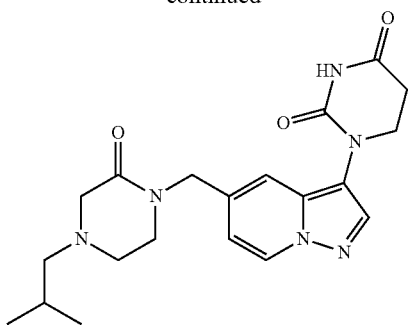

1-(5-((4-isobutyl-2-oxopiperazin-1-
yl)methyl)pyrazolo[1,5-a]pyridin-3-
yl)dihydropyrimidine-2,4(1H,3H)-dione

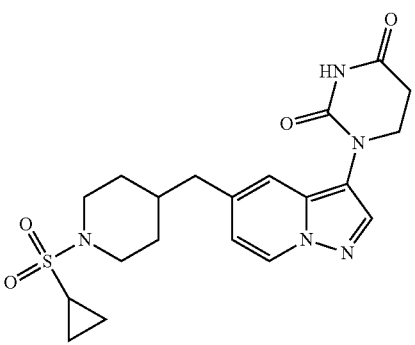

1-(5-((1-(cyclopropylsulfonyl)piperidin-4-
yl)methyl)pyrazolo[1,5-a]pyridin-3-
yl)dihydropyrimidine-2,4(1H,3H)-dione

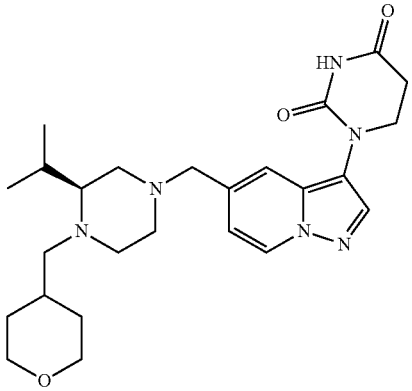

(S)-1-(5-((3-isopropyl-4-((tetrahydro-2H-
pyran-4-yl)methyl)piperazin-1-
yl)methyl)pyrazolo[1,5-a]pyridin-3-
yl)dihydropyrimidine-2,4(1H,3H)-dione

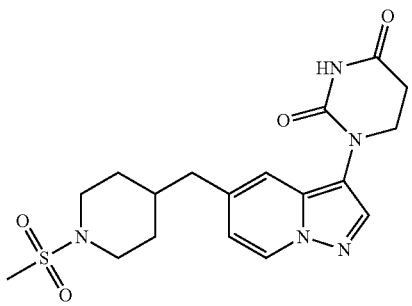

1-(5-((1-(methylsulfonyl)piperidin-4-
yl)methyl)pyrazolo[1,5-a]pyridin-3-
yl)dihydropyrimidine-2,4(1H,3H)-dione

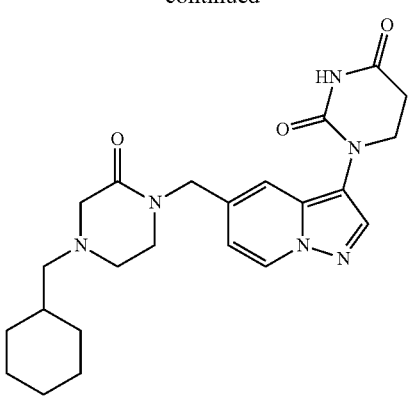

1-(5-((4-(cyclohexylmethyl)-2-oxopiperazin-1-
yl)methyl)pyrazolo[1,5-a]pyridin-3-
yl)dihydropyrimidine-2,4(1H,3H)-dione

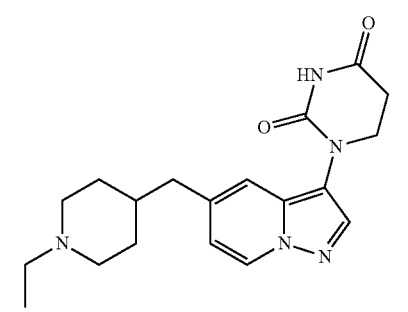

1-(5-((1-ethylpiperidin-4-
yl)methyl)pyrazolo[1,5-a]pyridin-3-
yl)dihydropyrimidine-2,4(1H,3H)-dione

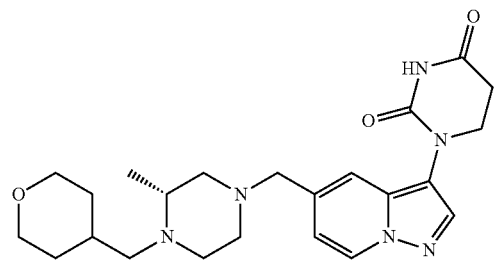

(R)-1-(5-((3-methyl-4-((tetrahydro-2H-pyran-
4-yl)methyl)piperazin-1-
yl)methyl)pyrazolo[1,5-a]pyridin-3-
yl)dihydropyrimidine-2,4(1H,3H)-dione

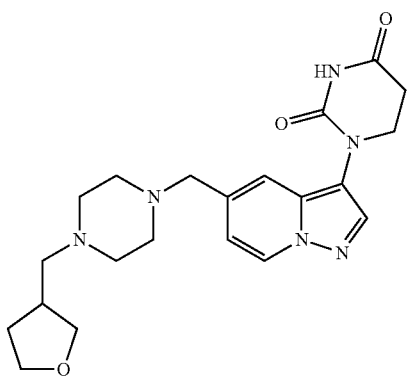

1-(5-((4-((tetrahydrofuran-3-
yl)methyl)piperazin-1-yl)methyl)pyrazolo[1,5-
a]pyridin-3-yl)dihydropyrimidine-2,4(1H,3H)-dione

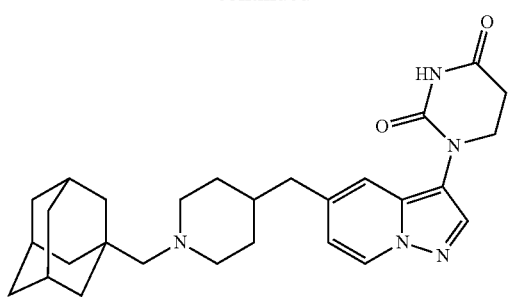

1-(5-((1-(((3r,5r,7r)-adamantan-1-yl)methyl)piperidin-4-yl)methyl)pyrazolo[1,5-a]pyridin-3-yl)dihydropyrimidine-2,4(1H,3H)-dione

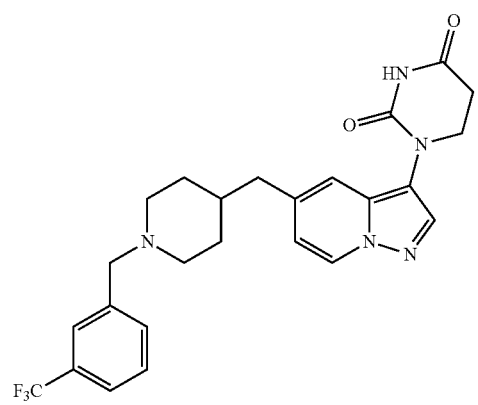

1-(5-((1-(3-(trifluoromethyl)benzyl)piperidin-4-yl)methyl)pyrazolo[1,5-a]pyridin-3-yl)dihydropyrimidine-2,4(1H,3H)-dione

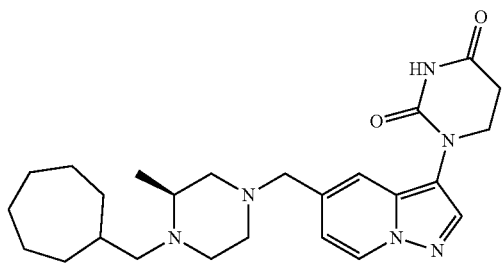

(S)-1-(5-((4-(cycloheptylmethyl)-3-methylpiperazin-1-yl)methyl)pyrazolo[1,5-a]pyridin-3-yl)dihydropyrimidine-2,4(1H,3H)-dione

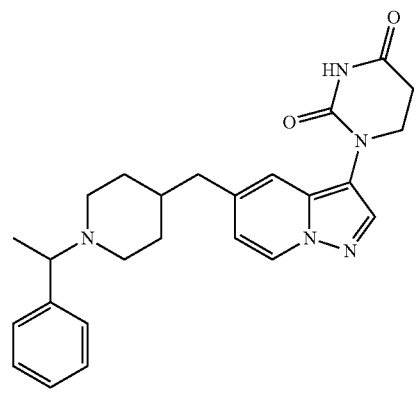

1-(5-((1-(1-phenylethyl)piperidin-4-yl)methyl)pyrazolo[1,5-a]pyridin-3-yl)dihydropyrimidine-2,4(1H,3H)-dione

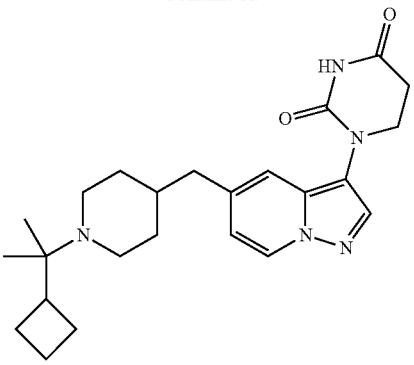

1-(5-((1-(2-cyclobutylpropan-2-yl)piperidin-4-yl)methyl)pyrazolo[1,5-a]pyridin-3-yl)dihydropyrimidine-2,4(1H,3H)-dione

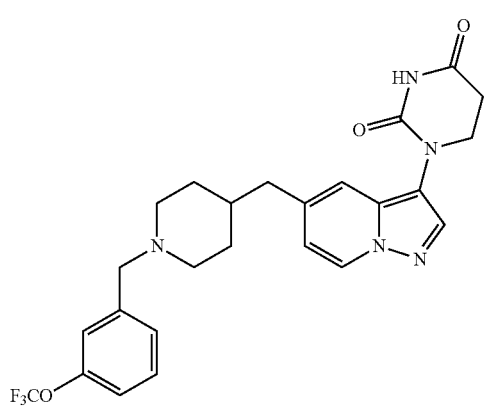

1-(5-((1-(3-(trifluoromethoxy)benzyl)piperidin-4-yl)methyl)pyrazolo[1,5-a]pyridin-3-yl)dihydropyrimidine-2,4(1H,3H)-dione

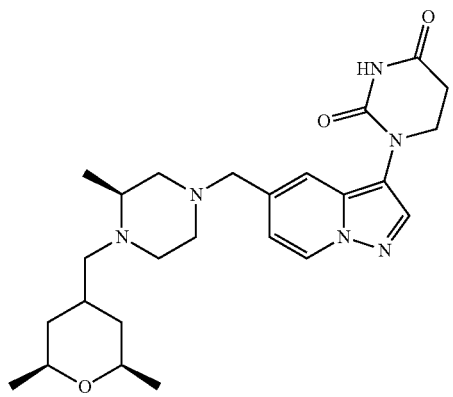

1-(5-(((3S)-4-(((2R,6S)-2,6-dimethyltetrahydro-2H-pyran-4-yl)methyl)-3-methylpiperazin-1-yl)methyl)pyrazolo[1,5-a]pyridin-3-yl)dihydropyrimidine-2,4(1H,3H)-dione

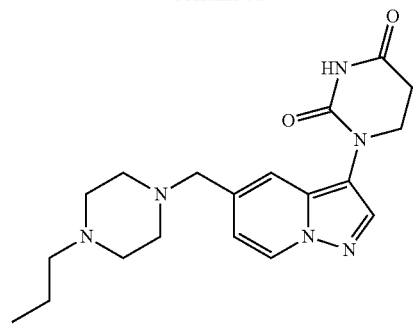

1-(5-((4-propylpiperazin-1-yl)methyl)pyrazolo[1,5-a]pyridin-3-yl)dihydropyrimidine-2,4(1H,3H)-dione

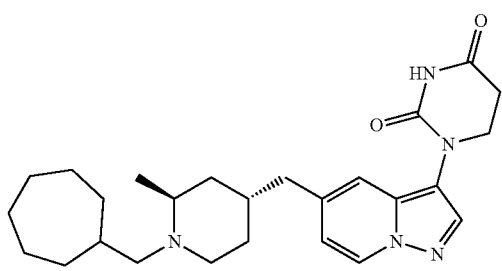

1-(5-(((2S,4R)-1-(cycloheptylmethyl)-2-methylpiperidin-4-yl)methyl)pyrazolo[1,5-a]pyridin-3-yl)dihydropyrimidine-2,4(1H,3H)-dione

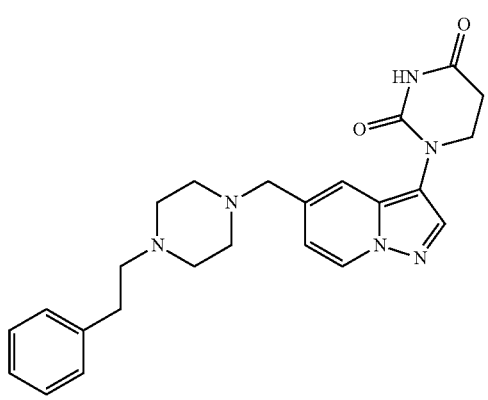

1-(5-((4-phenethylpiperazin-1-yl)methyl)pyrazolo[1,5-a]pyridin-3-yl)dihydropyrimidine-2,4(1H,3H)-dione

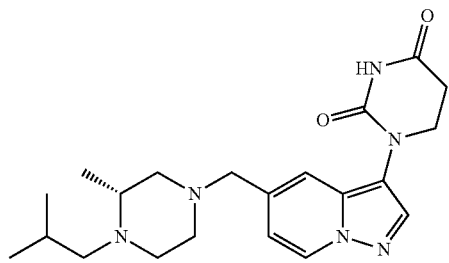

(R)-1-(5-((4-isobutyl-3-methylpiperazin-1-yl)methyl)pyrazolo[1,5-a]pyridin-3-yl)dihydropyrimidine-2,4(1H,3H)-dione

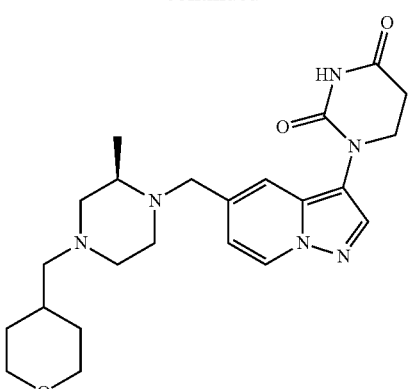

(R)-1-(5-((2-methyl-4-((tetrahydro-2H-pyran-4-yl)methyl)piperazin-1-yl)methyl)pyrazolo[1,5-a]pyridin-3-yl)dihydropyrimidine-2,4(1H,3H)-dione

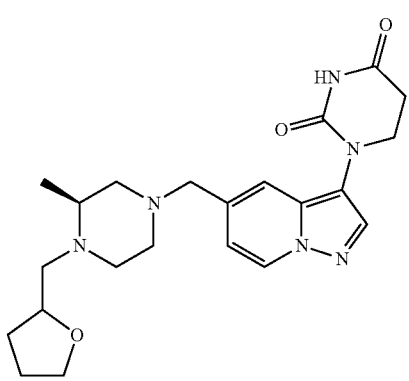

1-(5-(((3S)-3-methyl-4-((tetrahydrofuran-2-yl)methyl)piperazin-1-yl)methyl)pyrazolo[1,5-a]pyridin-3-yl)dihydropyrimidine-2,4(1H,3H)-dione

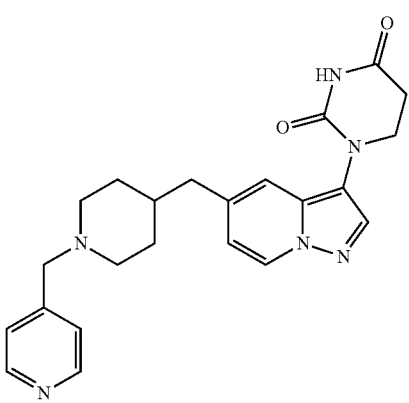

1-(5-((1-(pyridin-4-ylmethyl)piperidin-4-yl)methyl)pyrazolo[1,5-a]pyridin-3-yl)dihydropyrimidine-2,4(1H,3H)-dione -continued

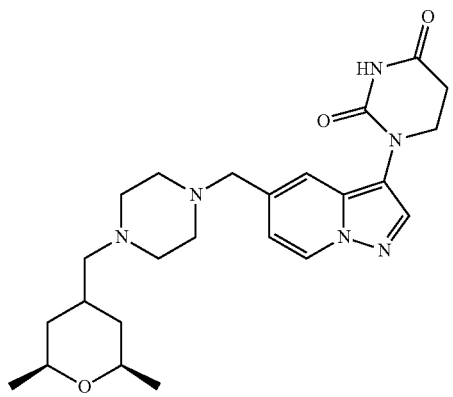

1-(5-(((4-(((2R,6S)-2,6-dimethyltetrahydro-2H-pyran-4-yl)methyl)piperazin-1-yl)methyl)pyrazolo[1,5-a]pyridin-3-yl)dihydropyrimidine-2,4(1H,3H)-dione

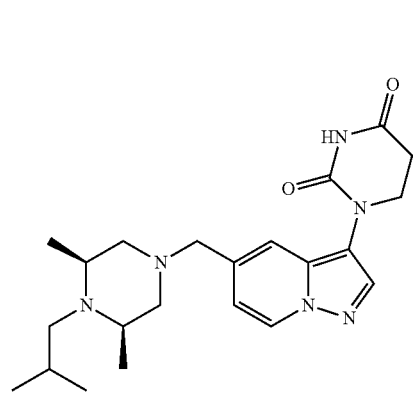

1-(5-(((3S,5R)-4-isobutyl-3,5-dimethylpiperazin-1-yl)methyl)pyrazolo[1,5-a]pyridin-3-yl)dihydropyrimidine-2,4(1H,3H)-dione

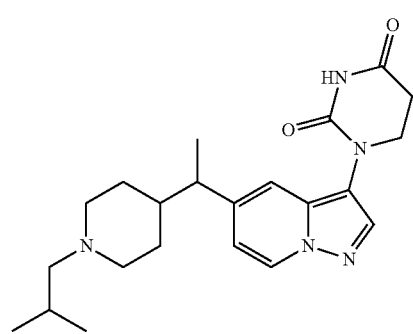

1-(5-(1-(1-isobutylpiperidin-4-yl)ethyl)pyrazolo[1,5-a]pyridin-3-yl)dihydropyrimidine-2,4(1H,3H)-dione -continued

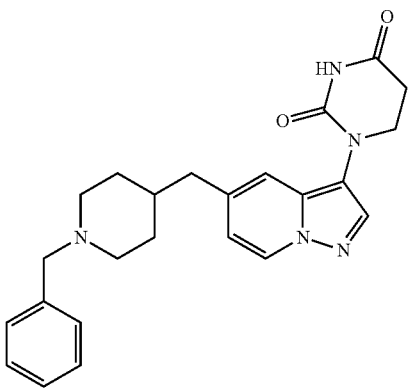

1-(5-((1-benzylpiperidin-4-yl)methyl)pyrazolo[1,5-a]pyridin-3-yl)dihydropyrimidine-2,4(1H,3H)-dione

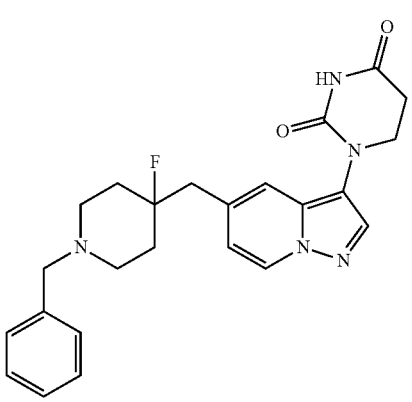

1-(5-((1-benzyl-4-fluoropiperidin-4-yl)methyl)pyrazolo[1,5-a]pyridin-3-yl)dihydropyrimidine-2,4(1H,3H)-dione

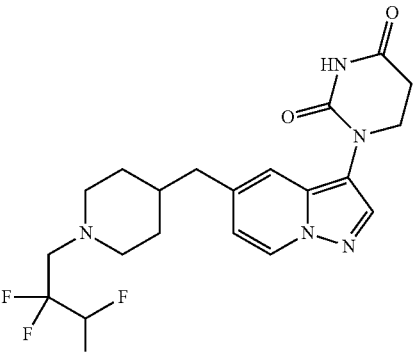

1-(5-((1-(2,2,3,3-tetrafluoropropyl)piperidin-4-yl)methyl)pyrazolo[1,5-a]pyridin-3-yl)dihydropyrimidine-2,4(1H,3H)-dione

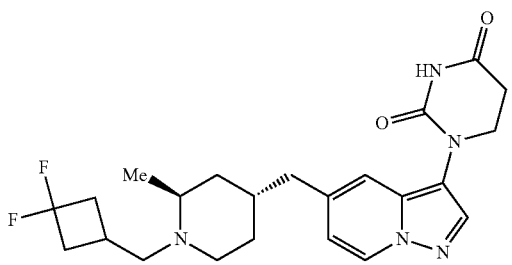

1-(5-(((2S,4R)-1-((3,3-difluorocyclobutyl)methyl)-2-methylpiperidin-4-yl)methyl)pyrazolo[1,5-a]pyridin-3-yl)dihydropyrimidine-2,4(1H,3H)-dione

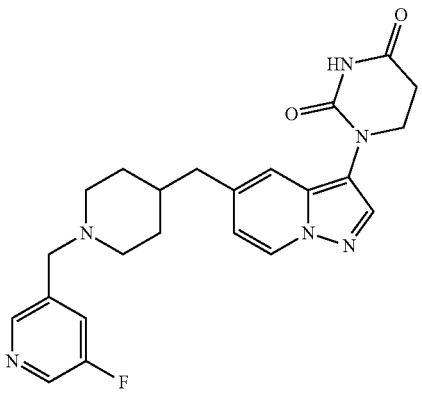

1-(5-((1-((5-fluoropyridin-3-yl)methyl)piperidin-4-yl)methyl)pyrazolo[1,5-a]pyridin-3-yl)dihydropyrimidine-2,4(1H,3H)-dione

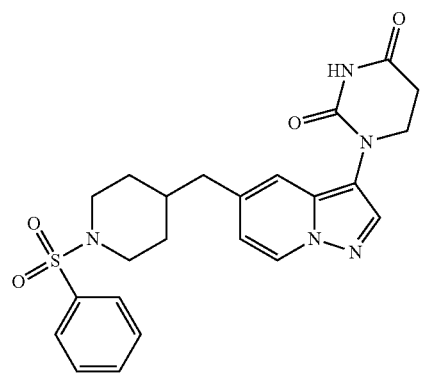

1-(5-((1-(phenylsulfonyl)piperidin-4-yl)methyl)pyrazolo[1,5-a]pyridin-3-yl)dihydropyrimidine-2,4(1H,3H)-dione

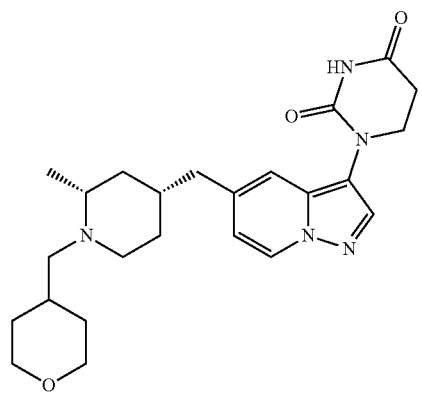

1-(5-(((2R,4R)-2-methyl-1-((tetrahydro-2H-pyran-4-yl)methyl)piperidin-4-yl)methyl)pyrazolo[1,5-a]pyridin-3-yl)dihydropyrimidine-2,4(1H,3H)-dione

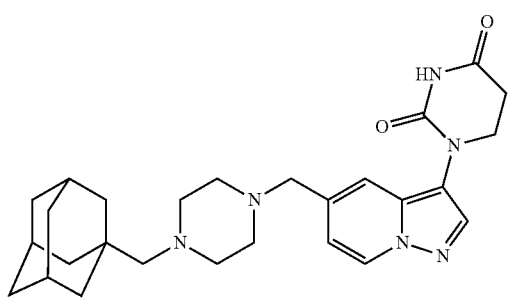

1-(5-((4-(((3r,5r,7r)-adamantan-1-yl)methyl)piperazin-1-yl)methyl)pyrazolo[1,5-a]pyridin-3-yl)dihydropyrimidine-2,4(1H,3H)-dione

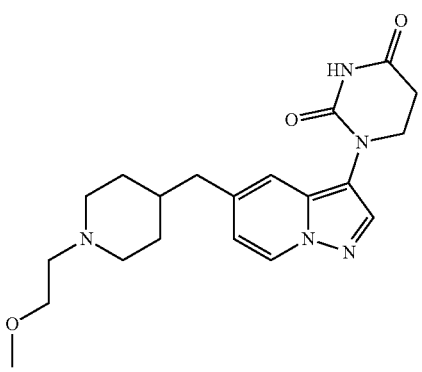

1-(5-((1-(2-methoxyethyl)piperidin-4-yl)methyl)pyrazolo[1,5-a]pyridin-3-yl)dihydropyrimidine-2,4(1H,3H)-dione -continued

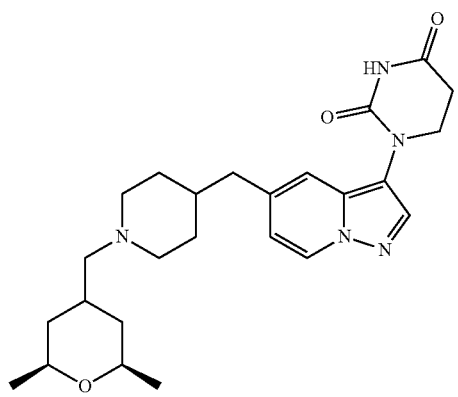

1-(5-(((2R,6S)-2,6-dimethyltetrahydro-2H-pyran-4-yl)methyl)piperidin-4-yl)methyl)pyrazolo[1,5-a]pyridin-3-yl)dihydropyrimidine-2,4(1H,3H)-dione

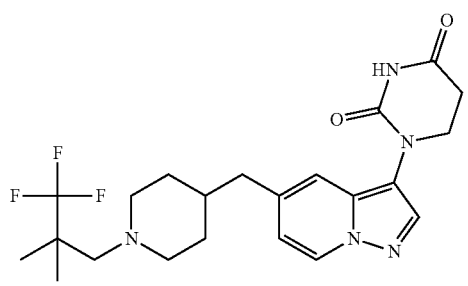

1-(5-((1-(3,3,3-trifluoro-2,2-dimethylpropyl)piperidin-4-yl)methyl)pyrazolo[1,5-a]pyridin-3-yl)dihydropyrimidine-2,4(1H,3H)-dione

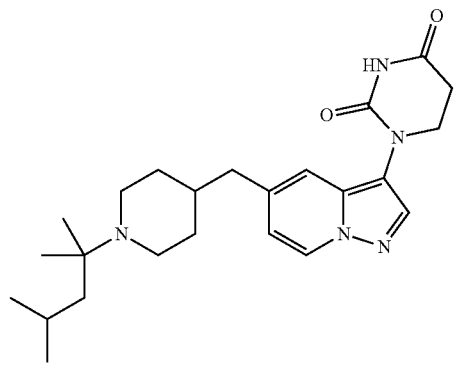

1-(5-((1-(2,4-dimethylpentan-2-yl)piperidin-4-yl)methyl)pyrazolo[1,5-a]pyridin-3-yl)dihydropyrimidine-2,4(1H,3H)-dione

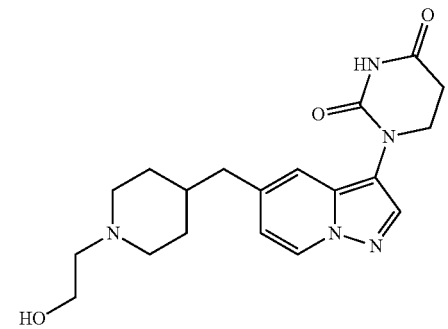

1-(5-((1-(2-hydroxyethyl)piperidin-4-yl)methyl)pyrazolo[1,5-a]pyridin-3-yl)dihydropyrimidine-2,4(1H,3H)-dione -continued

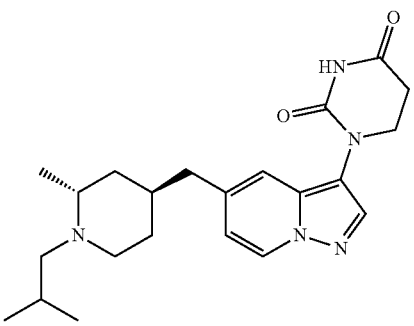

1-(5-(((2R,4S)-1-isobutyl-2-methylpiperidin-4-yl)methyl)pyrazolo[1,5-a]pyridin-3-yl)dihydropyrimidine-2,4(1H,3H)-dione

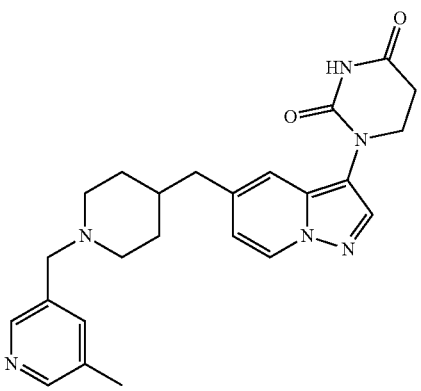

1-(5-((1-((5-methylpyridin-3-yl)methyl)piperidin-4-yl)methyl)pyrazolo[1,5-a]pyridin-3-yl)dihydropyrimidine-2,4(1H,3H)-dione

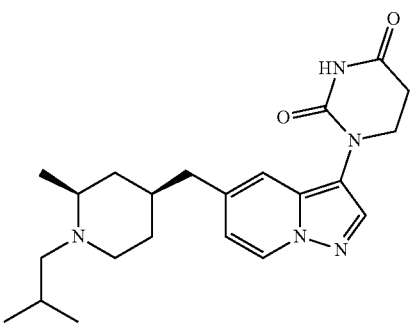

1-(5-(((2S,4S)-1-isobutyl-2-methylpiperidin-4-yl)methyl)pyrazolo[1,5-a]pyridin-3-yl)dihydropyrimidine-2,4(1H,3H)-dione

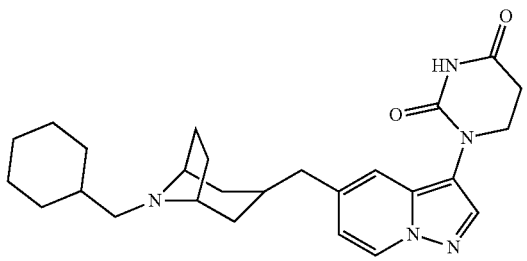

1-(5-((((1R,5S)-8-(cyclohexylmethyl)-8-azabicyclo[3.2.1]octan-3-yl)methyl)pyrazolo[1,5-a]pyridin-3-yl)dihydropyrimidine-2,4(1H,3H)-dione

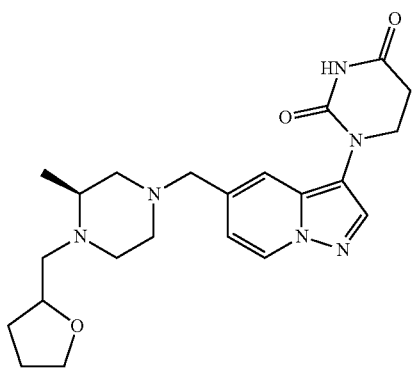

1-(5-(((3S)-3-methyl-4-((tetrahydrofuran-2-yl)methyl)piperazin-1-yl)methyl)pyrazolo[1,5-a]pyridin-3-yl)dihydropyrimidine-2,4(1H,3H)-dione

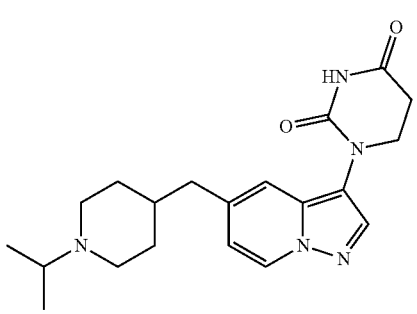

1-(5-((1-isopropylpiperidin-4-yl)methyl)pyrazolo[1,5-a]pyridin-3-yl)dihydropyrimidine-2,4(1H,3H)-dione

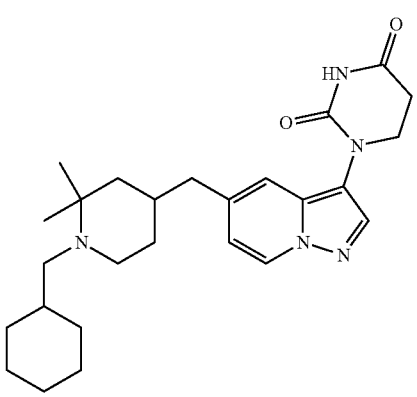

1-(5-((4-cyclohexylmethyl)-3,3-dimethylpiperazin-1-yl)methyl)pyrazolo[1,5-a]pyridin-3-yl)dihydropyrimidine-2,4(1H,3H)-dione

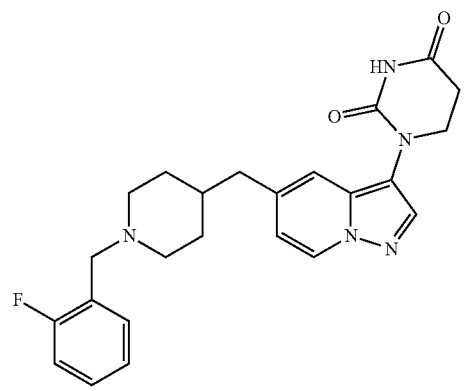

1-(5-((1-(2-fluorobenzyl)piperidin-4-yl)methyl)pyrazolo[1,5-a]pyridin-3-yl)dihydropyrimidine-2,4(1H,3H)-dione

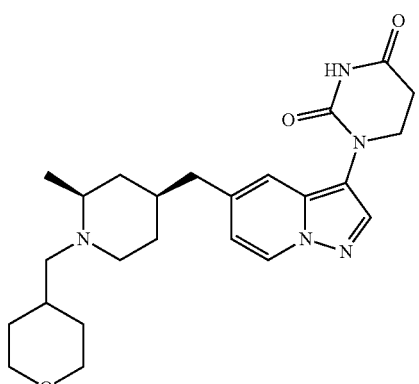

1-(5-(((2S,4S)-2-methyl-1-((tetrahydro-2H-pyran-4-yl)methyl)piperidin-4-yl)methyl)pyrazolo[1,5-a]pyridin-3-yl)dihydropyrimidine-2,4(1H,3H)-dione

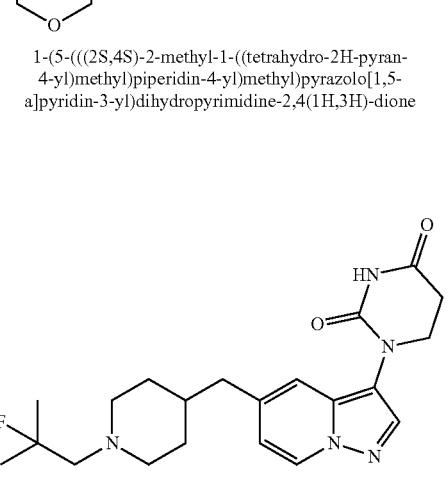

1-(5-((1-(2-fluoro-2-methylpropyl)piperidin-4-yl)methyl)pyrazolo[1,5-a]pyridin-3-yl)dihydropyrimidine-2,4(1H,3H)-dione

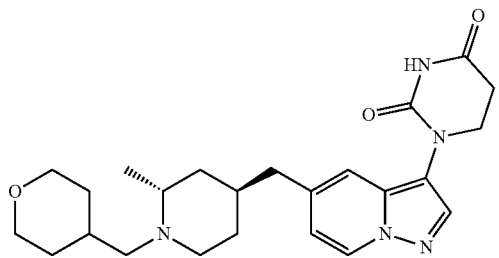

1-(5-(((2R,4S)-2-methyl-1-((tetrahydro-2H-pyran-4-yl)methyl)piperidin-4-yl)methyl)pyrazolo[1,5-a]pyridin-3-yl)dihydropyrimidine-2,4(1H,3H)-dione

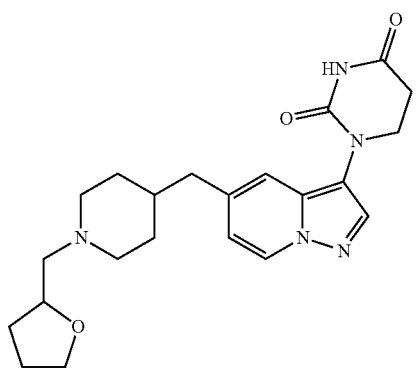

1-(5-((1-((tetrahydrofuran-2-yl)methyl)piperidin-
4-yl)methyl)pyrazolo[1,5-a]pyridin-
3-yl)dihydropyrimidine-2,4(1H,3H)-dione

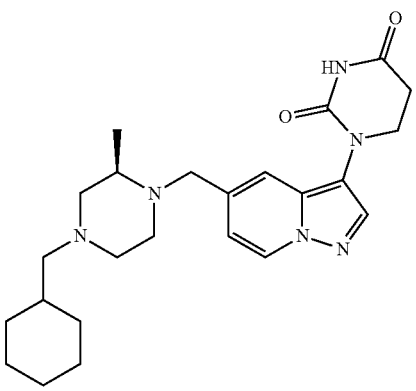

(R)-1-(5-((4-(cyclohexylmethyl)-2-methylpiperazin-1-
yl)methyl)pyrazolo[1,5-a]pyridin-3-yl)dihydropyrimidine-
2,4(1H,3H)-dione

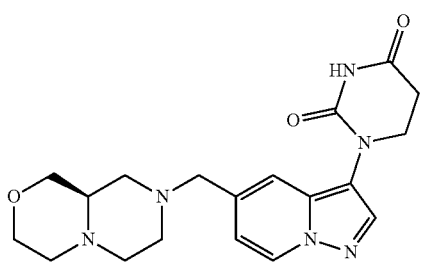

(R)-1-(5-((hexahydropyrazino[2,1-c][1,4]oxazin-
8(1H)-yl)methyl)pyrazolo[1,5-a]pyridin-3-
yl)dihydropyrimidine-2,4(1H,3H)-dione

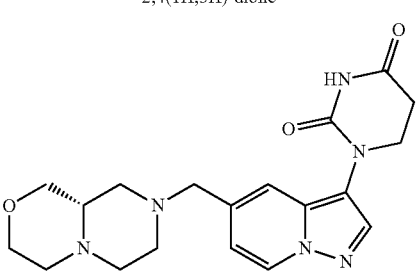

(S)-1-(5-((hexahydropyrazino[2,1-c][1,4]oxazin-
8(1H)-yl)methyl)pyrazolo[1,5-a]pyridin-3-
yl)dihydropyrimidine-2,4(1H,3H)-dione

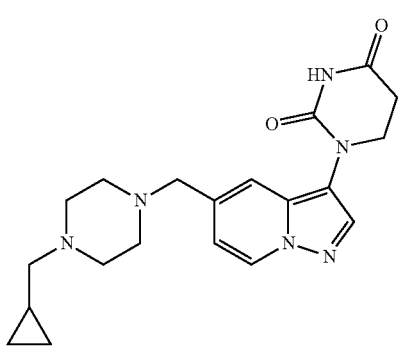

1-(5-((4-(cyclopropylmethyl)piperazin-1-
yl)methyl)pyrazolo[1,5-a]pyridin-3-
yl)dihydropyrimidine-2,4(1H,3H)-dione

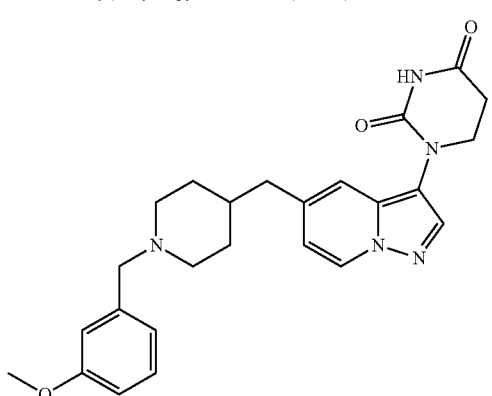

1-(5-((1-(3-methoxybenzyl)piperidin-4-
yl)methyl)pyrazolo[1,5-a]pyridin-3-
yl)dihydropyrimidine-2,4(1H,3H)-dione

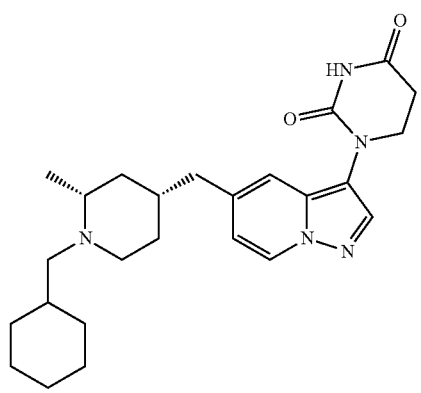

1-(5-(((2R,4R)-1-(cyclohexylmethyl)-2-methylpiperidin-4-
yl)methyl)pyrazolo[1,5-a]pyridin-3-yl)dihydropyrimidine-
2,4(1H,3H)-dione

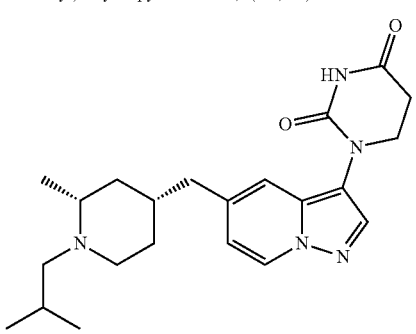

1-(5-(((2R,4R)-1-isobutyl-2-methylpiperidin-4-
yl)methyl)pyrazolo[1,5-a]pyridin-3-
yl)dihydropyrimidine-2,4(1H,3H)-dione

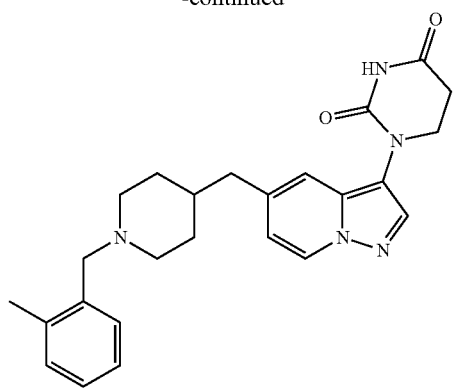

1-(5-((1-(2-methylbenzyl)piperidin-4-yl)methyl)pyrazolo[1,5-a]pyridin-3-yl)dihydropyrimidine-2,4(1H,3H)-dione

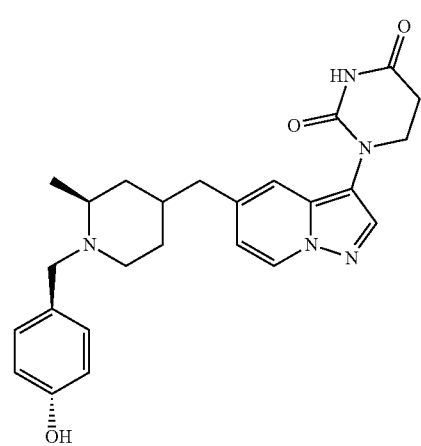

1-(5-(((S)-4-(((1r,4S)-4-hydroxycyclohexyl)methyl)-3-methylpiperzin-1-yl)methyl)pyrazolo[1,5-a]pyridin-3-yl)dihydropyrimidine-2,4(1H,3H)-dione

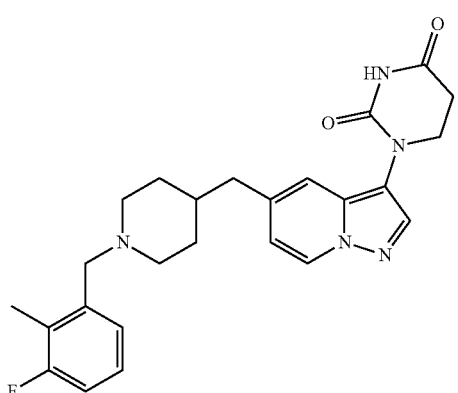

1-(5-((1-(3-fluoro-2-methylbenzyl)piperidin-4-yl)methyl)pyrazolo[1,5-a]pyridin-3-yl)dihydropyrimidine-2,4(1H,3H)-dione

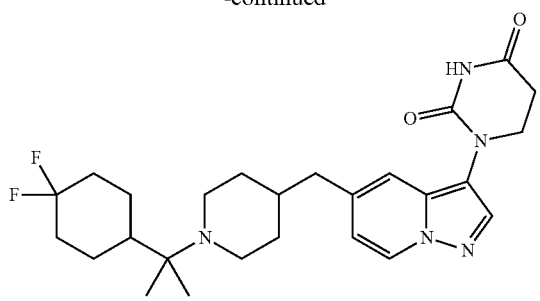

1-(5-((1-(2-(4,4-difluorocyclohexyl)propan-2-yl)piperidin-4-yl)methyl)pyrazolo[1,5-a]pyridin-3-yl)dihydropyrimidine-2,4(1H,3H)-dione

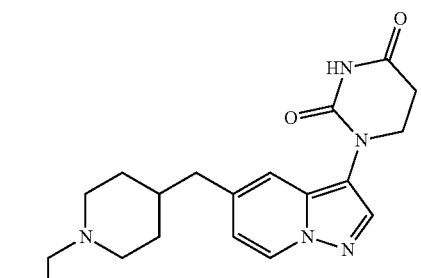

1-(5-((1-(2,2-difluoroethyl)piperidin-4-yl)methyl)pyrazolo[1,5-a]pyridin-3-yl)dihydropyrimidine-2,4(1H,3H)-dione

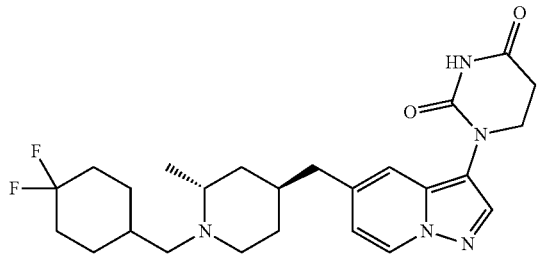

1(5-(((2R,4S)-1-((4,4-difluorocyclohexyl)methyl)-2-methylpiperidin-4-yl)methyl)pyrazolo[1,5-a]pyridin-3-yl)dihydropyrimidine-2,4(1H,3H)-dione

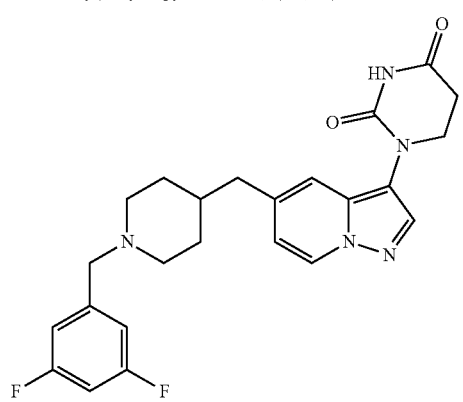

1-(5-((1-(3,5-difluorobenzyl)piperidin-4-yl)methyl)pyrazolo[1,5-a]pyridin-3-yl)dihydropyrimidine-2,4(1H,3H)-dione 97
-continued

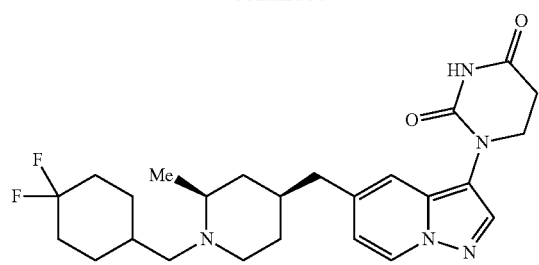

1(5-(((2S,4S)-1-((4,4-difluorocyclohexyl)methyl)-2-
methylpiperidin-4-yl)methyl)pyrazolo[1,5-a]pyridin-3-
yl)dihydropyrimidine-2,4(1H,3H)-dione

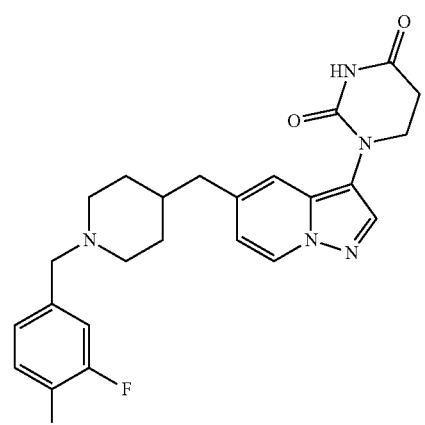

1-(5-((1-(3,4-difluorobenzyl)piperidin-4-
yl)methyl)pyrazolo[1,5-a]pyridin-3-
yl)dihydropyrimidine-2,4(1H,3H)-dione

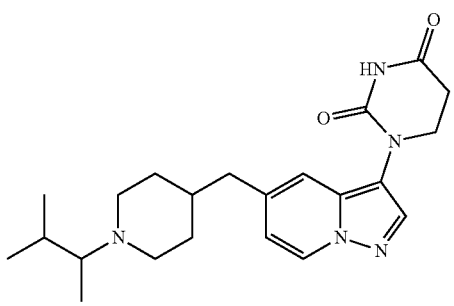

1-(5-((1-(3-methylbutan-2-yl)piperidin-4-
yl)methyl)pyrazolo[1,5-a]pyridin-3-
yl)dihydropyrimidine-2,4(1H,3H)-dione

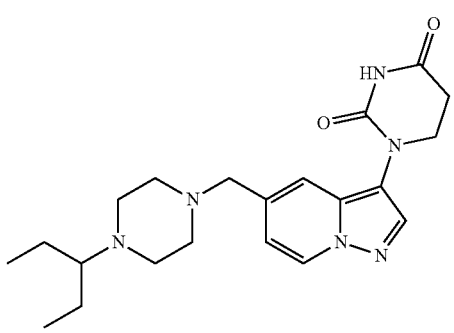

1-(5-((4-(pentan-3-yl)piperazin-1-
yl)methyl)pyrazolo[1,5-a]pyridin-3-
yl)dihydropyrimidine-2,4(1H,3H)-dione 98
-continued

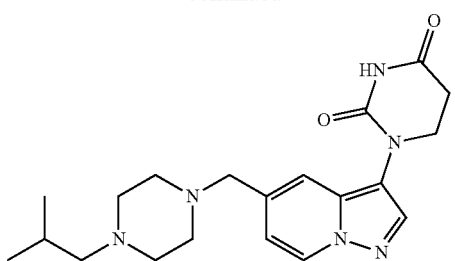

1-(5-((4-(3-methylbutan-2-yl)piperazin-1-
yl)methyl)pyrazolo[1,5-a]pyridin-3-
yl)dihydropyrimidine-2,4(1H,3H)-dione

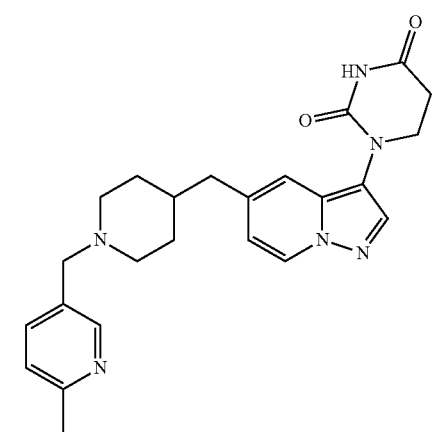

1-(5-((1-((6-methylpyridin-3-yl)methyl)piperidin-
4-yl)methyl)pyrazolo[1,5-a]pyridin-3-
yl)dihydropyrimidine-2,4(1H,3H)-dione

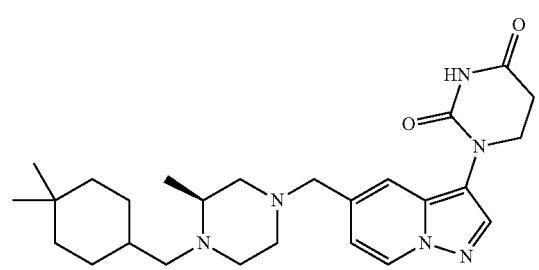

(S)-1-(5-((4-((4,4-dimethylcyclohexyl)methyl)-3-
methylpiperazin-1-yl)methyl)pyrazolo[1,5-a]pyridin-3-
yl)dihydropyrimidine-2,4(1H,3H)-dione

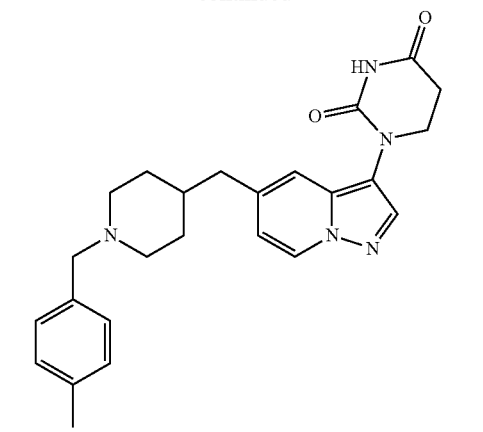

1-(5-((1-(4-methylbenzyl)piperidin-4-
yl)methyl)pyrazolo[1,5-a]pyridin-3-
yl)dihydropyrimidine-2,4(1H,3H)-dione

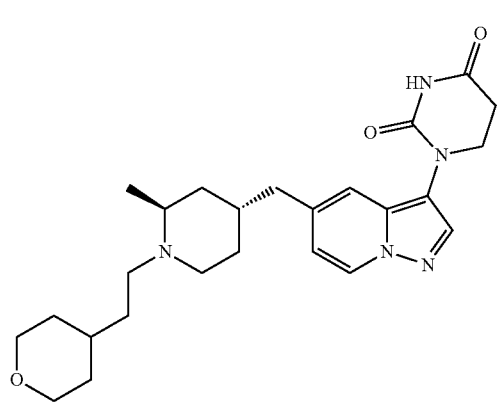

1(5-(((2S,4R)-2-methyl-1-(2-(tetrahydro-2H-pyran-4-
yl)ethyl)piperidin-4-yl)methyl)pyrazolo[1,5-a]pyridin-3-
yl)dihydropyrimidine-2,4(1H,3H)-dione

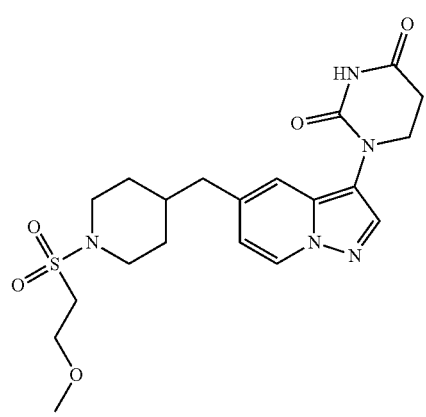

1-(5-((1-(2-methoxyethyl)sulfonyl)piperidin-4-
yl)methyl)pyrazolo[1,5-a]pyridin-3-
yl)dihydropyrimidine-2,4(1H,3H)-dione

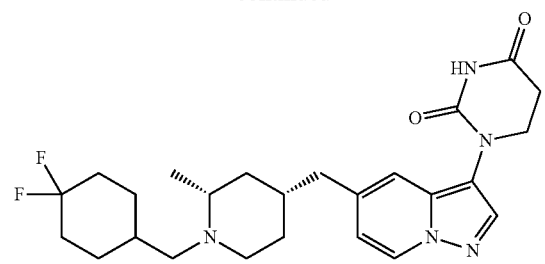

1(5-(((2S,4R)-1-((4,4-difluorocyclohexyl)methyl)-2-
methylpiperidin-4-yl)methyl)pyrazolo[1,5-a]pyridin-3-
yl)dihydropyrimidine-2,4(1H,3H)-dione

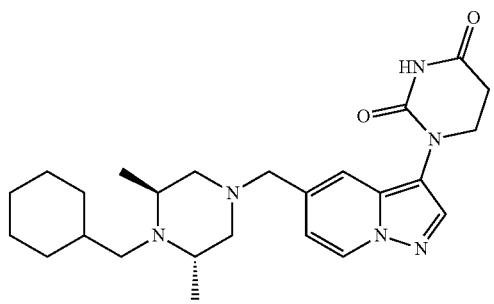

1-(5-(((3S,5S)-4-(cyclohexylmethyl)-3,5-dimethylpiperazin-
1-yl)methyl)pyrazolo[1,5-a]pyridin-3-yl)dihydropyrimidine-
2,4(1H,3H)-dione

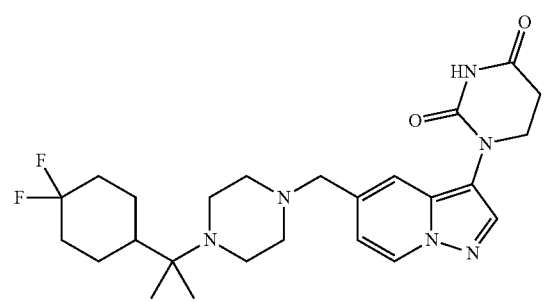

1-(5-((4-(2-(4,4-difluorocyclohexyl)propan-2-yl)piperazin-
1-yl)methyl)pyrazolo[1,5-a]pyridin-3-yl)dihydropyrimidine-
2,4(1H,3H)-dione

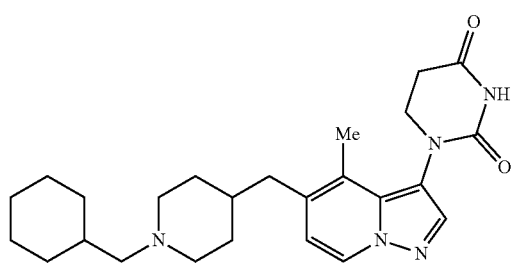

1-(5-((1-(cyclohexylmethyl)piperidin-4-
yl)methyl)-4-methylpyrazolo[1,5-a]pyridin-3-
yl)dihydropyrimidine-2,4(1H,3H)-dione

101

-continued

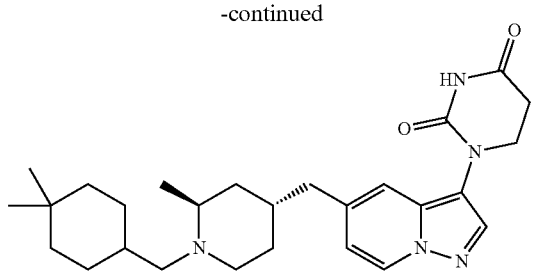

1-(5-(((2S,4R)-1-((4,4-dimethylcyclohexyl)methyl)-2-
methylpiperidin-4-yl)methyl)pyrazolo[1,5-a]pyridin-3-
yl)dihydropyrimidine-2,4(1H,3H)-dione

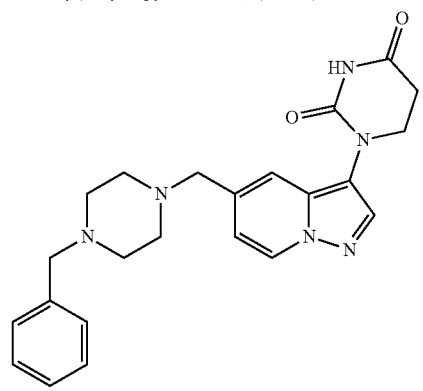

1-(5-((4-benzylpiperazin-1-
yl)methyl)pyrazolo[1,5-a]pyridin-3-
yl)dihydropyrimidine-2,4(1H,3H)-dione

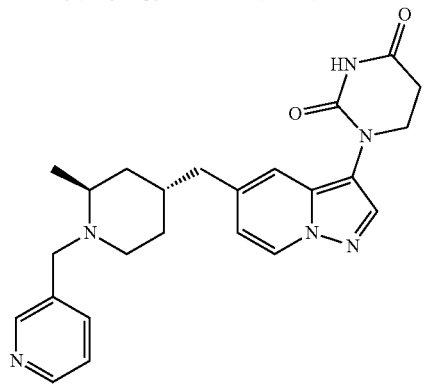

1-(5-(((2S,4R)-2-methyl-1-pyridin-3-
ylmethyl)piperidin-4-yl)methyl)pyrazolo[1,5-
a]pyridin-3-yl)dihydropyrimidine-2,4(1H,3H)-dione

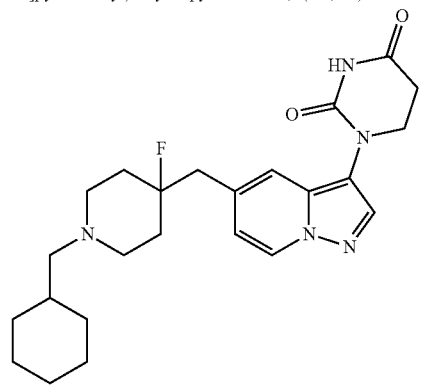

1-(5-((1-(cyclohexylmethyl)-4-fluoropiperidin-4-
yl)methyl)pyrazolo[1,5-a]pyridin-3-
yl)dihydropyrimidine-2,4(1H,3H)-dione

102

-continued

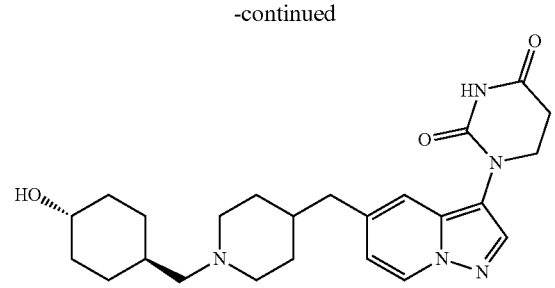

1-(5-((1-(((1r,4r)-4-hydroxycyclohexyl)methyl)piperidin-4-
yl)methyl)pyrazolo[1,5-a]pyridin-3-
yl)dihydropyrimidine-2,4(1H,3H)-dione

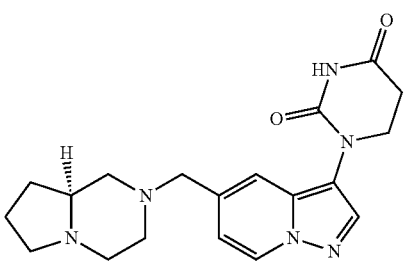

(S)-1-(5-((hexahydropyrrolo[1,2-a]pyrazin-
2(1H)-yl)methyl)pyrazolo[1,5-a]pyridin-3-
yl)dihydropyrimidine-2,4(1H,3H)-dione

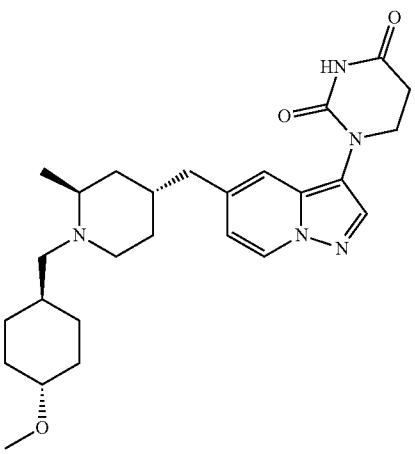

1-(5-(((2S,4R)-1-(((1r,4S)-4-methoxycyclohexyl)methyl)-2-
methylpiperidin-4-yl)methyl)pyrazolo[1,5-a]pyridin-3-
yl)dihydropyrimidine-2,4(1H,3H)-dione

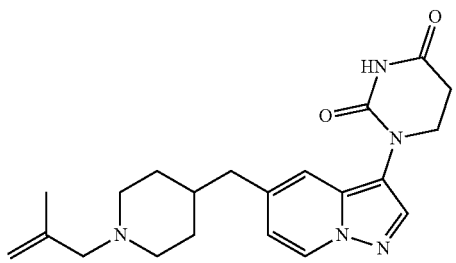

1-(5-((1-(2-methylallyl)piperidin-4-yl)methyl)pyrazolo[1,5-
a]pyridin-3-yl)dihydropyrimidine-2,4(1H,3H)-dione

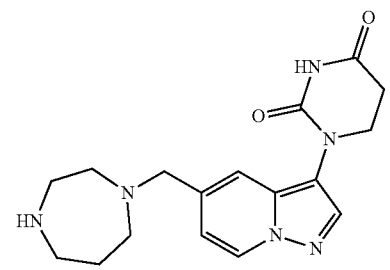

1-(5-((1,4-diazepan-1-yl)methyl)pyrazolo[1,5-a]pyridin-3-yl)dihydropyrimidine-2,4(1H,3H)-dione

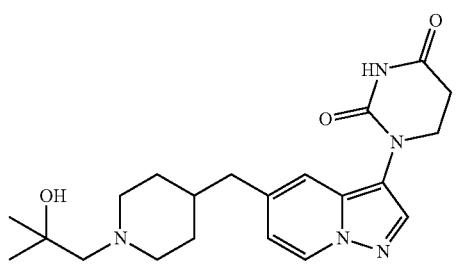

1-(5-((1-(2-hydroxy-2-methylpropyl)piperidin-4-yl)methyl)pyrazolo[1,5-a]pyridin-3-yl)dihydropyrimidine-2,4(1H,3H)-dione

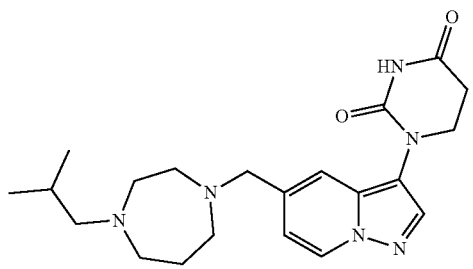

1-(5-((4-isobutyl-1,4-diazepan-1-yl)methyl)pyrazolo[1,5-a]pyridin-3-yl)dihydropyrimidine-2,4(1H,3H)-dione

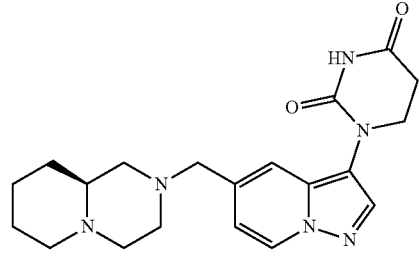

(S)-1-(5-((octahydro-2H-pyrido[1,2-a]pyrazin-2-yl)methyl)pyrazolo[1,5-a]pyridin-3-yl)dihydropyrimidine-2,4(1H,3H)-dione

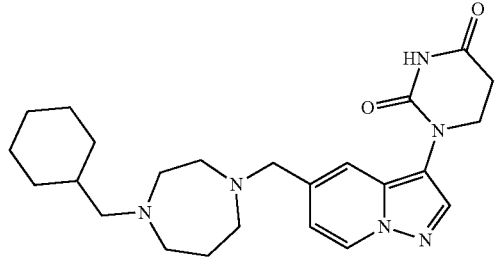

1-(5-((4-(cyclohexylmethyl)-1,4-diazepan-1-yl)methyl)pyrazolo[1,5-a]pyridin-3-yl)dihydropyrimidine-2,4(1H,3H)-dione

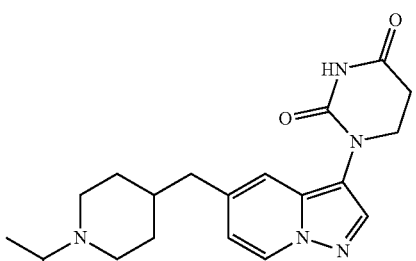

1-(5-((1-(1-(3-fluorophenyl)ethyl)piperidin-4-yl)methyl)pyrazolo[1,5-a]pyridin-3-yl)dihydropyrimidine-2,4(1H,3H)-dione

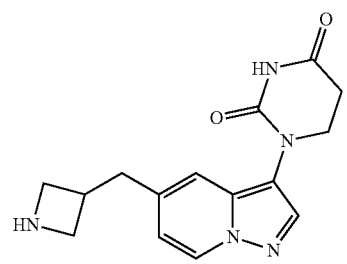

1-(5-(azetidin-3-ylmethyl)pyrazolo[1,5-a]pyridin-3-yl)dihydropyrimidine-2,4(1H,3H)-dione

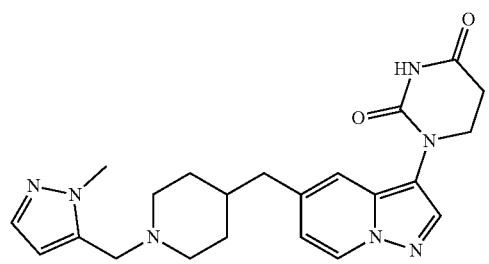

1-(5-((1-((1-methyl-1H-pyrazol-5-yl)methyl)piperidin-4-yl)methyl)pyrazolo[1,5-a]pyridin-3-yl)dihydropyrimidine-2,4(1H,3H)-dione

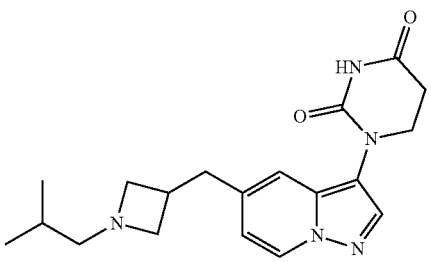

1-(5-((1-isobutylazetidin-3-yl)methyl)pyrazolo[1,5-a]pyridin-3-yl)dihydropyrimidine-2,4(1H,3H)-dione

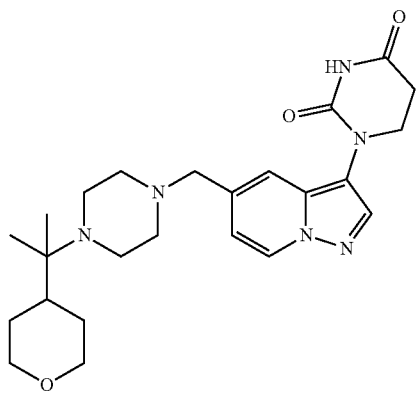

1-(5-((4-(2-(tetrahydro-2H-pyran-4-yl)propan-2-yl)piperazin-1-yl)methyl)pyrazolo[1,5-a]pyridin-3-yl)dihydropyrimidine-2,4(1H,3H)-dione

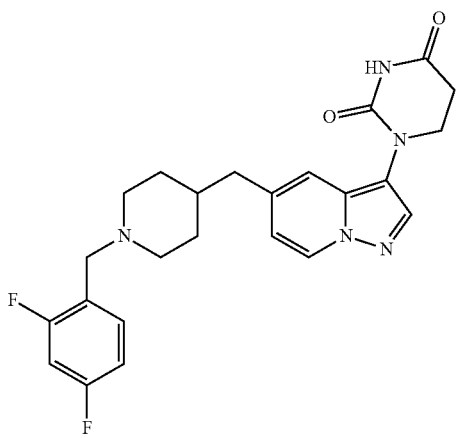

1-(5-((1-(2,4-difluorobenzyl)piperidin-4-yl)methyl)pyrazolo[1,5-a]pyridin-3-yl)dihydropyrimidine-2,4(1H,3H)-dione

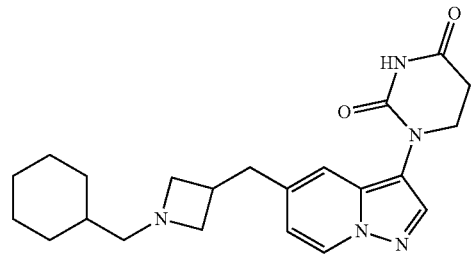

1-(5-((1-(cyclohexylmethyl)azetidin-3-yl)methyl)pyrazolo[1,5-a]pyridin-3-yl)dihydropyrimidine-2,4(1H,3H)-dione

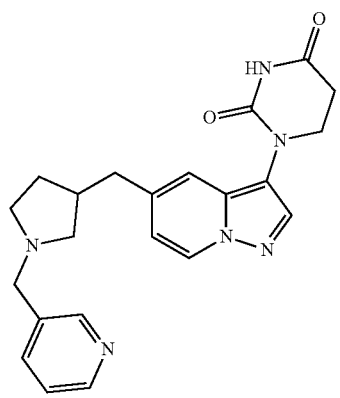

1-(5-((1-(pyridin-3-ylmethyl)pyrrolidin-3-yl)methyl)pyrazolo[1,5-a]pyridin-3-yl)dihydropyrimidine-2,4(1H,3H)-dione

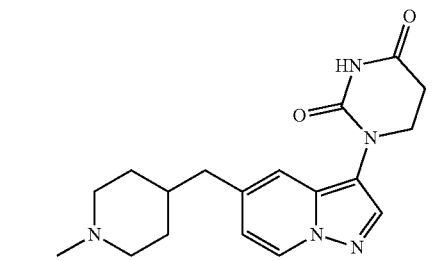

1-(5-((1-methylpiperidin-4-yl)methyl)pyrazolo[1,5-a]pyridin-3-yl)dihydropyrimidine-2,4(1H,3H)-dione

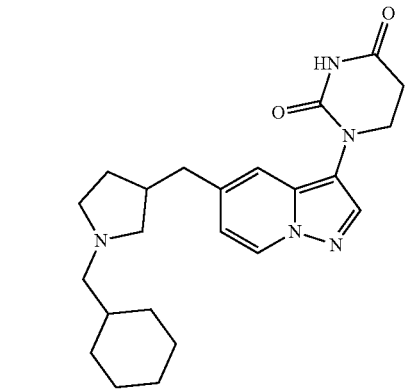

1-(5-((1-(cyclohexylmethyl)pyrrolidin-3-yl)methyl)pyrazolo[1,5-a]pyridin-3-yl)dihydropyrimidine-2,4(1H,3H)-dione

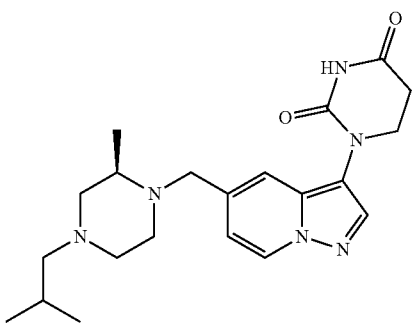

(R)-1-(5-((4-isobutyl-2-methylpiperazin-1-yl)methyl)pyrazolo[1,5-a]pyridin-3-yl)dihydropyrimidine-2,4(1H,3H)-dione

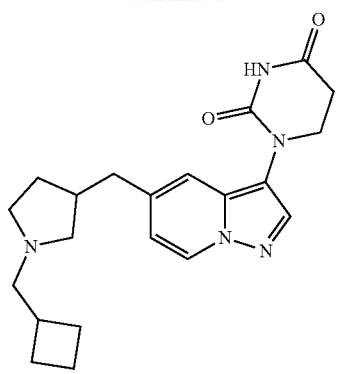

1-(5-((1-(cyclobutylmethyl)pyrrolidin-3-
yl)methyl)pyrazolo[1,5-a]pyridin-3-
yl)dihydropyrimidine-2,4(1H,3H)-dione

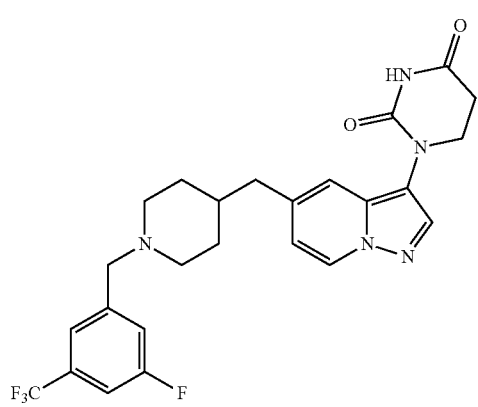

1-(5-((1-(3-fluoro-5-(trifluoromethyl)benzyl)piperidin-4-
yl)methyl)pyrazolo[1,5-a]pyridin-3-
yl)dihydropyrimidine-2,4(1H,3H)-dione

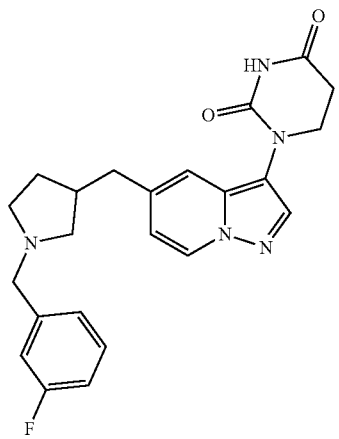

1-(5-((1-(3-fluorobenzyl))pyrrolidin-3-
yl)methyl)pyrazolo[1,5-a]pyridin-3-
yl)dihydropyrimidine-2,4(1H,3H)-dione

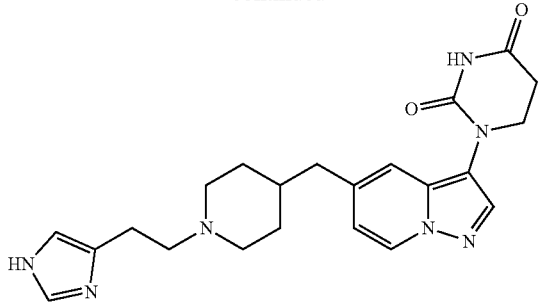

1-(5-((1-(2-(1H-imidazol-4-yl)ethyl)piperidin-4-
yl)methyl)pyrazolo[1,5-a]pyridin-3-
yl)dihydropyrimidine-2,4(1H,3H)-dione

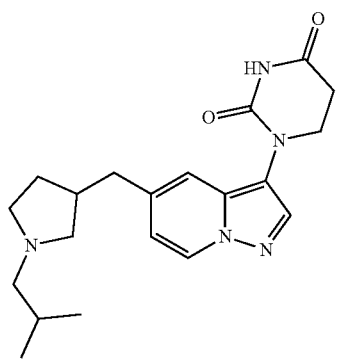

1-(5-((1-isobutylpyrrolidin-3-
yl)methyl)pyrazolo[1,5-a]pyridin-3-
yl)dihydropyrimidine-2,4(1H,3H)-dione

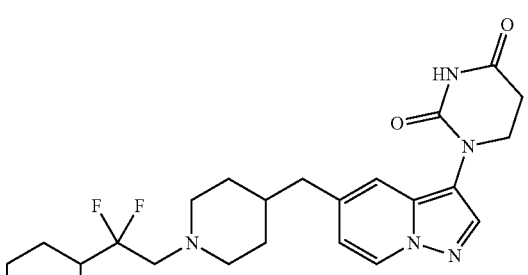

1-(5-((1-(2-cyclohexyl-2,2-difluoroethyl)piperidin-4-
yl)methyl)pyrazolo[1,5-a]pyridin-3-
yl)dihydropyrimidine-2,4(1H,3H)-dione

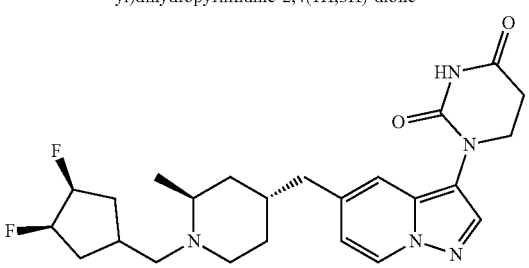

1-(5-(((2S,4R)-1-(((3R,4S)-3,4-difluorocyclopentyl)methyl)-
2-methylpiperidin-4-yl)methyl)pyrazolo[1,5-
a]pyridin-3-yl)dihydropyrimidine-2,4(1H,3H)-dione

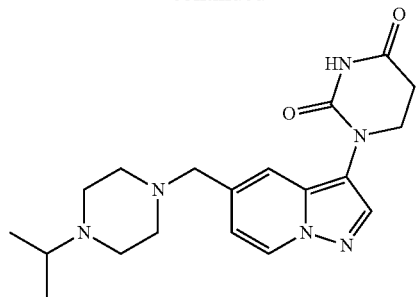

1-(5-((4-isopropylpiperazin-1-yl)methyl)pyrazolo[1,5-a]pyridin-3-yl)dihydropyrimidine-2,4(1H,3H)-dione

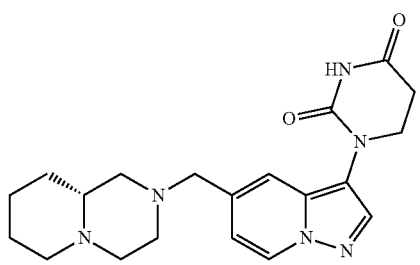

(R)-1-(5-((octahydro-2H-pyrido[1,2-a]pyrazin-2-yl)methyl)pyrazolo[1,5-a]pyridin-3-yl)dihydropyrimidine-2,4(1H,3H)-dione

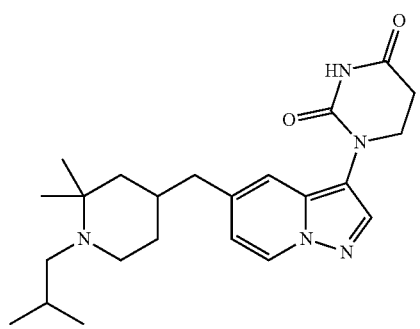

1-(5-((1-isobutyl-2,2-dimethylpiperidin-4-yl)methyl)pyrazolo[1,5-a]pyridin-3-yl)dihydropyrimidine-2,4(1H,3H)-dione

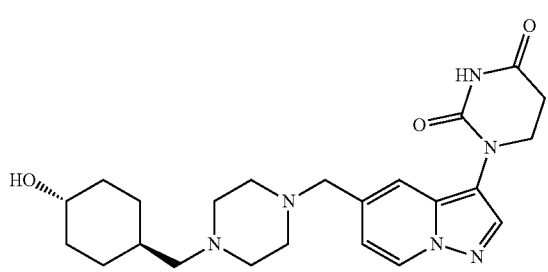

1-(5-((4-(((1r,4r)-4-hydroxycyclohexyl)methyl)piperazin-1-yl)methyl)pyrazolo[1,5-a]pyridin-3-yl)dihydropyrimidine-2,4(1H,3H)-dione

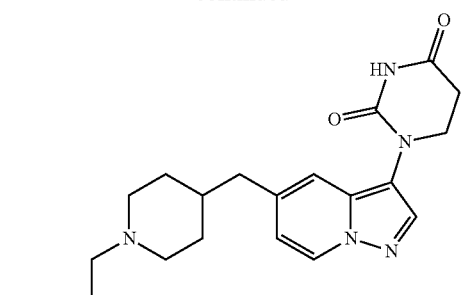

1-(5-((1-(2,3-difluorobenzyl)piperidin-4-yl)methyl)pyrazolo[1,5-a]pyridin-3-yl)dihydropyrimidine-2,4(1H,3H)-dione

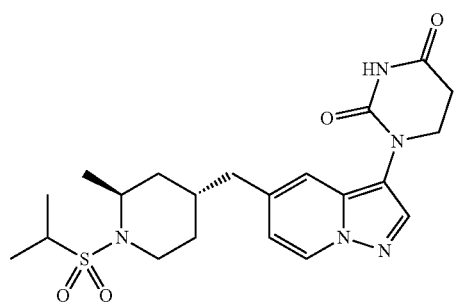

1-(5-(((2S,4R)-1-(isopropylsulfonyl)-2-methylpiperidin-4-yl)methyl)pyrazolo[1,5-a]pyridin-3-yl)dihydropyrimidine-2,4(1H,3H)-dione

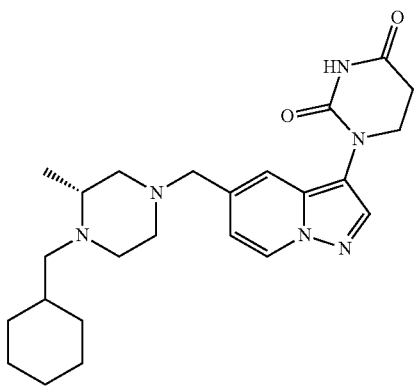

(R)-1-(5-((4-(cyclohexylmethyl)-3-methylpiperazin-1-yl)methyl)pyrazolo[1,5-a]pyridin-3-yl)dihydropyrimidine-2,4(1H,3H)-dione

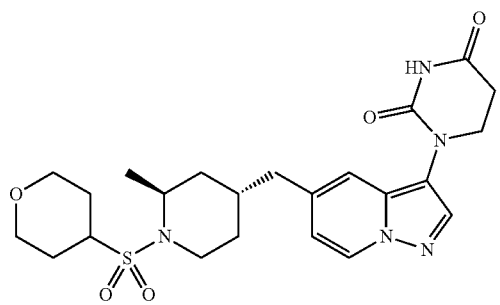

1-(5-(((2S,4R)-2-methyl-1-((tetrahydro-2H-pyran-4-)sulfonyl)piperidin-4-yl)methyl)pyrazolo[1,5-a]pyridin-3-yl)dihydropyrimidine-2,4(1H,3H)-dione

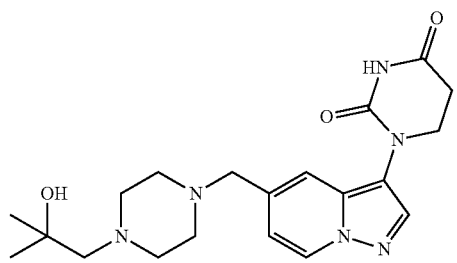

1-(5-((4-(2-hydroxy-2-methylpropyl)piperazin-
1-yl)methyl)pyrazolo[1,5-a]pyridin-3-
yl)dihydropyrimidine-2,4(1H,3H)-dione

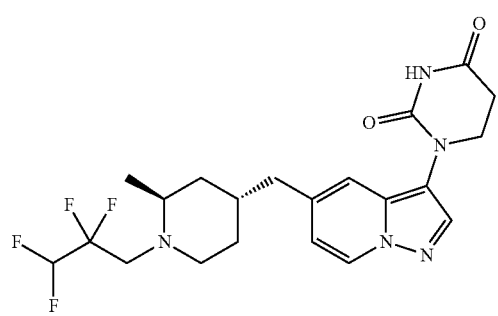

1-(5-(((2S,4R)-2-methyl-1-(2,2,3,3-
tetrafluoropropyl)piperidin-4-
yl)methyl)pyrazolo[1,5-a]pyridin-3-
yl)dihydropyrimidine-2,4(1H,3H)-dione

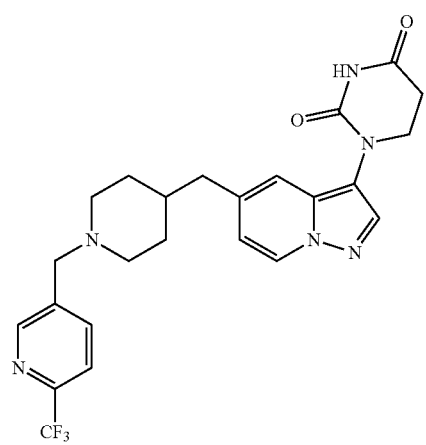

1-(5-((1-((6-(trifluoromethyl)pyridin-3-
yl)methyl)piperidin-4-yl)methyl)pyrazolo[1,5-
a]pyridin-3-yl)dihydropyrimidine-2,4(1H,3H)-dione

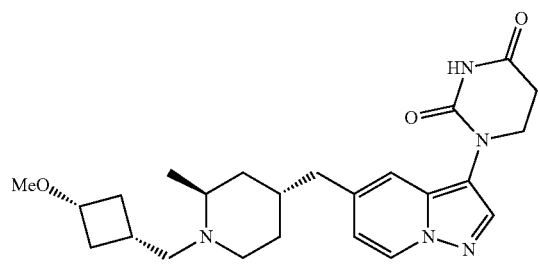

1-(5-(((2S,4R)-1-(((1s,3R)-3-methoxycyclobutyl)methyl)-
2-methylpiperidin-4-yl)methyl)pyrazolo[1,5-a]pyridin-
3-yl)dihydropyrimidine-2,4(1H,3H)-dione

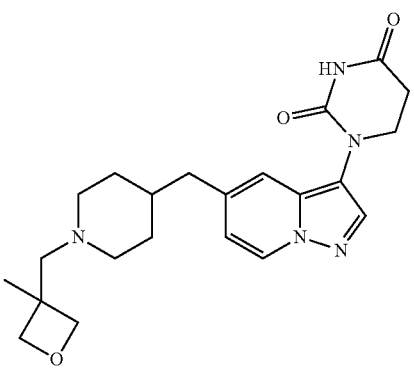

1-(5-(((1-((3-methyloxetan-3-
yl)methyl)piperidin-4-yl)methyl)pyrazolo[1,5-
a]pyridin-3-yl)dihydropyrimidine-2,4(1H,3H)-dione

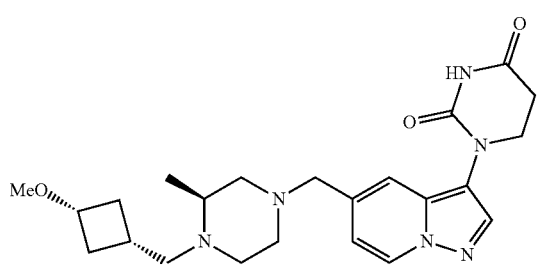

1-(5-(((S)-4-(((1s,3R)-3-methoxycyclobutyl)methyl)-
3-methylpiperazin-1-yl)methyl)pyrazolo[1,5-a]pyridin-
3-yl)dihydropyrimidine-2,4(1H,3H)-dione

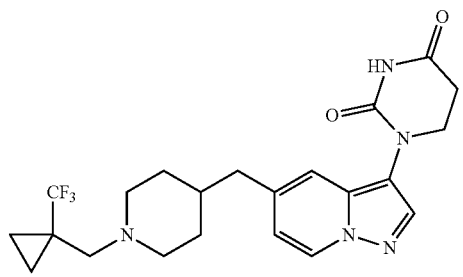

1-(5-((1-((1-
(trifluoromethyl)cyclopropyl)methyl)piperidin-
4-yl)methyl)pyrazolo[1,5-a]pyridin-3-
yl)dihydropyrimidine-2,4(1H,3H)-dione

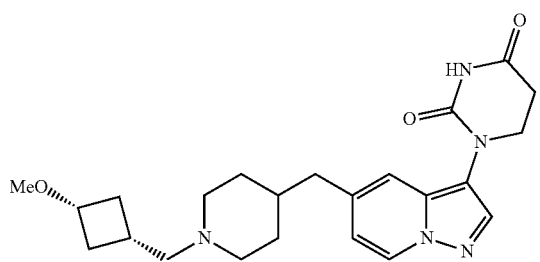

1-(5-((1-(((1s,3S)-3-
methoxycyclobutyl)methyl)piperidin-4-
yl)methyl)pyrazolo[1,5-a]pyridin-3-
yl)dihydropyrimidine-2,4(1H,3H)-dione

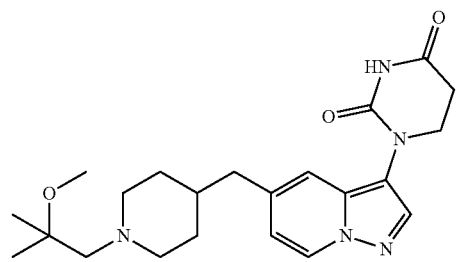

1-(5-((1-(2-methoxy-2-methylpropyl)piperidin-4-yl)methyl)pyrazolo[1,5-a]pyridin-3-yl)dihydropyrimidine-2,4(1H,3H)-dione

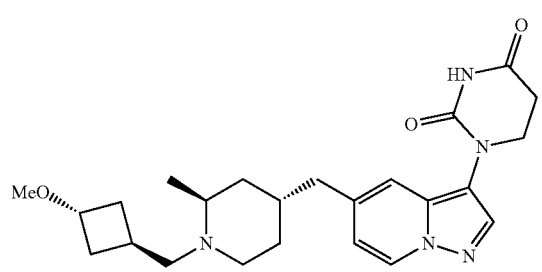

1-(5-(((2S,4R)-1-(((1r,3S)-3-methoxycyclobutyl)methyl)-2-methylpiperidin-4-yl)methyl)pyrazolo[1,5-a]pyridin-3-yl)dihydropyrimidine-2,4(1H,3H)-dione

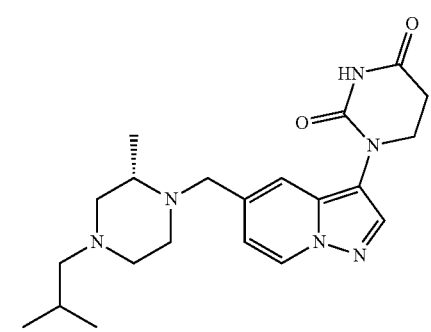

(S)-1-(5-((4-isobutyl-2-methylpiperazin-1-yl)methyl)pyrazolo[1,5-a]pyridin-3-yl)dihydropyrimidine-2,4(1H,3H)-dione

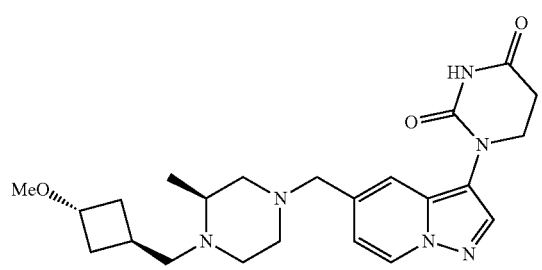

1-(5-(((S)-4-(((1r,3S)-3-methoxycyclobutyl)methyl)-3-methylpiperazin-1-yl)methyl)pyrazolo[1,5-a]pyridin-3-yl)dihydropyrimidine-2,4(1H,3H)-dione

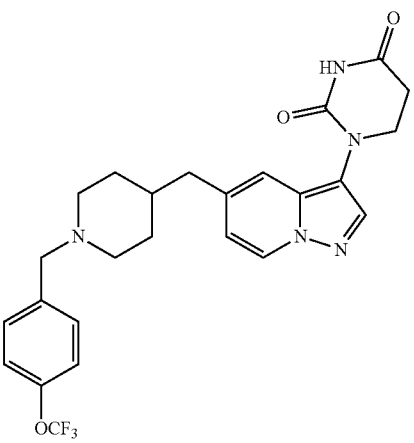
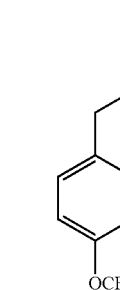

1-(5-((1-(4-(trifluoromethoxy)benzyl)piperidin-4-yl)methyl)pyrazolo[1,5-a]pyridin-3-yl)dihydropyrimidine-2,4(1H,3H)-dione

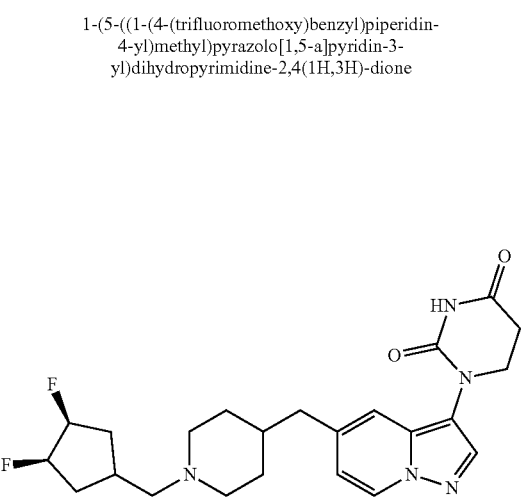

1-(5-((1-(((3R,4S)-3,4-difluorocyclopentyl)methyl)piperidin-4-yl)methyl)pyrazolo[1,5-a]pyridin-3-yl)dihydropyrimidine-2,4(1H,3H)-dione

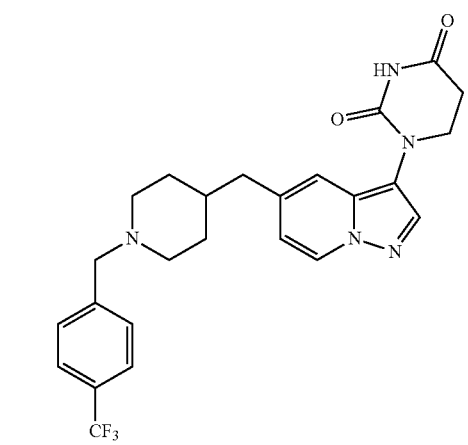

1-(5-((1-(4-(trifluoromethyl)benzyl)piperidin-4-yl)methyl)pyrazolo[1,5-a]pyridin-3-yl)dihydropyrimidine-2,4(1H,3H)-dione

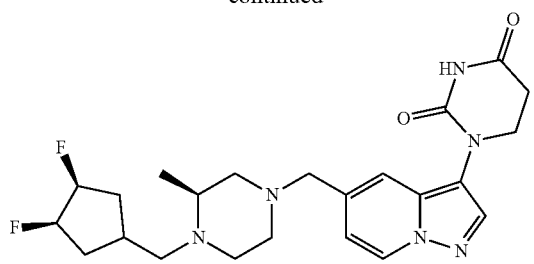

1-(5-(((3S)-4-(((3R,4S)-3,4-difluorocyclopentyl)methyl)-3-methylpiperazin-1-yl)methyl)pyrazolo[1,5-a]pyridin-3-yl)dihydropyrimidine-2,4(1H,3H)-dione

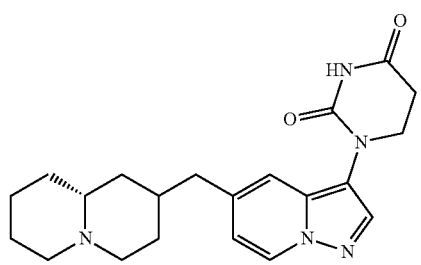

1-(5-(((9aR)-octahydro-2H-quinolizin-2-yl)methyl)pyrazolo[1,5-a]pyridin-3-yl)dihydropyrimidine-2,4(1H,3H)-dione

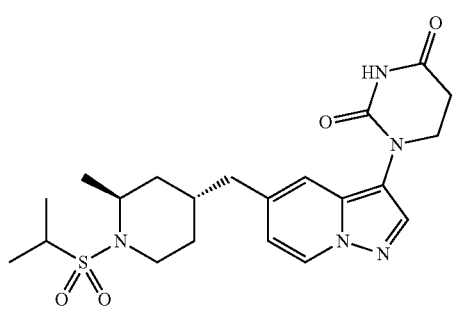

1-(5-(((2S,4R)-1-(isopropylsulfonyl)-2-methylpiperidin-4-yl)methyl)pyrazolo[1,5-a]pyridin-3-yl)dihydropyrimidine-2,4(1H,3H)-dione

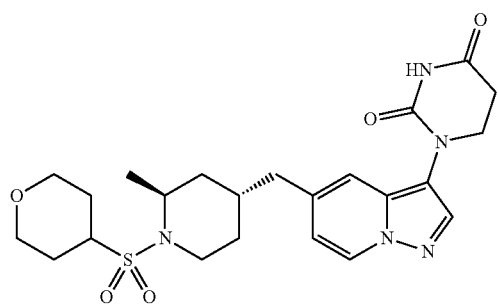

1-(5-(((2S,4R)-2-methyl-1-((tetrahydro-2H-pyran-4-yl)sulfonyl)piperidin-4-yl)methyl)pyrazolo[1,5-a]pyridin-3-yl)dihydropyrimidine-2,4(1H,3H)-dione

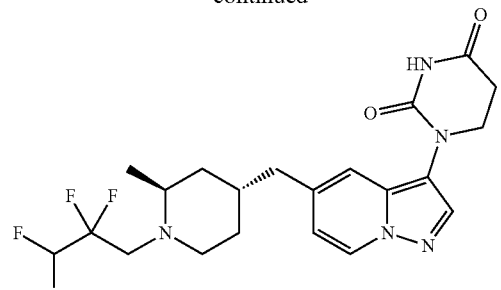

1-(5-(((2S,4R)-2-methyl-1-(2,2,3,3-tetrafluoropropyl)piperidin-4-yl)methyl)pyrazolo[1,5-a]pyridin-3-yl)dihydropyrimidine-2,4(1H,3H)-dione

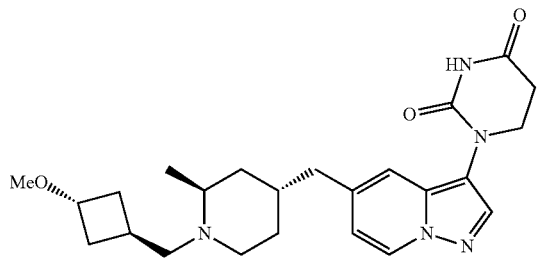

1-(5-(((2S,4R)-1-(((1r,3S)-3-methoxycyclobutyl)methyl)-2-methylpiperidin-4-yl)methyl)pyrazolo[1,5-a]pyridin-3-yl)dihydropyrimidine-2,4(1H,3H)-dione

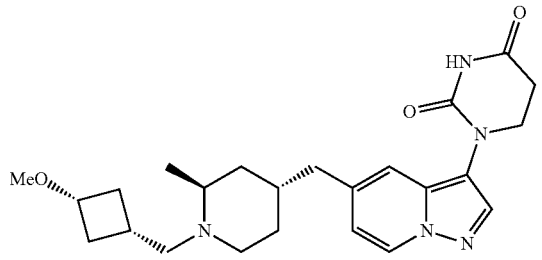

1-(5-(((2S,4R)-1-(((1s,3R)-3-methoxycyclobutyl)methyl)-2-methylpiperidin-4-yl)methyl)pyrazolo[1,5-a]pyridin-3-yl)dihydropyrimidine-2,4(1H,3H)-dione

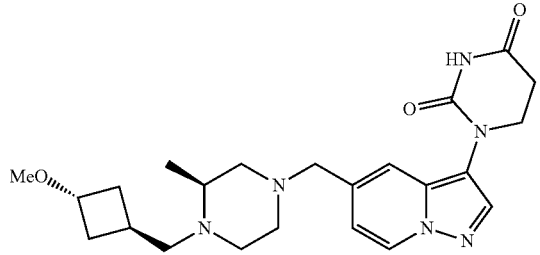

1-(5-(((S)-4-(((1r,3S)-3-methoxycyclobutyl)methyl)-3-methylpiperazin-1-yl)methyl)pyrazolo[1,5-a]pyridin-3-yl)dihydropyrimidine-2,4(1H,3H)-dione

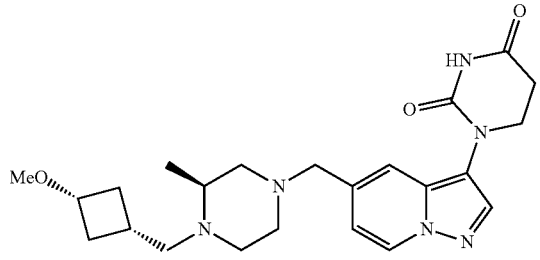

1-(5-(((S)-4-(((1s,3S)-3-methoxycyclobutyl)methyl)-3-methylpiperazin-1-yl)methyl)pyrazolo[1,5-a]pyridin-3-yl)dihydropyrimidine-2,4(1H,3H)-dione

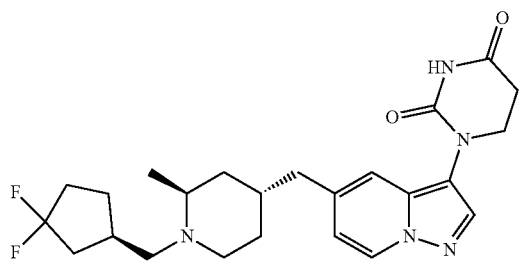

1-(5-(((2S,4R)-1-(((R)-3,3-
difluorocyclopentyl)methyl)-2-methylpiperidin-
4-yl)methyl)pyrazolo[1,5-a]pyridin-3-
yl)dihydropyrimidine-2,4(1H,3H)-dione

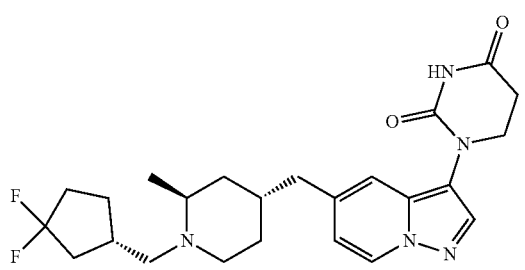

1-(5-(((2S,4R)-1-(((S)-3,3-
difluorocyclopentyl)methyl)-2-methylpiperidin-
4-yl)methyl)pyrazolo[1,5-a]pyridin-3-
yl)dihydropyrimidine-2,4(1H,3H)-dione

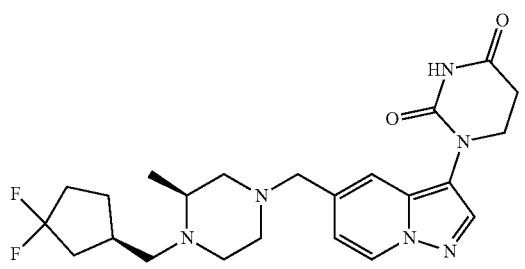

1-(5-(((S)-4-(((R)-3,3-
difluorocyclopentyl)methyl)-3-methylpiperazin-
1-yl)methyl)pyrazolo[1,5-a]pyridin-3-
yl)dihydropyrimidine-2,4(1H,3H)-dione

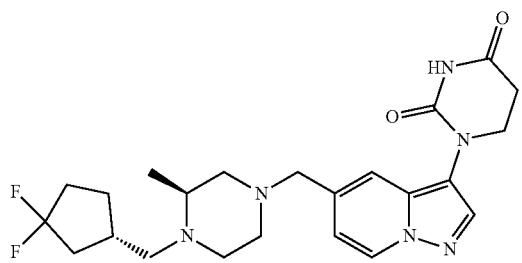

1-(5-(((S)-4-(((S)-3,3-
difluorocyclopentyl)methyl)-3-methylpiperazin-
1-yl)methyl)pyrazolo[1,5-a]pyridin-3-
yl)dihydropyrimidine-2,4(1H,3H)-dione

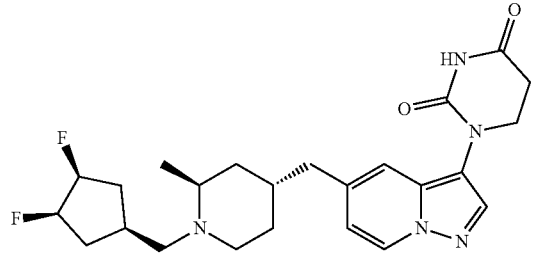

1-(5-(((2S,4R)-1-(((1r,3R,4S)-3,4-
difluorocyclopentyl)methyl)-2-methylpiperidin-
4-yl)methyl)pyrazolo[1,5-a]pyridin-
3-yl)dihydropyrimidine-2,4(1H,3H)-dione

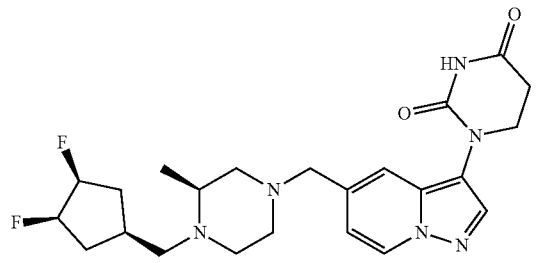

1-(5-(((S)-4-(((1r,3R,4S)-3,4-
difluorocyclopentyl)methyl)-3-methylpiperazin-
1-yl)methyl)pyrazolo[1,5-a]pyridin-
3-yl)dihydropyrimidine-2,4(1H,3H)-dione

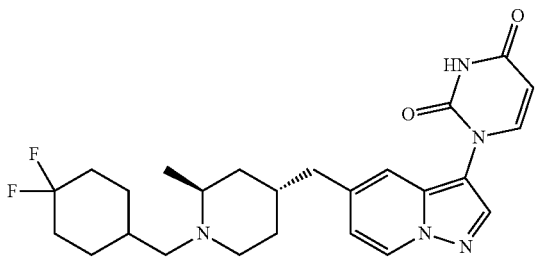

1-(5-(((2S,4R)-1-((4,4-
difluorocyclohexyl)methyl)-2-methylpiperidin-
4-yl)methyl)pyrazolo[1,5-a]pyridin-
3-yl)dihydropyrimidine-2,4(1H,3H)-dione


1-(5-(azepan-4-ylmethyl)pyrazolo[1,5-a]pyridin-
3-yl)dihydropyrimidine-2,4(1H,3H)-dione

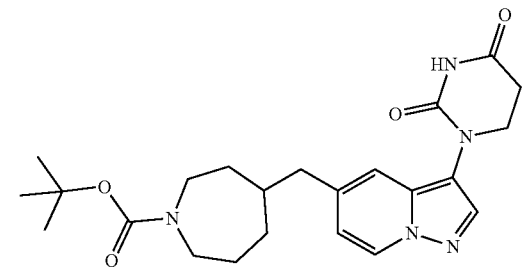

tert-butyl 4-((3-(2,4-dioxotetrahydropyrimidin-
1(2H)-yl)pyrazolo[1,5-a]pyridin-5-
yl)methyl)azepane-1-carboxylate

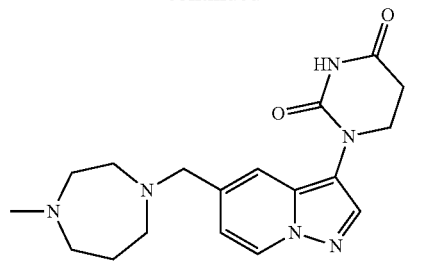

1-(5-((1-methylazepan-4-yl)methyl)pyrazolo[1,5-a]pyridin-3-yl)dihydropyrimidine-2,4(1H,3H)-dione

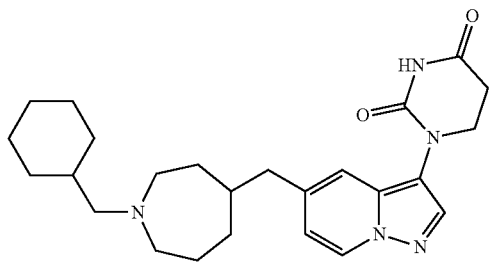

1-(5-((1-(cyclohexylmethyl)azepan-4-yl)methyl)pyrazolo[1,5-a]pyridin-3-yl)dihydropyrimidine-2,4(1H,3H)-dione

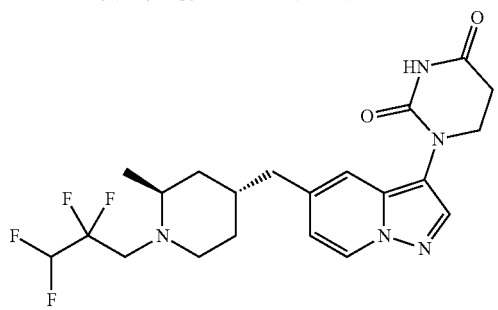

1-(5-(((2S,4R)-2-methyl-1-(2,2,3,3-tetrafluoropropyl)piperidin-4-yl)methyl)pyrazolo[1,5-a]pyridin-3-yl)dihydropyrimidine-2,4(1H,3H)-dione

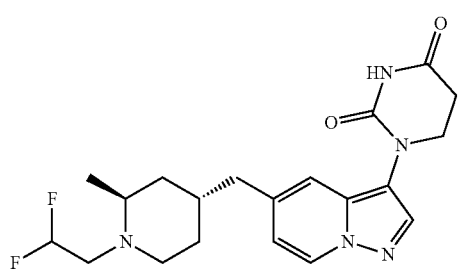

1-(5-(((2S,4R)-1-(2,2-difluoroethyl)-2-methylpiperidin-4-yl)methyl)pyrazolo[1,5-a]pyridin-3-yl)dihydropyrimidine-2,4(1H,3H)-dione

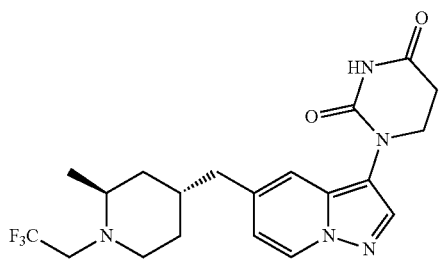

1-(5-(((2S,4R)-2-methyl-1-(2,2,2-trifluoroethyl)piperidin-4-yl)methyl)pyrazolo[1,5-a]pyridin-3-yl)dihydropyrimidine-2,4(1H,3H)-dione

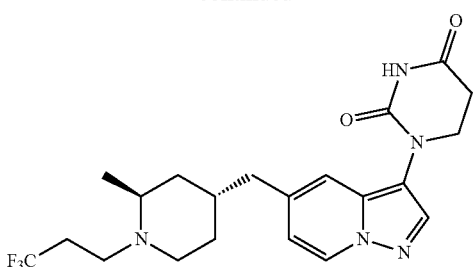

1-(5-(((2S,4R)-2-methyl-1-(3,3,3-trifluoropropyl)piperidin-4-yl)methyl)pyrazolo[1,5-a]pyridin-3-yl)dihydropyrimidine-2,4(1H,3H)-dione

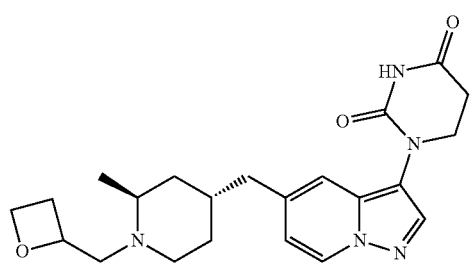

1-(5-(((2S,4R)-2-methyl-1-(oxetan-2-ylmethyl)piperidin-4-yl)methyl)pyrazolo[1,5-a]pyridin-3-yl)dihydropyrimidine-2,4(1H,3H)-dione

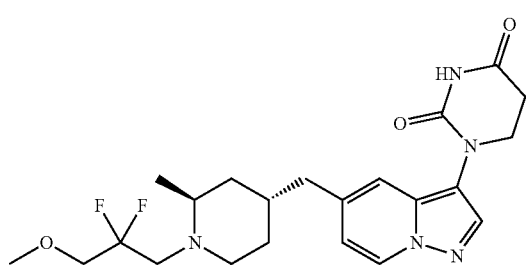

1-(5-(((2S,4R)-1-(2,2-difluoro-3-methoxypropyl)-2-methylpiperidin-4-yl)methyl)pyrazolo[1,5-a]pyridin-3-yl)dihydropyrimidine-2,4(1H,3H)-dione

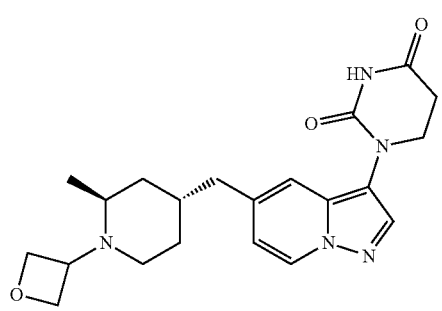

1-(5-(((2S,4R)-2-methyl-1-(oxetan-3-yl)piperidin-4-yl)methyl)pyrazolo[1,5-a]pyridin-3-yl)dihydropyrimidine-2,4(1H,3H)-dione

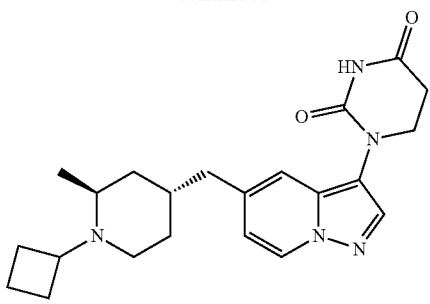

1-(5-(((2S,4R)-1-cyclobutyl-2-methylpiperidin-
4-yl)methyl)pyrazolo[1,5-a]pyridin-3-
yl)dihydropyrimidine-2,4(1H,3H)-dione

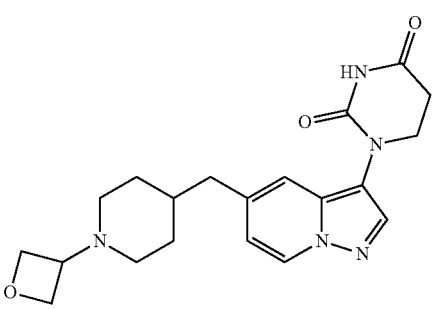

1-(5-((1-(oxetan-3-yl)piperidin-4-
yl)methyl)pyrazolo[1,5-a]pyridin-3-
yl)dihydropyrimidine-2,4(1H,3H)-dione

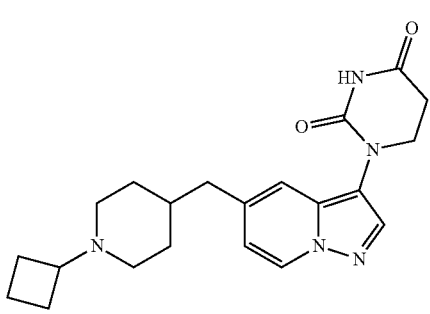

1-(5-((1-cyclobutylpiperidin-4-
yl)methyl)pyrazolo[1,5-a]pyridin-3-
yl)dihydropyrimidine-2,4(1H,3H)-dione

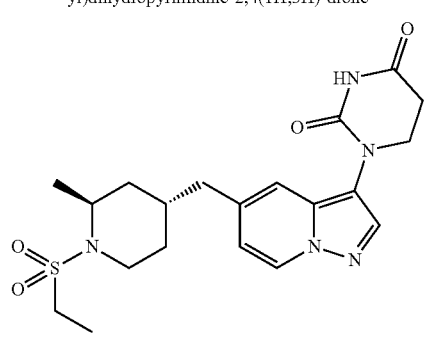

1-(5-(((2S,4R)-1-(ethylsulfonyl)-2-
methylpiperidin-4-yl)methyl)pyrazolo[1,5-
a]pyridin-3-yl)dihydropyrimidine-2,4(1H,3H)-dione

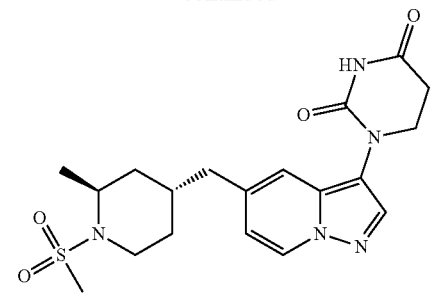

1-(5-(((2S,4R)-2-methyl-1-(methylsulfonyl)piperidin-
4-yl)methyl)pyrazolo[1,5-a]pyridin-3-
yl)dihydropyrimidine-2,4(1H,3H)-dione

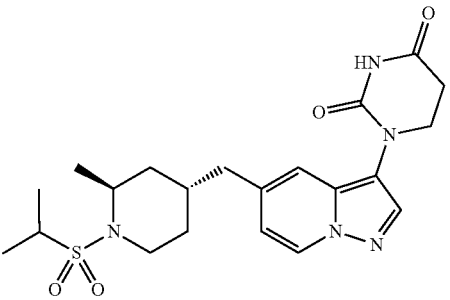

1-(5-(((2S,4R)-1-(isopropylsulfonyl)-2-
methylpiperidin-4-yl)methyl)pyrazolo[1,5-
a]pyridin-3-yl)dihydropyrimidine-2,4(1H,3H)-dione

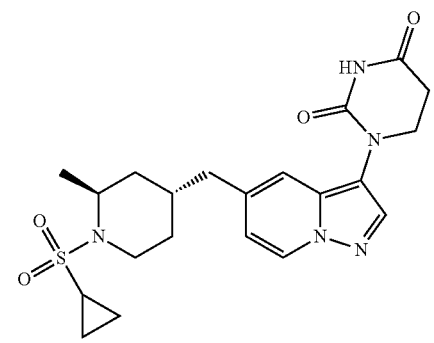

1-(5-(((2S,4R)-1-(cyclopropylsulfonyl)-2-
methylpiperidin-4-yl)methyl)pyrazolo[1,5-
a]pyridin-3-yl)dihydropyrimidine-2,4(1H,3H)-dione

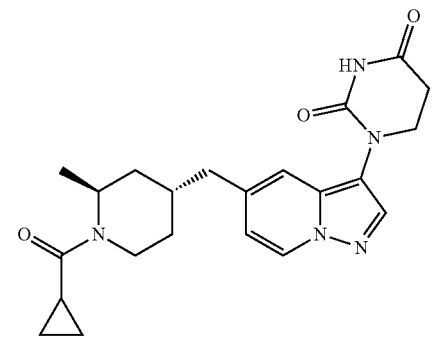

1-(5-(((2S,4R)-1-(cyclopropanecarbonyl)-2-
methylpiperidin-4-yl)methyl)pyrazolo[1,5-
a]pyridin-3-yl)dihydropyrimidine-2,4(1H,3H)-dione -continued

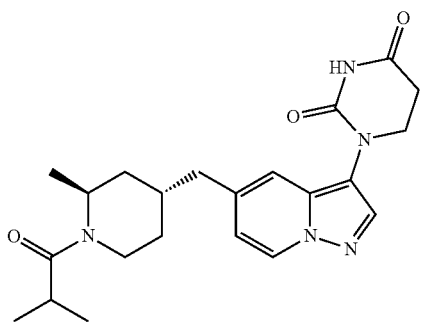

1-(5-(((2S,4R)-1-isobutyryl-2-methylpiperidin-4-yl)methyl)pyrazolo[1,5-a]pyridin-3-yl)dihydropyrimidine-2,4(1H,3H)-dione

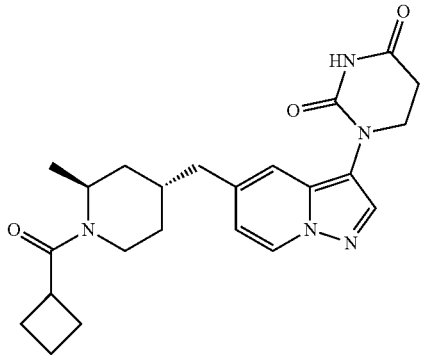

1-(5-(((2S,4R)-1-(cyclobutanecarbonyl)-2-methylpiperidin-4-yl)methyl)pyrazolo[1,5-a]pyridin-3-yl)dihydropyrimidine-2,4(1H,3H)-dione

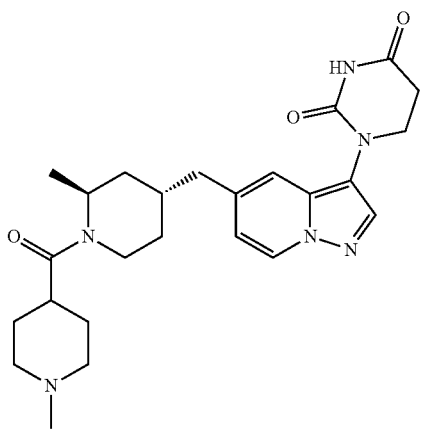

1-(5-(((2S,4R)-2-methyl-1-(1-methylpiperidine-4-carbonyl)piperidin-4-yl)methyl)pyrazolo[1,5-a]pyridin-3-yl)dihydropyrimidine-2,4(1H,3H)-dione -continued

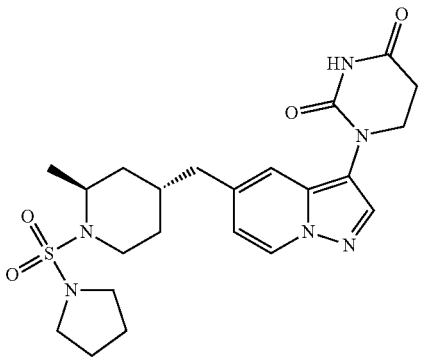

1-(5-(((2S,4R)-2-methyl-1-(pyrrolidin-1-ylsulfonyl)piperidin-4-yl)methyl)pyrazolo[1,5-a]pyridin-3-yl)dihydropyrimidine-2,4(1H,3H)-dione

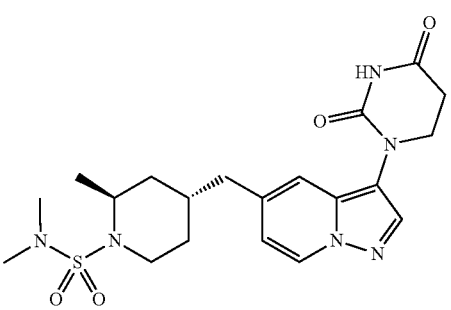

(2S,4R)-4-((3-(2,4-dioxotetrahydropyrimidin-1(2H)-yl)pyrazolo[1,5-a]pyridin-5-yl)methyl)-N,N,2-trimethylpiperidine-1-sulfonamide

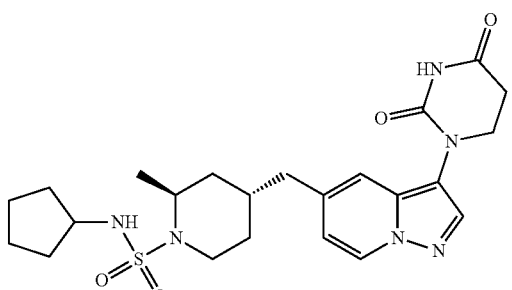

(2S,4R)-N-cyclopentyl-4-((3-(2,4-dioxotetrahydropyrimidin-1(2H)-yl)pyrazolo[1,5-a]pyridin-5-yl)methyl)-2-methylpiperidine-1-sulfonamide

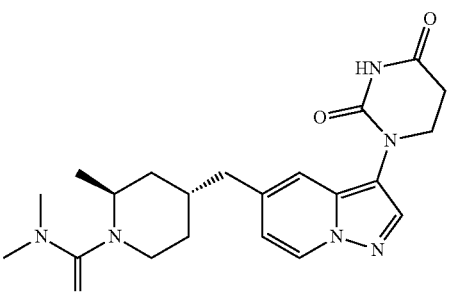

(2S,4R)-4-((3-(2,4-dioxotetrahydropyrimidin-1(2H)-yl)pyrazolo[1,5-a]pyridin-5-yl)methyl)-N,N,2-trimethylpiperidine-1-carboxamide

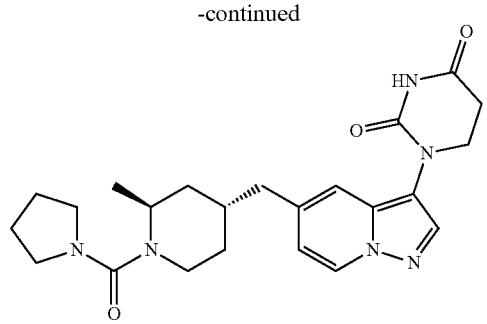

1-(5-(((2S,4R)-2-methyl-1-(pyrrolidin-1-carbonyl)piperidin-4-yl)methyl)pyrazolo[1,5-a]pyridin-3-yl)dihydropyrimidine-2,4(1H,3H)-dione

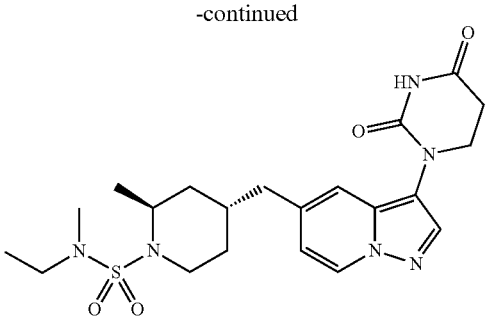

(2S,4R)-4-((3-(2,4-dioxotetrahydropyrimidin-1(2H)-yl)pyrazolo[1,5-a]pyridin-5-yl)methyl)-N-ethyl-N,2-dimethylpiperidine-1-carboxamide

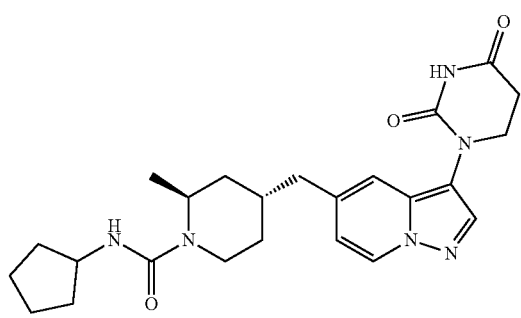

(2S,4R)-N-cyclopentyl-4-((3-(2,4-dioxotetrahydropyrimidin-1(2H)-yl)pyrazolo[1,5-a]pyridin-5-yl)methyl)-2-methylpiperidine-1-carboxamide

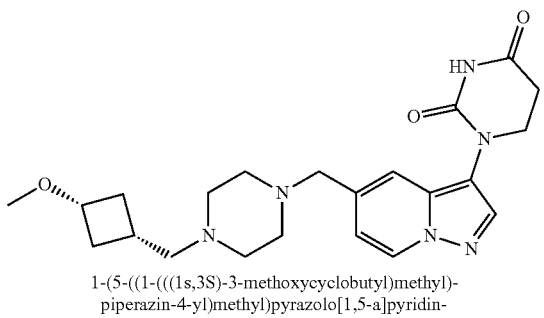

1-(5-((1-(((1s,3S)-3-methoxycyclobutyl)methyl)-piperazin-4-yl)methyl)pyrazolo[1,5-a]pyridin-3-yl)dihydropyrimidine-2,4(1H,3H)-dione

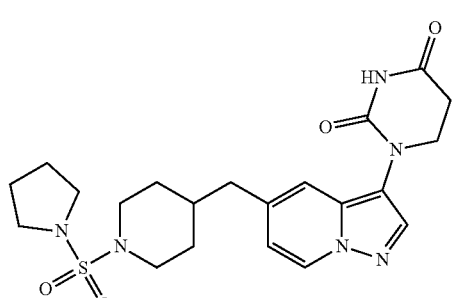

1-(5-((1-(pyrrolidin-1-ylsulfonyl)piperidin-4-yl)methyl)pyrazolo[1,5-a]pyridin-3-yl)dihydropyrimidine-2,4(1H,3H)-dione

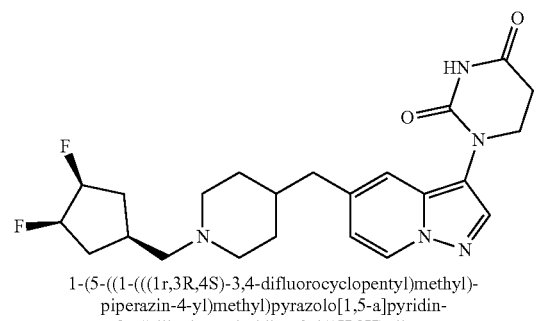

1-(5-((1-(((1r,3R,4S)-3,4-difluorocyclopentyl)methyl)-piperazin-4-yl)methyl)pyrazolo[1,5-a]pyridin-3-yl)dihydropyrimidine-2,4(1H,3H)-dione

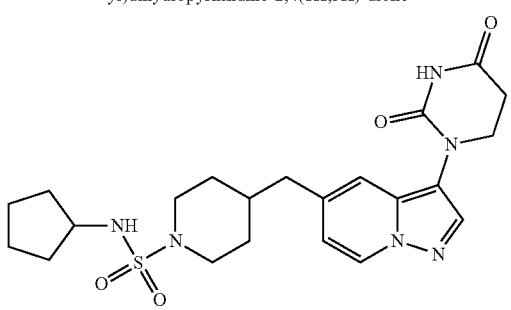

N-cyclopentyl-4-((3-(2,4-dioxotetrahydropyrimidin-1(2H)-yl)pyrazolo[1,5-a]pyridin-5-yl)methyl)piperidine-1-sulfonamide

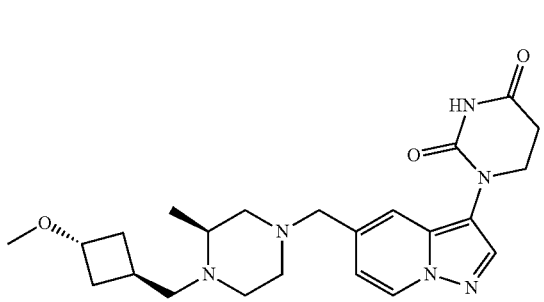

1-(5-(((2S,4R)-1-(((1r,3S)-3-methoxycyclobutyl)methyl)-2-methylpiperidin-4-yl)methyl)pyrazolo[1,5-a]pyridin-3-yl)dihydropyrimidine-2,4(1H,3H)-dione

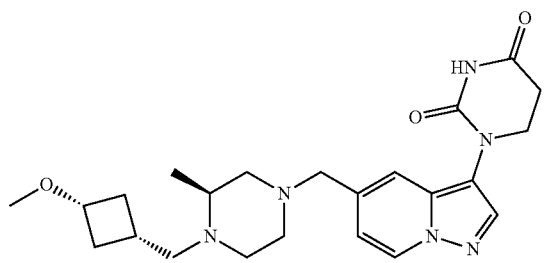

1-(5-(((2S,4R)-1-(((1s,3R)-3-methoxycyclobutyl)methyl)-2-methylpiperidin-4-yl)methyl)pyrazolo[1,5-a]pyridin-3-yl)dihydropyrimidine-2,4(1H,3H)-dione

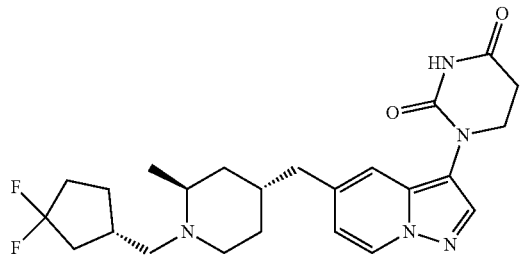

1-(5-(((2S,4R)-1-(((S)-3,3-difluorocyclopentyl)methyl)-2-methylpiperidin-4-yl)methyl)pyrazolo[1,5-a]pyridin-3-yl)dihydropyrimidine-2,4(1H,3H)-dione

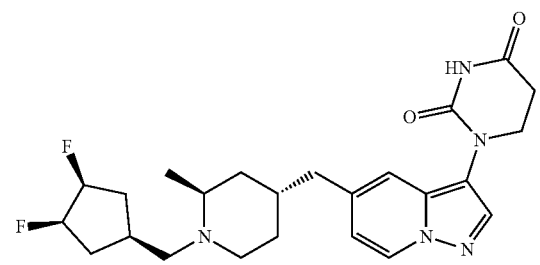

1-(5-(((2S,4R)-1-(((1r,3R,4S)-3,4-difluorocyclopentyl)methyl)-2-methylpiperidin-4-yl)methyl)pyrazolo[1,5-a]pyridin-3-yl)dihydropyrimidine-2,4(1H,3H)-dione

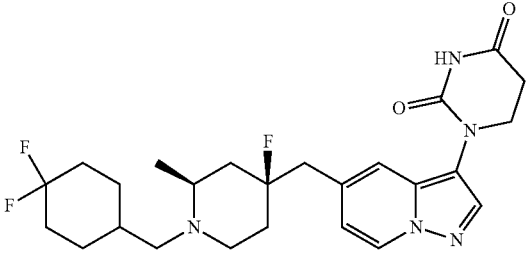

1-(5-(((2S,4S)-1-((4,4-difluorocyclohexyl)methyl)-4-fluoro-2-methylpiperidin-4-yl)methyl)pyrazolo[1,5-a]pyridin-3-yl)dihydropyrimidine-2,4(1H,3H)-dione

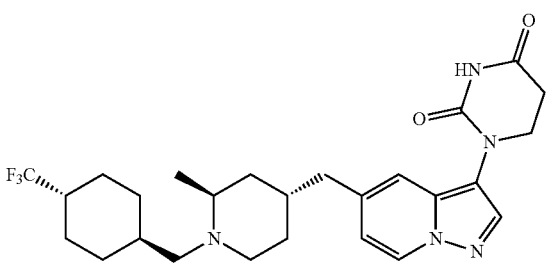

1-(5-(((2S,4R)-2-methyl-1-(((1r,4S)-4-(trifluoromethyl)cyclohexyl)methyl)piperidin-4-yl)methyl)pyrazolo[1,5-a]pyridin-3-yl)dihydropyrimidine-2,4(1H,3H)-dione

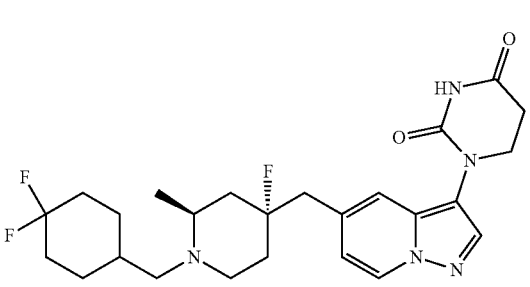

1-(5-(((2S,4R)-1-((4,4-difluorocyclohexyl)methyl)-4-fluoro-2-methylpiperidin-4-yl)methyl)pyrazolo[1,5-a]pyridin-3-yl)dihydropyrimidine-2,4(1H,3H)-dione 1-(5-(((2S,4R)-1-(((R)-3,3-difluorocyclopentyl)methyl)-2-methylpiperidin-4-yl)methyl)pyrazolo[1,5-a]pyridin-3-yl)dihydropyrimidine-2,4(1H,3H)-dione

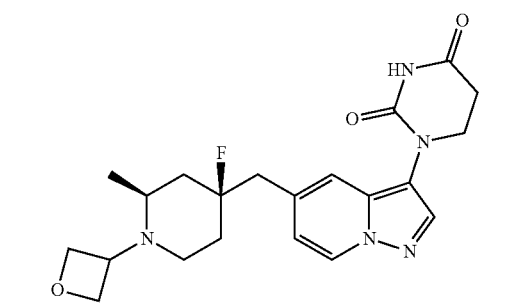

1-(5-(((2S,4S)-4-fluoro-2-methyl-1-(oxetan-3-yl)piperidin-4-yl)methyl)pyrazolo[1,5-a]pyridin-3-yl)dihydropyrimidine-2,4(1H,3H)-dione -continued

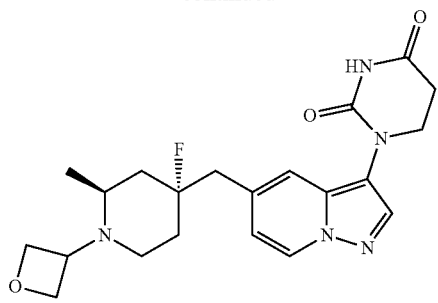

1-(5-(((2S,4R)-4-fluoro-2-methyl-1-(oxetan-3-yl)piperidin-4-yl)methyl)pyrazolo[1,5-a]pyridin-3-yl)dihydropyrimidine-2,4(1H,3H)-dione

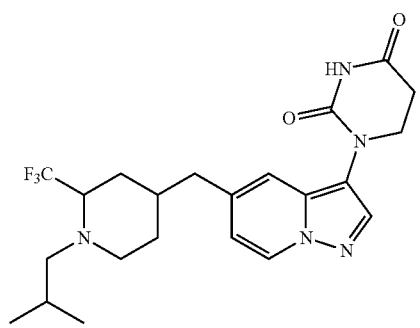

1-(5-((1-isobutyl-2-(trifluoromethyl)piperidin-4-yl)methyl)pyrazolo[1,5-a]pyridin-3-yl)dihydropyrimidine-2,4(1H,3H)-dione

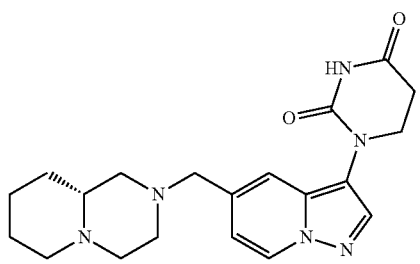

(R)-1-(5-((octahydro-2H-pyrido[1,2-a]pyrazin-2-yl)methyl)pyrazolo[1,5-a]pyridin-3-yl)dihydropyrimidine-2,4(1H,3H)-dione

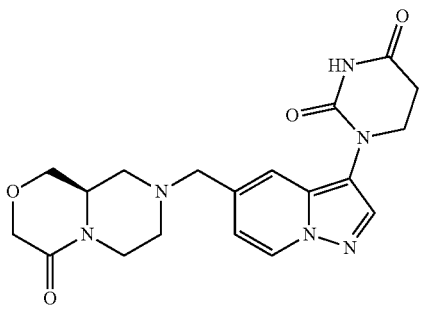

(R)-1-(5-((4-oxohexahydropyrazino[2,1-c][1,4]oxazin-8(1H)-yl)methyl)pyrazolo[1,5-a]pyridin-3-yl)dihydropyrimidine-2,4(1H,3H)-dione -continued

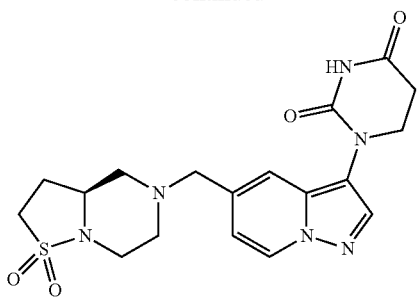

(S)-1-(5-(((1,1-dioxidohexahydro-5H-isothiazolo[2,3-a]pyrazin-5-yl)methyl)pyrazolo[1,5-a]pyridin-3-yl)dihydropyrimidine-2,4(1H,3H)-dione

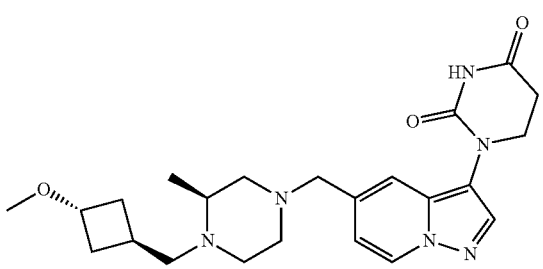

1-(5-(((S)-4-(((1r,3S)-3-methoxycyclobutyl)methyl)-3-methylpiperazin-1-yl)methyl)pyrazolo[1,5-a]pyridin-3-yl)dihydropyrimidine-2,4(1H,3H)-dione

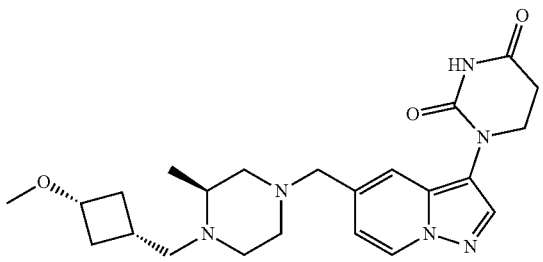

1-(5-(((S)-4-(((1s,3R)-3-methoxycyclobutyl)methyl)-3-methylpiperazin-1-yl)methyl)pyrazolo[1,5-a]pyridin-3-yl)dihydropyrimidine-2,4(1H,3H)-dione

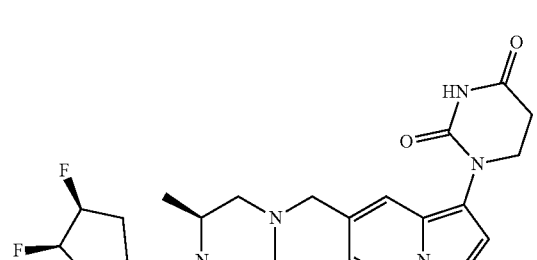

1-(5-(((S)-4-(((1r,3R,4S)-3,4-difluorocyclopentyl)methyl)-3-methylpiperazin-1-yl)methyl)pyrazolo[1,5-a]pyridin-3-yl)dihydropyrimidine-2,4(1H,3H)-dione

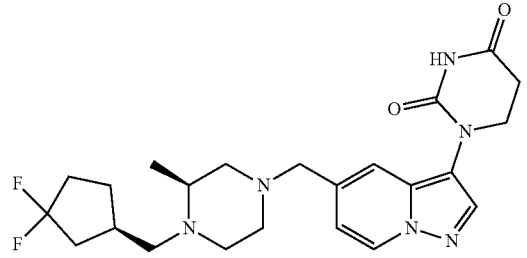

1-(5-(((S)-4-(((R)-3,3-
difluorocyclopentyl)methyl)-3-
methylpiperazin-1-yl)methyl)pyrazolo[1,5-
a]pyridin-3-yl)dihydropyrimidine-2,4(1H,3H)-dione

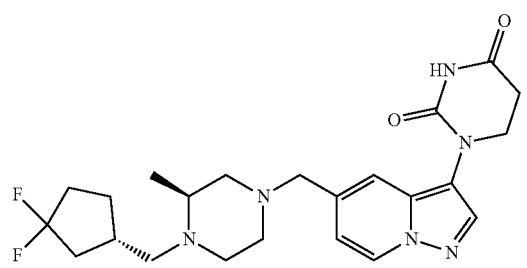

1-(5-(((S)-4-(((S)-3,3-
difluorocyclopentyl)methyl)-3-
methylpiperazin-1-yl)methyl)pyrazolo[1,5-
a]pyridin-3-yl)dihydropyrimidine-2,4(1H,3H)-dione

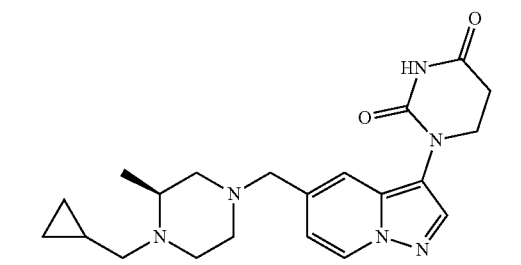

(S)-1-(5-((4-(cyclopropylmethyl)-3-
methylpiperazin-1-yl)methyl)pyrazolo[1,5-
a]pyridin-3-yl)dihydropyrimidine-2,4(1H,3H)-dione

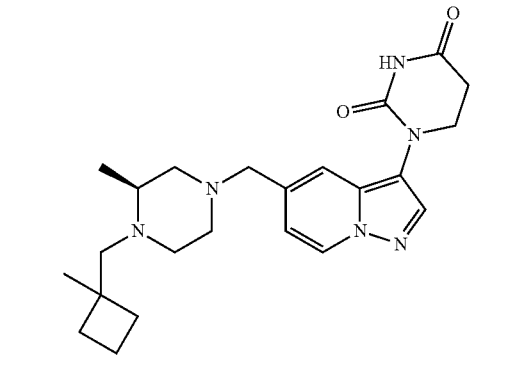

(S)-1-(5-((3-methyl-4-((1-
methylcyclobutyl)methyl)piperazin-1-
yl)methyl)pyrazolo[1,5-a]pyridin-3-
yl)dihydropyrimidine-2,4(1H,3H)-dione

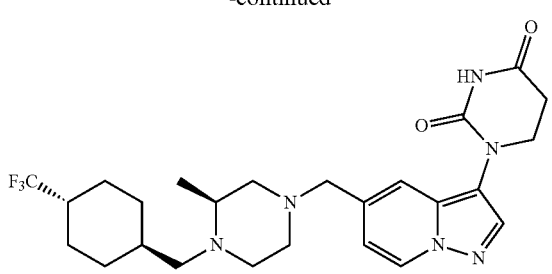

1-(5-(((S)-3-methyl-4-(((1r,4S)-4-
(trifluoromethyl)cyclohexyl)methyl)piperazin-
1-yl)methyl)pyrazolo[1,5-a]pyridin-3-
yl)dihydropyrimidine-2,4(1H,3H)-dione

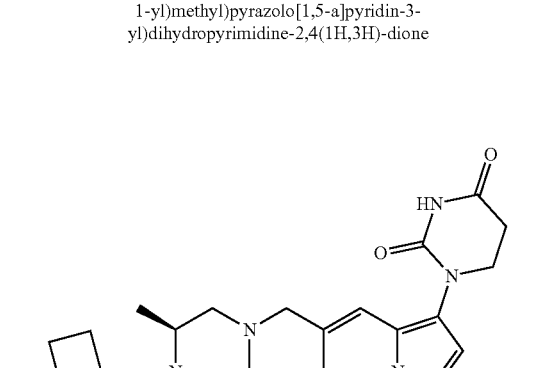

1-(5-(((S)-3-methyl-4-(oxetan-2-
ylmethyl)piperazin-1-yl)methyl)pyrazolo[1,5-
a]pyridin-3-yl)dihydropyrimidine-2,4(1H,3H)-dione

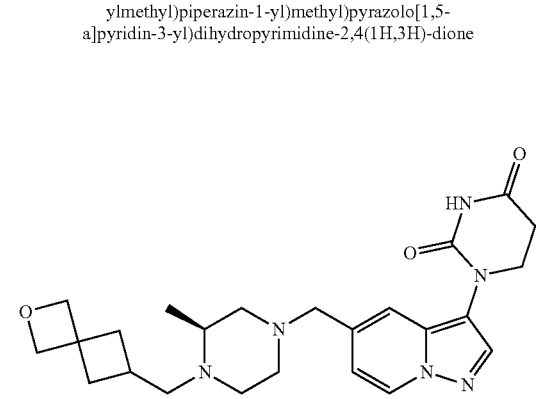

(S)-1-(5-((4-((2-oxaspiro[3.3]heptan-6-
yl)methyl)-3-methylpiperazin-1-
yl)methyl)pyrazolo[1,5-a]pyridin-3-
yl)dihydropyrimidine-2,4(1H,3H)-dione

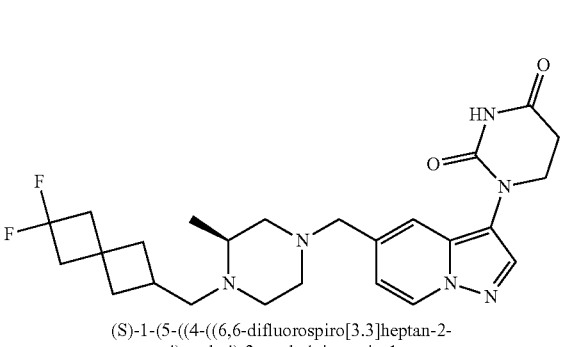

(S)-1-(5-((4-((6,6-difluorospiro[3.3]heptan-2-
yl)methyl)-3-methylpiperazin-1-
yl)methyl)pyrazolo[1,5-a]pyridin-3-
yl)dihydropyrimidine-2,4(1H,3H)-dione

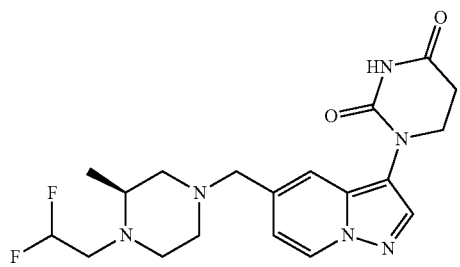

(S)-1-(5-((4-(2,2-difluoroethyl)-3-
methylpiperazin-1-yl)methyl)pyrazolo[1,5-
a]pyridin-3-yl)dihydropyrimidine-2,4(1H,3H)-dione

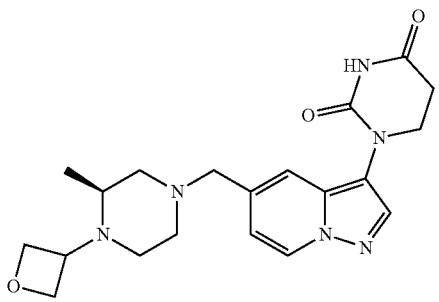

(S)-1-(5-((3-methyl-4-)oxetan-3-yl)piperazin-
1-yl)methyl)pyrazolo[1,5-a]pyridin-3-
yl)dihydropyrimidine-2,4(1H,3H)-dione

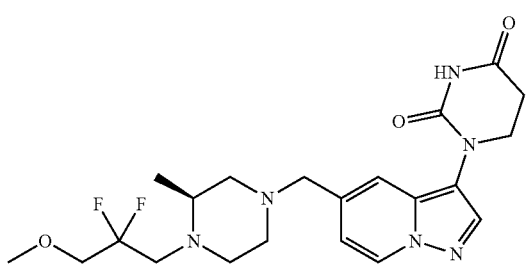

(S)-1-(5-((4-2,2-difluoro-3-methoxypropyl)-3-
methylpiperazin-1-yl)methyl)pyrazolo[1,5-
a]pyridin-3-yl)dihydropyrimidine-2,4(1H,3H)-dione

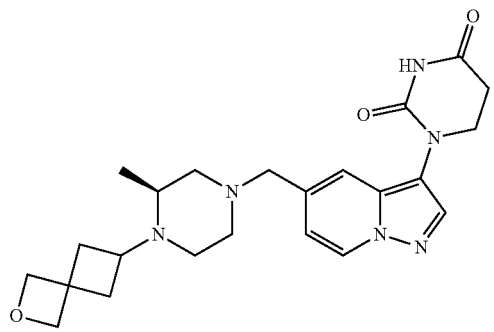

(S)-1-(5-((3-methyl-4-(2-oxaspiro[3.3]heptan-
6-yl)piperazin-1-yl)methyl)pyrazolo[1,5-
a]pyridin-3-yl)dihydropyrimidine-2,4(1H,3H)-dione

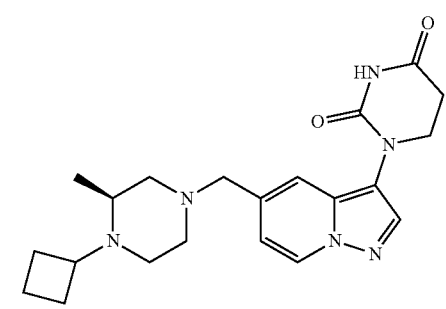

(S)-1-(5-((4-cyclobutyl-3-methylpiperazin-1-
yl)methyl)pyrazolo[1,5-a]pyridin-3-
yl)dihydropyrimidine-2,4(1H,3H)-dione

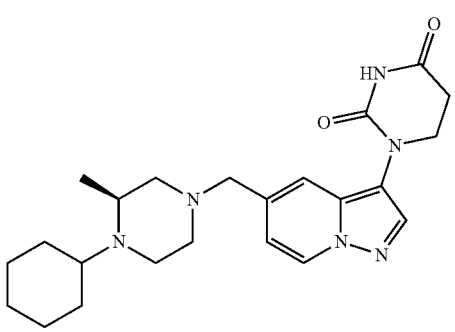

(S)-1-(5-((4-cyclohexyl-3-methylpiperazin-1-
yl)methyl)pyrazolo[1,5-a]pyridin-3-
yl)dihydropyrimidine-2,4(1H,3H)-dione

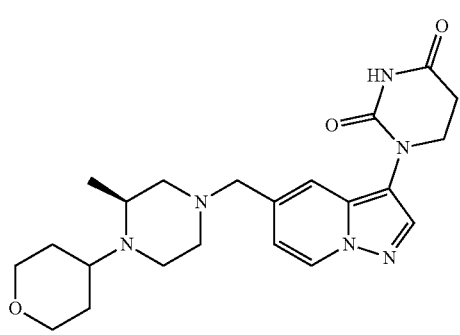

(S)-1-(5-((3-methyl-4-(tetrahydro-2H-pyran-4-
yl)piperazin-1-yl)methyl)pyrazolo[1,5-
a]pyridin-3-yl)dihydropyrimidine-2,4(1H,3H)-dione

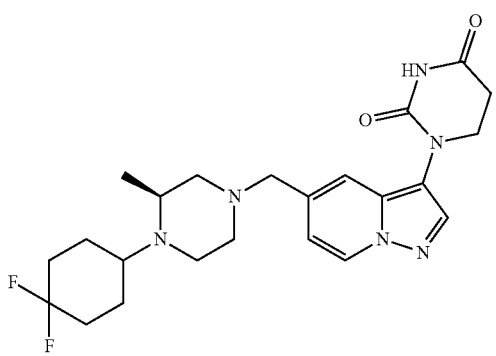

(S)-1-(5-((4-(4,4-difluorocyclohexyl)-3-
methylpiperazin-1-yl)methyl)pyrazolo[1,5-
a]pyridin-3-yl)dihydropyrimidine-2,4(1H,3H)-dione

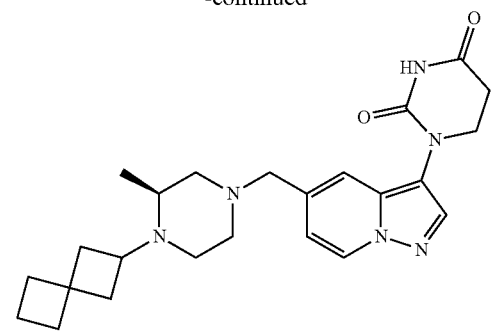

(S)-1-(5-((3-methyl-4-(spiro[3.3]heptan-2-yl)piperazin-1-yl)methyl)pyrazolo[1,5-a]pyridin-3-yl)dihydropyrimidine-2,4(1H,3H)-dione

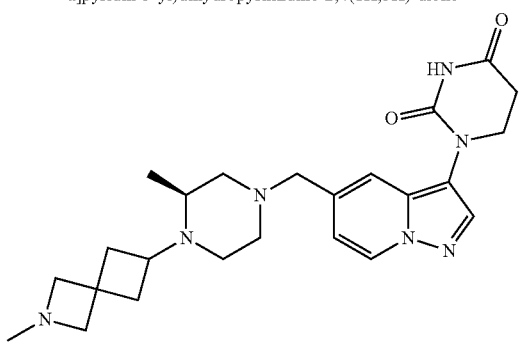

(S)-1-(5-((3-methyl-4-(2-methyl-2-azaspiro[3.3]heptan-6-yl)piperazin-1-yl)methyl)pyrazolo[1,5-a]pyridin-3-yl)dihydropyrimidine-2,4(1H,3H)-dione

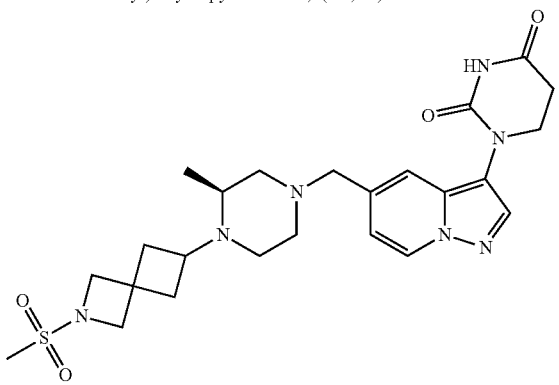

(S)-1-(5-((3-methyl-4-(2-methylsulfonyl)-2-azaspiro[3.3]heptan-6-yl)piperazin-1-yl)methyl)pyrazolo[1,5-a]pyridin-3-yl)dihydropyrimidine-2,4(1H,3H)-dione

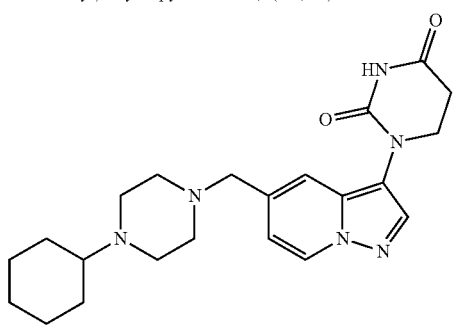

1-(5-((4-cyclohexylpiperazin-1-yl)methyl)pyrazolo[1,5-a]pyridin-3-yl)dihydropyrimidine-2,4(1H,3H)-dione

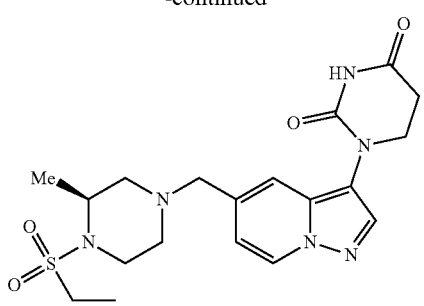

(S)-1-(5-((4-ethylsulfonyl)-3-methylpiperazin-1-yl)methyl)pyrazolo[1,5-a]pyridin-3-yl)dihydropyrimidine-2,4(1H,3H)-dione

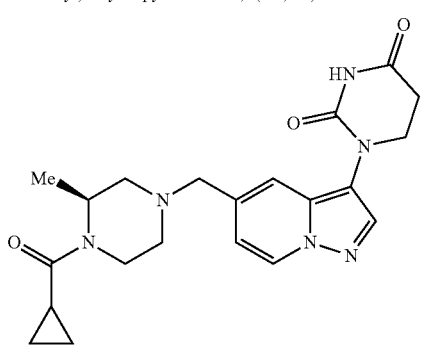

(S)-1-(5-((4-(cyclopropanecarbonyl)-3-methylpiperazin-1-yl)methyl)pyrazolo[1,5-a]pyridin-3-yl)dihydropyrimidine-2,4(1H,3H)-dione

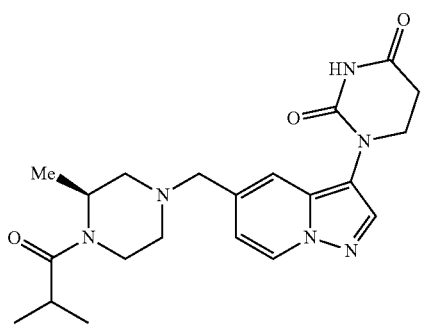

(S)-1-(5-((4-isobutyryl-3-methylpiperazin-1-yl)methyl)pyrazolo[1,5-a]pyridin-3-yl)dihydropyrimidine-2,4(1H,3H)-dione

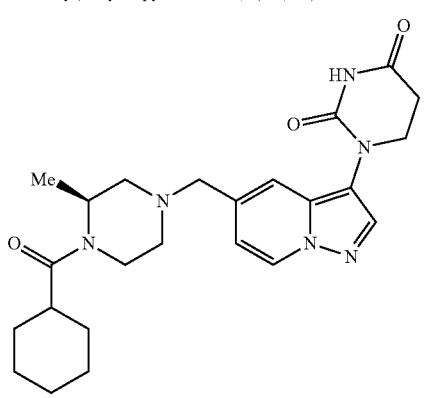

(S)-1-(5-((4-(cyclohexanecarbonyl)-3-methylpiperazin-1-yl)methyl)pyrazolo[1,5-a]pyridin-3-yl)dihydropyrimidine-2,4(1H,3H)-dione

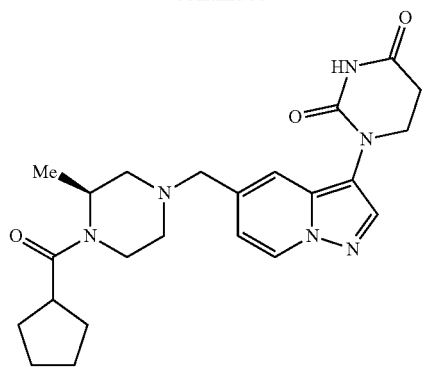

(S)-1-(5-((4-(cyclopentanecarbonyl)-3-
methylpiperazin-1-yl)methyl)pyrazolo[1,5-
a]pyridin-3-yl)dihydropyrimidine-2,4(1H,3H)-dione

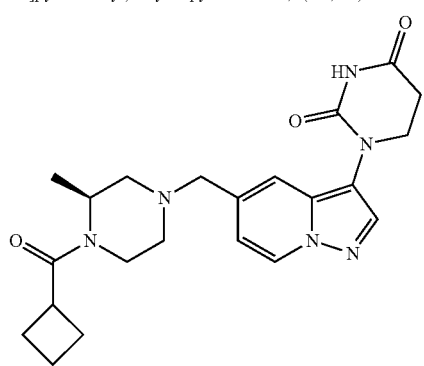

(S)-1-(5-((4-(cyclobutanecarbonyl)-3-
methylpiperazin-1-yl)methyl)pyrazolo[1,5-
a]pyridin-3-yl)dihydropyrimidine-2,4(1H,3H)-dione

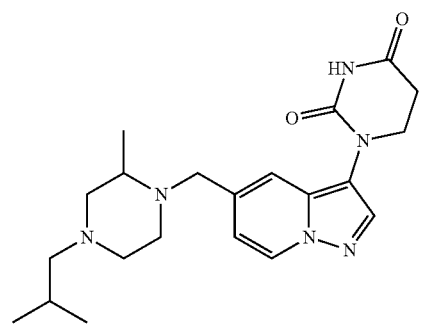

1-(5-(1-(4-isobutylpiperazin-1-
yl)ethyl)pyrazolo[1,5-a]pyridin-3-
yl)dihydropyrimidine-2,4(1H,3H)-dione

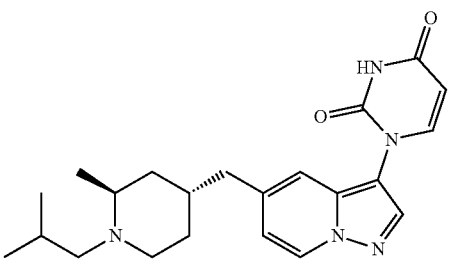

1-(5-(((2S,4R)-1-isobutyl-2-methylpiperidin-4-
yl)methyl)pyrazolo[1,5-a]pyridin-3-
yl)pyrimidine-2,4(1H,3H)-dione

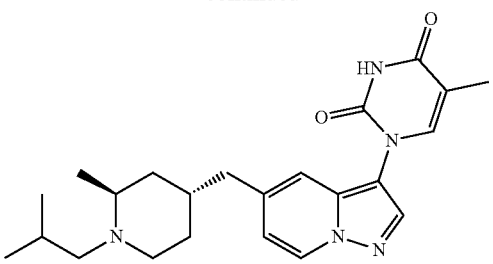

1-(5-(((2S,4R)-1-isobutyl-2-methylpiperidin-4-
yl)methyl)pyrazolo[1,5-a]pyridin-3-yl)-5-
methylpyrimidine-2,4(1H,3H)-dione

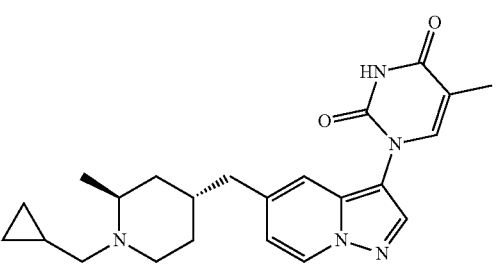

1-(5-(((2S,4R)-1-(cyclopropylmethyl)-2-
methylpiperidin-4-yl)methyl)pyrazolo[1,5-
a]pyridin-3-yl)-5-methylpyrimidine-2,4(1H,3H)-dione

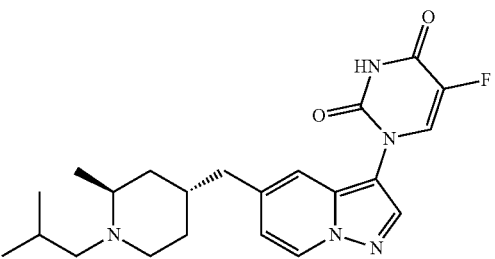

5-fluoro-1-(5-(((2S,4R)-1-isobutyl-2-
methylpiperidin-4-yl)methyl)pyrazolo[1,5-
a]pyridin-3-yl)pyrimidine-2,4(1H,3H)-dione

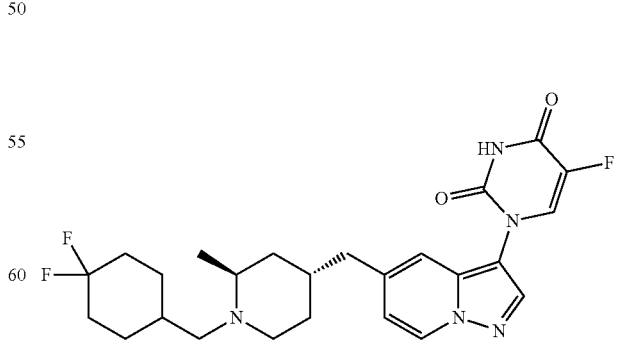

1-(5-(((2S,4R)-1-((4,4-
difluorocyclohexyl)methyl)-2-methylpiperidin-
4-yl)methyl)pyrazolo[1,5-a]pyridin-3-yl)-5-
fluoropyrimidine-2,4(1H,3H)-dione

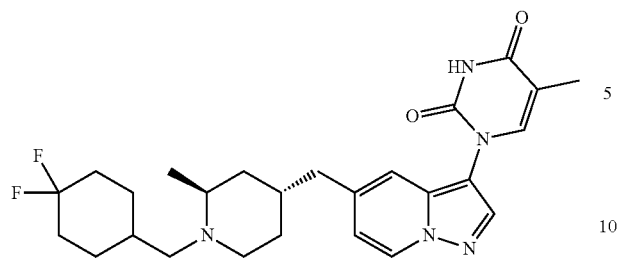

1-(5-(((2S,4R)-1-((4,4-difluorocyclohexyl)methyl)-2-methylpiperidin-4-yl)methyl)pyrazolo[1,5-a]pyridin-3-yl)-5-methylpyrimidine-2,4(1H,3H)-dione

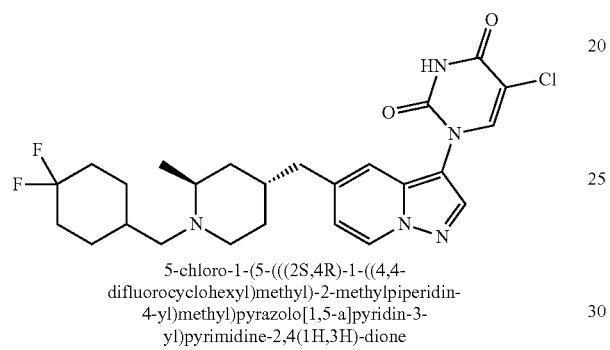

5-chloro-1-(5-(((2S,4R)-1-((4,4-difluorocyclohexyl)methyl)-2-methylpiperidin-4-yl)methyl)pyrazolo[1,5-a]pyridin-3-yl)pyrimidine-2,4(1H,3H)-dione


1-(5-(((2S,4R)-1-((4,4-difluorocyclohexyl)methyl)-2-methylpiperidin-4-yl)methyl)pyrazolo[1,5-a]pyridin-3-yl)-5-methoxypyrimidine-2,4(1H,3H)-dione

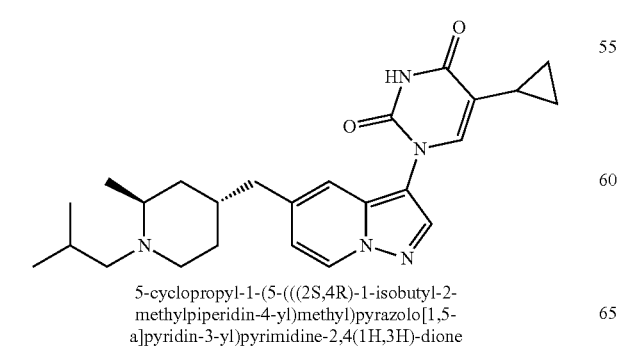

5-cyclopropyl-1-(5-(((2S,4R)-1-isobutyl-2-methylpiperidin-4-yl)methyl)pyrazolo[1,5-a]pyridin-3-yl)pyrimidine-2,4(1H,3H)-dione

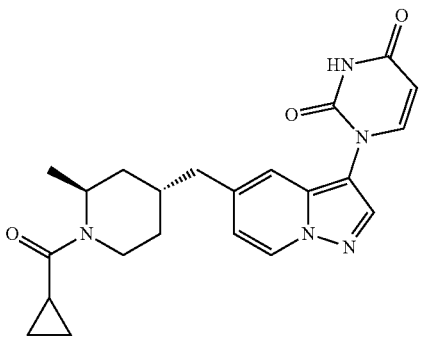

1-(5-(((2S,4R)-1-(cyclopropanecarbonyl)-2-methylpiperidin-4-yl)methyl)pyrazolo[1,5-a]pyridin-3-yl)pyrimidine-2,4(1H,3H)-dione

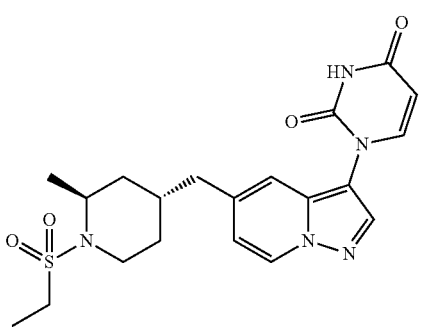

1-(5-(((2S,4R)-1-(ethylsulfonyl)-2-methylpiperidin-4-yl)methyl)pyrazolo[1,5-a]pyridin-3-yl)pyrimidine-2,4(1H,3H)-dione

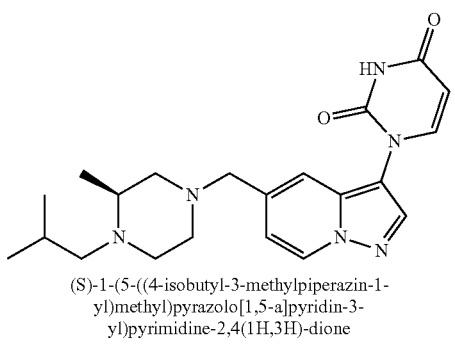

(S)-1-(5-((4-isobutyl-3-methylpiperazin-1-yl)methyl)pyrazolo[1,5-a]pyridin-3-yl)pyrimidine-2,4(1H,3H)-dione

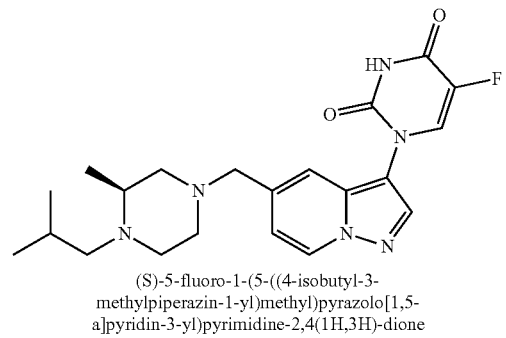

(S)-5-fluoro-1-(5-((4-isobutyl-3-methylpiperazin-1-yl)methyl)pyrazolo[1,5-a]pyridin-3-yl)pyrimidine-2,4(1H,3H)-dione -continued

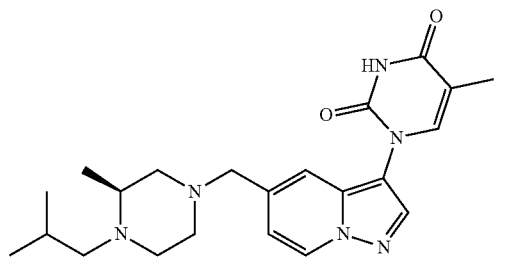

(S)-1-(5-((4-isobutyl-3-methylpiperazin-1-yl)methyl)pyrazolo[1,5-a]pyridin-3-yl)-5-methylpyrimidine-2,4(1H,3H)-dione

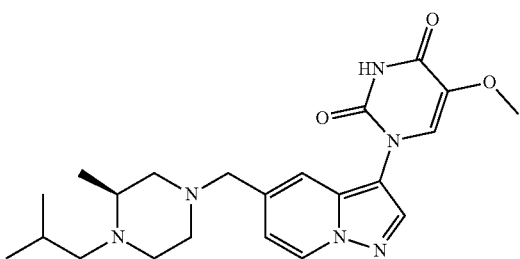

(S)-1-(5-((4-isobutyl-3-methylpiperazin-1-yl)methyl)pyrazolo[1,5-a]pyridin-3-yl)-5-methoxypyrimidine-2,4(1H,3H)-dione

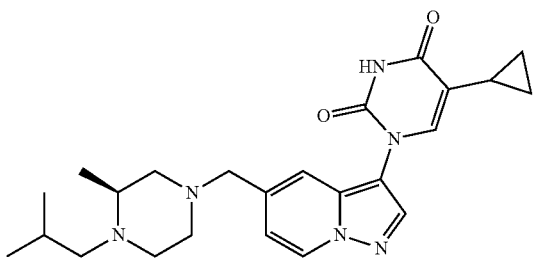

(S)-5-cyclopropyl-1-(5-((4-isobutyl-3-methylpiperazin-1-yl)methyl)pyrazolo[1,5-a]pyridin-3-yl)pyrimidine-2,4(1H,3H)-dione

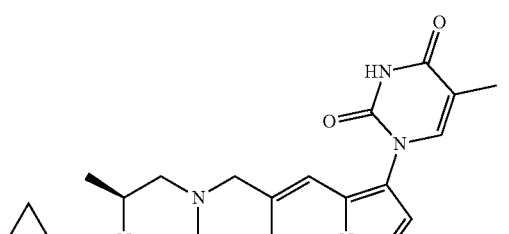

(S)-1-(5-((4-(cyclopropylmethyl)-3-methylpiperazin-1-yl)methyl)pyrazolo[1,5-a]pyridin-3-yl)-5-methylpyrimidine-2,4(1H,3H)-dione

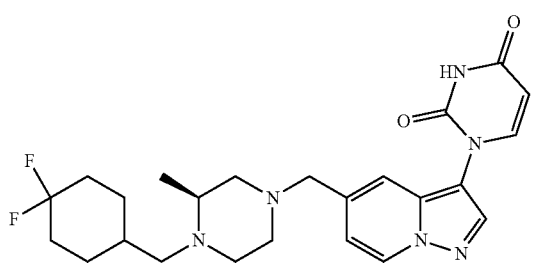

(S)-1-(5-((4-((4,4-difluorocyclohexyl)methyl)-3-methylpiperazin-1-yl)methyl)pyrazolo[1,5-a]pyridin-3-yl)pyrimidine-2,4(1H,3H)-dione Embodiment 49. The compound of any one of the preceding Embodiments, or a pharmaceutically acceptable salt, thereof, wherein the pharmaceutically acceptable salt is an acid addition salt.

Embodiment 50. A pharmaceutical composition comprising a therapeutically effective amount of a compound of any of Embodiments 1 to 49, or a pharmaceutically acceptable salt, hydrate, solvate, prodrug, stereoisomer, or tautomer thereof, and a pharmaceutically acceptable carrier or excipient.

Embodiment 51. A compound of any one of Embodiments 1 to 49, or a pharmaceutically acceptable salt, hydrate, solvate, prodrug, stereoisomer, or tautomer thereof, for use as a medicament.

Embodiment 52. A method of treating or preventing a disease or disorder in a subject in need thereof, the method comprising administering to the subject a therapeutically effective amount of a compound of any one of Embodiments 1 to 49, or a pharmaceutically acceptable salt, thereof.

Embodiment 53. A method of treating or preventing a disorder that is affected by the reduction of WIZ protein levels, in a subject in need thereof, the method comprising administering to the subject a therapeutically effective amount of a compound of any one of Embodiments 1 to 49, or a pharmaceutically acceptable salt, hydrate, solvate, prodrug, stereoisomer, or tautomer thereof.

Embodiment 54. A method of treating a disease or disorder that is affected by the modulation of WIZ protein levels comprising administering to the patient in need thereof a compound of any one of Embodiments 1 to 49, or a pharmaceutically acceptable salt, hydrate, solvate, prodrug, stereoisomer, or tautomer thereof.

Embodiment 55. A method of inhibiting WIZ protein expression in a subject in need thereof, the method comprising administering to the subject a therapeutically effective amount of a compound of any one of Embodiments 1 to 49, or a pharmaceutically acceptable salt, hydrate, solvate, prodrug, stereoisomer, or tautomer thereof.

Embodiment 56. A method of degrading WIZ protein in a subject in need thereof, the method comprising administering to the subject a therapeutically effective amount of a compound of any one of Embodiments 1 to 49, or a pharmaceutically acceptable salt, thereof.

Embodiment 57. A method of inhibiting, reducing, or eliminating the activity of WIZ protein or WIZ protein expression, the method comprising administering to the subject a compound of any one of Embodiments 1 to 49, or a pharmaceutically acceptable salt, hydrate, solvate, prodrug, stereoisomer, or tautomer thereof.

Embodiment 58. A method of inducing or promoting fetal hemoglobin in a subject in need thereof, the method comprising administering to the subject a therapeutically effective amount of a compound of any one of Embodiments 1 to 49, or a pharmaceutically acceptable salt, hydrate, solvate, prodrug, stereoisomer, or tautomer thereof.

Embodiment 59. A method of reactivating fetal hemoglobin production or expression in a subject in need thereof, the method comprising administering to the subject a therapeutically effective amount of a compound of any one of Embodiments 1 to 49, or a pharmaceutically acceptable salt, hydrate, solvate, prodrug, stereoisomer, or tautomer thereof.

Embodiment 60. A method of increasing fetal hemoglobin expression in a subject in need thereof, the method comprising administering to the subject a therapeutically effective amount of a compound of any one of Embodiments 1 to 49, or a pharmaceutically acceptable salt, hydrate, solvate, prodrug, stereoisomer, or tautomer thereof.

Embodiment 61. A method of treating a hemoglobinopathy, e.g., a beta-hemoglobinopathy, in a subject in need thereof, the method comprising administering to the subject a therapeutically effective amount of a compound of any one of Embodiments 1 to 49, or a pharmaceutically acceptable salt, hydrate, solvate, prodrug, stereoisomer, or tautomer thereof.

Embodiment 62. A method of treating a sickle cell disease in a subject in need thereof, the method comprising administering to the subject a therapeutically effective amount of a compound of any one of Embodiments 1 to 49, or a pharmaceutically acceptable salt, hydrate, solvate, prodrug, stereoisomer, or tautomer thereof.

Embodiment 63. A method of treating beta-thalassemia in a subject in need thereof, the method comprising administering to the subject a therapeutically effective amount of a compound of any one of Embodiments 1 to 49, or a pharmaceutically acceptable salt, hydrate, solvate, prodrug, stereoisomer, or tautomer thereof.

Embodiment 64. A method for reducing WIZ protein levels in a subject comprising the step of administering to a subject in need thereof a therapeutically effective amount of a compound of any one of Embodiments 1 to 49, or a pharmaceutically acceptable salt, hydrate, solvate, prodrug, stereoisomer, or tautomer thereof.

Embodiment 65. A compound of any one of Embodiments 1 to 49, or a pharmaceutically acceptable salt, hydrate, solvate, prodrug, stereoisomer, or tautomer thereof, for use in treating or preventing a disease or disorder in a subject in need thereof.

Embodiment 66. A compound of any one of Embodiments 1 to 49, or a pharmaceutically acceptable salt, hydrate, solvate, prodrug, stereoisomer, or tautomer thereof, for use in the treatment of a disease or disorder selected from sickle cell disease and beta-thalassemia.

Embodiment 67. A compound of any one of Embodiments 1 to 49, or a pharmaceutically acceptable salt, hydrate, solvate, prodrug, stereoisomer, or tautomer thereof, for use in treating or preventing a disorder that is affected by the inhibition of WIZ protein levels, in a subject in need thereof.

Embodiment 68. A compound of any one of Embodiments 1 to 49, or a pharmaceutically acceptable salt, hydrate, solvate, prodrug, stereoisomer, or tautomer thereof, for use in treating or preventing a disorder that is affected by the reduction of WIZ protein levels, in a subject in need thereof.

Embodiment 69. A compound of any one of Embodiments 1 to 49, or a pharmaceutically acceptable salt, hydrate, solvate, prodrug, stereoisomer, or tautomer thereof, for use in the treatment or prevention of a disease or disorder that is affected by the degradation of WIZ protein.

Embodiment 70. A compound of any one of Embodiments 1 to 49, or a pharmaceutically acceptable salt, hydrate, solvate, prodrug, stereoisomer, or tautomer thereof, for use in inhibiting, reducing, or eliminating the activity of WIZ protein or WIZ protein expression in a subject in need thereof.

Embodiment 71. A compound of any one of Embodiments 1 to 49, or a pharmaceutically acceptable salt, hydrate, solvate, prodrug, stereoisomer, or tautomer thereof, for use in inducing or promoting fetal hemoglobin in a subject in need thereof.

Embodiment 72. A compound of any one of Embodiments 1 to 49, or a pharmaceutically acceptable salt, hydrate, solvate, prodrug, stereoisomer, or tautomer thereof, for use in reactivating fetal hemoglobin production or expression in a subject in need thereof.

Embodiment 73. A compound of any one of Embodiments 1 to 49, or a pharmaceutically acceptable salt, hydrate, solvate, prodrug, stereoisomer, or tautomer thereof, for use in increasing fetal hemoglobin expression in a subject in need thereof.

Embodiment 74. A compound of any one of Embodiments 1 to 49, or a pharmaceutically acceptable salt, hydrate, solvate, prodrug, stereoisomer, or tautomer thereof, for use in treating a hemoglobinopathy in a subject in need thereof.

Embodiment 75. A compound of any one of Embodiments 1 to 49, or a pharmaceutically acceptable salt, hydrate, solvate, prodrug, stereoisomer, or tautomer thereof, for use in treating a sickle cell disease in a subject in need thereof.

Embodiment 76. A compound of any one of Embodiments 1 to 49, or a pharmaceutically acceptable salt, hydrate, solvate, prodrug, stereoisomer, or tautomer thereof, for use in treating beta-thalassemia in a subject in need thereof.

Embodiment 77. A compound of any one of Embodiments 1 to 49, or a pharmaceutically acceptable salt, hydrate, solvate, prodrug, stereoisomer, or tautomer thereof, for use in the treatment of a disease or disorder affected by an increase in fetal hemoglobin expression.

Embodiment 78. A compound of any one of Embodiments 1 to 49, or a pharmaceutically acceptable salt, hydrate, solvate, prodrug, stereoisomer, or tautomer thereof, for use in the treatment of a disease or disorder affected by the inhibition, reduction, or elimination of the activity of WIZ protein or WIZ protein expression.

Embodiment 79. A compound of any one of Embodiments 1 to 49, or a pharmaceutically acceptable salt, hydrate, solvate, prodrug, stereoisomer, or tautomer thereof, for use in the treatment of a disease or disorder affected by the induction or promotion of fetal hemoglobin.

Embodiment 80. A compound of any one of Embodiments 1 to 49, or a pharmaceutically acceptable salt, hydrate, solvate, prodrug, stereoisomer, or tautomer thereof, for use in the treatment of a disease or disorder affected by the reactivation of fetal hemoglobin production or expression.

Embodiment 81. A compound of any one of Embodiments 1 to 49, or a pharmaceutically acceptable salt, hydrate, solvate, prodrug, stereoisomer, or tautomer thereof, for use in inhibiting WIZ protein expression in a subject in need thereof.

Embodiment 82. A compound of any one of Embodiments 1 to 49, or a pharmaceutically acceptable salt, hydrate, solvate, prodrug, stereoisomer, or tautomer thereof, for use in degrading WIZ protein in a subject in need thereof.

Embodiment 83. Use of a compound of any one of Embodiments 1 to 49, or a pharmaceutically acceptable salt, hydrate, solvate, prodrug, stereoisomer, or tautomer thereof, in the manufacture of a medicament for treating a disease or disorder that is affected by the reduction of WIZ protein levels, inhibition of WIZ protein expression or degradation of WIZ protein.

Embodiment 84. Use of a compound of any one of Embodiments 1 to 49, or a pharmaceutically acceptable salt, hydrate, solvate, prodrug, stereoisomer, or tautomer thereof, in the manufacture of a medicament for treating a disease or disorder that is affected by inducing or promoting fetal hemoglobin.

Embodiment 85. Use of a compound of any one of Embodiments 1 to 49, or a pharmaceutically acceptable salt, hydrate, solvate, prodrug, stereoisomer, or tautomer thereof, in the manufacture of a medicament for treating a disease or disorder that is affected by reactivating fetal hemoglobin production or expression.

Embodiment 86. Use of a compound of any one of Embodiments 1 to 49, or a pharmaceutically acceptable salt, hydrate, solvate, prodrug, stereoisomer, or tautomer thereof, in the manufacture of a medicament for treating a disease or disorder that is affected by increasing fetal hemoglobin expression.

Embodiment 87. The use of a compound of any one of Embodiments 83 to 86, wherein the disease or disorder is selected from sickle cell disease and beta-thalassemia.

Embodiment 88. Use of a compound of any one of Embodiments 1 to 49, or a pharmaceutically acceptable salt, hydrate, solvate, prodrug, stereoisomer, or tautomer thereof, in the treatment of a disease or disorder that is affected by the reduction of WIZ protein levels, inhibition of WIZ protein expression or degradation of WIZ protein.

Embodiment 89. Use of a compound of any one of Embodiments 1 to 49, or a pharmaceutically acceptable salt, hydrate, solvate, prodrug, stereoisomer, or tautomer thereof, in the treatment of a disease or disorder that is affected by inducing fetal hemoglobin, reactivating fetal hemoglobin production or expression, or increasing fetal hemoglobin expression.

Embodiment 90. The use of Embodiment 88 or 89, wherein the disease or disorder is selected from sickle cell disease and beta-thalassemia.

Embodiment 91. A pharmaceutical combination comprising a compound of any one of Embodiments 1 to 49, or a pharmaceutically acceptable salt, hydrate, solvate, prodrug, stereoisomer, or tautomer thereof, and one or more additional therapeutic agent(s).

Depending on the choice of the starting materials and procedures, the compounds can be present in the form of one of the possible isomers or as mixtures thereof, for example as pure optical isomers, or as isomer mixtures, such as racemates and diastereomeric mixtures, depending on the number of asymmetric centres. The disclosure is meant to include all such possible isomers, including racemic mixtures, enantiomerically enriched mixtures, diastereomeric mixtures and optically pure forms. Optically active (R)- and (S)-isomers may be prepared using chiral synthons or chiral reagents, or resolved using conventional techniques. If the compound contains a disubstituted or trisubstituted cycloalkyl, the cycloalkyl substituent(s) may have a cis- or trans-configuration. The disclosure includes cis and trans configurations of substituted cycloalkyl groups as well as mixtures thereof. All tautomeric forms are also intended to be included. In particular, where a heteroaryl ring containing N as a ring atom is 2-pyridone, for example, tautomers where the carbonyl is depicted as a hydroxy (e.g., 2-hydroxypyridine) are included.

Pharmaceutically Acceptable Salts

As used herein, the terms "salt" or "salts" refers to an acid addition or base addition salt of a compound of the disclosure. "Salts" include in particular "pharmaceutically acceptable salts". The term "pharmaceutically acceptable salts" refers to salts that retain the biological effectiveness and properties of the compounds of this disclosure and, which typically are not biologically or otherwise undesirable. The compounds of the disclosure may be capable of forming acid and/or base salts by virtue of the presence of amino and/or carboxyl groups or groups similar thereto.

Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, formic acid, trifluoroacetic acid, and the like.

Pharmaceutically acceptable base addition salts can be formed with inorganic and organic bases. Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the disclosure provides compounds in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, formate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

In another aspect, the disclosure provides compounds in sodium, potassium, ammonium, calcium, magnesium, iron, silver, zinc, copper, isopropylamine, benzathine, cholinate, diethanolamine, diethylamine, lysine, meglumine, piperazine or tromethamine salt form.

Preferably, pharmaceutically acceptable salts of compounds of formulae (I), (Ia), (Ib), (Ic), (Id), and (Ie), are acid addition salts.

Isotopically Labelled Compounds

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, sulfur, fluorine, chlorine and iodine, such as $^{2}H$, $^{3}H$, $^{11}C$, $^{13}C$, $^{14}C$, $^{18}O$, $^{15}N$, $^{18}F$, $^{17}O$, $^{18}O$, $^{35}S$, $^{36}Cl$, $^{123}I$, $^{124}I$, $^{125}I$ respectively. The disclosure includes various isotopically labeled compounds as defined herein, for example those into which radioactive isotopes, such as $^{3}H$ and $^{14}C$, or those into which non-radioactive isotopes, such as $^{2}H$ and $^{13}C$ are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ compound may be particularly desirable for PET or SPECT studies. Isotopically-labeled compounds of formulae (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), and (Ie), can generally be prepared by conventional techniques known to those skilled in the art or by processes analogous to those described in the accompanying Examples and General Schemes (e.g., General Schemes 1 to 5) using an appropriate isotopically-labeled reagent in place of the non-labeled reagent previously employed.

In one embodiment of any aspect of the present disclosure, the hydrogens in the compound of Formula (I), Formula (I') or Formula (I") (and subformulae thereof) are present in their normal isotopic abundances. In a another embodiment, the hydrogens are isotopically enriched in deuterium (D), and in a particular embodiment of the disclosure the hydrogen(s) of the dihydrouracil (DHU) or the uracil portion in compounds of Formula (I) or Formula (I') are enriched in D, for example,

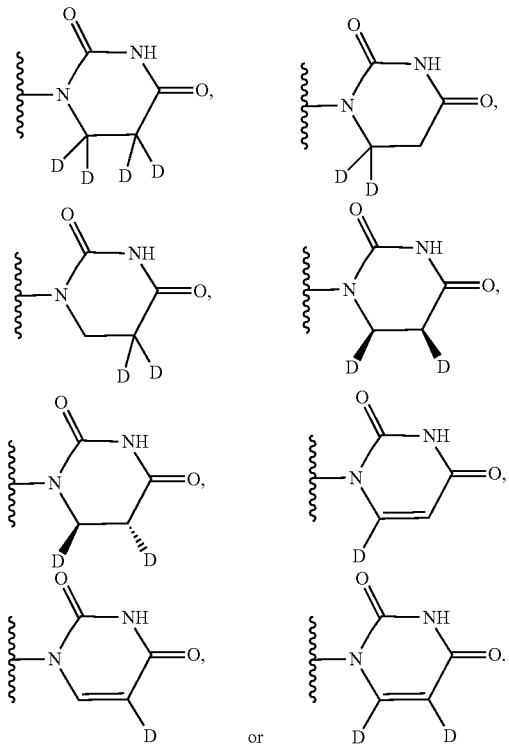

Deuterated dihydrouracil and uracil moities can be prepared as described in Hill, R. K. et al., Journal of Labelled Compounds and Radiopharmaceuticals, Vol. XXII, No. 2, p. 143-148.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formulae (I"), (I'), (I), (Ia"), (Ia'), (Ia), (Ib"), (Ib'), (b), (Ic"), (Ic'), (Ic), (Id"), (Id'), (Id), (Id-1), (Id-2), (Id-3), (Ie"), (Ie'), and (Ie). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this disclosure is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the disclosure include those wherein the solvent of crystallization may be isotopically substituted, e.g., $D_2O$, $d_6$-acetone, $d_6$-DMSO.

Compounds of the disclosure, i.e. compounds of formulae (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), and (Ie), that contain groups capable of acting as donors and/or acceptors for hydrogen bonds may be capable of forming co-crystals with suitable co-crystal formers. These co-crystals may be prepared from compounds of (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), and (Ie) by known co-crystal forming procedures. Such procedures include grinding, heating, co-subliming, co-melting, or contacting in solution compounds of formulae (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), and (Ie) with the co-crystal former under crystallization conditions and isolating co-crystals thereby formed. Suitable co-crystal formers include those described in WO 2004/078163.

All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed.

Any asymmetric center (e.g., carbon or the like) of the compound(s) of the disclosure can be present in racemic or enantiomerically enriched, for example the (R)-, (S)- or (R,S)-configuration. In certain embodiments, for example, as a mixture of enantiomers, each asymmetric center is present in at least 10% enantiomeric excess, at least 20% enantiomeric excess, at least 30% enantiomeric excess, at least 40% enantiomeric excess, at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess. In certain embodiments, for example, in enantiomerically enriched form, each asymmetric center is present in at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess. Thus, compounds of the disclosure can be present in a racemic mixture or in enantiomerically enriched form or in an enantiopure form or as a mixture of diastereoisomers.

In the formulae of the present application the term "⌀" on a C-sp$^3$ indicates the absolute stereochemistry, either (R) or (S). In the formulae of the present application the term "⌀" on a C-sp$^3$ indicates the absolute stereochemistry, either (R) or (S). In the formulae of the present application the term "⌀" on a C-sp$^3$ represents a covalent bond wherein the stereochemistry of the bond is not defined. This means that the term "╱" on a C-sp3 comprises an (S) configuration or an (R) configuration of the respective chiral centre. Furthermore, mixtures may also be present. Therefore, mixtures of stereoisomers, e.g., mixtures of enantiomers, such as racemates, and/or mixtures of diastereoisomers are encompassed by the present disclosure.

For the avoidance of doubt, where compound structures are drawn with undefined stereochemistry with respect to any R group, for example, to $R^2$ in formula (I), as represented by a bond (╱), this means the asymmetric center has either a (R)- or (S)-configuration, or exists as a mixture thereof and stated as such.

Accordingly, as used herein a compound of the disclosure can be in the form of one of the possible stereoisomers, rotamers, atropisomers, tautomers or mixtures thereof, for example, as substantially pure geometric (cis or trans) stereoisomers, diastereomers, optical isomers, racemates or mixtures thereof.

Any resulting mixtures of stereoisomers can be separated on the basis of the physicochemical differences of the constituents, into the pure or substantially pure geometric or optical isomers, diastereomers, racemates, for example, by chromatography and/or fractional crystallization.

Any resulting racemates of compounds of the disclosure or of intermediates can be resolved into the optical isomers (enantiomers) by known methods, e.g., by separation of the diastereomeric salts thereof, obtained with an optically active acid or base, and liberating the optically active acidic or basic compound. In particular, a basic moiety may thus be employed to resolve the compounds of the disclosure into their optical antipodes, e.g., by fractional crystallization of a salt formed with an optically active acid, e.g., tartaric acid, dibenzoyl tartaric acid, diacetyl tartaric acid, di-O,O'p-toluoyl tartaric acid, mandelic acid, malic acid or camphor-10-sulfonic acid. Racemic compounds of the disclosure or racemic intermediates can also be resolved by chiral chromatography, e.g., high pressure liquid chromatography (HPLC) using a chiral adsorbent.

Furthermore, the compounds of the disclosure, including their salts, can also be obtained in the form of their hydrates, or include other solvents used for their crystallization. The compounds of the disclosure may inherently or by design form solvates with pharmaceutically acceptable solvents (including water); therefore, it is intended that the disclosure embrace both solvated and unsolvated forms. The term "solvate" refers to a molecular complex of a compound of the disclosure (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water. The presence of solvates can be identified by a person of skill in the art with tools such as NMR.

The compounds of the disclosure, including salts, hydrates and solvates thereof, may inherently or by design form polymorphs.

Methods of Making

The compounds of the disclosure can be prepared in a number of ways well known to those skilled in the art of organic synthesis. By way of example, compounds of the present disclosure can be synthesized using the methods described below, together with synthetic methods known in the art of synthetic organic chemistry, or variations thereon as appreciated by those skilled in the art.

Generally, the compounds of formula (I″), formula (I) and formula (I′) can be prepared according to the Schemes provided infra.

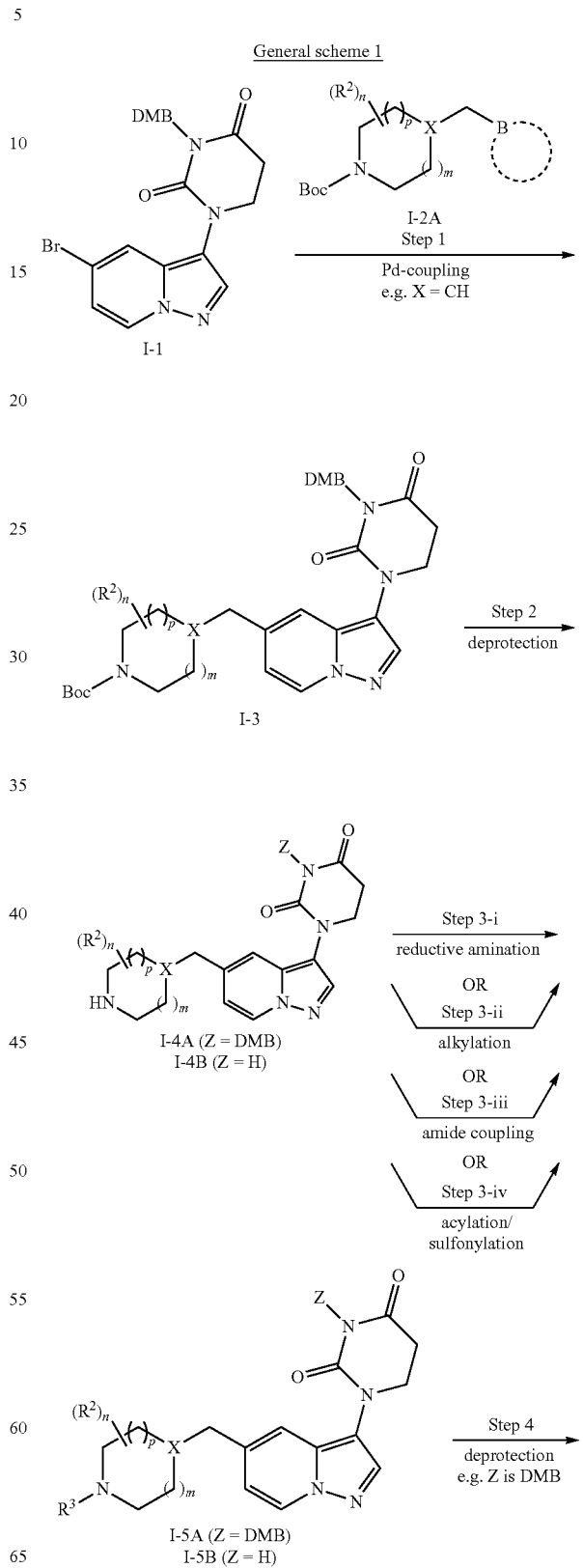

General scheme 1

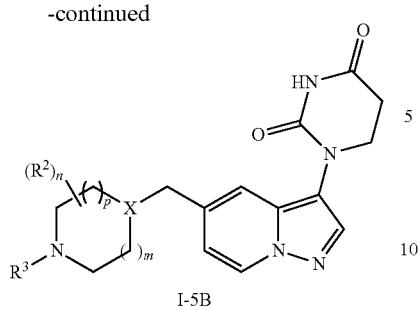

I-5B

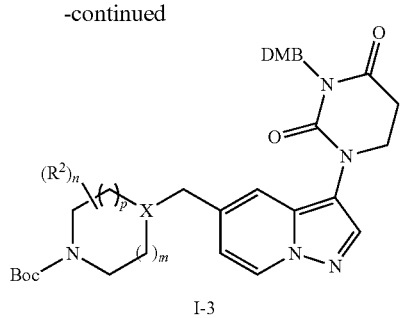

I-3

The starting materials for the above reaction scheme are commercially available or can be prepared according to methods known to one skilled in the art or by methods disclosed herein. In general, the compounds of the disclosure are prepared in the above reaction Scheme 1 as follows:

A cross-coupling reaction, such as a palladium (Pd)-catalysed coupling of I-1 with a boraneyl coupling partner of formula I-2A (prepared by hydroboration of an appropriate alkene with 9-BBN, for example) in the presence of a polar solvent, such as N,N-dimethylformamide (DMF), a suitable ligand such as dppf, and a base such as potassium carbonate ($K_2CO_3$) can provide the cross-coupled product 1-3 in Step 1, where X is CH. Removal of the protecting group (e.g., Boc) under acidic conditions at room temperature can provide the free amine I-4A, where Z=2,4-dimethoxybenzyl (DMB). Alternatively, removal of the protecting groups under acidic conditions and heating can provide I-4B (Step 2). I-4A and I-4B can then be converted respectively to I-5A and I-5B via a reductive amination (Step 3-i) with an appropriate aldehyde in the presence of a borohydride reagent, such as sodium borohydride acetate. Alternatively, by an alkylation reaction (Step 3-ii) with an appropriate alkyl halide, mesylate, tosylate or triflate in the presence of an amine or carbonate base and polar solvent, such as diisopropylethylamine (DIPEA) or potassium carbonate ($K_2CO_3$) and dimethylformamide (DMF). Alternatively, by an amide coupling reaction (Step 3-iii) of the compound with an appropriate carboxylic acid, an activating agent, such as HATU, and a base such as DIPEA, when $R^3$ forms an amide with the nitrogen to which it is attached. Alternatively, by an acylation or sulfonylation reaction (Step 3-iv) with an appropriate acyl chloride or sulfonyl chloride and a base such as DIPEA or TEA, where $R^3$ forms an amide or sulfonamide with the nitrogen to which it is attached. Removal of the protecting group of I-5A under acidic conditions and heating can provide I-5B (Step 4).

General scheme 2

II-2B
Step 1
Pd-coupling
e.g. X = N

The starting materials for the above reaction scheme are commercially available or can be prepared according to methods known to one skilled in the art or by methods disclosed herein. In general, the compounds of the disclosure are prepared in the above reaction Scheme 2 as follows:

A cross-coupling reaction, such as a palladium (Pd)-catalysed coupling of I-1 with a trifluoroborate (potassium salt) coupling partner of formula II-2B in the presence of an organic solvent such as toluene, and water, a phosphine ligand such as RuPhos or Xphos, and a base such as cesium carbonate ($Cs_2CO_3$) can provide the cross-coupled product 1-3 in Step 1, where X is N. Compound 1-3 as prepared in this manner, can be converted to compounds of formula I-5B by the methods of General Scheme 1, steps 2-4.

General scheme 3

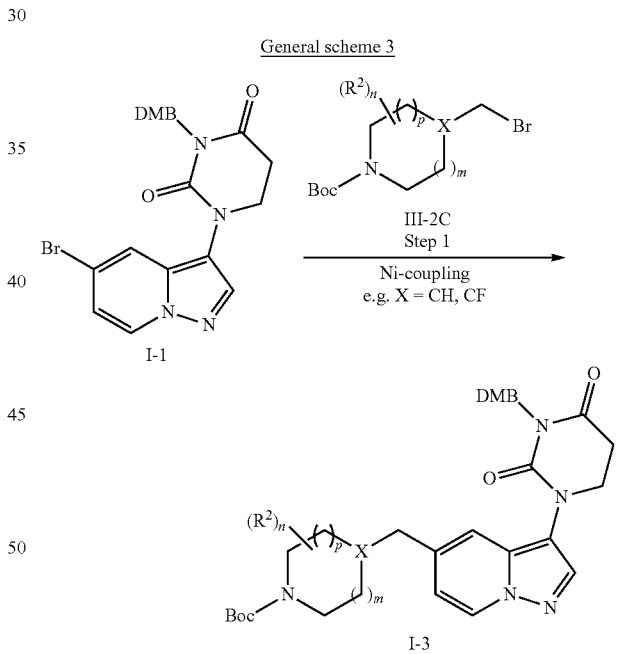

III-2C
Step 1
Ni-coupling
e.g. X = CH, CF

I-3

The starting materials for the above reaction scheme are commercially available or can be prepared according to methods known to one skilled in the art or by methods disclosed herein. In general, the compounds of the disclosure are prepared in the above reaction Scheme 3 as follows:

A cross-coupling reaction, such as a nickel (Ni)-catalysed coupling of I-1 with an alkyl bromide coupling partner of formula III-2C in the presence of a polar solvent such as DMA, a salt such as sodium iodide (NaI), zinc (Zn), and a ligand such as pyridine-2,6-bis(carboximidamide) dihydrochloride can provide the cross-coupled product 1-3 in Step 1, where X is CH or CF. Compound 1-3 as prepared in this manner, can be converted to compounds of formula 1-5B by the methods of General Scheme 1, steps 2-4.

General Scheme 4

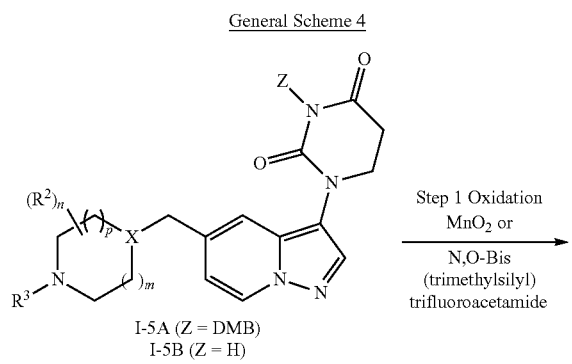

I-5A (Z = DMB)
I-5B (Z = H)

Step 1 Oxidation
MnO₂ or
N,O-Bis(trimethylsilyl)trifluoroacetamide

IV-5C

Step 2
deprotection
e.g. Z is DMB

IV-5D

In General Scheme 4, a compound of formula I-5A or I-5B is subjected to oxidation conditions, e.g., MnO₂, in a suitable solvent, such as toluene (e.g., at room temperature), or in the presence of N,O-bis(trimethylsilyl)trifluoroacetamide, to produce a compound of formula IV-5C (i.e., formula (I') when Z=H), followed by an optional deprotection step when the Z group represents a nitrogen protecting group, to give a compound of formula IV-5D (i.e., formula (I')).

General Scheme 5

I-5A (Z = DMB)

1) LDA, CH₃CH₂OCOCl
2) i) PhSeCl, Pyridine
   ii) H₂O₂

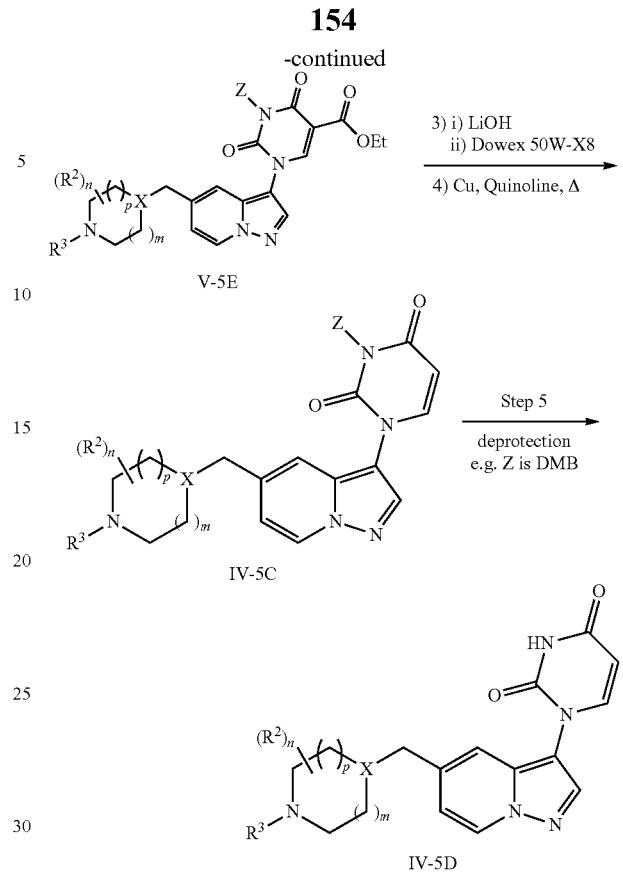

V-5E 3) i) LiOH
   ii) Dowex 50W-X8
4) Cu, Quinoline, Δ

IV-5C

Step 5
deprotection
e.g. Z is DMB

IV-5D

In General Scheme 5, a compound of formula 1-5A undergoes a Claisen condensation followed by selenation/oxidation/elimination sequence to give a compound of formula V-5E. Compound formula V-5E undergoes hydrolysis followed by a copper-catalysed decarboxylation to give a compound of formula IV-5C. Subsequent deprotection, e.g., under acidic conditions and heating, provides a compound of formula IV-5D (i.e., formula (I') or (I")).

For Schemes 1 to 5, X, R², R³, n, m and p are as defined herein, in particular according to any one of Embodiments 1 to 49.

In a further embodiment, there is provided a compound of formula I-1, which is

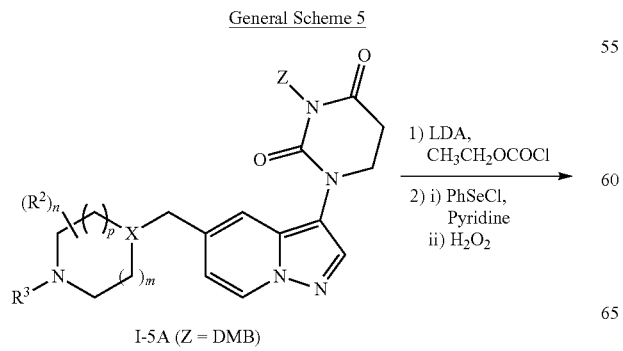

1-(5-bromopyrazolo[1,5-a]pyridin-3-yl)-3-(2,4-dimethoxybenzyl)dihydropyrimidine-2,4(1H,3H)-dione.

In a further embodiment, there is provided a compound of formula (X-1) or a salt thereof,

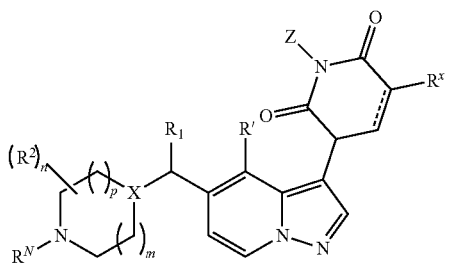

(X-1)

wherein:
=== is a single bond or a double bond;
X is selected from CH, CF, and N;
Z is selected from hydrogen and 2,4-dimethoxybenzyl (DMB);
$R^x$ is selected from hydrogen, $C_1$-$C_6$alkyl, halo (e.g., F, Cl), $C_1$-$C_6$alkoxyl, and $C_3$-$C_8$cycloalkyl;
$R^N$ is selected from hydrogen and a nitrogen protecting group PG (e.g., tert-butyloxycarbonyl (Boc));
R' is selected from hydrogen and $C_1$-$C_6$alkyl;
$R^1$ is selected from hydrogen and $C_1$-$C_6$alkyl;
each $R^2$ is independently selected from $C_1$-$C_6$alkyl, $C_1$-$C_6$haloalkyl, halo, and oxo, wherein the $C_1$-$C_6$alkyl is substituted with 0-1 occurrence of $R^{2a}$; or 2 $R^2$ on non-adjacent carbon atoms together with the non-adjacent carbon atoms to which they are attached form a bridging ring;
$R^{2a}$ is selected from $C_1$-$C_6$alkoxyl and hydroxyl;
n is 0, 1, 2, 3 or 4;
m is 0, 1 or 2; and
p is 0 or 1.

In a further embodiment, there is provided a compound of formula (X) or a salt thereof,

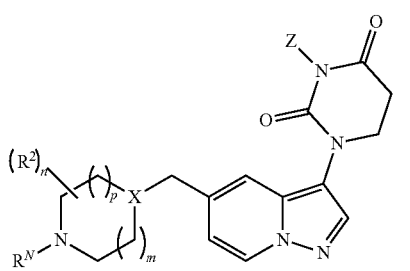

(X)

wherein:
X is selected from CH, CF, and N;
Z is selected from hydrogen and 2,4-dimethoxybenzyl (DMB);
$R^N$ is selected from hydrogen and a nitrogen protecting group PG (e.g., tert-butyloxycarbonyl (Boc))
each $R^2$ is independently selected from $C_1$-$C_6$alkyl, $C_1$-$C_6$haloalkyl, halo, and oxo, wherein the $C_1$-$C_6$alkyl is substituted with 0-1 occurrence of $R^{2a}$; or 2 $R^2$ on non-adjacent carbon atoms together with the non-adjacent carbon atoms to which they are attached form a bridging ring;
$R^{2a}$ is selected from $C_1$-$C_6$alkoxyl and hydroxyl;
n is 0, 1, 2, 3 or 4;
m is 0, 1 or 2; and
p is 0 or 1.

In an embodiment of formula (X-1) or (X), PG is an acid labile protecting group.

In an embodiment of formula (X-1) or (X), PG is the Boc protecting group (tert-butyloxycarbonyl).

In a further embodiment of formula (X-1) or (X), there is provided a compound or a salt thereof, selected from:
tert-butyl (2S,4R)-4-((3-(2,4-dioxo-3,4-dihydropyrimidin-1 (2H)-yl)pyrazolo[1,5-a]pyridin-5-yl)methyl)-2-methylpiperidine-1-carboxylate;
1-(5-(((2S,4R)-2-methylpiperidin-4-yl)methyl)pyrazolo[1,5-a]pyridin-3-yl)pyrimidine-2,4(1H,3H)-dione;
(S)-5-methyl-1-(5-((3-methylpiperazin-1-yl)methyl)pyrazolo[1,5-a]pyridin-3-yl)pyrimidine-2,4(1H,3H)-dione;
tert-butyl (S)-2-methyl-4-((3-(5-methyl-2,4-dioxo-3,4-dihydropyrimidin-1(2H)-yl)pyrazolo[1,5-a]pyridin-5-yl) methyl)piperazine-1-carboxylate;
tert-butyl (2S,4R)-2-methyl-4-((3-(5-methyl-2,4-dioxo-3,4-dihydropyrimidin-1(2H)-yl)pyrazolo[1,5-a]pyridin-5-yl) methyl)piperidine-1-carboxylate;
5-methyl-1-(5-(((2S,4R)-2-methylpiperidin-4-yl)methyl) pyrazolo[1,5-a]pyridin-3-yl)pyrimidine-2,4(1H,3H)-dione;
5-fluoro-1-(5-(((2S,4R)-2-methylpiperidin-4-yl)methyl) pyrazolo[1,5-a]pyridin-3-yl)pyrimidine-2,4(1H,3H)-dione;
tert-butyl (2S,4R)-4-((3-(5-fluoro-2,4-dioxo-3,4-dihydropyrimidin-1(2H)-yl)pyrazolo[1,5-a]pyridin-5-yl)methyl)-2-methylpiperidine-1-carboxylate;
(S)-5-fluoro-1-(5-((3-methylpiperazin-1-yl)methyl)pyrazolo[1,5-a]pyridin-3-yl)pyrimidine-2,4(1H,3H)-dione;
tert-butyl (S)-4-((3-(5-fluoro-2,4-dioxo-3,4-dihydropyrimidin-1(2H)-yl)pyrazolo[1,5-a]pyridin-5-yl)methyl)-2-methylpiperazine-1-carboxylate;
5-chloro-1-(5-(((2S,4R)-2-methylpiperidin-4-yl)methyl) pyrazolo[1,5-a]pyridin-3-yl)pyrimidine-2,4(1H,3H)-dione;
tert-butyl (2S,4R)-4-((3-(5-chloro-2,4-dioxo-3,4-dihydropyrimidin-1(2H)-yl)pyrazolo[1,5-a]pyridin-5-yl)methyl)-2-methylpiperidine-1-carboxylate;
5-methoxy-1-(5-(((2S,4R)-2-methylpiperidin-4-yl)methyl) pyrazolo[1,5-a]pyridin-3-yl)pyrimidine-2,4(1H,3H)-dione;
tert-butyl (2S,4R)-4-((3-(5-methoxy-2,4-dioxo-3,4-dihydropyrimidin-1 (2H)-yl)pyrazolo[1,5-a]pyridin-5-yl) methyl)-2-methylpiperidine-1-carboxylate;
(S)-5-methoxy-1-(5-((3-methylpiperazin-1-yl)methyl)pyrazolo[1,5-a]pyridin-3-yl)pyrimidine-2,4(1H,3H)-dione;
tert-butyl (S)-4-((3-(5-methoxy-2,4-dioxo-3,4-dihydropyrimidin-1(2H)-yl)pyrazolo[1,5-a]pyridin-5-yl)methyl)-2-methylpiperazine-1-carboxylate;
(S)-5-cyclopropyl-1-(5-((3-methylpiperazin-1-yl)methyl) pyrazolo[1,5-a]pyridin-3-yl)pyrimidine-2,4(1H,3H)-dione;
tert-butyl (S)-4-((3-(5-cyclopropyl-2,4-dioxo-3,4-dihydropyrimidin-1(2H)-yl)pyrazolo[1,5-a]pyridin-5-yl)methyl)-2-methylpiperazine-1-carboxylate;
5-cyclopropyl-1-(5-(((2S,4R)-2-methylpiperidin-4-yl) methyl)pyrazolo[1,5-a]pyridin-3-yl)pyrimidine-2,4(1H, 3H)-dione;
tert-butyl (2S,4R)-4-((3-(5-cyclopropyl-2,4-dioxo-3,4-dihydropyrimidin-1 (2H)-yl)pyrazolo[1,5-a]pyridin-5-yl) methyl)-2-methylpiperidine-1-carboxylate;
(S)-1-(5-((3-methylpiperazin-1-yl)methyl)pyrazolo[1,5-a] pyridin-3-yl)pyrimidine-2,4(1H,3H)-dione;

tert-butyl (S)-4-((3-(2,4-dioxo-3,4-dihydropyrimidin-1 (2H)-yl)pyrazolo[1,5-a]pyridin-5-yl)methyl)-2-methylpiperazine-1-carboxylate;

tert-butyl (2S,4R)-4-((3-(3-(3,4-dimethylbenzyl)-2,4-dioxotetrahydropyrimidin-1(2H)-yl)pyrazolo[1,5-a]pyridin-5-yl)methyl)-2-methylpiperidine-1-carboxylate;

3-(3,4-dimethylbenzyl)-1-(5-(((2S,4R)-2-methylpiperidin-4-yl)methyl)pyrazolo[1,5-a]pyridin-3-yl)dihydropyrimidine-2,4(1H,3H)-dione;

1-(5-(((2S,4R)-2-methylpiperidin-4-yl)methyl)pyrazolo[1,5-a]pyridin-3-yl)dihydropyrimidine-2,4(1H,3H)-dione;

tert-butyl 4-((3-(3-(3,4-dimethylbenzyl)-2,4-dioxotetrahydropyrimidin-1(2H)-yl)pyrazolo[1,5-a]pyridin-5-yl)methyl)piperazine-1-carboxylate;

3-(3,4-dimethylbenzyl)-1-(5-(piperazin-1-ylmethyl)pyrazolo[1,5-a]pyridin-3-yl)dihydropyrimidine-2,4(1H,3H)-dione;

1-(5-(piperazin-1-ylmethyl)pyrazolo[1,5-a]pyridin-3-yl)dihydropyrimidine-2,4(1H,3H)-dione;

tert-butyl 4-((3-(3-(3,4-dimethylbenzyl)-2,4-dioxotetrahydropyrimidin-1 (2H)-yl)pyrazolo[1,5-a]pyridin-5-yl)methyl)piperidine-1-carboxylate;

3-(3,4-dimethylbenzyl)-1-(5-(piperidin-4-ylmethyl)pyrazolo[1,5-a]pyridin-3-yl)dihydropyrimidine-2,4(1H,3H)-dione;

1-(5-(piperidin-4-ylmethyl)pyrazolo[1,5-a]pyridin-3-yl)dihydropyrimidine-2,4(1H,3H)-dione;

tert-butyl (S)-4-((3-(3-(3,4-dimethylbenzyl)-2,4-dioxotetrahydropyrimidin-1(2H)-yl)pyrazolo[1,5-a]pyridin-5-yl)methyl)-2-methylpiperazine-1-carboxylate;

(S)-3-(3,4-dimethylbenzyl)-1-(5-((3-methylpiperazin-1-yl)methyl)pyrazolo[1,5-a]pyridin-3-yl)dihydropyrimidine-2,4(1H,3H)-dione; and (S)-1-(5-((3-methylpiperazin-1-yl)methyl)pyrazolo[1,5-a]pyridin-3-yl)dihydropyrimidine-2,4(1H,3H)-dione.

In an embodiment of formula (X-1) or (X), the salt is selected from a HCl and TFA salt.

In a further aspect, the disclosure provides to a process for the preparation of a compound of formula (I), (I'), (I") or subformulae thereof, in free form or in pharmaceutically acceptable salt form, comprising the step of:

1) coupling an aryl bromide of formula (I-1) with a boraneyl coupling partner of formula I-2A or II-2B under cross coupling conditions, to give a compound of formula (I-3) as defined herein.

The boraneyl coupling partner of step 1 may optionally be prepared by hydroboration of a precursor alkene, e.g., with 9-BBN.

In a further aspect, the disclosure provides a process for the preparation of a compound of formula (I), (I'), (I") or subformulae thereof, in free form or in pharmaceutically acceptable salt form, comprising the step of:

1) coupling an aryl bromide of formula (I-1) with an alkyl bromide of formula (III-2C) under cross coupling conditions, to give a compound of formula (I-3) as defined herein.

Cross coupling reaction conditions for any of the aforementioned process steps or hereinafter involve the use of a Pd catalyst in the presence of a phosphine ligand, such as Pd(OAc)$_2$ and RuPhos or Xphos, and a base such as cesium carbonate (Cs$_2$CO$_3$), in the presence of a suitable solvent such as toluene, water, or a mixture thereof.

Cross coupling reaction conditions (e.g., in the case of an Sp$^2$-Sp$^3$ coupling) may alternatively involve the use of a Ni(II) complex, such as NiCl$_2$(DME), ligand, such as pyridine-2,6-bis(carboximidamide) dihydrochloride, additive such as NaI, a transmetalling agent such as Zn or Mn, a suitable solvent such as DMA, heating at a temperature of r.t. to 150° C., e.g., 70° C., for example, over a period of 12 hours.

In an embodiment of either process aspect described above, there is provided the further steps of:

2) deprotecting a compound of formula (I)-3 to give a compound of formula (I)-4A or (I)-4B as defined herein;

3-a) reacting a compound of formula (I)-4A or (I)-4B under reductive amination conditions to give a compound of formula (I)-5A or (I)-5B as defined herein; or 3-b) reacting a compound of formula (I)-4A or (I)-4B under alkylation conditions to give a compound of formula (I)-5A or (I)-5B as defined herein; or 3-c) reacting a compound of formula (I)-4A or (I)-4B under amide coupling conditions to give a compound of formula (I)-5A or (I)-5B as defined herein; or 3-d) reacting a compound of formula (I)-4A or (I)-4B under acylation or sulfonylation conditions to give a compound of formula (I)-5A or (I)-5B as defined herein; and 4) deprotecting the compound of formula (I)-5A to give a compound of formula (I) as described herein.

Reductive amination conditions for any of the aforementioned process steps or hereinafter involve the use of a corresponding aldehyde, a suitable hydride reagent, such as NaBH(OAc)$_3$, a suitable solvent, such as DMF, the reaction conducted at room temperature (r.t.).

Alkylation reaction conditions for any of the aforementioned process steps or hereinafter involve the use of a corresponding alkyl halide, mesylate, tosylate or triflate in the presence of a suitable base, such as DIPEA, or a carbonate base such as K$_2$CO$_3$, a polar solvent, such as DMF, the reaction conducted at a suitable temperature, such as r.t. to 100° C., e.g., 80° C., optionally, under microwave.

Amide coupling reaction conditions for any of the aforementioned process steps or hereinafter involve the use of a corresponding carboxylic acid, an activating agent, such as HATU, a suitable base, such as DIPEA or NMM, a suitable solvent, such as DMF, the reaction conducted at a suitable temperature, such as r.t., for a suitable amount of time, for example 12 hours.

Acylation or sulfonylation reaction conditions for any of the aforementioned process steps or hereinafter involve the use of a corresponding acyl chloride or sulfonyl chloride and a base such as DIPEA or TEA, in the presence of a suitable solvent such as DCM, the reaction conducted at a suitable temperature, such as r.t.

In a further embodiment there is provided a process for the preparation of a compound of formula (I') or (I"), comprising the step:

1) coupling an aryl bromide of formula

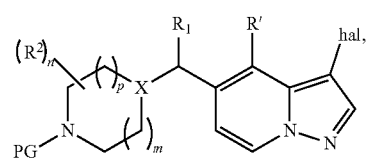

wherein hal is halo, preferably I, with

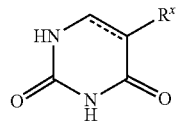

under cross coupling reaction conditions, to give a compound of formula

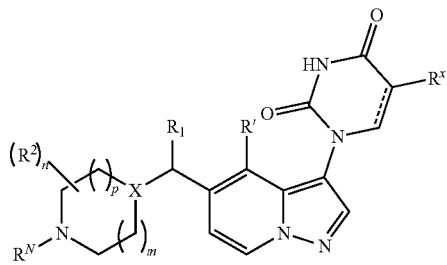

as defined herein, wherein ═ is a double bond or a single bond, $R^1$, R', X, $R^2$, n, m, p, $R^x$ are as defined herein, e.g., according to any one of enumerated Embodiments 1 to 49, PG is a nitrogen protecting group as defined herein, e.g., Boc, and $R^N$ is selected from hydrogen and a nitrogen protecting group PG (e.g., tert-butyloxycarbonyl (Boc)). In an embodiment, $R^1$ and R' are both hydrogen.

Cross coupling conditions for the aforementioned process may involve the use of copper as a catalyst, e.g., Ullmann reaction conditions. For example, reaction conditions may employ copper(I) iodide as a catalyst, a ligand, such as N-(2-cyanophenyl)picolinamide, a base, such as $K_3PO_4$, a suitable solvent, such as DMSO, heating at a temperature of r.t. to 130° C., e.g., 70 to 120° C., e.g., 110° C. The reaction may be heated over a period of 72 hours.

In a further embodiment there is provided a process for the preparation of a compound of formula (I), (I'), (I") or subformulae thereof, in free form or in pharmaceutically acceptable salt form according to any of General Schemes 1 to 5.

Compounds of formulae (I)-1, (X-1) and (X) as defined herein are useful in the preparation of compounds of the disclosure, e.g., compounds of formulae (I"), (I'), (I), (Ia"), (Ia'), (Ia), (Ib"), (Ib'), (Ic"), (Ic'), (Ic), (Id"), (Id'), (Id), (Id-1), (Id-2), (Id-3), (Ie"), (Ie'), and (Ie). Thus, in an aspect, the disclosure relates to a compound of formula (I)-1, (X-1) or (X) or salts thereof. In another aspect, the disclosure relates to the use of a compound of formula (I)-1, (X-1) or (X) or salts thereof in the manufacture of a compound of formulae (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), and (Ie). The disclosure further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Pharmaceutical Compositions

In another aspect, the disclosure provides a pharmaceutical composition comprising one or more compounds of described herein or a pharmaceutically acceptable salt, hydrate, solvate, prodrug, stereoisomer, or tautomer thereof, and one or more pharmaceutically acceptable carriers. As used herein, the term "pharmaceutical composition" refers to a compound of the disclosure, or a pharmaceutically acceptable salt, hydrate, solvate, prodrug, stereoisomer, or tautomer thereof, together with at least one pharmaceutically acceptable carrier, in a form suitable for oral or parenteral administration.

As used herein, the term "pharmaceutically acceptable carrier" refers to a substance useful in the preparation or use of a pharmaceutical composition and includes, for example, suitable diluents, solvents, dispersion media, surfactants, antioxidants, preservatives, isotonic agents, buffering agents, emulsifiers, absorption delaying agents, salts, drug stabilizers, binders, excipients, disintegration agents, lubricants, wetting agents, sweetening agents, flavoring agents, dyes, and combinations thereof, as would be known to those skilled in the art (see, for example, Remington The Science and Practice of Pharmacy, $22^{nd}$ Ed. Pharmaceutical Press, 2013, pp. 1049-1070).

In another aspect, the disclosure provides a pharmaceutical composition comprising a compound of the disclosure, or a pharmaceutically acceptable salt, hydrate, solvate, prodrug, stereoisomer, or tautomer thereof, and a pharmaceutically acceptable carrier. In a further embodiment, the composition comprises at least two pharmaceutically acceptable carriers, such as those described herein. For purposes of the disclosure, unless designated otherwise, solvates and hydrates are generally considered compositions. Preferably, pharmaceutically acceptable carriers are sterile. The pharmaceutical composition can be formulated for particular routes of administration such as oral administration, parenteral administration, and rectal administration, etc. In addition, the pharmaceutical compositions of the disclosure can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with one or more of:
a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol;
c) binders, e.g., magnesium aluminum silicate, starch paste, gelatin, tragacanth, methylcellulose, sodium carboxymethylcellulose and/or polyvinylpyrrolidone;
d) disintegrants, e.g., starches, agar, alginic acid or its sodium salt, or effervescent mixtures; and
e) absorbents, colorants, flavors and sweeteners.

In an embodiment, the pharmaceutical compositions are capsules comprising the active ingredient only.

Tablets may be either film coated or enteric coated according to methods known in the art.

Suitable compositions for oral administration include an effective amount of a compound of the disclosure in the form of tablets, lozenges, aqueous or oily suspensions, dispersible powders or granules, emulsion, hard or soft capsules, or syrups or elixirs, solutions or solid dispersion. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients, which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the disclosure with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The compounds of formulae (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), and (Ie) in free form or in pharmaceutically acceptable salt form, exhibit valuable pharmacological properties, e.g., WIZ modulating properties or WIZ degrading properties or HbF inducing properties e.g., as indicated in the in vitro tests as provided in the examples, and are therefore indicated for therapy or for use as research chemicals, e.g., as tool compounds.

Additional properties of the disclosed compounds include having good potency in the biological assays described herein, favorable safety profile, and possess favorable pharmacokinetic properties.

Diseases and Disorders

In an embodiment of the present disclosure, there is provided a compound of the disclosure, or a pharmaceutically acceptable salt, hydrate, solvate, prodrug, stereoisomer, or tautomer thereof, which is effective in reducing WIZ protein expression levels and/or inducing fetal hemoglobin (HbF) expression.

The compounds of the disclosure can be used to treat one or more of the diseases or disorders described herein below. In one embodiment, the disease or disorder is affected by the reduction of WIZ protein expression levels and/or induction of fetal hemoglobin protein expression levels. In another embodiment, the disease or disorder is a hemoglobinopathy, e.g., beta hemoglobinopathy, including sickle cell disease (SCD) and beta-thalassemia.

Methods of Use

All the aforementioned embodiments and embodiments hereinafter relating to the methods of reducing WIZ protein expression levels and/or inducing fetal hemoglobin (HbF) expression are equally applicable to:

A compound of the disclosure, or a pharmaceutically acceptable salt, hydrate, solvate, prodrug, stereoisomer, or tautomer thereof, for use in a method of reducing WIZ protein expression levels and/or inducing fetal hemoglobin (HbF) expression;

A compound of the disclosure, or a pharmaceutically acceptable salt, hydrate, solvate, prodrug, stereoisomer, or tautomer thereof, for use in the treatment of the aforementioned diseases or disorders according to the present disclosure;

Use of a compound of the disclosure, or a pharmaceutically acceptable salt, hydrate, solvate, prodrug, stereoisomer, or tautomer thereof, in the treatment of the aforementioned diseases or disorders according to the present disclosure; and A pharmaceutical composition comprising a compound of the disclosure, or a pharmaceutically acceptable salt, hydrate, solvate, prodrug, stereoisomer, or tautomer thereof, for use in the treatment of the aforementioned diseases or disorders according to the present disclosure.

Having regard to their activity as WIZ modulators or degraders, compounds of formulae (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), and (Ie) in free or pharmaceutically acceptable salt form, are useful in the treatment of conditions which may be treated by modulation of WIZ protein expression levels, reduction of WIZ protein expression levels, or induction of fetal hemoglobin (HbF), such as in a blood disorder, for example an inherited blood disorder, e.g., sickle cell disease, or beta-thalassemia. In one aspect, the disclosure provides a method of treating or preventing a disease or disorder in a subject in need thereof, the method comprising administering to the subject a therapeutically effective amount of a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof.

In another aspect, the disclosure provides a method of treating or preventing a disorder that is affected by the reduction of WIZ protein levels, in a subject in need thereof, the method comprising administering to the subject a therapeutically effective amount of a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof.

In another aspect, the disclosure provides a method of inhibiting WIZ protein expression in a subject in need thereof, the method comprising administering to the subject a therapeutically effective amount of a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof.

In another aspect, the disclosure provides a method of degrading WIZ protein in a subject in need thereof, the method comprising administering to the subject a therapeutically effective amount of a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof.

In another aspect, the disclosure provides a method of inhibiting, reducing, or eliminating the activity of WIZ protein or WIZ protein expression, the method comprising administering to the subject a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof.

In another aspect, the disclosure provides a method of inducing or promoting fetal hemoglobin in a subject in need thereof, the method comprising administering to the subject a therapeutically effective amount of a compound of (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof.

In another aspect, the disclosure provides a method of reactivating fetal hemoglobin production or expression in a subject in need thereof, the method comprising administering to the subject a therapeutically effective amount of a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof.

In another aspect, the disclosure provides a method of increasing fetal hemoglobin expression in a subject in need thereof, the method comprising administering to the subject a therapeutically effective amount of a compound of (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof.

In another aspect, the disclosure provides a method of treating a hemoglobinopathy, e.g., a beta-hemoglobinopathy, in a subject in need thereof, the method comprising administering to the subject a therapeutically effective amount of a compound of (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof.

In another aspect, the disclosure provides a method of treating a sickle cell disease in a subject in need thereof, the method comprising administering to the subject a therapeutically effective amount of a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof.

In another aspect, the disclosure provides a method of treating beta-thalassemia in a subject in need thereof, the method comprising administering to the subject a therapeutically effective amount of a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof.

In an embodiment, the beta-thalassemia major or intermedia is the result of homozygous null or compound heterozygous mutations resulting with beta-globin deficiency and the phenotypic complications of beta-thalassemia, whether transfusion-dependent or not.

In another aspect, the disclosure provides a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof for use in a method of treating or preventing a disease or disorder in a subject in need thereof, the method comprising administering to the subject a therapeutically effective amount of a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof.

In another aspect, the disclosure provides a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof for use in a method of treating or preventing a disorder that is affected by the reduction of WIZ protein levels, in a subject in need thereof, the method comprising administering to the subject a therapeutically effective amount of a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof.

In another aspect, the disclosure provides a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof for use in a method of inhibiting WIZ protein expression in a subject in need thereof, the method comprising administering to the subject a therapeutically effective amount of a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof.

In another aspect, the disclosure provides a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof for use in a method of degrading WIZ protein in a subject in need thereof, the method comprising administering to the subject a therapeutically effective amount of a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof.

In another aspect, the disclosure provides a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof for use in a method of inhibiting, reducing, or eliminating the activity of WIZ protein or WIZ protein expression, the method comprising administering to the subject a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof.

In another aspect, the disclosure provides a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof for use in a method of inducing or promoting fetal hemoglobin in a subject in need thereof, the method comprising administering to the subject a therapeutically effective amount of a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof.

In another aspect, the disclosure provides a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof for use in a method of reactivating fetal hemoglobin production or expression in a subject in need thereof, the method comprising administering to the subject a therapeutically effective amount of a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof.

In another aspect, the disclosure provides a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof for use in a method of increasing fetal hemoglobin expression in a subject in need thereof, the method comprising administering to the subject a therapeutically effective amount of a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof.

In another aspect, the disclosure provides a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof for use in a method of treating a hemoglobinopathy, e.g., a beta-hemoglobinopathy, in a subject in need thereof, the method comprising administering to the subject a therapeutically effective amount of a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof.

In another aspect, the disclosure provides a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof for use in a method of treating a sickle cell disease in a subject in need thereof, the method comprising administering to the subject a therapeutically effective amount of a compound of formula (I"), (I'), (I), (Ia"), (Ia'), (Ia), (Ib"), (Ib'), (2b), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof.

In another aspect, the disclosure provides a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof for use in a method of treating beta-thalassemia in a subject in need thereof, the method comprising administering to the subject a therapeutically effective amount of a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof.

In an embodiment, the beta-thalassemia major or intermedia is the result of homozygous null or compound heterozygous mutations resulting with beta-globin deficiency and the phenotypic complications of beta-thalassemia, whether transfusion-dependent or not.

Dosage

The pharmaceutical composition or combination of the disclosure can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated.

The above-cited dosage properties are demonstrable in vitro and in vivo tests using advantageously mammals, e.g., mice, rats, dogs, monkeys or isolated organs, tissues and preparations thereof. The compounds of the disclosure can be applied in vitro in the form of solutions, e.g., aqueous solutions, and in vivo either enterally, parenterally, advantageously intravenously, e.g., as a suspension or in aqueous solution. The dosage in vitro may range between about 10-3 molar and 10-9 molar concentrations. A therapeutically effective amount in vivo may range depending on the route of administration, between about 0.1-500 mg/kg, or between about 1-100 mg/kg.

The activity of a compound according to the disclosure can be assessed by the in vitro methods described in the Examples.

Combination Therapy

In another aspect, the disclosure provides a pharmaceutical combination comprising a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof, and one or more additional therapeutic agent(s) for simultaneous, separate or sequential use in therapy. In an embodiment, the additional therapeutic agent is a myelosuppressive agent, such as hydroxyurea.

Combination therapy includes the administration of the subject compounds in further combination with other biologically active ingredients (such as, but not limited to, a second and different antineoplastic agent or a therapeutic agent that targets HbF or another cancer target) and non-drug therapies (such as, but not limited to, surgery or radiation treatment). For instance, the compounds of the application can be used in combination with other pharmaceutically active compounds, preferably compounds that are able to enhance the effect of the compounds of the application.

The compound of the disclosure may be administered either simultaneously with, or before or after, one or more other therapeutic agents. The compound of the disclosure may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a compound of the disclosure. Thus, in one embodiment, the disclosure provides a combination comprising a therapeutically effective amount of a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), or a pharmaceutically acceptable salt, hydrate, solvate, prodrug, stereoisomer, or tautomer thereof and one or more additional therapeutically active agents.

In one embodiment, the disclosure provides a product comprising a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), and at least one other therapeutic agent as a combined preparation for simultaneous, separate or sequential use in therapy. In one embodiment, the therapy is the treatment of a disease or condition modulated by WIZ. Products provided as a combined preparation include a composition comprising the compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), and the other therapeutic agent(s) together in the same pharmaceutical composition, or the compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), and the other therapeutic agent(s) in separate form, e.g., in the form of a kit.

In one embodiment, the disclosure provides a pharmaceutical composition comprising a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie), and another therapeutic agent(s). Optionally, the pharmaceutical composition may comprise a pharmaceutically acceptable carrier, as described above.

In one embodiment, the disclosure provides a kit comprising two or more separate pharmaceutical compositions, at least one of which contains a compound of formula (I"), (I'), (I), (Ia"), (Ia'), (Ia), (Ib"), (Ib'), (Ib), (Ic"), (Ic'), (Ic), (Id"), (Id'), (Id), (Id-1), (Id-2), (Id-3), (Ie"), (Ie'), or (Ie). In one embodiment, the kit comprises means for separately retaining said compositions, such as a container, divided bottle, or divided foil packet. An example of such a kit is a blister pack, as typically used for the packaging of tablets, capsules and the like.

The kit of the disclosure may be used for administering different dosage forms, for example, oral and parenteral, for administering the separate compositions at different dosage intervals, or for titrating the separate compositions against one another. To assist compliance, the kit of the disclosure typically comprises directions for administration.

In the combination therapies of the disclosure, the compound of the disclosure and the other therapeutic agent may be manufactured and/or formulated by the same or different manufacturers. Moreover, the compound of the disclosure and the other therapeutic may be brought together into a combination therapy: (i) prior to release of the combination product to physicians (e.g., in the case of a kit comprising the compound of the disclosure and the other therapeutic agent); (ii) by the physician themselves (or under the guidance of the physician) shortly before administration; (iii) in the patient themselves, e.g., during sequential administration of the compound of the disclosure and the other therapeutic agent.

Preparation of Compounds

It is understood that in the following description, combinations of substituents and/or variables of the depicted formulae are permissible only if such combinations result in stable compounds.

It will also be appreciated by those skilled in the art that in the processes described below, the functional groups of intermediate compounds may need to be protected by suitable protecting groups. Such functional groups include hydroxy, phenol, amino and carboxylic acid. Suitable protecting groups for hydroxy or phenol include trialkylsilyl or diarylalkylsilyl (e.g., t-butyldimethylsilyl, t-butyldiphenylsilyl or trimethylsilyl), tetrahydropyranyl, benzyl, substituted benzyl, methyl, and the like. Suitable protecting groups for amino, amidino and guanidino include t-butoxycarbonyl, benzyloxycarbonyl, and the like. Suitable protecting groups for carboxylic acid include alkyl, aryl or arylalkyl esters.

Protecting groups may be added or removed in accordance with standard techniques, which are well-known to those skilled in the art and as described herein. The use of protecting groups is described in detail in J. F. W. McOmie, "Protective Groups in Organic Chemistry", Plenum Press, London and New York 1973; T. W. Greene and P. G. M. Wuts, "Greene's Protective Groups in Organic Synthesis", Fourth Edition, Wiley, New York 2007; P. J. Kocienski, "Protecting Groups", Third Edition, Georg Thieme Verlag, Stuttgart and New York 2005; and in "Methoden der organischen Chemie" (Methods of Organic Chemistry), Houben Weyl, 4th edition, Volume 15/I, Georg Thieme Verlag, Stuttgart 1974.

The protecting group may also be a polymer resin, such as a Wang resin or a 2-chlorotrityl-chloride resin.

The following reaction schemes illustrate methods to make compounds of this disclosure. It is understood that one skilled in the art would be able to make these compounds by similar methods or by methods known to one skilled in the art. In general, starting components and reagents may be obtained from sources such as Sigma Aldrich, Lancaster Synthesis, Inc., Maybridge, Matrix Scientific, TCI, and Fluorochem USA, Strem, other commercial vendors, or synthesized according to sources known to those skilled in the art, or prepared as described in this disclosure.

Analytical Methods, Materials, and Instrumentation

Unless otherwise noted, reagents and solvents were used as received from commercial suppliers. Proton nuclear magnetic resonance (NMR) spectra were obtained on either Bruker Avance spectrometer or Varian Oxford 400 MHz spectrometer unless otherwise noted. Spectra are given in ppm (δ) and coupling constants, J, are reported in Hertz. Tetramethylsilane (TMS) was used as an internal standard. Chemical shifts are reported in ppm relative to dimethyl sulfoxide (δ 2.50), methanol (δ 3.31), chloroform (δ 7.26) or other solvent as indicated in NMR spectral data. A small amount of the dry sample (2-5 mg) is dissolved in an appropriate deuterated solvent (1 mL). The chemical names were generated using ChemBioDraw Ultra v12 from CambridgeSoft.

Mass spectra (ESI-MS) were collected using a Waters System (Acquity UPLC and a Micromass ZQ mass spectrometer) or Agilent-1260 Infinity (6120 Quadrupole); all masses reported are the m/z of the protonated parent ions unless recorded otherwise. The sample was dissolved in a suitable solvent such as MeCN, DMSO, or MeOH and was injected directly into the column using an automated sample handler. The analysis is performed on Waters Acquity UPLC system (Column: Waters Acquity UPLC BEH C18 1.7 μm, 2.1×30 mm; Flow rate: 1 mL/min; 55° C. (column temperature); Solvent A: 0.05% formic acid in water, Solvent B: 0.04% formic acid in MeOH; gradient 95% Solvent A from 0 to 0.10 min; 95% Solvent A to 20% Solvent A from 0.10 to 0.50 min; 20% Solvent A to 5% Solvent A from 0.50 to 0.60 min; hold at 5% Solvent A from 0.6 min to 0.8 min; 5% Solvent A to 95% Solvent A from 0.80 to 0.90 min; and hold 95% Solvent A from 0.90 to 1.15 min.

Abbreviations

ACN acetonitrile
AcOH acetic acid
AIBN azobisisobutyronitrile
aq. aqueous
$B_2pin_2$ bis(pinacolato)diboron
9-BBN 9-borabicyclo[3.3.1]nonane
$Boc_2O$ di-tert-butyl dicarbonate
Bn benzyl
BnBr benzyl bromide
br broad
d doublet
dd doublet of doublets
ddd doublet of doublet of doublets
ddq doublet of doublet of quartets
ddt doublet of doublet of triplets
dq doublet of quartets
dt doublet of triplets
dtbbpy 4,4'-di-tert-butyl-2,2'-dipyridyl
dtd doublet of triplet of doublets
$Cs_2CO_3$ cesium carbonate
DCE 1,2-dichloroethane
DCM dichloromethane
DHP dihydropyran
DIBAL-H diisobutylaluminium hydride
DIPEA (DIEA) diisopropylethylamine
DIPEA N,N-diisopropylethylamine
DMA N,N-dimethylacetamide
DMAP 4-dimethylaminopyridine
DMB 2,4-dimethoxybenzyl
DME 1,2-dimethoxyethane
DMF N,N-dimethylformamide
DMP Dess-Martin periodinane or 1,1,1-Tris(acetyloxy)-1,1-dihydro-1,2-benziodoxol-3-(1H)-one
DMSO dimethylsulfoxide
$EC_{50}$ half maximal effective concentration
ELSD evaporative light scattering detector
EtOH ethanol
$Et_2O$ diethyl ether
$Et_3N$ triethylamine
EtOAc ethyl acetate
HATU 1-[bis(dimethylamino)methylene]-1H-1,2,3-triazolo[4,5-b]pyridinium 3-oxid hexafluorophosphate
HCl hydrogen chloride
hept heptet
HPLC high performance liquid chromatography
h or hr hour
HRMS high resolution mass spectrometry
g gram
g/min gram per minute
$IC_{50}$ half maximal inhibitory concentration
IPA (iPrOH) isopropyl alcohol
$Ir[(dF(CF_3)ppy)_2dtbbpy]PF_6$ [4,4'-Bis(1,1-dimethylethyl)-2,2'-bipyridine-N1,N1']bis[3,5-difluoro-2-[5-(trifluoromethyl)-2-pyridinyl-N]phenyl-C]Iridium(III) hexafluorophosphate
$K_2CO_3$ potassium carbonate
KI potassium iodide
KOAc potassium Acetate
$K_3PO_4$ tripotassium phosphate
LCMS liquid chromatography mass spectrometry
LDA lithium diisopropylamide
m multiplet
MeCN acetonitrile
MeOH methanol
mg milligram
MHz megahertz
min minutes
mL milliliter
mmol millimole
M molar
MS mass spectrometry
NaH sodium hydride
$NaHCO_3$ sodium bicarbonate
$NaBH(OAc)_3$ sodium triacetoxyborohydride
$Na_2SO_4$ sodium sulfate
NBS N-bromosuccinimide
NMM N-methylmorpholine
NMP N-methyl-2-pyrrolidone
NMR nuclear magnetic resonance
on overnight
Pd/C palladium on carbon
$PdCl_2(dppf)\cdot DCM$ [1,1'-bis(diphenylphosphino)ferrocene]dichloropalladium(II) complex with dichloromethane
$Pd(PPh_3)_4$ tetrakis(triphenylphosphine)palladium(0)
PMB para-methoxybenzyl
q quartet
qd quartet of doublets
quint quintet
quintd quintet of doublets
rbf round bottom flask
RockPhos G3 Pd [(2-di-tert-butylphosphino-3-methoxy-6-methyl-2',4',6'-triisopropyl-1,1'-biphenyl)-2-(2-aminobiphenyl)]palladium(II) methanesulfonate
rt or r.t. room temperature
Rt retention time
RuPhos dicyclohexyl(2',6'-diisopropoxy-[1,1'-biphenyl]-2-yl)phosphane
s singlet
SEM 2-(trimethylsilyl)ethoxymethyl
$SnBu_3$ tributyltin
t triplet
td triplet of doublets
tdd triplet of doublet of doublets TBAI tetrabutylammonium iodide
TEA (NEt$_3$) triethylamine
TFA trifluoroacetic acid
TfOH triflic Acid
THF tetrahydrofuran
THP tetrahydropyran
TMP 2,2,6,6-tetramethylpiperidine
Ts tosyl
tt triplet of triplets
ttd triplet of triplet of doublets
TLC thin-layer chromatography
UPLC ultra-Performance liquid Chromatography
XPhos Pd G2 chloro(2-dicyclohexylphosphino-2',4',6'-triisopropyl-1,1'-biphenyl)[2-(2'-amino-1,1'-biphenyl)]palladium(II)
μW or uW microwave Preparation of Intermediates Preparation of 3-(2,4-dimethoxybenzyl)dihydropyrimidine-2,4(1H,3H)-dione

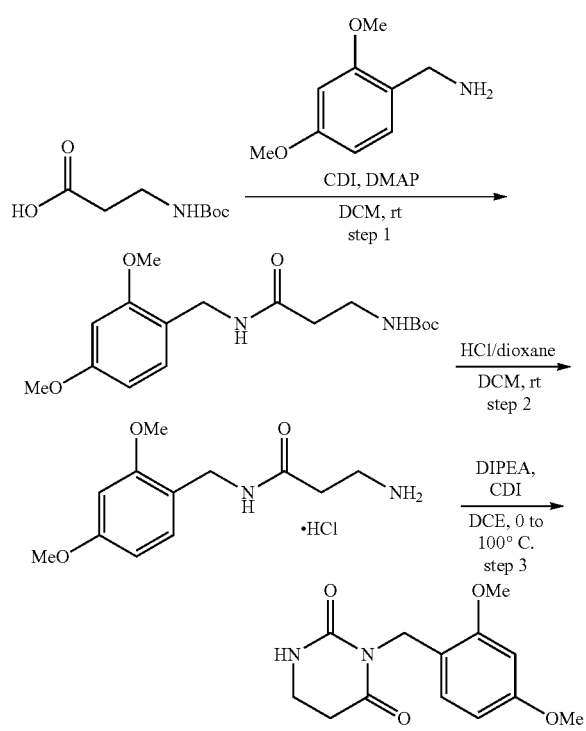

Step 1. tert-butyl (3-((2,4-dimethoxybenzyl)amino)-3-oxopropyl)carbamate

To a solution of 3-((tert-butoxycarbonyl)amino)propanoic acid (200 g, 1.06 mol, 1.00 eq) in DCM (1200 mL) was added CDI (189 g, 1.16 mol, 1.10 eq). The reaction mixture was stirred at 20° C. for 2 h. The reaction mixture was slowly added to a solution of (2,4-dimethoxyphenyl)methanamine (212 g, 1.27 mol, 191 mL, 1.20 eq) and DMAP (12.9 g, 106 mmol, 0.10 eq) in DCM (1000 mL). The solution was stirred at 20° C. for 12 h. The reaction mixture was slowly poured into water (2 L) and stirred at rt for 10 min. The organic phase was separated and the water phase was extracted with DCM (800 mL×2). The combined organic phase was washed with brine (1 L×2) and dried over Na$_2$SO$_4$, filtered and concentrated. The crude material was purified by silica gel chromatography (eluted with 50:1 to 2:1 petroleum ether:ethyl acetate) to give tert-butyl (3-((2,4-dimethoxybenzyl)amino)-3-oxopropyl)carbamate (210 g, 621 mmol, 59% yield) as a white solid. $^1$H NMR (400 MHz, DMSO-d6) δ 8.06 (t, J=5.6 Hz, 1H), 7.08-7.01 (m, 1H), 6.72 (br t, J=5.3 Hz, 1H), 6.55-6.51 (m, 1H), 6.46 (dd, J=2.4, 8.4 Hz, 1H), 4.13 (d, J=5.6 Hz, 2H), 3.77 (s, 3H), 3.73 (s, 3H), 3.13 (q, J=7.0 Hz, 2H), 2.28 (t, J=7.3 Hz, 2H), 1.37 (s, 9H).

Step 2. 3-amino-N-(2,4-dimethoxybenzyl)propanamide hydrochloride

To a solution of tert-butyl (3-((2,4-dimethoxybenzyl)amino)-3-oxopropyl)carbamate (210 g, 621 mmol, 1.00 eq) in DCM (1000 mL) was added HCl/dioxane (4 M, 1000 mL, 6.45 eq) and the solution was stirred at 20° C. for 5 h. The reaction mixture was concentrated to give 3-amino-N-(2,4-dimethoxybenzyl)propanamide hydrochloride (180 g, crude, HCl salt) as a white solid which was used in the next step without further purification. $^1$H NMR (400 MHz, DMSO-d6) δ 8.38 (br t, J=5.6 Hz, 1H), 8.07 (br s, 3H), 7.08 (d, J=8.3 Hz, 1H), 6.53 (d, J=2.4 Hz, 1H), 6.46 (dd, J=2.4, 8.3 Hz, 1H), 4.15 (d, J=5.6 Hz, 2H), 3.75 (d, J=15.6 Hz, 6H), 2.96 (sxt, J=6.3 Hz, 2H), 2.59-2.52 (m, 2H).

Step 3. 3-(2,4-dimethoxybenzyl)dihydropyrimidine-2,4(1H,3H)-dione

To a mixture of 3-amino-N-(2,4-dimethoxybenzyl)propanamide hydrochloride (180 g, 655 mmol, 1.00 eq) and DIPEA (212 g, 1.64 mol, 285 mL, 2.50 eq) in DCE (1200 mL) was added CDI (127 g, 786 mmol, 1.20 eq) at 0° C. The mixture was stirred at 0° C. for 0.5 h, then heated to 100° C. and stirred for 12 h. The reaction mixture was slowly poured into water (1000 mL) and stirred at 20° C. for 20 min. The organic phase was separated and the water phase was extracted with DCM (500 mL*2). The combined organic phases were washed with brine (500 mL*2), dried over Na$_2$SO$_4$, filtered and concentrated. The residue was purified by silica gel chromatography (45:1 to 0:1 petroleum ether: ethyl acetate) to give 3-(2,4-dimethoxybenzyl)dihydropyrimidine-2,4(1H,3H)-dione (120 g, 454 mmol, 69% yield) as a white solid. $^1$H NMR (400 MHz, CDCl$_3$) δ 6.99 (d, J=8.3 Hz, 1H), 6.48-6.37 (m, 2H), 5.79 (br s, 1H), 4.93 (s, 2H), 3.80 (d, J=15.3 Hz, 6H), 3.41 (dt, J=2.6, 6.8 Hz, 2H), 2.76 (t, J=6.8 Hz, 2H).

Preparation of potassium (R)-((4-(tert-butoxycarbonyl)-3-methylpiperazin-1-yl)methyl)trifluoroborate

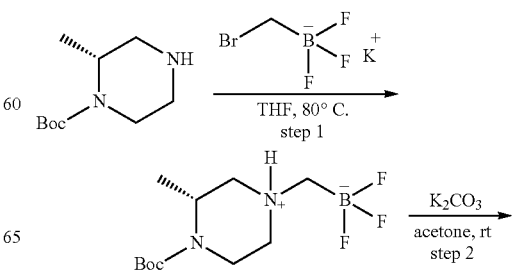

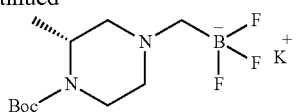

Step 1. (((3R)-4-(tert-butoxycarbonyl)-3-methylpiperazin-1-ium-1-yl)methyl)trifluoroborate To a solution of potassium (bromomethyl)trifluoroborate (2.00 g, 9.96 mmol) in THF (10 mL) was added tert-butyl (R)-2-methylpiperazine-1-carboxylate (2.09 g, 15.7 mmol). The reaction mixture was stirred at 80° C. for 16 h. The reaction mixture was filtered and the filter cake was washed with THF (2×10 mL), and the filter cake was collected and dried to give (((3R)-4-(tert-butoxycarbonyl)-3-methylpiperazin-1-ium-1-yl)methyl)trifluoroborate (4.3 g, crude) as a white solid. The crude was used in the next step without any other purification. $^1$H NMR (400 MHz, DMSO-d6) δ 8.45-8.44 (m, 1H), 4.31-2.92 (m, 1H), 3.87-3.82 (m, 1H), 3.67-3.54 (m, 1H), 3.27-3.04 (m, 2H), 2.99-2.77 (m, 2H), 1.99 (br s, 2H), 1.83-1.70 (m, 1H), 1.50-1.37 (m, 9H), 1.21 (br d, J=7.2 Hz, 3H).

Step 2. potassium (R)-((4-(tert-butoxycarbonyl)-3-methylpiperazin-1-yl)methyl)trifluoroborate To a solution of (((3R)-4-(tert-butoxycarbonyl)-3-methylpiperazin-1-ium-1-yl)methyl)trifluoroborate (4.3 g, crude) in acetone (20 mL) was added K$_2$CO$_3$ (2.10 g, 15.2 mmol) and the reaction mixture was stirred at 25° C. for 16 h. The reaction mixture was filtered and the filter cake was washed with acetone (2×10 mL), and the filtrate was concentrated to give potassium (R)-((4-(tert-butoxycarbonyl)-3-methylpiperazin-1-yl)methyl)trifluoroborate (1.1 g, crude) as a white solid. The crude material was used in the next step without any other purification. $^1$H NMR (400 MHz, DMSO-d6) δ 4.09 (br s, 1H), 3.79-3.60 (m, 1H), 3.51-3.21 (m, 1H), 2.98 (br s, 3H), 1.71-1.46 (m, 2H), 1.39 (s, 9H), 1.15 (d, J=7.2 Hz, 3H).

Additional Borate Salts Prepared by the Method Above:

The borate salts in the following table were prepared by the method of potassium (R)-((4-(tert-butoxycarbonyl)-3-methylpiperazin-1-yl)methyl)trifluoroborate using the appropriate commercially available piperazine in step 1 except where noted.

| Structure | Starting material |
|---|---|
| potassium (S)-((4-(tert-butoxycarbonyl)-3-ethylpiperazin-1-yl)methyl)trifluoroborate | tert-butyl (S)-2-ethylpiperazine-1-carboxylate |
| potassium (S)-((4-(tert-butoxycarbonyl)-3-isopropylpiperazin-1-yl)methyl)trifluoroborate | tert-butyl (S)-2-isopropylpiperazine-1-carboxylate |
| potassium ((4-(tert-butoxycarbonyl)-3,3-dimethylpiperazin-1-yl)methyl)trifluoroborate | tert-butyl 2,2-dimethylpiperazine-1-carboxylate |
| potassium (((1R,5S)-8-(tert-butoxycarbonyl)-3,8-diazabicyclo[3.2.1]octan-3-yl)methyl)trifluoroborate | tert-butyl (1R,5S)-3,8-diazabicyclo[3.2.1]octane-8-carboxylate |

-continued

| Structure | Starting material |
| --- | --- |
| potassium (((1R,4R)-5-(tert-butoxycarbonyl)-2,5-diazabicyclo[2.2.1]heptan-2-yl)methyl)trifluoroborate | tert-butyl (1R,4R)-2,5-diazabicyclo[2.2.1]heptane-2-carboxylate |
| potassium (((1S,4S)-5-(tert-butoxycarbonyl)-2,5-diazabicyclo[2.2.1]heptan-2-yl)methyl)trifluoroborate | tert-butyl (1S,4S)-2,5-diazabicyclo[2.2.1]heptane-2-carboxylate |
| potassium trifluoro((4-(3-methylbutan-2-yl)piperazin-1-yl)methyl)borate | 1-(3-methylbutan-2-yl)piperazine |
| potassium ((4-(tert-butoxycarbonyl)-1,4-diazepan-1-yl)methyl)trifluoroborate | tert-butyl 1,4-diazepane-1-carboxylate |
| potassium ((4-(cyclohexylmethyl)-3-oxopiperazin-1-yl)methyl)trifluoroborate | 1-(cyclohexylmethyl)piperazin-2-one [see *RSC Advances*, 2018, 8, 11163-11176] |
| potassium ((4-(2-cyclohexylethyl)-3-oxopiperazin-1-yl)methyl)trifluoroborate | 1-(2-cyclohexylethyl)piperazin-2-one [see *J. Med. Chem.* 1990, 33, 2590-2595] |
| potassium (R)-((4-(cyclohexylmethyl)-3-(methoxymethyl)piperazin-1-yl)methyl)trifluoroborate | (R)-1-(cyclohexylmethyl)-2-(methoxymethyl)piperazine hydrochloride [vide infra] |

-continued

| Structure | Starting material |
| --- | --- |
| potassium (R)-trifluoro((4-isobutyl-3-(methoxymethyl)piperazin-1-yl)methyl)borate | (R)-1-isobutyl-2-(methoxymethyl)piperazine hydrochloride [vide infra] |
| potassium (R)-((4-(cyclohexylmethyl)-3-(difluoromethyl)piperazin-1-yl)methyl)trifluoroborate | (R)-1-(cyclohexylmethyl)-2-(difluoromethyl)piperazine hydrochloride [vide infra] |
| potassium (R)-((3-(difluoromethyl)-4-isobutylpiperazin-1-yl)methyl)trifluoroborate | (R)-2-(difluoromethyl)-1-isobutylpiperazine hydrochloride [vide infra] |
| potassium trifluoro((4-(3,3,3-trifluoro-2,2-dimethylpropyl)piperazin-1-yl)methyl)borate | 1-(3,3,3-trifluoro-2,2-dimethylpropyl)piperazine hydrochloride [vide infra] |
| potassium (S)-trifluoro((hexahydro-pyrrolo[1,2-a]pyrazin-2(1H)-yl)methyl)borate | (S)-octahydropyrrolo[1,2-a]pyrazine |
| potassium (R)-trifluoro((hexahydro-pyrrolo[1,2-a]pyrazin-2(1H)-yl)methyl)borate | (R)-octahydropyrrolo[1,2-a]pyrazine |

| Structure | Starting material |
|---|---|
| potassium (S)-trifluoro((octahydro-2H-pyrido[1,2-a]pyrazin-2-yl)methyl)borate | (S)-octahydro-2H-pyrido[1,2-a]pyrazine |
| potassium (R)-trifluoro((hexahydropyrazino[2,1-c][1,4]oxazin-8(1H)-yl)methyl)borate | (R)-octahydropyrazino[2,1-c][1,4]oxazine |
| potassium (S)-trifluoro((hexahydropyrazino[2,1-c][1,4]oxazin-8(1H)-yl)methyl)borate | (S)-octahydropyrazino[2,1-c][1,4]oxazine |

Preparation of (R)-1-(cyclohexylmethyl)-2-(methoxymethyl)piperazine hydrochloride

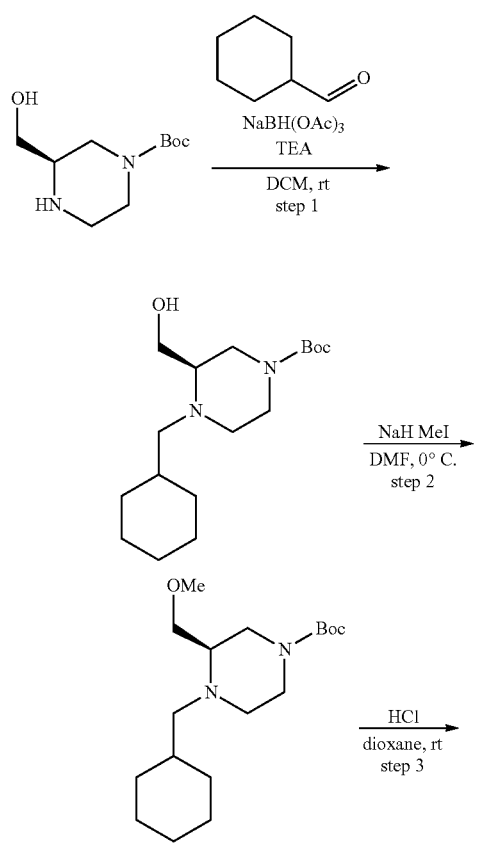

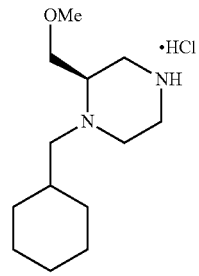

Step 1. tert-butyl (R)-4-(cyclohexylmethyl)-3-(hydroxymethyl)piperazine-1-carboxylate To a stirred solution of tert-butyl (R)-3-(hydroxymethyl)piperazine-1-carboxylate (6.0 g, 27.7 mmol) and cyclohexanecarbaldehyde (4.6 g, 41.6 mmol) dissolved in DCM (70 mL) was added Et₃N (11.7 mL, 83.2 mmol). The reaction mixture was stirred for 30 min at rt and then sodium triacetoxy borohydride (11.7 g, 55.5 mmol) was added in portions at 0° C. The reaction mixture was allowed to stirred at rt for 16 h. The reaction was diluted with DCM and water and the organic layer was dried over Na₂SO₄, filtered and concentrated. The crude compound was purified by silica gel chromotography (eluting with 10-20% EtOAc in hexanes) to afford tert-butyl (R)-4-(cyclohexylmethyl)-3-(hydroxymethyl)piperazine-1-carboxylate (4.2 g, 13.4 mmol, 48% yield). LCMS [M+H-tBu]⁺: 257.2.

Step 2. tert-butyl (R)-4-(cyclohexylmethyl)-3-(methoxymethyl)piperazine-1-carboxylate To a stirred solution of tert-butyl (R)-4-(cyclohexylmethyl)-3-(hydroxymethyl)piperazine-1-carboxylate (0.70 g, 2.2 mmol) in DMF (10 mL) cooled to 0° C. was added NaH (0.13 g, 3.36 mmol) under an inert atmosphere. The reaction mixture was stirred at 0° C. for 30 min and then MeI (0.47 g, 3.36 mmol) was added at 0° C. The reaction was diluted with EtOAc and water and the organic layer was dried over Na$_2$SO$_4$, filtered and concentrated. The crude compound was purified by silica gel chromotography (eluting with 10-20% EtOAc in hexanes) to afford tert-butyl (R)-4-(cyclohexylmethyl)-3-(methoxymethyl)piperazine-1-carboxylate (0.45 g, 1.37 mmol, 61%). LCMS [M+H]$^+$: 327.1

Step 3. (R)-1-(cyclohexylmethyl)-2-(methoxymethyl)piperazine hydrochloride

To a stirred solution of tert-butyl (R)-4-(cyclohexylmethyl)-3-(methoxymethyl)piperazine-1-carboxylate (0.45 g, 1.37 mmol) in DCM (7.0 mL) cooled to 0° C. was added a solution of HCl (4.0 M in dioxane, 4.0 mL). The reaction mixture was stirred at rt for 3 h and then concentrated. The crude compound was washed with diethyl ether to afford (R)-1-(cyclohexylmethyl)-2-(methoxymethyl)piperazine hydrochloride (0.40 g, crude). LCMS [M+H]$^+$: 227.1.

Preparation of (R)-1-isobutyl-2-(methoxymethyl)piperazine hydrochloride

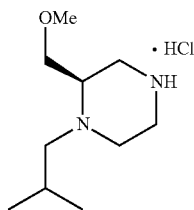

Prepared by the method of (R)-1-(cyclohexylmethyl)-2-(methoxymethyl)piperazine hydrochloride, using isobutyraldehyde in step 1. LCMS [M+H]$^+$: 187.1.

Preparation of (R)-1-(cyclohexylmethyl)-2-(difluoromethyl)piperazine hydrochloride

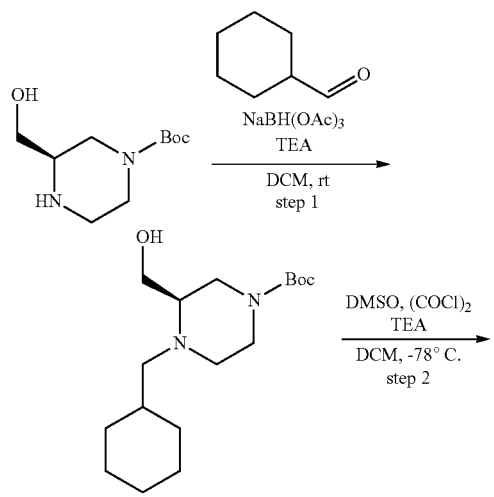

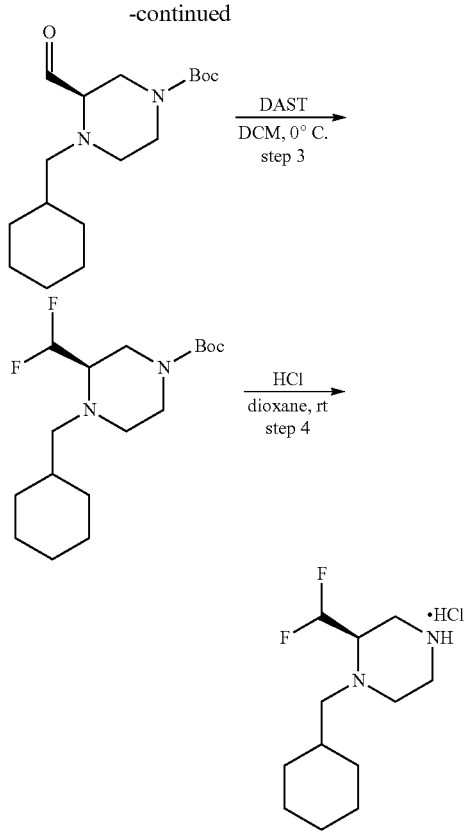

Step 1. tert-butyl (R)-4-(cyclohexylmethyl)-3-(hydroxymethyl)piperazine-1-carboxylate To a stirred solution of tert-butyl (R)-3-(hydroxymethyl)piperazine-1-carboxylate (6.0 g, 27.75 mmol) and cyclohexanecarbaldehyde (4.6 g, 41.62 mmol) in DCM (70 mL) was added Et$_3$N (11.69 mL, 83.25 mmol). The reaction mixture was stirred for 30 min at rt. Sodium triacetoxy borohydride (11.7 g, 55.50 mmol) was then added slowly at 0° C. The reaction mixture was stirred at rt for 16 h. After completion, the reaction was diluted with DCM and water and the organic layer was dried over Na$_2$SO$_4$, filtered and concentrated. The crude compound was purified by silica gel chromatography (eluting with 10-20% EtOAc in hexanes) to afford tert-butyl (R)-4-(cyclohexylmethyl)-3-(hydroxymethyl)piperazine-1-carboxylate (4.2 g, 13.44 mmol, 48% yield). LCMS [M+H-tBu]$^+$: 257.2.

Step 2. tert-butyl (R)-4-(cyclohexylmethyl)-3-formylpiperazine-1-carboxylate

To a stirred solution of oxalyl chloride (2.04 mL, 24.0 mmol) in DCM (25 mL) at −78° C. was added DMSO (3.41 mL, 48.0 mmol) dropwise under an inert atmosphere. The reaction mixture was stirred at −78° C. for 15 min and then a solution of tert-butyl (R)-4-(cyclohexylmethyl)-3-(hydroxymethyl)piperazine-1-carboxylate (2.5 g, 8.0 mmol) in DCM (5.0 mL) was added dropwise at −78° C. The reaction mixture was stirred at −78° C. for 1 h and Et$_3$N (11.24 mL, 80.01 mmol) was added slowly. The reaction mixture was stirred at −78° C. for 1 h and allowed to warm to rt. The reaction was diluted with DCM and water and the organic layer was dried over Na$_2$SO$_4$, filtered and concentrated to afford crude tert-butyl (R)-4-(cyclohexylmethyl)-3-formylpiperazine-1-carboxylate (2.7 g, crude). LCMS [M+H]+: 311.1.

Step 3. tert-butyl (R)-4-(cyclohexylmethyl)-3-(difluoromethyl)piperazine-1-carboxylate To a stirred solution of tert-butyl (R)-4-(cyclohexylmethyl)-3-formylpiperazine-1-carboxylate (2.7 g, 8.69 mmol) in DCM (30 mL) at 0° C. was added DAST (2.29 mL, 17.4 mmol) under an inert atmosphere. The reaction mixture was stirred at 0° C. for 2 h. After completion, the reaction was quenched with saturated aqueous NaHCO$_3$ solution and diluted with DCM. The organic layer was dried over Na$_2$SO$_4$, filtered and concentrated. The crude compound was purified by silica gel chromotography (eluting with 10-15% EtOAc in hexanes) to afford tert-butyl (R)-4-(cyclohexylmethyl)-3-(difluoromethyl)piperazine-1-carboxylate (0.41 g, 1.23 mmol, 14% yield). LCMS [M+H]+: 333.5.

Step 4. (R)-1-(cyclohexylmethyl)-2-(difluoromethyl)piperazine hydrochloride

To a stirred solution of tert-butyl (R)-4-(cyclohexylmethyl)-3-(difluoromethyl)piperazine-1-carboxylate (0.41 g, 1.2 mmol) in DCM (7.0 mL) at 0° C. was added a solution of HCl in dioxane (4.0 M, 4.0 mL). The reaction mixture was stirred at rt for 3 h. After completion, the mixture was concentrated and the crude compound was washed with diethyl ether to afford (R)-1-(cyclohexylmethyl)-2-(difluoromethyl)piperazine hydrochloride (0.33 g, 1.2 mmol, 100% yield). LCMS [M+H]+: 232.9.

Preparation of 1-(3,3,3-trifluoro-2,2-dimethylpropyl)piperazine hydrochloride

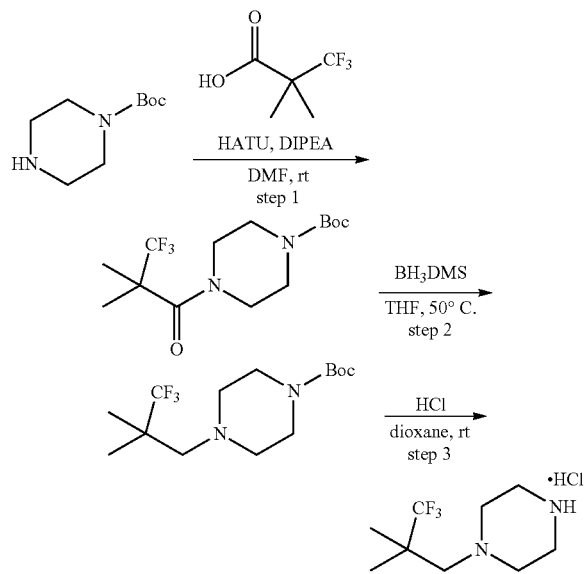

Step 1. tert-butyl 4-(3,3,3-trifluoro-2,2-dimethylpropanoyl)piperazine-1-carboxylate To a stirred solution of 3,3,3-trifluoro-2,2-dimethylpropanoic acid (1.0 g, 6.4 mmol) in DMF (15 mL) was added DIPEA (3.35 mL, 19.2 mmol) followed by HATU (3.65 g, 9.60 mmol) under inert atmosphere. The reaction mixture was stirred at rt for 15 min. After 15 min tert-butyl piperazine-1-carboxylate (1.43 g, 7.68 mmol) was added and the mixture was stirred at rt for 16 h. The reaction was poured into cold water and the precipitate was filtered and dried under vacuum to afford crude tert-butyl 4-(3,3,3-trifluoro-2,2-dimethylpropanoyl)piperazine-1-carboxylate (1.0 g, 3.08, 48% yield). LCMS [M+H-tBu]+: 269.1.

Step 2. tert-butyl 4-(3,3,3-trifluoro-2,2-dimethylpropyl)piperazine-1-carboxylate To a stirred solution of tert-butyl 4-(3,3,3-trifluoro-2,2-dimethylpropanoyl)piperazine-1-carboxylate (1.0 g, 3.08 mmol) in THF (15 mL) at 0° C. was added BH$_3$DMS (15.4 mL, 30.8 mmol, 1M in THF) under inert atmosphere. The reaction mixture was then stirred at 50° C. for 16 h. The reaction was quenched with MeOH and concentrate. The residue was dissolved in DCM and washed sequentially with a solution of aqueous 2M NaHCO$_3$ and brine. The organic layer was dried over Na$_2$SO$_4$, filtered and concentrated. The crude compound was purified by silica gel chromotography (eluting with 10-12% EtOAc in hexanes) to afford tert-butyl 4-(3,3,3-trifluoro-2,2-dimethylpropyl)piperazine-1-carboxylate (0.5 g, 1.61 mmol, 52% yield). LCMS [M+H-tBu]+: 254.9.

Step 3. 1-(3,3,3-trifluoro-2,2-dimethylpropyl)piperazine hydrochloride

To stirred solution of tert-butyl 4-(3,3,3-trifluoro-2,2-dimethylpropyl)piperazine-1-carboxylate (500 mg, 1.61 mmol) in DCM (7 mL) was added 4M HCl in dioxane (3 mL) and the mixture was stirred at rt for 2 h. The mixture was concentrated and the residue was washed with diethyl ether to afford 1-(3,3,3-trifluoro-2,2-dimethylpropyl)piperazine hydrochloride (500 mg, crude). LCMS [M+H]+: 211.2.

Preparation of (3-iodopyrazolo[1,5-a]pyridin-5-yl)methyl 4-methylbenzenesulfonate

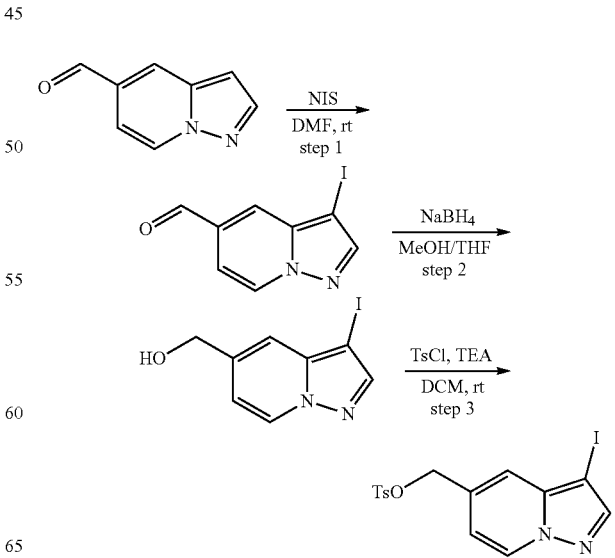

Step 1. 3-iodopyrazolo[1,5-a]pyridine-5-carbaldehyde

NIS (1.4 g, 5.92 mmol) was added to a solution of pyrazolo[1,5-a]pyridine-5-carbaldehyde (790 mg, 5.41 mmol) in DMF (10 mL) at 0° C. The mixture was then stirred at rt for 8 h. After completion, the reaction was quenched with water and the solid that precipitated was collected by filtration and dried under vacuum to afford 3-iodopyrazolo[1,5-a]pyridine-5-carbaldehyde (1.2 g, 4.4 mmol, 81% yield). LCMS [M+H]$^+$: 273.0.

Step 2. (3-iodopyrazolo[1,5-a]pyridin-5-yl)methanol

To a stirred solution of 3-iodopyrazolo[1,5-a]pyridine-5-carbaldehyde (1.2 g, 4.40 mmol) in MeOH:THF (2:1) (10 mL) was added NaBH$_4$ (250 mg, 6.60 mmol) at 0° C. The reaction mixture was stirred for 1 h and then concentrated. The residue was diluted with water and extracted with DCM. The organic layer was washed with brine, dried over Na$_2$SO$_4$, filtered and concentrated to afford (3-iodopyrazolo[1,5-a]pyridin-5-yl)methanol (800 mg, crude). LCMS [M+H]$^+$: 274.7.

Step 3. (3-iodopyrazolo[1,5-a]pyridin-5-yl)methyl 4-methylbenzenesulfonate

To a stirred solution of (3-iodopyrazolo[1,5-a]pyridin-5-yl)methanol (700 mg, 2.55 mmol) in DCM (10 mL) at 0° C. was added TEA (0.8 mL, 3.66 mmol). The mixture was stirred for 10 min and then tosyl chloride (610 mg, 3.06 mmol) and DMAP (38 mg, 0.25 mmol) were added. The reaction was stirred at rt for 1 h. The mixture was then diluted with DCM and water and the organic layer was dried over Na$_2$SO$_4$, filtered and concentrated to afford (3-iodopyrazolo[1,5-a]pyridin-5-yl)methyl 4-methylbenzenesulfonate (1.0 g, crude). The crude material was used without further purification.

Preparation of trans-3-methoxycyclobutane-1-carbaldehyde

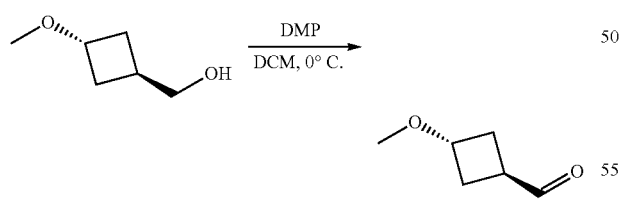

To a solution of trans-3-methoxycyclobutylmethanol [see WO2021/124172, 2021, A1] (0.30 g, 2.6 mmol, 1.0 eq) in DCM (15 mL) at 0° C. was added DMP (1.2 g, 2.8 mmol, 1.1 eq). The reaction mixture was stirred at 0° C. for 2 h. The reaction mixture was then concentrated. The crude material was purified by neutral alumina chromatography (eluted with 15% EtOAc in hexane) to give trans-3-methoxycyclobutane-1-carbaldehyde (0.21 g, 1.8 mmol, 71% yield) as a colorless oil.

Preparation of cis-3-methoxycyclobutane-1-carbaldehyde

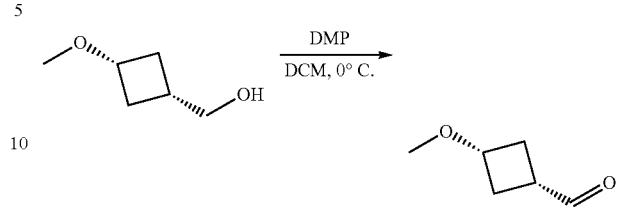

To a solution of cis-3-methoxycyclobutylmethanol [see WO2021/124172, 2021, A1] (0.10 g, 0.86 mmol, 1.0 eq) in DCM (7 mL) at 0° C. was added DMP (0.40 g, 0.94 mmol, 1.1 eq). The reaction mixture was stirred at 0° C. for 2 h. The reaction mixture was then concentrated. The crude material was diluted with Et$_2$O (10 mL) and filtered through celite, washing with additional Et$_2$O. The filtrate was concentrated to give crude cis-3-methoxycyclobutane-1-carbaldehyde (0.12 g, 1.1 mmol). The crude material was used in the next step without any other purification.

Preparation of (R)-3,3-difluorocyclopentane-1-carbaldehyde

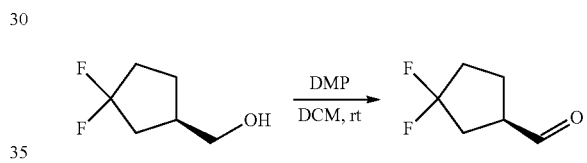

To a solution of (R)-(3,3-difluorocyclopentyl)methanol (0.230 g, 1.69 mmol), 1.0 eq) in DCM (5 mL) at 0° C. was added DMP (0.788 g, 1.86 mmol, 1.1 eq). The reaction mixture was stirred at rt for 2 h. The reaction mixture was then concentrated. The crude material was diluted with EtOAc (10 mL) and filtered through celite. The filtrate was washed with water, dried over MgSO$_4$, filtered and concentrated. The crude material was purified by neutral alumina chromatography (eluted with 20% EtOAc in hexane) to give (R)-3,3-difluorocyclopentane-1-carbaldehyde (0.13 g, 0.97 mmol, 57% yield) as a yellow oil.

Preparation of (S)-3,3-difluorocyclopentane-1-carbaldehyde

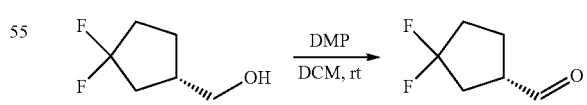

To a solution of (S)-(3,3-difluorocyclopentyl)methanol (0.170 g, 1.24 mmol), 1.0 eq) in DCM (10 mL) at 0° C. was added DMP (0.582 g, 1.37 mmol, 1.1 eq). The reaction mixture was stirred at rt for 2 h. The reaction mixture was then concentrated. The crude material was purified by neutral alumina chromatography (eluted with 20% EtOAc in hexane) to give (S)-3,3-difluorocyclopentane-1-carbaldehyde (0.15 g) as a colorless oil.

Preparation of (1r,3R,4S)-3,4-difluorocyclopentane-1-carbaldehyde

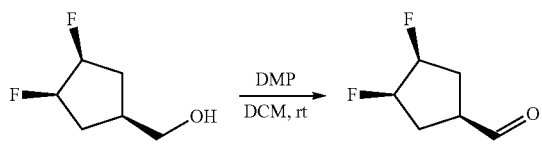 [SMILES: OC[C@H]1C[C@@H](F)[C@@H](F)C1 ; O=C[C@H]1C[C@@H](F)[C@@H](F)C1]

To a solution of ((1r,3R,4S)-3,4-difluorocyclopentyl)methanol [see EP2275414, 2011, A1] (0.170 g, 1.24 mmol), 1.0 eq) in DCM (10 mL) at 0° C. was added DMP (1.58 g, 3.74 mmol, 3.0 eq). The reaction mixture was stirred at rt for 2 h. The reaction mixture was then diluted with Et$_2$O and filtered through neutral alumina, washing with additional Et$_2$O. The filtrate containing crude (1r,3R,4S)-3,4-difluorocyclopentane-1-carbaldehyde was used in the next step without any other purification.

Preparation of 2-oxaspiro[3.3]heptane-6-carbaldehyde

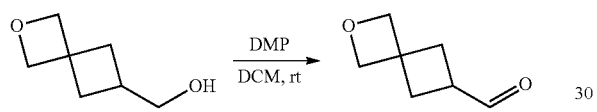

To a solution of (2-oxaspiro[3.3]heptan-6-yl)methanol (0.25 g, 1.95 mmol, 1.0 eq) in DCM (10 mL) at 0° C. was added DMP (1.65 g, 3.90 mmol, 2 eq). The reaction mixture was stirred at rt for 1 h. The reaction mixture was then filtered through celite and the filtrate was diluted with NaHCO$_3$ solution. The mixture was extracted with DCM and the DCM layer was washed with water, brine, dried over Na$_2$SO$_4$ and concentrated to give crude 2-oxaspiro[3.3]heptane-6-carbaldehyde (0.1 g) as a colorless oil. The crude material was used without further purification.

The borate salts in the following table were prepared by the method of potassium (R)-((4-(tert-butoxycarbonyl)-3-methylpiperazin-1-yl)methyl)trifluoroborate using the appropriate commercially available piperazine in step 1.

Preparation of potassium (S)-((1,1-dioxidohexahydro-5H-isothiazolo[2,3-a]pyrazin-5-yl)methyl)trifluoroborate

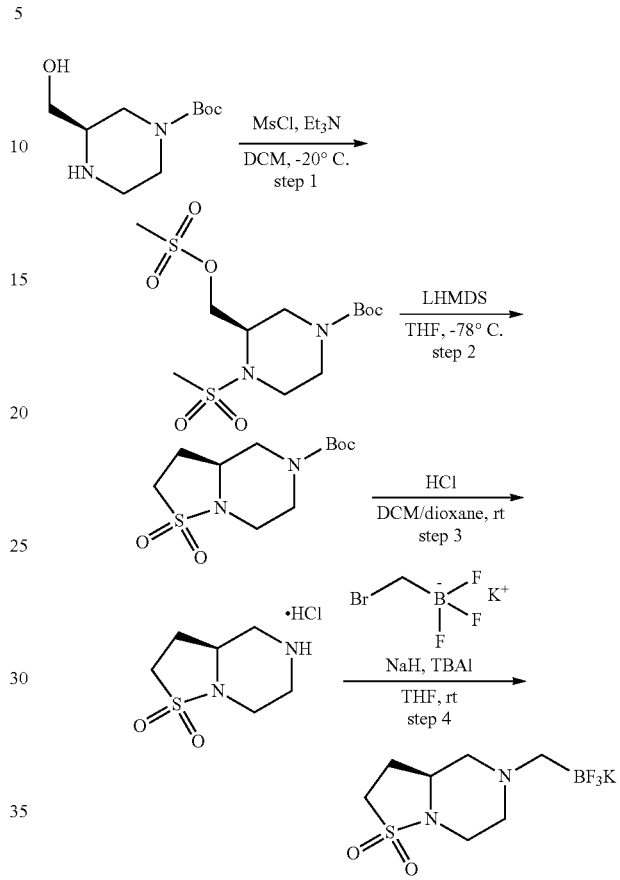

Step 1. tert-butyl (R)-4-(methylsulfonyl)-3-(((methylsulfonyl)oxy)methyl)piperazine-1-carboxylate To a solution of tert-butyl (R)-3-(hydroxymethyl)piperazine-1-carboxylate (4.00 g, 18.5 mmol) and Et$_3$N (5.15 mL, 37.0 mmol) in DCM (10 mL) at −20° C. was added

| Structure | Starting material |
|---|---|
| potassium (R)-trifluoro((octahydro-2H-pyrido[1,2-a]pyrazin-2-yl)methyl)borate | (R)-octahydro-2H-pyrido[1,2-a]pyrazine |
| potassium (R)-trifluoro((4-oxohexahydropyrazino[2,1-c][1,4]oxazin-8(1H)-yl)methyl)borate | (R)-hexahydropyrazino[2,1-c][1,4]oxazin-4(3H)-one | methanesulfonyl chloride (3.1 g, 27.7 mmol). The reaction mixture was stirred for 10 min and then diluted with a solution of saturated aqueous NaHCO$_3$. The mixture was extracted with DCM and the organic layer was dried over MgSO$_4$, filtered and concentrated. Silica gel column chromatography (eluting with 10% MeOH in DCM) provided tert-butyl (R)-4-(methylsulfonyl)-3-(((methylsulfonyl)oxy) methyl)piperazine-1-carboxylate (3.0 g, 8.1 mmol, 44% yield) as a gummy solid. The crude product was used in the next step without any other purification.

Step 2. tert-butyl (S)-hexahydro-5H-isothiazolo[2,3-a]pyrazine-5-carboxylate 1,1-dioxide To a solution of tert-butyl (R)-4-(methylsulfonyl)-3-(((methylsulfonyl)oxy)methyl)piperazine-1-carboxylate (3.0 g, 8.1 mmol) in THF (10 mL) at −78° C. was added a solution of LHMDS (1.0 M in THF, 24.3 mL, 24.3 mmol). The reaction mixture was stirred at −78° C. for 3 h and then diluted with a solution of saturated aqueous NaHCO$_3$. The mixture was extracted with DCM and the organic layer was dried over MgSO$_4$, filtered and concentrated. Silica gel column chromatography (eluting with 50% EtOAc in hexane) provided tert-butyl (S)-hexahydro-5H-isothiazolo [2,3-a]pyrazine-5-carboxylate 1,1-dioxide (2.5 g) as a white solid. $^1$H NMR (400 MHz, METHANOL-d4) b ppm 4.35-4.12 (m, 2H) 3.39-3.37 (m, 1H) 3.28-3.10 (m, 3H) 2.80-2.40 (m, 3H) 2.39-2.36 (m, 1H) 2.03-1.94 (m, 1H) 1.59 (s, 9H).

Step 3: (S)-hexahydro-2H-isothiazolo[2,3-a]pyrazine 1,1-dioxide hydrochloride

A solution of HCl (4.0 M in dioxane, 3 mL) was added to a solution of tert-butyl (S)-hexahydro-5H-isothiazolo[2,3-a] pyrazine-5-carboxylate 1,1-dioxide (2.5 g, 9.0 mmol) and the mixture was stirred for 2 h at rt. The reaction was then concentrated to give crude (S)-hexahydro-2H-isothiazolo[2, 3-a]pyrazine 1,1-dioxide hydrochloride which was used without further purification.

Step 4. potassium (S)-((1,1-dioxidohexahydro-5H-isothiazolo[2,3-a]pyrazin-5-yl)methyl)trifluoroborate To a solution of (S)-hexahydro-2H-isothiazolo[2,3-a] pyrazine 1,1-dioxide hydrochloride (1.7 g, 8.0 mmol) in THF (20 mL) was added NaH (0.461 g, 19.3 mmol), potassium (bromomethyl)trifluoroborate (1.9 g, 9.6 mmol) and tetrabutylammonium iodide (0.178 g, 0.482 mmol). The reaction mixture was stirred at rt for 16 h. The reaction mixture was then concentrated to give potassium (S)-((1,1-dioxidohexahydro-5H-isothiazolo[2,3-a]pyrazin-5-yl) methyl)trifluoroborate (3 g, crude) as a white solid.

Preparation of tert-butyl (2S)-4-(bromomethyl)-4-fluoro-2-methylpiperidine-1-carboxylate

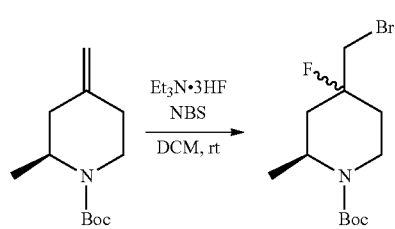 [SMILES: C=C1CCN(C(=O)OC(C)(C)C)[C@@H](C)C1 ; C[C@H]1CC(F)(CBr)CCN1C(=O)OC(C)(C)C]

To a solution of tert-butyl (S)-2-methyl-4-methylenepiperidine-1-carboxylate [see Example 71](400 mg, 1.89 mmol)) in DCM (10 mL) at 0° C. was added triethylamine trihydrofluoride (0.77 mL, 4.73 mmol). The reaction mixture was stirred at 0° C. for 30 min and then NBS (500 mg, 2.83 mmol) was added. The mixture was stirred at rt for 2 h. The reaction mixture was then basified with saturated aqueous NaHCO$_3$ solution and extracted with EtOAc. The organic layer was dried over sodium sulfate, filtered and concentrated. The crude product was purified by silica gel chromatography (eluted with 10% EtOAc/hexane) to give tert-butyl (2S)-4-(bromomethyl)-4-fluoro-2-methylpiperidine-1-carboxylate (0.35 g, 60% yield) as a mixture of diastereomers that was used without further purification.

Preparation of (cis)-4-(bromomethyl)-1-isobutyl-2-(trifluoromethyl)piperidine

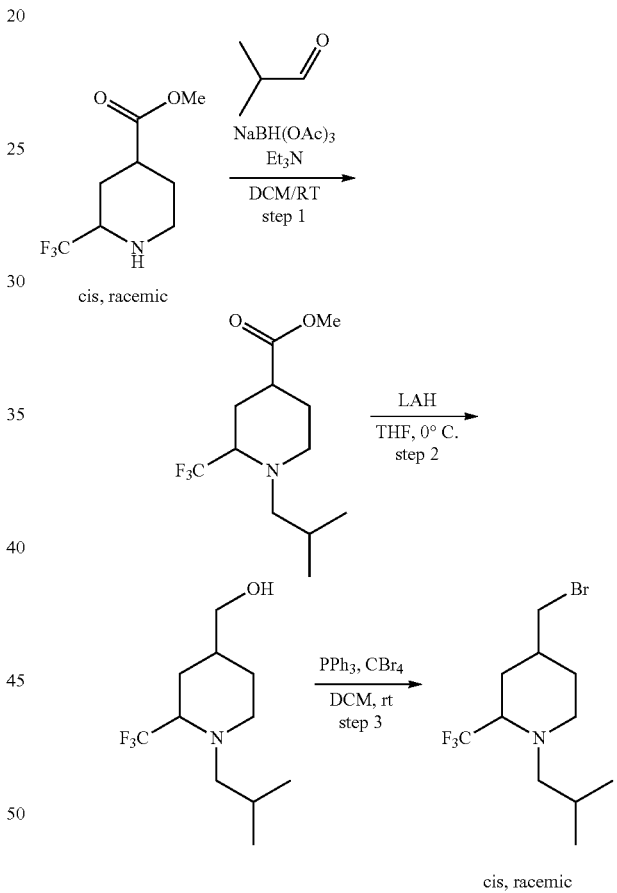

Step 1. (cis)-methyl 1-isobutyl-2-(trifluoromethyl) piperidine-4-carboxylate

Isobutyraldehyde (0.767 g, 10.7 mmol) and triethylamine (3.07 mL, 21.3 mmol) were added to a solution of (cis)-methyl 2-(trifluoromethyl)piperidine-4-carboxylate [see WO2021/158948, 2021, A1] (1.5 g, 7.1 mmol) in DCM (15 mL). The reaction mixture was stirred at rt for 30 min and then sodium triacetoxyborohydride (4.51 g, 21.3 mmol) was added. The reaction mixture was stirred at rt for 4 h and then quenched with a solution of saturated aqueous NaHCO$_3$ and extracted three times with DCM. The combined organic extracts were washed with brine, dried over Na₂SO₄, filtered and concentrated to give crude (cis)-methyl 1-isobutyl-2-(trifluoromethyl)piperidine-4-carboxylate (1.0 g) which was used without further purification.

Step 2. (cis)-(1-isobutyl-2-(trifluoromethyl)piperidin-4-yl)methanol

A solution of LAH (2M in THF, 1.02 mL, 2.05 mmol) was added to a solution of (cis)-methyl 1-isobutyl-2-(trifluoromethyl)piperidine-4-carboxylate (0.5 g, 1.87 mmol) in THF (5 mL) at 0° C. The mixture was stirred at 0° C. for 2 h and then quenched with EtOAc. The mixture was washed with a solution of saturated aqueous ammonium chloride and the organic layer was dried over Na₂SO₄, filtered and concentrated to give crude (cis)-(1-isobutyl-2-(trifluoromethyl)piperidin-4-yl)methanol (150 mg) which was used without further purification.

Step 3. (cis)-4-(bromomethyl)-1-isobutyl-2-(trifluoromethyl)piperidine

Triphenylphosphine (427 mg, 1.62 mmol) and carbon tetrabromide (537 mg, 1.62 mmol) were added in portions to a solution of (cis)-(1-isobutyl-2-(trifluoromethyl)piperidin-4-yl)methanol (130 mg, 0.54 mmol) in DCM (4 mL) at 0° C. The reaction mixture was stirred at rt for 2 h. After completion of the reaction, the mixture was diluted with DCM and washed with water. The organic layer was washed with brine, dried over Na₂SO₄, filtered and concentrated. The crude material was purified by silica gel chromatography (eluted with 0-50% EtOAc in hexanes) to afford (cis)-4-(bromomethyl)-1-isobutyl-2-(trifluoromethyl)piperidine (60 mg, 0.20 mmol, 37% yield).

PREPARATION OF EXAMPLE COMPOUNDS

Example 1. Preparation of 1-(5-((1-(cyclohexylmethyl)piperidin-4-yl)methyl)pyrazolo[1,5-a]pyridin-3-yl)dihydropyrimidine-2,4(1H,3H)-dione (Example 1)

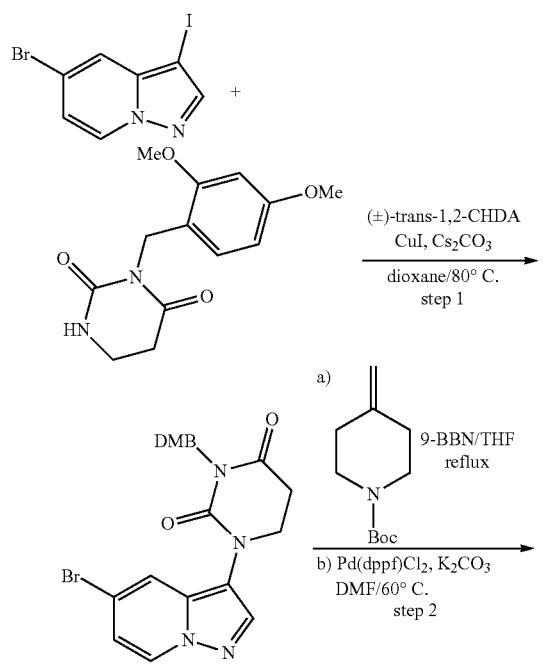

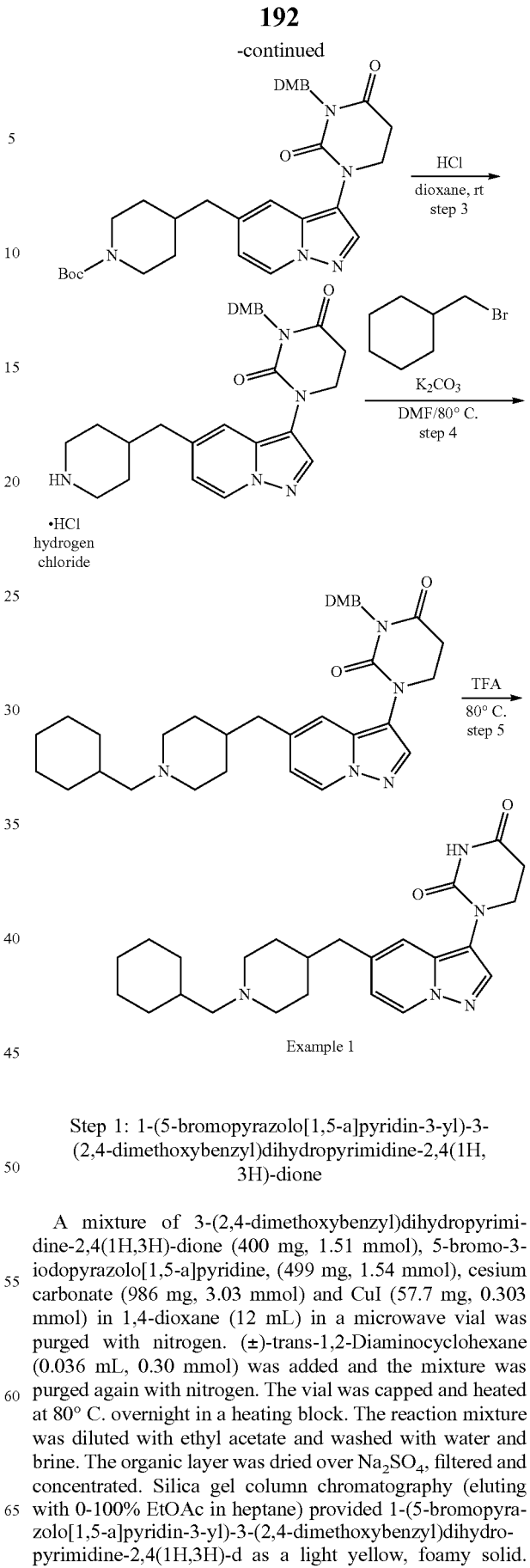

Step 1: 1-(5-bromopyrazolo[1,5-a]pyridin-3-yl)-3-(2,4-dimethoxybenzyl)dihydropyrimidine-2,4(1H,3H)-dione A mixture of 3-(2,4-dimethoxybenzyl)dihydropyrimidine-2,4(1H,3H)-dione (400 mg, 1.51 mmol), 5-bromo-3-iodopyrazolo[1,5-a]pyridine, (499 mg, 1.54 mmol), cesium carbonate (986 mg, 3.03 mmol) and CuI (57.7 mg, 0.303 mmol) in 1,4-dioxane (12 mL) in a microwave vial was purged with nitrogen. (±)-trans-1,2-Diaminocyclohexane (0.036 mL, 0.30 mmol) was added and the mixture was purged again with nitrogen. The vial was capped and heated at 80° C. overnight in a heating block. The reaction mixture was diluted with ethyl acetate and washed with water and brine. The organic layer was dried over Na₂SO₄, filtered and concentrated. Silica gel column chromatography (eluting with 0-100% EtOAc in heptane) provided 1-(5-bromopyrazolo[1,5-a]pyridin-3-yl)-3-(2,4-dimethoxybenzyl)dihydropyrimidine-2,4(1H,3H)-d as a light yellow, foamy solid.

LCMS [M+H]+: 459.2. $^1$H NMR (500 MHz, CDCl$_3$) δ 8.23 (dd, J=7.3, 0.8 Hz, 1H), 7.90 (s, 1H), 7.49 (dd, J=2.1, 0.8 Hz, 1H), 7.14 (d, J=8.9 Hz, 1H), 6.86 (dd, J=7.3, 2.1 Hz, 1H), 6.49-6.39 (m, 2H), 5.03 (s, 2H), 3.83 (s, 3H), 3.80 (m, 5H), 2.96 (t, J=6.6 Hz, 2H).

Step 2: tert-butyl 4-((3-(3-(2,4-dimethoxybenzyl)-2, 4-dioxotetrahydropyrimidin-1(2H)-yl)pyrazolo[1,5-a]pyridin-5-yl)methyl)piperidine-1-carboxylate a) A microwave vial containing tert-butyl 4-methylenepiperidine-1-carboxylate (500 mg, 2.53 mmol) was purged with nitrogen for 15 min and then a solution of 9-BBN (0.5M in THF, 5.07 mL, 2.53 mmol) was added. The vial was capped and the mixture was heated at 80° C. for 3.5 h and then cooled to rt.

b) The reaction mixture from part a was added by syringe to a microwave vial containing a mixture of 1-(5-bromopyrazolo[1,5-a]pyridin-3-yl)-3-(2,4-dimethoxybenzyl)dihydropyrimidine-2,4(1H,3H)-dione, (1048 mg, 2.281 mmol), K$_2$CO$_3$ (438 mg, 3.17 mmol) and PdCl$_2$(dppf)·CH$_2$Cl$_2$ adduct (54 mg, 0.066 mmol) in DMF (14 mL) and water (1.4 mL). The vial was capped and the reaction mixture was heated overnight at 60° C. The reaction mixture was then cooled to rt and diluted with ethyl acetate and washed sequentially with water and brine. The organic layer was dried over sodium sulfate, filtered and concentrated. Silica gel column chromatography (eluted with 0-100% EtOAc in heptane) provided tert-butyl 4-((3-(3-(2,4-dimethoxybenzyl)-2,4-dioxotetrahydropyrimidin-1(2H)-yl)pyrazolo[1,5-a]pyridin-5-yl)methyl)piperidine-1-carboxylate as a light yellow, foamy solid. LCMS [M+H]+: 578.4.

Step 3: 3-(2,4-dimethoxybenzyl)-1-(5-(piperidin-4-ylmethyl)pyrazolo[1,5-a]pyridin-3-yl)dihydropyrimidine-2,4(1H,3H)-dione hydrochloride A solution of HCl (4.0 M in dioxane, 15 ml, 60 mmol) was added to tert-butyl 4-((3-(3-(2,4-dimethoxybenzyl)-2,4-dioxotetrahydropyrimidin-1(2H)-yl)pyrazolo[1,5-a]pyridin-5-yl)methyl)piperidine-1-carboxylate (1270 mg, 2.154 mmol) and the mixture was stirred for 2 h at rt. The reaction was then concentrated to give crude 3-(2,4-dimethoxybenzyl)-1-(5-(piperidin-4-ylmethyl)pyrazolo[1,5-a]pyridin-3-yl)dihydropyrimidine-2,4(1H,3H)-dione hydrochloride. LCMS [M+H]+: 478.4.

Step 4: 1-(5-((1-(cyclohexylmethyl)piperidin-4-yl)methyl)pyrazolo[1,5-a]pyridin-3-yl)-3-(2,4-dimethoxybenzyl)dihydropyrimidine-2,4(1H,3H)-dione To a solution of 3-(2,4-dimethoxybenzyl)-1-(5-(piperidin-4-ylmethyl)pyrazolo[1,5-a]pyridin-3-yl)dihydropyrimidine-2,4(1H,3H)-dione hydrochloride (100 mg, 0.195 mmol) in DMF (3 mL) was added potassium carbonate (81 mg, 0.58 mmol) and (bromomethyl)cyclohexane (0.081 mL, 0.58 mmol). The mixture was heated at 80° C. for 4 h and then cooled to rt. The mixture was diluted with ethyl acetate and washed sequentially with water and brine. The organic layer was dried over sodium sulfate, filtered and concentrated to give crude 1-(5-((1-(cyclohexylmethyl)piperidin-4-yl)methyl)pyrazolo[1,5-a]pyridin-3-yl)-3-(2,4-dimethoxybenzyl)dihydropyrimidine-2,4(1H,3H)-dione. LCMS [M+H]+: 574.4.

Step 5: 1-(5-((1-(cyclohexylmethyl)piperidin-4-yl)methyl)pyrazolo[1,5-a]pyridin-3-yl)dihydropyrimidine-2,4(1H,3H)-dione TFA (2 mL, 26 mmol) was added to crude 1-(5-((1-(cyclohexylmethyl)piperidin-4-yl)methyl)pyrazolo[1,5-a]pyridin-3-yl)-3-(2,4-dimethoxybenzyl)dihydropyrimidine-2,4(1H,3H)-dione (30 mg, 0.0525 mmol) and the mixture was heated at 80° C. overnight. The mixture was then cooled to rt, concentrated and the residue was dissolved in toluene and concentrated again. The residue was dissolved in DMSO, filtered through a 1 micron filter and purified by reverse phase HPLC using ACN/Water/0.1% formic acid. The fractions containing the product were combined, frozen and lyophilized to afford a formate salt of 1-(5-((1-(cyclohexylmethyl)piperidin-4-yl)methyl)pyrazolo[1,5-a]pyridin-3-yl)dihydropyrimidine-2,4(1H,3H)-dione. LCMS [M+H]+: 424.3. $^1$H NMR (500 MHz, DMSO-d6) δ 10.44 (s, 1H), 8.58 (d, J=7.1 Hz, 1H), 8.16 (s, 1H), 8.00 (s, 1H), 7.37 (d, J=1.8 Hz, 1H), 6.79 (dd, J=7.2, 1.9 Hz, 1H), 3.77 (t, J=6.7 Hz, 2H), 3.59-3.26 (m, 2H), 3.19 (d, J=12.2 Hz, 3H), 2.79 (t, J=6.7 Hz, 2H), 2.60 (d, J=6.8 Hz, 2H), 2.56 (s, 1H), 1.82-1.58 (m, 9H), 1.41 (q, J=12.4 Hz, 2H), 1.30-1.09 (m, 3H), 0.96-0.82 (in, 2H).

The compounds in the following table were prepared by the method of Example 1, using the appropriate commercially available halide, mesylate, tosylate or triflate in step 4.

| Example No. | Structure | Mass [M + H] | $^1$H NMR |
|---|---|---|---|
| 2 | 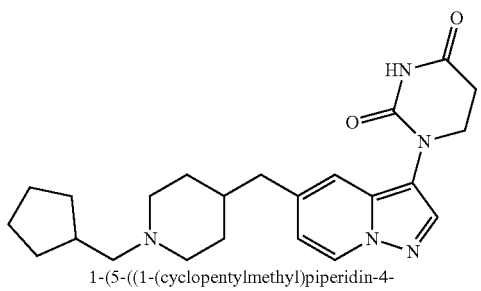  1-(5-((1-(cyclopentylmethyl)piperidin-4-yl)methyl)pyrazolo[1,5-a]pyridin-3-yl)dihydropyrimidine-2,4(1H,3H)-dione | 410.3 | (500 MHz, DMSO-d6) δ 10.45 (d, J = 4.6 Hz, 1H), 8.60 (d, J = 7.1 Hz, 1H), 8.01 (s, 1H), 7.45-7.26 (m, 1H), 6.80 (dd, J = 7.1, 1.9 Hz, 1H), 3.78 (td, J = 6.7, 2.8 Hz, 2H), 3.57-3.39 (m, 2H), 3.30-3.12 (m, 1H), 3.02 (dd, J = 7.2, 5.4 Hz, 2H), 2.87 (dt, J = 14.1, 10.6 Hz, 2H), 2.79 (t, J = 6.7 Hz, 2H), 2.62 (d, J = 6.6 Hz, 2H), 2.20 (h, J = 7.4 Hz, 1H), 1.94-1.70 (m, 4H), 1.62 (tdq, J = 9.7, 6.8, 3.8, 3.1 Hz, 2H),1.58-1.41 (m, 4H), 1.31-1.11 (m, 2H). |

-continued

| Example No. | Structure | Mass [M + H] | ¹H NMR |
|---|---|---|---|
| 3 | 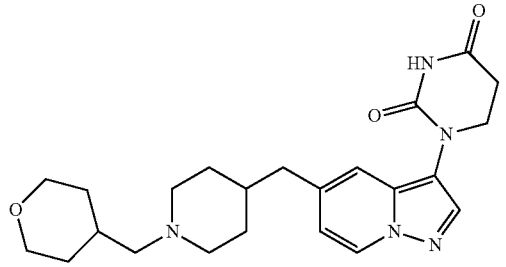 [SMILES: O=C1CCN(c2cnn3ccc(CC4CCN(CC5CCOCC5)CC4)cc23)C(=O)N1]<br>1-(5-((1-((tetrahydro-2H-pyran-4-yl)methyl)piperidin-4-yl)methyl)pyrazolo[1,5-a]pyridin-3-yl)dihydropyrimidine-2,4(1H,3H)-dione | 426.3 | (500 MHz, DMSO-d6) δ 10.45 (d, J = 5.4 Hz, 1H), 8.60 (dd, J = 7.2, 2.6 Hz, 1H), 8.02 (d, J = 2.3 Hz, 1H), 7.42-7.35 (m, 1H), 6.80 (dt, J = 7.2, 2.1 Hz, 1H), 3.85 (ddd, J = 11.6, 4.5, 1.9 Hz, 2H), 3.78 (td, J = 6.7, 3.5 Hz, 2H), 3.55-3.45 (m, 2H), 3.31 (td, J = 11.7, 2.1 Hz, 2H), 2.94 (t, J = 6.2 Hz, 2H), 2.87 (dt, J = 13.9, 10.9 Hz, 2H), 2.79 (t, J = 6.7 Hz, 2H), 2.62 (d, J = 6.6 Hz, 2H), 2.04 (ddt, J = 11.2, 7.3, 3.9 Hz, 1H), 1.92-1.71 (m, 3H), 1.69-1.58 (m, 2H), 1.56-1.42 (m, 2H), 1.22 (qd, J = 12.0, 4.5 Hz, 2H). |
| 4 | 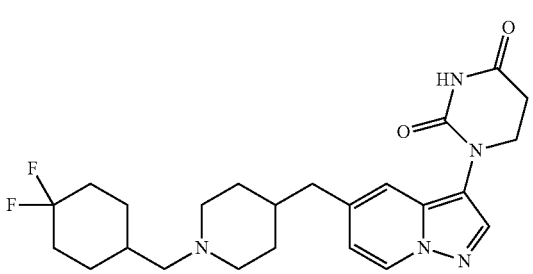 [SMILES: O=C1CCN(c2cnn3ccc(CC4CCN(CC5CCC(F)(F)CC5)CC4)cc23)C(=O)N1]<br>1-(5-((1-((4,4-difluorocyclohexyl)methyl)piperidin-4-yl)methyl)pyrazolo[1,5-a]pyridin-3-yl)dihydropyrimidine-2,4(1H,3H)-dione | 460.4 | (500 MHz, DMSO-d6) δ 10.36 (d, J = 5.1 Hz, 1H), 8.52 (d, J = 7.3 Hz, 1H), 7.93 (s, 1H), 7.29 (d, J = 15.4 Hz, 1H), 6.72 (d, J = 7.1 Hz, 1H), 3.69 (t, J = 6.8 Hz, 2H), 3.14 (s, 1H), 2.88 (t, J = 6.3 Hz, 2H), 2.79 (dd, J = 20.7, 8.9 Hz, 2H), 2.71 (t, J = 6.7 Hz, 2H), 2.54 (d, J = 6.5 Hz, 2H), 2.02-1.90 (m, 3H), 1.83-1.63 (m, 8H), 1.43 (q, J = 12.4, 11.6 Hz, 2H), 1.15 (q, J = 13.1 Hz, 2H). |
| 5 | 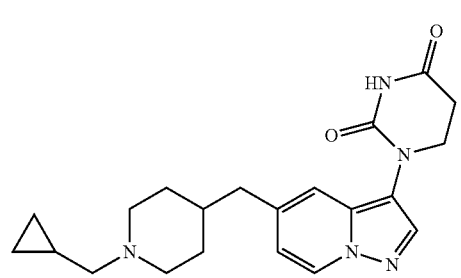 [SMILES: O=C1CCN(c2cnn3ccc(CC4CCN(CC5CC5)CC4)cc23)C(=O)N1]<br>1-(5-((1-(cyclopropylmethyl)piperidin-4-yl)methyl)pyrazolo[1,5-a]pyridin-3-yl)dihydropyrimidine-2,4(1H,3H)-dione | 382.2 | (500 MHz, DMSO-d6) δ 10.45 (d, J = 5.4 Hz, 1H), 8.60 (dd, J = 7.1, 3.0 Hz, 1H), 8.02 (d, J = 2.3 Hz, 1H), 7.39 (d, J = 1.8 Hz, 1H), 6.80 (dd, J = 7.2, 1.9 Hz, 1H), 5.77 (ddt, J = 17.0, 10.3, 6.7 Hz, 1H), 5.31-5.08 (m, 2H), 3.78 (td, J = 6.7, 3.3 Hz, 2H), 3.58-3.38 (m, 2H), 3.25 (d, J = 6.3 Hz, 1H), 3.15-3.03 (m, 2H), 2.96-2.83 (m, 2H), 2.79 (t, J = 6.8 Hz, 2H), 2.61 (d, J = 6.5 Hz, 2H), 2.43 (dtd, J = 9.7, 6.4, 1.6 Hz, 2H), 1.83 (d, J = 13.8 Hz, 2H), 1.43 (q, J = 13.1 Hz, 2H). |

| Example No. | Structure | Mass [M + H] | ¹H NMR |
|---|---|---|---|
| 6 | 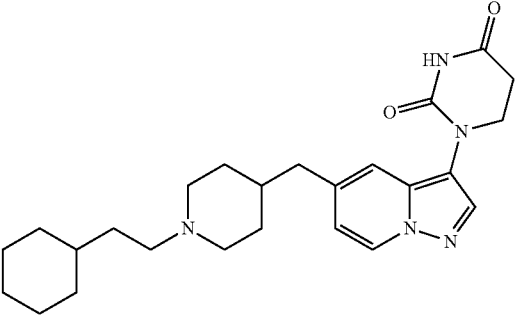 [SMILES: O=C1CCN(c2cnn3ccc(CC4CCN(CCC5CCCCC5)CC4)cc23)C(=O)N1]<br>1-(5-((1-(2-cyclohexylethyl)piperidin-4-yl)methyl)pyrazolo[1,5-a]pyridin-3-yl)dihydropyrimidine-2,4(1H,3H)-dione | 438.4 | (500 MHz, DMSO-d6) δ 10.45 (d, J = 5.6 Hz, 1H), 8.68-8.49 (m, 1H), 8.01 (d, J = 2.5 Hz, 1H), 7.46-7.24 (m, 1H), 6.80 (dd, J = 7.1, 1.9 Hz, 1H), 3.78 (t, J = 6.7 Hz, 2H), 3.53-3.41 (m, 2H), 3.28-3.10 (m, 1H), 3.03 (dt, J = 11.2, 5.3 Hz, 2H), 2.90-2.72 (m, 4H), 2.61 (d, J = 6.6 Hz, 2H), 1.83 (t, J = 15.3 Hz, 2H), 1.77-1.57 (m, 5H), 1.57-1.47 (m, 2H), 1.41 (q, J = 13.1 Hz, 2H), 1.18 (ddd, J = 26.1, 22.5, 12.0 Hz, 4H), 0.92 (q, J = 11.9 Hz, 2H). |
| 7 | 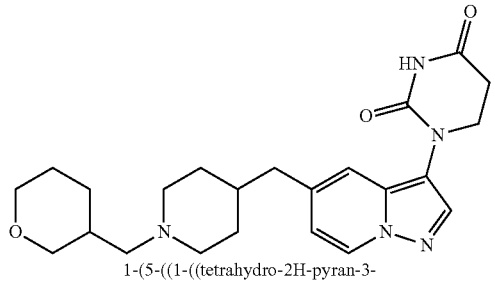<br>1-(5-((1-((tetrahydro-2H-pyran-3-yl)methyl)piperidin-4-yl)methyl)pyrazolo[1,5-a]pyridin-3-yl)dihydropyrimidine-2,4(1H,3H)-dione | 426.3 | 1H NMR (500 MHz, DMSO-d6) δ 10.36 (d, J = 4.0 Hz, 1H), 8.52 (d, J = 7.2 Hz, 1H), 7.93 (d, J = 2.0 Hz, 1H), 7.30 (s, 1H), 6.71 (dd, J = 7.2, 1.9 Hz, 1H), 3.75-3.67 (m, 4H), 3.62 (dt, J = 11.5, 4.2 Hz, 2H), 3.44 (s, 2H), 3.19-3.02 (m, 1H), 2.92-2.74 (m, 3H), 2.71 (t, J = 6.7 Hz, 2H), 2.58-2.51 (m, 2H), 1.92 (s, 1H), 1.72 (d, J = 14.5 Hz, 3H), 1.59-1.47 (m, 1H), 1.41 (dt, J = 13.5, 9.7 Hz, 3H), 1.31-1.14 (m, 1H). |
| 8 | 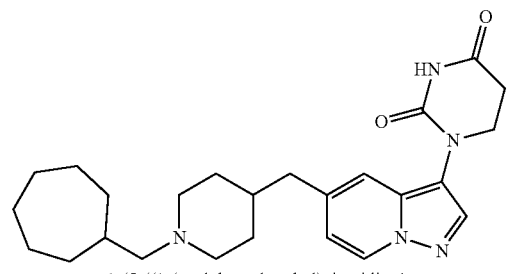<br>1-(5-((1-(cycloheptylmethyl)piperidin-4-yl)methyl)pyrazolo[1,5-a]pyridin-3-yl)dihydropyrimidine-2,4(1H,3H)-dione | 438.3 | (500 MHz, DMSO-d6) δ 10.45 (d, J = 4.7 Hz, 1H), 8.60 (dt, J = 7.2, 1.3 Hz, 1H), 8.02 (d, J = 1.6 Hz, 1H), 7.46-7.28 (m, 1H), 6.80 (dd, J = 7.2, 1.8 Hz, 1H), 3.78 (td, J = 6.7, 2.8 Hz, 2H), 3.47 (d, J = 12.2 Hz, 2H), 3.21 (s, 1H), 2.92-2.83 (m, 3H), 2.79 (td, J = 6.7, 1.8 Hz, 2H), 2.62 (d, J = 6.6 Hz, 2H), 2.00-1.66 (m, 6H), 1.65-1.38 (m, 10H), 1.27-1.09 (m, 2H). |
| 9 | 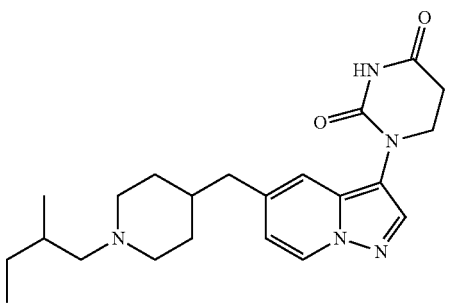 [SMILES: CCC(C)CN1CCC(Cc2ccn3ncc(N4CCC(=O)NC4=O)c3c2)CC1]<br>1-(5-((1-(2-methylbutyl)piperidin-4-yl)methyl)pyrazolo[1,5-a]pyridin-3-yl)dihydropyrimidine-2,4(1H,3H)-dione | 398.3 | (500 MHz, DMSO-d6) δ 10.44 (d, J = 4.6 Hz, 1H), 8.60 (s, 1H), 8.01 (s, 1H), 7.37 (d, J = 11.6 Hz, 1H), 6.79 (d, J = 7.2 Hz, 1H), 3.77 (t, J = 6.8 Hz, 2H), 3.46 (s, 2H), 3.21(s, 1H), 3.00-2.81 (m, 3H), 2.79 (t, J = 6.6 Hz, 2H), 2.62 (d, J = 6.5 Hz, 2H), 1.92- 1.71 (m, 4H), 1.65-1.33 (m, 3H), 1.16 (dq, J = 14.3, 7.2 Hz, 1H), 0.91 (dp, J = 23.0, 7.3, 6.9 Hz, 6H). |

| Example No. | Structure | Mass [M + H] | ¹H NMR |
|---|---|---|---|
| 10 | 1-(5-((1-(2-cyclohexylpropyl)piperidin-4-yl)methyl)pyrazolo[1,5-a]pyridin-3-yl)dihydropyrimidine-2,4(1H,3H)-dione | 452.3 | (500 MHz, DMSO-d6) δ 10.44 (s, 1H), 8.59 (d, J = 7.2 Hz, 1H), 8.01 (s, 1H), 7.36 (d, J = 11.5 Hz, 1H), 6.79 (d, J = 7.3 Hz, 1H), 3.77 (t, J = 6.6 Hz, 2H), 3.51 (d, J = 12.2 Hz, 4H), 3.21 (s, 1H), 3.01 (q, J = 6.3, 5.6 Hz, 1H), 2.97-2.70 (m, 4H), 2.62 (d, J = 6.5 Hz, 1H), 1.93-1.68 (m, 5H), 1.67-1.39 (m, 5H), 1.33-0.92 (m, 6H), 0.89 (d, J = 6.8 Hz, 3H). |
| 11 | 1-(5-((1-(2-(tetrahydro-2H-pyran-4-yl)ethyl)piperidin-4-yl)methyl)pyrazolo[1,5-a]pyridin-3-yl)dihydropyrimidine-2,4(1H,3H)-dione | 440.2 | (500 MHz, DMSO-d6) δ 10.44 (d, J = 5.6 Hz, 1H), 8.59 (d, J = 7.2 Hz, 1H), 8.00 (s, 1H), 7.37 (d, J = 13.5 Hz, 1H), 6.79 (d, J = 7.2 Hz, 1H), 3.88-3.79 (m, 2H), 3.77 (t, J = 6.7 Hz, 2H), 3.27 (q, J = 11.8 Hz, 4H), 3.04 (dt, J = 11.1, 5.4 Hz, 2H), 2.93-2.70 (m, 4H), 2.61 (d, J = 6.5 Hz, 2H), 1.83 (t, J = 14.6 Hz, 3H), 1.56 (d, J = 13.4 Hz, 5H), 1.40 (q, J = 13.0 Hz, 2H), 1.17 (qd, J = 12.2, 4.5 Hz, 2H). |
| 12 | 1-(5-((1-(heptan-4-yl)piperidin-4-yl)methyl)pyrazolo[1,5-a]pyridin-3-yl)dihydropyrimidine-2,4(1H,3H)-dione | 426.3 | (400 MHz, DMSO) δ 10.41 (s, 1H), 8.65 (s, 1H), 8.58 (d, J = 7.1 Hz, 1H), 7.99 (s, 1H), 7.36 (d, J = 1.8 Hz, 1H), 6.77 (dd, J = 7.2, 1.9 Hz, 1H), 3.76 (t, J = 6.7 Hz, 2H), 3.31 (d, J = 12.0 Hz, 2H), 3.05 (s, 1H), 3.02-2.92 (m, 2H), 2.78 (t, J = 6.7 Hz, 2H), 2.60 (d, J = 6.7 Hz, 2H), 1.92 (s, 1H), 1.84-1.61 (m, 4H), 1.56-1.39 (m, 4H), 1.34 (ddq, J = 13.6, 9.8, 7.0 Hz, 4H), 0.90 (t, J = 7.2 Hz, 6H). |
| 13 | 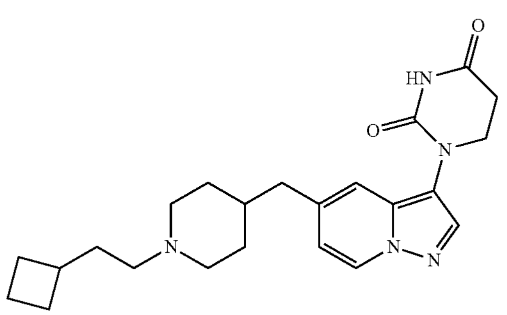 [SMILES: O=C1CCN(c2cnn3ccc(CC4CCN(CCC5CCC5)CC4)cc23)C(=O)N1] | 410.3 | (500 MHz, DMSO-d6) δ 10.43 (s, 1H), 8.59 (d, J = 7.2 Hz, 1H), 8.00 (s, 1H), 7.37 (d, J = 11.6 Hz, 1H), 6.79 (d, J = 7.1 Hz, 1H), 3.77 (t, J = 6.7 Hz, 2H), 3.21 (s, 1H), 3.00 (d, J = 8.3 Hz, 1H), 2.94-2.71 (m, 6H), 2.60 (d, J = 6.5 Hz, 2H), 2.23 (dq, J = 15.5, 7.7 Hz, 1H), 2.13-1.97 (m, 2H), 1.83 (dd, J = 17.2, 10.7 Hz, 5H), 1.72 (dd, J = 10.5, 6.2 |

| Example No. | Structure | Mass [M + H] | ¹H NMR |
|---|---|---|---|
| | 1-(5-((1-(2-cyclobutylethyl)piperidin-4-yl)methyl)pyrazolo[1,5-a]pyridin-3-yl)dihydropyrimidine-2,4(1H,3H)-dione | | Hz, 2H), 1.63 (h, J = 9.4 Hz, 2H), 1.40 (q, J = 13.1, 12.7 Hz, 2H). |
| 14 | 1-(5-((1-((tetrahydrofuran-3-yl)methyl)piperidin-4-yl)methyl)pyrazolo[1,5-a]pyridin-3-yl)dihydropyrimidine-2,4(1H,3H)-dione | 412.3 | (500 MHz, Methanol-d4) δ 8.34 (dd, J = 7.2, 0.9 Hz, 1H), 7.91 (s, 1H), 7.27 (dd, J = 2.0, 1.0 Hz, 1H), 6.73 (dd, J = 7.2, 1.9 Hz, 1H), 3.84 (dd, J = 8.8, 7.1 Hz, 1H), 3.81-3.74 (m, 3H), 3.66 (dt, J = 8.5, 7.5 Hz, 1H), 3.51 (t, J = 15.4 Hz, 2H), 3.37 (dd, J = 8.8, 6.5 Hz, 1H), 3.11-3.03 (m, 2H), 2.85 (t, J = 12.8 Hz, 2H), 2.79 (t, J = 6.8 Hz, 2H), 2.60 (dd, J = 6.8, 3.7 Hz, 3H), 2.10 (dtd, J = 12.6, 7.8, 4.8 Hz, 1H), 1.89 (dd, J = 29.1, 13.1 Hz, 3H), 1.58 (dq, J = 12.5, 7.6 Hz, 1H), 1.46 (q, J = 13.4 Hz, 2H). |
| 15 | 1-(5-((1-((tetrahydrofuran-2-yl)methyl)piperidin-4-yl)methyl)pyrazolo[1,5-a]pyridin-3-yl)dihydropyrimidine-2,4(1H,3H)-dione | 412.2 | (400 MHz, Methanol-d4) δ 8.43 (d, J = 7.2 Hz, 1H), 8.35 (s, 1H), 8.00 (s, 1H), 7.36 (s, 1H), 6.82 (d, J = 7.1 Hz, 1H), 4.25 (ddt, J = 10.0, 7.1, 3.7 Hz, 1H), 3.96-3.84 (m, 3H), 3.81 (q, J = 7.4 Hz, 1H), 3.61 (d, J = 12.4 Hz, 2H), 3.37-3.14 (m, 2H), 3.08 (dd, J = 13.3, 10.4 Hz, 1H), 3.04-2.92 (m, 2H), 2.88 (t, J = 6.8 Hz, 2H), 2.70 (d, J = 7.0 Hz, 2H), 2.21-2.07 (m, 1H), 2.06-1.85 (m, 5H), 1.68-1.48 (m, 3H). NH protons were not observed due to solvent exchange |
| 16 | 1-(5-((1-(2-cyclopentylethyl)piperidin-4-yl)methyl)pyrazolo[1,5-a]pyridin-3-yl)dihydropyrimidine-2,4(1H,3H)-dione | 424.3 | (500 MHz, DMSO-d6) δ 10.44 (d, J = 5.9 Hz, 1H), 8.59 (d, J = 7.2 Hz, 1H), 8.00 (s, 1H), J = 10.9 Hz, 1H), 6.79 (d, J = 7.2 Hz, 1H), 3.77 (t, J = 6.7 Hz, 2H), 3.22 (s, 1H), 2.99 (dt, J = 10.5, 5.0 Hz, 2H), 2.86 (t, J = 11.7 Hz, 2H), 2.82-2.72 (m, 3H), 2.60 (d, J = 6.6 Hz, 2H), 1.90-1.68 (m, 6H), 1.68-1.55 (m, 4H), 1.54-1.36 (m, 4H), 1.10 (d, J = 7.4 Hz, 2H). |

| Example No. | Structure | Mass [M + H] | ¹H NMR |
|---|---|---|---|
| 17 | 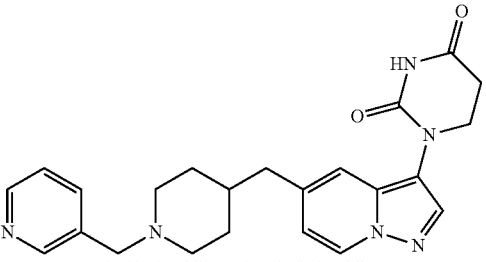 [SMILES: O=C1CCN(c2cnn3ccc(CC4CCN(Cc5cccnc5)CC4)cc23)C(=O)N1]<br>1-(5-(((1-(pyridin-3-ylmethyl)piperidin-4-yl)methyl)pyrazolo[1,5-a]pyridin-3-yl)dihydropyrimidine-2,4(1H,3H)-dione | 4193 | (500 MHz, DMSO-d6) δ 10.44 (s, 1H), 8.69 (dd, J = 5.1, 1.7 Hz, 2H), 8.59 (d, J = 7.1 Hz, 1H), 8.01 (s, 1H), 7.96 (dt, J = 7.9, 2.0 Hz, 1H), 7.56 (dd, J = 7.9, 4.9 Hz, 1H), 7.37 (s, 1H), 6.79 (dd, J = 7.1, 1.9 Hz, 1H), 4.35 (d, J = 4.0 Hz, 2H), 3.77 (t, J = 6.7 Hz, 2H), 3.39 (d, J = 12.0 Hz, 2H), 2.94 (q, J = 11.5 Hz, 2H), 2.79 (t, J = 6.7 Hz, 2H), 2.60 (d, J = 6.5 Hz, 2H), 2.00-1.69 (m, 3H), 1.51-1.23 (m, 2H). |
| 18 | 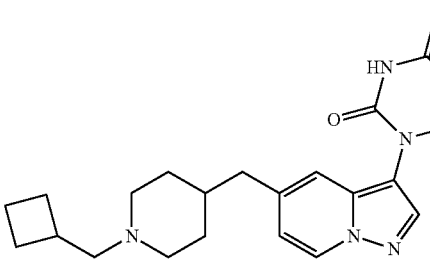<br>1-(5-((1-(cyclobutylmethyl)piperidin-4-yl)methyl)pyrazolo[1,5-a]pyridin-3-yl)dihydropyrimidine-2,4(1H,3H)-dione | 396.3 | (500 MHz, DMSO-d6) δ 10.45 (d, J = 6.0 Hz, 1H), 8.63-8.55 (m, 1H), 8.01 (d, J = 2.6 Hz, 1H), 7.38 (d, J = 1.8 Hz, 1H), 6.79 (dd, J = 7.2, 1.9 Hz, 1H), 3.77 (t, J = 6.7 Hz, 2H), 3.35 (d, J = 12.0 Hz, 2H), 3.26-3.13 (m, 1H), 3.08 (dd, J = 7.1, 5.1 Hz, 2H), 2.86 (t, J = 11.8 Hz, 3H), 2.75-2.64 (m, 1H), 2.60 (d, J = 6.6 Hz, 2H), 2.07 (dtd, J = 10.6, 6.8, 3.7 Hz, 2H), 1.98-1.69 (m, 7H), 1.41 (q, J = 13.1 Hz, 2H). |
| 19 | 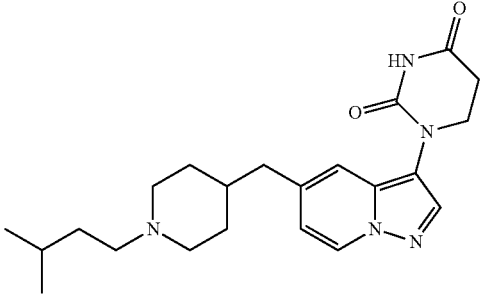 [SMILES: CC(C)CCN1CCC(Cc2ccn3ncc(N4CCC(=O)NC4=O)c3c2)CC1]<br>1-(5-((1-isopentylpiperidin-4-yl)methyl)pyrazolo[1,5-a]pyridin-3-yl)dihydropyrimidine-2,4(1H,3H)-dione | 398.4 | (500 MHz, DMSO-d6) δ 10.43 (s, 1H), 8.59 (d, J = 7.2 Hz, 1H), 8.00 (d, J = 2.8 Hz, 1H), 7.37 (d, J = 11.8 Hz, 1H), 6.79 (d, J = 7.1 Hz, 1H), 3.76 (dt, J = 7.0, 4.0 Hz, 2H), 3.27-3.10 (m, 2H), 3.01 (qd, J = 8.4, 5.1, 3.7 Hz, 2H), 2.93-2.67 (m, 4H), 2.68-2.55 (m, 2H), 1.80 (p, J = 20.8, 19.2 Hz, 3H), 1.59 (dt, J = 14.0, 7.9 Hz, 1H), 1.52 (t, J = 8.1 Hz, 2H), 1.40 (q, J = 13.5 Hz, 2H), 0.89 (d, J = 6.5 Hz, 6H). |
| 20 | 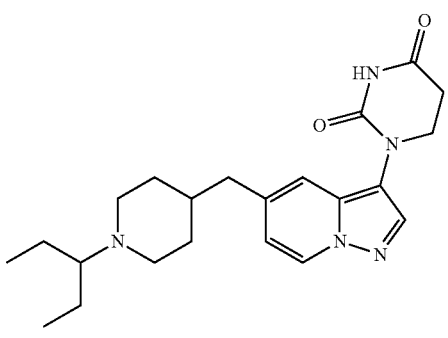 [SMILES: CCC(CC)N1CCC(Cc2ccn3ncc(N4CCC(=O)NC4=O)c3c2)CC1]<br>1-(5-((1-(pentan-3-yl)piperidin-4-yl)methyl)pyrazolo[1,5-a]pyridin-3-yl)dihydropyrimidine-2,4(1H,3H)-dione | 398.4 | (400 MHz, DMSO-d6) δ 10.42 (s, 1H), 8.59 (d, J = 7.2 Hz, 1H), 8.00 (d, J = 1.7 Hz, 1H), 7.37 (s, 1H), 6.78 (dd, J = 7.1, 1.9 Hz, 1H), 3.77 (t, J = 6.8 Hz, 2H), 3.34 (d, J = 12.0 Hz, 2H), 2.98 (d, J = 11.5 Hz, 3H), 2.78 (td, J = 6.9, 1.9 Hz, 2H), 2.61 (d, J = 6.7 Hz, 2H), 2.00-1.70 (m, 5H), 1.66-1.33 (m, 4H), 0.95 (td, J = 7.4, 1.8 Hz, 6H). |

| Example No. | Structure | Mass [M + H] | ¹H NMR |
|---|---|---|---|
| 21 | 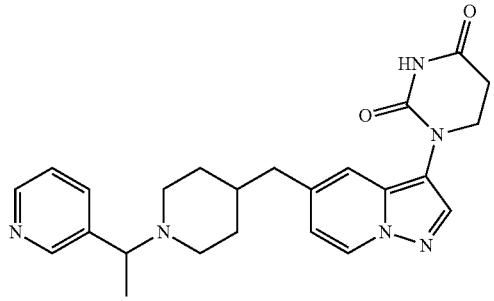 [SMILES: CC(c1cccnc1)N1CCC(Cc2ccn3ncc(N4CCC(=O)NC4=O)c3c2)CC1]<br>1-(5-((1-(1-(pyridin-3-yl)ethyl)piperidin-4-yl)methyl)pyrazolo[1,5-a]pyridin-3-yl)dihydropyrimidine-2,4(1H,3H)-dione | 433.4 | (500 MHz, DMSO-d6) δ 10.43 (s, 1H), 8.78-8.65 (m, 2H), 8.58 (d, J = 7.1 Hz, 1H), 8.15-7.94 (m, 2H), 7.71-7.55 (m, 1H), 7.35 (d, J = 1.6 Hz, 1H), 6.76 (dd, J = 7.2, 1.8 Hz, 1H), 4.62 (d, J = 7.9Hz, 2H), 3.76 (t, J = 6.7 Hz, 2H), 3.61 (d, J = 11.9 Hz, 1H), 3.30 (d, J = 12.1 Hz, 1H), 2.77 (q, J = 11.3, 9.0 Hz, 4H), 2.59 (d, J = 6.3 Hz, 1H), 1.81 (dd, J = 31.0, 11.2 Hz, 3H), 1.67 (d, J = 6.9 Hz, 3H), 1.45 (dt, J = 28.2, 13.6 Hz, 2H). |
| 22 | 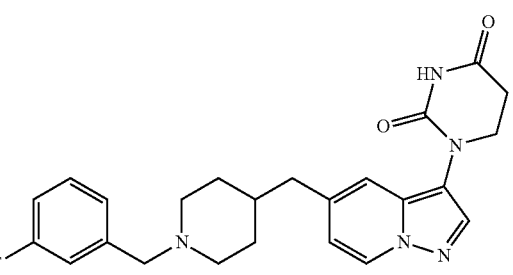<br>1-(5-((1-(3-fluorobenzyl)piperidin-4-yl)methyl)pyrazolo[1,5-a]pyridin-3-yl)dihydropyrimidine-2,4(1H,3H)-dione | 436.3 | (500 MHz, DMSO-d6) δ 10.45 (d, J = 14.1 Hz, 8.60 (dd, J = 10.0, 7.1 Hz, 1H), 8.01 (s, 1H), 7.54 (td, J = 8.0, 6.1 Hz, 1H), 7.49-7.26 (m, 4H), 6.79 (td, J = 7.2, 6.3, 1.9 Hz, 1H), 4.30 (d, J = 5.0 Hz, 2H), 3.77 (t, J = 6.7 Hz, 2H), 3.36 (d, J = 12.0 Hz, 2H), 2.91 (q, J = 11.6 Hz, 2H), 2.79 (t, J = 6.7 Hz, 2H), 2.60 (d, J = 6.5 Hz, 2H), 1.95-1.70 (m, 3H), 1.42 (q, J = 13.0 Hz, 2H). |
| 23 | 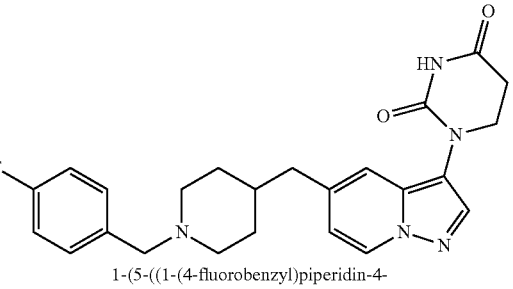<br>1-(5-((1-(4-fluorobenzyl)piperidin-4-yl)methyl)pyrazolo[1,5-a]pyridin-3-yl)dihydropyrimidine-2,4(1H,3H)-dione | 436.3 | (500 MHz, DMSO-d6) δ 10.42 (s, 1H), 8.57 (d, J = 7.2 Hz, 1H), 7.99 (s, 1H), 7.52 (dd, J = 8.6, 5.4 Hz, 2H), 7.37-7.28 (m, 3H), 6.77 (dd, J = 7.2, 1.9 Hz, 1H), 4.25 (d, J = 5.0 Hz, 2H), 3.75 (q, J = 6.4 Hz, 2H), 3.33 (d, J = 12.1 Hz, 2H), 2.87 (d, J = 12.0 Hz, 2H), 2.77 (t, J = 6.7 Hz, 2H), 2.58 (m, 3H), 1.83-1.73 (m, 2H), 1.44-1.35 (m, 2H). |
| 24 | 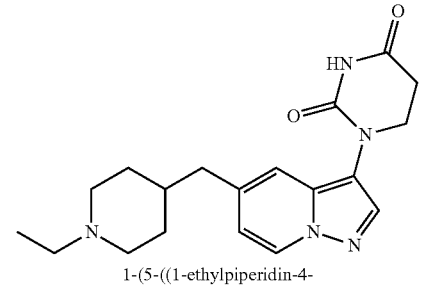<br>1-(5-((1-ethylpiperidin-4-yl)methyl)pyrazolo[1,5-a]pyridin-3-yl)dihydropyrimidine-2,4(1H,3H)-dione | 356.3 | (400 MHz, DMSO-d6) δ 10.42 (d, J = 4.5 Hz, 1H), 8.59 (dt, J = 7.1, 1.3 Hz, 1H), 8.00 (s, 1H), 7.45-7.31 (m, 1H), 6.79 (dd, J = 7.2, 1.9 Hz, 1H), 3.77 (t, J = 6.7 Hz, 2H), 3.45 (d, J = 12.2 Hz, 2H), 3.29-3.14 (m, 1H), 3.12-3.00 (m, 2H), 2.94-2.71 (m, 4H), 2.61 (d, J = 6.5 Hz, 2H), 1.82 (d, J = 13.5 Hz, 2H), 1.40 (q, J = 13.0 Hz, 2H), 1.19 (t, J = 7.3 Hz, 3H). |

| Example No. | Structure | Mass [M + H] | ¹H NMR |
|---|---|---|---|
| 25 | 1-(5-((1-(3-(trifluoromethyl)benzyl)piperidin-4-yl)methyl)pyrazolo[1,5-a]pyridin-3-yl)dihydropyrimidine-2,4(1H,3H)-dione | 486.3 | (500 MHz, DMSO-d6) δ 10.43 (s, 1H), 8.59 (d, J = 7.1 Hz, 1H), 8.01 (s, 1H), 7.91 (s, 1H), 7.86 (d, J = 7.7 Hz, 1H), 7.79 (d, J = 7.7 Hz, 1H), 7.73 (q, J = 7.7, 7.0 Hz, 1H), 7.37 (d, J = 1.8 Hz, 1H), 6.84-6.75 (m, 1H), 4.39 (d, J = 4.8 Hz, 2H), 3.77 (t, J = 6.7 Hz, 2H), 3.37 (d, J = 12.0 Hz, 2H), 2.94 (q, J = 11.5 Hz, 2H), 2.78 (t, J = 6.7 Hz, 2H), 2.61 (d, J = 6.5 Hz, 2H), 2.02-1.66 (m, 3H), 1.42 (q, J = 13.1 Hz, 2H). |
| 26 | 1-(5-((1-(1-phenylethyl)piperidin-4-yl)methyl)pyrazolo[1,5-a]pyridin-3-yl)dihydropyrimidine-2,4(1H,3H)-dione | 432.3 | (500 MHz, DMSO-d6) δ 10.43 (s, 1H), 8.57 (d, J = 7.1 Hz, 1H), 8.00 (s, 1H), 7.61-7.42 (m, 5H), 7.35 (s, 1H), 6.91-6.55 (m, 1H), 4.48 (dt, J = 11.9, 5.9 Hz, 1H), 3.76 (t, J = 6.7 Hz, 2H), 3.64 (d, J = 12.0 Hz, 1H), 3.29-3.10 (m, 1H), 2.87-2.63 (m, 4H), 2.59 (d, J = 6.3 Hz, 2H), 1.95-1.71 (m, 3H), 1.64 (d, J = 6.9 Hz, 3H), 1.44 (dq, J = 41.1, 12.9, 12.2 Hz, 2H). |
| 27 | 1-(5-((1-(3-(trifluoromethoxy)benzyl)piperidin-4-yl)methyl)pyrazolo[1,5-a]pyridin-3-yl)dihydropyrimidine-2,4(1H,3H)-dione | 502.3 | (500 MHz, DMSO-d6) δ 10.44 (s, 1H), 8.59 (d, J = 7.1 Hz, 1H), 8.01 (s, 1H), 7.70-7.58 (m, 1H), 7.60-7.47 (m, 3H), 7.37 (s, 1H), 6.92-6.64 (m, 1H), 4.34 (d, J = 4.9 Hz, 2H), 3.77 (t, J = 6.7 Hz, 2H), 3.36 (d, J = 12.0 Hz, 2H), 2.92 (q, J = 11.6 Hz, 2H), 2.79 (t, J = 6.7 Hz, 2H), 2.60 (d, J = 6.5 Hz, 2H), 1.79 (dd, J = 34.7, 12.8 Hz, 3H), 1.42 (q, J = 13.1 Hz, 2H). |
| 28 | 1-(5-((1-(pyridin-4-ylmethyl)piperidin-4-yl)methyl)pyrazolo[1,5-a]pyridin-3-yl)dihydropyrimidine-2,4(1H,3H)-dione | 419.3 | (500 MHz, DMSO-d6) δ 10.43 (s, 1H), 8.71 (s, 2H), 8.58 (d, J = 7.2 Hz, 1H), 8.00 (s, 1H), 7.51 (d, J = 5.1 Hz, 2H), 7.36 (s, 1H), 6.78 (dd, J = 7.1, 1.9 Hz, 1H), 4.32 (d, J = 4.7 Hz, 2H), 3.76 (t, J = 6.7 Hz, 2H), 3.37 (d, J = 11.9 Hz, 2H), 2.94 (d, J = 12.0 Hz, 2H), 2.78 (t, J = 6.7 Hz, 2H), 2.60 (d, J = 6.5 Hz, 2H), 1.82 (d, J = 14.8 Hz, 3H), 1.41 (q, J = 13.1 Hz, 2H). |

| Example No. | Structure | Mass [M + H] | ¹H NMR |
|---|---|---|---|
| 29 | 1-(5-((1-benzylpiperidin-4-yl)methyl)pyrazolo[1,5-a]pyridin-3-yl)dihydropyrimidine-2,4(1H,3H)-dione | 418.3 | (400 MHz, DMSO-d6) δ 10.42 (d, J = 12.8 Hz, 1H), 8.63-8.52 (m, 1H), 8.00 (d, J = 6.5 Hz,1H), 7.47 (s, 5H), 7.41-7.32 (m, 1H), 6.85-6.74 (m, 1H), 4.26 (d, J = 5.0 Hz, 2H), 3.76 (t, J = 6.7 Hz, 2H), 3.35 (d, J = 12.1 Hz, 2H), 2.90 (q, J = 11.7 Hz, 2H), 2.78 (t, J = 6.7 Hz, 2H), 2.59 (d, J = 6.4 Hz, 2H), 1.78 (dd, J = 25.2, 11.7 Hz, 3H), 1.41 (q, J = 13.1 Hz, 2H). |
| 30 | 1-(5-((1-(2,2,2-trifluoroethyl)piperidin-4-yl)methyl)pyrazolo[1,5-a]pyridin-3-yl)dihydropyrimidine-2,4(1H,3H)-dione | 410.3 | (500 MHz, DMSO-d6) δ 10.44 (s, 1H), 8.57 (dd, J = 7.1, 0.9 Hz, 1H), 8.00 (s, 1H), 7.36 (dd, J = 1.9, 0.9 Hz, 1H), 6.79 (dd, J = 7.2, 1.9 Hz, 1H), 4.18 (d, 2H), 3.77 (t, J = 6.7 Hz, 2H), 3.11 (d, J = 62.3 Hz, 3H), 2.79 (t, J = 6.7 Hz, 2H), 2.59 (d, J = 6.7 Hz, 3H), 2.56 (s, 1H), 1.67 (d, J = 13.8 Hz, 3H), 1.36 (d, J = 13.1 Hz, 2H). |
| 31 | 1-(5-((1-(2,2,3,3-tetrafluoropropyl)piperidin-4-yl)methyl)pyrazolo[1,5-a]pyridin-3-yl)dihydropyrimidine-2,4(1H,3H)-dione | 442.2 | (500 MHz, DMSO-d6) δ 10.44 (s, 1H), 8.56 (d, J = 7.4 Hz, 1H), 7.99 (s, 1H), 7.36 (s, 1H), 6.78 (dd, J = 7.1, 1.9 Hz, 1H), 6.50 (t, J = 52.4 Hz, 1H), 3.77 (t, J = 6.7 Hz, 2H), 3.59 (s, 4H), 2.93 (s, 2H), 2.79 (t, J = 6.7 Hz, 2H), 2.57 (d, J = 9.4 Hz, 2H), 2.45-2.05 (m, 1H), 1.61 (s, 3H), 1.37 (d, J = 56.0 Hz, 2H). |
| 32 | 1-(5-((1-((3,3-difluorocyclobutyl)methyl)piperidin-4-yl)methyl)pyrazolo[1,5-a]pyridin-3-yl)dihydropyrimidine-2,4(1H,3H)-dione | 432.1 | As formate salt-(400 MHz, CD₃OD) δ 8.44 (brs, 1H), 8.42 (d, J = 6.8 Hz, 1H), 7.99 (s, 1H), 7.36 (s, 1H), 6.82 (d, J = 7.2 Hz, 1H), 3.87 (t, J = 6.8 Hz, 2H), 3.45-3.42 (m, 2H), 3.20-3.19 (m, 2H), 2.89-2.40 (m, 11H), 1.92-1.88 (m, 3H), 1.55-1.53 (m, 2H) ppm. NH protons not observed due to solvent exchange |

-continued

| Example No. | Structure | Mass [M + H] | ¹H NMR |
|---|---|---|---|
| 33 | 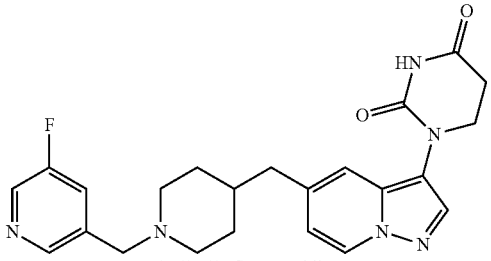 [SMILES: O=C1CCN(c2cnn3ccc(CC4CCN(Cc5cncc(F)c5)CC4)cc23)C(=O)N1]<br>1-(5-((1-((5-fluoropyridin-3-yl)methyl)piperidin-4-yl)methyl)pyrazolo[1,5-a]pyridin-3-yl)dihydropyrimidine-2,4(1H,3H)-dione | 437.4 | (500 MHz, DMSO-d6) δ 10.44 (s, 1H), 8.71 (d, J = 2.8 Hz, 1H), 8.68-8.50 (m, 2H), 8.01 (s, 1H), 7.89 (ddd, J = 9.6, 2.8, 1.7 Hz, 1H), 7.37 (d, J = 1.8 Hz, 1H), 6.79 (dd, J = 7.1, 1.9 Hz, 1H), 4.38 (d, J = 3.3 Hz, 2H), 3.77 (t, J = 6.7 Hz, 2H), 3.41 (d, J = 12.0 Hz, 2H), 3.01-2.87 (m, 2H), 2.79 (t, J = 6.7 Hz, 2H), 2.61 (d, J = 6.5 Hz, 2H), 1.98-1.69 (m, 3H), 1.41 (q, J = 13.1 Hz, 2H). |
| 34 | 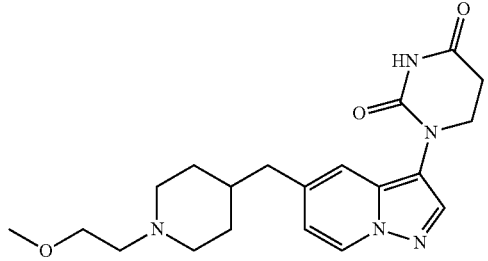 [SMILES: COCCN1CCC(Cc2ccn3ncc(N4CCC(=O)NC4=O)c3c2)CC1]<br>1-(5-((1-(2-methoxyethyl)piperidin-4-yl)methyl)pyrazolo[1,5-a]pyridin-3-yl)dihydropyrimidine-2,4(1H,3H)-dione | 386.3 | (500 MHz, DMSO-d6) δ 10.45 (d, J = 4.9 Hz, 1H), 8.60 (dd, J = 7.1, 3.2 Hz, 1H), 8.01 (d, J = 2.3 Hz, 1H), 7.42-7.32 (m, 1H), 6.80 (dd, J = 7.2, 1.9 Hz, 1H), 3.78 (td, J = 6.7, 2.8 Hz, 2H), 3.65 (dt, J = 10.0, 5.0 Hz, 2H), 3.47 (d, J = 12.0 Hz, 2H), 3.32 (d, J = 11.6 Hz, 3H), 3.24 (q, J = 5.1 Hz, 2H), 2.91 (q, J = 11.7 Hz, 2H), 2.79 (t, J = 6.7 Hz, 2H), 2.60 (d, J = 6.7 Hz, 2H), 1.81 (q, J = 12.7, 8.1 Hz, 3H), 1.48 (q, J = 12.9 Hz, 2H). |
| 35 | 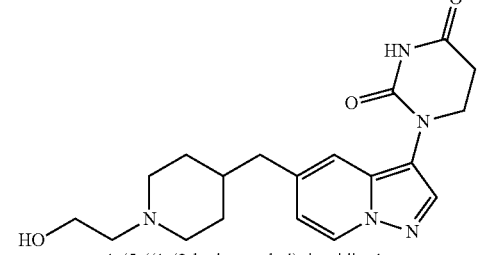<br>1-(5-((1-(2-hydroxyethyl)piperidin-4-yl)methyl)pyrazolo[1,5-a]pyridin-3-yl)dihydropyrimidine-2,4(1H,3H)-dione | 372.3 | (500 MHz, DMSO-d6) δ 10.45 (d, J = 5.1 Hz, 1H), 9.10 (s, 1H), 8.60 (dd, J = 7.2, 2.8 Hz, 1H), 8.01 (d, J = 2.2 Hz, 1H), 7.38 (d, J = 12.6 Hz, 1H), 6.80 (dd, J = 7.1, 1.9 Hz, 1H), 3.78 (t, J = 6.7 Hz, 2H), 3.72 (t, J = 5.3 Hz, 2H), 3.49 (d, J = 12.1 Hz, 2H), 3.24 (dd, J = 13.4, 7.7 Hz, 1H), 3.11 (q, J = 5.3 Hz, 2H), 2.90 (t, J = 11.7 Hz, 1H), 2.79 (td, J = 6.8, 2.2 Hz, 2H), 2.60 (d, J = 6.7 Hz, 2H), 1.94-1.66 (m, 3H), 1.49 (q, J = 13.1, 12.4 Hz, 2H). |
| 36 | 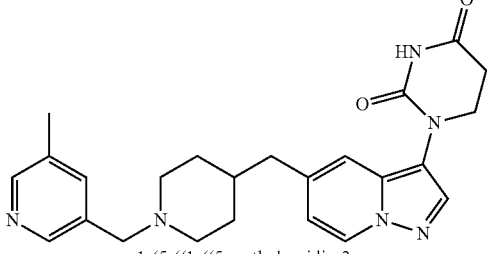<br>1-(5-((1-((5-methylpyridin-3-yl)methyl)piperidin-4-yl)methyl)pyrazolo[1,5-a]pyridin-3-yl)dihydropyrimidine-2,4(1H,3H)-dione | 433.2 | (500 MHz, DMSO-d6) δ 10.44 (s, 1H), 8.59 (d, J = 7.1 Hz, 1H), 8.55 (d, J = 2.1 Hz, 1H), 8.50 (d, J = 2.0 Hz, 1H), 8.01 (s, 1H), 7.87-7.69 (m, 1H), 7.43-7.25 (m, 1H), 6.79 (dd, J = 7.2, 1.9 Hz, 1H), 4.30 (d, J = 3.6 Hz, 2H), 3.77 (t, J = 6.7 Hz, 2H), 3.38 (d, J = 12.0 Hz, 2H), 2.93 (d, J = 11.2 Hz, 2H), 2.79 (t, J = 6.7 Hz, 2H), 2.60 (d, J = 6.5 Hz, 2H), 2.36 (s, 3H), 1.82 (q, J = 18.9, 17.6 Hz, 3H), 1.41 (q, J = 13.1 Hz, 2H). |

| Example No. | Structure | Mass [M + H] | ¹H NMR |
|---|---|---|---|
| 37 | 1-(5-((1-isopropylpiperidin-4-yl)methyl)pyrazolo[1,5-a]pyridin-3-yl)dihydropyrimidine-2,4(1H,3H)-dione | 370.3 | (500 MHz, DMSO-d6) δ 10.45 (s, 1H), 8.60 (d, J = 7.0 Hz, 1H), 8.01 (s, 1H), 7.39 (d, J = 1.8 Hz, 1H), 6.79 (dd, J = 7.3, 1.9 Hz, 1H), 3.78 (t, J = 6.7 Hz, 2H), 3.34 (d, J = 12.4 Hz, 2H), 3.26-3.18 (m, 1H), 2.92 (dt, J = (t, J = 6.8 Hz, 2H), 2.62 (d, J = 6.7 Hz, 2H), 1.97-1.78 (m, 3H), 1.45 (qd, J = 13.6, 3.7 Hz, 2H), 1.22 (d, J = 6.6 Hz, 6H). |
| 38 | 1-(5-((1-(2-fluorobenzyl)piperidin-4-yl)methyl)pyrazolo[1,5-a]pyridin-3-yl)dihydropyrimidine-2,4(1H,3H)-dione | 436.3 | (500 MHz, DMSO-d6) δ 10.44 (s, 1H), 8.59 (d, J = 7.1 Hz, 1H), 8.01 (s, 1H), 7.57 (dtd, J = 13.7, 7.5, 1.8 Hz, 2H), 7.41-7.28 (m, 3H), 6.85-6.75 (m, 1H), 4.33 (d, J = 4.8 Hz, 2H), 3.77 (t, J = 6.7 Hz, 2H), 3.40 (d, J = 12.0 Hz, 2H), 2.99 (d, J = 11.8 Hz, 2H), 2.79 (q, J = 6.5 Hz, 2H), 2.60 (d, J = 6.6 Hz, 2H), 1.82 (q, J = 20.3, 18.4 Hz, 3H), 1.43 (d, J = 13.0 Hz, 2H). |
| 39 | 1-(5-((1-(2-fluoro-2-methylpropyl)piperidin-4-yl)methyl)pyrazolo[1,5-a]pyridin-3-yl)dihydropyrimidine-2,4(1H,3H)-dione | 402.2 | (400 MHz, DMSO-d6) δ 10.42 (s, 1H), 8.59 (d, J = 7.3 Hz, 1H), 8.00 (s, 1H), 7.36 (d, J = 8.6Hz, 1H), 6.78 (d, J = 7.2 Hz, 1H), 3.77 (t, J = 6.7 Hz, 2H), 3.54 (s, 2H), 3.39 (d, J = 25.2 Hz, 2H), 3.01 (d, J = 11.9 Hz, 2H), 2.79 (t, J = 6.9 Hz, 2H), 2.65 (dd, J = 37.4, 7.6 Hz, 2H), 2.00-1.69 (m, 3H), 1.69-1.52 (m, 2H), 1.46 (dd, J = 21.5, 10.4 Hz, 6H). |
| 39a | 1-(5-((1-(2-methylallyl)piperidin-4-yl)methyl)pyrazolo[1,5-a]pyridin-3-yl)dihydropyrimidine-2,4(1H,3H)-dione Isolated during synthesis of Example 39 | 382.1 | (500 MHz, DMSO-d6) δ 10.45 (d, J = 5.0 Hz, 1H), 8.60 (dt, J = 7.2, 0.9 Hz, 1H), 8.02 (d, J = 2.3 Hz, 1H), 7.43-7.27 (m, 1H), 6.80 (dt, J = 7.2, 1.8 Hz, 1H), 5.32-5.21 (m, 1H), 5.16 (d, J = 1.7 Hz, 1H), 3.83-3.74 (m, 2H), 3.66 (d, J = 5.6 Hz, 1H), 3.52 (d, J = 12.1 Hz, 1H), 3.46-3.33 (m, 2H), 3.21-2.96 (m, 1H), 2.87 (t, J = 11.9 Hz, 1H), 2.79 (t, J = 6.7 Hz, 2H), 2.67-2.59 (m, 2H), 1.91-1.72 (m, 4H), 1.60 (td, J = 27.4, 25.3, 11.8 Hz, 1H), 1.47 (dd, J = 21.5, 12.9 Hz, 3H). |

| Example No. | Structure | Mass [M + H] | ¹H NMR |
|---|---|---|---|
| 40 | 1-(5-((1-(3-methoxybenzyl)piperidin-4-yl)methyl)pyrazolo[1,5-a]pyridin-3-yl)dihydropyrimidine-2,4(1H,3H)-dione | 448.4 | (500 MHz, DMSO-d6) δ 10.45 (d, J = 14.0 Hz, 1H), 8.60 (dd, J = 9.9, 7.1 Hz, 1H), 8.01 (d, J = 7.3 Hz, 1H), 7.56-7.30 (m, 2H), 7.19-6.96 (m, 3H), 6.80 (ddd, J = 12.4, 7.2, 1.9 Hz, 1H), 4.24 (d, J = 5.2 Hz, 2H), 3.78 (d, J = 12.4 Hz, 5H), 3.35 (d, J = 12.1 Hz, 2H), 2.91 (t, J = 11.8 Hz, 2H), 2.78 (t, J = 6.6 Hz, 2H), 2.60 (d, J = 6.5 Hz, 2H), 1.93-1.6 (m, 3H), 1.42 (q, J = 13.1 Hz, 2H). |
| 41 | 1-(5-((1-(2-methylbenzyl)piperidin-4-yl)methyl)pyrazolo[1,5-a]pyridin-3-yl)dihydropyrimidine-2,4(1H,3H)-dione | 432.3 | (500 MHz, DMSO-d6) δ 10.45 (d, J = 16.5 Hz, 1H), 8.60 (dd, J = 11.1, 7.1 Hz, 1H), 8.02 (d, J = 8.6 Hz, 1H), 7.48 (dd, J = 15.1, 7.7 Hz, 1H), 7.43-7.21 (m, 4H), 6.87-6.73 (m, 1H), 4.28 (d, J = 5.3 Hz, 2H), 3.77 (t, J = 6.7 Hz, 2H), 3.37 (d, J = 12.0 Hz, 2H), 3.05 (q, J = 11.6 Hz, 2H), 2.79 (q, J = 6.8 Hz, 2H), 2.61 (d, J = 6.6 Hz, 2H), 2.39 (s, 3H), 1.96-1.67 (m, 3H), 1.45 (q, J = 12.9 Hz, 2H). |
| 42 | 1-(5-((1-(3-fluoro-2-methylbenzyl)piperidin-4-yl)methyl)pyrazolo[1,5-a]pyridin-3-yl)dihydropyrimidine-2,4(1H,3H)-dione | 450.4 | (500 MHz, DMSO-d6) δ 10.44 (d, J = 16.3 Hz, 1H), 8.59 (d, J = 7.6 Hz, 1H), 8.00 (d, J = 3.3Hz, 1H), 7.54-7.21 (m, 4H), 6.78 (d, J = 7.6 Hz, 1H), 4.33 (t, J = 4.3 Hz, 2H), 3.77 (d, J = 8.0 Hz, 3H), 3.12-2.93 (m, 1H), 2.78 (d, J = 8.0 Hz, 2H), 2.61 (s, 2H), 2.35 (d, J = 17.2 Hz, 1H), 2.28 (s, 3H), 2.08 (d, J = 3.2 Hz, 1H), 1.96-1.67 (m, 3H), 1.42 (d, J = 13.4 Hz, 2H). |
| 43 | 1-(5-((1-(2,2-difluoroethyl)piperidin-4-yl)methyl)pyrazolo[1,5-a]pyridin-3-yl)dihydropyrimidine-2,4(1H,3H)-dione | 3923 | (500 MHz, Methanol-d4) δ 8.34 (d, J = 7.2 Hz, 1H), 7.91 (s, 1H), 7.27 (t, J = 1.3 Hz, 1H), 6.73 (dd, J = 7.1, 1.9 Hz, 1H), 6.30 (tt, J = 53.4, 3.6 Hz, 1H), 3.79 (t, J = 6 8 Hz, 2H), 3.57 (q, J = 14.1, 13.3 Hz, 4H), 3.06 (s, 2H), 2.79 (t, J = 6.7 Hz, 2H), 2.61 (d, J = 6.9 Hz, 2H), 1.87 (q, J = 13.3, 8.7 Hz, 3H), 1.52 (d, J = 13.6 Hz, 2H). |

| Example No. | Structure | Mass [M + H] | ¹H NMR |
|---|---|---|---|
| 44 | 1-(5-((1-(3,5-difluorobenzyl)piperidin-4-yl)methyl)pyrazolo[1,5-a]pyridin-3-yl)dihydropyrimidine-2,4(1H,3H)-dione | 454.3 | (500 MHz, DMSO-d6) δ 10.44 (d, J = 12.0 Hz, 1H), 8.59 (t, J = 7.9 Hz, 1H), 8.07-7.94 (m, 1H), 7.40 (t, J = 8.7 Hz, 1H), 7.36 (s, 1H), 7.28 (d, J = 7.0 Hz, 2H), 6.78 (d, J = 7.3 Hz, 1H), 4.29 (d, J = 5.0 Hz, 2H), 3.76 (t, J = 6.6 Hz, 2H), 3.18 (s, 1H), 2.89 (q, J = 11.4, 8.6 Hz, 2H), 2.78 (t, J = 6.7 Hz, 3H), 2.65-2.57 (m, 2H), 1.81 (q, J = 21.9, 19.6 Hz, 3H), 1.43 (q, J = 13.1 Hz, 2H). |
| 45 | 1-(5-((1-(3,4-difluorobenzyl)piperidin-4-yl)methyl)pyrazolo[1,5-a]pyridin-3-yl)dihydropyrimidine-2,4(1H,3H)-dione | 454.3 | (500 MHz, DMSO-d6) δ 10.44 (d, J = 13.2 Hz, 1H), 8.58 (d, J = 7.3 Hz, 1H), 8.01 (d, J = 7.1Hz, 1H), 7.58 (dt, J = 17.9, 8.9 Hz, 2H), 7.36 (s, 2H), 6.78 (d, J = 7.5 Hz, 1H), 4.27 (d, J = 5.0 Hz, 2H), 3.76 (t, J = 6.7 Hz, 2H), 3.34 (s, 2H), 2.89 (d, J = 11.7 Hz, 2H), 2.78 (t, J = 6.6 Hz, 2H), 2.66-2.57 (m, 2H), 1.98-1.69 (m, 3H), 1.50-1.29 (m, 2H). |
| 46 | 1-(5-((1-((6-methylpyridin-3-yl)methyl)piperidin-4-yl)methyl)pyrazolo[1,5-a]pyridin-3-yl)dihydropyrimidine-2,4(1H,3H)-dione | 433.2 | (500 MHz, DMSO-d6) δ 10.42 10.42 (s, 1H), 8.66-8.46 (m, 2H), 8.00 (s, 1H), 7.82 (dd, J = 8.0, 2.3 Hz, 1H), 7.49-7.30 (m, 2H), 6.87-6.58 (m, 1H), 4.28 (d, J = 4.5 Hz, 2H), 3.76 (t, J = 6.7 Hz, 2H), 3.36 (d, J = 13.0 Hz, 3H), 3.18 (s, 2H), 2.89 (dd, J = 14.6, 8.6 Hz, 2H), 2.78 (t, J = 6.7 Hz, 2H), 2.59 (d, J = 6.5 Hz, 2H), 1.80 (dt, J = 32.7, 15.1 Hz, 3H), 1.38 (q, J = 12.2 Hz, 2H). |
| 47 | 1-(5-((1-(4-methylbenzyl)piperidin-4-yl)methyl)pyrazolo[1,5-a]pyridin-3-yl)dihydropyrimidine-2,4(1H,3H)-dione | 432.3 | (500 MHz, DMSO-d6) δ 10.44 (d, J = 15.3 Hz, 1H), 9.18 (s, 1H), 8.59 (dd, J = 11.1, 7.2 Hz, 1H), 8.00 (d, J = 7.9 Hz, 1H), 7.41-7.35 (m, 2H), 7.28 (d, J = 7.8 Hz, 2H), 6.84-6.71 (m, 1H), 4.21 (d, J = 5.0 Hz, 2H), 3.76 (t, J = 6.7 Hz, 2H), 3.33 (d, J = 12.1 Hz, 2H), 2.87 (q, J = 11.7 Hz, 2H), 2.78 (q, J = 6.8 Hz, 2H), 2.59 (d, J = 6.5 Hz, 2H), 2.37-2.31 (m, 3H), 1.92-1.64 (m, 3H), 1.39 (q, J = 12.8 Hz, 2H). |

| Example No. | Structure | Mass [M + H] | ¹H NMR |
|---|---|---|---|
| 48 | 1-(5-((1-(1-(3-fluorophenyl)ethyl)piperidin-4-yl)methyl)pyrazolo[1,5-a]pyridin-3-yl)dihydropyrimidine-2,4(1H,3H)-dione | 450.2 | (500 MHz, DMSO-d6) δ 10.42 (s, 1H), 8.58 (dd, J = 11.5, 7.2 Hz, 1H), 8.00 (d, J = 7.0 Hz, 1H), 7.54 (dq, J = 14.8, 7.3 Hz, 1H), 7.46-7.24 (m, 4H), 6.85-6.60 (m, 1H), 4.56-4.46 (m, 1H), 3.76 (d, J = 6.7 Hz, 2H), 3.62 (d, J = 12.1 Hz, 1H), 3.22 (d, J = 13.1 Hz, 1H), 2.83-2.63 (m, 4H), 2.58 (d, J = 6.3 Hz, 2H), 1.92-1.70 (m, 3H), 1.62 (d, J = 6.9 Hz, 3H), 1.43 (dt, J = 40.7, 12.9 Hz, 2H). |
| 49 | 1-(5-((1-methylpiperidin-4-yl)methyl)pyrazolo[1,5-a]pyridin-3-yl)dihydropyrimidine-2,4(1H,3H)-dione | 342.2 | (500 MHz, DMSO-d6) δ 10.45 (d, J = 7.0 Hz, 1H), 8.60 (dt, J = 7.2, 2.1 Hz, 1H), 8.01 (d, J = 3.3 Hz, 1H), 7.55-7.08 (m, 1H), 6.80 (dd, J = 7.1, 1.9 Hz, 1H), 3.77 (t, J = 6.7 Hz, 2H), 3.40 (d, J = 12.1 Hz, 2H), 2.94-2.77 (m, 4H), 2.74 (d, J = 4.8 Hz, 3H), 2.60 (d, J = 6.5 Hz, 2H), 1.92-1.68 (m, 3H), 1.39 (q, J = 12.4, 11.7 Hz, 2H). |
| 50 | 1-(5-((1-(2,4-difluorobenzyl)piperidin-4-yl)methyl)pyrazolo[1,5-a]pyridin-3-yl)dihydropyrimidine-2,4(1H,3H)-dione | 454.4 | (500 MHz, DMSO-d6) δ 10.44 (s, 1H), 8.59 (d, J = 7.1 Hz, 1H), 8.01 (s, 1H), 7.64 (td, J = 8.6, 6.5 Hz, 1H), 7.47-7.38 (m, 1H), 7.37 (s, 1H), 7.26 (td, J = 8.5, 2.7 Hz, 1H), 6.78 (dd, J = 7.1, 1.9 Hz, 1H), 4.31 (d, J = 4.6 Hz, 2H), 3.77 (t, J = 6.7 Hz, 2H), 3.39 (d, J = 11.8 Hz, 2H), 2.97 (q, J = 11.8 Hz, 2H), 2.79 (t, J = 6.7 Hz, 2H), 2.60 (d, J = 6.6 Hz, 2H), 1.82 (q, J = 18.9, 16.6 Hz, 3H), 1.57-1.31 (m, 2H) |
| 51 | 1-(5-((1-(3-fluoro-5-(trifluoromethyl)benzyl)piperidin-4-yl)methyl)pyrazolo[1,5-a]pyridin-3-yl)dihydropyrimidine-2,4(1H,3H)-dione | 504.4 | (500 MHz, DMSO-d6) δ 10.36 (d, J = 11.7 Hz, 1H), 8.60-8.41 (m, 1H), 7.92 (d, J = 2.9 Hz, 1H), 7.90-7.56 (m, 3H), 7.29 (s, 1H), 6.70 (d, J = 7.6 Hz, 1H), 4.31 (s, 2H), 3.69 (d, J = 7.8 Hz, 2H), 3.12 (d, J = 15.6 Hz, 1H), 2.84 (t, J = 11.8 Hz, 2H), 2.69 (d, J = 7.6 Hz, 2H), 2.59-2.48 (m, 2H), 1.86-1.56 (m, 4H), 1.33 (q, J = 13.4, 12.9 Hz, 2H). |

| Example No. | Structure | Mass [M + H] | ¹H NMR |
|---|---|---|---|
| 52 | 1-(5-((1-(2-oxo-2-(piperidin-1-yl)ethyl)piperidin-4-yl)methyl)pyrazolo[1,5-a]pyridin-3-yl)dihydropyrimidine-2,4(1H,3H)-dione | 453.4 | (400 MHz, CD₃OD) δ 8.43 (d, J = 7.2 Hz, 1H), 8.31 (s, 2H), 8.00 (s, 1H), 7.36 (s, 1H), 7, 6.83 (d, J = 7.6 Hz, 1H), 4.10 (s, 2H), 3.88 (t, J = 6.4 Hz, 2H), 3.57-3.50 (m, 4H), 3.37-3.34 (m, 2H), 2.96-2.86 (m, 4H), 2.70 (d, J = 7.2 Hz, 2H), 1.93-1.89 (m, 3H), 1.69-1.56 (m, 7H). |
| 53 | 1-(5-((1-(2,3-difluorobenzyl)piperidin-4-yl)methyl)pyrazolo[1,5-a]pyridin-3-yl)dihydropyrimidine-2,4(1H,3H)-dione | 454.4 | (500 MHz, DMSO-d6) δ 10.43 (s, 1H), 8.58 (d, J = 7.2 Hz, 1H), 8.00 (s, 1H), 7.68-7.55 (m, 1H), 7.37 (d, J = 16.6 Hz, 3H), 6.83-6.72 (m, 1H), 4.37 (s, 2H), 3.76 (t, J = 6.7 Hz, 2H), 3.42 (s, 3H), 3.00 (d, J = 11.6 Hz, 1H), 2.78 (t, J = 6.6 Hz, 2H), 2.59 (d, J = 6.5 Hz, 2H), 1.82 (d, J = 14.7 Hz, 3H), 1.41 (d, J = 13.0 Hz, 2H). |
| 54 | 1-(5-((1-((6-(trifluoromethyl)pyridin-3-yl)methyl)piperidin-4-yl)methyl)pyrazolo[1,5-a]pyridin-3-yl)dihydropyrimidine-2,4(1H,3H)-dione | 487.1 | (500 MHz, DMSO-d6) δ 10.44 (s, 1H), 8.87 (d, J = 2.1 Hz, 1H), 8.59 (d, J = 7.1 Hz, 1H), 8.22 (dd, J = 8.1, 2.1 Hz, 1H), 8.06 (d, J = 8.1 Hz, 1H), 8.01 (s, 1H), 7.46-7.21 (m, 1H), 6.79 (dd, J = 7.2, 1.9 Hz, 1H), 4.45 (s, 2H), 3.77 (t, J = 6.7 Hz, 2H), 3.42 (d, J = 11.9 Hz, 2H), 2.96 (s, 2H), 2.79 (t, J = 6.7 Hz, 2H), 2.60 (d, J = 6.6 Hz, 2H), 1.98-1.73 (m, 3H), 1.53-1.21 (m, 2H). |
| 55 | 1-(5-((1-((1-(trifluoromethyl)cyclopropyl)methyl)piperidin-4-yl)methyl)pyrazolo[1,5-a]pyridin-3-yl)dihydropyrimidine-2,4(1H,3H)-dione | 450.1 | (400 MHz, DMSO-d6) δ 10.42 (s, 1H), 8.59 (d, J = 7.1 Hz, 1H), 8.00 (d, J = 1.7 Hz, 1H), 7.38 (s, 1H), 6.87-6.47 (m, 1H), 3.77 (t, J = 6.7 Hz, 2H), 3.62-3.35 (m, 4H), 3.29 (s, 1H), 2.94 (d, J = 11.5 Hz, 1H), 2.78 (t, J = 6.7 Hz, 2H), 2.61 (d, J = 6.1 Hz, 2H), 1.92-1.71 (m, 3H), 1.52 (t, J = 13.3 Hz, 2H), 1.16 (d, J = 42.2 Hz, 4H). |

| Example No. | Structure | Mass [M + H] | ¹H NMR |
|---|---|---|---|
| 56 | 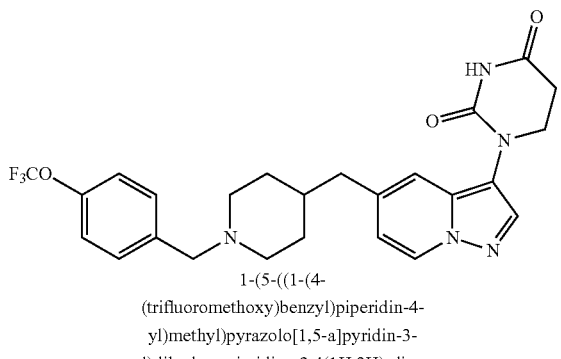<br>1-(5-((1-(4-(trifluoromethoxy)benzyl)piperidin-4-yl)methyl)pyrazolo[1,5-a]pyridin-3-yl)dihydropyrimidine-2,4(1H,3H)-dione | 502.3 | (500 MHz, DMSO-d6) δ 10.45 (d, J = 15.5 Hz, 1H), 8.59 (d, J = 7.1 Hz, 1H), 8.01 (s, 1H), 7.73-7.59 (m, 2H), 7.50 (d, J = 8.2 Hz, 2H), 7.37 (s, 1H), 6.87-6.71 (m, 1H), 4.32 (d, J = 5.0 Hz, 2H), 3.77 (t, J = 6.7 Hz, 2H), 3.36 (d, J = 12.0 Hz, 2H), 3.00-2.89 (m, 2H), 2.79 (t, J = 6.7 Hz, 2H), 2.60 (d, J = 6.5 Hz, 2H), 1.94-1.68 (m, 3H), 1.41 (q, J = 13.1 Hz, 2H). |
| 57 | 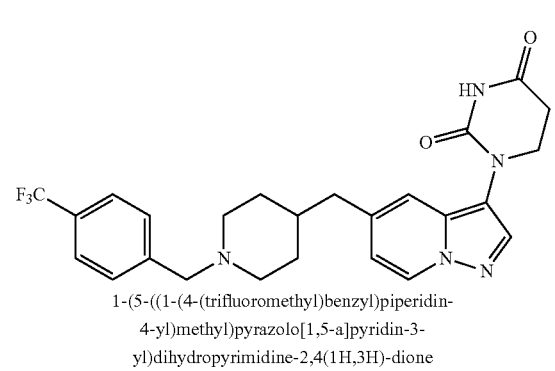<br>1-(5-((1-(4-(trifluoromethyl)benzyl)piperidin-4-yl)methyl)pyrazolo[1,5-a]pyridin-3-yl)dihydropyrimidine-2,4(1H,3H)-dione | 486.3 | (500 MHz, DMSO-d6) δ 10.43 (s, 1H), 8.59 (d, J = 7.1 Hz, 1H), 8.01 (s, 1H), 7.87 (d, J = 8.0Hz, 2H), 7.81-7.69 (m, 2H), 7.37 (s, 1H), 6.89-6.68 (m, 1H), 4.39 (d, J = 4.8 Hz, 2H), 3.77 (t, J = 6.7 Hz, 2H), 3.37 (d, J = 12.0 Hz, 2H), 2.93 (q, J = 11.7 Hz, 2H), 2.78 (t, J = 6.7 Hz, 2H), 2.60 (d, J = 6.5 Hz, 2H), 1.96-1.30-1.65 (m, 3H), 1.52-1.30 (m, 2H). |
| 58 | 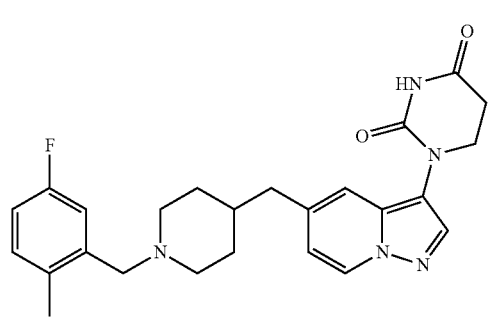 [SMILES: Cc1ccc(F)cc1CN1CCC(Cc2ccn3ncc(N4CCC(=O)NC4=O)c3c2)CC1]<br>1-(5-((1-(5-fluoro-2-methylbenzyl)piperidin-4-yl)methyl)pyrazolo[1,5-a]pyridin-3-yl)dihydropyrimidine-2,4(1H,3H)-dione | 450.4 | (500 MHz, DMSO-d6) δ 10.44 (d, J = 13.8 Hz, 1H), 8.59 (d, J = 7.7 Hz, 1H), 8.00 (d, J = 2.9 Hz, 1H), 7.35 (d, J = 10.7 Hz, 3H), 7.22 (d, J = 9.0 Hz, 1H), 6.78 (d, J = 7.2 Hz, 1H), 4.28 (s, 2H), 3.76 (t, J = 6.8 Hz, 2H), 3.05 (d, J = 12.0 Hz, 3H), 2.78 (d, J = 7.5 Hz, 2H), 2.61 (d, J = 6.5 Hz, 2H), 2.34 (s, 3H), 2.08 (d, J = 3.0 Hz, 1H), 1.81 (q, J = 18.9, 17.5 Hz, 3H), 1.56-1.27 (m, 2H). |
| 59 | 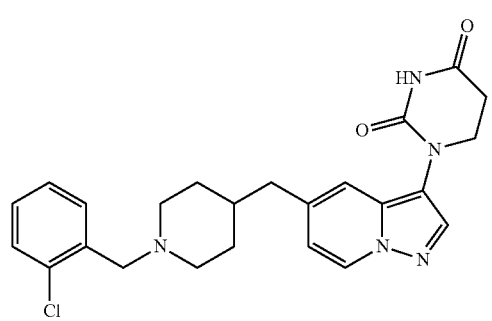 [SMILES: O=C1CCN(c2cnn3ccc(CC4CCN(Cc5ccccc5Cl)CC4)cc23)C(=O)N1]<br>1-(5-((1-(2-chlorobenzyl)piperidin-4-yl)methyl)pyrazolo[1,5-a]pyridin-3-yl)dihydropyrimidine-2,4(1H,3H)-dione | 452.4 | (500 MHz, DMSO-d6) δ 10.44 (d, J = 13.7 Hz, 1H), 8.58 (d, J = 7.8 Hz, 1H), 8.00 (d, J = 2.3 Hz, 1H), 7.64 (dd, J = 31.9, 7.8 Hz, 2H), 7.51 (q, J = 8.4 Hz, 2H), 7.35 (s, 1H), 6.88-6.61 (m, 1H), 4.40 (d, J = 4.9 Hz, 2H), 3.77 (d, J = 7.7 Hz, 3H), 3.08 (d, J = 11.7 Hz, 2H), 2.78 (d, J = 7.2 Hz, 2H), 2.69-2.55 (m, 2H), 2.08 (d, J = 2.7 Hz, 1H), 1.95-1.76 (m, 3H), 1.53-1.33 (m, 2H). |

| Example No. | Structure | Mass [M + H] | ¹H NMR |
|---|---|---|---|
| 60 | 1-(5-((1-(thiazol-2-ylmethyl)piperidin-4-yl)methyl)pyrazolo[1,5-a]pyridin-3-yl)dihydropyrimidine-2,4(1H,3H)-dione | 425.4 | (500 MHz, DMSO-d6) δ 10.44 (s, 1H), 8.59 (d, J = 7.1 Hz, 1H), 8.00 (d, J = 4.0 Hz, 2H), 7.95(d, J = 3.2 Hz, 1H), 7.38 (d, J = 1.4 Hz, 1H), 6.79 (dd, J = 7.2, 1.9 Hz, 1H), 4.72 (s, 2H), 3.77 (t, J = 6.7 Hz, 2H), 3.51 (d, J = 12.1 Hz, 2H), 3.02 (s, 2H), 2.79 (t, J = 6.7 Hz, 2H), 2.60 (d, J = 6.4 Hz, 2H), 1.83 (d, J = 14.2 Hz, 3H), 1.47 (d, J = 13.5 Hz, 2H). |
| 61 | 1-(5-((1-(4-methoxybenzyl)piperidin-4-yl)methyl)pyrazolo[1,5-a]pyridin-3-yl)dihydropyrimidine-2,4(1H,3H)-dione | 448.2 | (500 MHz, DMSO-d6) δ 10.45 (d, J = 16.0 Hz, 1H), 8.60 (dd, J = 11.3, 7.2 Hz, 1H), 8.01 (d, J = 8.0 Hz, 1H), 7.42-7.35 (m, 3H), 7.03 (dq, J = 9.5, 7.7, 7.1 Hz, 3H), 4.20 (d, J = 5.2 Hz, 2H), 3.82-3.74 (m, 4H), 3.34 (d, J = 12.0 Hz, 2H), 2.86 (q, J = 12.8, 12.0 Hz, 2H), 2.78 (t, J = 6.8 Hz, 2H), 2.60 (d, J = 6.4 Hz, 2H), 1.87-1.71 (m, 3H), 1.50-1.18 (m, 3H). |
| 62 | 1-(5-((1-(3,3,3-trifluoro-2,2-dimethylpropyl)piperidin-4-yl)methyl)pyrazolo[1,5-a]pyridin-3-yl)dihydropyrimidine-2,4(1H,3H)-dione | 452.0 | (400 MHz, CD₃OD) δ 8.44 (d, J = 7.2 Hz, 1H), 8.01 (s, 1H), 7.38 (s, 1H), 6.84 (d, J = 7.2 Hz, 1H), 3.89 (t, J = 6.8 Hz, 2H), 3.65 (s, 1H), 3.48 (s, 1H), 3.37-3.33 (m, 2H), 3.16-3.13 (m 2H), 2.89 (t, J = 6.8 Hz, 2H), 2.77-2.69 (m, 2H), 2.01-1.90 (m, 3H), 1.70-1.67 (m, 2H), 1.36 (s, 6H) ppm. NH proton not observed due to solvent exchange. |

Example 63. Preparation of 1-(5-((1-(piperidin-4-ylmethyl)piperidin-4-yl)methyl)pyrazolo[1,5-a]pyridin-3-yl)dihydropyrimidine-2,4(1H,3H)-dione (Example 63)

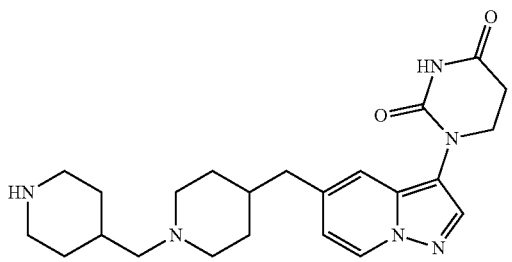 [SMILES: O=C1CCN(c2cnn3ccc(CC4CCN(CC5CCNCC5)CC4)cc23)C(=O)N1]

Prepared by the method of Example 1 using tert-butyl 4-(bromomethyl)piperidine-1-carboxylate in step 4 in place of (bromomethyl)cyclohexane. LCMS [M+H]+: 425.2. 1H NMR (500 MHz, DMSO-d6) δ 10.45 (d, J=6.6 Hz, 1H), 8.61 (dd, J=7.2, 3.9 Hz, 1H), 8.40 (d, J=11.9 Hz, 1H), 8.02 (d, J=3.2 Hz, 1H), 7.47-7.35 (m, 1H), 6.80 (dd, J=7.2, 1.9 Hz, 1H), 3.78 (td, J 6.7, 4.0 Hz, 2H), 3.51 (d, J=11.8 Hz, 2H), 3.30 (d, J=12.8 Hz, 2H), 2.98 (t, J=6.1 Hz, 2H), 2.94-2.82 (m, 4H), 2.79 (t, J=6.7 Hz, 2H), 2.62 (d, J=6.6 Hz, 2H), 2.09 (dt, J=7.7, 3.8 Hz, 1H), 1.84 (dq, J=29.1, 16.0, 14.5 Hz, 5H), 1.50 (q, J=13.1 Hz, 2H), 1.41-1.28 (in, 2H).

Examples 64 and 65. Preparation of 1-(5-((1-(((1r,4r)-4-methoxycyclohexyl)methyl)piperidin-4-yl)methyl)pyrazolo[1,5-a]pyridin-3-yl)dihydropyrimidine-2,4(1H,3H)-dione (Example 64) and 1-(5-((1-(((1s,4s)-4-methoxycyclohexyl)methyl)piperidin-4-yl)methyl)pyrazolo[1,5-a]pyridin-3-yl)dihydropyrimidine-2,4(1H,3H)-dione (Example 65)

cyclohexane. The stereoisomers were purified after step 5 by reverse-phase HPLC (eluting with using ACN/Water/0.1% TFA).

Example 64. 1-(5-((1-(((1r,4r)-4-methoxycyclohexyl)methyl)piperidin-4-yl)methyl)pyrazolo[1,5-a]pyridin-3-yl)dihydropyrimidine-2,4(1H,3H)-dione Eluted first, minor isomer. LCMS [M+H]+: 454.3. 1H NMR (500 MHz, DMSO-d6) δ 10.45 (d, J=4.6 Hz, 1H), 8.60 (d, J=7.1 Hz, 1H), 8.01 (s, 1H), 7.47-7.27 (m, 1H), 6.80 (dd, J=7.1, 1.9 Hz, 1H), 3.78 (td, J=6.7, 3.0 Hz, 2H), 3.47 (d, J=12.1 Hz, 2H), 3.24 (d, J=5.2 Hz, 4H), 3.05 (ddt, J=16.9, 10.7, 5.3 Hz, 1H), 2.93-2.83 (m, 3H), 2.79 (t, J=6.7 Hz, 2H), 2.62 (d, J=6.6 Hz, 2H), 2.00 (d, J=12.3 Hz, 2H), 1.92-1.63 (m, 6H), 1.49 (q, J=13.1 Hz, 2H), 1.19-1.07 (m, 2H), 0.98 (q, J=12.9 Hz, 2H).

Example 65. 1-(5-((1-(((1s,4s)-4-methoxycyclohexyl)methyl)piperidin-4-yl)methyl)pyrazolo[1,5-a]pyridin-3-yl)dihydropyrimidine-2,4(1H,3H)-dione Eluted second, major isomer. LCMS [M+H]+: 454.3. 1H NMR (500 MHz, Methanol-d4) δ 8.45 (d, J=7.1 Hz, 1H), 8.02 (s, 1H), 7.49-7.25 (m, 1H), 6.85 (dd, J=7.1, 1.8 Hz, 1H), 3.90 (t, J=6.8 Hz, 2H), 3.61-3.44 (m, 3H), 3.35 (s, 3H), 2.92 (dt, J=13.6, 6.9 Hz, 6H), 2.71 (d, J=7.1 Hz, 2H), 2.09-1.82 (m, 6H), 1.70-1.46 (m, 6H), 1.44-1.31 (m, 2H).

Example 66. Preparation of 1-(5-(((1R,5S)-8-(cyclohexylmethyl)-8-azabicyclo[3.2.1]octan-3-yl)methyl)pyrazolo[1,5-a]pyridin-3-yl)dihydropyrimidine-2,4(1H,3H)-dione Example 64

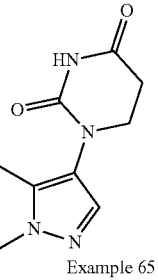

Example 65

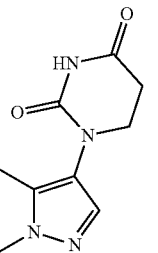

Prepared by the method of Example 1 using a commercially available mixture of cis and trans 1-(bromomethyl)-4-methoxycyclohexane in step 4 in place of (bromomethyl)

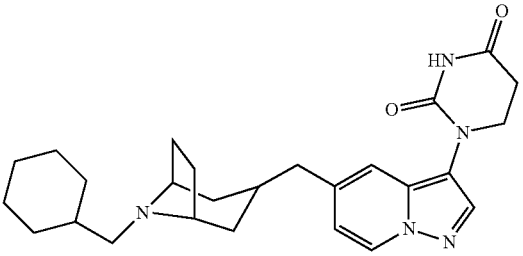 [SMILES: O=C1CCN(c2cnn3ccc(CC4CC5CCC(C4)N5CC4CCCCC4)cc23)C(=O)N1]

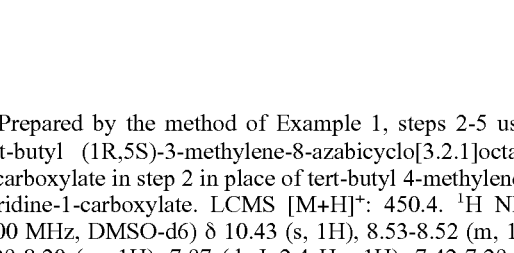

Prepared by the method of Example 1, steps 2-5 using tert-butyl (1R,5S)-3-methylene-8-azabicyclo[3.2.1]octane-8-carboxylate in step 2 in place of tert-butyl 4-methylenepiperidine-1-carboxylate. LCMS [M+H]+: 450.4. 1H NMR (400 MHz, DMSO-d6) δ 10.43 (s, 1H), 8.53-8.52 (m, 1H), 8.29-8.20 (m, 1H), 7.97 (d, J=2.4 Hz, 1H), 7.42-7.29 (m, 1H), 6.77 (d, J=7.2 Hz, 1H), 3.75-3.60 (m, 2H), 3.23 (br s, 2H), 2.84-2.70 (m, 3H), 2.24 (br s, 2H), 2.11-1.82 (m, 4H), 1.81-1.56 (m, 6H), 1.56-1.37 (m, 4H), 1.33-1.09 (m, 4H), 0.91-0.78 (m, 2H).

Example 67. Preparation of 1-(5-(((1R,5S)-8-isobutyl-8-azabicyclo[3.2.1]octan-3-yl)methyl)pyrazolo[1,5-a]pyridin-3-yl)dihydropyrimidine-2,4(1H,3H)-dione

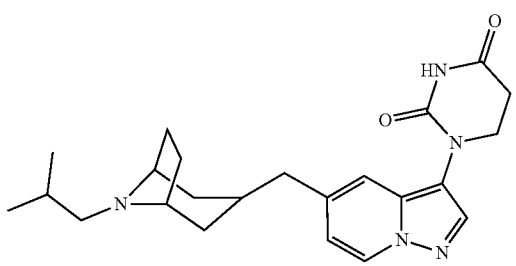 [SMILES: CC(C)CN1C2CCC1CC(Cc1ccn3ncc(N4CCC(=O)NC4=O)c3c1)C2]

Prepared by the method of Example 1, steps 2-5 using tert-butyl (1R,5S)-3-methylene-8-azabicyclo[3.2.1]octane-8-carboxylate in step 2 in place of tert-butyl 4-methylenepiperidine-1-carboxylate, and 1-iodo-2-methylpropane in step 4 in place of (bromomethyl)cyclohexane. LCMS [M+H]$^+$: 410.3. $^1$H NMR (400 MHz, CDCl$_3$) ppm 11.33 (s, 1H), 8.40 (m, J=6.8 Hz, 1H), 7.94 (s, 1H), 7.75 (s, 1H), 6.67 (m, J=7.3, 11.7 Hz, 1H), 3.93-3.84 (m, 4H), 3.19 (s, 1H), 2.97-2.89 (m, 3H), 2.78-2.71 (m, 4H), 2.42-2.25 (m, 2H), 2.15 (s, 1H), 1.92 (m, J=8.6 Hz, 2H), 1.68 (s, 3H), 1.14 (m J=6.4 Hz, 6H).

Example 68. Preparation of 1-(5-(((1R,5S)-8-(pyridin-3-ylmethyl)-8-azabicyclo[3.2.1]octan-3-yl)methyl)pyrazolo[1,5-a]pyridin-3-yl)dihydropyrimidine-2,4(1H,3H)-dione

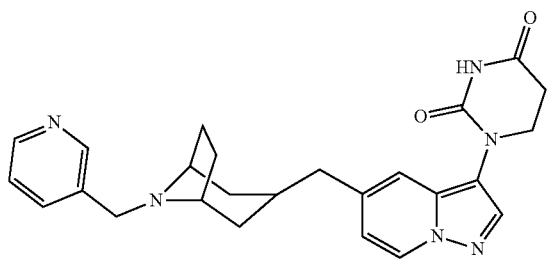 [SMILES: O=C1CCN(c2cnn3ccc(CC4CC5CCC(C4)N5Cc4cccnc4)cc23)C(=O)N1]

Prepared by the method of Example 1, steps 2-5 using tert-butyl (1R,5S)-3-methylene-8-azabicyclo[3.2.1]octane-8-carboxylate in step 2 in place of tert-butyl 4-methylenepiperidine-1-carboxylate, and 3-(bromomethyl)pyridine in step 4 in place of (bromomethyl)cyclohexane. LCMS [M+H]$^+$: 445.3. $^1$H NMR 1H NMR (400 MHz, METHANOL-d4) ppm=8.54 (s, 1H), 8.46-8.34 (m, 2H), 8.00-7.96 (m, 1H), 7.89 (m, J=7.8 Hz, 1H), 7.44-7.30 (m, 2H), 6.81 (d, J=2.1, 7.1 Hz, 1H), 3.88 (dt, J=4.6, 6.7 Hz, 2H), 3.60 (d, J=4.4 Hz, 2H), 3.18 (s, 2H), 2.89 (m, 3H), 2.58 (d, J=7.2 Hz, 1H), 2.23-2.17 (m, 1H), 2.10-2.03 (m, 2H), 1.94-1.81 (m, 1H), 1.68-1.60 (m, 1H), 1.49 (d, J=2.7, 8.7 Hz, 2H), 1.41 (m, J=13.9 Hz, 1H).

Example 69. Preparation of 1-(5-((1-(4-methoxypyrimidin-2-yl)piperidin-4-yl)methyl)pyrazolo[1,5-a]pyridin-3-yl)dihydropyrimidine-2,4(1H,3H)-dione

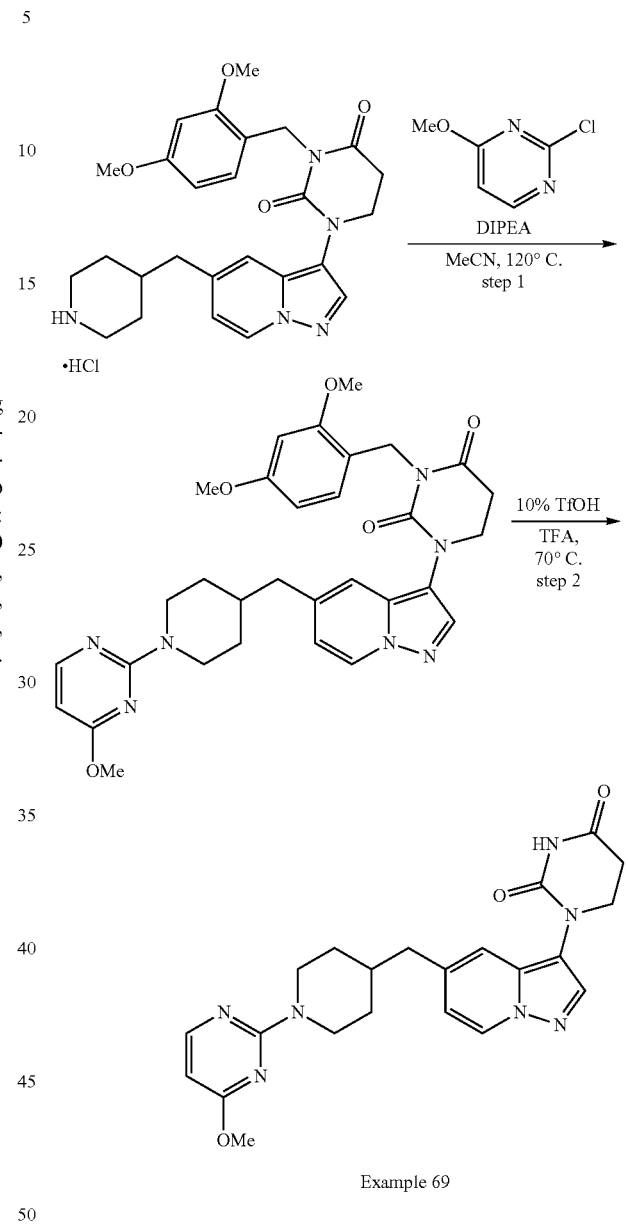

Example 69

Step 1. 3-(2,4-dimethoxybenzyl)-1-(5-((1-(4-methoxypyrimidin-2-yl)piperidin-4-yl)methyl)pyrazolo[1,5-a]pyridin-3-yl)dihydropyrimidine-2,4(1H,3H)-dione To a stirred solution of 3-(2,4-dimethoxybenzyl)-1-(5-(piperidin-4-ylmethyl)pyrazolo[1,5-a]pyridin-3-yl)dihydropyrimidine-2,4(1H,3H)-dione hydrochloride (100 mg, 0.209 mmol) and 2-chloro-4-methoxypyrimidine (30.2 mg, 0.209 mmol) in MeCN (1 mL) was added DIPEA (54 mL, 0.418 mmol). The mixture was stirred for 2 h at 120° C. After completion, the reaction was cooled to rt and diluted with EtOAc and water. The organic layer was dried over Na$_2$SO$_4$ and concentrate. The crude compound was purified by silica gel chromatography (eluting with 10% MeOH in DCM) to afford 3-(2,4-dimethoxybenzyl)-1-(5-((1-(4-methoxypyrimidin-2-yl)piperidin-4-yl)methyl)pyrazolo[1,5-a]pyridin-3-yl)dihydropyrimidine-2,4(1H,3H)-dione (90 mg, 0.153 mmol, 90% yield). LCMS [M+H]+: 586.3.

Step 2. 1-(5-((1-(4-methoxypyrimidin-2-yl)piperidin-4-yl)methyl)pyrazolo[1,5-a]pyridin-3-yl)dihydropyrimidine-2,4(1H,3H)-dione To a stirred solution of 3-(2,4-dimethoxybenzyl)-1-(5-((1-(4-methoxypyrimidin-2-yl)piperidin-4-yl)methyl)pyrazolo[1,5-a]pyridin-3-yl)dihydropyrimidine-2,4(1H,3H)-dione (90 mg, 0.145 mmol) in TFA (1 mL) was added TfOH (0.1 mL) and the reaction mixture was stirred at 70° C. for 2 h. After completion, the reaction was concentrate. The crude compound was purified by PREP HPLC using: Mobile Phase: A=0.1% HCOOH in water, B=Acetonitrile, Column: JUPITER Phenomenex (250 mm×21.2 mm), 5.0 µm, Flow: 20 mL/min. the collected fraction were concentrated under reduced pressure to afford 1-(5-((1-(4-methoxypyrimidin-2-yl)piperidin-4-yl)methyl)pyrazolo[1,5-a]pyridin-3-yl)dihydropyrimidine-2,4(1H,3H)-dione (25 mg, 0.053 mmol, 27% yield) as an off-white solid. LCMS [M+H]+: 436.2; HPLC: Rt=4.794 min. 1H NMR (400 MHz, Methanol-d4) δ 8.43 (d, J=7.1 Hz, 1H), 8.00 (s, 1H), 7.96 (d, J=6.4 Hz, 1H), 7.37 (s, 1H), 6.85 (dd, J=7.1, 1.8 Hz, 1H), 6.21 (d, J=6.5 Hz, 1H), 4.56 (d, J=9.6 Hz, 2H), 3.89 (t, J=6.8 Hz, 2H), 3.05 (t, J=12.9 Hz, 2H), 2.89 (t, J=6.8 Hz, 2H), 2.68 (d, J=7.3 Hz, 2H), 2.10-1.97 (m, 1H), 1.83 (d, J=13.2 Hz, 2H), 1.33 (qd, J=12.3, 3.3 Hz, 3H), NH proton not observed due to solvent exchange.

Example 70. Preparation of 1-(5-((1-(3-methylbutan-2-yl)piperidin-4-yl)methyl)pyrazolo[1,5-a]pyridin-3-yl)dihydropyrimidine-2,4(1H,3H)-dione Step 1. 1-(3-methylbutan-2-yl)-4-methylenepiperidine To a solution of 4-methylenepiperidine hydrochloride (2.0 g, 15 mmol) in DCM (20 mL) was added TEA (6.25 mL 44.9 mmol), TiCl4 (0.8 mL 7.48 mmol) and 3-methylbutan-2-one (1.4 g, 16.5 mmol). The mixture was stirred at rt for 12 h and then NaBH3CN (2.8 g, 45 mmol) was added. The reaction was stirred for 4 h at rt. After completion, the mixture was diluted with DCM and washed with water. The organic layer was dried over Na2SO4, filtered and concentrated to obtain 1-(3-methylbutan-2-yl)-4-methylenepiperidine (0.4 g, crude). 1H NMR (300 MHz, CDCl3) δ 4.60 (s, 2H), 2.61-2.53 (m, 2H), 2.36-2.31 (m, 2H), 2.25-2.09 (m, 4H), 1.65-1.59 (m, 1H), 1.11-1.06 (m, 3H), 0.96-0.92 (m, 3H), 0.89-0.85 (m, 3H).

Step 2. 1-(5-((1-(3-methylbutan-2-yl)piperidin-4-yl)methyl)pyrazolo[1,5-a]pyridin-3-yl)dihydropyrimidine-2,4(1H,3H)-dione (Example 70) was prepared from 1-(3-methylbutan-2-yl)-4-methylenepiperidine using the method of Example 1, steps 2 and 5, wherein 1-(3-methylbutan-2-yl)-4-methylenepiperidine was used in place of tert-butyl 4-methylenepiperidine-1-carboxylate. LCMS [M+H]+: 398.3. 1H NMR (300 MHz, CD3OD) δ 8.42 (d, J=7.2 Hz, 1H), 8.00 (s, 1H), 7.35 (s, 1H), 6.82 (dd, J=7.2 Hz, 1.2 Hz, 1H), 3.87 (t, J=6.4 Hz, 2H), 3.58-3.47 (m, 2H), 3.13-2.96 (m, 3H), 2.87 (t, J=6.8 Hz, 2H), 2.69 (d, J=6.4 Hz, 2H), 2.24-2.20 (m, 1H), 1.98-1.94 (m, 3H), 1.59-1.55 (m, 2H), 1.27 (d, J=6.8 Hz, 3H), 1.04 (d, J=6.8 Hz, 3H), 0.98 (d, J=6.8 Hz, 3H), NH proton not observed due to solvent exchange.

Example 71. Preparation of 1-(5-(((2S,4S)-1-(cyclohexylmethyl)-2-methylpiperidin-4-yl)methyl)pyrazolo[1,5-a]pyridin-3-yl)dihydropyrimidine-2,4(1H,3H)-dione

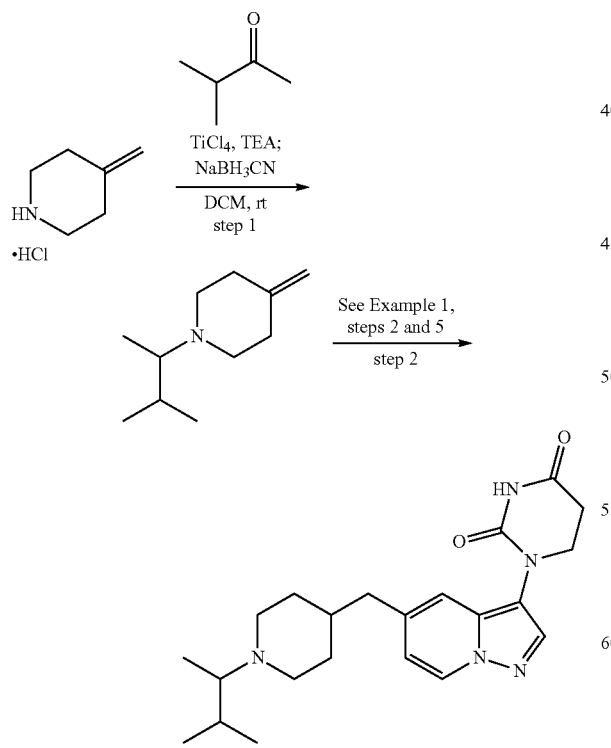

Example 70

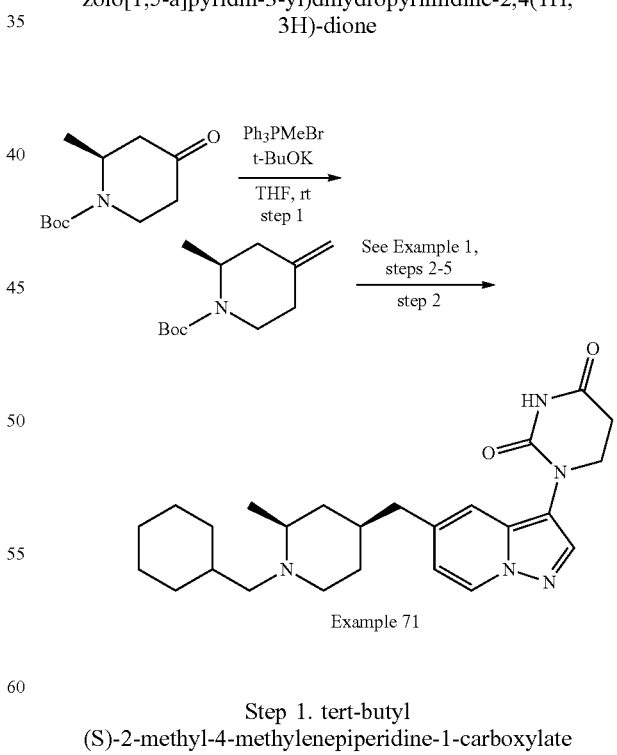

Example 71

Step 1. tert-butyl (S)-2-methyl-4-methylenepiperidine-1-carboxylate

To dry t-BuOK (1.58 g, 14.1 mmol) in THF (20 mL) was added methyltriphenylphosphonium bromide (5.02 g, 14.07 mmol) at 0° C., then the mixture was stirred at rt for 2 h. The mixture was cooled to 0° C. and a solution of tert-butyl (S)-2-methyl-4-oxopiperidine-1-carboxylate (2 g, 9.38 mmol) in THF (5 mL) was added slowly. The reaction mixture was stirred at rt for 14 h. The reaction mixture was quenched with a solution of saturated aqueous NH$_4$Cl (50 mL) and extracted with EtOAc (2×). The combined organic layers were concentrated to give the crude product. The crude product was purified by flash silica gel chromatography (eluted with 0-10% EtOAc/petroleum ether) to give tert-butyl (S)-2-methyl-4-methylenepiperidine-1-carboxylate (1.7 g, 8.1 mmol, 86% yield) as a yellow oil. $^1$H NMR (400 MHz, CDCl$_3$) δ 4.85 (d, J=1.6 Hz, 1H), 4.74 (d, J=1.6 Hz, 1H), 4.51-4.48 (m, 1H), 4.04-4.01 (m, 1H), 2.89-2.82 (m, 1H), 2.42-237 (m, 1H), 2.17-2.13 (m, 2H), 2.03-2.00 (m, 1H), 1.47 (s, 9H), 1.07 (d, J=6.8 Hz, 3H).

Step 2. 1-(5-(((2S,4S)-1-(cyclohexylmethyl)-2-methylpiperidin-4-yl)methyl)pyrazolo[1,5-a]pyridin-3-yl)dihydropyrimidine-2,4(1H,3H)-dione (Example 71) was prepared from tert-butyl (S)-2-methyl-4-methylenepiperidine-1-carboxylate using the method of Example 1, steps 2 to 5, wherein tert-butyl (S)-2-methyl-4-methylenepiperidine-1-carboxylate was used in place of tert-butyl 4-methylenepiperidine-1-carboxylate. The final product contained a minor amount of the trans isomer which was removed by SFC purification: Column: Chiralpak IG-3 50×4.6 mm I.D., 3 μm Mobile phase: Phase A for CO$_2$, and Phase B for IPA (0.05% DEA); Gradient elution: 40% IPA (0.05% DEA) in CO$_2$ Flow rate: 3 mL/min; Detector: PDA Column Temp: 35° C.; Back Pressure: 100 Bar. Product is peak 1, retention time 3.1 min. LCMS [M+H]$^+$: 438.3. $^1$H NMR (400 MHz, METHANOL-d4) δ 8.40 (d, J=7.2 Hz, 1H), 7.98 (s, 1H), 7.33 (s, 1H), 6.81-6.79 (m, 1H), 3.89-3.86 (m, 2H), 3.04 (br d, J=12.0 Hz, 1H), 2.89-2.87 (m, 2H), 2.66-2.56 (m, 3H), 2.20-1.84 (m, 4H), 1.75-1.44 (m, 8H), 1.37-1.11 (m, 5H), 1.10-1.03 (m, 3H), 0.99-0.81 (m, 2H).

The compounds in the following table were prepared by the method of Example 71, using the appropriate commercially available halide in the alkylation step.

| Example No. | Structure | Mass [M + H]$^+$ | $^1$H NMR |
|---|---|---|---|
| 72 | 1-(5-(((2S,4S)-1-isobutyl-2-methylpiperidin-4-yl)methyl)pyrazolo[1,5-a]pyridin-3-yl)dihydropyrimidine-2,4(1H,3H)-dione | 398.3 | (400 MHz, CD$_3$OD) δ 8.44 (d, J = 7.2 Hz, 1H), 8.37 (s, 1H), 8.01 (s, 1H), 7.37 (s, 1H), 6.84 (dd, J = 6.8 Hz, 1.2 Hz, 1H), 3.89 (t, J = 6.4 Hz, 2H), 3.62-3.60 (m, 1H), 3.20-3.14 (m, 3H), 2.92-2.87 (m, 3H), 2.84-2.79 (m, 1H), 2.70-2.66 (m, 3H), 2.10-2.05 (m, 2H), 1.93-1.90 (m, 2H), 1.55-1.45 (m, 2H), 1.37 (d, J = 6.4 Hz, 1H), 1.07-1.02 (m, 6H). |
| 73 | 1-(5-(((2S,4S)-2-methyl-1-((tetrahydro-2H-pyran-4-yl)methyl)piperidin-4-yl)methyl)pyrazolo[1,5-a]pyridin-3-yl)dihydropyrimidine-2,4(1H,3H)-dione | 440.1 | (400 MHz, CD$_3$OD) δ 8.44 (d, J = 7.2 Hz, 1H), 8.29 (s, 1H), 8.01 (s, 1H), 7.37 (s, 1H), 6.84 (dd, J = 7.2 Hz, 1.6 Hz, 1H), 3.98-3.94 (m, 2H), 3.89 (t, J = 6.4 Hz, 2H), 3.68-3.62 (m, 1H), 3.48-3.42 (m, 2H), 3.28-3.24 (m, 2H), 3.02-2.98 (m, 1H), 2.90-2.84 (m, 3H), 2.70-2.66 (m, 2H), 2.08-2.06 (m, 2H), 1.94-1.90 (m, 2H), 1.75-1.73 (m, 1H), 1.65-1.63 (m, 1H), 1.51-1.36 (m, 7H). |
| 74 | 1-(5-(((2S,4S)-1-((4,4-difluorocyclohexyl)methyl)-2-methylpiperidin-4-yl)methyl)pyrazolo[1,5-a]pyridin-3-yl)dihydropyrimidine-2,4(1H,3H)-dione | 474.2 | (400 MHz, CD$_3$OD) δ 8.43 (d, J = 6.4 Hz, 2H), 7.99 (s, 1H), 7.35 (s, 1H), 6.82 (dd, J = 6.8 Hz, 1.6 Hz, 1H), 3.89 (t, J = 6.8 Hz, 2H), 3.62-3.58 (m, 1H), 3.24-3.20 (m, 2H), 2.98-2.85 (m, 4H), 2.68 (d, J = 6.8 Hz, 1H), 2.07-2.04 (m, 3H), 1.91-1.81 (m, 7H), 1.42-1.33 (m, 7H). |

The compounds in the following table were prepared using the method of Example 71, wherein tert-butyl (R)-2-methyl-4-oxopiperidine-1-carboxylate was used in place of tert-butyl (S)-2-methyl-4-oxopiperidine-1-carboxylate and, using the appropriate commercially available halide in the alkylation step.

| Example No. | Structure | Mass [M + H]+ | 1H NMR |
|---|---|---|---|
| 75 | 1-(5-(((2R,4R)-2-methyl-1-((tetrahydro-2H-pyran-4-yl)methyl)piperidin-4-yl)methyl)pyrazolo[1,5-a]pyridin-3-yl)dihydropyrimidine-2,4(1H,3H)-dione | 440.2 | (400 MHz, Methanol-d4) δ 8.43 (d, J = 7.0 Hz, 1H), 8.35 (s, 1H), 8.00 (s, 1H), 7.36 (s, 1H), 6.82 (d, J = 7.1 Hz, 1H), 3.95 (dd, J = 11.8, 4.3 Hz, 2H), 3.88 (t, J = 6.7 Hz, 2H), 3.64 (s, 1H), 3.50-3.37 (m, 3H), 3.02 (d, J = 82.6 Hz, 5H), 2.88 (t, J = 6.8 Hz, 2H), 2.69 (d, J = 7.1 Hz, 2H), 1.99 (d, J = 53.6 Hz, 4H), 1.68 (dd, J = 37.8, 12.9 Hz, 2H), 1.56-1.31 (m, 8H). NH proton not observed due to solvent exchange |
| 76 | 1-(5-(((2R,4R)-1-(cyclohexylmethyl)-2-methylpiperidin-4-yl)methyl)pyrazolo[1,5-a]pyridin-3-yl)dihydropyrimidine-2,4(1H,3H)-dione | 438.2 | (400 MHz, Methanol-d4) δ 8.43 (d, J = 7.2 Hz, 1H), 8.01 (s, 1H), 7.36 (d, J = 1.7 Hz, 1H), 6.83 (dd, J = 7.3, 1.9 Hz, 1H), 3.89 (t, J = 6.8 Hz, 2H), 3.59 (d, J = 12.6 Hz, 1H), 3.27-3.09 (m, 2H), 2.89 (t, J = 6.7 Hz, 3H), 2.77 (dd, J = 13.3, 5.2 Hz, 1H), 2.72-2.61 (m, 3H), 2.05 (ddq, J = 11.9, 7.6, 3.8 Hz, 1H), 1.98-1.65 (m, 7H), 1.64-1.16 (m, 8H), 1.05 (dd, J = 16.5, 7.2 Hz, 2H). NH proton not observed due to solvent exchange |
| 77 | 1-(5-(((2R,4R)-1-isobutyl-2-methylpiperidin-4-yl)methyl)pyrazolo[1,5-a]pyridin-3-yl)dihydropyrimidine-2,4(1H,3H)-dione | 398.2 | (400 MHz, CD3OD) δ 8.50 (s, 1H), 8.43 (d, J = 7.2 Hz, 1H), 7.99 (s, 1H), 7.34 (s, 1H), 6.81 (dd, J = 7.2, 1.6 Hz, 1H), 3.87 (t, J = 7.2 Hz, 2H), 3.52-3.48 (m, 1H), 3.34 (m, 1H), 3.08-3.02 (m, 1H), 2.87 (t, J = 7.2 Hz, 2H), 2.80-2.74 (m, 1H), 2.67 (d, J = 6.8 Hz, 2H), 2.04-1.84 (m, 4H), 1.50-1.37 (m, 3H), 1.30 (d, J = 6.0 Hz, 3H), 1.01 (t, J = 6.4 Hz, 6H). |
| 78 | 1-(5-(((2R,4R)-1-((4,4-difluorocyclohexyl)methyl)-2-methylpiperidin-4-yl)methyl)pyrazolo[1,5-a]pyridin-3-yl)dihydropyrimidine-2,4(1H,3H)-dione | 474.4 | (400 MHz, Methanol-d4) δ 8.40 (d, J = 7.1 Hz, 1H), 7.98 (s, 1H), 7.34 (s, 1H), 6.81 (dd, J = 7.3, 1.8 Hz, 1H), 3.88 (t, J = 6.7 Hz, 2H), 3.06 (d, J = 11.6 Hz, 1H), 2.89 (t, J = 6.8 Hz, 2H), 2.65 (d, J = 11.8 Hz, 1H), 2.60 (d, J = 7.1 Hz, 2H), 2.19 (t, J = 7.5 Hz, 1H), 2.12-1.90 (m, 5H), 1.84-1.54 (m, 6H), 1.40-1.11 (m, 5H), 1.08 (d, J = 6.3 Hz, 3H). |

Example 79. Preparation of 1-(5-((1-isobutyl-2,2-dimethylpiperidin-4-yl)methyl)pyrazolo[1,5-a]pyridin-3-yl)dihydropyrimidine-2,4(1H,3H)-dione

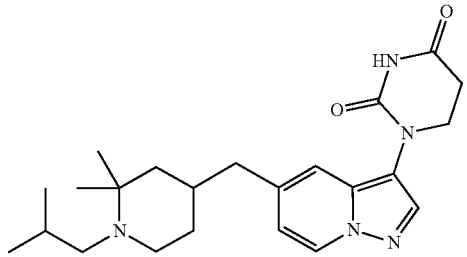 [SMILES: CC(C)CN1CCC(Cc2ccn3ncc(N4CCC(=O)NC4=O)c3c2)CC1(C)C]

Prepared using the method of Example 71 wherein tert-butyl 2,2-dimethyl-4-oxopiperidine-1-carboxylate was used in place of tert-butyl (S)-2-methyl-4-oxopiperidine-1-carboxylate. LCMS [M+H]+: 412.6. ¹H NMR (400 MHz, CD₃OD) δ 8.44 (d, J=7.2 Hz, 1H), 8.39 (s, 1H), 8.02 (s, 1H), 7.36 (s, 1H), 6.85-6.83 (m, 1H), 3.90 (t, J=7.2 Hz, 2H), 3.53-3.50 (m, 1H), 3.22-3.13 (m, 2H), 2.89 (t, J=6.8 Hz, 2H), 2.67-2.65 (m, 3H), 2.21 (brs, 1H), 2.03-1.82 (m, 3H), 1.65-1.52 (m, 2H), 1.43 (s, 3H), 1.36 (s, 3H), 1.10-1.06 (m, 6H).

Example 80. Preparation of 1-(5-((1-((cyclohexylmethyl)sulfonyl)piperidin-4-yl)methyl)pyrazolo[1,5-a]pyridin-3-yl)dihydropyrimidine-2,4(1H,3H)-dione

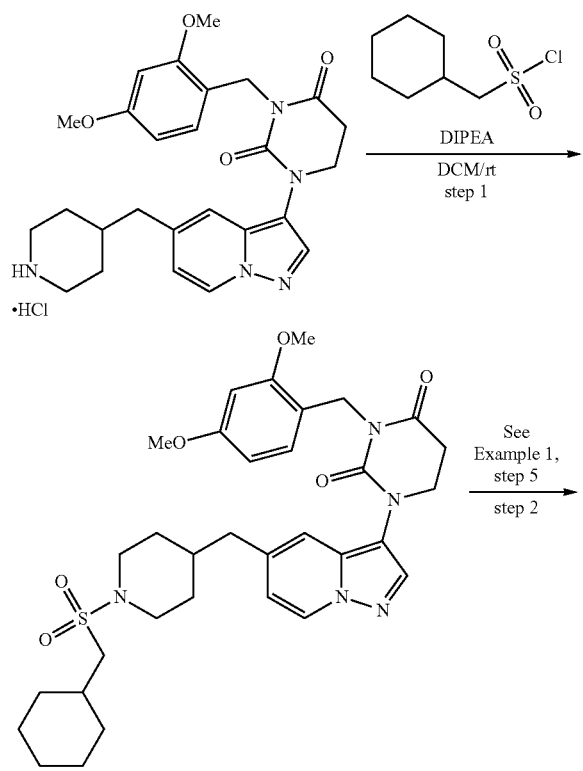

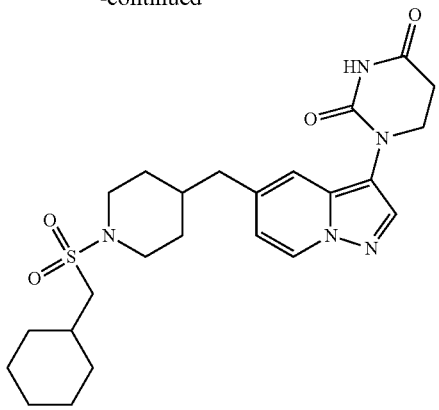

Example 80

Step 1: 1-(5-((1-((cyclohexylmethyl)sulfonyl)piperidin-4-yl)methyl)pyrazolo[1,5-a]pyridin-3-yl)-3-(2,4-dimethoxybenzyl)dihydropyrimidine-2,4(1H,3H)-dione DIPEA (0.042 mL, 0.24 mmol) and cyclohexylmethanesulfonyl chloride (14 mg, 0.073 mmol) were added to a solution of 3-(2,4-dimethoxybenzyl)-1-(5-(piperidin-4-ylmethyl)pyrazolo[1,5-a]pyridin-3-yl)dihydropyrimidine-2,4(1H,3H)-dione hydrochloride (25 mg, 0.049 mmol) in DCM (1.5 mL) at rt. The mixture was stirred at rt for 1 h, then diluted with DCM and washed sequentially with water and brine. The organic layer was dried over sodium sulfate, filtered and concentrated to give crude 1-(5-((1-((cyclohexylmethyl)sulfonyl)piperidin-4-yl)methyl)pyrazolo[1,5-a]pyridin-3-yl)-3-(2,4-dimethoxybenzyl)dihydropyrimidine-2,4(1H,3H)-dione (31 mg, 0.049 mmol). LCMS [M+H]+: 638.4.

Step 2: 1-(5-((1-((cyclohexylmethyl)sulfonyl)piperidin-4-yl)methyl)pyrazolo[1,5-a]pyridin-3-yl)dihydropyrimidine-2,4(1H,3H)-dione (Example 80) was prepared from 1-(5-((1-((cyclohexylmethyl)sulfonyl)piperidin-4-yl)methyl)pyrazolo[1,5-a]pyridin-3-yl)-3-(2,4-dimethoxybenzyl)dihydropyrimidine-2,4(1H,3H)-dione by the method of Example 1, step 5, wherein 1-(5-((1-((cyclohexylmethyl)sulfonyl)piperidin-4-yl)methyl)pyrazolo[1,5-a]pyridin-3-yl)-3-(2,4-dimethoxybenzyl)dihydropyrimidine-2,4(1H,3H)-dione was used in place of 1-(5-((1-(cyclohexylmethyl)piperidin-4-yl)methyl)pyrazolo[1,5-a]pyridin-3-yl)-3-(2,4-dimethoxybenzyl)dihydropyrimidine-2,4(1H,3)-dione. LCMS [M+H]: 488.3. ¹H NMR (500 MHz, DMSO-d6) δ 10.44 (s, 1H), 8.57 (d, J=7.1 Hz, 1 (H), 8.00 (s, 1H), 7.38 (d, J=1.7 Hz, 1H), 6.80 (dd, J=7.2, 1.9 Hz, 1H), 3.77 (t, J=6.7 Hz, 2H), 3.56 (d, J=12.2 Hz, 2H), 2.85 (d, J=6.2 Hz, 2H), 2.79 (t, J=6.7 Hz, 2H), 2.70 (td, J=12.1, 2.4 Hz, 2H), 2.60 (d, J=6.9 Hz, 2H), 1.92-1.78 (m, 3H), 1.79-1.64 (m, 5H), 1.59 (dd, J=10.3, 6.4 Hz, 1H), 1.31-1.19 (m, 4H), 1.18-1.00 (in, 3H).

The compounds in the following table were prepared by the method of Example 80, using the appropriate commercially available sulfonyl chloride or chloroformate in step 1.

| Example No. | Structure | Mass [M + H]+ | 1H NMR |
|---|---|---|---|
| 81 | 1-(5-((1-(cyclohexylsulfonyl)piperidin-4-yl)methyl)pyrazolo[1,5-a]pyridin-3-yl)dihydropyrimidine-2,4(1H,3H)-dione | 474.3 | (500 MHz, DMSO-d6) δ 10.44 (s, 1H), 8.56 (d, J = 7.0 Hz, 1H), 7.99 (s, 1H), 7.38 (t, J = 1.2 Hz, 1H), 6.79 (dd, J = 7.2, 1.9 Hz, 1H), 3.77 (t, J = 6.7 Hz, 2H), 3.70-3.49 (m, 2H), 3.06 (tt, J = 11.7,3.4 Hz, 1H), 2.92-2.71 (m, 4H), 2.59 (d, J = 7.2 Hz, 2H), 2.09-1.92 (m, 2H), 1.88-1.72 (m, 3H), 1.72-1.55 (m, 3H), 1.43-0.96 (m, 7H). |
| 82 | 1-(5-((1-(cyclohexylsulfonyl)piperidin-4-yl)methyl)pyrazolo[1,5-a]pyridin-3-yl)dihydropyrimidine-2,4(1H,3H)-dione | 460.4 | (500 MHz, DMSO-d6) δ 10.44 (s, 1H), 8.57 (d, J = 7.0 Hz, 1H), 7.99 (s, 1H), 7.37 (s, 1H), 6.79 (dd, J = 7.2, 1.9 Hz, 1H), 3.77 (t, J = 6.7 Hz, 2H), 3.62 (d, J = 13.3 Hz, 2H), 3.58 (d, J = 7.9 Hz, 1H, 2.82-2.74 (m, 4H), 2.60 (d, J = 7.1 Hz, 2H), 1.99-1.87 (m, 2H), 1.77 (dt, J = 14.1, 7.4 Hz, 3H), 1.67 (d, J = 13.0 Hz, 4H), 1.55 (t, J = 6.0 Hz, 2H), 1.21 (dt, J = 21.9, 10.9 Hz, 2H). |
| 83 | 1-(5-((1-((tetrahydro-2H-pyran-4-yl)sulfonyl)piperidin-4-yl)methyl)pyrazolo[1,5-a]pyridin-3-yl)dihydropyrimidine-2,4(1H,3H)-dione | 476.3 | (500 MHz, DMSO-d6) δ 10.44 (s, 1H), 8.57 (d, J = 7.1 Hz, 1H), 7.99 (s, 1H), 7.43-7.30 (m, 1H), 6.79 (dd, J = 7.2, 1.9 Hz, 1H), 3.94-3.88 (m, 2H), 3.77 (t, J = 6.7 Hz, 2H), 3.63 (d, J = 12.5 Hz, 2H), 3.39 (tt, J = 12.0, 3.8 Hz, 1H), 3.33 (td, J = 11.8, 2.0 Hz, 2H), 2.92-2.83 (m, 2H), 2.79 (t, J = 6.7 Hz, 2H), 2.60 (d, J = 7.1 Hz, 2H), 1.92-1.71 (m, 3H), 1.62 (dtd, J = 29.5, 13.0, 12.4, 4.1 Hz, 4H), 1.32-1.08 (m, 2H). |
| 84 | 1-(5-((1-((cyclopropylmethyl)sulfonyl)piperidin-4-yl)methyl)pyrazolo[1,5-a]pyridin-3-yl)dihydropyrimidine-2,4(1H,3H)-dione | 446.3 | (500 MHz, DMSO-d6) δ 10.44 (s, 1H), 8.57 (d, J = 7.1 Hz, 1H), 7.99 (s, 1H), 7.38 (d, J = 1.8 Hz, 1H), 6.80 (dd, J = 7.1, 1.8 Hz, 1H), 3.77 (t, J = 6.7 Hz, 2H), 3.61 (d, J = 12.3 Hz, 2H), 2.97 (d, J = 7.1 Hz, 2H), 2.85-2.71 (m, 4H), 2.60 (d, J = 7.0 Hz, 2H), 1.90-1.59 (m, 3H), 1.22 (qd, J = 12.3, 4.2 Hz, 2H), 0.98 (dqd, J = 15.1, 7.6, 4.8 Hz, 1H), 0.65-0.53 (m, 2H), 0.42-0.19 (m, 2H). |

| Example No. | Structure | Mass [M + H]⁺ | ¹H NMR |
|---|---|---|---|
| 85 | 1-(5-((1-(isopropylsulfonyl)piperidin-4-yl)methyl)pyrazolo[1,5-a]pyridin-3-yl) dihydropyrimidine-2,4(1H,3H)-dione | 434.3 | (500 MHz, DMSO-d6) δ 10.44 (s, 1H), 8.56 (dd, J = 7.1, 0.9 Hz, 1H), 7.99 (s, 1H), 7.38 (d, J = 1.7 Hz, 1H), 6.79 (dd, J = 7.2, 1.9 Hz, 1H), 3.77 (t, J = 6.7 Hz, 2H), 3.63 (d, J = 12.5 Hz, 2H), 3.29 (p, J = 6.8 Hz, 1H), 2.87-2.76 (m, 4H), 2.60 (d, J = 7.2 Hz, 2H), 1.77 (t, J = 4.8 Hz, 1H), 1.66 (d, J = 13.1 Hz, 2H), 1.21 (d, J = 6.8 Hz, 8H). |
| 86 | 1-(5-((1-(sec-butylsulfonyl)piperidin-4-yl)methyl)pyrazolo[1,5-a]pyridin-3-yl) dihydropyrimidine-2,4(1H,3H)-dione | 448.3 | (500 MHz, Methanol-d4) δ 8.31 (dd, J = 7.2, 0.9 Hz, 1H), 7.88 (s, 1H), 7.26 (dd, J = 1.9, 0.9 Hz, 1H), 6.73 (dd, J = 7.2, 1.9 Hz, 1H), 3.78 (t, J = 6.8 Hz, 2H), 3.71-3.62 (m, 2H), 2.93 (ddd, J = 9.3,6.8, 3.9 Hz, 1H), 2.84-2.73 (m, 4H), 2.55 (d, J = 7.3 Hz, 2H), 1.84 (dtd, J = 15.2, 7.6, 4.0 Hz, 1H), 1.73 (ddt, J = 11.4, 7.6, 3.8 Hz, 1H), 1.63 (d, J = 13.3 Hz, 2H), 1.40 (ddd, J = 13.7, 9.4, 7.4 Hz, 1H), 1.18 (d, J = 6.9 Hz, 5H), 0.91 (t, J = 7.5 Hz, 3H). |
| 87 | 1-(5-((1-(isobutylsulfonyl)piperidin-4-yl)methyl)pyrazolo[1,5-a]pyridin-3-yl) dihydropyrimidine-2,4(1H,3H)-dione | 448.3 | (500 MHz, DMSO-d6) δ 10.42 (s, 1H), 8.56 (d, J = 7.1 Hz, 1H), 7.99 (d, J = 1.7 Hz, 1H), 7.37 (s, 1H), 6.79 (d, J = 7.2 Hz, 1H), 3.76 (t, J = 6.7 Hz, 2H), 3.65-3.57 (m, 2H), 2.85 (d, J = 6.6 Hz, 2H, 2.78 (t, J = 6.7 Hz, 2H), 2.70 (t, J = 11.9 Hz, 2H), 2.59 (d, J = 6.9 Hz, 2H), 2.09 (hept, J = 6.6 Hz, 1H, 1.80-1.62 (m, 3H), 1.30-1.16 (m, 2H), 1.02 (dd, J = 6.8, 1.7 Hz, 6H). |
| 88 | 1-(5-((1-(benzylsulfonyl)piperidin-4-yl)methyl)pyrazolo[1,5-a]pyridin-3-yl) dihydropyrimidine-2,4(1H,3H)-dione | 482.3 | (500 MHz, DMSO-d6) δ 10.44 (s, 1H), 8.56 (d, J = 7.1 Hz, 1H), 8.00 (s, 1H), 7.50-7.26 (m, 6H), 6.78 (dd, J = 7.2, 1.9 Hz, 1H), 4.37 (s, 2H), 3.77 (t, J = 6.7 Hz, 2H), 3.54 (d, J = 12.4 Hz, 2H), 2.79 (t, J = 6.7 Hz, 2H), 2.67 (td, J = 12.4, 2.5 Hz, 2H), 2.57 (d, J = 7.1 Hz, 2H), 1.70 (tt, J = 7.4, 3.6 Hz, 1H, 1.63 (d, J = 13.2 Hz, 2H), 1.16 (qd, J = 12.2, 4.2 Hz, 2H). |

-continued

| Example No. | Structure | Mass [M + H]⁺ | ¹H NMR |
|---|---|---|---|
| 89 | 1-(5-((1-(cyclopropylsulfonyl)piperidin-4-yl)methyl)pyrazolo[1,5-a]pyridin-3-yl)dihydropyrimidine-2,4(1H,3H)-dione | 432.3 | (500 MHz, DMSO-d6) δ 10.44 (s, 1H), 8.57 (d, J = 7.1 Hz, 1H), 8.00 (s, 1H), 7.46-7.27 (m, 1H), 6.80 (dd, J = 7.1, 1.9 Hz, 1H), 3.78 (t, J = 6.7 Hz, 2H), 3.59 (d, J = 12.2 Hz, 2H), 2.84-2.73 (m, 4H), 2.61 (d, J = 7.0 Hz, 2H), 2.59-2.54 (m, 1H), 1.85-1.59 (m, 3H), 1.25 (qd, J = 12.3, 4.0 Hz, 2H, 1.06-0.82 (m, 4H). |
| 90 | 1-(5-((1-(methylsulfonyl)piperidin-4-yl)methyl)pyrazolo[1,5-a]pyridin-3-yl)dihydropyrimidine-2,4(1H,3H)-dione | 406.3 | (400 MHz, DMSO-d6) δ 10.41 (s, 1H), 8.56 (dd, J = 7.1, 0.9 Hz, 1H), 7.99 (s, 1H), 7.37 (dd, J = 1.9, 0.9 Hz, 1H), 6.79 (dd, J = 7.1, 1.9 Hz, 1H), 3.77 (t, J = 6.7 Hz, 2H), 3.54 (d, J = 11.6 Hz, 2H), 2.83 (s, 3H), 2.78 (t, J = 6.7 Hz, 2H), 2.71-2.57 (m, 4H), 1.77-1.64 (m, 3H), 1.27 (t, J = 11.8 Hz, 2H). |
| 91 | 1-(5-((1-(phenylsulfonyl)piperidin-4-yl)methyl)pyrazolo[1,5-a]pyridin-3-yl)dihydropyrimidine-2,4(1H,3H)-dione | 468.3 | (500 MHz, DMSO-d6) δ 10.42 (s, 1H), 8.52 (dd, J = 7.1, 0.9 Hz, 1H), 7.98 (s, 1H), 7.74-7.68 (m, 3H), 7.66-7.60 (m, 2H), 7.32 (t, J = 1.4 Hz, 1H), 6.72 (dd, J = 7.2, 1.9 Hz, 1H), 3.75 (t, J = 6.7 Hz, 2H), 3.65 (d, J = 12.0 Hz, 2H), 2.77 (t, J = 6.7 Hz, 2H), 2.56-2.53 (m, 2H), 2.19 (td, J = 12.0, 2.3 Hz, 2H), 1.77-1.42 (m, 3H), 1.24 (td, J = 12.3, 11.9, 4.0 Hz, 2H). |
| 92 | 1-(5-((1-((2-methoxyethyl)sulfonyl)piperidin-4-yl)methyl)pyrazolo[1,5-a]pyridin-3-yl)dihydropyrimidine-2,4(1H,3H)-dione | 450.2 | (500 MHz, Methanol-d4) δ 8.31 (dd, J = 7.2, 0.9 Hz, 1H), 7.88 (s, 1H), 7.26 (dd, J = 1.9, 0.9 Hz, 1H), 6.73 (dd, J = 7.2, 1.9 Hz, 1H), 3.78 (t, J = 6.8 Hz, 2H), 3.65-3.54 (m, 4H), 3.24 (s, 3H), 3.14 (t, J = 5.9 Hz, 2H), 2.79 (t, J = 6.8 Hz, 2H), 2.69 (td, J = 12.3, 2.4 Hz, 2H), 2.59-2.53 (m, 2H), 1.76-1.61 (m, 3H), 1.28-1.17 (m, 2H). |

-continued

| Example No. | Structure | Mass [M + H]⁺ | ¹H NMR |
|---|---|---|---|
| 93 | methyl 4-((3-(2,4-dioxotetrahydropyrimidin-1(2H)-yl)pyrazolo[1,5-a]pyridin-5-yl)methyl)piperidine-1-carboxylate | 386.3 | (400 MHz, DMSO-d6) δ 10.41 (s, 1H), 8.54 (dd, J = 7.1, 0.9 Hz, 1H), 7.98 (s, 1H), 7.35 (dd, J = 1.9, 1.0 Hz, 1H), 6.78 (dd, J = 7.1, 1.9 Hz, 1H), 3.94 (d, J = 13.0 Hz, 2H), 3.76 (t, J = 6.7 Hz, 2H), 3.57 (s, 3H), 2.78 (t, J = 6.7 Hz, 4H), 2.56 (d, J = 7.2 Hz, 2H), 1.85-1.76 (m, 1H), 1.59 (d, J = 13.0 Hz, 2H), 1.08 (qd, J = 12.3, 4.3 Hz, 2H). |
| 94 | phenyl 4-((3-(2,4-dioxotetrahydropyrimidin-1(2H)-yl)pyrazolo[1,5-a]pyridin-5-yl)methyl)piperidine-1-carboxylate | 448.3 | (500 MHz, DMSO-d6) δ 10.44 (s, 1H), 8.58 (dd, J = 7.1, 0.9 Hz, 1H), 8.00 (s, 1H), 7.46-7.35 (m, 3H), 7.27-7.19 (m, 1H), 7.15-7.06 (m, 2H), 6.82 (dd, J = 7.2, 1.9 Hz, 1H), 4.21-3.98 (m, 2H), 3.78 (t, J = 6.7 Hz, 2H), 2.99 (s, 1H), 2.80 (t, J = 6.7 Hz, 3H), 2.63 (d, J = 7.2 Hz, 2H), 1.88 (tt, J = 7.4, 3.7 Hz, 1H), 1.73-1.65 (m, 2H), 1.24 (s, 2H). |
| 95 | isobutyl 4-((3-(2,4-dioxotetrahydropyrimidin-1(2H)-yl)pyrazolo[1,5-a]pyridin-5-yl)methyl)piperidine-1-carboxylate | 428.3 | (500 MHz, DMSO-d6) δ 10.43 (s, 1H), 8.56 (d, J = 7.1 Hz, 1H), 7.99 (s, 1H), 7.36 (d, J = 1.8 Hz, 1H), 6.79 (dd, J = 7.1, 1.8 Hz, 1H), 3.97 (d, J = 13.2 Hz, 2H), 3.77 (dt, J = 6.7, 3.4 Hz, 5H), 2.79 (t, J = 6.7 Hz, 3H), 2.57 (d, J = 7.1 Hz, 2H), 1.96-1.73 (m, 2H), 1.66-1.54 (m, 2H), 1.10 (qd, J = 12.4, 4.3 Hz, 2H), 0.89 (d, J = 6.7 Hz, 6H). |
| 96 | cyclohexyl 4-((3-(2,4-dioxotetrahydropyrimidin-1(2H)-yl)pyrazolo[1,5-a]pyridin-5-yl)methyl)piperidine-1-carboxylate | 454.3 | (500 MHz, DMSO-d6) δ 10.43 (s, 1H), 8.56 (d, J = 7.1 Hz, 1H), 7.99 (s, 1H), 7.36 (s, 1H), 6.79 (dd, J = 7.2, 1.9 Hz, 1H), 4.54 (dt, J = 8.6, 4.5 Hz, 1H), 3.97 (d, J = 13.1 Hz, 2H), 3.77 (t, J = 6.7 Hz, 2H), 2.79 (t, J = 6.7 Hz, 4H), 2.57 (d, J = 7.2 Hz, 2H), 1.76 (d, J = 7.9 Hz, 3H), 1.69-1.56 (m, 4H), 1.53-1.20 (m, 6H), 1.09 (qd, J = 12.3, 4.2 Hz, 2H). |

Example 97. Preparation of tert-butyl 4-((3-(2,4-dioxotetrahydropyrimidin-1(2H)-yl)pyrazolo[1,5-a]pyridin-5-yl)methyl)piperidine-1-carboxylate (Example 97)

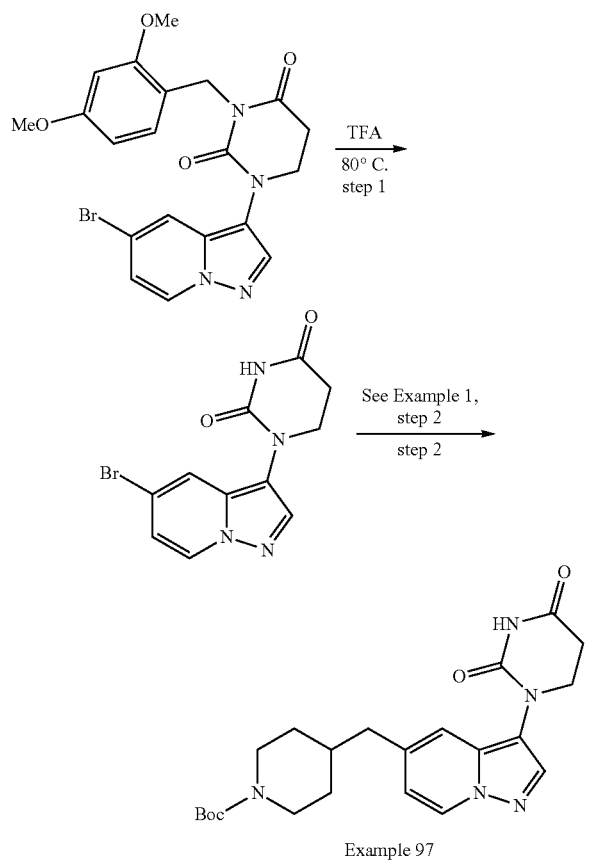

Example 97

Step 1. 1-(5-bromopyrazolo[1,5-a]pyridin-3-yl)dihydropyrimidine-2,4(1H,3H)-dione TFA (1.5 mL, 19 mmol) was added to 1-(5-bromopyrazolo[1,5-a]pyridin-3-yl)-3-(2,4-dimethoxybenzyl)dihydropyrimidine-2,4(1H,3H)-dione (95 mg, 0.21 mmol) and the mixture was heated at 80° C. overnight. The mixture was then cooled to rt, concentrated and the residue was dissolved in toluene and concentrated again to give crude 1-(5-bromopyrazolo[1,5-a]pyridin-3-yl)dihydropyrimidine-2,4(1H,3H)-dione as a TFA salt which was used without further purification. LCMS [M+H]+: 309.1.

Step 1. tert-butyl 4-((3-(2,4-dioxotetrahydropyrimidin-1(2H)-yl)pyrazolo[1,5-a]pyridin-5-yl)methyl)piperidine-1-carboxylate was prepared from 1-(5-bromopyrazolo[1,5-a]pyridin-3-yl)dihydropyrimidine-2,4(1H,3H)-dione using the method of Example 1, step 2, wherein 1-(5-bromopyrazolo[1,5-a]pyridin-3-yl)dihydropyrimidine-2,4(1H,3H)-dione was used in place of 1-(5-bromopyrazolo[1,5-a]pyridin-3-yl)-3-(2,4-dimethoxybenzyl)dihydropyrimidine-2,4(1H,3H)-dione. Purified by reverse phase HPLC using ACN/Water/0.1% TFA. LCMS [M+H]+: 428.3. $^1$H NMR (500 MHz, Methanol-d4) δ 8.30 (d, J=7.1 Hz, 1H), 7.88 (s, 1H), 7.25 (s, 1H), 6.72 (d, J=7.2 Hz, 1H), 3.95 (d, J=13.3 Hz, 2H), 3.78 (t, J=6.7 Hz, 2H), 2.79 (t, J=6.8 Hz, 2H), 2.61 (d, J=15.8 Hz, 2H), 2.53 (d, J=7.2 Hz, 2H), 1.74 (s, 1H), 1.56 (d, J=13.3 Hz, 2H), 1.34 (s, 9H), 1.13-0.98 (m, 2H).

Example 98. Preparation of 1-(5-((1-isobutyrylpiperidin-4-yl)methyl)pyrazolo[1,5-a]pyridin-3-yl)dihydropyrimidine-2,4(1H,3H)-dione

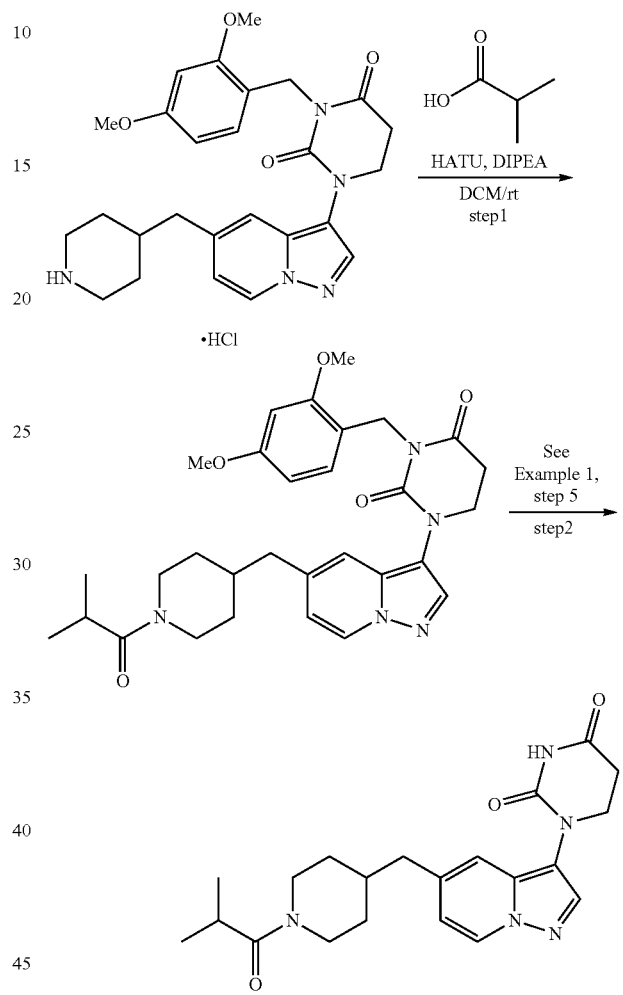

Example 98

Step 1: 3-(2,4-dimethoxybenzyl)-1-(5-((1-isobutyrylpiperidin-4-yl)methyl)pyrazolo[1,5-a]pyridin-3-yl)dihydropyrimidine-2,4(1H,3H)-dione HATU (28 mg, 0.073 mmol) and isobutyric acid (6.2 μl, 0.097 mmol) were added to a solution of 3-(2,4-dimethoxybenzyl)-1-(5-(piperidin-4-ylmethyl)pyrazolo[1,5-a]pyridin-3-yl)dihydropyrimidine-2,4(1H,3H)-dione hydrochloride (25 mg, 0.049 mmol) in DMF (1 mL) at rt. The mixture was stirred at rt for 5 min and then DIPEA (0.034 mL, 0.19 mmol) was added. The mixture was stirred at rt for 1 h and then diluted with ethyl acetate and washed sequentially with water and brine. The organic layer was dried over sodium sulfate, filtered and concentrated to give crude 3-(2,4-dimethoxybenzyl)-1-(5-((1-isobutyrylpiperidin-4-yl)methyl)pyrazolo[1,5-a]pyridin-3-yl)dihydropyrimidine-2,4(1H,3H)-dione (27 mg, 0.049 mmol). LCMS [M+H]+: 548.3.

Step 2: 1-(5-((1-isobutyrylpiperidin-4-yl)methyl)pyrazolo[1,5-a]pyridin-3-yl)dihydropyrimidine-2,4(1H,3H)-dione (Example 98) was prepared from 3-(2,4-dimethoxybenzyl)-1-(5-((1-isobutyrylpiperidin-4-yl)methyl)pyrazolo[1,5-a]pyridin-3-yl)dihydropyrimidine-2,4(1H,3H)-dione using the method of Example 1, step 5, wherein 3-(2,4-dimethoxybenzyl)-1-(5-((1-isobutyrylpiperidin-4-yl)methyl)pyrazolo[1,5-a]pyridin-3-yl)dihydropyrimidine-2,4(1H,31-)-dione was used in place of 1-(5-((1-(cyclohexylmethyl)piperidin-4-yl)methyl)pyrazolo[1,5-a]pyridin-3-yl)-3-(2,4-dimethoxybenzyl)dihydropyrimidine-2,4(1H,3)-dione. LCMS [M+H]: 488.3. $^1$H NMR (500 MHz, DMSO-d6) δ 10.43 (s, 1H), 8.56 (d, J=7.1 Hz, 1H), 7.99 (s, 1H), 7.37 (d, J=1.7 Hz, 1H), 6.80 (dd, J=7.1, 1.9 Hz, 1H), 4.39 (d, J=13.1 Hz, 1H), 3.93 (d, J=13.6 Hz, 1H), 3.77 (t, J=6.7 Hz, 2H), 2.97 (t, J=12.8 Hz, 1H), 2.86 (h, J=6.7 Hz, 1H), 2.79 (t, J=6.7 Hz, 2H), 2.58 (d, J=7.2 Hz, 2H), 2.47 (d, J=12.9 Hz, 1H), 1.86 (ddd, J=11.2, 7.5, 3.8 Hz, 1H), 1.73-1.56 (m, 2H), 1.22-1.01 (m, 2H), 0.99 (dd, J=12.3, 6.7 Hz, 6H).

The compounds in the following table were prepared by the method of Example 98, using the appropriate commercially available carboxylic acid in step 1.

| Example No. | Structure | Mass [M + H]$^+$ | $^1$H NMR |
|---|---|---|---|
| 99 | 1-(5-((1-(cyclohexanecarbonyl)piperidin-4-yl)methyl)pyrazolo[1,5-a]pyridin-3-yl)dihydropyrimidine-2,4(1H,3H)-dione | 438.4 | (500 MHz, DMSO-d6) δ 10.43 (s, 1H), 8.56 (d, J = 7.1 Hz, 1H), 7.99 (s, 1H), 7.37 (d, J = 1.8 Hz, 1H), 6.80 (dd, J = 7.1, 1.9 Hz, 1H), 4.38 (d, J = 13.2 Hz, 2H), 3.98-3.87 (m, 2H), 3.77 (t, J = 6.7 Hz, 2H), 2.95 (t, J = 12.8 Hz, 1H), 2.79 (t, J = 6.7 Hz, 2H), 2.57 (dd, J = 7.1, 4.1 Hz, 2H), 1.85 (ddd, J = 11.1, 7.3, 3.7 Hz, 1H), 1.76-1.52 (m, 7H), 1.30 (t, J = 10.4 Hz, 4H), 1.22-0.93 (m, 3H). |
| 100 | 1-(5-((1-(1-(trifluoromethyl)cyclopropane-1-carbonyl)piperidin-4-yl)methyl)pyrazolo[1,5-a]pyridin-3-yl)dihydropyrimidine-2,4(1H,3H)-dione | 464.2 | (400 MHz, DMSO-d6) δ 10.41 (s, 1H), 8.55 (dd, J = 7.5, 2.0 Hz, 1H), 7.98 (d, J = 2.0 Hz, 1H, 7.36 (s, 1H), 6.79 (dd, J = 7.2, 1.9 Hz, 1H), 4.23 (s, 2H), 3.76 (dd, J = 7.8, 5.8 Hz, 2H), 2.78 (dd, J = 7.7, 5.8 Hz, 2H), 2.58 (d, J = 6.9 Hz, 2H), 2.55 (d, J = 1.8 Hz, 2H), 1.87 (s, 1H), 1.67 (d, J = 13.1 Hz, 2H, 1.38-1.23 (m, 2H), 1.13 (d, J = 19.6 Hz, 4H). |
| 101 | 1-(5-((1-(benzoylpiperidin-4-yl)methyl)pyrazolo[1,5-a]pyridin-3-yl)dihydropyrimidine-2,4(1H,3H)-dione | 432.3 | (500 MHz, DMSO-d6) δ 10.43 (s, 1H), 8.62-8.39 (m, 1H), 7.99 (s, 1H), 7.48-7.42 (m, 3H), 7.37 (qt, J = 3.0, 1.7 Hz, 3H), 6.80 (dd, J = 7.2, 1.9 Hz, 1H), 4.47 (s, 2H), 3.77 (t, J = 6.7 Hz 2H) 3.56 (s, 1H) 3.00 (s, 1H), 2.79 (t, J = 6.7 Hz, 3H), 2.60 (s, 2H), 2.03-1.46 (m, 2H), 1.19 (s, 2H). |

-continued

| Example No. | Structure | Mass [M + H]+ | ¹H NMR |
|---|---|---|---|
| 102 | 1-(5-((1-(3-phenylpropanoyl)piperidin-4-yl)methyl)pyrazolo[1,5-a]pyridin-3-yl)dihydropyrimidine-2,4(1H,3H)-dione | 460.3 | (400 MHz, Methanol-d4) δ 8.40 (d, J = 7.1 Hz, 1H), 7.99 (s, 1H), 7.32 (s, 1H), 7.23 (ddd, J = 18.6, 13.0, 7.4 Hz, 5H), 6.80 (d, J = 7.2 Hz, 1H), 4.52 (d, J = 13.0 Hz, 1H), 3.87 (q, J = 9.5, 8.1 Hz, 3H), 2.97-2.85 (m, 5H), 2.79-2.45 (m, 5H), 1.86 (s, 1H), 1.69 (d, J = 13.4 Hz, 1H), 1.58 (d, J = 13.4 Hz, 1H), 1.30 (s, 1H), 1.17-1.00 (m, 1H), 0.93-0.76 (m, 1H). NH proton not observed due to solvent exchange. |
| 103 | 1-(5-((1-(3-cyclohexylpropanoyl)piperidin-4-yl)methyl)pyrazolo[1,5-a]pyridin-3-yl)dihydropyrimidine-2,4(1H,3H)-dione | 466.2 | (400 MHz, Methanol-d4) δ 8.40 (d, J = 7.0 Hz, 1H), 7.98 (s, 1H), 7.35 (s, 1H), 6.83 (d, J = 6.9 Hz, 1H), 4.50 (d, J = 13.2 Hz, 1H), 3.97-3.81 (m, 3H), 3.04 (t, J = 13.2 Hz, 1H), 2.88 (t, J = 6.6 Hz, 2H), 2.70-2.51 (m, 3H), 2.37 (dd, J = 9.5, 6.6 Hz, 2H), 1.93 (ddd, J = 13.5, 8.8, 5.1 Hz, 1H), 1.79-1.59 (m, 7H), 1.45 (q, J = 7.4 Hz, 2H), 1.33-1.06 (m, 6H), 0.91 (q, J = 13.7, 12.7 Hz, 2H). NH proton not observed due to solvent exchange. |

Example 104. Preparation of 1-(5-((1-acetylpiperidin-4-yl)methyl)pyrazolo[1,5-a]pyridin-3-yl)dihydropyrimidine-2,401H,3H)-dione

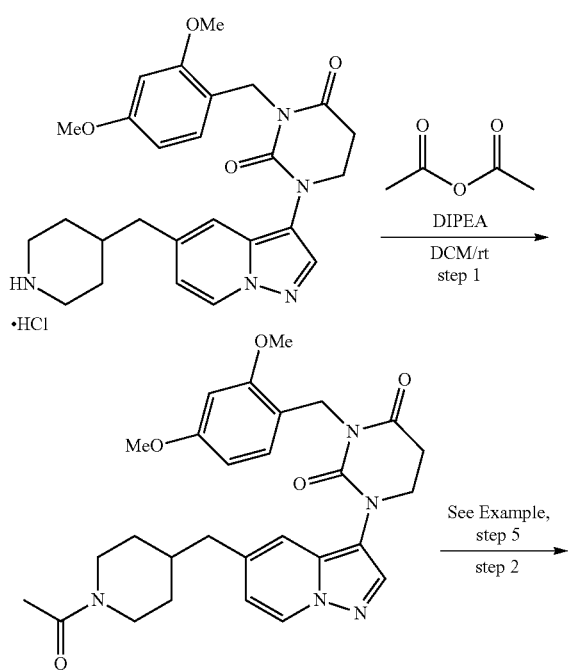

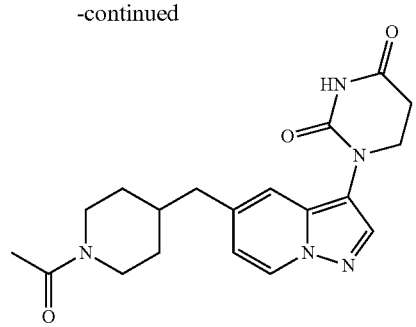

Example 104

Step 1. 1-(5-((1-acetylpiperidin-4-yl)methyl)pyrazolo[1,5-a]pyridin-3-yl)-3-(2,4-dimethoxybenzyl)dihydropyrimidine-2,4(1H,3H)-dione DIPEA (0.049 mL, 0.28 mmol) and acetic anhydride (0.016 mL, 0.17 mmol) were added to a solution of 3-(2,4-dimethoxybenzyl)-1-(5-(piperidin-4-ylmethyl)pyrazolo[1,5-a]pyridin-3-yl)dihydropyrimidine-2,4(1H,3H)-dione (27 mg, 0.057 mmol) in DCM (1.5 mL) at rt. The mixture was stirred at rt for 30 min and then partioned between DCM and water. The organic layer separated, washed with brine, dried over sodium sulfate, filtered and concentrated to give crude 1-(5-((1-acetylpiperidin-4-yl)methyl)pyrazolo[1,5-a]pyridin-3-yl)-3-(2,4-dimethoxybenzyl)dihydropyrimidine-2,4(1H,3H)-dione that was used without further purification. LCMS [M+H]: 520.4.

Step 2: 1-(5-((1-acetylpiperidin-4-yl)methyl)pyrazolo[1,5-a]pyridin-3-yl)dihydropyrimidine-2,4(1H,3H)-dione was prepared from 1-(5-((1-acetylpiperidin-4-yl)methyl)pyrazolo[1,5-a]pyridin-3-yl)-3-(2,4-dimethoxybenzyl)dihydropyrimidine-2,4(1H,3H)-dione using the method of Example 1, step 5, wherein 1-(5-((1-acetylpiperidin-4-yl)methyl)pyrazolo[1,5-a]pyridin-3-yl)-3-(2,4-dimethoxybenzyl)dihydropyrimidine-2,4(1H,3H)-dione was used in place of 1-(5-((1-(cyclohexylmethyl)piperidin-4-yl)methyl)pyrazolo[1,5-a]pyridin-3-yl)-3-(2,4-dimethoxybenzyl)dihydropyrimidine-2,4(1H,3H)-dione. LCMS [M+H]: 370.3. $^1$H NMR (400 MHz, DMSO-d6) δ 10.41 (s, 1H), 8.55 (d, J=7.2 Hz, 1H), 7.98 (s, 1H), 7.35 (d, J=1.6 Hz, 1H), 6.78 (dd, J=7.1, 1.8 Hz, 1H), 4.34 (d, J=13.1 Hz, 1H), 3.77 (q, J=6.3 Hz, 3H), 3.03-2.90 (m, 1H), 2.78 (t, J=6.7 Hz, 2H), 2.57 (d, J=7.2 Hz, 2H), 2.49-2.41 (m, 1H), 1.97 (s, 3H), 1.83 (ddd, J=10.9, 7.4, 3.6 Hz, 1H), 1.61 (t, J=12.6 Hz, 2H), 1.08 (dqd, J=47.6, 12.4, 4.2 Hz, 2H).

Example 105. Preparation of 1-(5-((1-(2-methoxy-2-methylpropyl)piperidin-4-yl)methyl)pyrazolo[1,5-a]pyridin-3-yl)dihydropyrimidine-2,4(1H,3H)-dione

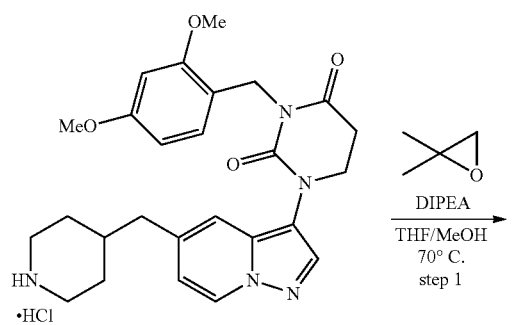

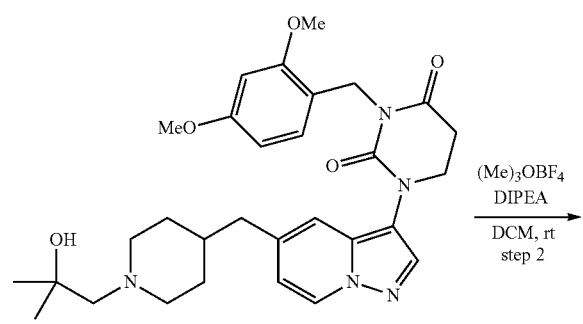

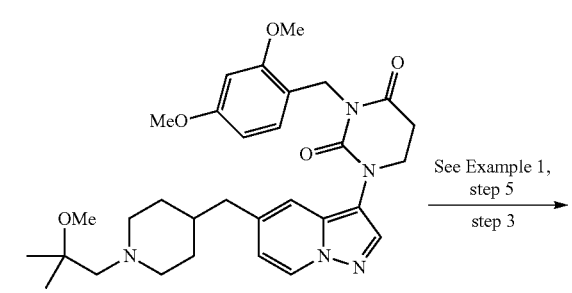

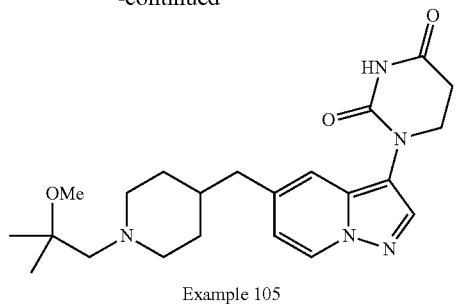

Example 105

Step 1. 3-(2,4-dimethoxybenzyl)-1-(5-((1-(2-hydroxy-2-methylpropyl)piperidin-4-yl)methyl)pyrazolo[1,5-a]pyridin-3-yl)dihydropyrimidine-2,4(1H,3H)-dione 2,2-Dimethyloxirane (63 mg, 0.87 mmol) and DIPEA (0.15 mL, 0.87 mmol) were added to a solution of 3-(2,4-dimethoxybenzyl)-1-(5-(piperidin-4-ylmethyl)pyrazolo[1,5-a]pyridin-3-yl)dihydropyrimidine-2,4(1H,3H)-dione (150 mg, 0.29 mmol) in THF (2 mL) and MeOH (2 mL) at rt. The mixture was heated at 70° C. overnight, then cooled to rt and concentrated to give crude 3-(2,4-dimethoxybenzyl)-1-(5-((1-(2-hydroxy-2-methylpropyl)piperidin-4-yl)methyl)pyrazolo[1,5-a]pyridin-3-yl)dihydropyrimidine-2,4(1H,3H)-dione which was used without further purification. LCMS [M+H]$^+$: 550.3.

Step 2. 3-(2,4-dimethoxybenzyl)-1-(5-((1-(2-methoxy-2-methylpropyl)piperidin-4-yl)methyl)pyrazolo[1,5-a]pyridin-3-yl)dihydropyrimidine-2,4(1H,3H)-dione Trimethyloxonium tetrafluoroborate (40 mg, 0.27 mmol) and DIPEA (0.072 mL, 0.41 mmol) were added to a solution of 3-(2,4-dimethoxybenzyl)-1-(5-((1-(2-hydroxy-2-methylpropyl)piperidin-4-yl)methyl)pyrazolo[1,5-a]pyridin-3-yl)dihydropyrimidine-2,4(1H,3H)-dione (40 mg, 0.068 mmol) in DCM (2 mL) at rt. The mixture was stirred at rt overnight, diluted with DCM and then washed sequentially with saturated aqueous NaHCO$_3$ solution and brine. The organic layer was dried over Na$_2$SO$_4$, filtered and concentrated to give crude 3-(2,4-dimethoxybenzyl)-1-(5-((1-(2-methoxy-2-methylpropyl)piperidin-4-yl)methyl)pyrazolo[1,5-a]pyridin-3-yl)dihydropyrimidine-2,4(1H,3H)-dione which was used without further purification. LCMS [M+H]$^+$: 564.3.

Step 3: 1-(5-((1-(2-methoxy-2-methylpropyl)piperidin-4-yl)methyl)pyrazolo[1,5-a]pyridin-3-yl)dihydropyrimidine-2,4(1H,3H)-dione was prepared from 3-(2,4-dimethoxybenzyl)-1-(5-((1-(2-methoxy-2-methylpropyl)piperidin-4-yl)methyl)pyrazolo[1,5-a]pyridin-3-yl)dihydropyrimidine-2,4(1H,3H)-dione using the method of Example 1, step 5, wherein 3-(2,4-dimethoxybenzyl)-1-(5-((1-(2-methoxy-2-methylpropyl)piperidin-4-yl)methyl)pyrazolo[1,5-a]pyridin-3-yl)dihydropyrimidine-2,4(1H,3H)-dione was used in place of 1-(5-((1-(cyclohexylmethyl)piperidin-4-yl)methyl)pyrazolo[1,5-a]pyridin-3-yl)-3-(2,4-dimethoxybenzyl)dihydropyrimidine-2,4(1H,3H)-dione. LCMS [M+H]$^+$: 414.4. $^1$H NMR (500 MHz, Methanol-d4) δ 8.46 (d, J=7.1 Hz, 1H), 8.03 (s, 1H), 7.39 (s, 1H), 6.86 (d, J=7.2 Hz, 1H), 3.90 (q, J=6.0 Hz, 4H), 3.45 (s, 3H), 3.30-3.12 (m, 4H), 2.90 (t, J=6.8

Hz, 2H), 2.78 (d, J=7.3 Hz, 2H), 2.04 (d, J=9.8 Hz, 1H), 1.96-1.77 (m, 4H), 1.46 (s, 6H).

Example 106. Preparation of 1-(5-((1-(2-hydroxy-2-methylpropyl)piperidin-4-yl)methyl)pyrazolo[1,5-a]pyridin-3-yl)dihydropyrimidine-2,4(1H,3H)-dione

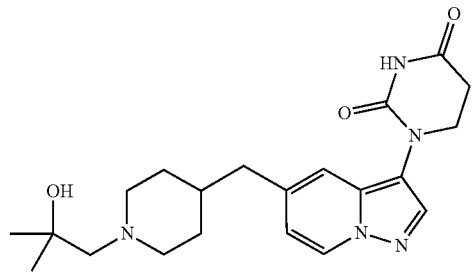 [SMILES: CC(C)(O)CN1CCC(Cc2ccn3ncc(N4CCC(=O)NC4=O)c3c2)CC1]

Prepared from 3-(2,4-dimethoxybenzyl)-1-(5-((1-(2-hydroxy-2-methylpropyl)piperidin-4-yl)methyl)pyrazolo[1,5-a]pyridin-3-yl)dihydropyrimidine-2,4(1H,3H)-dione (from step 2 of Example 105) by the method of Example 1, step 5, wherein 3-(2,4-dimethoxybenzyl)-1-(5-((1-(2-hydroxy-2-methylpropyl)piperidin-4-yl)methyl)pyrazolo[1,5-a]pyridin-3-yl)dihydropyrimidine-2,4(1H,3H)-dione was used in place of 1-(5-((1-(cyclohexylmethyl)piperidin-4-yl)methyl)pyrazolo[1,5-a]pyridin-3-yl)-3-(2,4-dimethoxybenzyl)dihydropyrimidine-2,4(1H,3H)-dione. LCMS [M+H]$^+$: 400.4. $^1$H NMR (400 MHz, DMSO-d6) δ 10.42 (s, 1H), 8.58 (dd, J=7.2, 2.8 Hz, 1H), 8.00 (s, 1H), 7.36 (d, J=3.2 Hz, 1H), 6.78 (dd, J=7.2, 1.8 Hz, 1H), 4.00-3.62 (m, 2H), 3.57 (d, J=12.8 Hz, 2H), 3.30-3.10 (m, 3H), 3.07-2.89 (m, 3H), 2.79 (t, J=6.6 Hz, 2H), 2.63 (dd, J=28.7, 7.0 Hz, 1H), 1.91 (d, J=53.7 Hz, 1H), 1.68 (dt, J=42.6, 14.6 Hz, 4H), 1.23 (d, J=5.3 Hz, 6H).

Example 107. Preparation of 1-(5-((1-((1-fluorocyclohexyl)methyl)piperidin-4-yl)methyl)pyrazolo[1,5-a]pyridin-3-yl)dihydropyrimidine-2,4(1H,3H)-dione

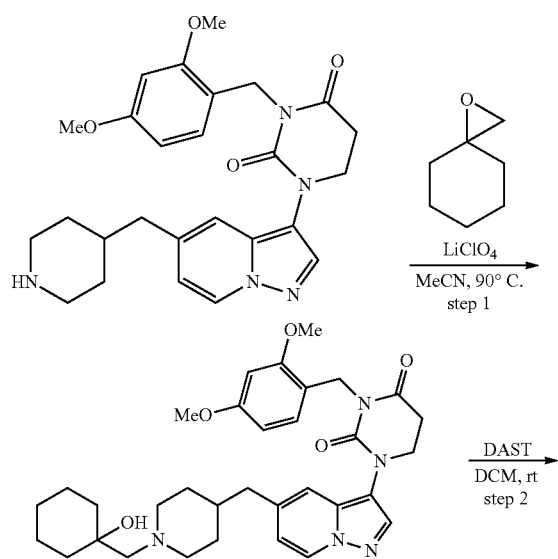

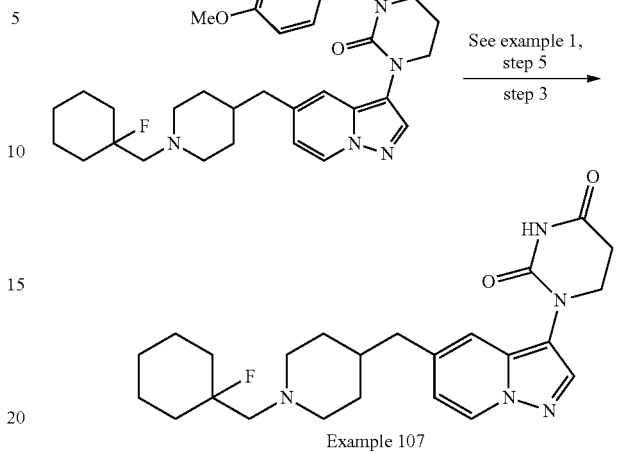

Example 107

Step 1. 3-(2,4-dimethoxybenzyl)-1-(5-((1-((1-hydroxycyclohexyl)methyl)piperidin-4-yl)methyl)pyrazolo[1,5-a]pyridin-3-yl)dihydropyrimidine-2,4(1H,3H)-dione To a stirred solution of 3-(2,4-dimethoxybenzyl)-1-(5-(piperidin-4-ylmethyl)pyrazolo[1,5-a]pyridin-3-yl)dihydropyrimidine-2,4(1H,3H)-dione (250 mg, 0.523 mmol) in acetonitrile (5.0 mL) was added lithium perchlorate (110 mg, 1.046 mmol). The reaction was stirred for 10 min followed by the addition of 1-oxaspiro[2.5]octane (293 mg, 2.61 mmol). The mixture was stirred at 90° C. for 4 h. After cooling to rt, the reaction was diluted with EtOAc and water. The organic layer was dried over Na$_2$SO$_4$, filtered and concentrated to give crude 3-(2,4-dimethoxybenzyl)-1-(5-((1-((1-hydroxycyclohexyl)methyl)piperidin-4-yl)methyl)pyrazolo[1,5-a]pyridin-3-yl)dihydropyrimidine-2,4(1H,3H)-dione (200 mg, crude). LCMS [M+H]$^+$: 590.3.

Step 2. 3-(2,4-dimethoxybenzyl)-1-(5-((1-((1-fluorocyclohexyl)methyl)piperidin-4-yl)methyl)pyrazolo[1,5-a]pyridin-3-yl)dihydropyrimidine-2,4(1H,3H)-dione To a stirred solution of 3-(2,4-dimethoxybenzyl)-1-(5-((1-((1-hydroxycyclohexyl)methyl)piperidin-4-yl)methyl)pyrazolo[1,5-a]pyridin-3-yl)dihydropyrimidine-2,4(1H,3H)-dione (80 mg, 0.135 mmol) in DCM (10 mL) at 0° C. was added DAST (43 mg, 0.271 mmol). The reaction was stirred at 0° C. for 1 h. The reaction was then diluted with DCM and water. The organic layer was dried over Na$_2$SO$_4$, filtered and concentrated to give crude 3-(2,4-dimethoxybenzyl)-1-(5-((1-((1-fluorocyclohexyl)methyl)piperidin-4-yl)methyl)pyrazolo[1,5-a]pyridin-3-yl)dihydropyrimidine-2,4(1H, 3H)-dione (50 mg, crude). LCMS [M+H]$^+$: 592.2.

Step 3: 1-(5-((1-((1-fluorocyclohexyl)methyl)piperidin-4-yl)methyl)pyrazolo[1,5-a]pyridin-3-yl)dihydropyrimidine-2,4(1H,3H)-dione (Example 107) was prepared from 3-(2,4-dimethoxybenzyl)-1-(5-((1-((1-fluorocyclohexyl)methyl)piperidin-4-yl)methyl)pyrazolo[1,5-a]pyridin-3-yl)dihydropyrimidine-2,4(1H,3H)-dione (10 mg, 0.016 mmol) using the method of Example 1, step 5, wherein 3-(2,4-dimethoxybenzyl)-1-(5-((1-((1-fluorocyclohexyl)methyl)piperidin-4-yl)methyl)pyrazolo[1,5-a]pyridin-3-yl)dihydropyrimidine-2,4(1H,3H)-dione was used in place of 1-(5-((1-(cyclohexylmethyl)piperidin-4-yl)methyl)pyrazolo[1,5-a]pyridin-3-yl)-3-(2,4-dimethoxybenzyl)dihydropyrimidine-2,4(1H,3H)-dione. The crude compound was purified by chiral HPLC::COLUMN: CHIRALPAK IG, 250 mm×20 mm×5 µm, MOBILE PHASE: HEXANE (A), 0.1% DEA in MeOH: EtOH, 1:1 (B), FLOW: 15 mL ISOCRATIC: 75(A): 25(B). The collected fractions were concentrated to afford 1-(5-((1-((1-fluorocyclohexyl)methyl)piperidin-4-yl)methyl)pyrazolo[1,5-a]pyridin-3-yl)dihydropyrimidine-2,4 (1H,3H)-dione (3 mg, 0.006 mmol, 33% yield) as an off-white solid. LCMS [M+H]$^+$: 442.3. HPLC Rt=4.95 min. $^1$H NMR (300 MHz, Methanol-d4) δ 8.40 (d, J=7.1 Hz, 1H), 7.98 (s, 1H), 7.34 (s, 1H), 6.81 (d, J=7.2 Hz, 1H), 3.88 (t, J=6.6 Hz, 2H), 2.98-2.84 (m, 4H), 2.61 (d, J=6.5 Hz, 2H), 2.42 (d, J=23.5 Hz, 2H), 2.07 (t, J=11.2 Hz, 2H), 1.82 (s, 2H), 1.69-1.47 (m, 10H), 1.43-1.24 (m, 3H). NH proton not observed due to solvent exchange.

Example 108. Preparation of 1-(5-(piperidin-4-ylmethyl)pyrazolo[1,5-a]pyridin-3-yl)dihydropyrimidine-2,4(1H,3H)-dione

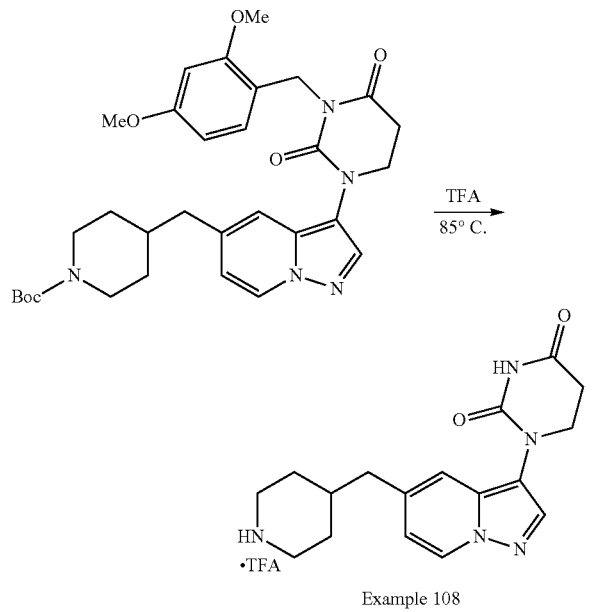

Example 108

TFA (25 mL, 5.28 mmol) was added to tert-butyl 4-((3-(3-(2,4-dimethoxybenzyl)-2,4-dioxotetrahydropyrimidin-1(2H)-yl)pyrazolo[1,5-a]pyridin-5-yl)methyl)piperidine-1-carboxylate (3.05 g, 5.28 mmol). The mixture was heated overnight at in a sealed vial at 85° C. The mixture was then cooled to rt and, concentrated and azeotropically dried with toluene to provide crude product (2.33 g, 5.28 mmol). A portion (~20 mg) of the crude material was dissolved in DMSO, filtered through a 1 micron filter and purified by reverse phase HPLC using ACN/Water/0.1% TFA. The fractions containing the product were combined, frozen and lyophilized to afford a TFA salt of 1-(5-(piperidin-4-ylmethyl)pyrazolo[1,5-a]pyridin-3-yl)dihydropyrimidine-2,4 (1H,3H)-dione (Example 108) (8 mg, 0.018 mmol). LCMS [M+H]$^+$: 328.3. $^1$H NMR (500 MHz, DMSO-d6) δ 10.44 (s, 1H), 8.59 (d, J=7.1 Hz, 1H), 8.52 (d, J=11.4 Hz, 1H), 8.23 (d, J=11.4 Hz, 1H), 8.01 (s, 1H), 7.39 (d, J=1.8 Hz, 1H), 6.80 (dd, J=7.2, 1.9 Hz, 1H), 3.77 (t, J=6.7 Hz, 2H), 3.26 (d, J=12.6 Hz, 2H), 2.90-2.76 (m, 4H), 2.61 (d, J=7.0 Hz, 2H), 1.89 (ddh, J=14.7, 7.3, 3.6 Hz, 1H), 1.80-1.72 (m, 2H), 1.35 (tdd, J=14.3, 12.0, 4.0 Hz, 2H).

Example 109. Preparation of 1-(5-((1-isobutylpiperidin-4-yl)methyl)pyrazolo[1,5-a]pyridin-3-yl)dihydropyrimidine-2,4(1H,3H)-dione

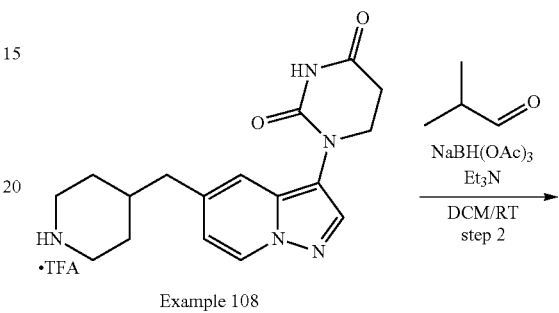

Example 108

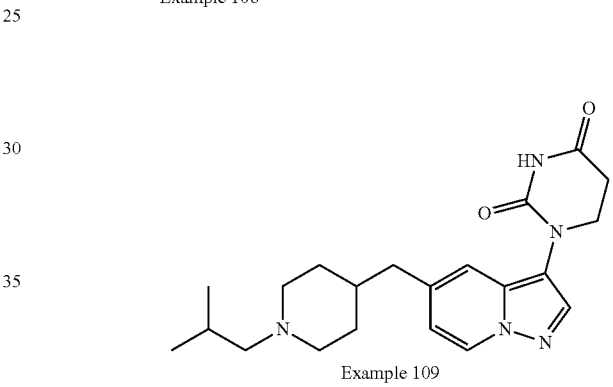

Example 109

Isobutyraldehyde (1.90 g, 26.4 mmol) and triethylamine (1.10 mL, 7.92 mmol) were added to a solution of 1-(5-(piperidin-4-ylmethyl)pyrazolo[1,5-a]pyridin-3-yl)dihydropyrimidine-2,4(1H,3H)-dione trifluoroacetate (Example 108) (2.33 g, 5.28 mmol) in DCM (30 mL) and MeOH (2 mL). The reaction mixture was stirred at rt for 30 min and then sodium triacetoxyborohydride (5.59 g, 26.4 mmol) was added. The reaction mixture was stirred overnight at rt and then quenched with a solution of saturated aqueous NaHCO$_3$ and extracted three times with DCM. The combined organic extracts were washed with brine, dried over Na$_2$SO$_4$, filtered and concentrated. Silica gel column chromatography (eluted with 0-100% EtOAc/EtOH (3:1), heptane and 0.1% TEA) provided a light brown solid which was triturated with diethyl ether to give 1-(5-((1-isobutylpiperidin-4-yl)methyl)pyrazolo[1,5-a]pyridin-3-yl)dihydropyrimidine-2,4(1H, 3H)-dione as an off white solid. (1055 mg, 2.738 mmol, 52% yield). LCMS [M+H]$^+$: 384.3. $^1$H NMR (500 MHz, DMSO-d6) δ 10.42 (s, 1H), 8.53 (d, J=7.1 Hz, 1H), 7.97 (d, J=1.4 Hz, 1H), 7.34 (s, 1H), 6.83-6.63 (m, 1H), 3.76 (t, J=6.6 Hz, 2H), 2.78 (t, J=6.8 Hz, 4H), 2.55 (d, J=6.5 Hz, 2H), 1.97 (d, J=7.4 Hz, 2H), 1.75 (dt, J=19.4, 9.2 Hz, 3H), 1.56 (d, J=11.5 Hz, 3H), 1.31-1.09 (m, 2H), 0.83 (d, J=6.5 Hz, 6H).

The compounds in the following table were prepared by the method of Example 109, using the appropriate commercially available aldehyde.

| Example No. | Structure | Mass [M + H]⁺ | ¹H NMR |
|---|---|---|---|
| 110 | 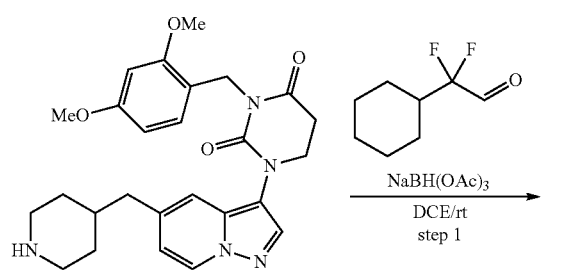

1-(5-((1-neopentylpiperidin-4-yl)methyl)pyrazolo[1,5-a]pyridin-3-yl)dihydropyrimidine-2,4(1H,3H)-dione | 398.4 | (400 MHz, DMSO-d6) δ 10.42 (s, 1H), 8.69-8.52 (m, 1H), 8.00 (d, J = 1.6 Hz, 1H), 7.36 (s, 1H), 6.78 (dd, J = 7.2, 1.8 Hz, 1H), 3.77 (dd, J = 7.5, 6.1 Hz, 2H), 3.47 (d, J = 12.3 Hz, 1H), 3.17 (s, 1H), 3.10-2.99 (m, 2H), 2.94 (d, J = 4.0 Hz, 2H), 2.79 (dd, J = 7.5, 6.0 Hz, 2H), 2.67 (d, J = 7.1 Hz, 1H, 2.61 (d, J = 6.5 Hz, 2H), 1.92 (d, J = 55.2 Hz, 1H), 1.81-1.48 (m, 4H), 1.03 (d, J = 1.3 Hz, 9H). |
| 111 | 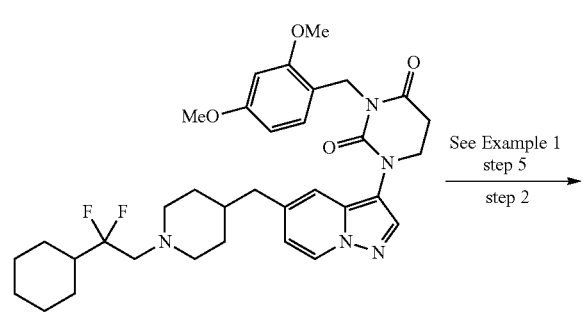

1-(5-((1-(pyridin-2ylmethyl)piperidin-4-yl)methyl)pyrazolo[1,5-a]pyridin-3-yl)dihydropyrimidine-2,4(1H,3H)-dione | 419.4 | (500 MHz, DMSO-d6) δ 10.43 (s, 1H), 8.68 (dd, J = 4.9, 1.7 Hz, 1H), 8.58 (d, J = 7.1 Hz, 1H, 8.00 (s, 1H), 7.93 (td, J = 7.7, 1.8 Hz, 1H), 7.59-7.44 (m, 2H), 7.37 (s, 1H), 6.79 (dd, J = 7.2, 1.9 Hz, 1H), 4.45 (s, 2H), 3.76 (t, J = 6.7 Hz, 2H), 3.40 (d, J = 13.0 Hz, 2H), 3.03 (t, J = 12.5 Hz, 2H), 2.78 (t, J = 6.7 Hz, 2H), 2.62 (d, J = 6.9 Hz, 2H), 2.00-1.73 (m, 3H), 1.64-1.44 (m, 2H). |

Example 112. Preparation of 1-(5-((1-(2-cyclohexyl-2,2-difluoroethyl)piperidin-4-yl)methyl)pyrazolo[1,5-a]pyridin-3-yl)dihydropyrimidine-2,4(1H,3H)-dione

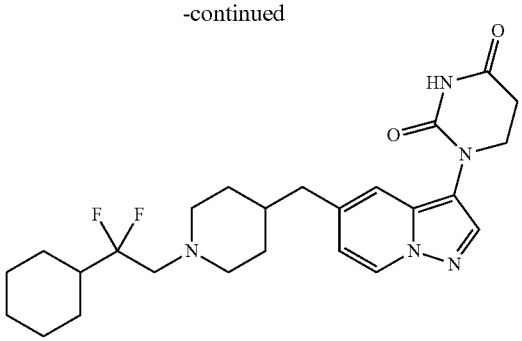

Example 112

Step 1. 1-(5-((1-(2-cyclohexyl-2,2-difluoroethyl)piperidin-4-yl)methyl)pyrazolo[1,5-a]pyridin-3-yl)-3-(2,4-dimethoxybenzyl)dihydropyrimidine-2,4(1H,3H)-dione To a solution of 3-(2,4-dimethoxybenzyl)-1-(5-(piperidin-4-ylmethyl)pyrazolo[1,5-a]pyridin-3-yl)dihydropyrimidine-2,4(1H,3H)-dione (200 mg, 0.419 mmol) and 2-cyclohexyl-2,2-difluoroacetaldehyde (1.36 g, 8.38 mmol) [see Org. Lett. 2009, 11, 943-946] in DCE (2 mL) was added NaBH(OAc)₃ (133 mg, 0.628 mmol) at rt, then the mixture was stirred for 16 h. The reaction mixture was diluted with water and then extracted with ethyl acetate. The organic layer was dried over Na₂SO₄, filtered and concentrated to give the crude product. The crude product was purified by prep-HPLC (column: Waters Xbridge C18 150×25 mm×10 μm; mobile phase: [water (0.225% FA)-ACN]; B %: 24%-54%, 10 min), the eluent was concentrated to remove MeCN and lyophilized to give 1-(5-((1-(2-cyclohexyl-2,2-difluoroethyl)

piperidin-4-yl)methyl)pyrazolo[1,5-a]pyridin-3-yl)-3-(2,4-dimethoxybenzyl)dihydropyrimidine-2,4(1H,3H)-dione (100 mg, 0.16 mmol, 38% yield) as a yellow solid. LCMS [M+H]⁺: 624.6.

Step 2: 1-(5-((1-(2-cyclohexyl-2,2-difluoroethyl)piperidin-4-yl)methyl)pyrazolo[1,5-a]pyridin-3-yl)dihydropyrimidine-2,4(1H,3H)-dione (Example 1112) was prepared from 1-(5-((1-(2-cyclohexyl-2,2-difluoroethyl)piperidin-4-yl)methyl)pyrazolo[1,5-a]pyridin-3-yl)-3-(2,4-dimethoxybenzyl)dihydropyrimidine-2,4(1H,3H)-dione using the method of Example 1, step 5, wherein 1-(5-((1-(2-cyclohexyl-2,2-difluoroethyl)piperidin-4-yl)methyl)pyrazolo[1,5-a]pyridin-3-yl)-3-(2,4-dimethoxybenzyl)dihydropyrimidine-2,4(1H,3H)-dione was used in place of 1-(5-((1-(cyclohexylmethyl)piperidin-4-yl)methyl)pyrazolo[1,5-a]pyridin-3-yl)-3-(2,4-dimethoxybenzyl)dihydropyrimidine-2,4(1H,3H)-dione. LCMS [M+H]⁺: 474.3. ¹H NMR (400 MHz, DMSO-d6) δ 10.41 (s, 1H), 8.53 (d, J=6.8 Hz, 1H), 7.97 (s, 1H), 7.34 (s, 1H), 6.77-6.75 (m, 1H), 3.76-3.73 (m, 2H), 2.85-2.82 (m, 2H), 2.78-2.75 (m, 2H), 2.70-2.59 (m, 2H), 2.55-2.52 (m, 2H), 2.08-2.07 (m, 2H), 1.99-1.85 (m, 1H), 1.85-1.67 (m, 4H), 1.64-1.61 (m, 1H), 1.55-1.52 (m, 3H), 1.27-1.05 (m, 7H).

The compounds in the following table were prepared by the method of Example 112, using the appropriate commercially available aldehyde and TEA or DIPEA (2 equiv) in step 1.

| Example No. | Structure | Mass [M + H]⁺ | ¹H NMR |
|---|---|---|---|
| 113 | 1-(5-((1-(((2R,6S)-2,6-dumethyltetrahydro-2H-pyran-4-yl)methyl)piperidin-4-yl)methyl)pyrazolo[1,5-a]pyridin-3-yl)dihydropyrimidine-2,4(1H,3H)-dione | 454.3 | (300 MHz, Methanol-d4) 8.39 (d, J = 7.2 Hz, 1H), 8.31 (s, 1H), 7.96 (s, 1H), 7.34 (s, 1H), 6.79 (d, J = 7.2 Hz, 1H), 3.84 (t, J = 6.8 Hz, 2H), 3.68-3.38 (m, 4H), 3.33-3.19 (m, 1H), 2.98-2.79 (m, 5H), 2.65 (d, J = 6.7 Hz, 2H), 2.47-2.03 (m, 1H), 2.02-1.81 (m, 3H), 1.77-1.33 (m, 5H), 1.14 (d, J = 6.4 Hz, 3H), 1.09 (d, J = 6.0 Hz, 2H), 0.86 (q, J = 11.8 Hz, 1H). NH protons not observed due to solvent exchange |
| 114 | 1-(5-((1-((1-methyl-1H-pyrazol-5-yl)methyl)piperidin-4-yl)methyl)pyrazolo[1,5-a]pyridin-3-yl)dihydropyrimidine-2,4(1H,3H)-dione | 422.2 | (400 MHz, CD₃OD): δ 8.44 (d, J = 7.2 Hz, 1H), 8.02 (s, 1H), 7.56 (s, 1H), 7.36 (s, 1H), 6.83 (d, J = 6.8 Hz, 1H), 6.56 (s, 1H), 4.47 (s, 2H), 3.95 (s, 3H), 3.89 (t, J = 6.8 Hz, 2H), 3.57-3.54 (m, 2H), 3.05 (m, 2H), 2.89 (t, J = 7.2 Hz, 2H), 2.71-2.69 (m, 2H), 2.01-1.97 (m, 3H), 1.53 (m, 2H) ppm. NH proton not observed due to solvent exchange |
| 115 | 1-(5-((1-(thiazol-4-ylmethyl)piperidin-4-yl)methyl)pyrazolo[1,5-a]pyridin-3-yl)dihydropyrimidine-2,4(1H,3H)-dione | 425.0 | (400 MHz, Methanol-d4) δ 9.09 (d, J = 2.0 Hz, 1H), 8.42 (d, J = 7.1 Hz, 1H), 8.36 (s, 1H), 8.00 (s, 1H), 7.80 (d, J = 2.0 Hz, 1H), 7.36 (s, 1H), 6.82 (dd, J = 7.6, 1.6 Hz, 1H), 4.38 (s, 2H), 3.88 (t, J = 6.8 Hz, 2H), 3.45 (d, J = 12.5 Hz, 2H), 2.98-2.85 (m, 4H), 2.69 (d, J = 6.7 Hz, 2H), 1.91 (d, J = 15.0 Hz, 3H), 1.54 (q, J = 13.1 Hz, 2H). NH protons not observed due to solvent exchange |

| Example No. | Structure | Mass [M + H]⁺ | ¹H NMR |
|---|---|---|---|
| 116 | 1-(5-((1-(((1-methyl-1H-imidazol-4-yl)methyl)piperidin-4-yl)methyl) pyrazolo[1,5-a]pyridin-3-yl)dihydropyrimidine-2,4(1H,3H)-dione | 422.2 | (400 MHz, Methanol-d4) δ 9.04 (s, 1H), 8.43 (d, J = 6.9 Hz, 1H), 8.06-8.01 (m, 1H), 7.83 (s, 1H), 7.39 (d, J = 6.5 Hz, 1H), 6.88-6.80 (m, 1H), 4.47 (s, 2H), 3.97 (s, 3H), 3.88 (t, J = 6.8 Hz, 2H), 3.56 (d, J = 11.9 Hz, 2H), 3.06 (t, J = 12.8 Hz, 2H), 2.89 (t, J = 6.8 Hz, 3H), 2.70 (d, J = 6.7 Hz, 2H). NH proton not observed due to solvent exchange. |
| 117 | 1-(5-((1-(((3r,5r,7r)-adamantan-1-yl)methyl)piperidin-4-yl)methyl) pyrazolo[1,5-a]pyridin-3-yl)dihydropyrimidine-2,4(1H,3H)-dione | 476.3 | (400 MHz, CD₃OD) δ 8.42.8.40 (m, 2H), 7.98 (s, 1H), 7.34 (s, 1H), 6.07 (d, J = 6.8 Hz, 1H), 3.86 (t, J = 7.2 Hz, 2H), 3.48.3.38 (brs, 2H), 3.15 (s, 2H), 2.88-2.84 (m, 4H), 2.69 (d, J = 6.8 Hz, 2H), 2.01-1.65 (s, 1H). Two protons not integrated due to peak broadening. NH proton not observed due to solvent exchange. |

Example 118. Preparation of 1-(5-((1-(((3-methyl-oxetan-3-yl)methyl)piperidin-4-yl)methyl)pyrazolo[1,5-a]pyridin-3-yl)dihydropyrimidine-2,4(1H,3H)-dione

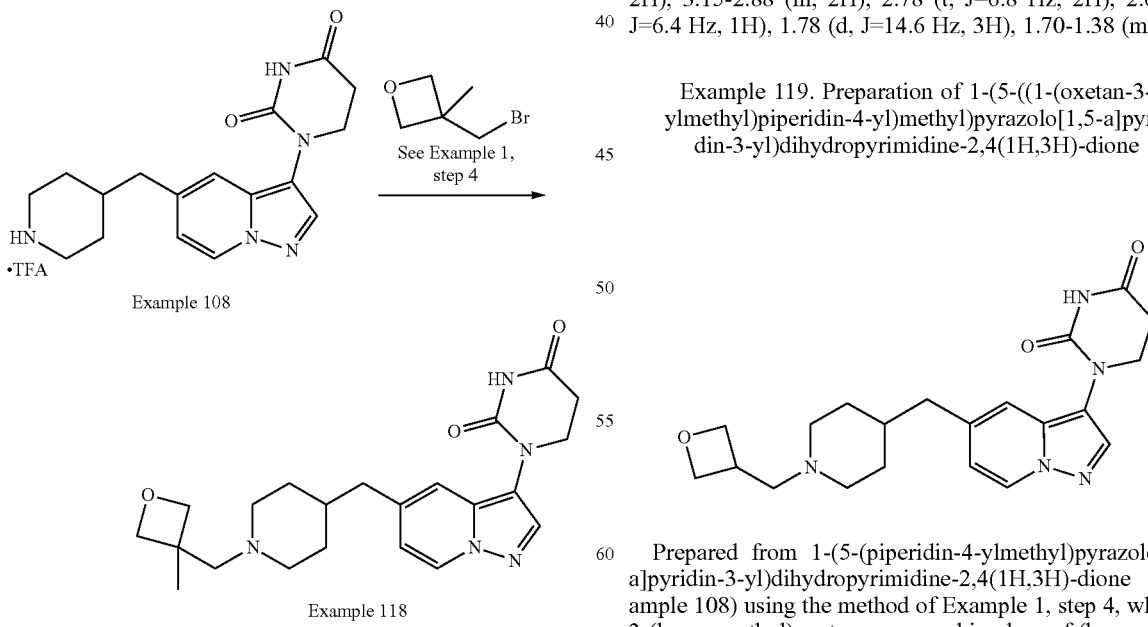

Example 118

Prepared from 1-(5-(piperidin-4-ylmethyl)pyrazolo[1,5-a]pyridin-3-yl)dihydropyrimidine-2,4(1H,3H)-dione (Example 108) using the method of Example 1, step 4, wherein 3-(bromomethyl)-3-methyloxetane was used in place of (bromomethyl)cyclohexane. LCMS [M+H]⁺: 412.3. ¹H NMR (400 MHz, DMSO-d6) δ 10.42 (s, 1H), 8.70-8.39 (m, 1H), 8.00 (d, J=1.9 Hz, 1H), 7.37 (s, 1H), 6.78 (dd, J=7.2, 2.0 Hz, 1H), 4.45 (d, J=6.2 Hz, 2H), 4.24-4.20 (m, 2H), 3.82-3.67 (m, 3H), 3.60-3.31 (m, 3H), 3.22 (d, J=12.2 Hz, 2H), 3.15-2.88 (m, 2H), 2.78 (t, J=6.8 Hz, 2H), 2.60 (d, J=6.4 Hz, 1H), 1.78 (d, J=14.6 Hz, 3H), 1.70-1.38 (m, 4H).

Example 119. Preparation of 1-(5-((1-(oxetan-3-ylmethyl)piperidin-4-yl)methyl)pyrazolo[1,5-a]pyridin-3-yl)dihydropyrimidine-2,4(1H,3H)-dione Prepared from 1-(5-(piperidin-4-ylmethyl)pyrazolo[1,5-a]pyridin-3-yl)dihydropyrimidine-2,4(1H,3H)-dione (Example 108) using the method of Example 1, step 4, wherein 3-(bromomethyl)oxetane was used in place of (bromomethyl)cyclohexane. LCMS [M+H]⁺: 398.4. ¹H NMR (500 MHz, Methanol-d4) δ 8.45 (d, J=7.2 Hz, 1H), 8.03 (d, J=1.8 Hz, 1H), 7.38 (s, 1H), 6.84 (d, J=7.2 Hz, 1H), 4.84 (d, J=7.1 Hz, 2H), 4.50 (t, J=6.0 Hz, 1H), 3.90 (t, J=6.7 Hz, 2H), 3.77-3.67 (m, 1H), 3.67-3.42 (m, 4H), 3.29-3.23 (m, 1H), 3.04-2.88 (m, 4H), 2.77-2.65 (m, 2H), 2.12-1.92 (m, 3H), 1.53 (t, J=14.3 Hz, 2H).

Example 120. Preparation of 1-(5-((1-(2-(1H-imidazol-4-yl)ethyl)piperidin-4-yl)methyl)pyrazolo[1,5-a]pyridin-3-yl)dihydropyrimidine-2,4(1H,3H)-dione

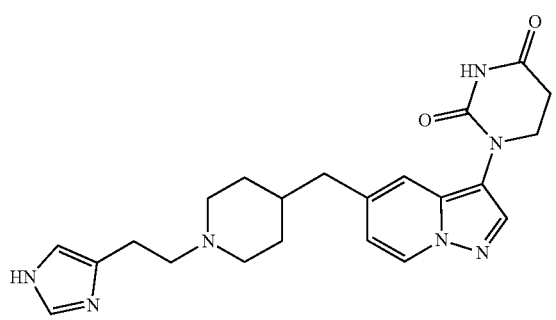 [SMILES: O=C1CCN(c2cnn3ccc(CC4CCN(CCc5c[nH]cn5)CC4)cc23)C(=O)N1]

Prepared from 1-(5-(piperidin-4-ylmethyl)pyrazolo[1,5-a]pyridin-3-yl)dihydropyrimidine-2,4(1H,3H)-dione (Example 108) using the method of Example 1, step 4, wherein 4-(2-chloroethyl)-1H-imidazole was used in place of (bromomethyl)cyclohexane and with the addition of KI (1.5 equiv). LCMS [M+H]$^+$: 422.4. $^1$H NMR (500 MHz, DMSO-d6) δ 10.43 (s, 1H), 9.73-9.28 (m, 1H), 9.02 (s, 1H), 8.59 (d, J=7.1 Hz, 1H), 8.00 (s, 1H), 7.53 (s, 1H), 7.37 (s, 1H), 6.79 (dd, J=7.1, 1.9 Hz, 1H), 3.76 (t, J=6.7 Hz, 2H), 3.56-3.43 (m, 2H), 3.39-3.29 (m, 2H), 3.10 (t, J=7.9 Hz, 2H), 3.02-2.87 (m, 2H), 2.78 (t, J=6.7 Hz, 2H), 2.65-2.56 (m, 2H), 1.96-1.77 (m, 3H), 1.52-1.38 (m, 2H).

Example 121. Preparation of 1-(5-((1-(3-hydroxy-2-(hydroxymethyl)propyl)piperidin-4-yl)methyl)pyrazolo[1,5-a]pyridin-3-yl)dihydropyrimidine-2,4(1H,3H)-dione

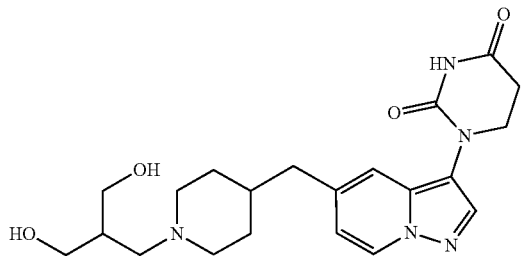 [SMILES: O=C1CCN(c2cnn3ccc(CC4CCN(CC(CO)CO)CC4)cc23)C(=O)N1]

Prepared from 1-(5-((1-(oxetan-3-ylmethyl)piperidin-4-yl)methyl)pyrazolo[1,5-a]pyridin-3-yl)dihydropyrimidine-2,4(1H,3H)-dione (Example 119) using the method of Example 1, step 5, wherein 1-(5-((1-(oxetan-3-ylmethyl)piperidin-4-yl)methyl)pyrazolo[1,5-a]pyridin-3-yl)dihydropyrimidine-2,4(1H,3H)-dione was used in place of 1-(5-((1-(cyclohexylmethyl)piperidin-4-yl)methyl)pyrazolo[1,5-a]pyridin-3-yl)-3-(2,4-dimethoxybenzyl)dihydropyrimidine-2,4(1H,3H)-dione. LCMS [M+H]$^+$: 416.3. $^1$H NMR (500 MHz, Methanol-d4) δ 8.45 (d, J=7.2 Hz, 1H), 8.03 (d, J=1.6 Hz, 1H), 7.40 (d, J=11.5 Hz, 1H), 6.86 (dd, J=9.2, 7.1 Hz, 1H), 5.51 (d, J=1.5 Hz, 1H), 3.91 (t, J=6.6 Hz, 2H), 3.77-3.67 (m, 4H), 3.58 (dd, J=10.7, 7.6 Hz, 2H), 3.43-3.36 (m, 1H), 3.25 (d, J=6.8 Hz, 2H), 3.02-2.88 (m, 4H), 2.72 (d, J=6.8 Hz, 2H), 2.32 (s, 1H), 2.02 (t, J=18.4 Hz, 3H), 1.55 (q, J=13.2 Hz, 2H).

Example 122. Preparation of 1-(5-((1-(2-methoxybenzyl)piperidin-4-yl)methyl)pyrazolo[1,5-a]pyridin-3-yl)dihydropyrimidine-2,4(1H,3H)-dione

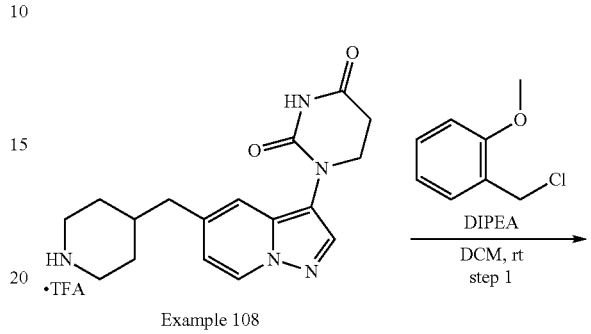

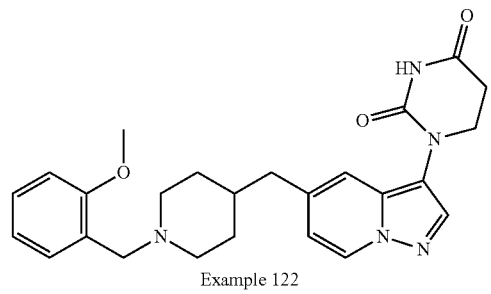

DIPEA (0.053 mL, 0.31 mmol) and 1-(chloromethyl)-2-methoxybenzene (11 mg, 0.073 mmol) were added to a solution of 1-(5-(piperidin-4-ylmethyl)pyrazolo[1,5-a]pyridin-3-yl)dihydropyrimidine-2,4(1H,3H)-dione (Example 108) (20 mg, 0.061 mmol) in DCM. The mixture was stirred at rt for 30 min. Additional 1-(chloromethyl)-2-methoxybenzene (11 mg, 0.073 mmol) and DIPEA (0.053 mL, 0.31 mmol) were added and the mixture was stirred for 2 h at rt. The reaction was then diluted with DCM and washed sequentially with water and brine. The organic layer was dried over sodium sulfate, filtered and concentrated. The residue was dissolved in DMSO, filtered through a 1 micron filter and purified by reverse phase HPLC using ACN/water/0.1% TFA. The fractions containing the product were combined, frozen and lyophilized to afford a TFA salt of 1-(5-((1-(2-methoxybenzyl)piperidin-4-yl)methyl)pyrazolo[1,5-a]pyridin-3-yl)dihydropyrimidine-2,4(1H,3H)-dione (2.3 mg, 0.0039 mmol, 6% yield). LCMS [M+H]$^+$: 448.2. $^1$H NMR (500 MHz, DMSO-d6) δ 10.45 (d, J=14.6 Hz, 1H), 8.60 (dd, J=12.9, 7.2 Hz, 1H), 8.01 (d, J=8.5 Hz, 1H), 7.54-7.42 (m, 2H), 7.42-7.33 (m, 1H), 7.14 (d, J=8.3 Hz, 1H), 7.05 (q, J=7.8 Hz, 1H), 6.78 (dd, J=7.2, 1.9 Hz, 1H), 4.22 (d, J=4.9 Hz, 2H), 3.84 (s, 3H), 3.77 (t, J=6.7 Hz, 2H), 3.36 (d, J=12.1 Hz, 2H), 2.95 (d, J=11.6 Hz, 2H), 2.78 (t, J=6.8 Hz, 2H), 2.59 (d, J=6.7 Hz, 2H), 1.95-1.70 (m, 3H), 1.44 (q, J=12.2, 11.0 Hz, 2H).

Example 123. Preparation of 1-(5-((1-(cyclohexyl-methyl)-4-fluoropiperidin-4-yl)methyl)pyrazolo[1,5-a]pyridin-3-yl)dihydropyrimidine-2,4(1H,3H)-dione

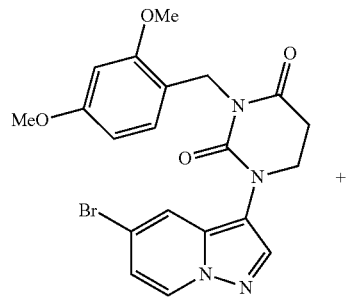

+

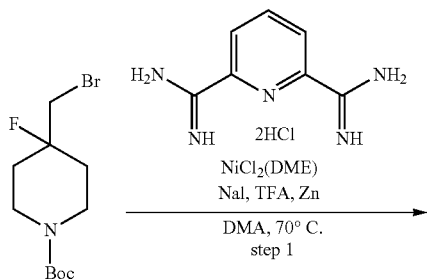

NiCl₂(DME)
NaI, TFA, Zn
DMA, 70° C.
step 1

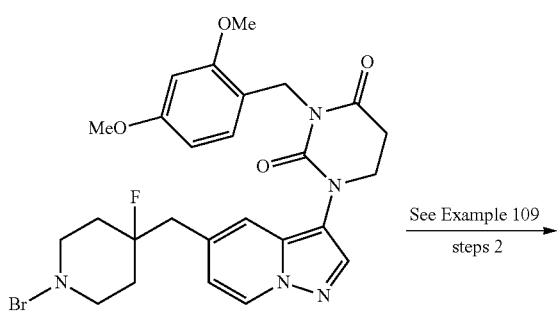

See Example 109
steps 2

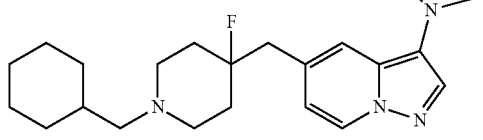

Example 123

Step 1. tert-butyl 4-((3-(3-(2,4-dimethoxybenzyl)-2,4-dioxotetrahydropyrimidin-1(2H)-yl)pyrazolo[1,5-a]pyridin-5-yl)methyl)-4-fluoropiperidine-1-carboxylate To an oven-dried vial was added tert-butyl 4-(bromomethyl)-4-fluoropiperidine-1-carboxylate (0.308 g, 1.04 mmol), 1-(5-bromopyrazolo[1,5-a]pyridin-3-yl)-3-(2,4-dimethoxybenzyl)dihydropyrimidine-2,4(1H,3H)-dione (0.367 g, 0.8 mmol), NiCl₂(DME) (8.8 mg, 0.040 mmol), pyridine-2,6-bis(carboximidamide) dihydrochloride (9.4 mg, 0.040 mmol), NaI (0.030 g, 0.20 mmol) and Zn (0.105 g, 1.60 mmol). The vial was sealed with a septum cap, evacuated and refilled with nitrogen 3 times. DMA (2.7 mL) and TFA (6 μl, 0.08 mmol) were added and the reaction was stirred at rt for 2 min. The vial was carefully evacuated and refilled with nitrogen 3 times to remove any H₂. The reaction was then heated overnight at 70° C., forming a brown reaction mixture. The reaction was cooled to rt, diluted with EtOAc and filtered through a plug of silica gel, eluting with EtOAc. The eluent was concentrated and the residue was purified by silica gel column chromatography (eluted with 0-100% EtOAc in heptane) to give tert-butyl 4-((3-(3-(2,4-dimethoxybenzyl)-2,4-dioxotetrahydro pyrimidin-1(2H)-yl) pyrazolo[1,5-a]pyridin-5-yl)methyl)-4-fluoropiperidine-1-carboxylate (0.47 g, 0.80 mmol, 98% yield, purity 70%). LCMS [M+H]⁺: 596.4. The product was used without further purification.

Step 2: 1-(5-((1-(cyclohexylmethyl)-4-fluoropiperidin-4-yl)methyl)pyrazolo[1,5-a]pyridin-3-yl)dihydropyrimidine-2,4(1H,3H)-dione was prepared from tert-butyl 4-((3-(3-(2,4-dimethoxybenzyl)-2,4-dioxotetrahydropyrimidin-1(2H)-yl)pyrazolo[1,5-a]pyridin-5-yl)methyl)-4-fluoropiperidine-1-carboxylate using the method of Example 109, wherein cyclohexanecarbaldehyde was used in place of isobutyraldehyde. LCMS [M+H]⁺: 442.2. ¹H NMR (400 MHz, DMSO-d6) δ 10.44 (s, 1H), 8.62 (dd, J=7.1, 0.9 Hz, 1H), 8.04 (d, J=1.9 Hz, 1H), 7.43 (d, J=30.9 Hz, 1H), 6.92-6.71 (m, 1H), 3.81-3.74 (m, 2H), 3.43 (d, J=12.2 Hz, 2H), 3.28-2.86 (m, 6H), 2.82-2.73 (m, 2H), 2.14-1.84 (m, 4H), 1.82-1.53 (m, 6H), 1.18 (dt, J=30.0, 12.3 Hz, 3H),1.01-0.84 (m, 2H).

Example 124. Preparation of 1-(5-((4-fluoro-1-isobutylpiperidin-4-yl)methyl)pyrazolo[1,5-a]pyridin-3-yl)dihydropyrimidine-2,4(1H,3H)-dione Prepared using the method of Example 123, wherein isobutyraldehyde was used in place of cyclohexanecarbaldehyde. LCMS [M+H]⁺: 402.4. ¹H NMR (400 MHz, DMSO-d6) δ 10.44 (s, 1H), 8.62 (d, J=7.0 Hz, 1H), 8.04 (d, J=1.9 Hz, 1H), 7.47 (s, 1H), 6.82 (d, J=7.3 Hz, 1H), 3.78 (t, J=6.8 Hz, 2H), 3.44 (d, J=12.5 Hz, 2H), 3.15-2.89 (m, 6H), 2.83-2.73 (m, 2H), 2.17-1.87 (m, 5H), 0.93 (dd, J=6.7, 2.0 Hz, 6H).

Example 125. Preparation of 1-(5-((1-(cyclobutylmethyl)-4-fluoropiperidin-4-yl)methyl)pyrazolo[1,5-a]pyridin-3-yl)dihydropyrimidine-2,4(1H,3H)-dione

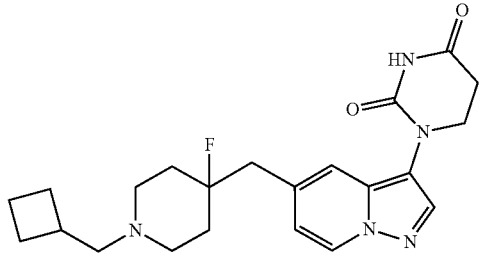 [SMILES: O=C1CCN(c2cnn3ccc(CC4(F)CCN(CC5CCC5)CC4)cc23)C(=O)N1]

Prepared using the method of Example 123, wherein cyclobutanecarbaldehyde was used in place of cyclohexanecarbaldehyde. LCMS [M+H]+: 402.4. ¹H NMR (400 MHz, DMSO-d6) δ 10.44 (s, 1H), 8.61 (dd, J=7.2, 1.0 Hz, 1H), 8.04 (s, 1H), 7.46 (d, J=1.6 Hz, 1H), 6.93-6.73 (m, 1H), 3.78 (t, J=6.7 Hz, 2H), 3.34 (d, J=12.3 Hz, 2H), 3.23-2.93 (m, 6H), 2.79 (t, J=6.8 Hz, 2H), 2.67 (p, J=7.3, 6.9 Hz, 1H), 2.15-1.92 (m, 5H), 1.91-1.71 (m, 5H).

Example 126. Preparation of 1-(5-((1-benzyl-4-fluoropiperidin-4-yl)methyl)pyrazolo[1,5-a]pyridin-3-yl)dihydropyrimidine-2,4(1H,3H)-dione

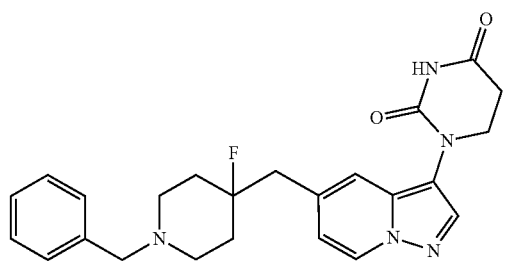 [SMILES: O=C1CCN(c2cnn3ccc(CC4(F)CCN(Cc5ccccc5)CC4)cc23)C(=O)N1]

Prepared from tert-butyl 4-((3-(3-(2,4-dimethoxybenzyl)-2,4-dioxotetrahydropyrimidin-1(2H)-yl)pyrazolo[1,5-a]pyridin-5-yl)methyl)-4-fluoropiperidine-1-carboxylate using the method of Example 1, steps 3 to 5, wherein benzyl bromide was used in place of (bromomethyl)cyclohexane. LCMS [M+H]+: 436.2. ¹H NMR (500 MHz, DMSO-d6) δ 10.44 (s, 1H), 8.61 (d, J=7.1 Hz, 1H), 8.03 (s, 1H), 7.46 (d, J=16.6 Hz, 6H), 6.80 (d, J=7.3 Hz, 1H), 4.34 (d, J=5.1 Hz, 2H), 3.77 (t, J=6.6 Hz, 2H), 3.21-3.01 (m, 6H), 2.77 (t, J=6.7 Hz, 2H), 2.64 (s, 1H), 2.07-1.80 (m, 3H).

Example 127. Preparation of 1-(5-((1-(cyclohexylmethyl)piperidin-4-yl)methyl)-4-methylpyrazolo[1,5-a]pyridin-3-yl)dihydropyrimidine-2,4(1H,3H)-dione

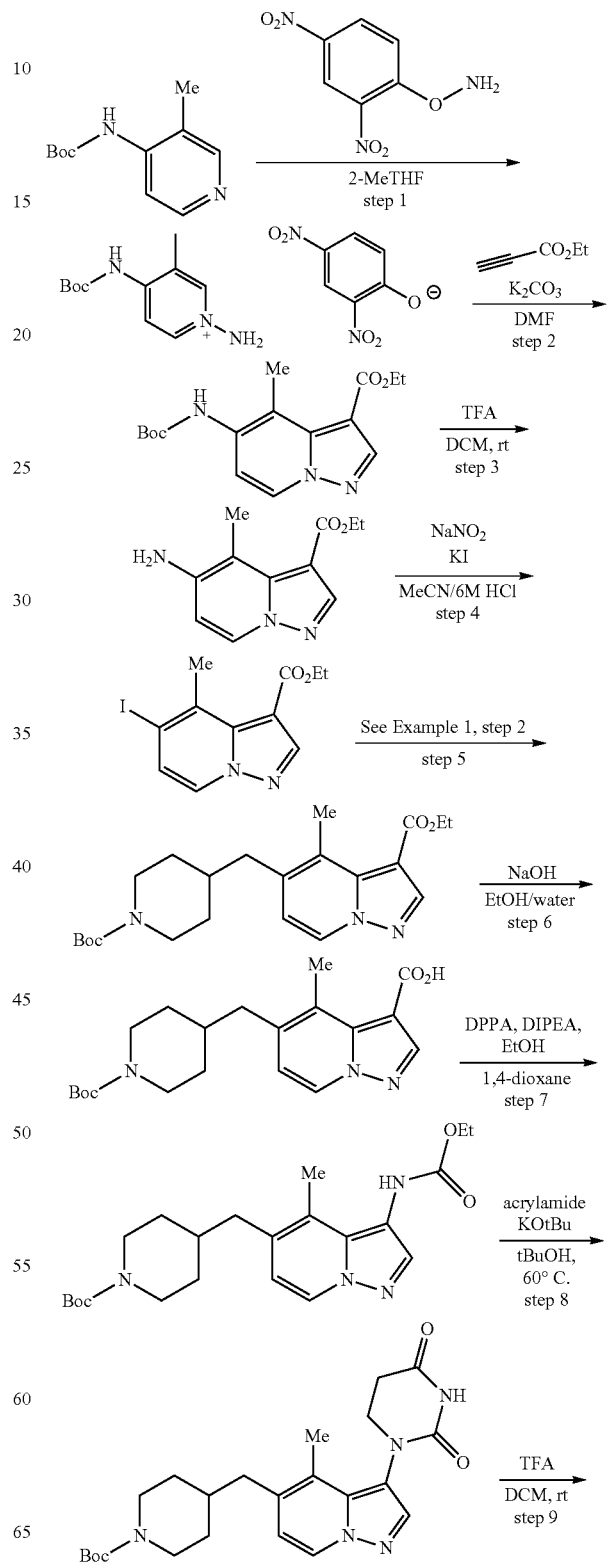

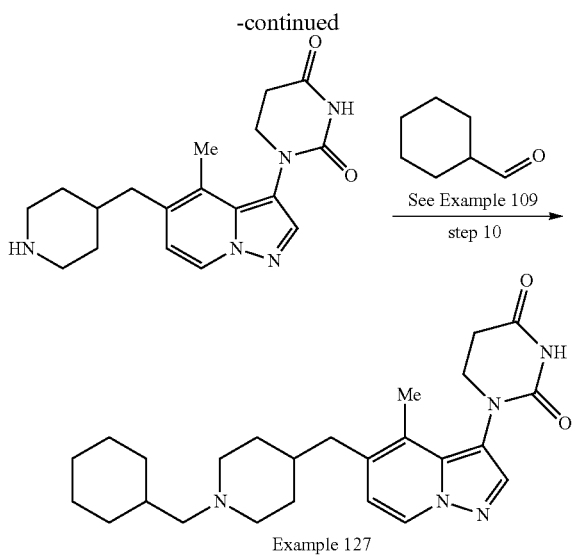

Example 127

Step 1. 1-amino-4-((tert-butoxycarbonyl)amino)-3-methylpyridin-1-ium 2,4-dinitrophenolate tert-Butyl (3-methylpyridin-4-yl)carbamate (2.447 g, 10.0 mmol) and O-(2,4-dinitrophenyl)hydroxylamine (2.19 g, 11.0 mmol) were added to a reaction flask. 2-MeTHF (20 mL) was added and the reaction was heated to at 40° C. for 1 h, then stirred at rt overnight. Additional O-(2,4-dinitrophenyl)hydroxylamine (600 mg, 3.00 mmol, 0.3 eq) was added and the reaction stirred for another 2 h at 40° C. The reaction was diluted with isopropanol and concentrated to give a yellow solid which was suspended in cold IPA, filtered and dried to give 1-amino-4-((tert-butoxycarbonyl)amino)-3-methylpyridin-1-ium 2,4-dinitrophenolate (5.5 g, crude) which was used without further purification. LCMS [M]+: 224.1.

Step 2. ethyl 5-((tert-butoxycarbonyl)amino)-4-methylpyrazolo[1,5-a]pyridine-3-carboxylate Potassium carbonate (5.60 g, 40.5 mmol) was added to a mixture of 1-amino-4-((tert-butoxycarbonyl)amino)-3-methylpyridin-1-ium 2,4-dinitrophenolate (5.5 g, 13.5 mmol) in DMF (13.5 mL) at 0° C. After 5 min, ethyl propiolate (1.50 mL, 14.8 mmol) was added and the reaction was stirred at 0° C. and allowed to warm to rt overnight. Two regioisomers were present by LCMS. The reaction was concentrated and the residue was suspended in water, filtered and the solid was purified by silica gel chromatography to give ethyl 5-((tert-butoxycarbonyl)amino)-4-methylpyrazolo[1,5-a]pyridine-3-carboxylate (849 mg, 2.66 mmol, 20% yield) as a single regiosiomer. LCMS [M+H]+: 320. $^1$H NMR (500 MHz, CDCl$_3$) δ 8.37 (d, J=1.8 Hz, 1H), 8.34 (d, J=7.6 Hz, 1H), 7.80 (d, J=7.6 Hz, 1H), 6.58 (s, 1H), 4.37-4.27 (m, 2H), 2.77 (d, J=1.8 Hz, 3H), 1.55 (d, J=1.7 Hz, 9H), 1.39 (td, J=7.1, 1.8 Hz, 3H).

Step 3. ethyl 5-amino-4-methylpyrazolo[1,5-a]pyridine-3-carboxylate

TFA (3.3 mL) was added to a solution of ethyl 5-((tert-butoxycarbonyl)amino)-4-methylpyrazolo[1,5-a]pyridine-3-carboxylate (850 mg, 2.66 mmol) in DCM (10 mL) at rt. The reaction was stirred at rt for 1 h and then concentrated. The residue was azeotropically dried with toluene to give ethyl 5-amino-4-methylpyrazolo[1,5-a]pyridine-3-carboxylate (850 mg, 2.66 mmol) as a light yellow solid. LCMS [M+H]+: 220.

Step 4. ethyl 5-iodo-4-methylpyrazolo[1,5-a]pyridine-3-carboxylate

A solution of sodium nitrite (37.9 mg, 0.550 mmol) in water (0.50 mL) was added dropwise to a suspension of ethyl 5-amino-4-methylpyrazolo[1,5-a]pyridine-3-carboxylate (167 mg, 0.5 mmol) in MeCN (0.83 mL) and aqueous 6 M HCl (2.5 mL) at 0° C. The reaction turned bright yellow and was stirred at 0° C. for 1 h. A solution of potassium iodide (166 mg, 1.00 mmol) in water (0.50 mL) was added dropwise to the vigorously stirring reaction; the reaction turned dark brown and bubbled and a precipitate formed. After 15 min, the reaction was diluted with water, filtered and the solid was washed with water. The solid was then dissolved in EtOH/DCM and concentrated. The solid was suspended in cold methanol, filtered and dried to give ethyl 5-iodo-4-methylpyrazolo[1,5-a]pyridine-3-carboxylate (141 mg, 0.427 mmol, 85% yield) as a light yellow solid. LCMS [M+H]+: 331.

Step 5. ethyl 5-((1-(tert-butoxycarbonyl)piperidin-4-yl)methyl)-4-methylpyrazolo[1,5-a]pyridine-3-carboxylate Prepared from ethyl 5-iodo-4-methylpyrazolo[1,5-a]pyridine-3-carboxylate by the method of Example 1, step 2, wherein ethyl 5-iodo-4-methylpyrazolo[1,5-a]pyridine-3-carboxylate was used in place of 1-(5-bromopyrazolo[1,5-a]pyridin-3-yl)-3-(2,4-dimethoxybenzyl)dihydropyrimidine-2,4(1H,3H)-dione. LCMS [M+H-tBu]+: 346.1.

Step 6. 5-((1-(tert-butoxycarbonyl)piperidin-4-yl)methyl)-4-methylpyrazolo[1,5-a]pyridine-3-carboxylic acid Sodium hydroxide (360 mg, 9.00 mmol) was added to a solution of ethyl 5-((1-(tert-butoxycarbonyl)piperidin-4-yl)methyl)-4-methylpyrazolo[1,5-a]pyridine-3-carboxylate (723 mg, 1.80 mmol) in EtOH (7.2 mL) and water (1.8 mL). The mixture was heated at 60° C. for 3 h, then cooled to rt and concentrated. The residue was dissolved in water, filtered and then aqueous 6 M HCl was added dropwise until the product precipitated. The supernatant was decanted and the solid was washed with water, dried and purified by silica gel chromatography (eluted with 0-50% of (1% AcOH in 3:1 EtOAc/EtOH) in heptane) to give 5-((1-(tert-butoxycarbonyl)piperidin-4-yl)methyl)-4-methylpyrazolo[1,5-a]pyridine-3-carboxylic acid (636 mg, 1.703 mmol, 95% yield) as an off-white solid. LCMS [M+H-tBu]+: 318.

Step 7. tert-butyl 4-((3-((ethoxycarbonyl)amino)-4-methylpyrazolo[1,5-a]pyridin-5-yl)methyl)piperidine-1-carboxylate DIPEA (675 µl, 3.86 mmol) was added to a solution of 5-((1-(tert-butoxycarbonyl)piperidin-4-yl)methyl)-4-methylpyrazolo[1,5-a]pyridine-3-carboxylic acid (481 mg, 1.29 mmol) in dioxane (4.3 mL) at rt. The bright yellow mixture was stirred at rt for 3 h, then EtOH (1.5 mL, 25.8 mmol) was added and the reaction was heated at 100° C. for 15 min. The reaction was cooled to rt, diluted with water and brine and extracted with EtOAc. The organic layer was dried over Na₂SO₄, filtered and concentrated. The residue was purified by silica gel chromatography (eluted with 0-60% EtOAc/heptane) to give tert-butyl 4-((3-((ethoxycarbonyl)amino)-4-methylpyrazolo[1,5-a]pyridin-5-yl)methyl)piperidine-1-carboxylate (479 mg, 1.150 mmol, 89% yield) as a colorless oil. LCMS [M+H-tBu]⁺: 361.

Step 8. tert-butyl 4-((3-(2,4-dioxotetrahydropyrimidin-1(2H)-yl)-4-methylpyrazolo[1,5-a]pyridin-5-yl)methyl)piperidine-1-carboxylate Acrylamide (14.2 mg, 0.200 mmol) and tert-butyl 4-((3-((ethoxycarbonyl)amino)-4-methylpyrazolo[1,5-a]pyridin-5-yl)methyl)piperidine-1-carboxylate (41.7 mg, 0.1 mmol) were added to a vial followed by tBuOH (0.5 mL) and potassium tert-butoxide (110 µl, 0.110 mmol) (1.0 M in THF)—the reaction turned light yellow. The mixture was heated at 60° C. overnight. The reaction was quenched with saturated aqueous NaHCO₃ and water. The mixture was extracted with EtOAC, dried over Na₂SO₄, filtered and concentrated to give crude tert-butyl 4-((3-(2,4-dioxotetrahydropyrimidin-1(2H)-yl)-4-methylpyrazolo[1,5-a]pyridin-5-yl)methyl)piperidine-1-carboxylate (39 mg, 0.088 mmol, 88% yield). LCMS [M+H-Boc]⁺: 342.

Step 9. 1-(4-methyl-5-(piperidin-4-ylmethyl)pyrazolo[1,5-a]pyridin-3-yl)dihydropyrimidine-2,4(1H,3H)-dione TFA (215 µl) was added to a solution of tert-butyl 4-((3-(2,4-dioxotetrahydropyrimidin-1(2H)-yl)-4-methylpyrazolo[1,5-a]pyridin-5-yl)methyl)piperidine-1-carboxylate (38 mg, 0.086 mmol) in DCM (645 µl) at rt. The reaction was stirred at rt for 30 min and was then concentrated to give crude 1-(4-methyl-5-(piperidin-4-ylmethyl)pyrazolo[1,5-a]pyridin-3-yl)dihydropyrimidine-2,4(1H,3H)-dione that was used without further purification. LCMS [M+H]: 342.

Step 10. 1-(5-((1-(cyclohexylmethyl)piperidin-4-yl)methyl)-4-methylpyrazolo[1,5-a]pyridin-3-yl)dihydropyrimidine-2,4(1H,3H)-dione Prepared from 1-(4-methyl-5-(piperidin-4-ylmethyl)pyrazolo[1,5-a]pyridin-3-yl)dihydropyrimidine-2,4(1H,3H)-dione by the method of Example 109, wherein cyclohexanecarbaldehyde was used in place of isobutyraldehyde. LCMS [M+H]⁺: 438.5. ¹H NMR (500 MHz, DMSO-d6) δ 10.45 (H, 1H), 8.60 (s, 1H), 8.44 (d, J=7.1 Hz, 1H), 7.98 (s, 1H), 6.73 (d, J=7.1 Hz, 1H), 3.79 (dt, J=13.3, 7.1 Hz, 1H), 3.65 (dt, J=12.6, 6.4 Hz, 2H), 2.88-2.80 (m, 3H), 2.76 (t, J=6.8 Hz, 2H), 2.68-2.59 (m, 2H), 2.35 (s, 3H), 1.86-1.58 (m, 10H), 1.53 (d, J=12.6 Hz, 2H), 1.33-1.07 (m, 4H), 0.92 (d, J=12.8 Hz, 2H).

The compounds in the following table were prepared by the method of Example 1, using tert-butyl 3-methylenepyrrolidine-1-carboxylate in step 2 and the appropriate commercially available halide in step 4.

| Example No. | Structure | Mass [M + H]⁺ | ¹H NMR |
|---|---|---|---|
| 128 | 1-(5-((1-(cyclohexylmethyl)pyrrolidin-3-yl)methyl)pyrazolo[1,5-a]pyridin-3-yl)dihydropyrimidine-2,4(1H,3H)-dione | 410.3 | (500 MHz, Methanol-d4) δ 8.35 (d, J = 7.2 Hz, 1H), 7.93 (s, 1H), 7.30 (d, J = 6.9 Hz, 1H, 6.75 (d, J = 7.2 Hz, 1H), 3.80 (t, J = 6.5 Hz, 2H), 3.73-3.42 (m, 2H), 2.95 (t, J = 7.2 Hz, 2H), 2.87-2.71 (m, 5H), 2.70-2.58 (m, 1H), 2.21-2.02 (m, 1H), 1.84 (q, J = 10.8, 9.0 Hz, 1H), 1.65 (dd, J = 35.6,13.5 Hz, 6H), 1.19 (ddd, J = 41.2, 25.5, 12.9 Hz, 4H), 0.93 (d, J = 12.3 Hz, 2H). |
| 129 | 1-(5-((1-(pyridin-3-ylmethyl)pyrrolidin-3-yl)methyl)pyrazolo[1,5-a]pyridin-3-yl)dihydropyrimidine-2,4(1H,3H)-dione | 405.3 | (500 MHz, DMSO-d6) δ 10.45 (d, J = 3.2 Hz, 1H), 8.73 (dd, J = 6.0, 2.1 Hz, 1H), 8.66 (d, J = 5.5 Hz, 1H), 8.60 (d, J = 7.2 Hz, 1H), 8.02 (d, J = 5.0 Hz, 1H), 7.96 (d, J = 7.9 Hz, 1H), 7.61-7.48 (m, 1H), 7.39 (d, J = 23.9 Hz, 1H), 6.81 (td, J = 5.1, 2.6 Hz, 1H), 4.45 (t, J = 5.1 Hz, 2H), 3.77 (q, J = 6.0 Hz, 2H), 3.58-3.25 (m, 3H), 3.16 (dd, J = 11.6, 6.1 Hz, 1H), 3.02-2.55 (m, 5H), 2.25-1.94 (m, 1H), 1.91-1.55 (m, 1H). |

-continued

| Example No. | Structure | Mass [M + H]⁺ | ¹H NMR |
|---|---|---|---|
| 130 | 1-(5-((1-(cyclobutylmethyl)pyrrolidin-3-yl)methyl)pyrazolo[1,5-a]pyridin-3-yl)dihydropyrimidine-2,4(1H,3H)-dione | 382.3 | (500 MHz, DMSO-d6) δ 10.45 (s, 1H), 8.60 (d, J = 7.1 Hz, 1H), 8.02 (s, 1H), 7.39 (d, J = 16.8 Hz, 1H), 6.82 (ddd, J = 6.5, 4.2, 1.7 Hz, 1H), 3.83-3.72 (m, 2H), 3.50 (dq, J = 14.3, 6.4 Hz, 2H), 3.19 (q, J = 7.0 Hz, 3H), 3.15-2.95 (m, 1H), 2.85-2.69 (m, 5H), 2.60 (tt, J = 19.8, 9.2 Hz, 1H), 2.18-1.95 (m, 3H), 1.89 (ddt, J = 12.3, 8.4, 3.6 Hz, 1H), 1.83-1.71 (m, 4H). |
| 131 | 1-(5-((1-(3-fluorobenzyl)pyrrolidin-3-yl)methyl)pyrazolo[1,5-a]pyridin-3-yl)dihydropyrimidine-2,4(1H,3H)-dione | 422.3 | (500 MHz, Methanol-d4) δ 8.34 (d, J = 7.1 Hz, 1H), 7.92 (s, 1H), 7.41 (q, J = 7.3 Hz, 1H, 7.30 (s, 1H), 7.21 (dd, J = 14.6, 8.6 Hz, 2H), 7.14 (t, J = 8.7 Hz, 1H), 6.74 (d, J = 7.2 Hz, 1H), 4.31 (s, 2H), 3.79 (t, J = 6.7 Hz, 2H), 3.45 (d, J = 26.2 Hz, 2H), 3.07 (s, 1H), 2.88 (t, J = 10.8 Hz, 1H), 2.79 (t, J = 6.7 Hz, 4H), 2.63 (s, 1H), 2.13 (d, J = 61.3 Hz, 1H), 1.93-1.56 (m, 1H). |
| 132 | 1-(5-((1-isobutylpyrrolidin-3-yl)methyl)pyrazolo[1,5-a]pyridin-3-yl)dihydropyrimidine-2,4(1H,3H)-dione | 370.3 | (500 MHz, DMSO-d6) δ 10.45 (s, 1H), 8.61 (d, J = 7.2 Hz, 1H), 8.02 (s, 1H), 7.39 (d, J = 13.4 Hz, 1H), 6.82 (ddd, J = 7.2, 3.7, 1.9 Hz, 1H), 3.78 (t, J = 6.7 Hz, 2H), 3.50 (m, 1H), 3.30-3.13 (m, 2H), 3.00 (dt, J = 9.8, 6.6 Hz, 2H), 2.88-2.71 (m, 5H), 2.61 (dd, J = 18.5, 9.7 Hz, 1H), 2.19-1.88 (m, 2H), 1.86-1.55 (m, 1H), 0.95 (dd, J = 6.6, 4.1 Hz, 6H). |

Example 133. Preparation of 1-(5-(azetidin-3-ylmethyl)pyrazolo[1,5-a]pyridin-3-yl)dihydropyrimidine-2,4(1H,3H)-dione

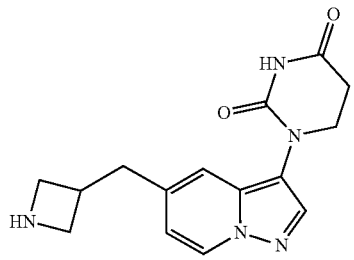 [SMILES: O=C1CCN(c2cnn3ccc(CC4CNC4)cc23)C(=O)N1]

Prepared using the method of Example 1, steps 2 and 5, wherein tert-butyl 3-methyleneazetidine-1-carboxylate was used in place of tert-butyl 4-methylenepiperidine-1-carboxylate. LCMS [M+H]+: 300.0. $^1$H NMR (300 MHz, CD$_3$OD) δ 8.53 (s, 1H), 8.44 (d, J=7.2 Hz, 1H), 8.01 (s, 1H), 7.37 (s, 1H), 6.82-6.79 (m, 1H), 4.09 (t, J=8.7 Hz, 2H), 3.92-3.86 (m, 4H), 3.34 (m, 1H), 3.03 (d, J=8.1 Hz, 2H), 2.88 (t, J=7.2 Hz, 2H).

Example 134. Preparation of 1-(5-((1-isobutylazetidin-3-yl)methyl)pyrazolo[1,5-a]pyridin-3-yl)dihydropyrimidine-2,4(1H,3H)-dione

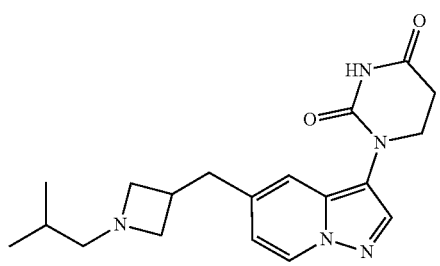 [SMILES: CC(C)CN1CC(Cc2ccn3ncc(N4CCC(=O)NC4=O)c3c2)C1]

Prepared from 1-(5-(azetidin-3-ylmethyl)pyrazolo[1,5-a]pyridin-3-yl)dihydropyrimidine-2,4(1H,3H)-dione (Example 133) using the method of Example 109, wherein 1-(5-(azetidin-3-ylmethyl)pyrazolo[1,5-a]pyridin-3-yl)dihydropyrimidine-2,4(1H,3H)-dione was used in place of 1-(5-(piperidin-4-ylmethyl)pyrazolo[1,5-a]pyridin-3-yl)dihydropyrimidine-2,4(1H,3H)-dione trifluoroacetate. LCMS [M+H]+: 356.3. $^1$H NMR (300 MHz, CD$_3$OD) δ 8.55 (s, 1H), 8.43 (d, J=7.2 Hz, 1H), 8.01 (s, 1H), 7.37 (s, 1H), 6.81-6.79 (m, 1H), 3.96-3.87 (m, 4H), 3.63-3.61 (m, 2H), 3.13-3.09 (m, 1H), 3.00 (d, J=8.0 HZ, 2H), 2.89 (d, J=7.2 Hz, 2H), 2.79 (d, J=6.8 Hz, 2H), 1.84-1.81 (m, 1H), 0.96 (d, J=6.8 Hz, 6H), NH proton not observed due to solvent exchange.

Example 135. Preparation of 1-(5-((1-(cyclohexylmethyl)azetidin-3-yl)methyl)pyrazolo[1,5-a]pyridin-3-yl)dihydropyrimidine-2,4(1H,3H)-dione

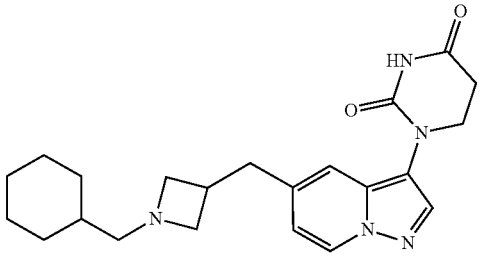 [SMILES: O=C1CCN(c2cnn3ccc(CC4CN(CC5CCCCC5)C4)cc23)C(=O)N1]

Prepared from 1-(5-(azetidin-3-ylmethyl)pyrazolo[1,5-a]pyridin-3-yl)dihydropyrimidine-2,4(1H,3H)-dione (Example 133) using the method of Example 109, wherein 1-(5-(azetidin-3-ylmethyl)pyrazolo[1,5-a]pyridin-3-yl)dihydropyrimidine-2,4(1H,3H)-dione was used in place of 1-(5-(piperidin-4-ylmethyl)pyrazolo[1,5-a]pyridin-3-yl)dihydropyrimidine-2,4(1H,3H)-dione trifluoroacetate and cyclohexanecarbaldehyde was used in place of isobutyraldehyde. LCMS [M+H]+: 396.1. $^1$H NMR (300 MHz, CD$_3$OD) δ 8.54 (s, 1H), 8.42 (d, J=7.2 Hz, 1H), 8.00 (s, 1H), 7.35 (s, 1H), 6.80-6.77 (m, 1H), 3.95-3.86 (m, 4H), 3.62-3.56 (m, 2H), 3.09-3.07 (m, 1H), 2.99-2.97 (m, 2H), 2.88 (d, J=6.6 Hz, 2H), 2.80-2.78 (m, 2H), 1.73-1.70 (m, 5H), 1.51 (s, 1H), 1.30-0.95 (m, 5H).

Example 136. Preparation of 1-(5-((1-(2-(tetrahydro-2H-pyran-4-yl)propan-2-yl)piperidin-4-yl)methyl)pyrazolo[1,5-a]pyridin-3-yl)dihydropyrimidine-2,4(1H,3H)-dione

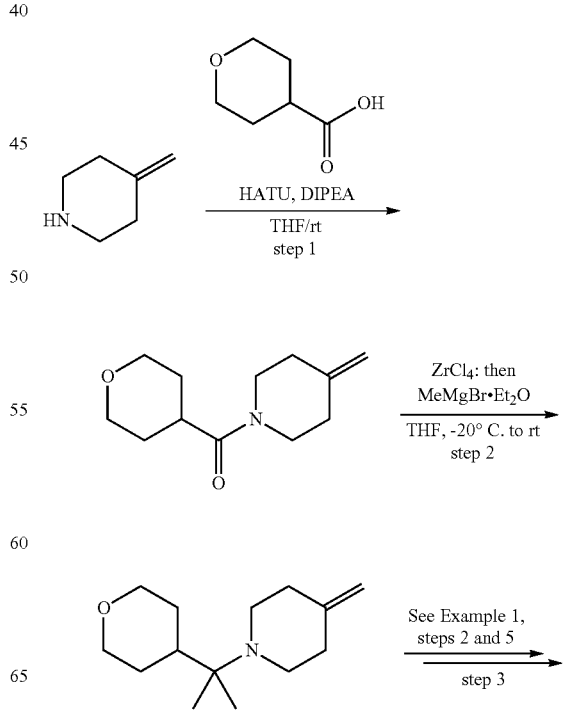

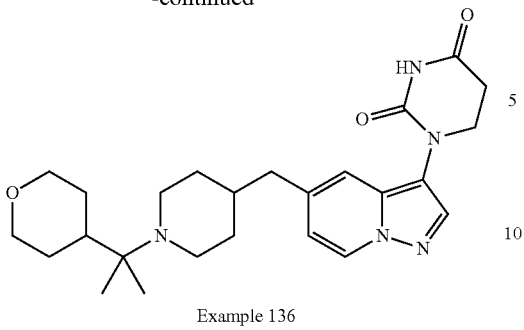

Example 136

Step 1. (4-methylenepiperidin-1-yl)(tetrahydro-2H-pyran-4-yl)methanone

To a stirred solution of tetrahydro-2H-pyran-4-carboxylic acid (4.0 g, 27.7 mmol) in THF (80 mL) was added HATU (15.81 g, 41.60 mmol), DIPEA (14.2 mL, 83.2 mmol) at 0° C. The mixture was stirred for 10 min followed by the addition of a solution of 4-methylenepiperidine (4.41 g, 33.3 mmol) in THF (20 mL). The reaction mixture was then stirred at rt for 12 h. The reaction was then quenched with water and extracted with EtOAc. The organic layer was washed with brine, dried over $Na_2SO_4$, filtered and concentrated. The crude material was purified by silica gel chromotography (eluting with 50% EtOAc in hexanes) to afford (4-methylenepiperidin-1-yl)(tetrahydro-2H-pyran-4-yl)methanone (3.8 g, 18.1 mmol, 59% yield). LCMS $[M+H]^+$: 210.0.

Step 2. 4-methylene-1-(2-(tetrahydro-2H-pyran-4-yl)propan-2-yl)piperidine

To a stirred solution of (4-methylenepiperidin-1-yl)(tetrahydro-2H-pyran-4-yl)methanone (1.0 g, 4.7 mmol) in THF (12 mL) was added $ZrCl_4$ (1.09 g, 4.7 mmol) at −20° C. and the mixture was stirred for 30 min. A solution of MeMgBr·Et$_2$O (9.4 mL, 28.2 mmol, 3.0 M) was added and the mixture was stirred for 10 min at −20° C. and then at rt for 2 h. After completion, the reaction was quenched with water (10 mL) and extracted with EtOAc. The organic layer was washed with brine, dried over $Na_2SO_4$, filtered and concentrated. The crude material was purified by silica gel chromotography (eluting with 50% EtOAc in hexanes) to afford 4-methylene-1-(2-(tetrahydro-2H-pyran-4-yl)propan-2-yl)piperidine (250 mg, 1.12 mmol, 24% yield). LCMS $[M+H]^+$: 224.0.

Step 3: 1-(5-((1-(2-(tetrahydro-2H-pyran-4-yl)propan-2-yl)piperidin-4-yl)methyl)pyrazolo[1,5-a]pyridin-3-yl)dihydropyrimidine-2,4(1H,3H)-dione was prepared from 4-methylene-1-(2-(tetrahydro-2H-pyran-4-yl)propan-2-yl)piperidine using the method of Example 1, steps 2 and 5, wherein was used in place of 4-methylene-1-(2-(tetrahydro-2H-pyran-4-yl)propan-2-yl)piperidine was used in place of tert-butyl 4-methylenepiperidine-1-carboxylate. LCMS $[M+H]^+$: 454.2. $^1$H NMR (400 MHz, DMSO-d6): δ 10.44 (s, 1H), 8.59 (d, J=7.2 Hz, 1H), 8.00 (s, 1H), 7.83 (s, 1H), 7.35 (s, 1H), 6.78 (d, J=6.8 Hz, 1H), 3.91-3.88 (m, 2H), 3.74 (t, J=6.8 Hz, 2H), 3.28 (s, 2H), 2.96-2.93 (m, 2H), 2.78 (t, J=6.4 Hz, 2H), 2.61-2.59 (m, 2H), 2.42 (brs, 1H), 2.02-1.80 (m, 5H), 1.58-1.48 (m, 4H), 1.35-1.28 (m, 2H), 1.20 (s, 6H).

Example 137. Preparation of 1-(5-((1-(2-methyl-1-(tetrahydro-2H-pyran-4-yl)propan-2-yl)piperidin-4-yl)methyl)pyrazolo[1,5-a]pyridin-3-yl)dihydropyrimidine-2,4(1H,3H)-dione

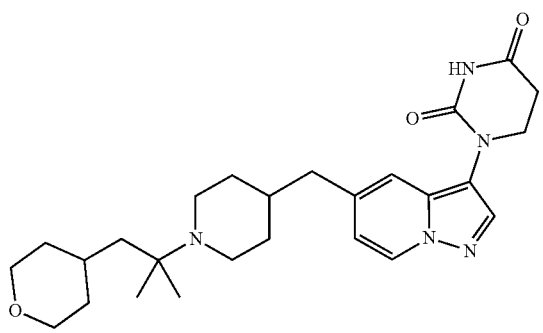 [SMILES: CC(C)(CC1CCOCC1)N1CCC(Cc2ccn3ncc(N4CCC(=O)NC4=O)c3c2)CC1]

Prepared using the method of Example 136, wherein 2-(tetrahydro-2H-pyran-4-yl)acetic acid was used in place of tetrahydro-2H-pyran-4-carboxylic acid. LCMS $[M+H]^+$: 468.3. $^1$H NMR (400 MHz, DMSO-d6) δ 10.44 (s, 1H), 8.60 (d, J=7.1 Hz, 1H), 8.28 (t, J=8.3 Hz, 1H), 8.00 (s, 1H), 7.36 (s, 1H), 6.78 (d, J=7.1 Hz, 1H), 3.84-3.72 (m, 4H), 3.47 (s, 1H), 3.29 (t, J=11.4 Hz, 2H), 2.90 (q, J=11.7 Hz, 2H), 2.78 (t, J=6.7 Hz, 2H), 2.61 (d, J=6.4 Hz, 2H), 1.92 (s, 2H), 1.85 (d, J=14.6 Hz, 2H), 1.68-1.52 (m, 5H), 1.46 (t, J=12.9 Hz, 2H), 1.38-1.13 (m, 3H), 1.30 (s, 6H).

Example 138. Preparation of 1-(5-((1-(2-cyclobutylpropan-2-yl)piperidin-4-yl)methyl)pyrazolo[1,5-a]pyridin-3-yl)dihydropyrimidine-2,4(1H,3H)-dione

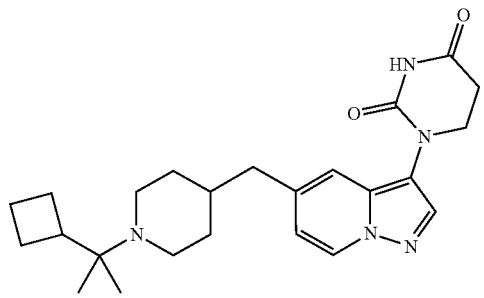 [SMILES: CC(C)(C1CCC1)N1CCC(Cc2ccn3ncc(N4CCC(=O)NC4=O)c3c2)CC1]

Prepared using the method of Example 136, wherein cyclobutanecarboxylic acids was used in place of tetrahydro-2H-pyran-4-carboxylic acid. LCMS $[M+H]^+$: 424.3. $^1$H NMR (400 MHz, Methanol-d4) δ 8.43 (d, J=7.2 Hz, 1H), 8.01 (s, 1H), 7.36 (s, 1H), 7.08 (s, 1H), 6.83 (dd, J=7.1, 1.9 Hz, 1H), 3.89 (t, J=6.8 Hz, 2H), 3.58-3.48 (m, 2H), 2.97-2.86 (m, 3H), 2.82-2.74 (m, 1H), 2.68 (d, J=6.7 Hz, 1H), 2.64 (d, J=5.9 Hz, 2H), 2.09-1.90 (m, 6H), 1.50-1.26 (m, 10H).

Example 139. Preparation of 1-(5-((1-(2,4-dimethylpentan-2-yl)piperidin-4-yl)methyl)pyrazolo[1,5-a]pyridin-3-yl)dihydropyrimidine-2,4(1H,3H)-dione

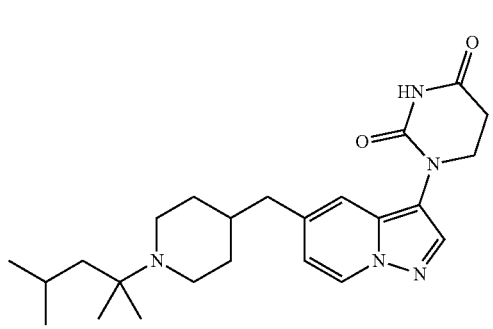 [SMILES: CC(C)CC(C)(C)N1CCC(Cc2ccn3ncc(N4CCC(=O)NC4=O)c3c2)CC1]

Prepared using the method of Example 136, wherein 3-methylbutanoic acid was used in place of tetrahydro-2H-pyran-4-carboxylic acid. LCMS [M+H]+: 426.3. 1H NMR (300 MHz, Methanol-d4) δ 8.53 (s, 1H), 8.43 (d, J=7.2 Hz, 1H), 8.01 (s, 1H), 7.38 (s, 1H), 6.84 (d, J=7.3 Hz, 1H), 3.89 (t, J=6.8 Hz, 2H), 3.71-3.48 (m, 3H), 2.97 (t, J=12.2 Hz, 2H), 2.89 (t, J=6.6 Hz, 3H), 2.69 (d, J=6.3 Hz, 2H), 2.00 (d, J=13.2 Hz, 3H), 1.75 (hept, J=6.3 Hz, 1H), 1.63 (d, J=5.4 Hz, 2H), 1.61-1.49 (m, 3H), 1.41 (s, 6H), 1.03 (d, J=6.6 Hz, 6H). NH proton not observed due to solvent exchange.

Example 140. Preparation of 1-(5-((1-(2-(4,4-difluorocyclohexyl)propan-2-yl)piperidin-4-yl)methyl)pyrazolo[1,5-a]pyridin-3-yl)dihydropyrimidine-2,4(1H,3H)-dione

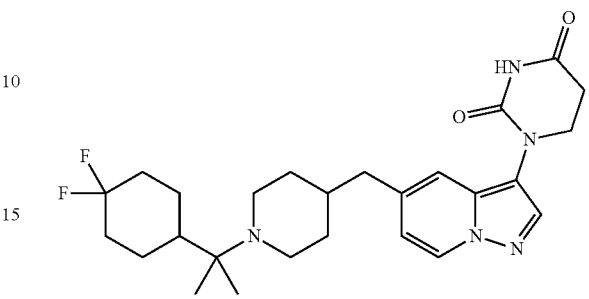

Prepared using the method of Example 136, wherein 4,4-difluorocyclohexane-1-carboxylic acid was used in place of tetrahydro-2H-pyran-4-carboxylic acid. LCMS [M+H]+: 488.4. 1H NMR (400 MHz, CD3OD): δ 8.43 (d, J=7.2 Hz, 1H), 8.00 (s, 1H), 7.35 (s, 1H), 6.82 (dd, J=7.6 Hz, 2.0 Hz, 1H), 3.87 (t, J=6.8 Hz, 2H), 3.59 (d, J=12.4 Hz, 2H), 3.06-2.98 (m, 2H), 2.87 (t, J=6.8 Hz, 2H), 2.70 (d, J=6.8 Hz, 2H), 2.08-2.10 (m, 2H), 2.01-1.75 (m, 8H), 1.64-1.46 (m, 4H), 1.33 (m, 6H). NH proton not observed due to solvent exchange.

Example 141. Preparation of 1-(5-(((2S,4R)-1-((4,4-difluorocyclohexyl)methyl)-2-methylpiperidin-4-yl)methyl)pyrazolo[1,5-a]pyridin-3-yl)dihydropyrimidine-2,4(1H,3H)-dione

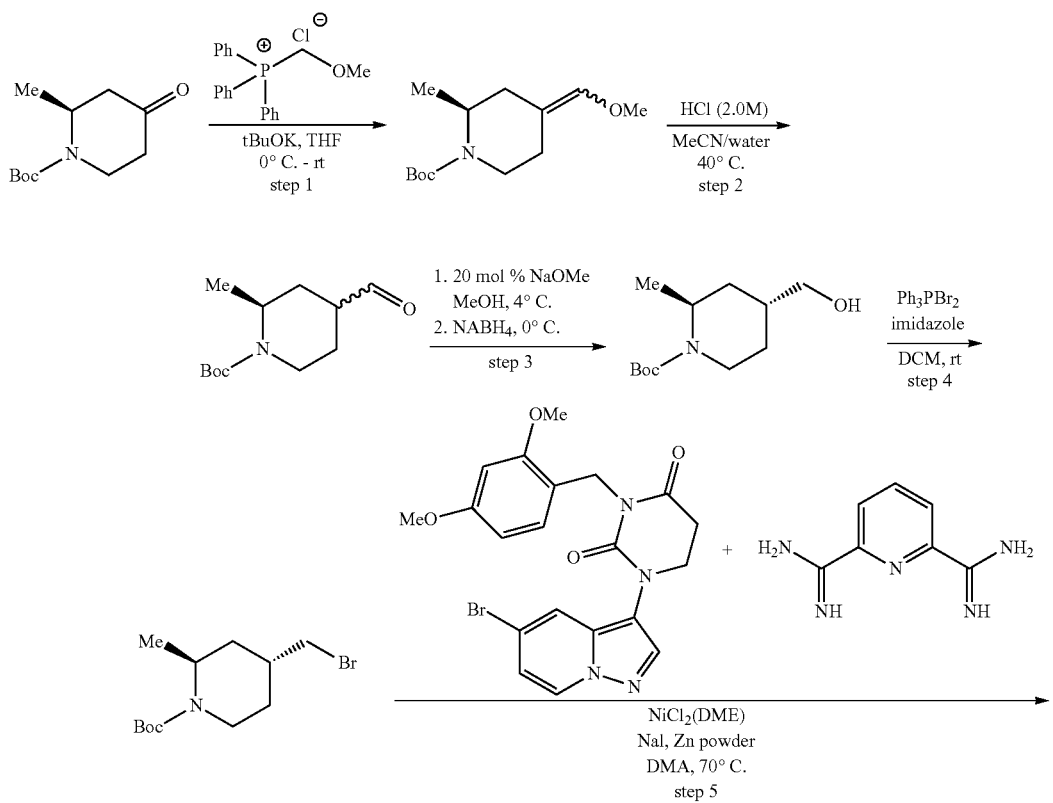

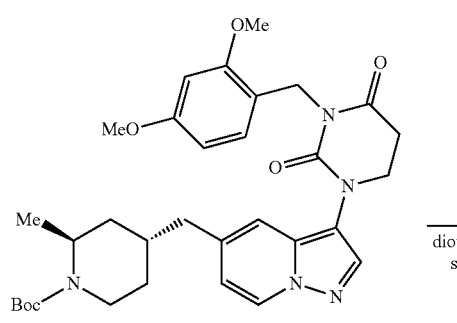
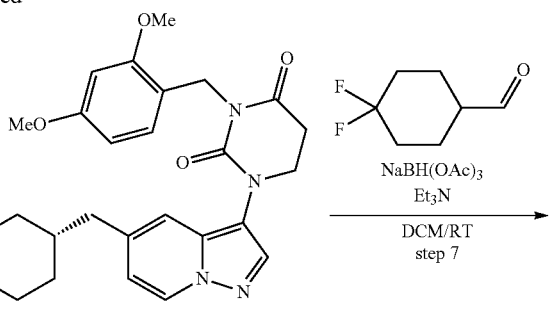
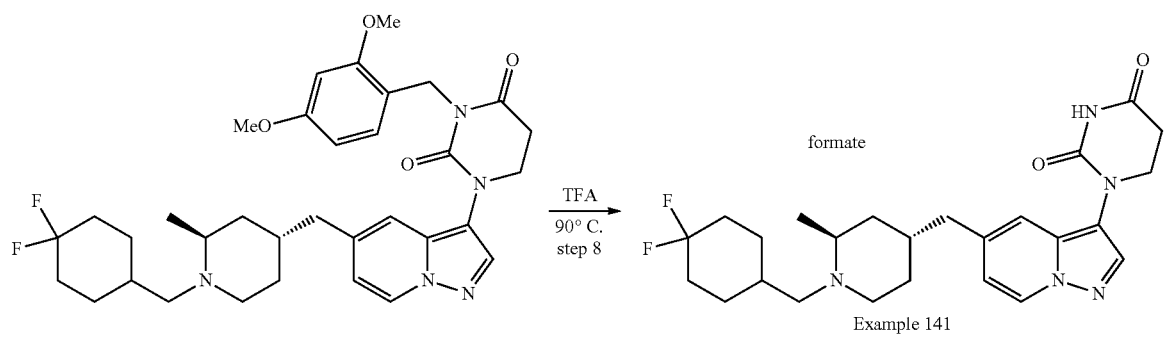

Example 141

Step 1. tert-butyl (S)-4-(methoxymethylene)-2-methylpiperidine-1-carboxylate A solution of KOtBu (63.78 mL, 63.78 mmol, 1M in THF) was added dropwise to a stirred suspension of (methoxymethyl)triphenylphosphonium chloride (21.86 g, 63.78 mmol) in THF (70 mL) at 0° C. The red solution was stirred for 30 min at rt and then cooled again to 0° C. A solution of tert-butyl (S)-2-methyl-4-oxopiperidine-1-carboxylate (8.0 g, 37.5 mmol) in THF (30 mL) was added and the reaction mixture was stirred at rt for 16 h. The reaction mixture was quenched with a solution of saturated aqueous NH$_4$Cl and extracted with EtOAc. The organic layer was washed with brine, dried over Na$_2$SO$_4$, filtered and concentrated. The crude material was purified by silica gel chromotography (eluting with 15-20% EtOAc in hexanes) to afford tert-butyl (S)-4-(methoxymethylene)-2-methylpiperidine-1-carboxylate (7.5 g, 31 mmol, 82% yield) as a mixture of E:Z isomers. LCMS [M+H-tBu]$^+$: 186. $^1$H NMR (300 MHz, CDCl$_3$) δ 5.96 (s, 1H), 5.78 (s, 1H), 4.46-4.39 (m, 2H), 4.00-3.89 (m, 2H), 3.56 (s, 3H), 3.53 (s, 3H), 2.86-2.74 (m, 2H), 2.62-2.47 (m, 2H), 2.31-2.24 (m, 1H), 2.02-1.94 (m, 4H), 1.90-1.81 (m, 3H), 1.46 (s, 18H) 1.04 (d, J=6.6 Hz, 3H).

Step 2. tert-butyl (2S)-4-formyl-2-methylpiperidine-1-carboxylate

A solution of HCl (2.0 M in water, 75 mL) was added to a solution of tert-butyl (S)-4-(methoxymethylene)-2-methylpiperidine-1-carboxylate (7.5 g, 31 mmol) in MeCN (220 mL) at rt. The reaction was heated to 40° C. and stirred for 40 min. The reaction was then cooled to rt and quenched by addition of solid NaHCO$_3$. Brine was added and the reaction was extracted with EtOAc 3 times. The combined organic layers were dried over Na$_2$SO$_4$, filtered and concentrated to give crude tert-butyl (2S)-4-formyl-2-methylpiperidine-1-carboxylate as a ~5:1 mixture of cis:trans isomers (7 g, 31 mmol). The crude material was used in the next reaction without further purification. LCMS [M+H-tBu]$^+$: 172.

Step 3. tert-butyl (2S,4R)-4-(hydroxymethyl)-2-methylpiperidine-1-carboxylate NaOMe (335 mg, 6.15 mmol) was added to a stirred solution of crude tert-butyl (2S)-4-formyl-2-methylpiperidine-1-carboxylate (7 g, 31 mmol) in MeOH (70 mL) at 0° C. The reaction mixture was kept at 4° C. for 24 h. After 24 h the reaction mixture was placed in an ice bath, NaBH$_4$ (4.65 g, 123 mmol) was added at 0° C. and the reaction was then stirred at rt for 10 min. The reaction mixture was quenched with water and extracted with EtOAc. The organic layer was washed with brine, dried over Na$_2$SO$_4$, filtered and concentrated. The crude material was purified by silica gel chromatography (eluted with 20% EtOAc in hexanes) to afford tert-butyl (2S,4R)-4-(hydroxymethyl)-2-methylpiperidine-1-carboxylate (5.4 g, 76% yield). LCMS [M+H-tBu]$^+$: 174. $^1$H NMR (400 MHz, CDCl$_3$) δ 4.45-4.41 (m, 1H), 3.99-3.94 (m, 1H), 3.38-3.35 (m, 2H), 2.90 (brs, 1H), 1.87-1.84 (m, 1H), 1.75-1.72 (m, 1H), 1.65-1.62 (m, 1H), 1.46 (s, 9H), 1.32-1.25 (m, 2H), 1.17 (d, J=6.4 Hz, 3H), 1.05-1.01 (s, 1H).

Step 4. tert-butyl (2S,4R)-4-(bromomethyl)-2-methylpiperidine-1-carboxylate

Triphenylphosphine dibromide (1.2 g, 28.5 mmol) was added to a solution of imidazole (2.10 g, 30.6 mmol) and tert-butyl (2S,4R)-4-(hydroxymethyl)-2-methylpiperidine-1-carboxylate (5.4 g, 23.5 mmol in DCM (50 mL) at 0° C. The reaction mixture was stirred at rt for 16 h. After completion of the reaction, the mixture was diluted with DCM and washed with water. The organic layer was washed with brine, dried over $Na_2SO_4$, filtered and concentrated. The crude material was purified by silica gel chromotography (eluted with 10% EtOAc in hexanes) to afford tert-butyl (2S,4R)-4-(bromomethyl)-2-methylpiperidine-1-carboxylate (3.5 g, 12.2 mmol, 50% yield). LCMS $[M+H-tBu]^+$: 236. $^1H$ NMR (300 MHz, $CDCl_3$) δ 4.45 (brs, 1H), 4.01 (brs, 1H), 3.30-3.20 (m, 2H), 2.88-2.80 (m, 1H), 2.04-1.94 (m, 1H), 1.85-1.81 (m, 1H), 1.70-1.65 (m, 1H), 1.29-1.03 (m, 15H).

Step 5. tert-butyl (2S,4R)-4-((3-(3-(2,4-dimethoxybenzyl)-2,4-dioxotetrahydropyrimidin-1(2H)-yl) pyrazolo[1,5-a]pyridin-5-yl)methyl)-2-methylpiperidine-1-carboxylate Zn powder was activated by taking commercial material and stirring it vigorously in a solution of aqueous 1M HCl for 10 min. The material was then filtered and the large chunks were broken up with a spatula. The solids were washed with distilled water, followed by EtOH, followed by $Et_2O$. The solids were then heated at 50° C. overnight under vacuum.

To an oven-dried 2-necked flask was added tert-butyl (2S,4R)-4-(bromomethyl)-2-methylpiperidine-1-carboxylate (2.98 g, 10.2 mmol), 1-(5-bromopyrazolo[1,5-a]pyridin-3-yl)-3-(2,4-dimethoxybenzyl)dihydropyrimidine-2,4(1H,3H)-dione (3.90 g, 8.5 mmol), $NiCl_2(DME)$ (0.093 g, 0.425 mmol), pyridine-2,6-bis(carboximidamide) dihydrochloride (0.100 g, 0.425 mmol), Zn powder (1.11 g, 17.0 mmol) and sodium iodide (0.319 g, 2.125 mmol). The flask was sealed with a septum and evacuated and refilled with argon 3 times. DMA (34.0 mL, degassed by bubbling argon through for several min) was added and the reaction was stirred at 70° C. overnight. The reaction was cooled to rt and poured into water and a grey precipitate formed which was collected by filtration. The solid was diluted with EtOH (200 mL) and filtered through celite (washed with EtOH) to remove Zn solids. The filtrate was concentrated and the crude material was purified by silica gel chromatography (eluted with 10-100% of (3:1 EtOAc/EtOH w/0.1% $Et_3N$)/heptane) to give tert-butyl (2S,4R)-4-((3-(3-(2,4-dimethoxybenzyl)-2,4-dioxotetrahydropyrimidin-1(2H)-yl)pyrazolo[1,5-a]pyridin-5-yl)methyl)-2-methylpiperidine-1-carboxylate (4.30 g, 6.69 mmol, 79% yield) as an off-white solid. LCMS $[M+H-Boc]^+$: 492.2.

Step 6. 3-(2,4-dimethoxybenzyl)-1-(5-(((2S,4R)-2-methylpiperidin-4-yl)methyl)pyrazolo[1,5-a]pyridin-3-yl)dihydropyrimidine-2,4(1H,3H)-dione hydrochloride A solution of HCl (4.0 M in dioxane, 40 mL) was added to tert-butyl (2S,4R)-4-((3-(3-(2,4-dimethoxybenzyl)-2,4-dioxotetrahydropyrimidin-1(2H)-yl)pyrazolo[1,5-a]pyridin-5-yl)methyl)-2-methylpiperidine-1-carboxylate (5.1 g, 8.61 mmol) and the mixture was stirred at rt for 3 h and then concentrated. The crude compound was triturated with diethyl ether to afford 3-(2,4-dimethoxybenzyl)-1-(5-(((2S,4R)-2-methylpiperidin-4-yl)methyl)pyrazolo[1,5-a]pyridin-3-yl)dihydropyrimidine-2,4(1H,3H)-dione hydrochloride (4.8 g, crude). LCMS $[M+H]^+$: 492.3.

Step 7. 1-(5-(((2S,4R)-1-((4,4-difluorocyclohexyl)methyl)-2-methylpiperidin-4-yl)methyl)pyrazolo[1,5-a]pyridin-3-yl)-3-(2,4-dimethoxybenzyl)dihydropyrimidine-2,4(1H,3H)-dione TEA (3.3 mL, 23.7 mmol) and 4,4-difluorocyclohexane-1-carbaldehyde (1.4 g, 9.48 mmol) were added to a solution of 3-(2,4-dimethoxybenzyl)-1-(5-(((2S,4R)-2-methylpiperidin-4-yl)methyl)pyrazolo[1,5-a]pyridin-3-yl)dihydropyrimidine-2,4(1H,3H)-dione hydrochloride (2.5 g, 4.74 mmol) in DCM (25 mL) at rt and the mixture was stirred for 1.5 h. The reaction was then cooled to 0° C. and sodium triacetoxyborohydride (2.00 g, 9.48 mmol) was added. The reaction mixture was stirred for 16 h at rt. After completion, the reaction was diluted with DCM and water and the organic layer was dried over $Na_2SO_4$, filtered and concentrated to afford crude 1-(5-(((2S,4R)-1-((4,4-difluorocyclohexyl)methyl)-2-methylpiperidin-4-yl)methyl)pyrazolo[1,5-a]pyridin-3-yl)-3-(2,4-dimethoxybenzyl) dihydropyrimidine-2,4(1H,3H)-dione (1.7 g, crude). LCMS $[M+H]^+$: 624.5.

Step 8. 1-(5-(((2S,4R)-1-((4,4-difluorocyclohexyl)methyl)-2-methylpiperidin-4-yl)methyl)pyrazolo[1,5-a]pyridin-3-yl)dihydropyrimidine-2,4(1H,3H)-dione TFA (3 mL) was added to crude 1-(5-(((2S,4R)-1-((4,4-difluorocyclohexyl)methyl)-2-methylpiperidin-4-yl)methyl)pyrazolo[1,5-a]pyridin-3-yl)-3-(2,4-dimethoxybenzyl)dihydropyrimidine-2,4(1H,3H)-dione. The reaction mixture was stirred for 16 h at 90° C. and then concentrated. The crude compound was purified by reverse-phase HPLC using: Mobile Phase: A=0.1% HCOOH in WATER, B=Acetonitrile, Column: X SELECT (250 mm×21.2 mm), 5.0 μm, Flow: 20 mL/min. The collected fractions were concentrated under reduced pressure to obtain the product as a formate salt. The product was dissolved in 20% MeOH in DCM, washed with a solution of saturated aqueous $NaHCO_3$ and concentrated to give 1-(5-(((2S,4R)-1-((4,4-difluorocyclohexyl)methyl)-2-methylpiperidin-4-yl)methyl)pyrazolo[1,5-a]pyridin-3-yl)dihydropyrimidine-2,4(1H,3H)-dione (554 mg, 1.05 mmol, 48% yield) as an off-white solid. HPLC: 98.40% [Rt=4.893 min]. LCMS $[M+H]^+$: 474.5. $^1H$ NMR (500 MHz, DMSO-d6) δ 10.42 (s, 1H), 8.54 (d, J=7.1 Hz, 1H), 7.98 (s, 1H), 7.34 (s, 1H), 6.78 (dd, J=7.3, 1.9 Hz, 1H), 3.76 (t, J=6.7 Hz, 2H), 2.91 (s, 1H), 2.79 (t, J=6.7 Hz, 2H), 2.53 (d, J=9.4 Hz, 2H), 2.45-2.34 (m, 2H), 2.27-2.12 (m, 2H), 2.04-1.92 (m, 2H), 1.92-1.85 (m, 1H), 1.85-1.67 (m, 4H), 1.60-1.47 (m, 2H), 1.47-1.35 (d, 2H), 1.24-1.14 (m, 1H), 1.13-1.00 (m, 2H), 0.88 (d, J=6.5 Hz, 3H).

The compounds in the following table were prepared by the method of Example 141, using the appropriate commercially available aldehyde in step 7.

| Example No. | Structure | Mass [M + H]+ | 1H NMR |
|---|---|---|---|
| 142 | 1-(5-(((2S,4R)-2-methyl-1-((tetrahydro-2H-pyran-4-yl)methyl) piperidin-4-yl)methyl)pyrazolo[1,5-a]pyridin-3-yl)dihydropyrimidine-2,4(1H,3H)-dione | 440.5 | (500 MHz, DMSO-d6) δ 10.42 (s, 1H), 8.54 (d, J = 7.1 Hz, 1H), 7.98 (s, 1H), 7.34 (s, 1H), 6.77 (dd, J = 7.2, 1.9 Hz, 1H), 3.82 (d, J = 11.3 Hz, 2H), 3.76 (t, J = 6.7 Hz, 2H), 3.26 (t, J = 11.5 Hz, 2H), 3.18 (d, J = 5.3 Hz, 1H), 2.91 (d, J = 6.2 Hz, 1H), 2.78 (t, J = 6.7 Hz, 2H), 2.54 (s, 1H), 2.46-2.33 (m, 2H), 2.19 (qd, J = 12.5, 6.9 Hz, 2H), 1.88 (s, 1H), 1.56 (dd, J = 44.9, 16.0 Hz, 4H), 1.47-1.35 (m, 2H), 1.25-1.14 (m, 1H), 1.14-1.00 (m, 2H), 0.88 (d, J = 6.5 Hz, 3H). |
| 143 | 1-(5-(((2S,4R)-1-(cyclohexylmethyl)-2-methylpiperidin-4-yl)methyl) pyrazolo[1,5-a]pyridin-3-yl)dihydropyrimidine-2,4(1H,3H)-dione | 438.3 | (400 MHz, METHANOL-d4) δ = 8.40 (d, J = 7.2 Hz, 1H), 7.98 (s, 1H), 7.33 (s, 1H), 6.81-6.79 (m, 1H), 3.89-3.86 (m, 2H), 3.04 (br d, J = 12.0 Hz, 1H), 2.89-2.87 (m, 2H), 2.66-2.56 (m, 3H), 2.20-1.84 (m, 4H), 1.75-1.44 (m, 8H), 1.37-1.11 (m, 5H), 1.10-1.03 (m, 3H), 0.99-0.81 (m, 2H) |
| 144 | 1-(5-(((2S,4R)-1-(cyclopentylmethyl)-2-methylpiperidin-4-yl)methyl) pyrazolo[1,5-a]pyridin-3-yl)dihydropyrimidine-2,4(1H,3H)-dione | 424.5 | (500 MHz, DMSO-d6) δ 10.41 (s, 1H), 8.52 (d, J = 7.1 Hz, 1H), 7.96 (s, 1H), 7.33 (s, 1H), 6.76 (d, J = 7.1 Hz, 1H), 3.75 (t, J = 6.7 Hz, 2H), 3.29 (s, 1H), 2.93 (s, 1H), 2.77 (t, J = 6.7 Hz, 2H), 2.50 (p, J = 1.8 Hz, 3H), 2.28-2.13 (m, 2H), 2.02-1.93 (m, 1H), 1.86 (s, 1H), 1.70-1.05 (m, 13H), 0.86 (d, J = 6.6 Hz, 3H). |
| 145 | 1-(5-(((2S,4R)-1-isobutyl-2-methylpiperidin-4-yl)methyl) pyrazolo[1,5-a]pyridin-3-yl)dihydropyrimidine-2,4(1H,3H)-dione | 398.4 | (500 MHz, Methanol-d4) δ 8.41 (d, J = 7.2 Hz, 1H), 7.99 (s, 1H), 7.35 (d, J = 1.8 Hz, 1H), 6.82 (dd, J = 7.2, 1.8 Hz, 1H), 3.89 (t, J = 6.8 Hz, 2H), 3.09-2.98 (m, 1H), 2.90 (t, J = 6.8 Hz, 2H), 2.64-2.60 (m, 2H), 2.59-2.51 (m, 2H), 2.30-2.18 (m, 2H), 2.05-1.95 (m, 1H), 1.82-1.72 (m, 1H), 1.68-1.61 (m, 1H), 1.59-1.50 (m, 2H), 1.43-1.33 (m, 1H), 0.99 (d, J = 6.6 Hz, 3H), 0.93 (d, J = 4.0 Hz, 3H), 0.92 (d, J = 4.1 Hz, 3H). |

| Example No. | Structure | Mass [M + H]+ | ¹H NMR |
|---|---|---|---|
| 146 | 1-(5-(((2S,4R)-1-(cyclobutylmethyl)-2-methylpiperidin-4-yl)methyl)pyrazolo[1,5-a]pyridin-3-yl)dihydropyrimidine-2,4(1H,3H)-dione | 410.5 | (400 MHz, DMSO-d6) δ 10.45 (d, J = 3.9 Hz, 1H), 8.58 (d, J = 7.1 Hz, 1H), 8.00 (d, J = 2.2 Hz, 1H), 7.35 (d, J = 5.1 Hz, 1H), 6.79 (d, J = 7.7 Hz, 1H), 3.76 (td, J = 6.8, 3.0 Hz, 2H), 3.54 (d, J = 47.4 Hz, 2H), 3.38-3.17 (m, 2H), 3.16-2.94 (m, 3H), 2.77 (t, J = 6.8 Hz, 2H), 2.73-2.59 (m, 2H), 2.18-1.98 (m, 3H), 1.95-1.53 (m, 7H), 1.25 (m, 3H). |
| 147 | 1-(5-(((2S,4R)-1-(cycloheptylmethyl)-2-methylpiperidin-4-yl)methyl)pyrazolo[1,5-a]pyridin-3-yl)dihydropyrimidine-2,4(1H,3H)-dione | 452.4 | (400 MHz, CD3OD) δ 8.43 (d, J = 6.8 Hz, 1H), 8.00 (s, 1H), 7.36 (s, 1H), 6.81 (dd, J = 7.2 Hz, 2.0 Hz, 1H), 3.89 (t, J = 6.4 Hz, 2H), 3.12 (bm, 2H), 2.90-2.68 (m, 5H), 2.20 (bm, 2H), 1.81-1.30 (m, 21H). NH proton not observed due to solvent exchange |
| 148 | 1-(5-(((2S,4R)-2-methyl-1-(2-(tetrahydro-2H-pyran-4-yl)ethyl)piperidin-4-yl)methyl)pyrazolo[1,5-a]pyridin-3-yl)dihydropyrimidine-2,4(1H,3H)-dione | 454.1 | (300 MHz, CD3OD) δ 8.49 (s, 1H), 8.43 (d, J = 7.2 Hz, 1H), 8.00 (s, 1H), 7.36 (s, 1H), 6.83 (d, J = 6.0 Hz, 1H), 3.93-3.86 (m, 4H), 3.60 (s, 1H), 3.46-3.36 (m, 3H), 3.23 (s, 2H), 3.08-3.04 (m, 3H), 2.88 (t, J = 6.6 Hz, 2H), 2.69-2.67 (m, 2H), 2.02-1.98 (s, 1H), 1.84-1.63 (m, 7H), 1.32-1.30 (m, 5H). |
| 149 | 1-(5-(((2S,4R)-1-((4,4-dimethylcyclohexyl)methyl)-2-methylpiperidin-4-yl)methyl)pyrazolo[1,5-a]pyridin-3-yl)dihydropyrimidine-2,4(1H,3H)-dione | 466.2 | (300 MHz, Methanol-d4) δ 8.43 (m, 2H), 8.01 (s, 1H), 7.36 (d, J = 1.8 Hz, 1H), 6.83 (dd, J = 7.2, 1.8 Hz, 1H), 3.88 (t, J = 6.8 Hz, 2H), 3.71 (s, 1H), 3.24 (m, 2H), 2.96 (s, 1H), 2.88 (t, J = 6.8 Hz, 2H), 2.69 (s, 2H), 2.22 (s, 1H), 1.73 (dd, J = 59.4, 16.0 Hz, 7H), 1.53-1.16 (m, 10H), 0.93 (d, J = 3.0 Hz, 6H). |

| Example No. | Structure | Mass [M + H]+ | 1H NMR |
|---|---|---|---|
| 150 | 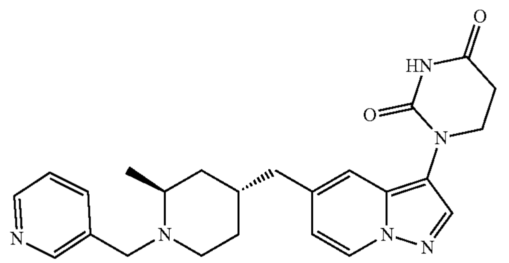 [SMILES: C[C@H]1C[C@H](Cc2ccn3ncc(N4CCC(=O)NC4=O)c3c2)CCN1Cc1cccnc1] | 433.0 | (300 MHz, CD3OD) δ 8.60 (s, 1H), 8.53-8.51 (m, 1H), 8.42-8.39 (m, 2H), 7.98 (s, 1H), 7.96-7.94 (m, 1H), 7.48-7.46 (m, 1H), 7.34 (s, 1H), 6.84 (d, J = 7.5 Hz, 1.3 Hz, 1H), 4.04-4.02 (m, 2H) 3.87 (t, J = 6.9 Hz, 2H), 2.91-2.85 (m, 4H), 2.67-2.65 (m, 3H), 2.18-2.16 (s, 2H), 1.71-1.69 (m, 3H), 1.28 (s, 3H). |

1-(5-(((2S,4R)-2-methyl-1-(pyridin-3-ylmethyl)piperidin-4-yl)methyl)pyrazolo[1,5-a]pyridin-3-yl)dihydropyrimidine-2,4(1H,3H)-dione Example 151. Preparation of 1-(5-((1-(((1r,4r)-4-hydroxycyclohexyl)methyl)piperidin-4-yl)methyl)pyrazolo[1,5-a]pyridin-3-yl)dihydropyrimidine-2,4(1H,3H)-dione Example 152. Preparation of 1-(5-(((2S,4R)-1-((3,3-difluorocyclobutyl)methyl)-2-methylpiperidin-4-yl)methyl)pyrazolo[1,5-a]pyridin-3-yl)dihydropyrimidine-2,4(1H,3H)-dione

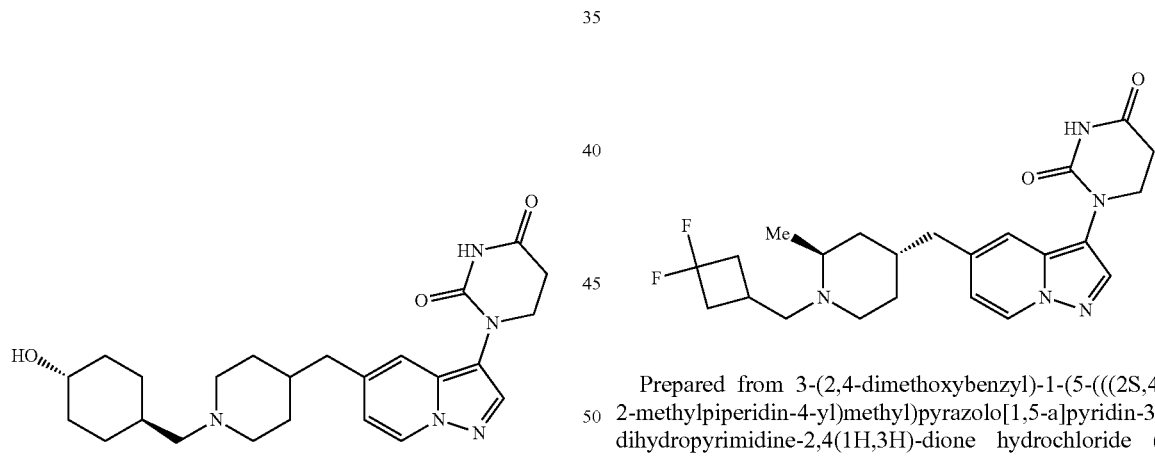

Prepared from 3-(2,4-dimethoxybenzyl)-1-(5-(((2S,4R)-2-methylpiperidin-4-yl)methyl)pyrazolo[1,5-a]pyridin-3-yl)dihydropyrimidine-2,4(1H,3H)-dione hydrochloride (see Example 141, step 6) using the method of Example 1, steps 4 to 5, wherein 3-(bromomethyl)-1,1-difluorocyclobutane was used in place of (bromomethyl)cyclohexane. LCMS [M+H]+: 446.3. 1H NMR (400 MHz, CD3OD) δ 8.51 (s, 1H), 8.43 (d, J=7.1 Hz, 1H), 8.00 (s, 1H), 7.36 (s, 1H), 6.83 (dd, J=7.2, 1.9 Hz, 1H), 3.89 (t, J=6.8 Hz, 2H), 3.48 (s, 1H), 3.08 (d, J=41.8 Hz, 3H), 2.89 (t, J=6.8 Hz, 2H), 2.76 (d, J=7.6 Hz, 2H), 2.68 (d, J=7.2 Hz, 2H), 2.43 (d, J=29.2 Hz, 3H), 2.18 (d, J=10.5 Hz, 1H), 1.90-1.62 (m, 3H), 1.51 (s, 1H), 1.37-1.17 (m, 4H). NH proton not observed due to solvent exchange.

Prepared using the method of Example 141, steps 7-8, wherein trans-4-(benzyloxy)cyclohexane-1-carbaldehyde [see WO2020/232470, 2020, A1] was used in place of 4,4-difluorocyclohexane-1-carbaldehyde. LCMS [M+H]+: 440.1. 1H NMR (400 MHz, CD3OD) δ 8.42 (s, 1H), 8.00 (s, 1H), 7.36 (s, 1H), 6.98 (d J=5.6 Hz, 1H), 3.87 (t, J=6.8 Hz, 2H), 3.56-3.48 (m, 2H), 2.93-2.85 (m, 6H), 2.68-2.65 (m, 2H), 1.97-1.80 (m, 7H), 1.58-1.55 (m, 2H), 1.29-1.27 (m, 4H), 1.11-1.08 (m, 2H), NH and OH protons not observed due to solvent exchange.

The compounds in the following table were prepared from tert-butyl (R)-2-methyl-4-oxopiperidine-1-carboxylate using the method of Example 141, wherein the appropriate commercially available aldehydes were used in step 7.

| Example No. | Structure | Mass [M + H]+ | 1H NMR |
|---|---|---|---|
| 153 | 1-(5-(((2R,4S)-1-isobutyl-2-methylpiperidin-4-yl)methyl)pyrazolo[1,5-a]pyridin-3-yl)dihydropyrimidine-2,4(1H,3H)-dione | 398.2 | (400 MHz, CD$_3$OD) δ 8.49 (s, 1H), 8.44 (d, J = 6.8 Hz, 1H), 7.98 (s, 1H), 7.35 (s, 1H), 6.81 (d, J = 6.0 Hz, 1H), 3.94-3.84 (m, 4H), 3.65 (s, 1H), 3.45-3.40 (m, 2H), 3.17 (s, 2H), 2.91-2.84 (m, 3H), 2.67-2.63 (m, 2H), 2.09 (s, 1H), 2.01 (s, 1H), 1.85-1.58 (m, 5H), 1.39-1.30 (m, 6H). |
| 154 | 1-(5-(((2R,4S)-2-methyl-1-((tetrahydro-2H-pyran-4-yl)methyl)piperidin-4-yl)methyl)pyrazolo[1,5-a]pyridin-3-yl)dihydropyrimidine-2,4(1H,3H)-dione | 440.1 | (400 MHz, CD$_3$OD) δ 8.51 (s, 1H), 8.41 (d, J = 7.2 Hz, 1H), 7.98 (s, 1H), 7.34 (s, 1H), 6.82-6.80 (m, 1H), 3.86 (t, J = 6.4 Hz, 2H), 3.68 (s, 1H), 3.19 (s, 2H), 2.88-2.84 (s, 4H), 2.68-2.66 (m, 2H), 2.19 (s, 1H), 2.08-2.02 (m, 1H) 1.86-1.72 (m, 4H), 1.64-1.60 (m, 2H), 1.33-1.27 (m, 3H, 1.04-1.00 (m, 6H). |
| 155 | 1-(5-(((2R,4S)-1-((4,4-difluorocyclohexyl)methyl)-2-methylpiperidin-4-yl)methyl)pyrazolo[1,5-a]pyridin-3-yl)dihydropyrimidine-2,4(1H,3H)-dione | 474.4 | (400 MHz, CD$_3$OD) δ 8.52 (s, 1H), 8.41 (d, J = 6.8 Hz, 1H), 7.99 (s, 1H), 7.34 (s, 1H), 6.83-6.81 (m, 1H), 3.87 (t, J = 7.2 Hz, 2H), 2.89-2.86 (m, 3H), 2.66-2.65 (m, 2H), 2.12-2.04 (m, 4H), 1.88-1.70 (m, 7H), 1.50 (brs, 2H), 1.20 (s, 3H). |

Example 156. Preparation of 1-(5-((4-(cyclohexylmethyl)piperazin-1-yl)methyl)pyrazolo[1,5-a]pyridin-3-yl)dihydropyrimidine-2,4(1H,3H)-dione -continued

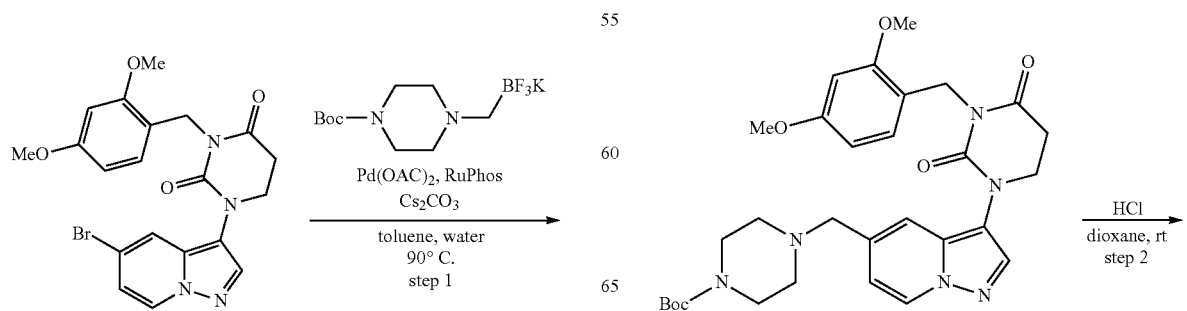

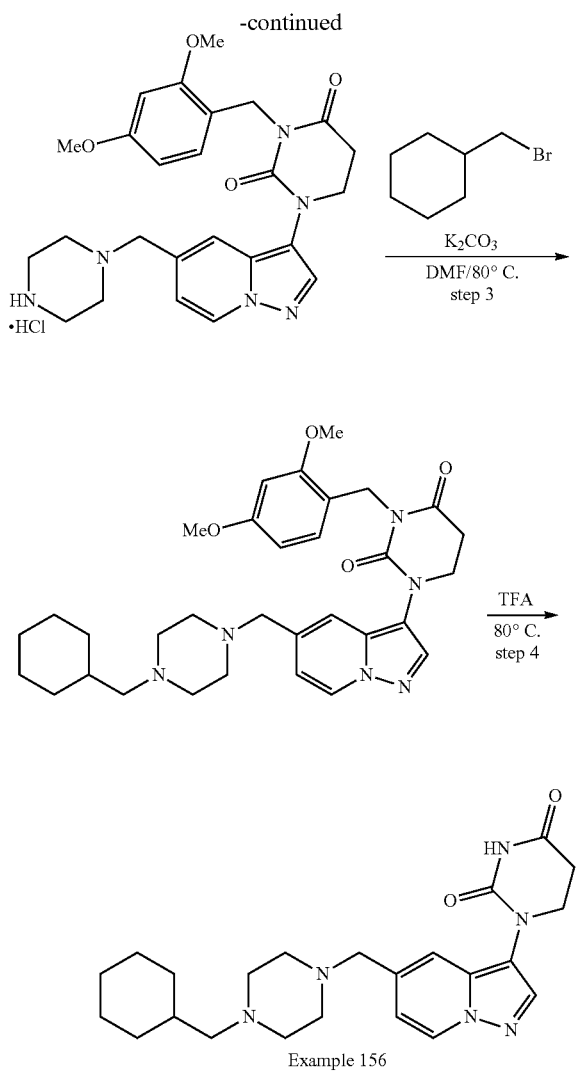

Example 156

Step 1: tert-butyl 4-((3-(3-(2,4-dimethoxybenzyl)-2,4-dioxotetrahydropyrimidin-1(2H)-yl)pyrazolo[1,5-a]pyridin-5-yl)methyl)piperazine-1-carboxylate To a suspension of 1-(5-bromopyrazolo[1,5-a]pyridin-3-yl)-3-(2,4-dimethoxybenzyl)dihydropyrimidine-2,4(1H,3H)-dione (45 mg, 0.098 mmol) in toluene (2 mL) and water (0.2 mL) at room temperature was added Cs$_2$CO$_3$ (128 mg, 0.392 mmol), potassium {[4-(tert-butoxycarbonyl)-1-piperazinyl]methyl}(trifluoro)borate (60.0 mg, 0.196 mmol) and RuPhos (9.14 mg, 0.020 mmol), followed by Pd(OAc)$_2$ (2.2 mg, 9.8 µmol). The mixture was stirred at 90° C. for 3 h, then cooled to rt and partitioned between EtOAc and water. The organic layer was separated, washed with brine, dried over sodium sulfate, filtered and concentrated to give crude tert-butyl 4-((3-(3-(2,4-dimethoxybenzyl)-2,4-dioxotetrahydropyrimidin-1(2H)-yl)pyrazolo[1,5-a]pyridin-5-yl)methyl)piperazine-1-carboxylate (56 mg, 0.098 mmol). LCMS [M+H]$^+$: 579.4. The crude material was used without further purification.

Step 2: 3-(2,4-dimethoxybenzyl)-1-(5-(piperazin-1-ylmethyl)pyrazolo[1,5-a]pyridin-3-yl)dihydropyrimidine-2,4(1H,3H)-dione hydrochloride A solution of HCl (4.0 M in dioxane, 2 mL, 8 mmol) was added to tert-butyl 4-((3-(3-(2,4-dimethoxybenzyl)-2,4-dioxotetrahydropyrimidin-1(2H)-yl)pyrazolo[1,5-a]pyridin-5-yl)methyl)piperazine-1-carboxylate (55 mg, 0.095 mmol) and the mixture was stirred for 2 h at rt. The reaction was then concentrated to give crude 3-(2,4-dimethoxybenzyl)-1-(5-(piperazin-1-ylmethyl)pyrazolo[1,5-a]pyridin-3-yl)dihydropyrimidine-2,4(1H,3H)-dione hydrochloride (46 mg, 0.095 mmol) which was used without further purification. LCMS [M+H]$^+$: 479.4.

Step 3: 1-(5-((4-(cyclohexylmethyl)piperazin-1-yl)methyl)pyrazolo[1,5-a]pyridin-3-yl)-3-(2,4-dimethoxybenzyl)dihydropyrimidine-2,4(1H,3H)-dione To a solution of 3-(2,4-dimethoxybenzyl)-1-(5-(piperazin-1-ylmethyl)pyrazolo[1,5-a]pyridin-3-yl)dihydropyrimidine-2,4(1H,3H)-dione hydrochloride (22 mg, 0.043 mmol) in DMF (1 mL) was added potassium carbonate (30 mg, 0.21 mmol) and (bromomethyl)cyclohexane (0.012 mL, 0.085 mmol). The mixture was heated at 80° C. for 4 h and then cooled to rt. The mixture was diluted with ethyl acetate and washed sequentially with water and brine. The organic layer was dried over sodium sulfate, filtered and concentrated to give crude 1-(5-((4-(cyclohexylmethyl)piperazin-1-yl)methyl)pyrazolo[1,5-a]pyridin-3-yl)-3-(2,4-dimethoxybenzyl)dihydropyrimidine-2,4(1H,3H)-dione (25 mg, 0.043 mmol) which was used without further purification. LCMS [M+H]$^+$: 575.4.

Step 4: 1-(5-((4-(cyclohexylmethyl)piperazin-1-yl)methyl)pyrazolo[1,5-a]pyridin-3-yl)dihydropyrimidine-2,4(1H,3H)-dione TFA (1.5 mL, 19 mmol) was added to crude 1-(5-((4-(cyclohexylmethyl)piperazin-1-yl)methyl)pyrazolo[1,5-a]pyridin-3-yl)-3-(2,4-dimethoxybenzyl)dihydropyrimidine-2,4(1H,3H)-dione (24 mg, 0.042 mmol) and the mixture was heated at 80° C. overnight. The mixture was then cooled to rt, concentrated and the residue was dissolved in toluene and concentrated again. The residue was dissolved in DMSO, filtered through a 1 micron filter and purified by reverse phase HPLC using ACN/Water/0.1% TFA. The fractions containing the product were combined, frozen and lyophilized to afford a TFA salt of 1-(5-((4-(cyclohexylmethyl)piperazin-1-yl)methyl)pyrazolo[1,5-a]pyridin-3-yl)dihydropyrimidine-2,4(1H,3H)-dione (5.5 mg, 10 umol, 24% yield). LCMS [M+H]$^+$: 425.3. $^1$H NMR (500 MHz, DMSO-d6) δ 10.48 (s, 1H), 8.66 (d, J=7.2 Hz, 1H), 8.06 (s, 1H), 7.53 (s, 1H), 6.91 (d, J=6.9 Hz, 1H), 4.59 (s, 6H), 3.80 (t, J=6.7 Hz, 2H), 3.72 (s, 1H), 3.47 (s, 1H), 3.01 (s, 4H), 2.80 (t, J=6.7 Hz, 2H), 1.69 (td, J=29.6, 13.7 Hz, 6H), 1.21 (dq, J=36.0, 12.2 Hz, 3H), 0.95 (q, J=11.9 Hz, 2H).

The compounds in the following table were prepared by the method of Example 156, using the appropriate commercially available halide, mesylate or triflate in step 4.

| Example No. | Structure | Mass [M + H]+ | 1H NMR |
|---|---|---|---|
| 157 | 1-(5-((4-((4,4-difluorocyclohexyl)methyl)piperazin-1-yl)methyl)pyrazolo[1,5-a]pyridin-3-yl)dihydropyrimidine-2,4(1H,3H)-dione | 461.4 | (500 MHz, DMSO-d6) δ 10.48 (s, 1H), 8.67 (d, J = 7.2 Hz, 1H), 8.07 (s, 1H), 7.55 (s, 1H), 7.01-6.71 (m, 1H), 3.79 (d, J = 6.7 Hz, 4H), 3.49 (d, J = 29.6 Hz, 4H), 3.02 (s, 6H), 2.80 (t, J = 6.7 Hz, 2H), 2.04 (d, J = 9.1 Hz, 2H), 1.94-1.66 (m, 5H), 1.23 (d, J = 12.9 Hz, 2H). |
| 158 | 1-(5-((4-(cycloheptylmethyl)piperazin-1-yl)methyl)pyrazolo[1,5-a]pyridin-3-yl)dihydropyrimidine-2,4(1H,3H)-dione | 439.3 | (500 MHz, DMSO-d6) δ 10.48 (s, 1H), 8.66 (d, J = 7.2 Hz, 1H), 8.07 (s, 1H), 7.54 (s, 1H), 6.91 (dd, J = 7.1, 1.8 Hz, 1H), 4.27 (s, 4H), 3.80 (t, J = 6.7 Hz, 4H), 3.57-3.32 (m, 2H), 2.95 (d, J = 71.8 Hz, 5H), 2.80 (t, J = 6.7 Hz, 2H), 1.72 (ddt, J = 13.8, 6.8, 3.1 Hz, 2H), 1.67-1.51 (m, 4H), 1.52-1.38 (m, 4H), 1.27-1.13 (m, 2H). |
| 159 | 1-(5-((4-(cyclopentylmethyl)piperazin-1-yl)methyl)pyrazolo[1,5-a]pyridin-3-yl)dihydropyrimidine-2,4(1H,3H)-dione | 411.2 | (500 MHz, DMSO-d6) δ 10.48 (s, 1H), 8.67 (d, J = 7.1 Hz, 1H), 8.07 (s, 1H), 7.56 (s, 1H), 6.92 (dd, J = 7.1, 1.9 Hz, 1H), 4.85 (s, 4H), 3.80 (t, J = 6.7 Hz, 4H), 3.51 (s, 1H), 3.09 (s, 5H), 2.80 (t, J = 6.7 Hz, 2H), 2.20 (p, J = 7.7 Hz, 1H), 1.94-1.71 (m, 2H), 1.70-1.39 (m, 4H), 1.37-1.06 (m, 2H). |
| 160 | 1-(5-((4-((tetrahydro-2H-pyran-4-yl)methyl)piperazin-1-yl)methyl)pyrazolo[1,5-a]pyridin-3-yl)dihydropyrimidine-2,4(1H,3H)-dione | 427.3 | (500 MHz, DMSO-d6) δ 10.49 (s, 1H), 8.68 (dd, J = 7.1, 0.9 Hz, 1H), 8.08 (s, 1H), 7.58 (s, 1H), 6.93 (dd, J = 7.2, 1.9 Hz, 1H), 3.97-3.70 (m, 6H), 3.65-3.36 (m, 2H), 3.31 (td, J = 11.7, 2.0 Hz, 2H), 3.03 (d, J = 59.1 Hz, 6H), 2.80 (t, J = 6.7 Hz, 4H), 2.01 (s, 1H), 1.63 (ddd, J = 12.9, 4.1, 2.0 Hz, 2H), 1.34-1.07 (m, 2H). |

| Example No. | Structure | Mass [M + H]+ | ¹H NMR |
|---|---|---|---|
| 161 | 1-(5-((4-((tetrahydro-2H-pyran-4-yl)ethyl)piperazin-1-yl)methyl)pyrazolo[1,5-a]pyridin-3-yl)dihydropyrimidine-2,4(1H,3H)-dione | 441.2 | (500 MHz, DMSO-d6) δ 10.47 (s, 1H), 8.65 (dd, J = 7.2, 0.9 Hz, 1H), 8.06 (s, 1H), 7.52 (s, 1H), 6.90 (dd, J = 7.1, 1.8 Hz, 1H), 4.45 (t, J = 6.5 Hz, 1H), 3.86-3.78 (m, 4H), 3.45 (t, J = 6.6 Hz, 2H), 3.27 (tdd, J = 11.7, 4.2, 2.0 Hz, 4H), 3.08 (d, J = 47.4 Hz, 4H), 2.80 (t, J = 6.7 Hz, 2H), 1.62-1.51 (m, 5H), 1.36 (q, J = 6.7 Hz, 1H), 1.26-1.08 (m, 4H). |
| 162 | 1-(5-((4-((tetrahydro-2H-pyran-3-yl)methyl)piperazin-1-yl)methyl)pyrazolo[1,5-a]pyridin-3-yl)dihydropyrimidine-2,4(1H,3H)-dione | 427.2 | (500 MHz, DMSO-d6) δ 10.49 (s, 1H), 8.67 (d, J = 7.1 Hz, 1H), 8.08 (s, 1H), 7.57 (s, 1H), 6.92 (dd, J = 7.2, 1.8 Hz, 1H), 5.00 (s, 6H), 4.01-3.76 (m, 4H), 3.71 (dt, J = 11.3, 4.2 Hz, 1H), 3.36 (ddd, J = 11.2, 9.7, 3.0 Hz, 2H), 3.31-2.84 (m, 5H), 2.80 (t, J = 6.7 Hz, 2H), 1.98 (s, 1H), 1.87-1.76 (m, 1H), 1.66-1.38 (m, 2H), 1.38-1.17 (m, 1H). |
| 163 | 1-(5-((4-propylpiperazin-1-yl)methyl)pyrazolo[1,5-a]pyridin-3-yl)dihydropyrimidine-2,4(1H,3H)-dione | 371.2 | (400 MHz, DMSO-d6) δ 10.44 (s, 1H), 8.63 (d, J = 7.1 Hz, 1H), 8.04 (d, J = 2.4 Hz, 1H), 7.51 (s, 1H), 6.89 (dd, J = 7.2, 1.8 Hz, 1H), 4.41 (s, 3H), 3.78 (dd, J = 7.8, 5.7 Hz, 2H), 3.69 (s, 2H), 3.45 (s, 2H), 3.02 (d, J = 8.5 Hz, 5H), 2.78 (td, J = 6.7, 2.2 Hz, 2H), 1.71-1.47 (m, 2H), 0.90 (t, J = 7.3 Hz, 3H). |
| 164 | 1-(5-((4-(pentan-3-yl)piperazin-1-yl)methyl)pyrazolo[1,5-a]pyridin-3-yl)dihydropyrimidine-2,4(1H,3H)-dione | 399.3 | (500 MHz, DMSO-d6) δ 10.48 (s, 1H), 8.65 (d, J = 6.7 Hz, 1H), 8.06 (d, J = 4.9 Hz, 1H), 7.57 (d, J = 37.0 Hz, 1H), 6.92 (d, J = 7.1 Hz, 1H), 4.56-3.26 (m, 8H), 3.05 (s, 5H), 2.80 (t, J = 6.7 Hz, 2H), 1.77 (s, 2H), 1.61 (s, 2H), 0.94 (t, J = 7.4 Hz, 6H). |

| Example No. | Structure | Mass [M + H]⁺ | ¹H NMR |
|---|---|---|---|
| 165 | 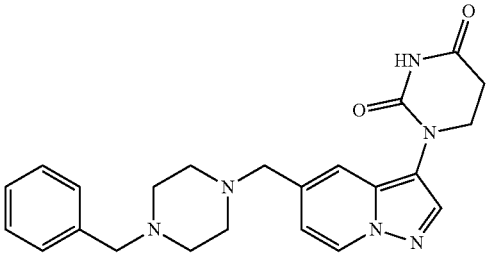 [SMILES: O=C1CCN(c2cnn3ccc(CN4CCN(Cc5ccccc5)CC4)cc23)C(=O)N1]<br>1-(5-((4-benzylpiperazin-1-yl)methyl)pyrazolo[1,5-a]pyridin-3-yl)dihydropyrimidine-2,4(1H,3H)-dione | 419.3 | (500 MHz, DMSO-d6) δ 10.48 (s, 1H), 8.67 (d, J = 7.2 Hz, 1H), 8.08 (s, 1H), 7.56 (s, 1H), 7.48 (d, J = 4.8 Hz, 5H), 6.92 (dd, J = 7.2, 1.8 Hz, 1H), 4.24 (s, 2H), 3.79 (t, J = 6.7 Hz, 4H), 3.00 (d, J = 92.9 Hz, 5H), 2.79 (t, J = 6.7 Hz, 3H), 2.56 (s, 2H). |
| 166 | 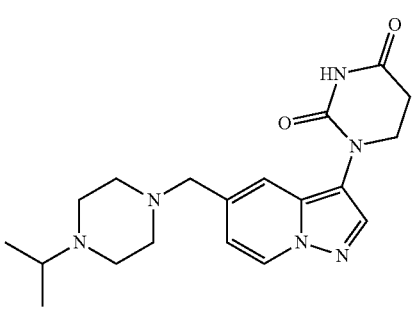 [SMILES: CC(C)N1CCN(Cc2ccn3ncc(N4CCC(=O)NC4=O)c3c2)CC1]<br>1-(5-((4-isopropylpiperazin-1-yl)methyl)pyrazolo[1,5-a]pyridin-3-yl)dihydropyrimidine-2,4(1H,3H)-dione | 371.2 | (500 MHz, DMSO-d6) δ 10.47 (s, 1H), 8.65 (dd, J = 7.1, 0.9 Hz, 1H), 8.06 (s, 1H), 7.54 (s, 1H), 6.92 (dd, J = 7.2, 1.8 Hz, 1H), 4.56 (s, 2H), 3.88-3.65 (m, 4H), 3.60-3.33 (m, 3H), 3.07 (s, 4H), 2.80 (t, J = 6.7 Hz, 2H), 1.26 (d, J = 6.6 Hz, 6H). |
| 167 | 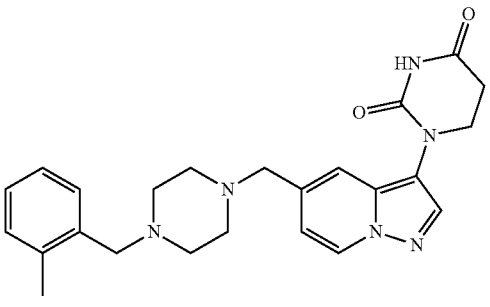 [SMILES: Cc1ccccc1CN1CCN(Cc2ccn3ncc(N4CCC(=O)NC4=O)c3c2)CC1]<br>1-(5-((4-(2-methylbenzyl)piperazin-1-yl)methyl)pyrazolo[1,5-a]pyridin-3-yl)dihydropyrimidine-2,4(1H,3H)-dione | 433.4 | (500 MHz, DMSO-d6) δ 10.49 (s, 1H), 8.69 (d, J = 7.1 Hz, 1H), 8.09 (s, 1H), 7.59 (s, 1H), 7.40 (s, 1H), 7.28 (dt, J = 14.0, 7.1 Hz, 3H), 7.01-6.83 (m, 1H), 4.27 (s, 4H), 3.80 (t, J = 6.7 Hz, 4H), 3.02 (d, J = 112.7 Hz, 6H), 2.79 (t, J = 6.7 Hz, 2H), 2.38 (s, 3H). |
| 168 | 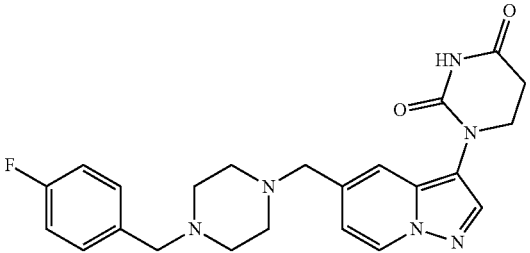 [SMILES: O=C1CCN(c2cnn3ccc(CN4CCN(Cc5ccc(F)cc5)CC4)cc23)C(=O)N1]<br>1-(5-((4-(4-fluorobenzyl)piperazin-1-yl)methyl)pyrazolo[1,5-a]pyridin-3-yl)dihydropyrimidine-2,4(1H,3H)-dione | 437.2 | (500 MHz, DMSO-d6) δ 10.48 (s, 1H), 8.67 (d, J = 7.2 Hz, 1H), 8.07 (s, 1H), 7.63-7.45 (m, 3H), 7.30 (t, J = 8.6 Hz, 2H), 6.92 (dd, J = 7.2, 1.8 Hz, 1H), 4.20 (s, 2H), 3.79 (t, J = 6.7 Hz, 6H), 3.08 (s, 6H), 2.79 (t, J = 6.7 Hz, 2H). |

-continued

| Example No. | Structure | Mass [M + H]+ | 1H NMR |
|---|---|---|---|
| 169 | 1-(5-((4-(2-fluoro-2-methylpropyl)piperazin-1-yl)methyl)pyrazolo[1,5-a]pyridin-3-yl)dihydropyrimidine-2,4(1H,3H)-dione | 403.2 | (400 MHz, DMSO-d6) δ 10.50 (s, 1H), 8.73 (d, J = 7.1 Hz, 1H), 8.12 (s, 1H), 7.65 (d, J = 34.0 Hz, 1H), 6.98 (d, J = 7.2 Hz, 1H), 3.81 (q, J = 6.0, 5.3 Hz, 6H), 3.07 (s, 8H), 2.79 (dd, J = 7.4, 6.0 Hz, 2H), 1.34 (d, J = 21.4 Hz, 6H). |
| 170 | 1-(5-((4-(3-fluorobenzyl)piperazin-1-yl)methyl)pyrazolo[1,5-a]pyridin-3-yl)dihydropyrimidine-2,4(1H,3H)-dione | 437.3 | (500 MHz, DMSO-d6) δ 10.49 (s, 1H), 8.69 (d, J = 7.1 Hz, 1H), 8.09 (s, 1H), 7.60 (s, 1H), 7.50 (td, J = 7.9, 6.1 Hz, 1H), 7.37-7.15 (m, 3H), 6.94 (dd, J = 7.3, 1.8 Hz, 1H), 4.67 (s, 2H), 4.05 (d, J = 80.5 Hz, 4H), 3.80 (t, J = 6.7 Hz, 2H), 2.98 (d, J = 72.5 Hz, 6H), 2.79 (t, J = 6.7 Hz, 2H). |
| 171 | 1-(5-((4-(2,2,2-trifluoroethyl)piperazin-1-yl)methyl)pyrazolo[1,5-a]pyridin-3-yl)dihydropyrimidine-2,4(1H,3H)-dione | 411.3 | (500 MHz, DMSO-d6) δ 10.54 (s, 1H), 8.77 (d, J = 7.3 Hz, 1H), 8.15 (s, 1H), 7.72 (s, 1H), 6.98 (d, J = 7.2 Hz, 1H), 4.39 (s, 2H), 3.82 (t, J = 6.7 Hz, 2H), 3.33 (s, 4H), 3.10 (dd, J = 47.4, 18.5 Hz, 4H, 2.79 (t, J = 6.7 Hz, 2H), 2.68 (d, J = 37.2 Hz, 2H). |
| 172 | 1-(5-((4-(1-trifluoromethyl)cyclopropyl)piperazin-1-yl)methyl)pyrazolo[1,5-a]pyridin-3-yl)dihydropyrimidine-2,4(1H,3H)-dione | 451.2 | (500 MHz, DMSO-d6) δ 10.54 (s, 1H), 8.76 (d, J = 7.1 Hz, 1H), 8.15 (s, 1H), 7.73 (s, 1H), 7.00 (dd, J = 7.2, 1.8 Hz, 1H), 4.53 (d, J = 195.2 Hz, 8H), 3.83 (t, J = 6.7 Hz, 2H), 3.21 (d, J = 131.0 Hz, 4H), 2.80 (t, J = 6.7 Hz, 2H), 1.01 (s, 2H), 0.79 (s, 2H). |

| Example No. | Structure | Mass [M + H]+ | 1H NMR |
|---|---|---|---|
| 173 | 1-(5-((4-(2,2,3,3-tetrafluoropyl)piperazin-1-yl)methyl)pyrazolo[1,5-a]pyridin-3-yl)dihydropyrimidine-2,4(1H,3H)-dione | 443.3 | (500 MHz, DMSO-d6) δ 10.46 (s, 1H), 8.70 (d, J = 7.1 Hz, 1H), 8.07 (s, 1H), 7.66 (s, 1H), 6.91 (d, J = 7.2 Hz, 1H), 6.44 (tt, J = 52.3, 5.3 Hz, 1H), 4.31 (s, 2H), 3.75 (t, J = 6.7 Hz, 2H), 3.31 (s, 2H), 3.05 (t, J = 15.1 Hz, 4H), 2.93 (d, J = 12.8 Hz, 2H), 2.72 (t, J = 6.7 Hz, 2H), 2.67-2.53 (m, 2H). |
| 174 | 1-(5-((4-(3,3-difluorocyclobutyl)methyl)piperazin-1-yl)methyl)pyrazolo[1,5-a]pyridin-3-yl)dihydropyrimidine-2,4(1H,3H)-dione | 433.4 | (400 MHz, Methanol-d4) δ 8.48 (d, J = 7.2 Hz, 1H), 8.04 (s, 1H), 7.54 (s, 1H), 6.99 (dd, J = 7.2, 1.9 Hz, 1H), 4.88 (br. s, 2H), 3.90 (t, J = 6.8 Hz, 2H), 3.76 (s, 2H), 3.58-3.37 (m, 2H), 3.30-3.22 (m, 1H), 3.22-3.01 (m, 4H), 2.89 (t, J = 6.8 Hz, 2H), 2.87-2.74 (m, 2H), 2.67-2.52 (m, 2H), 2.52-2.36 (m, 2H). NH proton not observed due to solvent exchange |
| 175 | 1-(5-((4-(1-(pyridin-3-yl)ethyl)piperazin-1-yl)methyl)pyrazolo[1,5-a]pyridin-3-yl)dihydropyrimidine-2,4(1H,3H)-dione | 434.3 | (500 MHz, DMSO-d6) δ 10.51 (s, 1H), 8.79-8.60 (m, 3H), 8.14-7.98 (m, 2H), 7.76-7.58 (m, 2H), 6.95 (dd, J = 7.1, 1.9 Hz, 1H), 4.14 (s, 6H), 3.80 (t, J = 6.7 Hz, 2H), 3.52-2.84 (m, 5H), 2.79 (t, J = 6.7 Hz, 2H), 1.48 (s, 3H). |
| 176 | 1-(5-((4-(pyridin-4-ylmethyl)piperazin-1-yl)methyl)pyrazolo[1,5-a]pyridin-3-yl)dihydropyrimidine-2,4(1H,3H)-dione | 420.3 | (500 MHz, DMSO-d6) δ 10.53 (s, 1H), 8.80-8.61 (m, 3H), 8.14 (s, 1H), 7.70 (s, 3H), 6.99 (d, J = 7.0 Hz, 1H), 4.45 (s, 4H), 4.28 (s, 4H), 3.82 (t, J = 6.7 Hz, 2H), 3.00 (s, 4H), 2.80 (t, J = 6.7 Hz, 2H). |

-continued

| Example No. | Structure | Mass [M + H]+ | 1H NMR |
|---|---|---|---|
| 177 | 1-(5-((4-((tetrahydrofuran-3-yl)methyl)piperazin-1-yl)methyl) pyrazolo[1,5-a]pyridin-3-yl)dihydropyrimidine-2,4(1H,3H)-dione | 413.4 | (500 MHz, DMSO-d6) δ 10.48 (s, 1H), 8.67 (d, J = 7.1 Hz, 1H), 8.07 (s, 1H), 7.56 (s, 1H), 6.92 (dd, J = 7.2, 1.9 Hz, 1H), 4.61 (s, 4H), 3.92-3.71 (m, 6H), 3.64 (dt, J = 8.4, 7.4 Hz, 1H), 3.57-3.43 (m, 1H), 3.39 (dd, J = 8.6, 6.4 Hz, 1H), 3.08 (s, 5H), 2.80 (t, J = 6.7 Hz, 2H), 2.64-2.56 (m, 1H), 2.07 (td, J = 12.7, 7.7 Hz, 1H), 1.59 (dq, J = 12.3, 7.4 Hz, 1H). |
| 178 | 1-(5-((4-phenethylpiperazin-1-yl)methyl) pyrazolo[1,5-a]pyridin-3-yl)dihydropyrimidine-2,4(1H,3H)-dione | 433.3 | (400 MHz, CDCl3) δ 8.42-8.29 (m, 1H), 7.93 (s, 1H), 7.66 (br s, 1H), 7.34-7.27 (m, 3H), 7.25-7.17 (m, 3H), 6.91-6.89 (m, 1H), 3.90 (t, J = 6.8 Hz, 2H), 3.56 (s, 2H), 2.97-2.86 (m, 4H), 2.86-2.51 (m, 10H). |

Examples 179 and 180. Preparation of 1-(5-((4-(((1r,4r)-4-methoxycyclohexyl)methyl)piperazin-1-yl)methyl)pyrazolo[1,5-a]pyridin-3-yl)dihydropyrimidine-2,4(1H,3H)-dione (Example 179) and 1-(5-((4-(((1s,4s)-4-methoxycyclohexyl)methyl)piperazin-1-yl)methyl)pyrazolo[1,5-a]pyridin-3-yl)dihydropyrimidine-2,4(1H,3H)-dione (Example (180)

(Example 179)

(Example 180)

Prepared using the method of Example 156 using a commercially available mixture of cis and trans 1-(bromomethyl)-4-methoxycyclohexane in place of (bromomethyl)cyclohexane. The stereoisomers were purified after the final step by reverse-phase HPLC (eluting with using ACN/Water/0.1% TFA).

Example 179. 1-(5-((4-(((1r,4r)-4-methoxycyclohexyl)methyl)piperazin-1-yl)methyl)pyrazolo[1,5-a]pyridin-3-yl)dihydropyrimidine-2,4(1H,3H)-dione Eluted first, minor isomer. LCMS [M+H]+: 455.2. 1H NMR (500 MHz, DMSO-d6) δ 10.48 (s, 1H), 8.66 (d, J=7.2 Hz, 1H), 8.07 (s, 1H), 7.54 (s, 1H), 6.91 (dd, J=7.3, 1.8 Hz, 1H), 4.59 (s, 4H), 3.80 (t, J=6.7 Hz, 4H), 3.42 (d, J=45.9 Hz, 1H), 3.24 (s, 3H), 3.06 (ddd, J=14.6, 10.7, 4.2 Hz, 6H), 2.80 (t, J=6.7 Hz, 2H), 2.01 (d, J=12.1 Hz, 2H), 1.86-1.54 (m, 3H), 1.20-0.77 (m, 4H).

Example 180. 1-(5-((4-(((1s,4s)-4-methoxycyclohexyl)methyl)piperazin-1-yl)methyl)pyrazolo[1,5-a]pyridin-3-yl)dihydropyrimidine-2,4(1H,3H)-dione Eluted second, major isomer. LCMS [M+H]⁺: 455.2. ¹H NMR (500 MHz, DMSO-d6) δ 10.48 (s, 1H), 8.66 (d, J=7.2 Hz, 1H), 8.07 (s, 1H), 7.54 (s, 1H), 6.91 (dd, J=7.1, 1.8 Hz, 1H), 4.60 (s, 4H), 3.80 (t, J=6.7 Hz, 4H), 3.47 (s, 1H), 3.38 (d, J=4.9 Hz, 1H), 3.21 (s, 3H), 3.02 (s, 5H), 2.80 (t, J=6.7 Hz, 2H), 1.91-1.62 (m, 3H), 1.56-1.36 (m, 4H), 1.32-1.18 (m, 2H).

Example 181. Preparation of 1-(5-((4-(2-(4,4-difluorocyclohexyl)propan-2-yl)piperazin-1-yl)methyl)pyrazolo[1,5-a]pyridin-3-yl)dihydropyrimidine-2,4(1H,3H)-dione

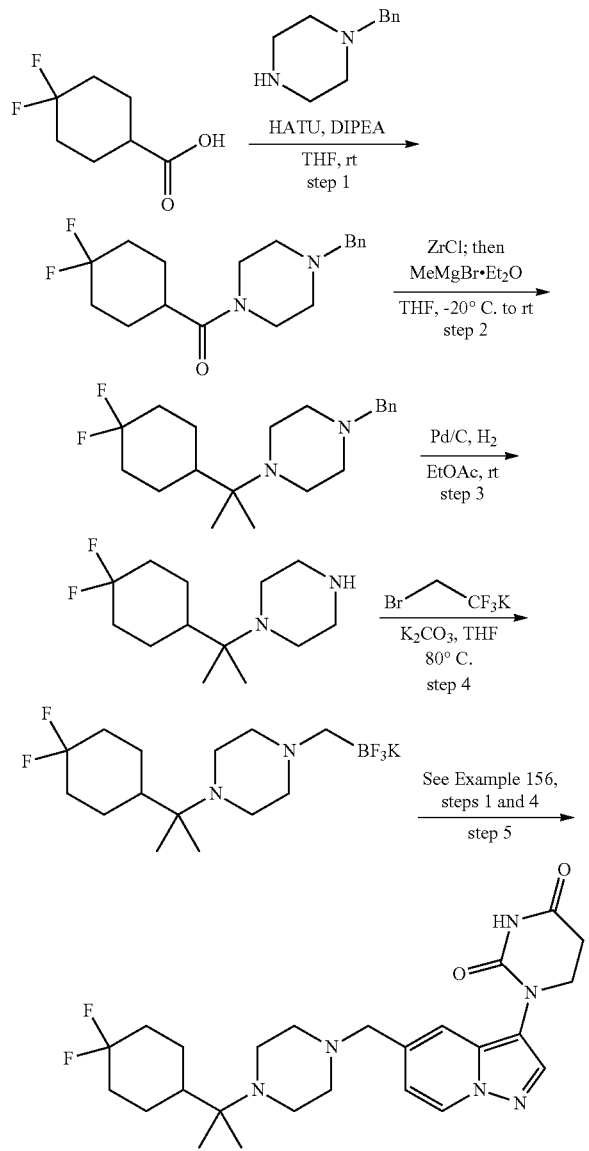

Example 181

Step 1. (4-benzylpiperazin-1-yl)(4,4-difluorocyclohexyl)methanone

HATU (8.26 g, 21.9 mmol) and DIPEA (9.53 mL, 54.75 mmol) were added to a solution of 4,4-difluorocyclohexane-1-carboxylic acid (3.0 g, 18.25 mmol) in THF (10 mL) at 0° C. The mixture was stirred for 10 min and then 1-benzylpiperazine (3.2 g, 18.3 mmol) was added and the reaction was stirred for 16 h at rt. The reaction mixture was quenched with water and extracted with EtOAc. The organic layer was washed with brine, dried over Na₂SO₄, filtered and concentrated. The crude material was purified by silica gel chromotography (eluting with 50% EtOAc in hexane) to afford (4-benzylpiperazin-1-yl)(4,4-difluorocyclohexyl)methanone (1.5 g, 4.65 mmol, 25% yield). LCMS [M+H]⁺: 323.5.

Step 2. 1-benzyl-4-(2-(4,4-difluorocyclohexyl)propan-2-yl)piperazine

To a stirred solution of (4-benzylpiperazin-1-yl)(4,4-difluorocyclohexyl)methanone (1.5 g, 4.65 mmol) in THF (10 mL) was added ZrCl₄ (1.84 g, 4.65 mmol) at −20° C. and the mixture was stirred for 30 min. A solution of MeMgBr·Et₂O (9.4 mL, 28.2 mmol, 3.0 M) was added and the mixture was stirred for 10 min at −20° C. and then at rt for 16 h. After completion, the reaction was quenched with water (10 mL) and extracted with EtOAc. The organic layer was washed with brine, dried over Na₂SO₄, filtered and concentrated. The crude material was purified by silica gel chromotography (eluting with 10-15% EtOAc in hexanes) to afford 1-benzyl-4-(2-(4,4-difluorocyclohexyl)propan-2-yl)piperazine (500 mg, 1.49 mmol, 31% yield).

Step 3. 1-(2-(4,4-difluorocyclohexyl)propan-2-yl)piperazine

To a stirred solution of 1-benzyl-4-(2-(4,4-difluorocyclohexyl)propan-2-yl)piperazine (500 mg, 1.49 mmol) in EtOAc (15 mL) under an inert atmosphere was added Pd/C (100 mg) at rt. The flask was evacuated and refilled with hydrogen from a balloon and stirred at RT for 36 h. The reaction was then purged with argon and filtered through celite. The filtrate was concentrated to give crude 1-(2-(4,4-difluorocyclohexyl)propan-2-yl)piperazine (400 mg, crude). The material was used without further purification.

Step 4. potassium ((4-(2-(4,4-difluorocyclohexyl)propan-2-yl)piperazin-1-yl)methyl)trifluoroborate To a stirred solution of 1-(2-(4,4-difluorocyclohexyl)propan-2-yl)piperazine (400 mg, 1.62 mmol) in THF (10 mL) at rt was added K₂CO₃ (448 mg, 3.25 mmol) and potassium (bromomethyl)trifluoroborate (326 mg, 1.62 mmol). The reaction was stirred for 12 h at 80° C. and then cooled to rt and concentrated to afford potassium ((4-(2-(4,4-difluorocyclohexyl)propan-2-yl)piperazin-1-yl)methyl)trifluoroborate (1.5 g, crude). The material was used without further purification.

Step 5: 1-(5-((4-(2-(4,4-difluorocyclohexyl)propan-2-yl)piperazin-1-yl)methyl)pyrazolo[1,5-a]pyridin-3-yl)dihydropyrimidine-2,4(1H,3H)-dione was prepared from potassium ((4-(2-(4,4-difluorocyclohexyl)propan-2-yl)piperazin-1-yl)methyl)trifluoroborate by the method of Example 156, steps 1 and 4, wherein potassium ((4-(2-(4,4-difluorocyclohexyl)propan-2-yl)piperazin-1-yl)methyl)trifluoroborate was used in place of potassium {[4-(tert-butoxycarbonyl)-1-piperazinyl]methyl}(trifluoro)borate. LCMS [M+H]⁺: 489.2. ¹H NMR (400 MHz, Methanol-d4) δ 8.51 (d, J=6.9 Hz, 1H), 8.06 (s, 1H), 7.54 (d, J=14.9 Hz, 1H), 7.00 (dd, J=7.4, 1.8 Hz, 1H), 3.91 (t, J=6.7 Hz, 2H), 3.48 (s, 3H), 3.26-3.10 (m, 2H), 2.89 (t, J=6.7 Hz, 2H), 2.67 (s, 3H), 2.16 (d, J=23.5 Hz, 2H), 1.82 (d, J=14.0 Hz, 4H), 1.55-1.18 (m, 7H). 4 protons not integrated due to peak broadening. NH proton not observed due to solvent exchange.

Example 182. Preparation of 1-(5-((4-(2-(tetrahydro-2H-pyran-4-yl)propan-2-yl)piperazin-1-yl)methyl)pyrazolo[1,5-a]pyridin-3-yl)dihydropyrimidine-2,4(1H,3H)-dione

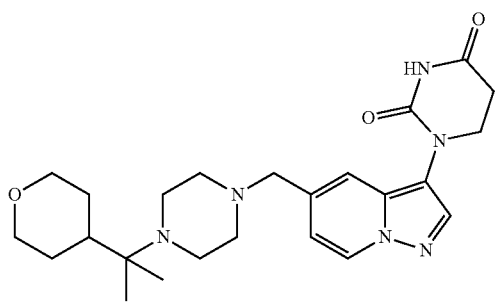 [SMILES: CC(C)(C1CCOCC1)N1CCN(Cc2ccn3ncc(N4CCC(=O)NC4=O)c3c2)CC1]

Prepared using the method of 181, wherein tetrahydro-2H-pyran-4-carboxylic acid was used in place of 4,4-difluorocyclohexane-1-carboxylic acid. LCMS [M+H]+: 474.8. 1H NMR (400 MHz, DMSO-d6) δ 10.46 (s, 1H), 8.74, (s, 1H), 8.62 (s, 1H), 8.13 (s, 1H), 8.03 (s, 1H), 7.48 (s, 1H), 6.90 (s, 1H), 3.89 (d, J=11.0 Hz, 2H), 3.78 (t, J=6.5 Hz, 2H), 3.63 (s, 1H), 3.32 (s, 9H), 2.78 (t, J=6.7 Hz, 2H), 1.85 (d, J=110.7 Hz, 2H), 1.52 (d, J=12.5 Hz, 2H), 1.43-1.07 (m, 6H), 0.86 (s, 3H).

Example 183. Preparation of 1-(5-((4-(2-hydroxy-2-methylpropyl)piperazin-1-yl)methyl)pyrazolo[1,5-a]pyridin-3-yl)dihydropyrimidine-2,4(1H,3H)-dione

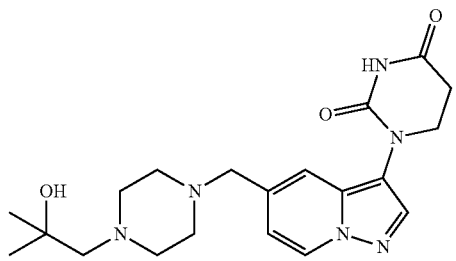

Prepared using the method of Example 106, wherein 3-(2,4-dimethoxybenzyl)-1-(5-(piperazin-1-ylmethyl)pyrazolo[1,5-a]pyridin-3-yl)dihydropyrimidine-2,4(1H,3H)-dione was used in place of 3-(2,4-dimethoxybenzyl)-1-(5-((1-(2-hydroxy-2-methylpropyl)piperidin-4-yl)methyl)pyrazolo[1,5-a]pyridin-3-yl)dihydropyrimidine-2,4(1H,3H)-dione. LCMS [M+H]+: 401.4. 1H NMR (400 MHz, DMSO-d6) δ 10.46 (s, 1H), 8.66 (d, J=7.1 Hz, 1H), 8.07 (d, J=1.7 Hz, 1H), 7.56 (s, 1H), 6.92 (dd, J=7.3, 1.9 Hz, 1H), 4.70 (s, 4H), 3.96-3.67 (m, 4H), 3.29 (s, 2H), 2.97 (d, J=36.7 Hz, 5H), 2.79 (t, J=6.8 Hz, 2H), 1.22 (d, J=1.8 Hz, 6H).

Example 184. Preparation of 1-(5-((4-(1-(trifluoromethyl)cyclopropane-1-carbonyl)piperazin-1-yl)methyl)pyrazolo[1,5-a]pyridin-3-yl)dihydropyrimidine-2,4(1H,3H)-dione

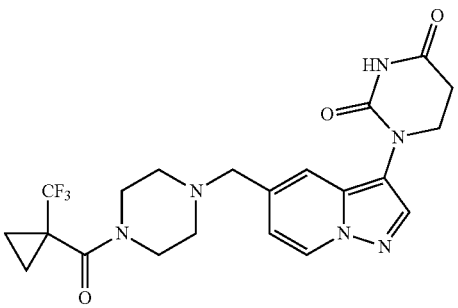 [SMILES: O=C1CCN(c2cnn3ccc(CN4CCN(C(=O)C5(C(F)(F)F)CC5)CC4)cc23)C(=O)N1]

Prepared using the method of Example 98, wherein 3-(2,4-dimethoxybenzyl)-1-(5-(piperazin-1-ylmethyl)pyrazolo[1,5-a]pyridin-3-yl)dihydropyrimidine-2,4(1H,3H)-dione hydrochloride was used in place of 3-(2,4-dimethoxybenzyl)-1-(5-(piperidin-4-ylmethyl)pyrazolo[1,5-a]pyridin-3-yl)dihydropyrimidine-2,4(1H,3H)-dione hydrochloride and 1-(trifluoromethyl)cyclopropane-1-carboxylic acid was used in place of isobutyric acid. LCMS [M+H]+: 465.2. 1H NMR (400 MHz, DMSO-d6) δ 10.51 (d, J=2.2 Hz, 1H), 8.76 (d, J=7.1 Hz, 1H), 8.14 (d, J=1.9 Hz, 1H), 7.72 (s, 1H), 6.99 (dd, J=7.2, 2.0 Hz, 1H), 4.34 (s, 2H), 3.82 (td, J=6.4, 1.8 Hz, 2H), 3.64 (s, 4H), 3.19 (s, 4H), 2.79 (t, J=6.7 Hz, 2H), 1.47-0.84 (m, 4H).

Example 185. Preparation of 1-(5-((4-(isopropylsulfonyl)piperazin-1-yl)methyl)pyrazolo[1,5-a]pyridin-3-yl)dihydropyrimidine-2,4(1H,3H)-dione

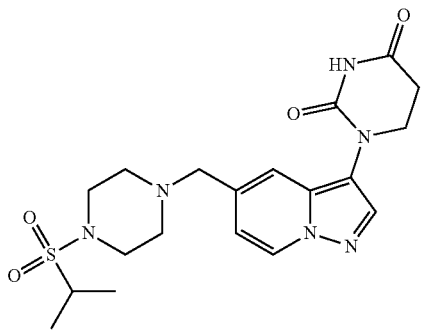 [SMILES: CC(C)S(=O)(=O)N1CCN(Cc2ccn3ncc(N4CCC(=O)NC4=O)c3c2)CC1]

Prepared using the method of Example 80, wherein 3-(2,4-dimethoxybenzyl)-1-(5-(piperazin-1-ylmethyl)pyrazolo[1,5-a]pyridin-3-yl)dihydropyrimidine-2,4(1H,3H)-dione hydrochloride was used in place of 3-(2,4-dimethoxybenzyl)-1-(5-(piperidin-4-ylmethyl)pyrazolo[1,5-a]pyridin-3-yl)dihydropyrimidine-2,4(1H,3H)-dione hydrochloride and propane-2-sulfonyl chloride was used in place of cyclohexylmethanesulfonyl chloride. LCMS [M+H]+: 435.4. 1H NMR (500 MHz, DMSO-d6) δ 10.45 (s, 1H), 8.67 (d, J=6.7 Hz, 1H), 8.06 (s, 1H), 7.62 (s, 1H), 6.90 (d, J=7.4 Hz, 1H), 4.27 (bs, 4H), 3.74 (t, J=6.6 Hz, 2H), 3.23-2.83 (m, 4H), 2.72 (t, J=6.7 Hz, 2H), 1.16 (d, J=6.8 Hz, 6H) (missing proton obscured by water peak).

Example 186. Preparation of 1-(5-((4-isobutylpiperazin-1-yl)methyl)pyrazolo[1,5-a]pyridin-3-yl)dihydropyrimidine-2,4(1H,3H)-dione

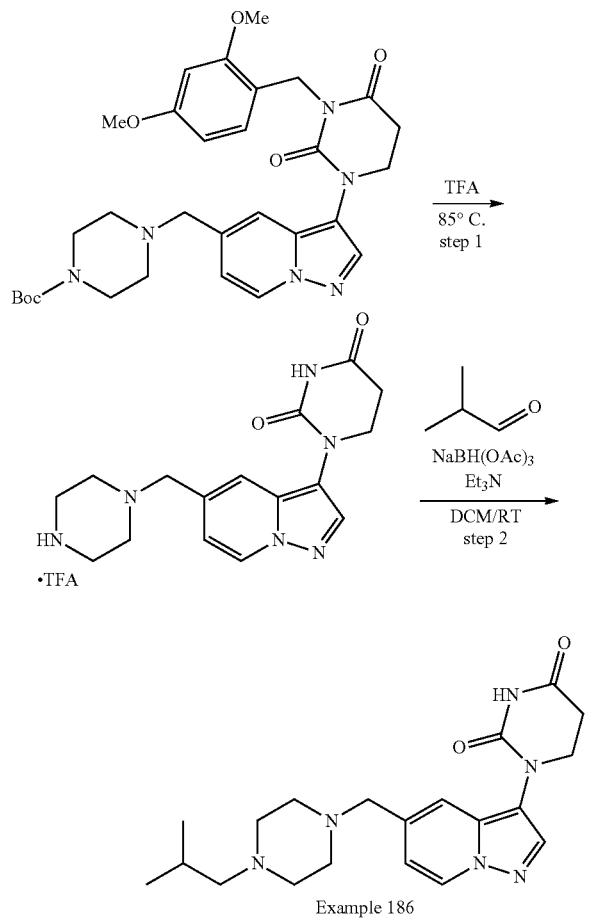

Example 186

Step 1. 1-(5-(piperazin-1-ylmethyl)pyrazolo[1,5-a]pyridin-3-yl)dihydropyrimidine-2,4(1H,3H)-dione TFA (4 ml, 52 mmol) was added to tert-butyl 4-((3-(3-(2,4-dimethoxybenzyl)-2,4-dioxotetrahydropyrimidin-1(2H)-yl)pyrazolo[1,5-a]pyridin-5-yl)methyl)piperazine-1-carboxylate (200 mg, 0.346 mmol). The mixture was heated overnight at in a sealed vial at 85° C. The mixture was then cooled to rt and, concentrated and azeotropically dried with toluene to provide crude 1-(5-(piperazin-1-ylmethyl)pyrazolo[1,5-a]pyridin-3-yl)dihydropyrimidine-2,4(1H,3H)-dione trifluoroacetate which was used without further purification. LCMS [M+H]$^+$: 329.2.

Step 2: 1-(5-((4-isobutylpiperazin-1-yl)methyl)pyrazolo[1,5-a]pyridin-3-yl)dihydropyrimidine-2,4(1H, 3H)-dione Isobutyraldehyde (10 mg, 0.14 mmol) and triethylamine (0.014 mL, 0.10 mmol) were added to a solution of 1-(5-(piperazin-1-ylmethyl)pyrazolo[1,5-a]pyridin-3-yl)dihydropyrimidine-2,4(1H,3H)-dione trifluoroacetate (30 mg, 0.068 mmol) in DCM (2 mL) and MeOH (2 mL). The reaction mixture was stirred at rt for 10 min and then sodium triacetoxyborohydride (43 mg, 0.20 mmol) was added. The reaction mixture was stirred overnight at rt and then quenched with a solution of saturated aqueous NaHCO$_3$ and extracted three times with DCM. The combined organic extracts were washed with brine, dried over Na$_2$SO$_4$, filtered and concentrated. The residue was dissolved in DMSO, filtered through a 1 micron filter and purified by reverse phase HPLC using ACN/Water/0.1% TFA. The fractions containing the product were combined, frozen and lyophilized to afford a TFA salt of 1-(5-((4-isobutylpiperazin-1-yl)methyl)pyrazolo[1,5-a]pyridin-3-yl)dihydropyrimidine-2,4(1H,3H)-dione (12 mg, 0.023 mmol, 33% yield). LCMS [M+H]$^+$: 385.3. $^1$H NMR (500 MHz, DMSO-d6) δ 10.46 (s, 1H), 8.56 (d, J=7.1 Hz, 1H), 8.05 (s, 1H), 7.50 (s, 1H), 6.89 (d, J=7.1 Hz, 1H), 3.79 (t, J=6.7 Hz, 2H), 3.72-3.55 (m, 4H), 3.41 (s, 4H), 3.00 (d, J=39.0 Hz, 4H), 2.79 (t, J=6.7 Hz, 2H), 2.11-1.98 (m, 1H), 0.94 (d, J=6.6 Hz, 6H).

The compounds in the following table were prepared by the method of Example 186, using the appropriate commercially available aldehyde in step 2.

| Example No. | Structure | Mass [M + H]$^+$ | $^1$H NMR |
|---|---|---|---|
| 187 | 1-(5-((4-(2-cyclohexylethyl)piperazin-1-yl)methyl)pyrazolo[1,5-a]pyridin-3-yl)dihydropyrimidine-2,4(1H,3H)-dione | 439.3 | (500 MHz, DMSO-d6) δ 10.38 (s, 1H), 8.56 (d, J = 7.1 Hz, 1H), 7.97 (s, 1H), 7.43 (s, 1H), 6.81 (dd, J = 7.2, 1.8 Hz, 1H), 3.71 (t, J = 6.7 Hz, 2H), 3.59 (s, 4H), 3.09-2.80 (m, 6H), 2.71 (t, J = 6.7 Hz, 2H), 2.37 (d, J = 31.0 Hz, 2H), 1.64-1.50 (m, 5H), 1.49-1.38 (m, 2H), 1.12 (tddd, J = 24.2, 21.4, 9.8, 6.5 Hz, 4H), 0.84 (q, J = 11.2 Hz, 2H). |

| Example No. | Structure | Mass [M + H]+ | 1H NMR |
|---|---|---|---|
| 188 | 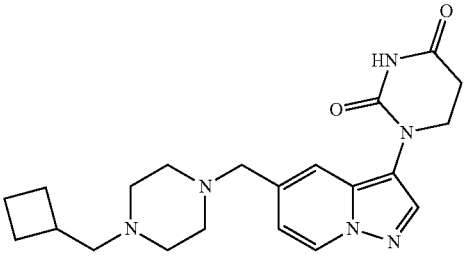 [SMILES: O=C1CCN(c2cnn3ccc(CN4CCN(CC5CCC5)CC4)cc23)C(=O)N1]<br>1-(5-((4-(cyclobutylmethyl)piperazin-1-yl)methyl)pyrazolo[1,5-a]pyridin-3-yl)dihydropyrimidine-2,4(1H,3H)-dione | 397.3 | (500 MHz, DMSO-d6) δ 10.46 (s, 1H), 8.63 (d, J = 7.1 Hz, 1H), 8.04 (s, 1H), 7.50 (s, 1H), 6.88 (dd, J = 7.2, 1.8 Hz, 1H), 3.78 (t, J = 6.7 Hz, 4H), 3.35 (s, 2H), 3.14 (s, 2H), 2.99 (s, 4H), 2.79 (t, J = 6.7 Hz, 2H), 2.73-2.60 (m, 1H), 2.40 (d, J = 29.5 Hz, 2H), 2.13-2.01 (m, 2H), 1.95-1.84 (m, 1H), 1.84-1.69 (m, 3H). |
| 189 | 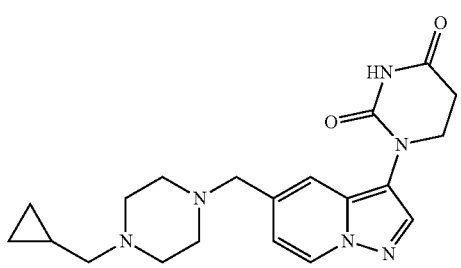 [SMILES: O=C1CCN(c2cnn3ccc(CN4CCN(CC5CC5)CC4)cc23)C(=O)N1]<br>1-(5-((4-(cyclopropylmethyl)piperazin-1-yl)methyl)pyrazolo[1,5-a]pyridin-3-yl)dihydropyrimidine-2,4(1H,3H)-dione | 383.4 | (500 MHz, DMSO-d6) δ 10.48 (s, 1H), 8.66 (dd, J = 7.2, 0.9 Hz, 1H), 8.06 (s, 1H), 7.54 (s, 1H), 6.91 (dd, J = 7.2, 1.9 Hz, 1H), 3.84-3.72 (m, 5H), 3.55 (s, 3H), 3.25-2.94 (m, 6H), 2.80 (t, J = 6.7 Hz, 2H), 1.05 (dh, J = 10.5, 2.8 Hz, 1H), 0.74-0.54 (m, 2H), 0.44-0.21 (m, 2H). |
| 190 | 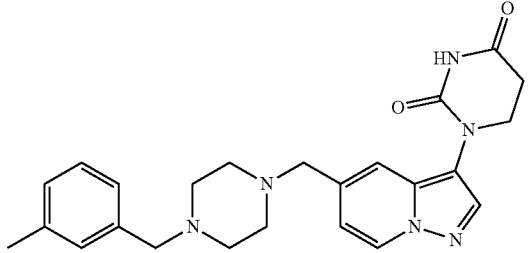 [SMILES: Cc1cccc(CN2CCN(Cc3ccn4ncc(N5CCC(=O)NC5=O)c4c3)CC2)c1]<br>1-(5-((4-(3-methylbenzyl)piperazin-1-yl)methyl)pyrazolo[1,5-a]pyridin-3-yl)dihydropyrimidine-2,4(1H,3H)-dione | 433.2 | (500 MHz, DMSO-d6) δ 10.39 (s, 1H), 8.57 (d, J = 7.2 Hz, 1H), 7.98 (s, 1H), 7.44 (s, 1H), 7.23 (d, J = 36.8 Hz, 4H), 6.82 (d, J = 7.3 Hz, 1H), 4.43-4.03 (m, 6H), 3.71 (t, J = 6.7 Hz, 5H), 3.19 (s, 1H), 2.95 (s, 2H), 2.71 (t, J = 6.7 Hz, 2H), 2.26 (s, 3H). |
| 191 | 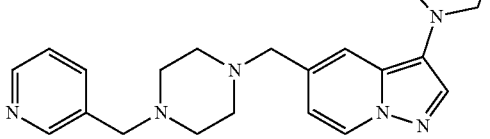<br>1-(5-((4-(pyridin-3-ylmethyl)piperazin-1-yl)methyl)pyrazolo[1,5-a]pyridin-3-yl)dihydropyrimidine-2,4(1H,3H)-dione | 420.3 | (500 MHz, Methanol-d4) δ 8.66 (s, 1H), 8.61 (d, J = 5.4 Hz, 1H), 8.48 (d, J = 7.2 Hz, 1H), 8.23 (s, 1H), 8.01 (s, 1H), 7.74 (d, J = 6.8 Hz, 1H), 7.59 (s, 1H), 6.90 (dd, J = 7.3, 1.9 Hz, 1H), 4.14 (s, 2H), 3.88 (s, 2H), 3.82 (t, J = 6.7 Hz, 2H), 3.07 (s, 4H), 2.86 (s, 3H), 2.79 (t, J = 6.7 Hz, 3H). |

Example 192. Preparation of (S)-1-(5-((4-(cyclohexylmethyl)-3-methylpiperazin-1-yl)methyl)pyrazolo[1,5-a]pyridin-3-yl)dihydropyrimidine-2,4(1H,3H)-dione

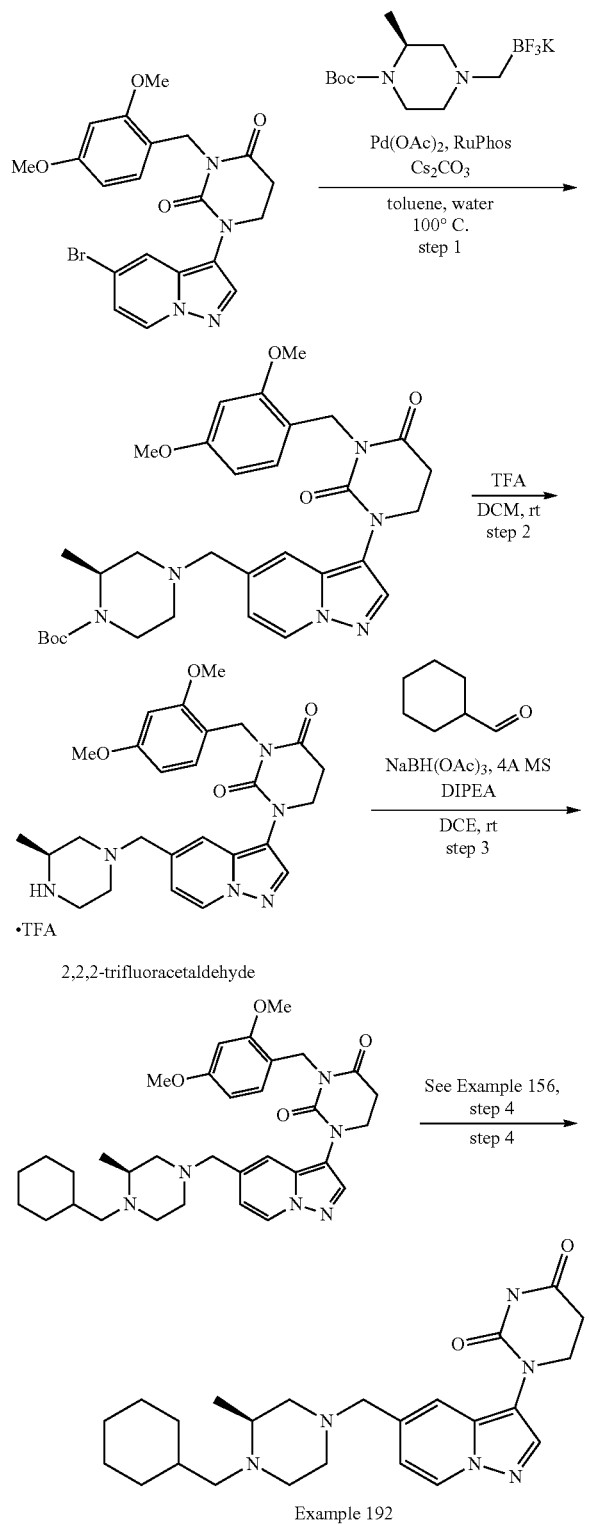

Example 192

Step 1. tert-butyl (S)-4-((3-(3-(2,4-dimethoxybenzyl)-2,4-dioxotetrahydropyrimidin-1 (2H)-yl)pyrazolo[1,5-a]pyridin-5-y)methyl)-2-methylpiperazine-1-carboxylate To a suspension of 1-(5-bromopyrazolo[1,5-a]pyridin-3-yl)-3-(2,4-dimethoxybenzyl)dihydropyrimidine-2,4(1H, 3H)-dione (1.2 g, 2.61 mmol) in toluene (20 mL) and water (2 mL) at room temperature was added Cs$_2$CO$_3$ (2.55 g, 7.84 mmol), tert-butyl (S)-2-methyl-4-((trifluoro-I4-boraneyl)methyl)piperazine-1-carboxylate, potassium salt (3.35 g, 10.45 mmol) [see Chem Med Chem, 2016, 11, 2640-2648] and RuPhos (242 mg, 0.52 mmol), followed by Pd(OAc)$_2$ (59 mg, 0.26 mmol). The mixture was stirred at 100° C. overnight, then cooled to rt and partitioned between EtOAc and water. The organic layer was separated, washed with brine, dried over sodium sulfate, filtered and concentrated. Silica gel column chromatography [eluted with 0-100% EtOAc/EtOH (3:1) in heptane] provided tert-butyl (S)-4-((3-(3-(2,4-dimethoxybenzyl)-2,4-dioxotetrahydropyrimidin-1 (2H)-yl)pyrazolo[1,5-a]pyridin-5-yl)methyl)-2-methylpiperazine-1-carboxylate, (1.12 g, 2.61 mmol, 71% yield) as an off-white foamy solid. LCMS [M+H]$^+$: 593.4.

Step 2. (S)-3-(2,4-dimethoxybenzyl)-1-(5-((3-methylpiperazin-1-yl)methyl)pyrazolo[1,5-a]pyridin-3-yl) dihydropyrimidine-2,4(1H,3H)-dione trifluoroacetate TFA (4 mL, 2 mmol) was added to a solution of tert-butyl (S)-4-((3-(3-(2,4-dimethoxybenzyl)-2,4-dioxotetrahydropyrimidin-1(2H)-yl)pyrazolo[1,5-a]pyridin-5-yl)methyl)-2-methylpiperazine-1-carboxylate (1.2 g, 2.0 mmol) in DCM (12 mL) and the mixture was stirred for 2 h at rt. The reaction was then concentrated and dried azeotropically with toluene to give crude (S)-3-(2,4-dimethoxybenzyl)-1-(5-((3-methylpiperazin-1-yl)methyl)pyrazolo[1,5-a]pyridin-3-yl) dihydropyrimidine-2,4(1H,3H)-dione trifluoroacetate (1.2 g, 1.4 mmol) which was used without further purification. LCMS [M+H]$^+$: 493.2.

Step 3. (S)-1-(5-((4-(cyclohexylmethyl)-3-methylpiperazin-1-yl)methyl)pyrazolo[1,5-a]pyridin-3-yl)-3-(2,4-dimethoxybenzyl)dihydropyrimidine-2,4 (1H,3H)-dione To a solution of (S)-3-(2,4-dimethoxybenzyl)-1-(5-((3-methylpiperazin-1-yl)methyl)pyrazolo[1,5-a]pyridin-3-yl) dihydropyrimidine-2,4(1H,3H)-dione (100 mg, 0.20 mmol) in DCE (2 mL) was added cyclohexanecarbaldehyde (21 mg, 0.20 mmol), NaBH(OAc)$_3$ (120 mg, 0.60 mmol), 4A MS (100 mg) and DIPEA (113 mg, 0.15 mL, 0.95 mmol). The reaction was stirred at rt for 2 h. The suspension was filtered through a pad of Celite and the filtrate was diluted with a solution of saturated aqueous NaHCO$_3$ and extracted with DCM. The organic layer was dried over Na$_2$SO$_4$, filtered and concentrated to give (S)-1-(5-((4-(cyclohexylmethyl)-3-methylpiperazin-1-yl)methyl)pyrazolo[1,5-a]pyridin-3-yl)-3-(2,4-dimethoxybenzyl)dihydropyrimidine-2,4(1H,3H)-dione (200 mg, 0.34 mmol, 72% purity). The crude product was used in the next step without any other purification. LCMS [M+H]$^+$: 589.2.

Step 4: (S)-1-(5-((4-(cyclohexylmethyl)-3-methylpiperazin-1-yl)methyl)pyrazolo[1,5-a]pyridin-3-yl)dihydropyrimidine-2,4(1H,3H)-dione (Example 192) was prepared using the method of Example 156, step 4, wherein (S)-1-(5-((4-(cyclohexylmethyl)-3-methylpiperazin-1-yl)methyl)

pyrazolo[1,5-a]pyridin-3-yl)-3-(2,4-dimethoxybenzyl)dihydropyrimidine-2,4(1H,3H)-dione was used in place of 1-(5-((4-(cyclohexylmethyl)piperazin-1-yl)methyl)pyrazolo[1,5-a]pyridin-3-yl)-3-(2,4-dimethoxybenzyl) dihydropyrimidine-2,4(1H,3H)-dione. LCMS [M+H]: 439.1. $^1$H NMR (400 MHz, DMSO-d6) δ 10.43 (s, 1H), 8.57-8.55 (m, 1H), 8.00 (s, 1H), 7.43 (s, 1H), 6.88-6.86 (m, 1H), 3.76 (s, 2H), 3.45-3.44 (m, 2H), 2.80-2.72 (t, 3H), 2.57 (br s, 1H), 2.47-2.40 (m, 1H), 2.35-2.26 (N, 1H), 2.23-2.08 (m, 2H), 2.03-1.77 (m, 3H), 1.63 (br s, 4H), 1.42-1.39 (m, 1H), 1.30-1.02 (m, 4H), 0.92-0.91 (m, 3H), 0.87-0.70 (s, 2H).

The compounds in the following table were prepared from 3-(2,4-dimethoxybenzyl)-1-(5-(piperazin-1-ylmethyl)pyrazolo[1,5-a]pyridin-3-yl)dihydropyrimidine-2,4(1H,3H)-dione hydrochloride by the method of Example 192, steps 3-4 using the appropriate commercially available aldehyde in step 3.

| Example No. | Structure | Mass [M + H]⁺ | $^1$H NMR |
|---|---|---|---|
| 193 | 1-(5-((4-(((2R,6S)-2,6-dimethyltetrahydro-2H-pyran-4-yl)methyl)piperazin-1-yl)methyl)pyrazolo[1,5-a]pyridin-3-yl)dihydropyrimidine-2,4(1H,3H)-dione | 455.2 | (400 MHz, CD$_3$OD) δ 8.46 (d, J = 7.2 Hz, 1H), 8.44 (s, 1H), 8.02 (s, 1H), 7.51 (s, 1H), 6.99 (d, J = 4.4 Hz, H), 3.88 (t, J = 6.6 Hz, 2H), 3.69-3.48 (m, 4H), 3.08 (m, 4H), 2.90-2.77 (m, 7H), 2.31 (s, 1H), 2.19 (s, 1H), 1.74-1.42 (m, 3H), 1.18-1.11 (m, 6H), 0.88-0.84 (m, 1H). |
| 194 | 1-(5-((4-(((3r,5r,7r)-adamantan-1-yl)methyl)piperazin-1-yl)methyl)pyrazolo[1,5-a]pyridin-3-yl)dihydropyrimidine-2,4(1H,3H)-dione | 477.2 | (400 MHz, Methanol-d4) δ 8.49 (s, 1H), 8.46 (d, J = 7.2 Hz, 1H), 8.02 (s, 1H), 7.51 (s, 1H), 6.99 (dd, J = 7.4, 1.6 Hz, 1H), 3.89 (t, J = 6.7 Hz, 2H), 3.64 (s, 2H), 2.89 (t, J = 6.8 Hz, 2H), 2.78 (s, 4H), 2.63 (s, 4H), 2.23 (s, 2H), 1.96 (s, 3H), 1.76 (d, J = 12.4 Hz, 3H), 1.68 (d, J = 12.2 Hz, 3H), 1.57 (d, J = 3.0 Hz, 6H). NH proton not observed due to solvent exchange |
| 195 | 1-(5-((4-((1-methyl-1H-pyrazol-5-yl)methyl)piperazin-1-yl)methyl)pyrazolo[1,5-a]pyridin-3-yl)dihydropyrimidine-2,4(1H,3H)-dione | 423.2 | (400 MHz, CD$_3$OD) δ 8.58 (d, J = 7.6 Hz, 1H), 8.11 (s, 1H), 7.70 (s, 1H), 7.45 (d, J = 1.6 Hz, 1H), 7.02 (d, J = 7.6 Hz, 1H), 6.34 (d, J = 1.6 Hz, 1H), 4.24 (s, 2H), 3.94-3.91 (m, 7H), 3.23 (brs, 4H), 2.91-2.88 (m, 6H). |

| Example No. | Structure | Mass [M + H]⁺ | ¹H NMR |
|---|---|---|---|
| 196 | 1-(5-((4-((1-methyl-1H-imidazol-4-yl)methyl)piperazin-1-yl)methyl)pyrazolo[1,5-a]pyridin-3-yl)dihydropyrimidine-2,4(1H,3H)-dione | 422.8 | (400 MHz, Methanol-d4) δ 8.86 (s, 1H), 8.61 (d, J = 7.2 Hz, 1H), 8.13 (s, 1H), 7.80 (d, J = 1.8 Hz, 1H), 7.51 (s, 1H), 7.01 (dd, J = 7.6, 1.9 Hz, 1H), 4.42 (s, 2H), 3.92 (m, 5H), 3.75 (s, 2H), 3.38 (bs, 3H), 2.90 (bm, 7H). NH proton not observed due to solvent exchange |
| 197 | 1-(5-((4-(thiazol-4-ylmethyl)piperazin-1-yl)methyl)pyrazolo[1,5-a]pyridin-3-yl)dihydropyrimidine-2,4(1H,3H)-dione | 425.8 | (400 MHz, Methanol-d4) δ 9.11 (d, J = 1.9 Hz, 1H), 8.50 (d, J = 7.1 Hz, 1H), 8.06 (s, 1H), 7.82 (d, J = 2.0 Hz, 1H), 7.58 (s, 1H), 6.99 (dd, J = 7.1, 1.9 Hz, 1H), 4.44 (s, 2H), 3.96-3.84 (m, 4H), 3.19-2.66 (m, 8H). 2 protons not integrated due to broadening. NH proton not observed due to solvent exchange. |

The compounds in the following table were prepared by the method of Example 192, using the appropriate commercially available aldehyde in step 3.

| Example No. | Structure | Mass [M + H]⁺ | ¹H NMR |
|---|---|---|---|
| 198 | (S)-1-(5-((4-(cycloheptylmethyl)-3-methylpiperazin-1-yl)methyl)pyrazolo[1,5-a]pyridin-3-yl)dihydropyrimidine-2,4(1H,3H)-dione | 453.0 | (400 MHz, CD₃OD): δ 8.45 (d, J = 6.8 Hz, 1H), 8.02 (s, 1H), 7.50 (s, 1H), 6.99 (d, J = 6.8 Hz, 1H), 3.89 (t, J = 7.2 Hz, 2H), 3.63-3.54 (s, 2H), 2.91-2.79 (m, 6H), 3.14-3.07 (m, 2H), 2.87 (t, J = 6.8 Hz, 2H), 2.48-2.16 (m, 1H), 1.86-1.47 (m, 12H), 1.21-1.14 (m, 5H), ppm. NH proton not observed due to solvent exchange. |

| Example No. | Structure | Mass [M + H]+ | ¹H NMR |
|---|---|---|---|
| 199 | 1-(5-(((3S)-4-(((2R,6S)-2,6-dimethyltetrahydro-2H-pyran-4-yl)methyl)-3-methylpiperazin-1-yl)methyl)pyrazolo[1,5-a]pyridin-3-yl)dihydropyrimidine-2,4(1H,3H)-dione | 469.3 | (400 MHz, Methanol-d4) δ 8.56 (dd, J = 7.0, 2.7 Hz, 1H), 8.09 (d, J = 2.0 Hz, 1H), 7.67 (s, 1H), 7.00 (dd, J = 7.3, 1.8 Hz, 1H), 4.14 (s, 1H), 3.91 (t, J = 6.8 Hz, 2H), 3.99-3.37 (m, 8H), 3.12 (s, 3H), 2.89 (t, J = 6.8 Hz, 2H), 2.46-1.95 (m, 1H), 1.81-1.49 (m, 2H), 1.43 (d, J = 6.6 Hz, 3H), 1.29 (s, 1H), 1.22-1.10 (m, 6H), 1.04-0.84 (m, 2H). NH proton not observed due to solvent exchange. |
| 200 | (S)-1-(5-((4-((4,4-dimethylcyclohexyl)methyl)-3-methylpiperazin-1-yl)methyl)pyrazolo[1,5-a]pyridin-3-yl)dihydropyrimidine-2,4(1H,3H)-dione | 467.3 | (400 MHz, CD₃OD) δ 8.46-8.43 (m, 2H), 8.02 (s, 1H), 7.48 (s, 1H), 6.99-6.97 (m, 1H), 3.88 (t, J = 7.2 Hz, 2H), 3.64-3.62 (m, 2H), 3.48-3.40 (m, 2H), 3.12-2.40 (m, 8H), 1.68-1.23 (m, 12H), 0.92 (d, J = 2.4 Hz, 6H). NH proton not observed due to solvent exchange. |

Example 201. Preparation of 1-(5-(((S)-4-(((1r,4S)-4-hydroxycyclohexyl)methyl)-3-methylpiperazin-1-yl)methyl)pyrazolo[1,5-a]pyridin-3-yl)dihydropyrimidine-2,4(1H,3H)-dione

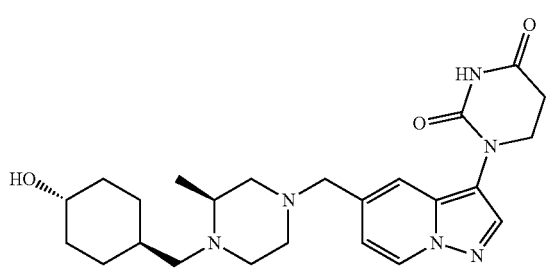 [SMILES: C[C@H]1CN(Cc2ccn3ncc(N4CCC(=O)NC4=O)c3c2)CCN1C[C@H]1CC[C@H](O)CC1]

Prepared using the method of Example 192, steps 3-4, wherein trans-4-(benzyloxy)cyclohexane-1-carbaldehyde (see WO2020/232470, 2020, A1 which is incorporated herein by reference) was used in place of cyclohexanecarbaldehyde. LCMS [M+H]: 455.2. ¹H NMR (400 MHz, Methanol-d4) δ 8.44 (d, J=7.1 Hz, 1H), 8.00 (d, J=11.5 Hz, 1H), 7.38 (s, 1H), 6.83 (d, J=6.2 Hz, 1H), 3.88 (t, J=6.8 Hz, 2H), 3.63-3.44 (m, 3H), 2.96-2.85 (m, 6H), 2.73-2.64 (m, 2H), 2.08-1.72 (m, 7H), 1.58 (q, J=12.1, 11.1 Hz, 2H), 1.37-1.22 (m, 4H), 1.11 (q, J=12.5 Hz, 2H), NH and OH protons not observed due to solvent exchange.

The compounds in the following table were prepared from (S)-3-(2,4-dimethoxybenzyl)-1-(5-((3-methylpiperazin-1-yl)methyl)pyrazolo[1,5-a]pyridin-3-yl)dihydropyrimidine-2,4(1H,3H)-dione trifluoroacetate by the method of Example 156, steps 3-4 using the appropriate commercially available halide, mesylate or triflate in step 3.

| Example No. | Structure | Mass [M + H]+ | 1H NMR |
|---|---|---|---|
| 202 | (S)-1-(5-((3-methyl-4-((tetrahydro-2H-pyran-4-yl)methyl)piperazin-1-yl)methyl)pyrazolo[1,5-a]pyridin-3-yl)dihydropyrimidine-2,4(1H,3H)-dione | 441.3 | (500 MHz, DMSO-d6) δ 10.43 (s, 1H), 8.57 (d, J = 7.1 Hz, 1H), 8.01 (s, 1H), 7.44 (s, 1H), 6.88 (dd, J = 7.2, 1.8 Hz, 1H), 3.81 (d, J = 11.6 Hz, 2H), 3.77 (t, J = 6.7 Hz, 2H), 3.49-3.38 (m, 2H), 3.30-3.19 (m, 2H), 2.78 (t, J = 6.7 Hz, 3H), 2.56 (d, J = 12.1 Hz, 2H), 2.46 (d, J = 12.2 Hz, 1H), 2.36 (d, J = 12.4 Hz, 1H), 2.18 (t, J = 10.5 Hz, 2H), 1.92 (s, 2H), 1.66 (d, J = 12.4 Hz, 2H), 1.51 (d, J = 13.0 Hz, 1H), 1.22-1.00 (m, 2H), 0.94 (d, J = 6.2 Hz, 3H). |
| 203 | (S)-1-(5-((4-isobutyl-3-methylpiperazin-1-yl)methyl)pyrazolo[1,5-a]pyridin-3-yl)dihydropyrimidine-2,4(1H,3H)-dione | 399.4 | (500 MHz, Methanol-d4) δ 8.46 (dd, J = 7.1, 0.9 Hz, 1H), 8.02 (s, 1H), 7.51 (dd, J = 1.9, 1.0 Hz, 1H), 7.01 (dd, J = 7.2, 1.8 Hz, 1H), 3.91 (t, J = 6.7 Hz, 2H), 3.63-3.49 (m, 2H), 2.91 (t, J = 6.8 Hz, 3H), 2.73 (dd, J = 28.7, 10.7 Hz, 2H), 2.39 (dd, J = 71.2, 21.3 Hz, 4H), 2.02 (d, J = 45.3 Hz, 2H), 1.81 (s, 1H), 1.04 (d, J = 6.2 Hz, 3H), 0.93 (dd, J = 7.7, 6.6 Hz, 6H). |
| 204 | (S)-1-(5-((4-isopentyl-3-methylpiperazin-1-yl)methyl)pyrazolo[1,5-a]pyridin-3-yl)dihydropyrimidine-2,4(1H,3H)-dione | 413.4 | (400 MHz, DMSO-d6) δ 10.44 (s, 1H), 8.62 (d, J = 7.2 Hz, 1H), 8.04 (s, 1H), 7.49 (s, 1H), 6.89 (dd, J = 7.1, 1.8 Hz, 1H), 3.78 (t, J = 6.7 Hz, 2H), 3.62 (s, 3H), 3.29 (s, 2H), 3.00 (s, 4H), 2.79 (t, J = 6.7 Hz, 2H), 2.44-2.18 (m, 2H), 1.72-1.40 (m, 3H), 1.29 (dd, J = 29.4, 6.4 Hz, 3H), 0.92 (t, J = 6.1 Hz, 6H). |
| 205 | (S)-1-(5-((4-((3,3-difluorocyclobutyl)methyl)-3-methylpiperazin-1-yl)methyl)pyrazolo[1,5-a]pyridin-3-yl)dihydropyrimidine-2,4(1H,3H)-dione | 447.3 | (500 MHz, DMSO-d6) δ 10.43 (s, 1H), 8.57 (dd, J = 7.2, 0.9 Hz, 1H), 8.01 (s, 1H), 7.51-7.23 (m, 1H), 6.88 (dd, J = 7.2, 1.8 Hz, 1H), 3.77 (t, J = 6.7 Hz, 2H), 3.49-3.42 (m, 2H), 2.83-2.70 (m, 4H), 2.60 (q, J = 14.0, 11.8 Hz, 4H), 2.37 (s, 1H), 2.32-2.12 (m, 6H), 1.91 (s, 1H), 0.95 (d, J = 6.2 Hz, 3H). |

-continued

| Example No. | Structure | Mass [M + H]+ | 1H NMR |
|---|---|---|---|
| 206 | (S)-1-(5-((3-methyl-4-(2-(tetrahydro-2H-pyran-4-yl)ethyl)piperazin-1-yl)methyl)pyrazolo[1,5-a]pyridin-3-yl)dihydropyrimidine-2,4(1H,3H)-dione | 455.4 | (400 MHz, DMSO-d6) δ 10.44 (s, 1H), 8.74-8.50 (m, 1H), 8.04 (s, 1H), 7.49 (s, 1H), 6.89 (dd, J = 7.2, 1.8 Hz, 1H), 3.84 (dd, J = 11.0, 4.1 Hz, 2H), 3.78 (t, J = 6.7 Hz, 2H), 3.64 (s, 3H), 3.50 (d, J = 11.4 Hz, 1H), 3.41-3.19 (m, 4H), 3.00 (d, J = 14.8 Hz, 4H), 2.79 (t, J = 6.7 Hz, 2H), 2.26 (d, J = 11.8 Hz, 1H), 1.59 (d, J = 13.9 Hz, 5H), 1.22 (dd, J = 22.3, 9.4 Hz, 5H). |
| 207 | (S)-1-(5-((4-((4,4-difluorocyclohexyl)methyl)-3-methylpiperazin-1-yl)methyl)pyrazolo[1,5-a]pyridin-3-yl)dihydropyrimidine-2,4(1H,3H)-dione | 475.2 | (500 MHz, DMSO-d6) δ 10.43 (s, 1H), 8.57 (d, J = 7.1 Hz, 1H), 8.01 (s, 1H), 7.44 (s, 1H), 6.88 (dd, J = 7.2, 1.8 Hz, 1H), 3.77 (t, J = 6.7 Hz, 2H), 3.50-3.40 (m, 2H), 2.78 (t, J = 6.7 Hz, 2H), 2.68-2.53 (m, 2H), 2.50-2.28 (m, 4H), 2.17 (dt, J = 19.9, 10.0 Hz, 2H), 2.05-1.64 (m, 8H), 1.09 (dt, J = 45.2, 11.8 Hz, 2H), 0.94 (d, J = 6.1 Hz, 3H). |
| 208 | (S)-1-(5-((3-methyl-4-(pyridin-3-ylmethyl)piperazin-1-yl)methyl)pyrazolo[1,5-a]pyridin-3-yl)dihydropyrimidine-2,4(1H,3H)-dione | 434.4 | (400 MHz, DMSO-d6) δ 10.41 (br s, 1H), 8.56 (d, J = 7.2 Hz, 1H), 8.48 (d, J = 1.6 Hz, 1H), 8.46-8.43 (m, 1H), 8.00 (s, 1H), 7.69 (d, J = 8.0 Hz, 1H), 7.43 (s, 1H), 7.37-7.31 (m, 1H), 6.90-6.84 (m, 1H), 3.95 (d, J = 14.0 Hz, 1H), 3.78-3.74 (m, 2H), 3.52-3.42 (m, 3H), 3.23 (d, J = 14.0 Hz, 1H), 2.79-2.75 (m, 2H), 2.64-2.55 (m, 3H), 2.17 (d, J = 8.0 Hz, 2H), 2.04-1.93 (m, 1H), 1.07 (d, J = 6.0 Hz, 3H). |

| Example No. | Structure | Mass [M + H]+ | 1H NMR |
|---|---|---|---|
| 209 | 1-(5-(((3S)-3-methyl-4-((tetrahydrofuran-2-yl)methyl)piperazin-1-yl)methyl)pyrazolo[1,5-a]pyridin-3-yl)dihydropyrimidine-2,4(1H,3H)-dione | 427.0 | (400 MHz, Methanol-d4) δ 8.62 (d, J = 7.2 Hz, 1H), 8.15 (s, 1H), 7.89 (s, 1H), 7.05 (d, J = 7.3 Hz, 1H), 4.56 (s, 2H), 4.27 (q, J = 8.1 Hz, 1H), 4.14 (s, 1H), 4.05-3.74 (m, 7H), 3.74-3.50 (m, 3H), 3.50-3.20 (m, 3H), 2.91 (t, J = 6.8 Hz, 2H), 2.20 (dq, J = 12.8, 6.4 Hz, 1H), 2.09-1.87 (m, 2H), 1.77-1.57 (m, 1H), 1.48 (d, J = 6.6 Hz, 3H). NH proton not observed due to solvent exchange. |

Example 203 (alternate synthesis). Preparation of (S)-1-(5-((4-isobutyl-3-methylpiperazin-1-yl)methyl)pyrazolo[1,5-a]pyridin-3-yl)dihydropyrimidine-2,4(1H,3H)-dione (Example 203)

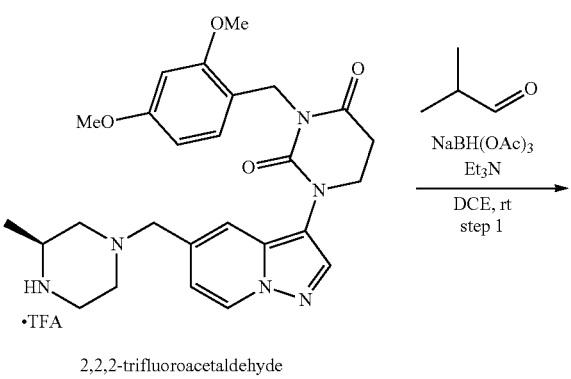

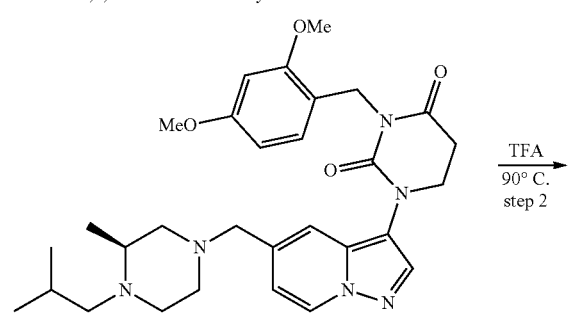

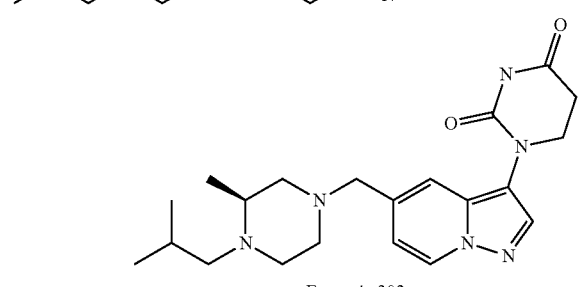

Example 203

Step 1. (S)-3-(2,4-dimethoxybenzyl)-1-(5-((4-isobutyl-3-methylpiperazin-1-yl)methyl)pyrazolo[1,5-a]pyridin-3-yl)dihydropyrimidine-2,4(1H,3H)-dione To a solution of (S)-3-(2,4-dimethoxybenzyl)-1-(5-((3-methylpiperazin-1-yl)methyl)pyrazolo[1,5-a]pyridin-3-yl)dihydropyrimidine-2,4(1H,3H)-dione trifluoroacetate (2.2 g, 3.6 mmol) in DCM (20 mL) was added Et₃N (0.51 mL, 3.6 mmol) followed by isobutyraldehyde (1.31 g, 18.1 mmol). The mixture was stirred at rt for 30 min and then NaBH(OAc)₃ (3.84 g, 18.1 mmol) was added. The reaction was stirred overnight at rt. The reaction was quenched with a solution of saturated aqueous NaHCO₃ and extracted with DCM. The organic layer was dried over Na₂SO₄, filtered and concentrated. Silica gel column chromatography (eluting with 10-100% EtOAc (containing 25% EtOH) in hexane) provided (S)-3-(2,4-dimethoxybenzyl)-1-(5-((4-isobutyl-3-methylpiperazin-1-yl)methyl)pyrazolo[1,5-a]pyridin-3-yl)dihydropyrimidine-2,4(1H,3H)-dione (1.25 g, 2.28 mmol, 63% yield) as a white solid. LCMS [M+H]+: 549.3.

Step 2. (S)-1-(5-((4-isobutyl-3-methylpiperazin-1-yl)methyl)pyrazolo[1,5-a]pyridin-3-yl)dihydropyrimidine-2,4(1H,3H)-dione (Example 203)

TFA (10 mL) was added to (S)-3-(2,4-dimethoxybenzyl)-1-(5-((4-isobutyl-3-methylpiperazin-1-yl)methyl)pyrazolo[1,5-a]pyridin-3-yl)dihydropyrimidine-2,4(1H,3H)-dione (1.25 g, 2.28 mmol). The reaction mixture was stirred for 16 h at 90° C. and then concentrated. The crude material was dissolved in DCM and washed with a solution of saturated aqueous NaHCO₃. The layers were separated and the aqueous layer was extracted with DCM. The combined organic layers were washed with brine, dried over Na₂SO₄, filtered and concentrated. Silica gel column chromatography (eluting with 10-100% EtOAc (containing 25% EtOH) in hexane) provided (S)-1-(5-((4-isobutyl-3-methylpiperazin-1-yl)methyl)pyrazolo[1,5-a]pyridin-3-yl)dihydropyrimidine-2,4(1H,3H)-dione (800 mg, 1.97 mmol, 86% yield). LCMS [M+H]+: 399.4. ¹H NMR (500 MHz, Methanol-d4) δ 8.46 (dd, J=7.1, 0.9 Hz, 1H), 8.02 (s, 1H), 7.51 (dd, J=1.9, 1.0 Hz, 1H), 7.01 (dd, J=7.2, 1.8 Hz, 1H), 3.91 (t, J=6.7 Hz, 2H), 3.63-3.49 (m, 2H), 2.91 (t, J=6.8 Hz, 3H), 2.73 (dd, J=28.7, 10.7 Hz, 2H), 2.39 (dd, J=71.2, 21.3 Hz, 4H), 2.02 (d, J=45.3 Hz, 2H), 1.81 (s, 1H), 1.04 (d, J=6.2 Hz, 3H), 0.93 (dd, J=7.7, 6.6 Hz, 6H).

Examples 210 and 211. Preparation of 1-(5-(((S)-4-(((1r,4S)-4-methoxycyclohexyl)methyl)-3-methylpiperazin-1-yl)methyl)pyrazolo[1,5-a]pyridin-3-yl)dihydropyrimidine-2,4(1H,3H)-dione (Example 210) and 1-(5-(((S)-4-(((1s,4R)-4-methoxycyclohexyl)methyl)-3-methylpiperazin-1-yl)methyl)pyrazolo[1,5-a]pyridin-3-yl)dihydropyrimidine-2,4(1H,3H)-dione (Example 211)

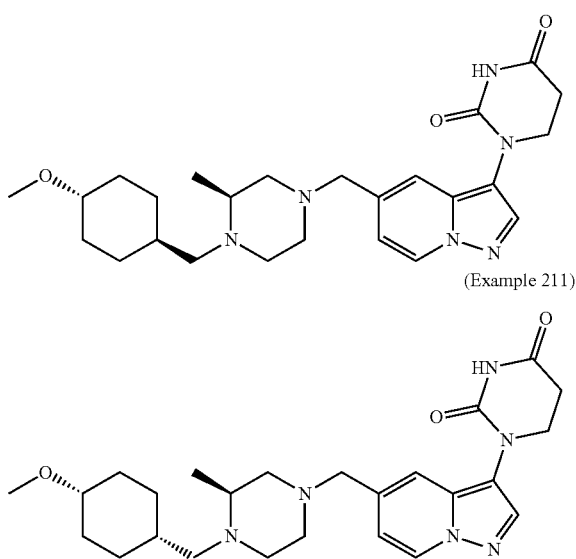

(Example 210)

(Example 211)

Prepared using the method of Example 202, wherein a commercially available mixture of cis and trans 1-(bromomethyl)-4-methoxycyclohexane was used in place of trans-4-(benzyloxy)cyclohexane-1-carbaldehyde. The stereoisomers were purified after the final step by reverse-phase HPLC (eluting with using ACN/Water/0.1% TFA).

Example 210. 1-(5-(((S)-4-(((1r,4S)-4-methoxycyclohexyl)methyl)-3-methylpiperazin-1-yl)methyl)pyrazolo[1,5-a]pyridin-3-yl)dihydropyrimidine-2,4(1H,3H)-dione Eluted first, minor isomer. LCMS [M+H]$^+$: 469.3. $^1$H NMR (400 MHz, DMSO-d6) δ 10.45 (s, 1H), 8.64 (d, J=7.2 Hz, 1H), 8.05 (s, 1H), 7.52 (s, 1H), 6.90 (dd, J=7.2, 1.8 Hz, 1H), 4.99 (s, 4H), 3.79 (t, J=6.7 Hz, 2H), 3.72 (s, 2H), 3.23 (s, 4H), 3.13-2.94 (m, 4H), 2.79 (t, J=6.7 Hz, 3H), 2.37 (d, J=30.0 Hz, 1H), 2.00 (s, 2H), 1.92-1.57 (m, 2H), 1.26 (s, 3H), 1.07 (dt, J=37.0, 13.5 Hz, 4H).

Example 211. 1-(5-(((S)-4-(((1s,4R)-4-methoxycyclohexyl)methyl)-3-methylpiperazin-1-yl)methyl)pyrazolo[1,5-a]pyridin-3-yl)dihydropyrimidine-2,4(1H,3H)-dione Eluted second, major isomer. LCMS [M+H]$^+$: 469.3. $^1$H NMR 400 MHz, DMSO-d6) δ 10.44 (s, 1H), 8.63 (d, J=7.2 Hz, 1H), 8.04 (s, 1H), 7.50 (s, 1H), 6.90 (dd, J=7.2, 1.8 Hz, 1H), 3.78 (t, J=6.7 Hz, 2H), 3.67 (s, 5H), 3.23 (s, 3H), 3.20 (s, 3H), 3.17-2.84 (m, 4H), 2.79 (t, J=6.7 Hz, 2H), 2.46-2.21 (m, 1H), 1.92-1.69 (m, 3H), 1.55 (s, 1H), 1.51-1.29 (m, 4H), 1.25 (s, 3H).

Example 212. Preparation of (S)-1-(5-((4-(cycloheptylmethyl)-3-methylpiperazin-1-yl)methyl)pyrazolo[1,5-a]pyridin-3-yl)dihydropyrimidine-2,4(1H,3H)-dione

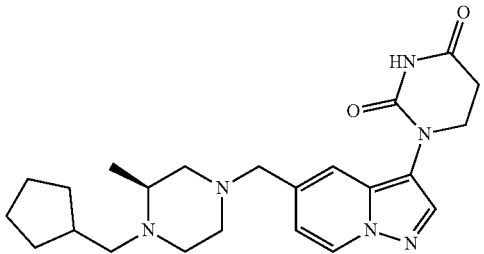 [SMILES: C[C@H]1CN(Cc2ccn3ncc(N4CCC(=O)NC4=O)c3c2)CCN1CC1CCCC1]

Prepared using the method of Example 186, wherein tert-butyl (S)-4-((3-(3-(2,4-dimethoxybenzyl)-2,4-dioxotetrahydropyrimidin-1(2H)-yl)pyrazolo[1,5-a]pyridin-5-yl)methyl)-2-methylpiperazine-1-carboxylate was used in place of tert-butyl 4-((3-(3-(2,4-dimethoxybenzyl)-2,4-dioxotetrahydropyrimidin-1(2H)-yl)pyrazolo[1,5-a]pyridin-5-yl)methyl)piperazine-1-carboxylate, and cyclopentanecarbaldehyde was used in place of isobutyraldehyde. LCMS [M+H]$^+$: 425.3. $^1$H NMR (400 MHz, DMSO-d6) δ 10.44 (s, 1H), 8.63 (d, J=7.2 Hz, 1H), 8.04 (s, 1H), 7.51 (s, 1H), 6.90 (dd, J=7.2, 1.9 Hz, 1H), 4.39 (s, 3H), 3.78 (t, J=6.7 Hz, 2H), 3.61 (d, J=44.7 Hz, 3H), 3.30 (d, J=20.9 Hz, 2H), 3.00 (d, J=14.0 Hz, 3H), 2.79 (t, J=6.7 Hz, 2H), 2.18 (s, 1H), 1.79 (d, J=20.7 Hz, 2H), 1.58 (ddd, J=38.4, 7.7, 4.0 Hz, 4H), 1.42-1.10 (m, 5H).

Example 213. Preparation of (S)-1-(5-((4-(cyclobutylmethyl)-3-methylpiperazin-1-yl)methyl)pyrazolo[1,5-a]pyridin-3-yl)dihydropyrimidine-2,4(1H,3H)-dione

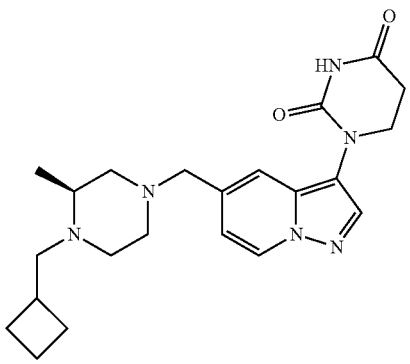 [SMILES: C[C@H]1CN(Cc2ccn3ncc(N4CCC(=O)NC4=O)c3c2)CCN1CC1CCC1]

Prepared using the method of Example 186, wherein tert-butyl (S)-4-((3-(3-(2,4-dimethoxybenzyl)-2,4-dioxotetrahydropyrimidin-1(2H)-yl)pyrazolo[1,5-a]pyridin-5-yl)methyl)-2-methylpiperazine-1-carboxylate was used in place of tert-butyl 4-((3-(3-(2,4-dimethoxybenzyl)-2,4-dioxotetrahydropyrimidin-1(2H)-yl)pyrazolo[1,5-a]pyridin-5- yl)methyl)piperazine-1-carboxylate, and cyclobutanecarbaldehyde was used in place of isobutyraldehyde. LCMS [M+H]⁺: 411.5. ¹H NMR (500 MHz, DMSO-d6) δ 10.44 (s, 1H), 8.58 (d, J=7.1 Hz, 1H), 8.02 (s, 1H), 7.45 (s, 1H), 6.89 (dd, J=7.1, 1.8 Hz, 1H), 3.78 (t, J=6.7 Hz, 2H), 3.47 (s, 2H), 2.79 (t, J=6.7 Hz, 2H), 2.76-2.57 (m, 3H), 2.56 (s, 2H), 2.14 (d, J=47.7 Hz, 3H), 1.99 (s, 3H), 1.92-1.73 (m, 3H), 1.65 (s, 2H), 1.03 (d, J=50.1 Hz, 3H).

The compounds in the following table were prepared using the method of Example 192, wherein potassium (R)-((4-(tert-butoxycarbonyl)-3-methylpiperazin-1-yl)methyl)trifluoroborate was used in place of tert-butyl (S)-2-methyl-4-((trifluoro-l4-boraneyl)methyl)piperazine-1-carboxylate, potassium salt and the appropriate commercially available aldehyde was used in place of cyclohexanecarbaldehyde.

| Example No. | Structure | Mass [M + H]⁺ | ¹H NMR |
|---|---|---|---|
| 214 | (R)-1-(5-((4-(cyclohexylmethyl)-3-methylpiperazin-1-yl)methyl)pyrazolo[1,5-a]pyridin-3-yl)dihydropyrimidine-2,4(1H,3H)-dione | 439.1 | (400 MHz, DMSO-d6) δ 10.43 (s, 1H), 8.60-8.54 (m, 1H), 8.00 (s, 1H), 7.44 (s, 1H), 6.89-6.86 (m, 1H), 3.79-3.75 (m, 2H), 3.51-3.39 (m, 2H), 2.81-2.71 (m, 3H), 2.58-2.52 (m, 2H), 2.45-2.39 (m, 1H), 2.36-2.26 (m, 1H), 2.24-2.06 (m, 2H), 2.00-1.75 (m, 3H), 1.63 (br s, 4H), 1.47-1.35 (m, 1H), 1.29-1.07 (m, 3H), 0.92 (d, J = 6.0 Hz, 3H), 0.89-0.69 (m, 2H). |
| 215 | (R)-1-(5-((3-methyl-4-(pyridin-3-ylmethyl)piperazin-1-yl)methyl)pyrazolo[1,5-a]pyridin-3-yl)dihydropyrimidine-2,4(1H,3H)-dione | 434.1 | (400 MHz, CDCl₃) δ 8.55 (d, J = 1.8 Hz, 1H), 8.49-8.47 (m, 1H), 8.35 (d, J = 7.2 Hz, 1H), 8.09-7.88 (m, 2H), 7.67-7.64 (m, 1H), 7.29 (s, 1H), 7.27-7.25 (m, 1H), 6.89-6.87 (m, 1H), 4.02-3.99 (m, 1H), 3.88 (t, J = 6.8 Hz, 2H), 3.48 (s, 2H), 3.24-3.21 (m, 1H), 2.90 (t, J = 6.8 Hz, 2H), 2.71-2.50 (m, 4H), 2.25-2.23 (m, 2H), 2.07-2.06 (m, 1H), 1.14 (d, J = 6.4 Hz, 3H). |
| 216 | (R)-1-(5-((4-isobutyl-3-methylpiperazin-1-yl)methyl)pyrazolo[1,5-a]pyridin-3-yl)dihydropyrimidine-2,4(1H,3H)-dione | 399.0 | (400 MHz, Methanol-d4) δ 8.53 (s, 1H), 8.45 (d, J = 7.3 Hz, 1H), 8.02 (s, 1H), 7.50 (s, 1H), 6.99 (dd, J = 7.2, 2.0 Hz, 1H), 4.73-4.50 (m, 1H), 3.89 (t, J = 6.8 Hz, 2H), 3.63 (d, J = 13.5 Hz, 1H), 3.58 (d, J = 13.5 Hz, 1H), 3.19 (d, J = 12.0 Hz, 1H), 2.89 (t, J = 6.8 Hz, 2H), 2.87-2.71 (m, 4H), 2.65 (s, 1H), 2.53-2.19 (m, 3H), 1.93 (hept, J = 6.1 Hz, 2H), 1.18 (d, J = 6.2 Hz, 3H), 0.98 (d, J = 6.0 Hz, 3H), 0.96 (s, 3H). NH proton not observed due to solvent exchange |

-continued

| Example No. | Structure | Mass [M + H]+ | 1H NMR |
|---|---|---|---|
| 217 | (R)-1-(5-((3-methyl-4-((tetrahydro-2H-pyran-4-yl)methyl)piperazin-1-yl)methyl)pyrazolo[1,5-a]pyridin-3-yl)dihydropyrimidine-2,4(1H,3H)-dione | 441.3 | (400 MHz, Methanol-d4) δ 8.53 (d, J = 7.2 Hz, 1H), 8.46 (d, J = 7.2 Hz, 1H), 8.03 (s, 1H), 7.51 (s, 1H), 7.00 (dd, J = 7.2, 1.8 Hz, 1H), 3.98-3.87 (m, 4H), 3.63 (d, J = 13.6 Hz, 1H), 3.58 (d, J = 13.6 Hz, 1H), 3.50-3.37 (m, 2H), 3.16 (dt, J = 12.2, 3.4 Hz, 1H), 2.90 (t, J = 6.8 Hz, 2H), 2.87-2.76 (m, 4H), 2.62 (t, J = 10.9 Hz, 1H), 2.45 (t, J = 10.7 Hz, 1H), 2.36 (dd, J = 11.2, 4.4 Hz, 1H), 2.29-2.18 (m, 1H), 1.97-1.84 (m, 1H), 1.78 (ddd, J = 13.3, 4.0, 2.1 Hz, 1H), 1.66-1.58 (m, 1H), 1.38-1.21 (m, 2H), 1.17 (d, J = 6.2 Hz, 3H). NH proton not observed due to solvent exchange |

The compounds in the following table were prepared using the method of Example 192, wherein potassium (R)-((4-(tert-butoxycarbonyl)-2-methylpiperazin-1-yl)methyl)trifluoroborate [see *J. Med. Chem.* 2012, 55, 7796-7816] was used in place of tert-butyl (S)-2-methyl-4-((trifluoro-l4-boraneyl)methyl)piperazine-1-carboxylate, potassium salt, and the appropriate commercially available aldehyde was used in place of cyclohexanecarbaldehyde.

| Example No. | Structure | Mass [M + H]+ | 1H NMR |
|---|---|---|---|
| 218 | (R)-1-(5-((4-(cyclohexylmethyl)-2-methylpiperazin-1-yl)methyl)pyrazolo[1,5-a]pyridin-3-yl)dihydropyrimidine-2,4(1H,3H)-dione | 439.1 | (400 MHz, DMSO-d6) δ 10.43 (s, 1H), 8.40 (d, J = 7.2 Hz, 1H), 7.99 (s, 1H), 7.43 (s, 1H), 6.88-6.84 (m, 1H), 3.96-3.91 (m, 1H), 3.76 (t, J = 6.8 Hz, 2H), 3.19-3.15 (m, 1H), 2.77 (t, J = 6.8 Hz, 2H), 2.62-2.51 (m, 3H), 2.44 (br s, 1H), 2.19-2.09 (m, 1H), 2.07-1.95 (m, 3H), 1.88-1.86 (m, 1H), 1.76-1.56 (m, 5H), 1.50-1.37 (m, 1H, 1.25-1.03 (m, 6H), 0.84-0.75 (m, 2H). |
| 219 | (R)-1-(5-((2-methyl-4-((tetrahydro-2H-pyran-4-yl)methyl)piperazin-1-yl)methyl)pyrazolo[1,5-a]pyridin-3-yl)dihydropyrimidine-2,4(1H,3H)-dione | 441.2 | (400 MHz, Methanol-d4) δ 8.63 (d, J = 7.2 Hz, 1H), 8.14 (d, J = 2.2 Hz, 1H), 7.81 (d, J = 5.4 Hz, 1H), 7.05-6.94 (m, 1H), 4.89-4.88 (m, 2H), 4.29-4.16 (m, 1H), 4.00-3.85 (m, 5H), 3.84-3.66 (m, 2H), 3.66-3.55 (m, 1H), 3.50-3.41 (m, 2H), 3.26-3.05 (m, 4H), 2.90 (t, J = 6.8 Hz, 2H), 2.24-2.08 (m, 1H), 1.78-1.47 (m, 5H), 1.45-1.30 (m, 3H). NH protons not observed due to solvent exchange. |

| Example No. | Structure | Mass [M + H]⁺ | ¹H NMR |
|---|---|---|---|
| 220 | (R)-1-(5-((4-isobutyl-3-methylpiperazin-1-yl)methyl)pyrazolo[1,5-a]pyridin-3-yl)dihydropyrimidine-2,4(1H,3H)-dione | 399.3 | (400 MHz, CD$_3$OD) δ 8.46 (s, 1H), 8.45 (d, J = 6.8 Hz, 1H), 8.01 (s, 1H), 7.50 (s, 1H), 6.99-6.96 (m, 1H), 4.18 (d, J = 14.0 Hz, 2H), 3.88 (d, J = 6.8 Hz, 2H), 3.12-3.08 (m, 2H), 2.88 (t, J = 6.4 Hz, 2H), 2.72-2.37 (m, 7H), 1.99-1.95 (m, 1H), 1.23 (d, J = 6.0 Hz, 3H), 0.97 (d, J = 6.4 Hz, 6H). |

The compounds in the following table were prepared using the method of Example 192, wherein potassium (S)-((4-(tert-butoxycarbonyl)-2-methylpiperazin-1-yl)methyl)trifluoroborate [see *J. Med. Chem.* 2012, 55, 7796-7816] was used in place of tert-butyl (S)-2-methyl-4-((trifluoro-I4-boraneyl)methyl)piperazine-1-carboxylate, potassium salt and the appropriate commercially available aldehyde was used in place of cyclohexanecarbaldehyde.

| Example No. | Structure | Mass [M + H]⁺ | ¹H NMR |
|---|---|---|---|
| 221 | (S)-1-(5-((4-(cyclohexylmethyl)-2-methylpiperazin-1-yl)methyl)pyrazolo[1,5-a]pyridin-3-yl)dihydropyrimidine-2,4(1H,3H)-dione | 439.1 | (400 MHz, DMSO-d6) δ = 10.43 (br s, 1H), 8.55 (d, J = 7.2 Hz, 1H), 7.99 (s, 1H), 7.43 (s, 1H), 6.93-6.81 (m, 1H), 3.94 (d, J = 13.8 Hz, 1H), 3.78-3.74 (m, 2H), 3.17 (d, J = 13.8 Hz, 1H), 2.78-2.75 (m, 2H), 2.63-2.52 (m, 3H), 2.47-2.41 (m, 1H), 2.19-1.96 (m, 4H), 1.87 (d, J = 8.6 Hz, 1H), 1.76-1.57 (m, 5H), 1.49-1.37 (m, 1H), 1.24-1.05 (m, 6H), 0.90-0.69 (m, 2H). |
| 222 | (S)-1-(5-((4-isobutyl-2-methylpiperazin-1-yl)methyl)pyrazolo[1,5-a]pyridin-3-yl)dihydropyrimidine-2,4(1H,3H)-dione | 399.0 | (400 MHz, DMSO-D6) δ 10.44 (s, 1H), 8.60-8.57 (m, 1H), 8.31 (s, 1H), 8.13 (s, 1H), 8.01 (d, J = 2.4 Hz, 1H), 7.46 (s, 1H), 6.87-6.88 (m, 1H), 4.00 (m, 1H), 3.76 (t, J = 6.4 Hz, 2H), 3.55-3.50 (m, 1H), 2.92-2.08 (m, 6H), 2.32-2.10 (m, 3H), 1.85 (s, 1H), 1.13 (d, J = 6.0 Hz, 3H), 0.87 (d, J = 6.4 Hz, 6H). |

| Example No. | Structure | Mass [M + H]⁺ | ¹H NMR |
|---|---|---|---|
| 223 | (S)-1-(5-((2-methyl-4-((tetrahydro-2H-pyran-4-yl)methyl)piperazin-1-yl)methyl)pyrazolo[1,5-a]pyridin-3-yl)dihydropyrimidine-2,4(1H,3H)-dione | 440.8 | (400 MHz, Methanol-d4) δ 8.48 (d, J = 7.4 Hz, 1H), 8.04 (s, 1H), 7.54 (s, 1H), 6.98 (d, J = 7.1 Hz, 1H), 4.30 (s, 1H), 4.00-3.85 (m, 4H), 3.45 (t, J = 12.0 Hz, 4H), 3.16-2.77 (m, 8H), 2.55 (s, 1H), 2.11 (s, 1H), 1.69 (d, J = 13.2 Hz, 3H), 1.34 (d, J = 17.8 Hz, 5H). NH protons not observed due to solvent exchange. |
| 224 | (S)-1-(5-((4-(cyclobutylmethyl)-2-methylpiperazin-1-yl)methyl)pyrazolo[1,5-a]pyridin-3-yl)dihydropyrimidine-2,4(1H,3H)-dione | 411.1 | (400 MHz, Methanol-d4) δ 8.46 (d, J = 7.2 Hz, 1H), 8.37 (s, 1H), 8.02 (s, 1H), 7.50 (s, 1H), 6.97 (dd, J = 7.2, 1.9 Hz, 1H), 4.20 (d, J = 14.3 Hz, 1H), 3.89 (t, J = 6.8 Hz, 2H), 3.32-3.20 (m, 1H), 3.08 (s, 2H), 2.97-2.86 (m, 4H), 2.75 (d, J = 8.0 Hz, 3H), 2.41 (s, 1H), 2.18 (d, J = 7.8 Hz, 2H), 2.02 (d, J = 7.5 Hz, 1H), 1.87 (s, 3H), 1.35-1.28 (m, 2H), 1.26 (d, J = 4.9 Hz, 4H). NH protons not observed due to solvent exchange. |
| 225 | 1-(5-(((2S)-2-methyl-4-((tetrahydrofuran-2-yl)methyl)piperazin-1-yl)methyl)pyrazolo[1,5-a]pyridin-3-yl)dihydropyrimidine-2,4(1H,3H)-dione | 427.1 | (400 MHz, DMSO-d6) δ 10.44 (s, 1H), 8.58 (d, J = 7.3 Hz, 1H), 8.13 (s, 1H), 8.01 (s, 1H), 7.46 (s, 1H), 6.86 (d, J = 7.2 Hz, 1H), 4.06-3.94 (m, 2H), 3.82-3.71 (m, 3H), 3.63 (q, J = 8.6, 7.9 Hz, 1H), 3.10-2.85 (m, 3H), 2.77 (t, J = 6.7 Hz, 2H), 2.72-2.54 (m, 5H), 2.37-2.19 (m, 2H), 1.94 (qd, J = 12.4, 6.7 Hz, 1H), 1.86-1.72 (m, 2H), 1.46 (dq, J = 12.0, 7.8 Hz, 1H), 1.11 (d, J = 6.0 Hz, 3H). NH protons not observed due to solvent exchange. |

Example 226. Preparation of (S)-1-(5-((4-((3,3-difluorocyclobutyl)methyl)-2-methylpiperazin-1-yl)methyl)pyrazolo[1,5-a]pyridin-3-yl)dihydropyrimidine-2,4(1H,3H)-dione

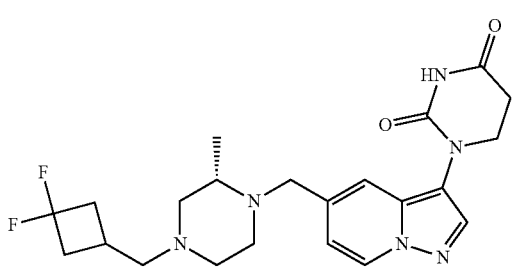 [SMILES: C[C@H]1CN(CC2CC(F)(F)C2)CCN1Cc1ccn2ncc(N3CCC(=O)NC3=O)c2c1]

Prepared using the method of Example 156 wherein potassium (S)-((4-(tert-butoxycarbonyl)-2-methylpiperazin-1-yl)methyl)trifluoroborate [see *J. Med. Chem.* 2012, 55, 7796-7816] was used in place of potassium ((4-(tert-butoxycarbonyl)piperazin-1-yl)methyl)trifluoroborate and (3,3-difluorocyclobutyl)methyl 4-methylbenzenesulfonate was used in place of (bromomethyl)cyclohexane. LCMS [M+H]$^+$: 447.0. $^1$H NMR (400 MHz, Methanol-d4) δ 8.45 (d, J=7.1 Hz, 1H), 8.37 (s, 1H), 8.01 (s, 1H), 7.51 (s, 1H), 6.98 (dd, J=7.1, 1.8 Hz, 1H), 4.19 (d, J=13.7 Hz, 1H), 3.89 (t, J=6.8 Hz, 2H), 3.34-3.27 (m, 1H), 3.07-2.94 (m, 2H), 2.89 (t, J=6.8 Hz, 2H), 2.86-2.63 (m, 6H), 2.53 (t, J=11.2 Hz, 1H), 2.49-2.24 (m, 5H), 1.23 (d, J=6.2 Hz, 3H), NH proton not observed due to solvent exchange.

Example 227. Preparation of (S)-1-(5-((3-ethyl-4-((tetrahydro-2H-pyran-4-yl)methyl)piperazin-1-yl)methyl)pyrazolo[1,5-a]pyridin-3-yl)dihydropyrimidine-2,4(1H,3H)-dione

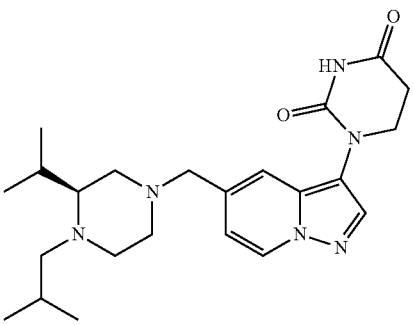

Prepared using the method of Example 192, wherein potassium (S)-((4-(tert-butoxycarbonyl)-3-ethylpiperazin-1-yl)methyl)trifluoroborate was used in place of tert-butyl (S)-2-methyl-4-((trifluoro-l4-boraneyl)methyl)piperazine-1-carboxylate, potassium salt and tetrahydro-2H-pyran-4-carbaldehyde was used in place of cyclohexanecarbaldehyde. LCMS [M+H]$^+$: 455.5. $^1$H NMR (400 MHz, Methanol-d4) δ 8.48 (d, J=7.2 Hz, 1H), 8.23 (s, 1H), 8.04 (s, 1H), 7.52 (s, 1H), 7.00 (dd, J=7.3, 1.9 Hz, 1H), 3.96 (dd, J=11.5, 4.2 Hz, 2H), 3.90 (t, J=6.8 Hz, 2H), 3.86-3.50 (m, 4H), 3.50-3.39 (m, 2H), 3.28-2.51 (m, 9H), 1.96 (d, J=78.4 Hz, 3H), 1.75 (d, J=13.3 Hz, 2H), 1.66 (d, J=13.2 Hz, 1H), 1.49-1.31 (m, 2H), 0.96 (t, J=7.4 Hz, 3H), NH proton not observed due to solvent exchange.

Example 228. Preparation of (S)-1-(5-((3-ethyl-4-isobutylpiperazin-1-yl)methyl)pyrazolo[1,5-a]pyridin-3-yl)dihydropyrimidine-2,4(1H,3H)-dione

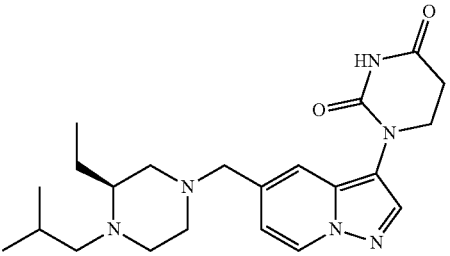 [SMILES: CC[C@H]1CN(Cc2ccn3ncc(N4CCC(=O)NC4=O)c3c2)CCN1CC(C)C]

Prepared using the method of Example 192, wherein (S)-((4-(tert-butoxycarbonyl)-3-ethylpiperazin-1-yl)methyl)trifluoroborate was used in place of tert-butyl (S)-2-methyl-4-((trifluoro-l4-boraneyl)methyl)piperazine-1-carboxylate, potassium salt and isobutyraldehyde was used in place of cyclohexanecarbaldehyde. LCMS [M+H]$^+$: 413.3. $^1$H NMR (400 MHz, Methanol-d4) δ 8.48 (d, J=7.1 Hz, 1H), 8.37 (s, 1H), 8.04 (s, 1H), 7.51 (s, 1H), 7.00 (d, J=7.2 Hz, 1H), 3.90 (t, J=6.6 Hz, 2H), 3.74 (d, J=13.7 Hz, 1H), 3.63 (d, J=13.7 Hz, 1H), 3.48 (s, 1H), 3.23-3.01 (m, 3H), 2.89 (t, J=7.0 Hz, 5H), 2.75-2.50 (m, 2H), 2.12-1.99 (m, 1H), 1.95-1.69 (m, 2H), 1.05 (t, J=6.1 Hz, 6H), 0.96 (t, J=7.4 Hz, 3H), NH proton not observed due to solvent exchange.

Example 229. Preparation of (S)-1-(5-((4-isobutyl-3-isopropylpiperazin-1-yl)methyl)pyrazolo[1,5-a]pyridin-3-yl)dihydropyrimidine-2,4(1H,3H)-dione Prepared using the method of Example 192, wherein (S)-((4-(tert-butoxycarbonyl)-3-isopropylpiperazin-1-yl)methyl)trifluoroborate was used in place of tert-butyl (S)-2-methyl-4-((trifluoro-l4-boraneyl)methyl)piperazine-1-carboxylate, potassium salt and isobutyraldehyde was used in place of cyclohexanecarbaldehyde. LCMS [M+H]$^+$: 427.5. $^1$H NMR (400 MHz, Methanol-d4) δ 8.48 (d, J=7.4 Hz, 1H), 8.07 (s, 1H), 8.04 (s, 1H), 7.53 (s, 1H), 7.00 (dd, J=6.9, 1.8 Hz, 1H), 3.90 (t, J=6.8 Hz, 2H), 3.86-3.53 (m, 3H), 3.41-2.95 (m, 4H), 2.89 (t, J=6.8 Hz, 2H), 2.55 (d, J=44.4 Hz, 4H), 2.12 (s, 1H), 1.11-1.01 (m, 9H), 1.00 (s, 3H), NH proton not observed due to solvent exchange.

Example 230. (Preparation of (S)-1-(5-((3-isopropyl-4-((tetrahydro-2H-pyran-4-yl)methyl)piperazin-1-yl)methyl)pyrazolo[1,5-a]pyridin-3-yl)dihydropyrimidine-2,4(1H,3H)-dione

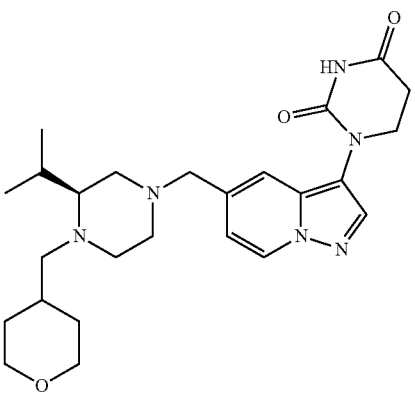 [SMILES: CC(C)[C@H]1CN(Cc2ccn3ncc(N4CCC(=O)NC4=O)c3c2)CCN1CC1CCOCC1]

Prepared using the method of Example 192, wherein (S)-((4-(tert-butoxycarbonyl)-3-isopropylpiperazin-1-yl)methyl)trifluoroborate was used in place of tert-butyl (S)-2-methyl-4-((trifluoro-l4-boraneyl)methyl)piperazine-1-carboxylate, potassium salt and tetrahydro-2H-pyran-4-carbaldehyde was used in place of cyclohexanecarbaldehyde. LCMS [M+H]$^+$: 469.2. $^1$H NMR (400 MHz, Methanol-d4) δ 8.49 (d, J=7.2 Hz, 1H), 8.30 (s, 1H), 8.04 (s, 1H), 7.55 (s, 1H), 7.00 (dd, J=7.2, 1.8 Hz, 1H), 3.95 (dd, J=11.5, 4.2 Hz, 2H), 3.90 (t, J=6.8 Hz, 2H), 3.85 (d, J=13.7 Hz, 1H), 3.72 (d, J=13.6 Hz, 1H), 3.53-3.38 (m, 3H), 3.18-2.92 (m, 5H), 2.89 (t, J=6.8 Hz, 2H), 2.59 (t, J=10.8 Hz, 2H), 2.50 (dd, J=12.6, 10.0 Hz, 1H), 2.41-2.28 (m, 1H), 2.07-1.94 (m, 1H), 1.79 (d, J=13.4 Hz, 1H), 1.65 (d, J=13.2 Hz, 1H), 1.44-1.25 (m, 2H), 1.01 (d, J=6.8 Hz, 3H), 0.95 (d, J=6.8 Hz, 3H), NH proton not observed due to solvent exchange.

Example 231. Preparation of 1-(5-((4-(cyclohexylmethyl)-3,3-dimethylpiperazin-1-yl)methyl)pyrazolo[1,5-a]pyridin-3-yl)dihydropyrimidine-2,4(1H,3H)-dione

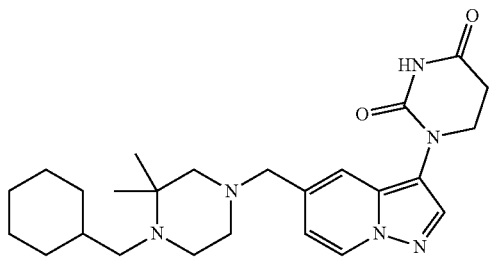 [SMILES: CC1(C)CN(Cc2ccn3ncc(N4CCC(=O)NC4=O)c3c2)CCN1CC1CCCCC1]

Prepared using the method of Example 192, wherein ((4-(tert-butoxycarbonyl)-3,3-dimethylpiperazin-1-yl)methyl)trifluoroborate was used in place of tert-butyl (S)-2-methyl-4-((trifluoro-l4-boraneyl)methyl)piperazine-1-carboxylate, potassium salt. LCMS [M+H]$^+$: 453.3. $^1$H NMR (400 MHz, Methanol-d4) δ 8.52 (s, 1H), 8.46 (d, J=7.2 Hz, 1H), 8.02 (s, 1H), 7.49 (s, 1H), 7.00 (dd, J=7.4, 1.7 Hz, 1H), 3.89 (t, J=6.8 Hz, 2H), 3.61 (s, 2H), 2.89 (t, J=6.8 Hz, 2H), 2.99-2.32 (m, 5H), 1.92-1.59 (m, 6H), 1.42-1.15 (m, 10H), 1.04 (q, J=11.4 Hz, 2H), NH proton not observed due to solvent exchange.

Example 232. Preparation of 1-(5-((3,3-dimethyl-4-((tetrahydro-2H-pyran-4-yl)methyl)piperazin-1-yl)methyl)pyrazolo[1,5-a]pyridin-3-yl)dihydropyrimidine-2,4(1H,3H)-dione

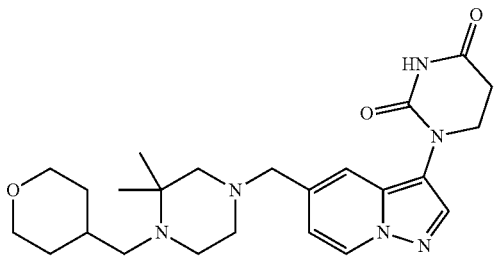 [SMILES: CC1(C)CN(Cc2ccn3ncc(N4CCC(=O)NC4=O)c3c2)CCN1CC1CCOCC1]

Prepared using the method of Example 192, wherein ((4-(tert-butoxycarbonyl)-3,3-dimethylpiperazin-1-yl)methyl)trifluoroborate was used in place of tert-butyl (S)-2-methyl-4-((trifluoro-l4-boraneyl)methyl)piperazine-1-carboxylate, potassium salt and tetrahydro-2H-pyran-4-carbaldehyde was used in place of cyclohexanecarbaldehyde. LCMS [M+H]$^+$: 455.1. $^1$H NMR (300 MHz, Methanol-d4) δ 8.45 (d, J=7.2 Hz, 1H), 8.27 (s, 1H), 8.01 (s, 1H), 7.47 (s, 1H), 6.98 (d, J=7.3 Hz, 1H), 3.94 (d, J=12.8 Hz, 1H), 3.88 (t, J=6.8 Hz, 2H), 3.71-3.31 (m, 9H), 3.05 (s, 5H), 2.87 (t, J=6.7 Hz, 2H), 2.08-1.58 (m, 3H), 1.32 (d, J=24.2 Hz, 7H). NH proton not observed due to solvent exchange.

Example 233. Preparation of 1-(5-((4-isobutyl-3,3-dimethylpiperazin-1-yl)methyl)pyrazolo[1,5-a]pyridin-3-yl)dihydropyrimidine-2,4(1H,3H)-dione

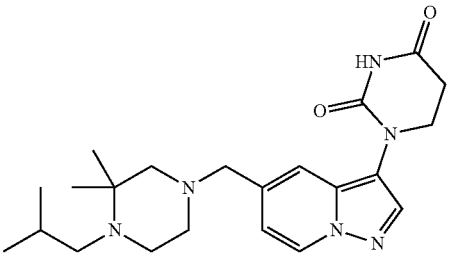 [SMILES: CC(C)CN1CCN(Cc2ccn3ncc(N4CCC(=O)NC4=O)c3c2)CC1(C)C]

Prepared using the method of Example 192, wherein ((4-(tert-butoxycarbonyl)-3,3-dimethylpiperazin-1-yl)methyl)trifluoroborate was used in place of tert-butyl (S)-2-methyl-4-((trifluoro-l4-boraneyl)methyl)piperazine-1-carboxylate, potassium salt and isobutyraldehyde was used in place of cyclohexanecarbaldehyde. LCMS [M+H]$^+$: 413.3. $^1$H NMR (300 MHz, Methanol-d4) δ 8.47 (d, J=7.1 Hz, 1H), 8.03 (s, 1H), 7.50 (s, 1H), 7.00 (d, J=7.1 Hz, 1H), 3.90 (t, J=6.7 Hz, 2H), 3.81-3.36 (m, 2H), 3.11 (d, J=39.0 Hz, 2H), 2.89 (t, J=6.8 Hz, 2H), 2.83-2.42 (m, 3H), 2.01 (ddd, J=25.6, 12.6, 5.4 Hz, 2H), 1.59-1.20 (m, 8H), 1.08 (d, J=6.5 Hz, 6H).

Example 234. Preparation of 1-(5-(((1R,4R)-5-(cyclohexylmethyl)-2,5-diazabicyclo[2.2.1]heptan-2-yl)methyl)pyrazolo[1,5-a]pyridin-3-yl)dihydropyrimidine-2,4(1H,3H)-dione

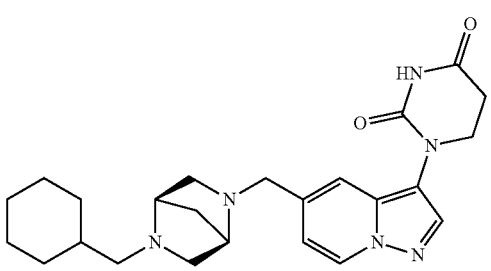 [SMILES: O=C1CCN(c2cnn3ccc(CN4C[C@H]5C[C@@H]4CN5CC4CCCCC4)cc23)C(=O)N1]

Prepared using the method of Example 192, wherein potassium (((1R,4R)-5-(tert-butoxycarbonyl)-2,5-diazabicyclo[2.2.1]heptan-2-yl)methyl)trifluoroborate was used in place of tert-butyl (S)-2-methyl-4-((trifluoro-I4-boraneyl)methyl)piperazine-1-carboxylate. LCMS [M+H]⁺: 437.2.

Example 235. Preparation of 1-(5-(((1R,4R)-5-(pyridin-3-ylmethyl)-2,5-diazabicyclo[2.2.1]heptan-2-yl)methyl)pyrazolo[1,5-a]pyridin-3-yl)dihydropyrimidine-2,4(1H,3H)-dione

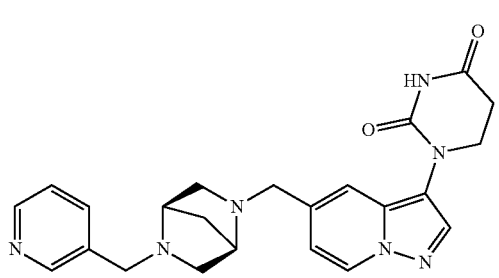 [SMILES: O=C1CCN(c2cnn3ccc(CN4C[C@H]5C[C@@H]4CN5Cc4cccnc4)cc23)C(=O)N1]

Prepared using the method of Example 192, wherein potassium (((1R,4R)-5-(tert-butoxycarbonyl)-2,5-diazabicyclo[2.2.1]heptan-2-yl)methyl)trifluoroborate was used in place of tert-butyl (S)-2-methyl-4-((trifluoro-I4-boraneyl)methyl)piperazine-1-carboxylate and using nicotinaldehyde was used in place of cyclohexanecarbaldehyde. LCMS [M+H]⁺: 432.2. ¹H NMR (400 MHz, CD₃OD) δ 8.80 (brs, 1H), 8.60 (d, J=7.2 Hz, 1H), 8.42 (m, 1H), 8.13 (s, 1H), 7.90 (brs, 1H), 7.77 (s, 1H), 7.07 (d, J=7.2 Hz, 1H), 4.49-4.44 (m, 1H), 4.32-4.20 (m, 3H), 4.08-3.87 (m, 5H), 3.62-3.61 (m, 3H), 3.04-3.01 (m, 1H), 2.90 (t, J=6.8 Hz, 2H), 2.31 (s, 2H), NH proton not observed due to solvent exchange.

Example 236. Preparation of 1-(5-(((1S,4S)-5-(cyclohexylmethyl)-2,5-diazabicyclo[2.2.1]heptan-2-yl)methyl)pyrazolo[1,5-a]pyridin-3-yl)dihydropyrimidine-2,4(1H,3H)-dione

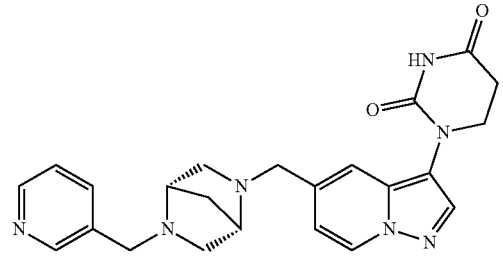 [SMILES: O=C1CCN(c2cnn3ccc(CN4C[C@@H]5C[C@H]4CN5Cc4cccnc4)cc23)C(=O)N1]

Prepared using the method of Example 192, wherein potassium (((1S,4S)-5-(tert-butoxycarbonyl)-2,5-diazabicyclo[2.2.1]heptan-2-yl)methyl)trifluoroborate was used in place of tert-butyl (S)-2-methyl-4-((trifluoro-I4-boraneyl)methyl)piperazine-1-carboxylate. LCMS [M+H]⁺: 437.2. ¹H NMR (400 MHz, Methanol-d4) δ 8.46 (d, J=7.2 Hz, 1H), 8.03 (s, 1H), 7.52 (s, 1H), 7.02 (d, J=7.4 Hz, 1H), 4.23 (s, 1H), 3.97-3.86 (m, 2H), 3.83-3.54 (m, 2H), 3.28 (s, 1H), 3.19-2.95 (m, 3H), 2.95-2.84 (m, 2H), 2.84-2.61 (m, 1H), 2.23 (d, J=11.7 Hz, 1H), 2.13-2.04 (m, 1H), 1.91-1.69 (m, 6H), 1.59 (s, 1H), 1.42-1.20 (m, 4H), 1.15-0.95 (m, 2H), NH proton not observed due to solvent exchange.

Example 237. Preparation of 1-(5-(((1S,4S)-5-(pyridin-3-ylmethyl)-2,5-diazabicyclo[2.2.1]heptan-2-yl)methyl)pyrazolo[1,5-a]pyridin-3-yl)dihydropyrimidine-2,4(1H,3H)-dione Prepared using the method of Example 192, wherein potassium (((1S,4S)-5-(tert-butoxycarbonyl)-2,5-diazabicyclo[2.2.1]heptan-2-yl)methyl)trifluoroborate was used in place of tert-butyl (S)-2-methyl-4-((trifluoro-I4-boraneyl)methyl)piperazine-1-carboxylate and nicotinaldehyde was used in place of cyclohexanecarbaldehyde. LCMS [M+H]⁺: 432.1. ¹H NMR (400 MHz, Methanol-d4) δ 8.83 (s, 1H), 8.75 (d, J=5.6 Hz, 1H), 8.59 (d, J=7.3 Hz, 1H), 8.52 (d, J=8.1 Hz, 1H), 8.12 (s, 1H), 7.96 (t, J=6.9 Hz, 1H), 7.78 (s, 1H), 7.07 (dd, J=7.2, 1.9 Hz, 1H), 4.49 (d, J=13.3 Hz, 1H), 4.33 (d, J=13.2 Hz, 1H), 4.28 (s, 1H), 4.20 (d, J=14.7 Hz, 1H), 4.05 (d, J=14.7 Hz, 1H), 3.93 (t, J=6.8 Hz, 2H), 3.84 (s, 1H), 3.62 (d, J=11.8 Hz, 1H), 3.38-3.19 (m, 2H), 3.01 (dd, J=12.0, 2.7 Hz, 1H), 2.89 (t, J=6.8 Hz, 2H), 2.31 (s, 2H), NH proton not observed due to solvent exchange.

Example 238. Preparation of 1-(5-(((1S,4S)-5-(isopropylsulfonyl)-2,5-diazabicyclo[2.2.1]heptan-2-yl)methyl)pyrazolo[1,5-a]pyridin-3-yl)dihydropyrimidine-2,4(1H,3H)-dione

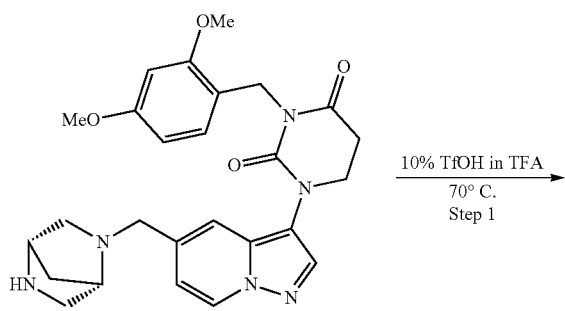

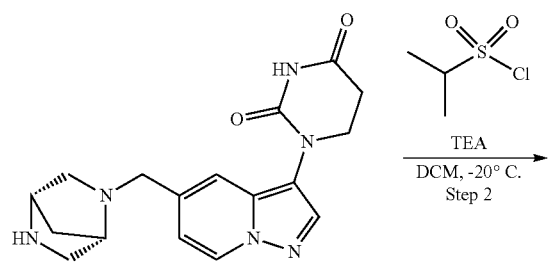

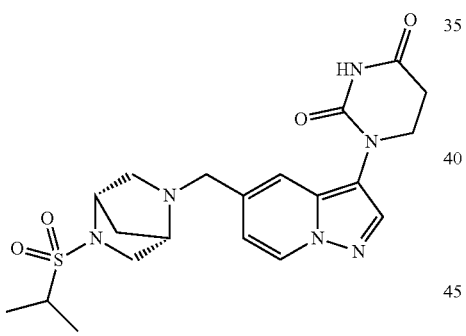

Example 238

Step 1. 1-(5-(((1S,4S)-2,5-diazabicyclo[2.2.1]heptan-2-yl)methyl)pyrazolo[1,5-a]pyridin-3-yl)dihydropyrimidine-2,4(1H,3H)-dione To a stirred solution of 1-(5-(((1S,4S)-2,5-diazabicyclo[2.2.1]heptan-2-yl)methyl)pyrazolo[1,5-a]pyridin-3-yl)-3-(2,4-dimethoxybenzyl)dihydropyrimidine-2,4(1H,3H)-dione (175 mg, 0.32 mmol) [prepared in Example 236] in TFA (5 mL) was added TfOH (0.2 mL) and the reaction mixture was stirred for 2 h at 70° C. The reaction was concentrated under to afford crude compound. The crude compound was dissolved in 10% MeOH in DCM and basified with Amberlyst-A21 (free base) resin and then filtered. The filtrate was concentrated to afford 1-(5-(((1S,4S)-2,5-diazabicyclo[2.2.1]heptan-2-yl)methyl)pyrazolo[1,5-a]pyridin-3-yl)dihydropyrimidine-2,4(1H,3H)-dione (150 mg, crude). LCMS [M+H]$^+$: 341.3.

Step 2. 1-(5-(((1S,4S)-5-(isopropylsulfonyl)-2,5-diazabicyclo[2.2.1]heptan-2-yl)methyl)pyrazolo[1,5-a]pyridin-3-yl)dihydropyrimidine-2,4(1H,3H)-dione To a stirred solution of 1-(5-(((1S,4S)-2,5-diazabicyclo[2.2.1]heptan-2-yl)methyl)pyrazolo[1,5-a]pyridin-3-yl)dihydropyrimidine-2,4(1H,3H)-dione (130 mg, 0.38 mmol) in DCM (5 mL) was added Et$_3$N (0.076 mL, 0.76 mmol) and propane-2-sulfonyl chloride (0.035 mL, 0.45 mmol) at −20° C. The reaction mixture was stirred for 2 h at 0° C. and then quenched with methanol and concentrated to afford the crude compound. The crude compound was purified by PREP HPLC using: Mobile Phase: A=0.1% TFA in water, B=Acetonitrile, Column: ATLANTIS (250 mm×21.2 mm), 5.0µ, Flow: 20 mL/min. the collected fraction were concentrated under reduced pressure to afford 1-(5-(((1S,4S)-5-(isopropylsulfonyl)-2,5-diazabicyclo[2.2.1]heptan-2-yl)methyl)pyrazolo[1,5-a]pyridin-3-yl)dihydropyrimidine-2,4(1H,3H)-dione (12 mg, 0.022 mmol, 5.8% yield) as an off-white solid. LCMS [M+H]$^+$: 447.2. HPLC: Rt=5.406 min. $^1$H NMR (400 MHz, Methanol-d4) δ 8.63 (dd, J=7.2, 3.1 Hz, 1H), 8.15 (d, J=1.7 Hz, 1H), 7.83 (d, J=2.8 Hz, 1H), 7.07 (dd, J=7.4, 2.1 Hz, 1H), 4.59 (dd, J=13.5, 7.5 Hz, 3H), 4.44 (d, J=12.3 Hz, 1H), 3.95 (t, J=6.8 Hz, 2H), 3.72 (s, 2H), 3.50 (d, J=9.1 Hz, 1H), 2.91 (t, J=6.8 Hz, 2H), 2.47 (d, J=12.0 Hz, 1H), 2.23 (d, J=13.0 Hz, 1H), 1.49 (d, J=2.2 Hz, 2H), 1.35 (d, J=6.8 Hz, 6H), NH proton not observed due to solvent exchange.

Example 239. Preparation of 1-(5-(((1R,4R)-5-(isopropylsulfonyl)-2,5-diazabicyclo[2.2.1]heptan-2-yl)methyl)pyrazolo[1,5-a]pyridin-3-yl)dihydropyrimidine-2,4(1H,3H)-dione

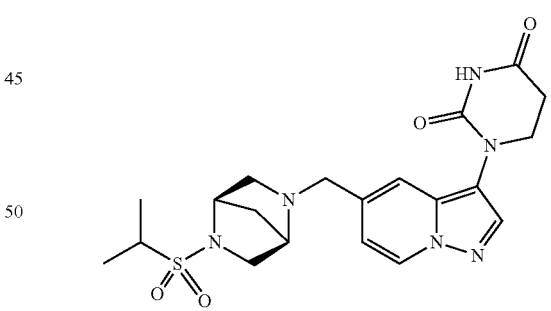

Prepared from using the method of Example 238, wherein 1-(5-(((1R,4R)-2,5-diazabicyclo[2.2.1]heptan-2-yl)methyl)pyrazolo[1,5-a]pyridin-3-yl)-3-(2,4-dimethoxybenzyl)dihydropyrimidine-2,4(1H,3H)-dione [prepared in Example 234] was used in place of 1-(5-(((1S,4S)-2,5-diazabicyclo[2.2.1]heptan-2-yl)methyl)pyrazolo[1,5-a]pyridin-3-yl)-3-(2,4-dimethoxybenzyl)dihydropyrimidine-2,4(1H,3H)-dione. LCMS [M+H]$^+$: 446.8.

Example 240. Preparation of 1-(5-((4-(3-methylbutan-2-yl)piperazin-1-yl)methyl)pyrazolo[1,5-a]pyridin-3-yl)dihydropyrimidine-2,4(1H,3H)-dione (Example 240)

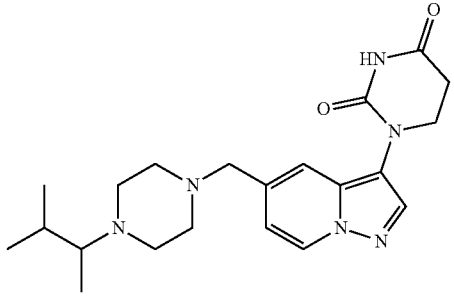 [SMILES: CC(C)C(C)N1CCN(Cc2ccn3ncc(N4CCC(=O)NC4=O)c3c2)CC1]

Prepared using the method of Example 156, steps 1 and 4, wherein potassium trifluoro((4-(3-methylbutan-2-yl)piperazin-1-yl)methyl)borate was used in place of potassium {[4-(tert-butoxycarbonyl)-1-piperazinyl]methyl}(trifluoro)borate. LCMS [M+H]+: 399.0. 1H NMR (400 MHz, Methanol-d4) δ 8.47 (d, J=7.1 Hz, 1H), 8.39 (s, 1H), 8.03 (s, 1H), 7.52 (s, 1H), 6.99 (d, J=7.2 Hz, 1H), 3.90 (t, J=6.7 Hz, 2H), 3.70 (s, 2H), 3.31 (m, 4H), 3.07 (d, J=6.5 Hz, 1H), 2.89 (t, J=6.8 Hz, 2H), 2.81 (bs, 4H), 2.30-2.16 (m, 1H), 1.25 (d, J=6.7 Hz, 3H), 1.04 (d, J=6.7 Hz, 3H), 0.97 (d, J=6.7 Hz, 3H).

Example 241. Preparation of 1-(5-((4-(3,3,3-trifluoro-2,2-dimethylpropyl)piperazin-1-yl)methyl)pyrazolo[1,5-a]pyridin-3-yl)dihydropyrimidine-2,4(1H,3H)-dione

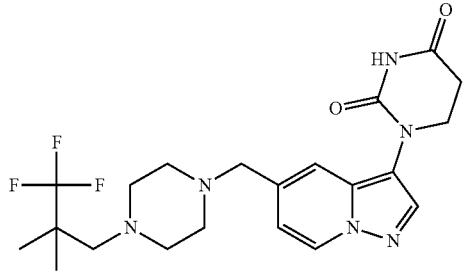 [SMILES: CC(C)(CN1CCN(Cc2ccn3ncc(N4CCC(=O)NC4=O)c3c2)CC1)C(F)(F)F]

Prepared using the method of Example 156, steps 1 and 4, wherein potassium trifluoro((4-(3,3,3-trifluoro-2,2-dimethylpropyl)piperazin-1-yl)methyl)borate was used in place of potassium {[4-(tert-butoxycarbonyl)-1-piperazinyl]methyl}(trifluoro)borate. LCMS [M+H]+: 453.2. 1H NMR (400 MHz, Methanol-d4) δ 8.61 (d, J=7.0 Hz, 1H), 8.13 (s, 1H), 7.75 (s, 1H), 7.00 (dd, J=7.3, 1.9 Hz, 1H), 4.35 (s, 2H), 3.93 (t, J=6.8 Hz, 2H), 3.48 (d, J=12.2 Hz, 1H), 3.08 (t, J=11.8 Hz, 1H), 2.98-2.67 (m, 8H), 2.55 (d, J=10.8 Hz, 2H), 1.14 (d, J=2.1 Hz, 6H). NH proton not observed due to solvent exchange.

Example 242. Preparation of 1-(5-((4-(cyclohexylmethyl)-3-oxopiperazin-1-yl)methyl)pyrazolo[1,5-a]pyridin-3-yl)dihydropyrimidine-2,4(1H,3H)-dione

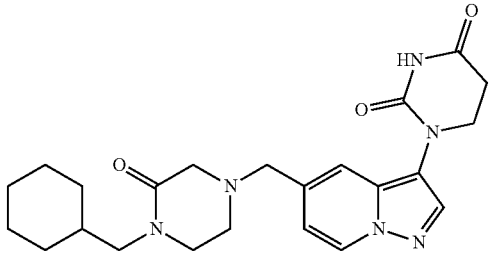 [SMILES: O=C1CCN(c2cnn3ccc(CN4CCN(CC5CCCCC5)C(=O)C4)cc23)C(=O)N1]

Prepared using the method of Example 156, steps 1 and 4, wherein potassium ((4-(cyclohexylmethyl)-3-oxopiperazin-1-yl)methyl)trifluoroborate was used in place of potassium {[4-(tert-butoxycarbonyl)-1-piperazinyl]methyl}(trifluoro)borate. LCMS [M+H]+: 439.2. 1H NMR (400 MHz, Methanol-d4) δ 8.50 (d, J=7.1 Hz, 1H), 8.04 (s, 1H), 7.57 (s, 1H), 7.00 (dd, J=7.1, 1.8 Hz, 1H), 3.90 (t, J=6.7 Hz, 2H), 3.81 (s, 2H), 3.43 (t, J=5.5 Hz, 2H), 3.38-3.31 (m, 2H), 3.25 (d, J=7.2 Hz, 2H), 2.89 (t, J=6.8 Hz, 4H), 1.80-1.59 (m, 6H), 1.24 (q, J=9.3, 6.0 Hz, 3H), 0.97 (q, J=11.9 Hz, 2H), NH proton not observed due to solvent exchange.

Example 243. Preparation of 1-(5-((4-(2-cyclohexylethyl)-3-oxopiperazin-1-yl)methyl)pyrazolo[1,5-a]pyridin-3-yl)dihydropyrimidine-2,4(1H,3H)-dione

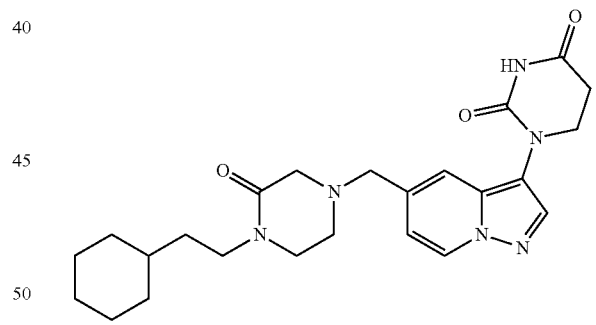

Prepared using the method of Example 156, steps 1 and 4, wherein potassium ((4-(2-cyclohexylethyl)-3-oxopiperazin-1-yl)methyl)trifluoroborate was used in place of potassium {[4-(tert-butoxycarbonyl)-1-piperazinyl]methyl}(trifluoro)borate. LCMS [M+H]+: 452.9. 1H NMR (400 MHz, Methanol-d4) δ 8.52 (d, J=7.2 Hz, 1H), 8.06 (s, 1H), 7.62-7.58 (m, 1H), 7.00 (dd, J=7.1, 1.9 Hz, 1H), 4.01-3.78 (m, 3H), 3.51-3.38 (m, 5H), 3.12-2.96 (m, 2H), 2.89 (t, J=6.8 Hz, 2H), 1.83-1.60 (m, 5H), 1.46 (dt, J=9.7, 6.8 Hz, 2H), 1.37-1.15 (m, 5H), 0.96 (qd, J=14.1, 12.9, 4.4 Hz, 2H), NH proton not observed due to solvent exchange.

Example 244. Preparation of (R)-1-(5-((4-(cyclo-hexylmethyl)-3-(methoxymethyl)piperazin-1-yl)methyl)pyrazolo[1,5-a]pyridin-3-yl)dihydropyrimidine-2,4(1H,3H)-dione

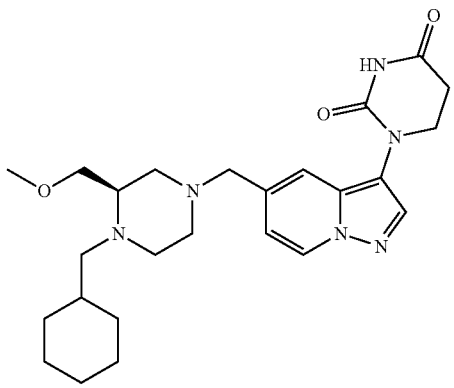 [SMILES: COC[C@H]1CN(Cc2ccn3ncc(N4CCC(=O)NC4=O)c3c2)CCN1CC1CCCCC1]

Prepared using the method of Example 156, steps 1 and 4, wherein potassium (R)-((4-(cyclohexylmethyl)-3-(methoxymethyl)piperazin-1-yl)methyl)trifluoroborate was used in place of potassium {[4-(tert-butoxycarbonyl)-1-piperazinyl]methyl}(trifluoro)borate. LCMS [M+H]⁺: 469.4. ¹H NMR (400 MHz, Methanol-d4) δ 8.46 (s, 1H), 8.45 (s, 1H), 8.02 (s, 1H), 7.49 (s, 1H), 3.89 (t, J=6.8 Hz, 2H), 3.70-3.53 (m, 4H), 3.36 (s, 4H), 3.19 (s, 1H), 3.03 (dd, J=12.0, 8.2 Hz, 1H), 2.97-2.82 (m, 5H), 2.67-2.47 (m, 3H), 1.90 (d, J=13.1 Hz, 1H), 1.82-1.63 (m, 5H), 1.41-1.18 (m, 4H), 1.09-0.92 (m, 2H), NH proton not observed due to solvent exchange.

Example 245. Preparation of (R)-1-(5-((4-isobutyl-3-(methoxymethyl)piperazin-1-yl)methyl)pyrazolo[1,5-a]pyridin-3-yl)dihydropyrimidine-2,4(1H,3H)-dione

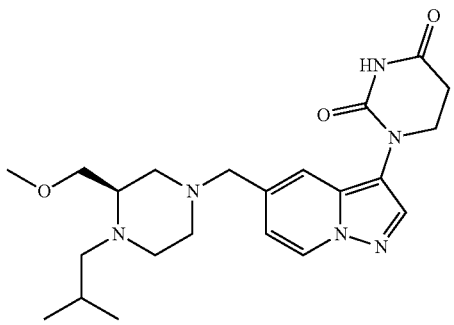 [SMILES: COC[C@H]1CN(Cc2ccn3ncc(N4CCC(=O)NC4=O)c3c2)CCN1CC(C)C]

Prepared using the method of Example 156, steps 1 and 4, wherein potassium (R)-trifluoro((4-isobutyl-3-(methoxymethyl)piperazin-1-yl)methyl)borate was used in place of potassium {[4-(tert-butoxycarbonyl)-1-piperazinyl]methyl}(trifluoro)borate. LCMS [M+H]⁺: 429.3. ¹H NMR (400 MHz, Methanol-d4) δ 8.46 (d, J=7.1 Hz, 1H), 8.42 (1H, s) 8.02 (s, 1H), 7.50 (s, 1H), 6.98 (d, J=7.1 Hz, 1H), 3.89 (t, J=6.7 Hz, 2H), 3.73-3.56 (m, 4H), 3.45 (d, J=13.1 Hz, 1H), 3.37 (s, 3H), 3.31 (s, 1H), 3.12-2.96 (m, 2H), 2.94-2.84 (m, 4H), 2.72 (dd, J=13.0, 5.5 Hz, 1H), 2.67-2.55 (m, 2H), 2.05 (h, J=6.8 Hz, 1H), 1.03 (d, J=6.8 Hz, 3H), 1.01 (d, J=6.8 Hz, 3H), NH proton not observed due to solvent exchange.

Example 246. Preparation of (R)-1-(5-((4-(cyclo-hexylmethyl)-3-(difluoromethyl)piperazin-1-yl)methyl)pyrazolo[1,5-a]pyridin-3-yl)dihydropyrimidine-2,4(1H,3H)-dione

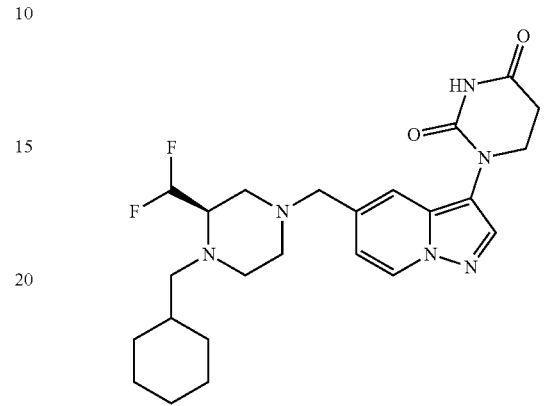

Prepared using the method of Example 156, steps 1 and 4, wherein potassium (R)-((4-(cyclohexylmethyl)-3-(difluoromethyl)piperazin-1-yl)methyl)trifluoroborate was used in place of potassium {[4-(tert-butoxycarbonyl)-1-piperazinyl]methyl}(trifluoro)borate. LCMS [M+H]⁺: 475.4. ¹H NMR (400 MHz, Methanol-d4) δ 8.56 (d, J=7.2 Hz, 1H), 8.09 (s, 1H), 7.66 (s, 1H), 7.01 (dd, J=7.4, 2.0 Hz, 1H), 6.35 (t, J=54.3 Hz, 1H), 4.12 (s, 1H), 3.92 (t, J=6.8 Hz, 2H), 3.53 (t, J=17.9 Hz, 1H), 3.10 (d, J=49.1 Hz, 4H), 2.89 (t, J=6.8 Hz, 3H), 2.59 (s, 1H), 2.12 (dd, J=35.5, 24.8 Hz, 1H), 1.98-1.45 (m, 7H), 1.26 (dq, J=21.1, 12.4, 11.8 Hz, 4H), 1.08-0.83 (m, 2H), NH proton not observed due to solvent exchange.

Example 247. Preparation of (R)-1-(5-((3-(difluoromethyl)-4-isobutylpiperazin-1-yl)methyl)pyrazolo[1,5-a]pyridin-3-yl)dihydropyrimidine-2,4(1H,3H)-dione

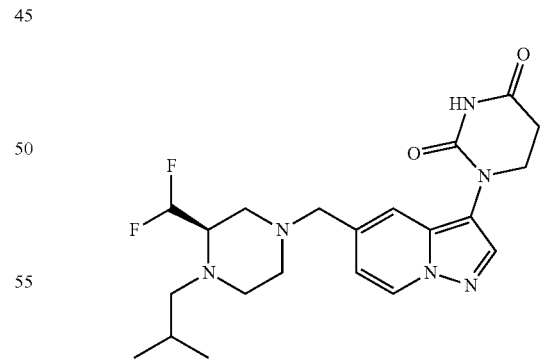

Prepared using the method of Example 156, steps 1 and 4, wherein potassium (R)-((3-(difluoromethyl)-4-isobutylpiperazin-1-yl)methyl)trifluoroborate was used in place of potassium {[4-(tert-butoxycarbonyl)-1-piperazinyl]methyl}(trifluoro)borate. LCMS [M+H]⁺: 434.7. ¹H NMR (400 MHz, Methanol-d4) δ 8.58 (d, J=7.2 Hz, 1H), 8.11 (s, 1H), 7.70 (s, 1H), 7.01 (dd, J=7.1, 1.9 Hz, 1H), 6.34 (t, J=54.1 Hz, 1H), 4.23 (d, J=24.8 Hz, 2H), 3.92 (t, J=6.7 Hz, 2H), 3.38 (s, 2H), 3.12 (m, 4H), 2.90 (t, J=6.7 Hz, 4H), 2.52 (s, 1H), 1.90 (s, 1H), 1.04-0.84 (m, 6H), NH proton not observed due to solvent exchange.

Example 248. Preparation of 1-(5-((1,4-diazepan-1-yl)methyl)pyrazolo[1,5-a]pyridin-3-yl)dihydropyrimidine-2,4(1H,3H)-dione

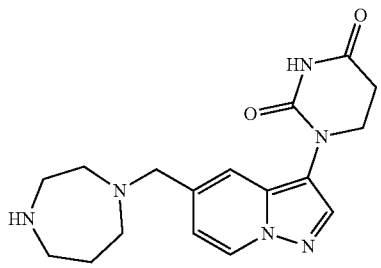 [SMILES: O=C1CCN(c2cnn3ccc(CN4CCCNCC4)cc23)C(=O)N1]

Prepared using the method of Example 192, steps 1 and 4, wherein potassium ((4-(tert-butoxycarbonyl)-1,4-diazepan-1-yl)methyl)trifluoroborate was used in place of tert-butyl (S)-2-methyl-4-((trifluoro-l4-boraneyl)methyl)piperazine-1-carboxylate, potassium salt. LCMS [M+H]⁺: 343.1. ¹H NMR (400 MHz, Methanol-d4) δ 8.56 (t, J=6.8 Hz, 1H), 8.10 (d, J=4.4 Hz, 1H), 7.71 (d, J=21.5 Hz, 1H), 7.14-6.99 (m, 1H), 4.27 (d, J=44.9 Hz, 2H), 3.92 (t, J=6.7 Hz, 2H), 3.68 (t, J=4.7 Hz, 2H), 3.60-3.50 (m, 3H), 3.45-3.37 (m, 2H), 3.26 (s, 1H), 2.89 (t, J=6.8 Hz, 2H), 2.29-2.16 (m, 2H), NH proton not observed due to solvent exchange.

Example 249. Preparation of 1-(5-((4-(cyclohexylmethyl)-1,4-diazepan-1-yl)methyl)pyrazolo[1,5-a]pyridin-3-yl)dihydropyrimidine-2,4(1H,3H)-dione

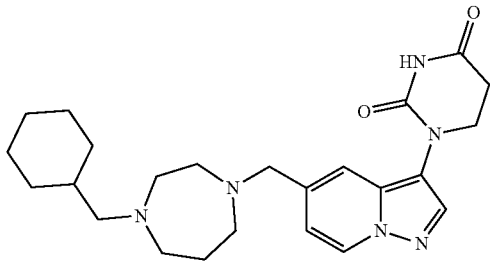 [SMILES: O=C1CCN(c2cnn3ccc(CN4CCCN(CC5CCCCC5)CC4)cc23)C(=O)N1]

Prepared using the method of Example 192, wherein potassium ((4-(tert-butoxycarbonyl)-1,4-diazepan-1-yl)methyl)trifluoroborate was used in place of tert-butyl (S)-2-methyl-4-((trifluoro-l4-boraneyl)methyl)piperazine-1-carboxylate, potassium salt. LCMS [M+H]⁺: 439.2. ¹H NMR (400 MHz, Methanol-d4) δ 8.52 (d, J=7.2 Hz, 1H), 8.07 (s, 1H), 7.61 (s, 1H), 7.03 (dd, J=7.3, 2.0 Hz, 1H), 4.02 (s, 2H), 3.91 (t, J=6.8 Hz, 2H), 3.51 (s, 4H), 3.23 (s, 1H), 3.14-3.03 (m, 5H), 2.90 (t, J=6.8 Hz, 2H), 2.25-2.10 (m, 2H), 1.87-1.66 (m, 6H), 1.44-1.19 (m, 4H), 1.07 (t, J=11.7 Hz, 2H), NH proton not observed due to solvent exchange.

Example 250. Preparation of 1-(5-((4-isobutyl-1,4-diazepan-1-yl)methyl)pyrazolo[1,5-a]pyridin-3-yl)dihydropyrimidine-2,4(1H,3H)-dione

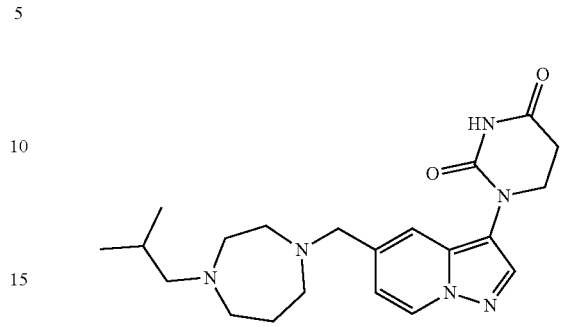

Prepared using the method of Example 192, wherein potassium ((4-(tert-butoxycarbonyl)-1,4-diazepan-1-yl)methyl)trifluoroborate was used in place of tert-butyl (S)-2-methyl-4-((trifluoro-l4-boraneyl)methyl)piperazine-1-carboxylate, potassium salt and isobutyraldehyde was used in place of cyclohexanecarbaldehyde. LCMS [M+H]⁺: 399.3. ¹H NMR (400 MHz, CD₃OD) δ 8.44 (d, J=7.2 Hz, 1H), 8.01 (s, 1H), 7.49 (s, 1H), 7.02 (d, J=6.6 Hz, 1H), 3.88 (t, J=7.2 Hz, 2H), 3.73 (s, 2H), 3.14-3.07 (m, 4H), 2.90-2.69 (m, 8H), 1.97 (m, 3H), 0.97 (d, J=6.6 Hz, 6H), NH proton not observed due to solvent exchange.

Example 251. Preparation of 1-(5-(((1R,5S)-8-(3-fluorobenzyl)-3,8-diazabicyclo[3.2.1]octan-3-yl)methyl)pyrazolo[1,5-a]pyridin-3-yl)dihydropyrimidine-2,4(1H,3H)-dione

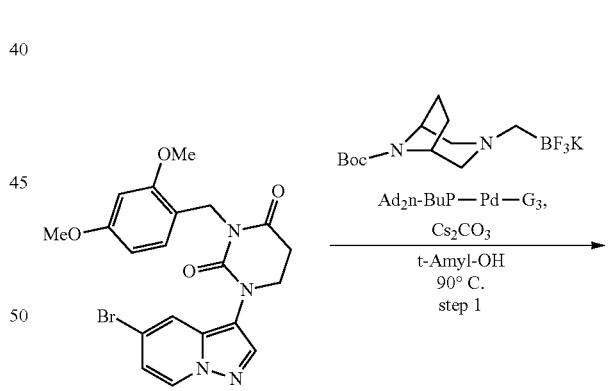

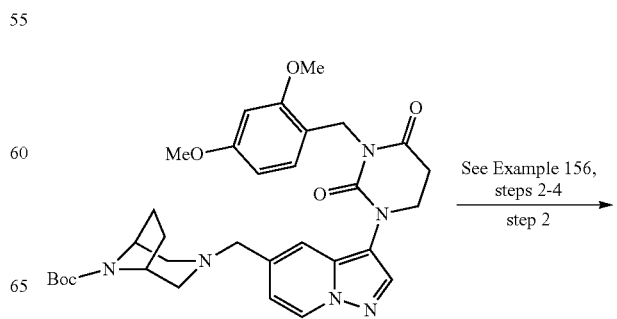

355

-continued

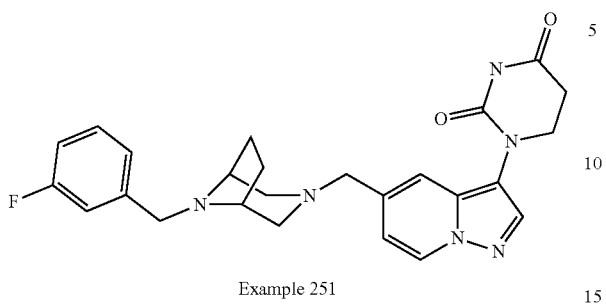

Example 251

Step 1. tert-butyl (1R,5S)-3-((3-(3-(2,4-dimethoxybenzyl)-2,4-dioxotetrahydropyrimidin-1(2H)-yl)pyrazolo[1,5-a]pyridin-5-yl)methyl)-3,8-diazabicyclo[3.2.1]octane-8-carboxylate To a suspension of 1-(5-bromopyrazolo[1,5-a]pyridin-3-yl)-3-(2,4-dimethoxybenzyl)dihydropyrimidine-2,4(1H,3H)-dione (600 mg, 1.30 mmol) in t-amyl-OH (6 mL) at rt was added Cs₂CO₃ (2.6 mL, 1.5 M aqueous solution), potassium (((1R,5S)-8-(tert-butoxycarbonyl)-3,8-diazabicyclo[3.2.1]octan-3-yl)methyl)trifluoroborate (518 mg, 1.56 mmol) and Ad₂n-BuP-Pd-G₃ (44 mg, 0.06 mmol) in the glove-box. The reaction mixture was stirred at 90° C. for 16 h under inert atmosphere. The reaction mixture was then filtered and concentrated. The crude product was purified by silica gel chromatography (eluted with ethyl acetate in petroleum ether) to give tert-butyl (1R,5S)-3-((3-(3-(2,4-dimethoxybenzyl)-2,4-dioxotetrahydropyrimidin-1(2H)-yl)pyrazolo[1,5-a]pyridin-5-yl)methyl)-3,8-diazabicyclo[3.2.1]octane-8-carboxylate as a light yellow solid. LCMS [M+H]⁺: 605.2.

Step 2: 1-(5-(((1R,5S)-8-(3-fluorobenzyl)-3,8-diazabicyclo[3.2.1]octan-3-yl)methyl)pyrazolo[1,5-a]pyridin-3-yl)dihydropyrimidine-2,4(1H,3H)-dione was prepared. using the method of Example 156, steps 2-4, wherein tert-butyl (1R,5S)-3-((3-(3-(2,4-dimethoxybenzyl)-2,4-dioxotetrahydropyrimidin-1(2H)-yl)pyrazolo[1,5-a]pyridin-5-yl)methyl)-3,8-diazabicyclo[3.2.1]octane-8-carboxylate was used in place of tert-butyl 4-((3-(3-(2,4-dimethoxybenzyl)-2,4-dioxotetrahydropyrimidin-1(2H)-yl)pyrazolo[1,5-a]pyridin-5-yl)methyl)piperazine-1-carboxylate and 1-(bromomethyl)-3-fluorobenzene was used in place of (bromomethyl)cyclohexane. LCMS [M+H]⁺: 463.1. ¹H NMR (400 MHz, DMSO-d6) δ=10.43 (br s, 1H), 8.57 (d, J=7.2 Hz, 1H), 7.99 (s, 1H), 7.41 (s, 1H), 7.38-7.28 (m, 1H), 7.20-7.17 (m, 2H), 7.07-6.98 (m, 1H), 6.91-6.88 (m, 1H), 3.76 (t, J=6.8 Hz, 2H), 3.49-3.47 (m, 4H), 3.04 (br s, 2H), 2.76 (t, J=6.8 Hz, 2H), 2.54-2.52 (m, 2H), 2.32-2.25 (m, 2H), 1.94-1.83 (m, 2H), 1.81-1.71 (m, 2H).

356

Example 252. Preparation of 1-(5-(((1R,5S)-8-(cyclohexylmethyl)-3,8-diazabicyclo[3.2.1]octan-3-yl)methyl)pyrazolo[1,5-a]pyridin-3-yl)dihydropyrimidine-2,4(1H,3H)-dione

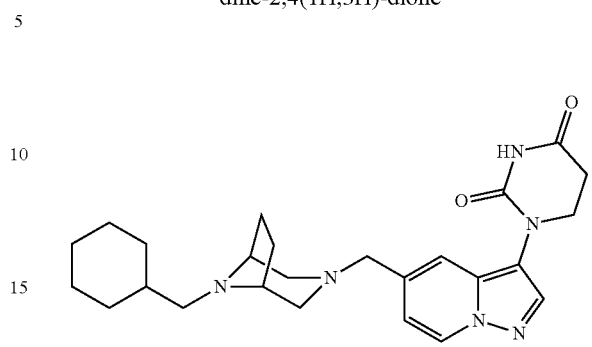

Prepared using the method of Example 156, steps 2-4, wherein tert-butyl (1R,5S)-3-((3-(3-(2,4-dimethoxybenzyl)-2,4-dioxotetrahydropyrimidin-1(2H)-yl)pyrazolo[1,5-a]pyridin-5-yl)methyl)-3,8-diazabicyclo[3.2.1]octane-8-carboxylate was used in place of tert-butyl 4-((3-(3-(2,4-dimethoxybenzyl)-2,4-dioxotetrahydropyrimidin-1(2H)-yl)pyrazolo[1,5-a]pyridin-5-yl)methyl)piperazine-1-carboxylate. LCMS [M+H]⁺: 451.1. ¹H NMR (400 MHz, DMSO-d6) δ 10.43 (br s, 1H), 8.56 (d, J=7.1 Hz, 1H), 7.99 (s, 1H), 7.40 (s, 1H), 6.89-6.87 (m, 1H), 3.75 (t, J=6.8 Hz, 2H), 3.45-3.42 (m, 2H), 3.01 (br s, 2H), 2.76 (t, J=6.8 Hz, 2H), 2.48 (br s, 2H), 2.24-2.21 (m, 2H), 2.06 (d, J=7.2 Hz, 2H), 1.87-1.53 (m, 9H), 1.09 (br s, 4H), 0.91-0.74 (m, 2H).

Example 253. Preparation of 1-(5-(((1R,5S)-8-(pyridin-3-ylmethyl)-3,8-diazabicyclo[3.2.1]octan-3-yl)methyl)pyrazolo[1,5-a]pyridin-3-yl)dihydropyrimidine-2,4(1H,3H)-dione

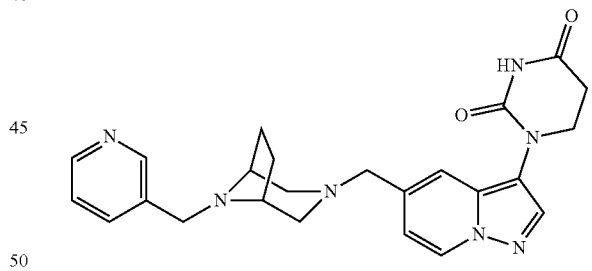

Prepared using the method of Example 192, steps 2-4, wherein tert-butyl (1R,5S)-3-((3-(3-(2,4-dimethoxybenzyl)-2,4-dioxotetrahydropyrimidin-1(2H)-yl)pyrazolo[1,5-a]pyridin-5-yl)methyl)-3,8-diazabicyclo[3.2.1]octane-8-carboxylate was used in place of tert-butyl (S)-4-((3-(3-(2,4-dimethoxybenzyl)-2,4-dioxotetrahydropyrimidin-1(2H)-yl)pyrazolo[1,5-a]pyridin-5-yl)methyl)-2-methylpiperazine-1-carboxylate and nicotinaldehyde was used in place of cyclohexanecarbaldehyde. The reductive amination was carried out with NaBH₃CN, ZnCl₂, and DIPEA in THF/EtOH. LCMS [M+H]⁺: 446.1. ¹H NMR (400 MHz, CDCl₃) δ 8.58 (d, J=2.0 Hz, 1H), 8.50-8.48 (m, 1H), 8.35 (d, J=7.2 Hz, 1H), 7.92 (s, 1H), 7.79-7.67 (m, 2H), 7.27-7.24 (m, 2H), 6.91-6.90 (m, 1H), 3.88 (t, J=6.7 Hz, 2H), 3.51 (d, J=16.0 Hz, 4H), 3.10 (br s, 2H), 2.91 (t, J=6.8 Hz, 2H), 2.57-2.55 (m, 2H), 2.39-2.37 (m, 2H), 1.99-1.84 (m, 4H).

Example 254. Preparation of 1-(5-((4-isobutyl-2-oxopiperazin-1-yl)methyl)pyrazolo[1,5-a]pyridin-3-yl)dihydropyrimidine-2,4(1H,3H)-dione

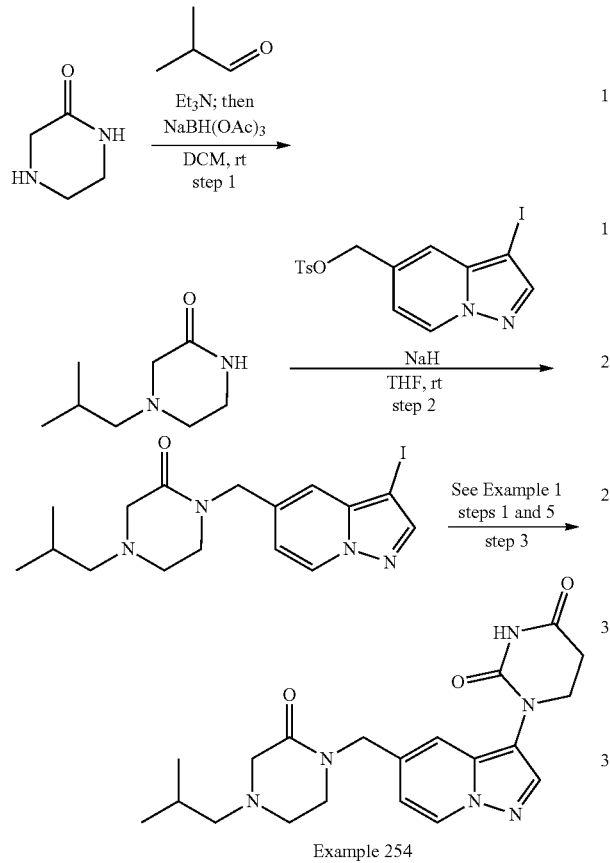

Example 254

Step 1. 4-isobutylpiperazin-2-one

To a stirred solution of piperazin-2-one (500 mg, 4.99 mmol) in DCM (20 mL) was added TEA (2.0 mL 14.97 mmol) and isopropyl aldehyde (720 mg, 9.98 mmol) at rt. The mixture was stirred for 30 min and then NaBH(OAc)$_3$ (2.1 g, 9.98 mmol) was added. The reaction was stirred at rt for 4 h and then diluted with DCM and water. The organic layer was dried over Na$_2$SO$_4$, filtered and concentrated to afford 4-isobutylpiperazin-2-one (500 mg, crude). LCMS [M+H]$^+$: 157.0.

Step 2. 1-((3-iodopyrazolo[1,5-a]pyridin-5-yl)methyl)-4-isobutylpiperazin-2-one To a stirred solution of 4-isobutylpiperazin-2-one (184 mg, 1.16 mmol) in THF (5 mL) at 0° C. was added NaH (88.0 mg, 2.23 mmol). The mixture was stirred for 30 min and allowed to warm to rt. A solution of (3-iodopyrazolo[1,5-a]pyridin-5-yl)methyl 4-methylbenzenesulfonate (500 mg, 1.16 mmol) in THF (5 mL) was added and the reaction was stirred for 1 h at rt. The reaction was diluted with EtOAc and water, the organic layer was dried over Na$_2$SO$_4$, filtered and concentrated. The crude material was purified by silica gel chromatography (eluted with 60% EtOAc in hexanes) to afford 1-((3-iodopyrazolo[1,5-a]pyridin-5-yl)methyl)-4-isobutylpiperazin-2-one (130 mg). LCMS [M+H]$^+$: 413.0.

Step 3: 1-(5-((4-isobutyl-2-oxopiperazin-1-yl)methyl)pyrazolo[1,5-a]pyridin-3-yl)dihydropyrimidine-2,4(1H,3H)-dione was prepared using the method of Example 1, steps 1 and 5, wherein 1-((3-iodopyrazolo[1,5-a]pyridin-5-yl)methyl)-4-isobutylpiperazin-2-one was used in place of 5-bromo-3-iodopyrazolo[1,5-a]pyridine. LCMS [M+H]$^+$: 399.1. $^1$H NMR (400 MHz, DMSO-d6): δ 10.45 (s, 1H), 8.60 (d, J=7.6 Hz, 1H), 8.16 (brs, 2H), 8.03 (s, 1H), 7.43 (s, 1H), 6.73 (d, J=7.2 Hz, 1H), 4.54 (s, 2H), 3.77 (t, J=6.4 Hz, 2H), 3.23-3.21 (m, 2H), 3.05 (s, 2H), 2.77 (t, J=6.8 Hz, 2H), 2.60-2.50 (m, 2H), 2.11-2.09 (m, 2H), 1.78-1.72 (m, 1H), 0.85 (d, J=6.4 Hz, 6H).

Example 255. Preparation of 1-(5-((4-(cyclohexylmethyl)-2-oxopiperazin-1-yl)methyl)pyrazolo[1,5-a]pyridin-3-yl)dihydropyrimidine-2,4(1H,3H)-dione

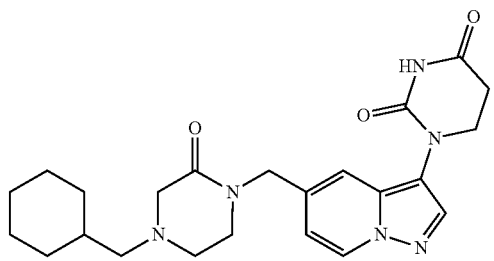 [SMILES: O=C1CCN(c2cnn3ccc(CN4CCN(CC5CCCCC5)CC4=O)cc23)C(=O)N1]

Prepared using the method of Example 254, wherein cyclohexanecarbaldehyde was used in place of isopropyl aldehyde. LCMS [M+H]$^+$: 439.2. $^1$H NMR (400 MHz, DMSO-d6) δ 10.45 (s, 1H), 8.60 (d, J=7.3 Hz, 1H), 8.33 (s, 1H), 8.03 (s, 1H), 7.43 (s, 1H), 6.73 (dd, J=7.3, 1.9 Hz, 1H), 4.54 (s, 2H), 3.77 (t, J=6.7 Hz, 2H), 3.21 (t, J=5.4 Hz, 2H), 3.04 (s, 2H), 2.77 (t, J=6.7 Hz, 2H), 2.58 (t, J=5.5 Hz, 2H), 2.53-2.50 (m, 1H), 2.14 (d, J=7.3 Hz, 2H), 1.76-1.56 (m, 5H), 1.47 (ddt, J=10.3, 6.2, 3.3 Hz, 1H), 1.29-1.07 (m, 3H), 0.82 (q, J=11.5 Hz, 2H).

Example 256. Preparation of 1-(5-(((3S,5R)-3,5-dimethyl-4-((tetrahydro-2H-pyran-4-yl)methyl)piperazin-1-yl)methyl)pyrazolo[1,5-a]pyridin-3-yl)dihydropyrimidine-2,4(1H,3H)-dione

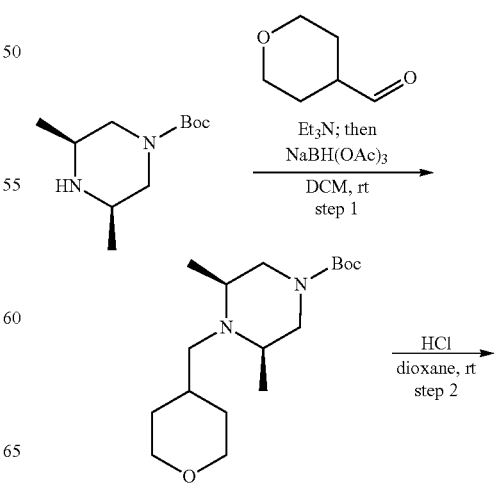

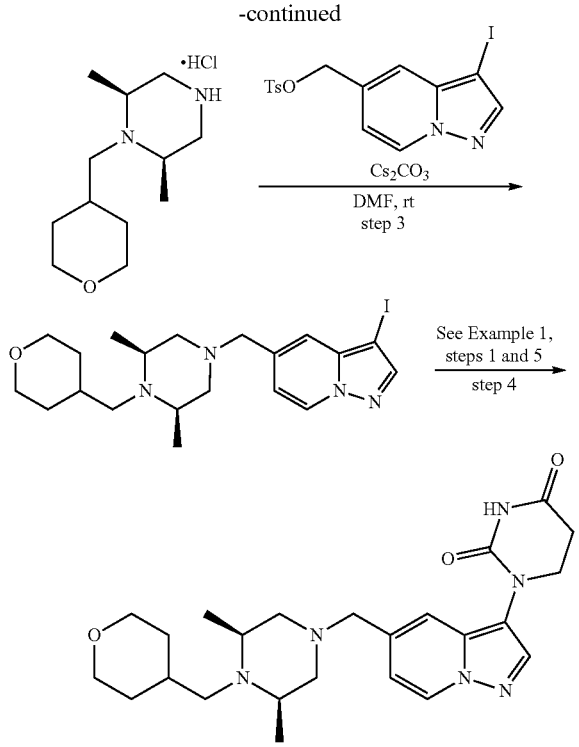

Example 256

Step 1. tert-butyl (3S,5R)-3,5-dimethyl-4-((tetrahydro-2H-pyran-4-yl)methyl)piperazine-1-carboxylate To a stirred solution of tert-butyl (3S,5R)-3,5-dimethylpiperazine-1-carboxylate (200 mg, 0.933 mmol) in DCM (5 mL) 0° C. was added tetrahydro-2H-pyran-4-carbaldehyde (159 mg, 1.39 mmol) and TEA (0.39 mL, 2.79 mmol). The mixture was stirred for 30 min and then NaBH(OAc)$_3$ (395 mg, 1.86 mmol) was added and the mixture was stirred for 2 h at rt. The reaction was diluted with DCM and water the organic layer was dried over Na$_2$SO$_4$, filtered and concentrated. The crude compound was purified by silica gel chromotography (eluting with 10% MeOH in DCM) to obtain tert-butyl (3S,5R)-3,5-dimethyl-4-((tetrahydro-2H-pyran-4-yl)methyl)piperazine-1-carboxylate (200 mg, 0.64 mmol, 69% yield). LCMS [M+H]$^+$: 313.2.

Step 2. (2S,6R)-2,6-dimethyl-1-((tetrahydro-2H-pyran-4-yl)methyl)piperazine hydrochloride To a stirred solution of tert-butyl (3S,5R)-3,5-dimethyl-4-((tetrahydro-2H-pyran-4-yl)methyl)piperazine-1-carboxylate (200 mg, 0.64 mmol) in DCM (2 mL) was added 4M HCl in dioxane (2 mL) and the mixture was stirred for 2 h at rt. The reaction was then concentrated to afford crude (2S,6R)-2,6-dimethyl-1-((tetrahydro-2H-pyran-4-yl)methyl)piperazine hydrochloride (200 mg, crude) which was used without further purification. LCMS [M+H]$^+$: 213.2.

Step 3. 5-(((3S,5R)-3,5-dimethyl-4-((tetrahydro-2H-pyran-4-yl)methyl)piperazin-1-yl)methyl)-3-iodopyrazolo[1,5-a]pyridine To a stirred solution of (3-iodopyrazolo[1,5-a]pyridin-5-yl)methyl 4-methylbenzenesulfonate (200 mg, 0.467 mmol) in DMF (4.0 mL) was added Cs$_2$CO$_3$ (456 mg, 1.401 mmol). The mixture was stirred for 30 min at 0° C. and then a solution of (2S,6R)-2,6-dimethyl-1-((tetrahydro-2H-pyran-4-yl)methyl)piperazine hydrochloride (99.1 mg, 0.467 mmol) in DMF (1 mL) was added. The mixture was stirred for 1 h at rt. The reaction was diluted with EtOAc and water and the organic layer was dried over Na$_2$SO$_4$, filtered and concentrated. The crude compound was purified by silica gel chromotography (eluting with 30% EtOAc in hexanes) to obtain 5-(((3S,5R)-3,5-dimethyl-4-((tetrahydro-2H-pyran-4-yl)methyl)piperazin-1-yl)methyl)-3-iodopyrazolo[1,5-a]pyridine (80 mg, 0.17 mmol, 40% yield). LCMS [M+H]$^+$: 469.0.

Step 4: 1-(5-(((3S,5R)-3,5-dimethyl-4-((tetrahydro-2H-pyran-4-yl)methyl)piperazin-1-yl)methyl)pyrazolo[1,5-a]pyridin-3-yl)dihydropyrimidine-2,4(1H,3H)-dione was prepared using the method of Example 1, steps 1 and 5, wherein 5-(((3S,5R)-3,5-dimethyl-4-((tetrahydro-2H-pyran-4-yl)methyl)piperazin-1-yl)methyl)-3-iodopyrazolo[1,5-a]pyridine was used in place of 5-bromo-3-iodopyrazolo[1,5-a]pyridine. LCMS [M+H]$^+$: 455.4. $^1$H NMR (400 MHz, CD$_3$OD): δ 8.46 (d, J=7.2 Hz, 1H), 8.02 (s, 1H), 7.49 (s, 1H), 6.99-6.97 (m, 1H), 3.97-3.87 (m, 4H), 3.63 (s, 2H), 3.42 (t, J=11.6 Hz, 4H), 3.05-2.98 (m, 4H), 2.88 (t, J=6.4 Hz, 2H), 2.30-2.25 (m, 2H), 1.94-1.93 (m, 2H), 1.79-1.75 (m, 2H), 1.42-1.28 (m, 7H).

Example 257. Preparation of 1-(5-(((3S,5R)-4-isobutyl-3,5-dimethylpiperazin-1-yl)methyl)pyrazolo[1,5-a]pyridin-3-yl)dihydropyrimidine-2,4(1H,3H)-dione

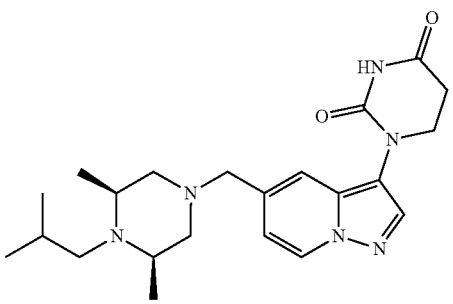 [SMILES: CC(C)CN1[C@H](C)CN(Cc2ccn3ncc(N4CCC(=O)NC4=O)c3c2)C[C@@H]1C]

Prepared using the method of Example 256, wherein isobutyraldehyde was used in place of tetrahydro-2H-pyran-4-carbaldehyde. LCMS [M+H]$^+$: 413.2. $^1$H NMR (400 MHz, Methanol-d4) b 8.46 (d, J=7.1 Hz, 1H), 8.03 (s, 1H), 7.50 (s, 1H), 6.99 (dd, J=7.1, 1.8 Hz, 1H), 3.90 (t, J=6.7 Hz, 2H), 3.60 (s, 2H), 3.30-3.13 (m, 2H), 3.00-2.77 (m, 6H), 2.21 (t, J=10.7 Hz, 2H), 2.00-1.85 (m, 1H), 1.26 (s, 2H), 1.25 (s, 2H), 1.05 (s, 2H), 1.04 (s, 2H). NH proton not observed due to solvent exchange.

Example 258. Preparation of 1-(5-(((3S,5S)-4-(cyclohexylmethyl)-3,5-dimethylpiperazin-1-yl)methyl)pyrazolo[1,5-a]pyridin-3-yl)dihydropyrimidine-2,4(1H,3H)-dione

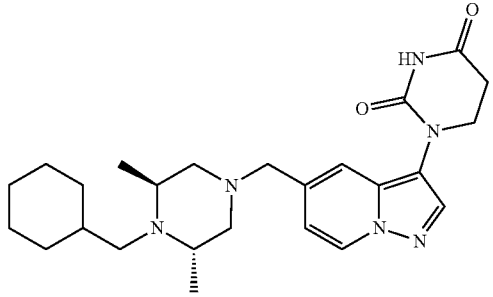 [SMILES: C[C@H]1CN(Cc2ccn3ncc(N4CCC(=O)NC4=O)c3c2)C[C@H](C)N1CC1CCCCC1]

Prepared using the method of Example 256, wherein tert-butyl (3S,5S)-3,5-dimethylpiperazine-1-carboxylate was used in place of tert-butyl (3S,5R)-3,5-dimethylpiperazine-1-carboxylate and cyclohexanecarbaldehyde was used in place of tetrahydro-2H-pyran-4-carbaldehyde. LCMS [M+H]$^+$: 453.2. $^1$H NMR (400 MHz, Methanol-d4) δ 8.51 (d, J=7.3 Hz, 1H), 8.06 (s, 1H), 7.56 (s, 1H), 7.01 (d, J=7.7 Hz, 1H), 3.95-3.64 (m, 6H), 3.20-2.49 (m, 8H), 1.91-1.65 (m, 6H), 1.59-1.17 (m, 9H), 1.08 (q, J=12.0 Hz, 2H). NH proton not observed due to solvent exchange.

Example 259. Preparation of 1-(5-(((3S,5S)-4-isobutyl-3,5-dimethylpiperazin-1-yl)methyl)pyrazolo[1,5-a]pyridin-3-yl)dihydropyrimidine-2,4(1H,3H)-dione (Example 259)

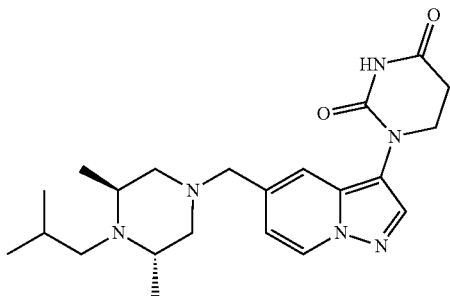 [SMILES: CC(C)CN1[C@@H](C)CN(Cc2ccn3ncc(N4CCC(=O)NC4=O)c3c2)C[C@@H]1C]

Prepared using the method of Example 256, wherein tert-butyl (3S,5S)-3,5-dimethylpiperazine-1-carboxylate was used in place of tert-butyl (3S,5R)-3,5-dimethylpiperazine-1-carboxylate and isobutyraldehyde was used in place of tetrahydro-2H-pyran-4-carbaldehyde. LCMS [M+H]$^+$: 413.2. $^1$H NMR (400 MHz, Methanol-d4) δ 8.47 (d, J=7.3 Hz, 1H), 8.07 (s, 1H), 8.03 (s, 1H), 7.49 (s, 1H), 7.00 (d, J=7.1 Hz, 1H), 3.90 (t, J=6.7 Hz, 2H), 3.82 (s, 1H), 3.76-3.51 (m, 3H), 3.09 (dd, J=13.4, 9.7 Hz, 1H), 3.04-2.93 (m, 2H), 2.93-2.75 (m, 3H), 2.62 (d, J=12.5 Hz, 1H), 2.46 (t, J=11.2 Hz, 1H), 2.16-2.01 (m, 1H), 1.50-1.33 (m, 7H), 1.06 (t, J=6.9 Hz, 7H). NH proton not observed due to solvent exchange.

Example 260. Preparation of (S)-1-(5-((hexahydropyrrolo[1,2-a]pyrazin-2(1H)-yl)methyl)pyrazolo[1,5-a]pyridin-3-yl)dihydropyrimidine-2,4(1H,3H)-dione (Example 260)

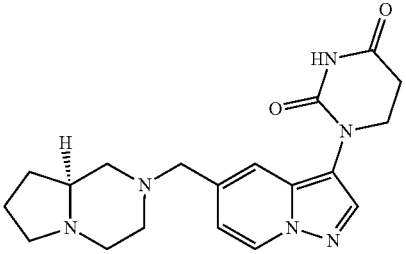 [SMILES: O=C1CCN(c2cnn3ccc(CN4CCN5CCC[C@H]5C4)cc23)C(=O)N1]

Prepared using the method of Example 156, steps 1 and 4, wherein potassium (S)-trifluoro((hexahydropyrrolo[1,2-a]pyrazin-2(1H)-yl)methyl)borate was used in place of potassium {[4-(tert-butoxycarbonyl)-1-piperazinyl]methyl}(trifluoro)borate. LCMS [M+H]$^+$: 369.3. $^1$H NMR (400 MHz, METHANOL-d4) δ 8.46 (d, J=7.2 Hz, 1H), 8.03 (s, 1H), 7.52 (d, J=0.4 Hz, 1H), 7.03-7.01 (m, 1H), 3.93-3.89 (m, 2H), 3.74-3.57 (m, 2H), 3.12-2.99 (m, 3H), 2.95-2.82 (m, 3H), 2.42-2.29 (m, 2H), 2.25-2.19 (m, 2H), 2.05-1.95 (m, 1H), 1.91-1.78 (m, 3H), 1.50-1.36 (m, 1H).

Example 261. Preparation of (R)-1-(5-((hexahydropyrrolo[1,2-a]pyrazin-2(1H)-yl)methyl)pyrazolo[1,5-a]pyridin-3-yl)dihydropyrimidine-2,4(1H,3H)-dione

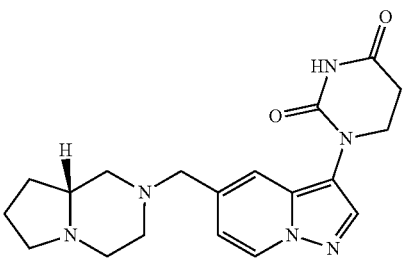 [SMILES: O=C1CCN(c2cnn3ccc(CN4CCN5CCC[C@@H]5C4)cc23)C(=O)N1]

Prepared using the method of Example 156, steps 1 and 4, wherein potassium (R)-trifluoro((hexahydropyrrolo[1,2-a]pyrazin-2(1H)-yl)methyl)borate was used in place of potassium {[4-(tert-butoxycarbonyl)-1-piperazinyl]methyl}(trifluoro)borate. LCMS [M+H]$^+$: 369.1. $^1$H NMR (400 MHz, METHANOL-d4) δ=8.47-8.41 (m, 1H), 8.01 (s, 1H), 7.50 (d, J=0.8 Hz, 1H), 7.06-6.92 (m, 1H), 3.95-3.86 (m, 2H), 3.71-3.60 (m, 2H), 3.10-2.97 (m, 3H), 2.93-2.83 (m, 3H), 2.39-2.29 (m, 2H), 2.21 (d, J=8.8 Hz, 2H), 2.01-1.96 (m, 1H), 1.86-1.74 (m, 3H), 1.47-1.33 (m, 1H).

Example 262. Preparation of (S)-1-(5-((octahydro-2H-pyrido[1,2-a]pyrazin-2-yl)methyl)pyrazolo[1,5-a]pyridin-3-yl)dihydropyrimidine-2,4(1H,3H)-dione

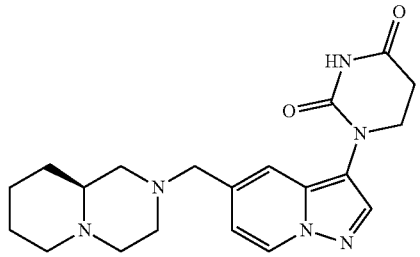 [SMILES: O=C1CCN(c2cnn3ccc(CN4CCN5CCCC[C@H]5C4)cc23)C(=O)N1]

Prepared using the method of Example 156, steps 1 and 4, wherein potassium (S)-trifluoro((octahydro-2H-pyrido[1,2-a]pyrazin-2-yl)methyl)borate was used in place of potassium {[4-(tert-butoxycarbonyl)-1-piperazinyl]methyl}(trifluoro)borate. LCMS [M+H]$^+$: 383.1. $^1$H NMR (400 MHz, Methanol-d4) δ 8.48 (d, J=7.2 Hz, 1H), 8.04 (s, 1H), 7.54 (s, 1H), 6.99 (dd, J=7.2, 1.9 Hz, 1H), 4.88 (br. s, 2H), 3.90 (t, J=6.8 Hz, 2H), 3.76 (s, 2H), 3.58-3.37 (m, 2H), 3.22-3.01 (m, 3H), 2.89 (t, J=6.8 Hz, 2H), 2.87-2.74 (m, 2H), 2.67-2.52 (m, 2H), 2.52-2.36 (m, 2H).

Example 263. Preparation of (R)-1-(5-((hexahydropyrazino[2,1-c][1,4]oxazin-8(1H)-yl)methyl)pyrazolo[1,5-a]pyridin-3-yl)dihydropyrimidine-2,4(1H,3H)-dione

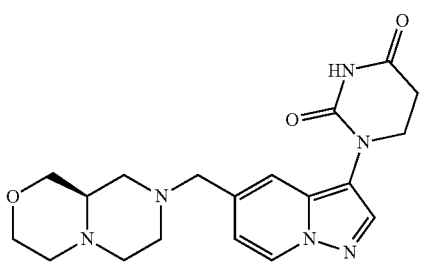 [SMILES: O=C1CCN(c2cnn3ccc(CN4CCN5CCOC[C@H]5C4)cc23)C(=O)N1]

Prepared using the method of Example 156, steps 1 and 4, Wherein potassium (R)-trifluoro((hexahydropyrazino[2,1-c][1,4]oxazin-8(1H)-yl)methyl)borate was used in place of potassium {[4-(tert-butoxycarbonyl)-1-piperazinyl]methyl}(trifluoro)borate. LCMS [M+H]$^+$: 385.3. $^1$H NMR (400 MHz, Methanol-d4) δ 8.44 (d, J=7.1 Hz, 1H), 8.25 (s, 1H), 8.00 (s, 1H), 7.50 (s, 1H), 6.97 (dd, J=7.1, 1.8 Hz, 1H), 3.91-3.82 (m, 3H), 3.72-3.58 (m, 4H), 3.24 (d, J=11.1 Hz, 1H), 2.98-2.71 (m, 6H), 2.61-2.38 (m, 4H), 1.99 (t, J=10.9 Hz, 1H). NH proton not observed due to solvent exchange.

Example 264. Preparation of (S)-1-(5-((hexahydropyrazino[2,1-c][1,4]oxazin-8(1H)-yl)methyl)pyrazolo[1,5-a]pyridin-3-yl)dihydropyrimidine-2,4(1H,3H)-dione

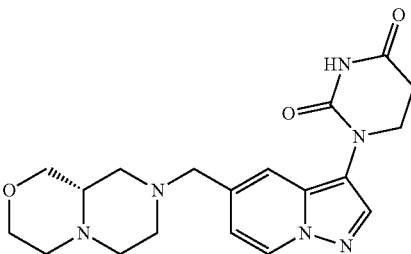

Prepared using the method of Example 156, steps 1 and 4, wherein potassium (S)-trifluoro((hexahydropyrazino[2,1-c][1,4]oxazin-8(1H)-yl)methyl)borate was used in place of potassium {[4-(tert-butoxycarbonyl)-1-piperazinyl]methyl}(trifluoro)borate. LCMS [M+H]$^+$: 385.2. $^1$H NMR (400 MHz, CD$_3$OD) δ 8.45 (d, J=7.2 Hz, 1H), 8.24 (brs, 1H), 8.01 (s, 1H), 7.50 (s, 1H), 6.98 (dd, J=7.2 Hz, 1.2 Hz, 1H), 3.89-3.84 (m, 3H), 3.72-3.61 (m, 4H), 3.27-3.24 (m, 1H), 2.97-2.78 (m, 6H), 2.62-2.44 (m, 4H), 2.03-1.98 (m, 1H).

Example 265. Preparation of 1-(5-(((2S,4R)-1-(((1r,4S)-4-methoxycyclohexyl)methyl)-2-methylpiperidin-4-yl)methyl)pyrazolo[1,5-a]pyridin-3-yl)dihydropyrimidine-2,4(1H,3H)-dione

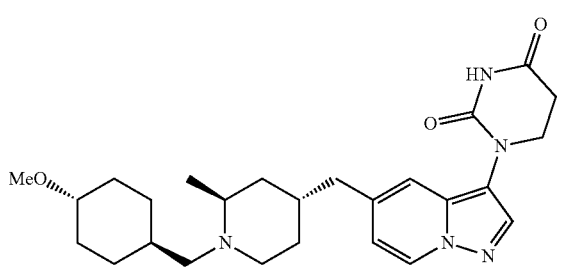 [SMILES: CO[C@H]1CC[C@H](CN2CC[C@@H](Cc3ccn4ncc(N5CCC(=O)NC5=O)c4c3)C[C@@H]2C)CC1]

Prepared using the method of Example 141, wherein trans-4-methoxycyclohexane-1-carbaldehyde was used in place of 4,4-difluorocyclohexane-1-carbaldehyde. LCMS [M+H]$^+$: 468.1. $^1$H NMR (400 MHz, CD$_3$OD) δ 8.55 (s, 1H), 8.43 (d, J=7.2 Hz, 1H), 8.01 (s, 1H), 7.36 (s, 1H), 6.83 (dd, J=7.1, 1.9 Hz, 1H), 3.89 (t, J=6.7 Hz, 2H), 3.62 (s, 1H), 3.35 (s, 3H), 3.16 (ddd, J=15.1, 7.5, 4.4 Hz, 3H), 2.89 (t, J=6.7 Hz, 4H), 2.68 (d, J=7.3 Hz, 1H), 2.25-2.07 (m, 3H), 1.96-1.56 (m, 7H), 1.38-1.04 (m, 8H).

Example 266. Preparation of 1-(5-((1-(((1r,4r)-4-ethoxycyclohexyl)methyl)piperidin-4-yl)methyl)pyrazolo[1,5-a]pyridin-3-yl)dihydropyrimidine-2,4(1H,3H)-dione

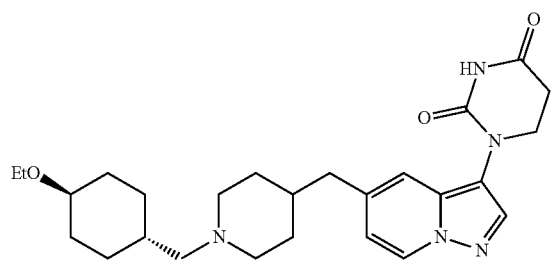 [SMILES: CCO[C@H]1CC[C@H](CN2CCC(Cc3ccn4ncc(N5CCC(=O)NC5=O)c4c3)CC2)CC1]

Prepared using the method of Example 192, steps 3-4, wherein trans-4-ethoxycyclohexane-1-carbaldehyde [see US2016/122318, 2016, A1] was used in place of cyclohexanecarbaldehyde. LCMS [M+H]$^+$: 468.2. $^1$H NMR (500 MHz, DMSO-d6) δ 10.45 (d, J=4.5 Hz, 1H), 8.60 (dt, J=7.1, 1.4 Hz, 1H), 8.02 (d, J=1.8 Hz, 1H), 7.46-7.28 (m, 1H), 6.80 (dd, J=7.2, 1.9 Hz, 1H), 3.78 (td, J=6.7, 2.8 Hz, 2H), 3.45 (p, J=6.6 Hz, 4H), 3.26-3.08 (m, 2H), 2.92-2.83 (m, 3H), 2.79 (td, J=6.7, 2.0 Hz, 2H), 2.61 (d, J=6.6 Hz, 2H), 1.98 (d, J=12.1 Hz, 2H), 1.92-1.65 (m, 6H), 1.49 (q, J=13.1 Hz, 2H), 1.11 (s, 2H), 1.09 (t, J=7.0 Hz, 3H), 0.99 (dd, J=14.4, 11.3 Hz, 2H).

Example 267. Preparation of 1-(5-(1-(1-isobutylpiperidin-4-yl)ethyl)pyrazolo[1,5-a]pyridin-3-yl)dihydropyrimidine-2,4(1H,3H)-dione

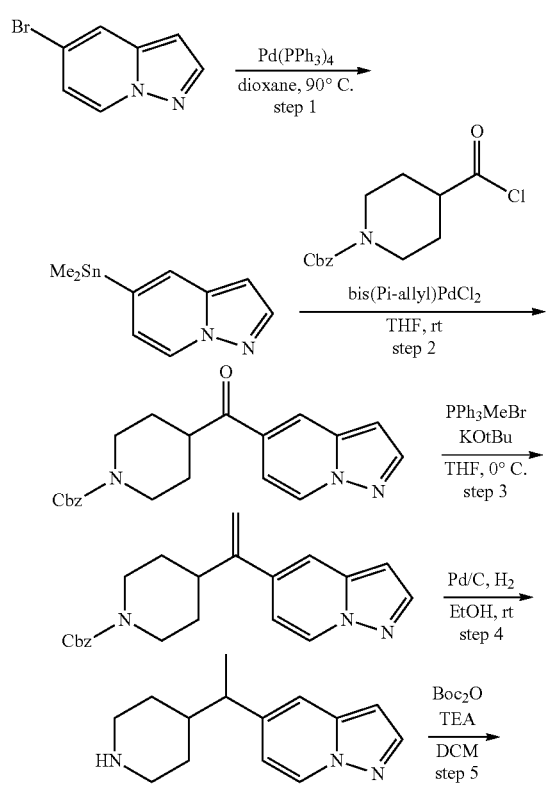

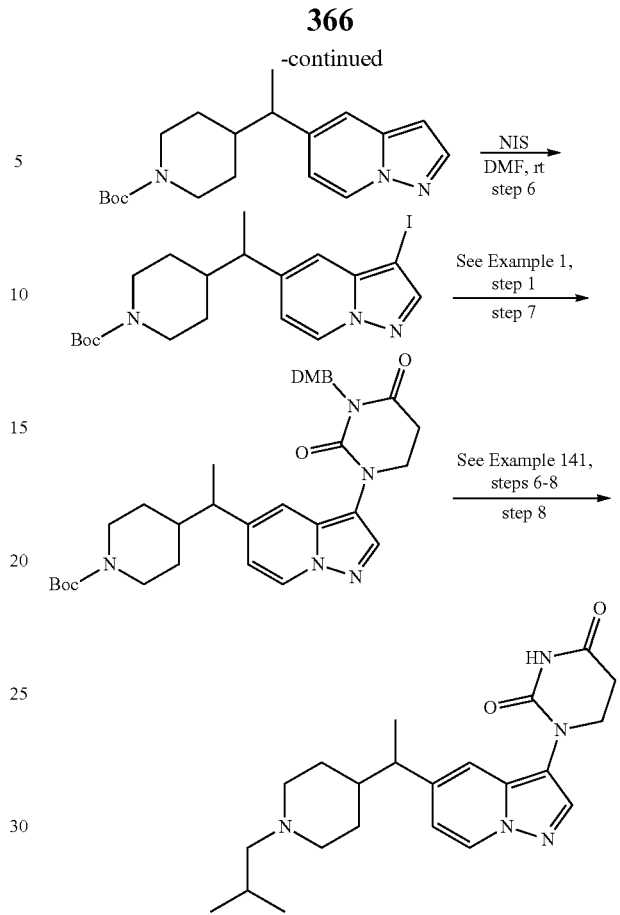

Example 267

Step 1. 5-(trimethylstannyl)pyrazolo[1,5-a]pyridine

To a stirred solution of 5-bromopyrazolo[1,5-a]pyridine (3 g, 15.2 mmol) in dioxane (40 mL) was added Pd(PPh$_3$)$_4$ (877 mg, 0.76 mmol), Hexamethylditin (4.97 g, 15.2 mmol) and the reaction was stirred for 4 h at 90° C. After completion, the reaction mixture was filtered through celite and concentrated to afford 5-(trimethylstannyl)pyrazolo[1,5-a]pyridine (3.2 g, crude). The material was used without further purification. LCMS [M+H]$^+$: 282.9.

Step 2. benzyl 4-(pyrazolo[1,5-a]pyridine-5-carbonyl)piperidine-1-carboxylate To a stirred solution of 5-(trimethylstannyl)pyrazolo[1,5-a]pyridine (3.0 g. 10.7 mmol) in THF (30 mL) was added benzyl 4-(chlorocarbonyl)piperidine-1-carboxylate (3.0 g, 10.7 mmol) and the solution was de-gassed by bubbling nitrogen through it for 10 min. Allylpalladium(II) chloride dimer (390 mg, 1.07 mmol) and molecular sieves (500 mg) were added and the reaction was stirred for 4 h at 60° C. After completion, the reaction mixture was concentrated. The crude compound was purified by silica gel chromotography (eluting with 50% EtOAc in hexanes) to afford benzyl 4-(pyrazolo[1,5-a]pyridine-5-carbonyl)piperidine-1-carboxylate (1.8 g, 4.95 mmol, 46% yield). LCMS [M+H]$^+$: 364.0.

Step 3. benzyl 4-(1-(pyrazolo[1,5-a]pyridin-5-yl)vinyl)piperidine-1-carboxylate To a stirred solution of methyl triphenylphosphonium bromide (1.47 g, 4.12 mmol) in THF (10 mL) at 0° C., was slowly added 1M KOtBu (4.1 mL, 4.12 mmol) resulting in a yellow color. The reaction mixture was stirred at rt for 30 min and then a solution of benzyl 4-(pyrazolo[1,5-a]pyridine-5-carbonyl)piperidine-1-carboxylate (0.50 g, 1.37 mmol) in THF (2 mL) was added dropwise to at 0° C. The reaction mixture was allowed to stirred at rt for 3 h. After completion, the reaction was quenched with a solution of saturated aqueous NH₄Cl and the mixture was diluted with ethyl acetate and washed with water. The organic layer was dried over Na₂SO₄, filtered and concentrated. The crude compound was purified by silica gel chromatography (eluting with 30% EtOAc in hexanes) to afford benzyl 4-(1-(pyrazolo[1,5-a]pyridin-5-yl)vinyl)piperidine-1-carboxylate (0.21 g, 0.58 mmol, 42% yield). ¹H NMR (400 MHz, CD₃OD) b 8.41 (d, J=7.2 Hz, 1H), 7.93 (d, J=2.1 Hz, 1H), 7.45 (s, 1H), 7.36-7.30 (m, 4H), 6.76 (dd, J=7.2 Hz, 2.1 Hz, 1H), 6.49 (d, J=2.1 Hz, 1H), 5.34 (s, 1H), 5.13-5.11 (m, 3H), 4.28 (s, 2H), 2.89-2.82 (m, 2H), 2.63-2.56 (m, 2H), 1.85-1.81 (m, 2H), 1.43-1.40 (m, 2H).

Step 4. 5-(1-(piperidin-4-yl)ethyl)pyrazolo[1,5-a]pyridine

To a stirred solution of benzyl 4-(1-(pyrazolo[1,5-a]pyridin-5-yl)vinyl)piperidine-1-carboxylate (0.20 g, 0.55 mmol) in EtOH (10 mL) under a nitrogen atmosphere was added Pd/C (0.10 g). The flask was evacuated and refilled with hydrogen from a balloon and stirred for 16 h at rt. After completion, the reaction mixture was filtered through celite and washed through with EtOH. The filtrate was concentrated to afford 5-(1-(piperidin-4-yl)ethyl)pyrazolo[1,5-a]pyridine (0.18 g, crude). The compound was used in the next step without further purification.

Step 5. tert-butyl 4-(1-(pyrazolo[1,5-a]pyridin-5-yl)ethyl)piperidine-1-carboxylate To a stirred solution of 5-(1-(piperidin-4-yl)ethyl)pyrazolo[1,5-a]pyridine (0.18 g, 0.78 mmol) in DCM (7 mL) at 0° C. was added Et₃N (0.33 mL, 2.4 mmol) followed by di-tert-butyl dicarbonate (0.26 g, 1.17 mmol) and DMAP (9.59 mg, 0.078 mmol). The reaction mixture was stirred at rt for 16 h. After completion, the reaction was diluted with water and extracted with EtOAc. The organic layer was washed with brine, dried over Na₂SO₄, filtered and concentrated. The crude compound was purified by silica gel chromatography (eluting with 10-15% EtOAc in hexanes) to afford tert-butyl 4-(1-(pyrazolo[1,5-a]pyridin-5-yl)ethyl)piperidine-1-carboxylate (110 mg, 0.33 mmol, 42% yield). ¹H NMR (300 MHz, CD₃OD) δ 8.39 (d, J=7.5 Hz, 1H), 7.91 (s, 1H), 6.56 (dd, J=7.2 Hz, 2.1 Hz, 1H), 6.40 (d, J=1.2 Hz, 1H), 2.65-2.45 (m, 3H), 1.84-1.80 (m, 1H), 1.61-1.49 (m, 1H), 1.43-1.38 (m, 10H), 1.28-1.02 (m, 6H).

Step 6. tert-butyl 4-(1-(3-iodopyrazolo[1,5-a]pyridin-5-yl)ethyl)piperidine-1-carboxylate To a stirred solution of tert-butyl 4-(1-(pyrazolo[1,5-a]pyridin-5-yl)ethyl)piperidine-1-carboxylate (0.10 g 0.30 mmol) in DMF (5 mL) at 0° C. was added NIS (68.2 mg, 0.30 mmol) under an inert atmosphere. The reaction mixture was stirred at rt for 3 h. After completion, the reaction was quenched with water and the yellow precipitate that formed was collected by filtration. The solid was washed with water and dried under vacuum to afford tert-butyl 4-(1-(3-iodopyrazolo[1,5-a]pyridin-5-yl)ethyl)piperidine-1-carboxylate (120 mg, 0.26 mmol, 86% yield). LCMS [M+H]⁺: 456.0.

Step 7: tert-butyl 4-(1-(3-(3-(2,4-dimethoxybenzyl)-2,4-dioxotetrahydropyrimidin-1(2H)-yl)pyrazolo[1,5-a]pyridin-5-yl)ethyl)piperidine-1-carboxylate was prepared using the method of Example 1, step 1, wherein tert-butyl 4-(1-(3-iodopyrazolo[1,5-a]pyridin-5-yl)ethyl)piperidine-1-carboxylate was used in place of 5-bromo-3-iodopyrazolo[1,5-a]pyridine. LCMS [M+H]⁺: 592.2.

Step 8: 1-(5-(1-(1-isobutylpiperidin-4-yl)ethyl)pyrazolo[1,5-a]pyridin-3-yl)dihydropyrimidine-2,4(1H,3H)-dione was prepared using the method of Example 141, steps 6-8, wherein tert-butyl 4-(1-(3-(3-(2,4-dimethoxybenzyl)-2,4-dioxotetrahydropyrimidin-1(2H)-yl)pyrazolo[1,5-a]pyridin-5-yl)ethyl)piperidine-1-carboxylate was used in place of tert-butyl (2S,4R)-4-((3-(3-(2,4-dimethoxybenzyl)-2,4-dioxotetrahydropyrimidin-1(2H)-yl)pyrazolo[1,5-a]pyridin-5-yl)methyl)-2-methylpiperidine-1-carboxylate and isobutyraldehyde was used in place of 4,4-difluorocyclohexane-1-carbaldehyde. LCMS [M+H]⁺: 398.3. ¹H NMR (400 MHz, Methanol-d4) b 8.51 (s, 1H), 8.43 (d, J=7.2 Hz, 1H), 8.01 (s, 1H), 7.36 (s, 1H), 6.84 (dd, J=7.4, 1.9 Hz, 1H), 3.89 (t, J=6.8 Hz, 2H), 3.74-3.61 (m, 1H), 3.23-3.14 (m, 2H), 2.95 (s, 1H), 2.89 (t, J=6.7 Hz, 2H), 2.69 (d, J=7.2 Hz, 2H), 2.21 (s, 1H), 2.06 (d, J=19.5 Hz, 2H), 1.81 (dd, J=37.0, 15.2 Hz, 7H), 1.59 (s, 1H), 1.35 (t, J=11.2 Hz, 5H).

Example 268. Preparation of 1-(5-(((2S,4R)-1-((4,4-difluorocyclohexyl)methyl)-2-methylpiperidin-4-yl)methyl)pyrazolo[1,5-a]pyridin-3-yl)pyrimidine-2,4(1H,3H)-dione

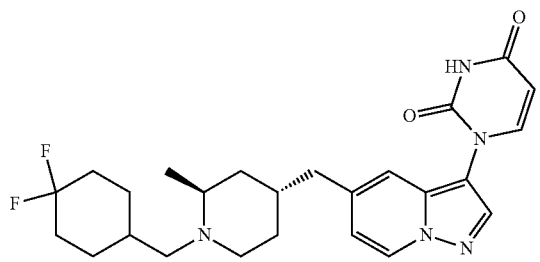 [SMILES: C[C@H]1C[C@H](Cc2ccn3ncc(-n4ccc(=O)[nH]c4=O)c3c2)CCN1CC1CCC(F)(F)CC1]

Methanesulfonic acid (2.0 mL, 31 mmol) was added to 1-(5-(((2S,4R)-1-((4,4-difluorocyclohexyl)methyl)-2-methylpiperidin-4-yl)methyl)pyrazolo[1,5-a]pyridin-3-yl)-3-(2,4-dimethoxybenzyl)dihydropyrimidine-2,4(1H,3H)-dione (1.24 g, 1.99 mmol) in DCM (8 mL). The resulting pale red solution was stirred overnight at 40° C. The reaction mixture was quenched with 50% aqueous sodium bicarbonate solution and extracted with 4:1 dichloromethane:trifluoroethanol three times. The combined organic phases were dried over Na₂SO₄, filtered and concentrated. The crude material was purified by silica gel chromatography (eluting with 15-100% 3:1 EtOAc:EtOH in heptane, 0.1% TEA as modifier) to afford impure product. The material was further purified by C18 reverse phase chromatography (eluting with 25-75% acetonitrile in water, 0.1% NH₄OH as modifier) and the product-containing fractions were assembled and poured into a pH 7 phosphate buffered solution. The aqueous phase was extracted with 4:1 dichloromethane:trifluoroethanol three times. The combined organic phases were concentrated in vacuo, diluted with 2:1 acetonitrile:water (3 mL) and lyophilized to afford 1-(5-(((2S,4R)-1-((4,4-difluorocyclohexyl)methyl)-2-methylpiperidin-4-yl)methyl)pyrazolo[1,5-a]pyridin-3-yl)pyrimidine-2,4(1H,3H)-dione (3.5 mg, 0.0072 mmol, 0.36% yield) as a white solid. LCMS [M+H]⁺:

472.3. ¹H NMR (400 MHz, DMSO-d₆) δ 11.48 (s, 1H), 8.61 (d, J=7.1 Hz, 1H), 8.12 (s, 1H), 7.70 (d, J=7.8 Hz, 1H), 7.33 (s, 1H), 6.85 (dd, J=7.2, 1.8 Hz, 1H), 5.69 (d, J=7.8 Hz, 1H), 2.96-2.83 (m, 1H), 2.57-2.50 (m, 2H), 2.46-2.35 (m, 2H), 2.17 (qd, J=12.5, 7.2 Hz, 2H), 2.02-1.90 (m, 2H), 1.90-1.84 (m, 1H), 1.84-1.62 (m, 4H), 1.59-1.44 (m, 2H), 1.44-1.33 (m, 2H), 1.22-1.12 (m, 1H), 1.05 (q, J=13.7, 12.7 Hz, 2H), 0.86 (d, J=6.6 Hz, 3H).

Example 269. Preparation of 1-(5-(azepan-4-ylmethyl)pyrazolo[1,5-a]pyridin-3-yl)dihydropyrimidine-2,4(1H,3H)-dione

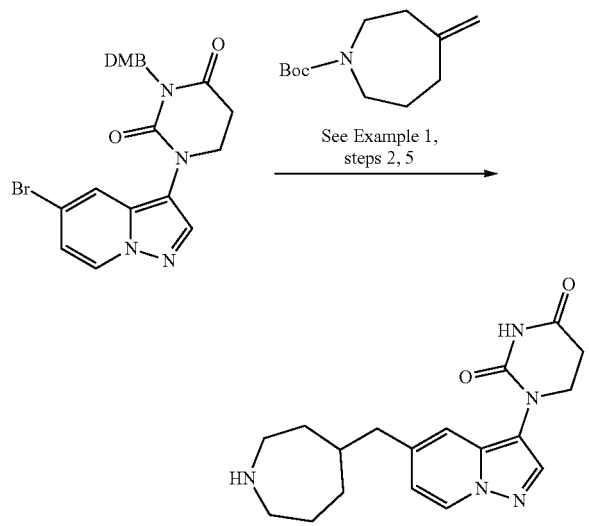

Prepared using the method of Example 1, steps 2 and 5, wherein tert-butyl 4-methyleneazepane-1-carboxylate [see WO2021/158829, 2021, A1] was used in place of tert-butyl 4-methylenepiperidine-1-carboxylate in step 2. LCMS [M+H]⁺: 341.8. ¹H NMR (400 MHz, CD₃OD) δ 8.43 (s, 1H), 8.41 (s, 1H), 8.00 (d, J=2.2 Hz, 1H), 7.36 (s, 1H), 6.84 (dd, J=7.1, 2.0 Hz, 1H), 3.88 (td, J=6.8, 2.1 Hz, 2H), 3.28-3.21 (m, 2H), 3.20-3.04 (m, 2H), 2.89 (td, J=6.8, 1.8 Hz, 2H), 2.75-2.61 (m, 2H), 2.09-1.89 (m, 4H), 1.86-1.73 (m, 1H), 1.62 (ddt, J=18.5, 13.0, 6.5 Hz, 1H), 1.46-1.29 (m, 1H). Missing NH due to solvent exchange.

Example 270. Preparation of tert-butyl 4-((3-(2,4-dioxotetrahydropyrimidin-1(2H)-yl)pyrazolo[1,5-a]pyridin-5-yl)methyl)azepane-1-carboxylate

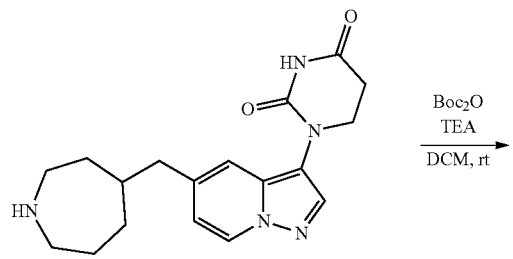

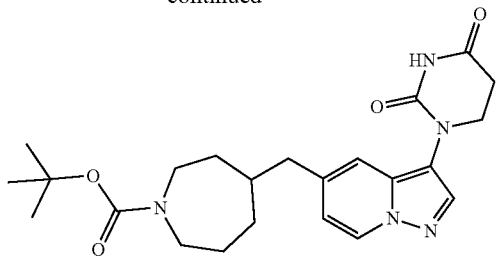

TEA (0.061 mL, 0.44 mmol) and di-tert-butyl dicarbonate (0.015 mL, 0.32 mmol) were added to a solution of 1-(5-(azepan-4-ylmethyl)pyrazolo[1,5-a]pyridin-3-yl)dihydropyrimidine-2,4(1H,3H)-dione (Example 269) (100 mg, 0.21 mmol) in DCM (5 mL) at rt. The mixture was stirred at rt for 4 h and then partioned between DCM and water. The organic layer was separated, washed with brine, dried over sodium sulfate, filtered and concentrated. The residue was dissolved in DMSO, filtered through a 1 micron filter and purified by reverse phase HPLC using ACN/Water/0.1% formic acid. The fractions containing the product were combined, frozen and lyophilized to afford tert-butyl 4-((3-(2,4-dioxotetrahydropyrimidin-1(2H)-yl)pyrazolo[1,5-a]pyridin-5-yl)methyl)azepane-1-carboxylate as an off-white solid. LCMS [M+H-tBu]⁺: 385.9. ¹H NMR (400 MHz, CD₃OD) δ 8.40 (d, J=7.1 Hz, 1H), 7.98 (d, J=2.7 Hz, 1H), 7.34 (s, 1H), 6.82 (dd, J=7.1, 1.9 Hz, 1H), 3.88 (t, J=6.7 Hz, 2H), 3.55 (dt, J=16.6, 5.4 Hz, 1H), 3.37 (dd, J=15.6, 8.8 Hz, 2H), 3.25-3.12 (m, 1H), 2.89 (t, J=6.8 Hz, 2H), 2.64 (d, J=7.1 Hz, 2H), 1.90-1.73 (m, 4H), 1.56 (s, 1H), 1.45 (d, J=5.7 Hz, 9H), 1.40-1.19 (m, 2H). Missing NH due to solvent exchange.

Example 271. Preparation of 1-(5-((1-methylazepan-4-yl)methyl)pyrazolo[1,5-a]pyridin-3-yl)dihydropyrimidine-2,4(1H,3H)-dione

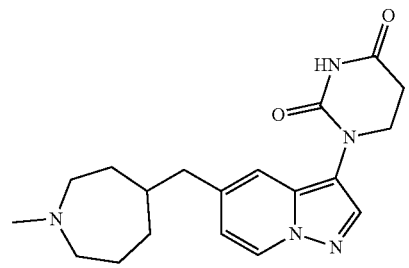 [SMILES: CN1CCCC(Cc2ccn3ncc(N4CCC(=O)NC4=O)c3c2)CC1]

Prepared from 1-(5-(azepan-4-ylmethyl)pyrazolo[1,5-a]pyridin-3-yl)dihydropyrimidine-2,4(1H,3H)-dione (Example 269) using the method of Example 109, wherein paraformaldehyde was used in place of isobutyraldehyde. LCMS [M+H]⁺: 355.9. ¹H NMR (400 MHz, CD₃OD) δ8.46-8.35 (m, 2H), 8.00 (s, 1H), 7.35 (s, 1H), 6.83 (dd, J=7.0, 1.9 Hz, 1H), 3.89 (t, J=6.8 Hz, 2H), 3.22 (d, J=12.2 Hz, 3H), 2.94-2.83 (m, 5H), 2.74-2.60 (m, 2H), 2.09 (ddt, J=10.3, 7.2, 3.6 Hz, 1H), 2.01-1.80 (m, 4H), 1.77-1.65 (m, 1H), 1.48-1.28 (m, 2H).

Example 272. Preparation of 1-(5-((1-(cyclohexylmethyl)azepan-4-yl)methyl)pyrazolo[1,5-a]pyridin-3-yl)dihydropyrimidine-2,4(1H,3H)-dione

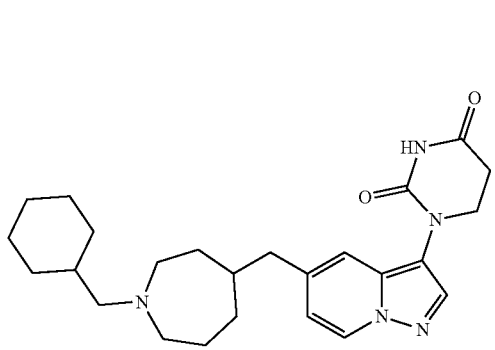 [SMILES: O=C1CCN(c2cnn3ccc(CC4CCCN(CC5CCCCC5)CC4)cc23)C(=O)N1]

Prepared from 1-(5-(azepan-4-ylmethyl)pyrazolo[1,5-a]pyridin-3-yl)dihydropyrimidine-2,4(1H,3H)-dione (Example 269) using the method of Example 109, wherein cyclohexanecarbaldehyde was used in place of isobutyraldehyde. LCMS [M+H]+: 438.2. $^1$H NMR (400 MHz, CD$_3$OD) δ 8.42 (d, J=7.3 Hz, 1H), 8.38 (s, 1H), 8.01 (s, 1H), 7.35 (s, 1H), 6.83 (dd, J=7.1, 1.9 Hz, 1H), 3.89 (t, J=6.7 Hz, 2H), 3.41 (s, 2H), 3.22 (s, 2H), 2.98 (d, J=6.7 Hz, 2H), 2.89 (t, J=6.8 Hz, 2H), 2.68 (qd, J=13.5, 7.1 Hz, 2H), 2.11-1.61 (m, 12H), 1.45-1.16 (m, 4H), 1.04 (q, J=12.1 Hz, 2H).

Example 273. Preparation of 1-(5-(((2S,4R)-2-methyl-1-(2,2,3,3-tetrafluoropropyl)piperidin-4-yl)methyl)pyrazolo[1,5-a]pyridin-3-yl)dihydropyrimidine-2,4(1H,3H)-dione

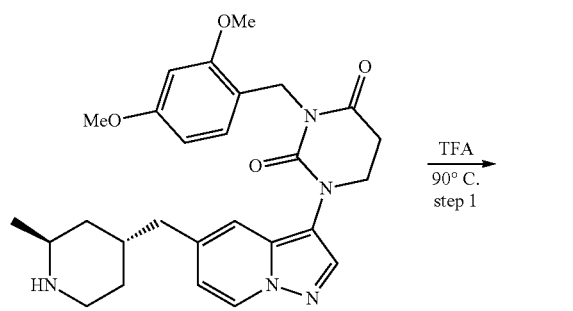

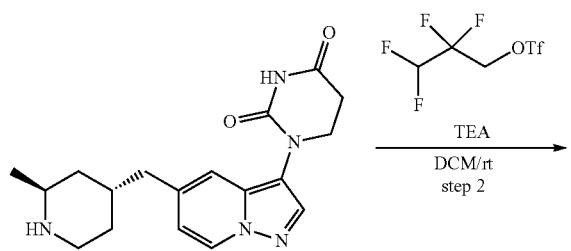

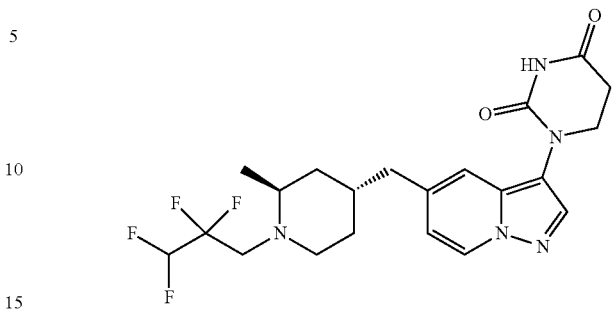

Step 1: 1-(5-(((2S,4R)-2-methylpiperidin-4-yl)methyl)pyrazolo[1,5-a]pyridin-3-yl)dihydropyrimidine-2,4(1H,3H)-dione TFA (2 mL) was added to 3-(2,4-dimethoxybenzyl)-1-(5-(((2S,4R)-2-methylpiperidin-4-yl)methyl)pyrazolo[1,5-a]pyridin-3-yl)dihydropyrimidine-2,4(1H,3H)-dione (340 mg, 0.57 mmol). The reaction mixture was stirred for 16 h at 90° C. and then concentrated. The residue was taken up in DCM, stirred with basic resin, filtered and concentrated again. The crude material was triturated sequentially with pentane and diethyl ether to provide crude 1-(5-(((2S,4R)-2-methylpiperidin-4-yl)methyl)pyrazolo[1,5-a]pyridin-3-yl)dihydropyrimidine-2,4(1H,3H)-dione (360 mg) as a yellow semi solid. LCMS [M+H]+: 341.9.

Step 2: 1-(5-(((2S,4R)-2-methyl-1-(2,2,3,3-tetrafluoropropyl)piperidin-4-yl)methyl)pyrazolo[1,5-a]pyridin-3-yl)dihydropyrimidine-2,4(1H,3H)-dione To a solution of 1-(5-(((2S,4R)-2-methylpiperidin-4-yl)methyl)pyrazolo[1,5-a]pyridin-3-yl)dihydropyrimidine-2,4(1H,3H)-dione (150 mg, 0.43 mmol) DCM (5 mL) was added triethylamine (131 mg, 1.29 mmol) and 2,2,3,3-tetrafluoropropyl trifluoromethanesulfonate (137 mg, 0.51 mmol). The reaction mixture was allowed to stir for 16 h at rt. The reaction mixture was diluted with water (20 mL) and extracted with DCM (2×30 mL). The organic layer was washed with brine solution (10 mL), dried over sodium sulfate and concentrated. The crude material was purified by reverse phase HPLC using ACN/Water/0.1% formic acid. The fractions containing the product were combined, frozen and lyophilized to afford 1-(5-(((2S,4R)-2-methyl-1-(2,2,3,3-tetrafluoropropyl)piperidin-4-yl)methyl)pyrazolo[1,5-a]pyridin-3-yl)dihydropyrimidine-2,4(1H,3H)-dione as a white solid. LCMS [M+H]+: 456.1. $^1$H NMR (300 MHz, CD$_3$OD) δ 8.40 (d, J=7.1 Hz, 1H), 8.23 (s, 1H), 7.98 (s, 1H), 7.33 (s, 1H), 6.81 (dd, J=7.1, 1.9 Hz, 1H), 6.39-5.96 (m, 1H), 3.88 (t, J=6.8 Hz, 2H), 3.04 (d, J=14.0 Hz, 2H), 2.89 (t, J=6.8 Hz, 3H), 2.81-2.69 (m, 1H), 2.62 (dd, J=17.2, 5.7 Hz, 3H), 2.00 (d, J=23.6 Hz, 1H), 1.65-1.47 (m, 3H), 1.35-1.27 (m, 1H), 1.02 (d, J=6.7 Hz, 3H).

Example 274. Preparation of 1-(5-(((2S,4R)-1-(2,2-difluoroethyl)-2-methylpiperidin-4-yl)methyl)pyrazolo[1,5-a]pyridin-3-yl)dihydropyrimidine-2,4(1H,3H)-dione

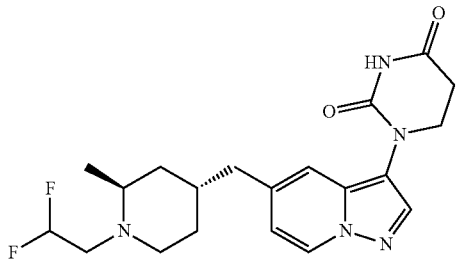 [SMILES: C[C@H]1C[C@H](Cc2ccn3ncc(N4CCC(=O)NC4=O)c3c2)CCN1CC(F)F]

Prepared by the method of Example 273 wherein 2,2-difluoroethyl trifluoromethanesulfonate was used in place of 2,2,3,3-tetrafluoropropyl trifluoromethanesulfonate in step 2. LCMS [M+H]+: 406.2. ¹H NMR (400 MHz, MeOD) δ 8.41 (dd, J=7.2, 0.9 Hz, 1H), 8.17 (s, 1H), 7.99 (s, 1H), 7.34 (dd, J=1.9, 1.0 Hz, 1H), 6.82 (dd, J=7.2, 1.9 Hz, 1H), 5.98 (tt, J=55.7, 4.2 Hz, 1H), 3.88 (t, J=6.8 Hz, 2H), 3.21 (d, J=6.5 Hz, 1H), 3.05-2.92 (m, 2H), 2.89 (t, J=6.8 Hz, 2H), 2.81 (dd, J=8.0, 3.4 Hz, 2H), 2.64 (d, J=7.3 Hz, 2H), 2.10-1.99 (m, 1H), 1.69 (dd, J=13.5, 3.9 Hz, 1H), 1.60 (dd, J=7.5, 4.2 Hz, 2H), 1.47-1.36 (m, 1H), 1.10 (d, J=6.7 Hz, 3H). NH proton not observed due to solvent exchange.

Example 275. Preparation of 1-(5-(((2S,4R)-2-methyl-1-(2,2,2-trifluoroethyl)piperidin-4-yl)methyl)pyrazolo[1,5-a]pyridin-3-yl)dihydropyrimidine-2,4(1H,3H)-dione

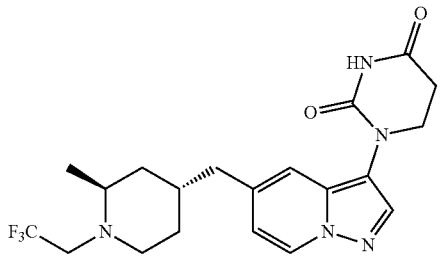 [SMILES: C[C@H]1C[C@H](Cc2ccn3ncc(N4CCC(=O)NC4=O)c3c2)CCN1CC(F)(F)F]

Prepared by the method of Example 273 wherein 2,2,2-trifluoroethyl trifluoromethanesulfonate was used in place of 2,2,3,3-tetrafluoropropyl trifluoromethanesulfonate in step 2. LCMS [M+H]+: 424.0. ¹H NMR (400 MHz, MeOD) δ 8.40 (dd, J=7.2, 0.9 Hz, 1H), 7.98 (s, 1H), 7.34 (dd, J=1.9, 0.9 Hz, 1H), 6.81 (dd, J=7.2, 1.8 Hz, 1H), 3.88 (t, J=6.8 Hz, 2H), 3.17-2.95 (m, 3H), 2.89 (t, J=6.8 Hz, 2H), 2.81-2.65 (m, 2H), 2.61 (d, J=7.3 Hz, 2H), 1.97 (h, J=6.1 Hz, 1H), 1.66-1.49 (m, 3H), 1.34 (dtd, J=12.9, 10.7, 4.4 Hz, 1H), 1.02 (d, J=6.6 Hz, 3H). NH proton not observed due to solvent exchange.

Example 276. Preparation of 1-(5-(((2S,4R)-2-methyl-1-(3,3,3-trifluoropropyl)piperidin-4-yl)methyl)pyrazolo[1,5-a]pyridin-3-yl)dihydropyrimidine-2,4(1H,3H)-dione

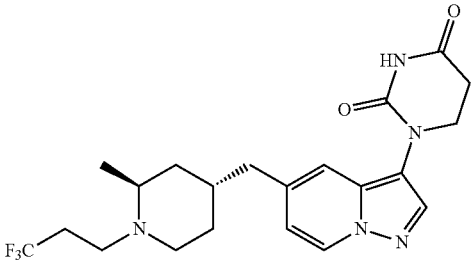 [SMILES: C[C@H]1C[C@H](Cc2ccn3ncc(N4CCC(=O)NC4=O)c3c2)CCN1CCC(F)(F)F]

Prepared by the method of Example 273 wherein 3,3,3-trifluoropropyl trifluoromethanesulfonate was used in place of 2,2,3,3-tetrafluoropropyl trifluoromethanesulfonate in step 2. LCMS [M+H]+: 438.0. ¹H NMR (400 MHz, MeOD) δ 8.42 (d, J=7.2 Hz, 1H), 7.99 (s, 1H), 7.35 (s, 1H), 6.83 (dd, J=7.2, 1.9 Hz, 1H), 3.88 (t, J=6.8 Hz, 2H), 2.98 (s, 2H), 2.89 (t, J=6.8 Hz, 2H), 2.66 (d, J=7.3 Hz, 2H), 2.53 (s, 2H), 2.15-2.00 (m, 2H), 1.84-1.56 (m, 4H), 1.51-1.39 (m, 2H), 1.16 (d, J=6.7 Hz, 3H). NH proton not observed due to solvent exchange.

Example 277. Preparation of 1-(5-(((2S,4R)-2-methyl-1-(oxetan-2-ylmethyl)piperidin-4-yl)methyl)pyrazolo[1,5-a]pyridin-3-yl)dihydropyrimidine-2,4(1H,3H)-dione

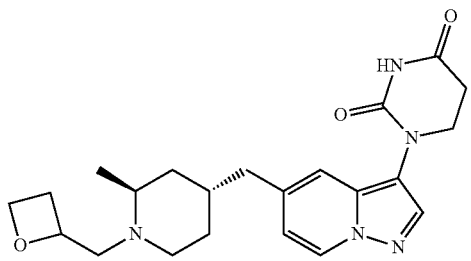

Prepared from 1-(5-(((2S,4R)-2-methylpiperidin-4-yl)methyl)pyrazolo[1,5-a]pyridin-3-yl)dihydropyrimidine-2,4(1H,3H)-dione by the method of Example 109 wherein oxetane-2-carbaldehyde was used in place of isobutyraldehyde. LCMS [M+H]+: 412.0. ¹H NMR (400 MHz, MeOD) δ 8.44 (s, 1H), 8.42 (s, 1H), 8.01 (s, 1H), 7.36 (s, 1H), 6.86-6.79 (m, 1H), 5.39-5.21 (m, 1H), 5.20-4.99 (m, 1H), 4.76-4.52 (m, 3H), 4.43-4.26 (m, 2H), 3.89 (t, J=6.8 Hz, 2H), 3.63 (s, 1H), 3.23-3.00 (m, 2H), 2.89 (t, J=6.8 Hz, 2H), 2.82-2.48 (m, 4H), 2.03 (d, J=6.0 Hz, 1H), 1.89-1.57 (m, 2H), 1.40-1.25 (m, 3H).

Example 278. Preparation of 1-(5-(((2S,4R)-1-(2,2-difluoro-3-methoxypropyl)-2-methylpiperidin-4-yl)methyl)pyrazolo[1,5-a]pyridin-3-yl)dihydropyrimidine-2,4(1H,3H)-dione

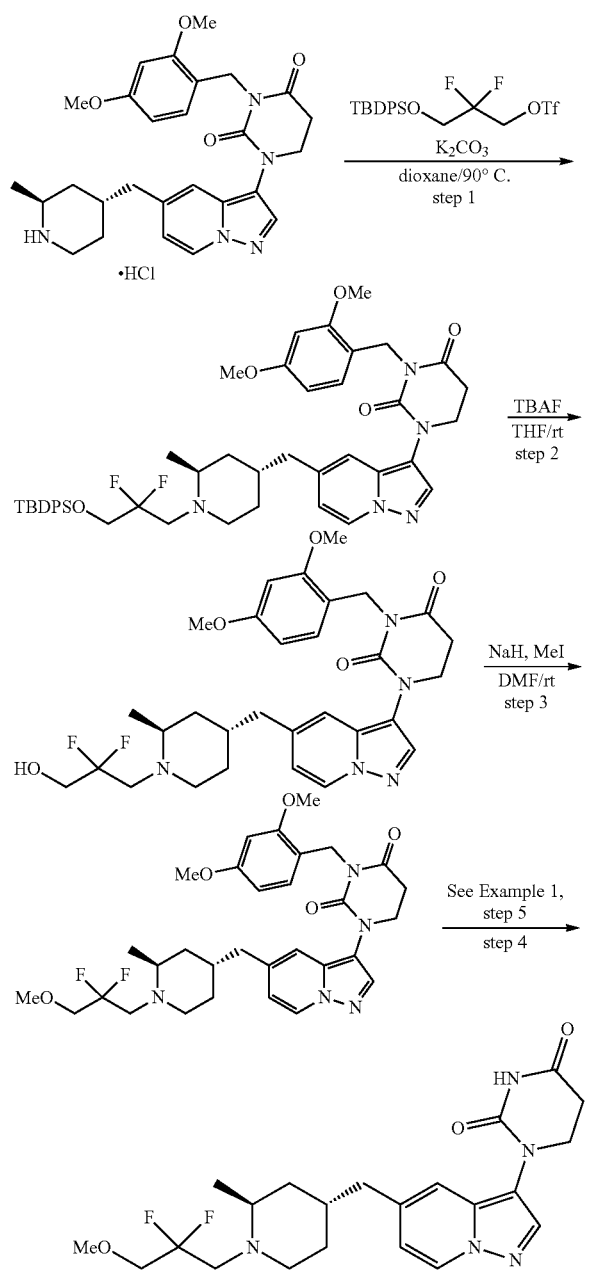

Step 1: 1-(5-(((2S,4R)-1-(3-((tert-butyldiphenylsilyl)oxy)-2,2-difluoropropyl)-2-methylpiperidin-4-yl)methyl)pyrazolo[1,5-a]pyridin-3-yl)-3-(2,4-dimethoxybenzyl)dihydropyrimidine-2,4(1H,3H)-dione To a mixture of 3-(2,4-dimethoxybenzyl)-1-(5-(((2S,4R)-2-methylpiperidin-4-yl)methyl)pyrazolo[1,5-a]pyridin-3-yl)dihydropyrimidine-2,4(1H,3H)-dione hydrochloride (0.17 g, 0.32 mmol) and K₂CO₃ (0.133 g, 0.96 mmol) in dioxane (5 mL) was added 3-((tert-butyldiphenylsilyl)oxy)-2,2-difluoropropyl trifluoromethanesulfonate (0.156 g, 0.32 mmol). The reaction mixture was stirred at 90° C. for 16 h. The reaction mixture was cooled to rt and diluted with water and saturated aqueous NaHCO₃ solution. The mixture was extracted with DCM and the organic layer was dried over Na₂SO₄, filtered, and concentrated to afford crude 1-(5-(((2S,4R)-1-(3-((tert-butyldiphenylsilyl)oxy)-2,2-difluoropropyl)-2-methylpiperidin-4-yl)methyl)pyrazolo[1,5-a]pyridin-3-yl)-3-(2,4-dimethoxybenzyl)dihydropyrimidine-2,4(1H,3H)-dione (0.24 g) that was used without further purification. LCMS [M+H]⁺: 824.6.

Step 2: 1-(5-(((2S,4R)-1-(2,2-difluoro-3-hydroxypropyl)-2-methylpiperidin-4-yl)methyl)pyrazolo[1,5-a]pyridin-3-yl)-3-(2,4-dimethoxybenzyl)dihydropyrimidine-2,4(1H,3H)-dione To a solution of 1-(5-(((2S,4R)-1-(3-((tert-butyldiphenylsilyl)oxy)-2,2-difluoropropyl)-2-methylpiperidin-4-yl)methyl)pyrazolo[1,5-a]pyridin-3-yl)-3-(2,4-dimethoxybenzyl)dihydropyrimidine-2,4(1H,3H)-dione (0.24 g, 0.29 mmol) in THF (3 mL) was added TBAF (1.0 M in THF, 2 mL) and the reaction mixture was stirred at room temperature for 2 h. The reaction mixture was diluted with water and extracted with DCM. The organic layer was dried over Na₂SO₄, filtered, and concentrated to afford crude 1-(5-(((2S,4R)-1-(2,2-difluoro-3-hydroxypropyl)-2-methylpiperidin-4-yl)methyl)pyrazolo[1,5-a]pyridin-3-yl)-3-(2,4-dimethoxybenzyl)dihydropyrimidine-2,4(1H,3H)-dione (0.11 g, 0.15 mmol) as a brown solid. LCMS [M+H]⁺: 586.1.

Step 3: 1-(5-(((2S,4R)-1-(2,2-difluoro-3-methoxypropyl)-2-methylpiperidin-4-yl)methyl)pyrazolo[1,5-a]pyridin-3-yl)-3-(2,4-dimethoxybenzyl)dihydropyrimidine-2,4(1H,3H)-dione To a stirred solution of 1-(5-(((2S,4R)-1-(2,2-difluoro-3-hydroxypropyl)-2-methylpiperidin-4-yl)methyl)pyrazolo[1,5-a]pyridin-3-yl)-3-(2,4-dimethoxybenzyl)dihydropyrimidine-2,4(1H,3H)-dione (80 mg, 0.136 mmol) in DMF (2 mL) was added sodium hydride (10 mg, 0.41 mmol) at 0° C. After 5 min, methyl iodide (39 mg, 0.27 mmol) was added and the reaction mixture was stirred at room temperature for 10 min. The reaction mixture was diluted with water and extracted with EtOAc. The organic layer was washed with brine, dried over Na₂SO₄, filtered, and concentrated. Silica gel column chromatography (eluting with 30% EtOAc in hexane) provided 1-(5-(((2S,4R)-1-(2,2-difluoro-3-methoxypropyl)-2-methylpiperidin-4-yl)methyl)pyrazolo[1,5-a]pyridin-3-yl)-3-(2,4-dimethoxybenzyl)dihydropyrimidine-2,4(1H,3H)-dione (80 mg). LCMS [M+H]⁺: 600.2.

Step 4: 1-(5-(((2S,4R)-1-(2,2-difluoro-3-methoxypropyl)-2-methylpiperidin-4-yl)methyl)pyrazolo[1,5-a]pyridin-3-yl)dihydropyrimidine-2,4(1H,3H)-dione (Example 278) was prepared from 1-(5-(((2S,4R)-1-(2,2-difluoro-3-methoxypropyl)-2-methylpiperidin-4-yl)methyl)pyrazolo[1,5-a]pyridin-3-yl)-3-(2,4-dimethoxybenzyl)dihydropyrimidine-2,4(1H,3H)-dione by the method of Example 1, step 5, wherein 1-(5-(((2S,4R)-1-(2,2-difluoro-3-methoxypropyl)-2-methylpiperidin-4-yl)methyl)pyrazolo[1,5-a]pyridin-3-yl)-3-(2,4-dimethoxybenzyl)dihydropyrimidine-2,4(1H,3H)-dione was used in place of 1-(5-((1-(cyclohexylmethyl)piperidin-4-yl)methyl)pyrazolo[1,5-a]pyridin-3-yl)-3-(2,4-dimethoxybenzyl)dihydropyrimidine-2,4(1H,3H)-dione. LCMS [M+H]⁺: 450.0. ¹H NMR (400 MHz, MeOD) δ 8.42-8.36 (m, 1H), 8.24 (s, 1H), 7.98 (s, 1H), 7.33 (s, 1H), 6.81 (dd, J=7.3, 1.9 Hz, 1H), 3.88 (t, J=6.8 Hz, 2H), 3.65 (q, J=12.9 Hz, 2H), 3.41 (s, 3H), 2.95 (d, J=15.0 Hz, 1H), 2.89 (t, J=6.8 Hz, 2H), 2.85-2.68 (m, 3H), 2.60 (d, J=7.2 Hz, 2H), 2.02 (q, J=7.7 Hz, 2H), 1.61 (d, J=12.3 Hz, 2H), 1.54 (dd, J=7.7, 4.0 Hz, 2H), 1.04 (d, J=6.7 Hz, 3H).

Example 279. Preparation of 1-(5-(((2S,4R)-2-methyl-1-(oxetan-3-yl)piperidin-4-yl)methyl)pyrazolo[1,5-a]pyridin-3-yl)dihydropyrimidine-2,4(1H,3H)-dione

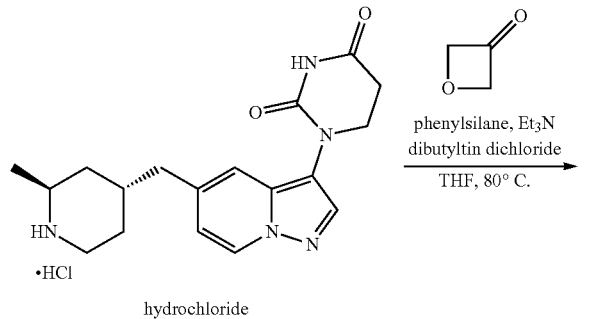

To a solution of 1-(5-(((2S,4R)-2-methylpiperidin-4-yl)methyl)pyrazolo[1,5-a]pyridin-3-yl)dihydropyrimidine-2,4(1H,3H)-dione hydrochloride (180 mg, 0.41 mmol) in THF (10 mL) was added oxetan-3-one (85 mg, 1.2 mmol), dibutyltin dichloride (62 mg, 0.20 mmol), and triethylamine (0.2 mL, 1.2 mmol). The mixture was stirred at 80° C. for 1 h and then cooled to 0° C. and phenylsilane (45 mg, 0.41 mmol) was added. The reaction was stirred in a capped vial at 80° C. for 4 h. The reaction was cooled to rt, diluted with DCM and washed sequentially with water and brine. The organic layer was dried over Na$_2$SO$_4$, filtered and concentrated. The crude material was purified by reverse phase HPLC using ACN/water/0.1% formic acid. The fractions containing the product were combined, frozen and lyophilized to afford 1-(5-(((2S,4R)-2-methyl-1-(oxetan-3-yl)piperidin-4-yl)methyl)pyrazolo[1,5-a]pyridin-3-yl)dihydropyrimidine-2,4(1H,3H)-dione as white solid. LCMS [M+H]$^+$: 398.2. $^1$H NMR (400 MHz, MeOD) δ 8.44 (dd, J=7.2, 0.9 Hz, 1H), 8.01 (s, 1H), 7.36 (d, J=1.8 Hz, 1H), 6.83 (dd, J=7.2, 1.9 Hz, 1H), 4.84-4.74 (m, 3H), 4.52 (s, 1H), 3.89 (t, J=6.8 Hz, 2H), 3.81 (s, 1H), 3.24-3.02 (m, 2H), 2.89 (t, J=6.8 Hz, 2H), 2.67 (d, J=9.1 Hz, 2H), 2.25 (d, J=19.4 Hz, 1H), 2.00-1.20 (m, 8H). NH proton not observed due to solvent exchange.

Example 280. Preparation of 1-(5-(((2S,4R)-1-cyclobutyl-2-methylpiperidin-4-yl)methyl)pyrazolo[1,5-a]pyridin-3-yl)dihydropyrimidine-2,4(1H,3H)-dione

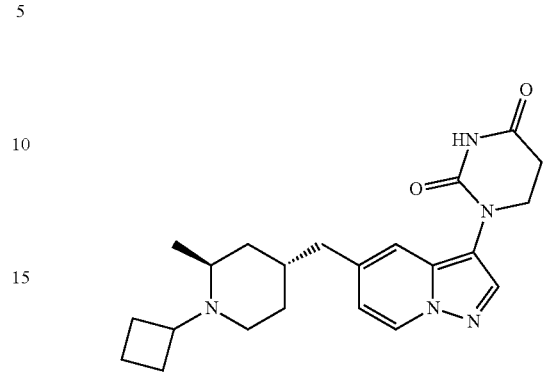

Prepared using the method of Example 279 wherein cyclobutanone was used in place of oxetan-3-one. LCMS [M+H]$^+$: 396.0. $^1$H NMR (400 MHz, MeOD) δ 8.44 (s, 1H), 8.01 (s, 1H), 7.36 (s, 1H), 6.83 (dd, J=7.2, 1.9 Hz, 1H), 3.89 (t, J=6.8 Hz, 2H), 3.70 (s, 1H), 3.14 (s, 1H), 2.89 (t, J=6.8 Hz, 2H), 2.68 (d, J=7.0 Hz, 2H), 2.31 (s, 2H), 2.25-2.12 (m, 3H), 1.95-1.80 (m, 4H), 1.30 (s, 7H). NH proton not observed due to solvent exchange.

Example 281. Preparation of 1-(5-((1-(oxetan-3-yl)piperidin-4-yl)methyl)pyrazolo[1,5-a]pyridin-3-yl)dihydropyrimidine-2,4(1H,3H)-dione

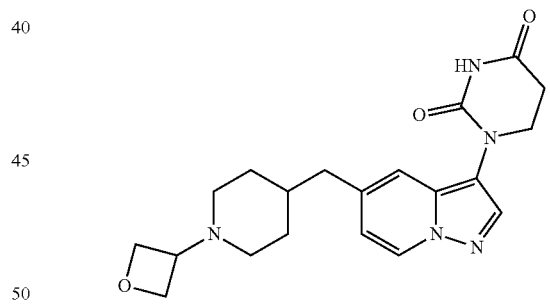

Prepared using the method of Example 279 wherein 1-(5-(piperidin-4-ylmethyl)pyrazolo[1,5-a]pyridin-3-yl)dihydropyrimidine-2,4(1H,3H)-dione was used in place of 1-(5-(((2S,4R)-2-methylpiperidin-4-yl)methyl)pyrazolo[1,5-a]pyridin-3-yl)dihydropyrimidine-2,4(1H,3H)-dione. LCMS [M+H]$^+$: 384.1. $^1$H NMR (400 MHz, MeOD) δ 8.42 (dd, J=7.1, 0.9 Hz, 1H), 8.25 (s, 1H), 7.99 (s, 1H), 7.39-7.31 (m, 1H), 6.82 (dd, J=7.2, 1.9 Hz, 1H), 4.75 (t, J=7.1 Hz, 2H), 4.67 (t, J=6.6 Hz, 2H), 3.88 (t, J=6.8 Hz, 3H), 3.09 (d, J=11.7 Hz, 2H), 2.89 (t, J=6.8 Hz, 2H), 2.68 (d, J=6.8 Hz, 2H), 2.30 (t, J=12.1 Hz, 2H), 1.88-1.78 (m, 3H), 1.45 (td, J=14.3, 7.4 Hz, 2H).

Example 282. Preparation of 1-(5-((1-cyclobutylpiperidin-4-yl)methyl)pyrazolo[1,5-a]pyridin-3-yl)dihydropyrimidine-2,4(1H,3H)-dione

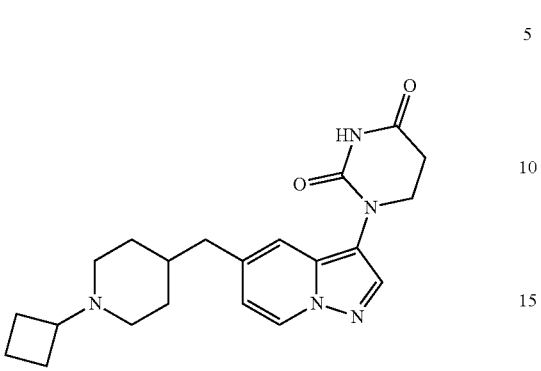

Prepared using the method of Example 279 wherein 1-(5-(piperidin-4-ylmethyl)pyrazolo[1,5-a]pyridin-3-yl)dihydropyrimidine-2,4(1H,3H)-dione was used in place of 1-(5-(((2S,4R)-2-methylpiperidin-4-yl)methyl)pyrazolo[1,5-a]pyridin-3-yl)dihydropyrimidine-2,4(1H,3H)-dione and cyclobutanone was used in place of oxetan-3-one. LCMS [M+H]+: 382.0. ¹H NMR (400 MHz, MeOD) δ 8.43 (d, J=7.2 Hz, 1H), 8.01 (s, 1H), 7.37 (s, 1H), 6.83 (dd, J=7.2, 1.8 Hz, 1H), 3.88 (t, J=6.8 Hz, 2H), 3.59 (s, 1H), 3.41 (d, J=12.2 Hz, 2H), 3.35 (s, 2H), 2.89 (t, J=6.8 Hz, 2H), 2.78-2.65 (m, 3H), 2.36-2.26 (m, 2H), 2.17 (d, J=13.8 Hz, 2H), 2.04-1.79 (m, 4H), 1.49 (d, J=13.3 Hz, 2H). NH proton not observed due to solvent exchange.

Example 283. Preparation of 1-(5-(((2S,4R)-1-(ethylsulfonyl)-2-methylpiperidin-4-yl)methyl)pyrazolo[1,5-a]pyridin-3-yl)dihydropyrimidine-2,4(1H,3H)-dione

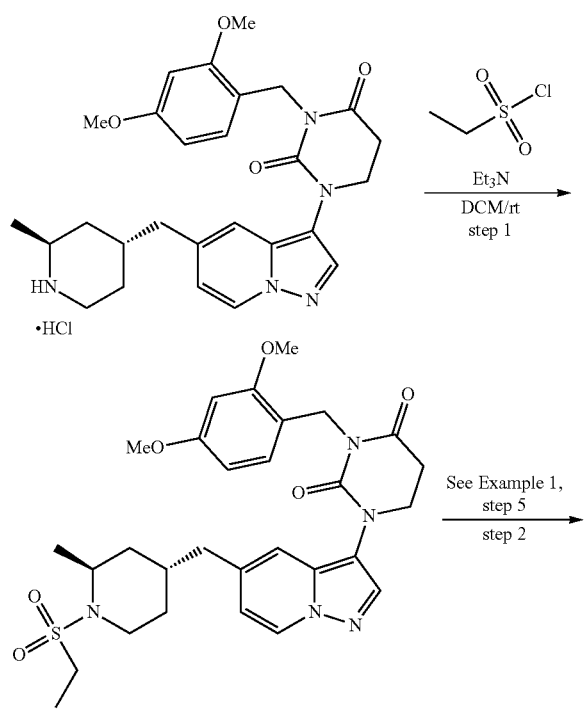

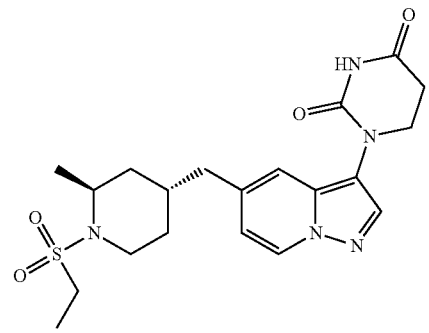

Step 1: 3-(2,4-dimethoxybenzyl)-1-(5-(((2S,4R)-1-(ethylsulfonyl)-2-methylpiperidin-4-yl)methyl)pyrazolo[1,5-a]pyridin-3-yl)dihydropyrimidine-2,4(1H,3H)-dione Triethylamine (0.066 mL, 0.47 mmol) and ethylsulfonyl chloride (37 mg, 0.28 mmol) were added to a solution of 3-(2,4-dimethoxybenzyl)-1-(5-(((2S,4R)-2-methylpiperidin-4-yl)methyl)pyrazolo[1,5-a]pyridin-3-yl)dihydropyrimidine-2,4(1H,3H)-dione hydrochloride (50 mg, 0.095 mmol) in DCM (2 mL) at 0° C. The mixture was stirred at rt for 2 h, then diluted with DCM and washed with brine. The organic layer was dried over sodium sulfate, filtered and concentrated to give crude 3-(2,4-dimethoxybenzyl)-1-(5-(((2S,4R)-1-(ethylsulfonyl)-2-methylpiperidin-4-yl)methyl)pyrazolo[1,5-a]pyridin-3-yl)dihydropyrimidine-2,4(1H,3H)-dione, which was used without further purification. LCMS [M+H]+: 584.4.

Step 2: 1-(5-(((2S,4R)-1-(ethylsulfonyl)-2-methylpiperidin-4-yl)methyl)pyrazolo[1,5-a]pyridin-3-yl)dihydropyrimidine-2,4(1H,3H)-dione (Example 283) was prepared from 3-(2,4-dimethoxybenzyl)-1-(5-(((2S,4R)-1-(ethylsulfonyl)-2-methylpiperidin-4-yl)methyl)pyrazolo[1,5-a]pyridin-3-yl)dihydropyrimidine-2,4(1H,3H)-dione by the method of Example 1, step 5, wherein 3-(2,4-dimethoxybenzyl)-1-(5-(((2S,4R)-1-(ethylsulfonyl)-2-methylpiperidin-4-yl)methyl)pyrazolo[1,5-a]pyridin-3-yl)dihydropyrimidine-2,4(1H,3H)-dione was used in place of 1-(5-((1-(cyclohexylmethyl)piperidin-4-yl)methyl)pyrazolo[1,5-a]pyridin-3-yl)-3-(2,4-dimethoxybenzyl)dihydropyrimidine-2,4(1H,3H)-dione. LCMS [M+H]+: 434.1. ¹H NMR (500 MHz, DMSO) δ 10.44 (s, 1H), 8.57 (dd, J=7.1, 0.9 Hz, 1H), 7.99 (s, 1H), 7.37 (dd, J=1.9, 0.9 Hz, 1H), 6.81 (dd, J=7.2, 1.9 Hz, 1H), 4.12-4.00 (m, 1H), 3.77 (t, J=6.7 Hz, 2H), 3.61-3.45 (m, 1H), 3.15-2.92 (m, 3H), 2.79 (t, J=6.7 Hz, 2H), 2.54 (d, J=7.4 Hz, 2H), 2.03 (dd, J=7.6, 3.9 Hz, 1H), 1.65-1.49 (m, 2H), 1.37 (td, J=12.9, 5.4 Hz, 1H), 1.25-1.15 (m, 6H), 1.11 (td, J=12.6, 4.6 Hz, 1H).

The compounds in the following table were prepared by the method of Example 283, using the appropriate commercially available sulfonyl chloride in step 1.

| Example No. | Structure | Mass [M + H]+ | ¹H NMR |
|---|---|---|---|
| 284 | 1-(5-(((2S,4R)-2-methyl-1-(methylsulfonyl)piperidin-4-yl)methyl)pyrazolo[1,5-a]pyridin-3-yl)dihydropyrimidine-2,4(1H,3H)-dione | 420.1 | (500 MHZ, DMSO-d6) δ 10.44 (s, 1H), 8.57 (dd, J = 7.1, 0.9 Hz, 1H), 8.00 (s, 1H), 7.36 (dd, J = 1.9, 0.9 Hz, 1H), 6.81 (dd, J = 7.1, 1.9 Hz, 1H), 4.10 (t, J = 6.6 Hz, 1H), 3.77 (t, J = 6.8 Hz, 2H), 3.58-3.49 (m, 1H), 2.98 (td, J = 13.2, 2.7 Hz, 1H), 2.91 (s, 3H), 2.79 (t, J = 6.7 Hz, 2H), 2.57-2.53 (m, 2H), 2.10-1.94 (m, 1H), 1.60 (d, J = 13.0 Hz, 1H), 1.55-1.48 (m, 1H), 1.40 (td, J = 12.9, 5.3 Hz, 1H), 1.27-1.06 (m, 4H). |
| 285 | 1-(5-(((2S,4R)-1-(isopropylsulfonyl)-2-methylpiperidin-4-yl)methyl)pyrazolo[1,5-a]pyridin-3-yl)dihydropyrimidine-2,4(1H,3H)-dione | 448.2 | (500 MHZ, DMSO-d6) δ 10.44 (s, 1H), 8.57 (d, J = 7.1 Hz, 1H), 7.99 (s, 1H), 7.37 (s, 1H), 6.81 (dd, J = 7.1, 1.8 Hz, 1H), 4.12 - 3.99 (m, 1H), 3.77 (t, J = 6.7 Hz, 2H), 3.00 (ddp, J = 21.1, 14.8, 6.7 Hz, 2H), 2.79 (t, J = 6.7 Hz, 2H), 2.00 (d, J = 22.1 Hz, 2H), 1.71-1.47 (m, 4H), 1.37 (td, J = 12.7, 5.3 Hz, 2H), 1.26-1.07 (m, 5H), 0.98 (t, J = 7.4 Hz, 4H). |
| 286 | 1-(5-(((2S,4R)-1-(cyclopropylsulfonyl)-2-methylpiperidin-4-yl)methyl)pyrazolo[1,5-a]pyridin-3-yl)dihydropyrimidine-2,4(1H,3H)-dione | 446.1 | (400 MHZ, MeOD) δ 8.41 (dd, J = 7.2, 0.9 Hz, 1H), 7.99 (s, 1H), 7.35 (dd, J = 1.9, 0.9 Hz, 1H), 6.83 (dd, J = 7.2, 1.8 Hz, 1H), 4.20 (t, J = 7.0 Hz, 1H), 3.88 (t, J = 6.8 Hz, 2H), 3.70-3.60 (m, 1H), 3.13 (td, J = 13.3, 2.7 Hz, 1H), 2.89 (t, J = 6.8 Hz, 2H), 2.61 (d, J = 7.1 Hz, 2H), 2.53-2.37 (m, 1H), 2.21-2.05 (m, 1H), 1.75-1.59 (m, 2H), 1.51 (td, J = 12.8, 5.3 Hz, 1H), 1.33-1.23 (m, 4H), 1.07-0.96 (m, 4H). Missing NH due to solvent exchange. |

Example 287. Preparation of 1-(5-(((2S,4R)-1-(cyclopropanecarbonyl)-2-methylpiperidin-4-yl)methyl)pyrazolo[1,5-a]pyridin-3-yl)dihydropyrimidine-2,4(1H,3H)-dione

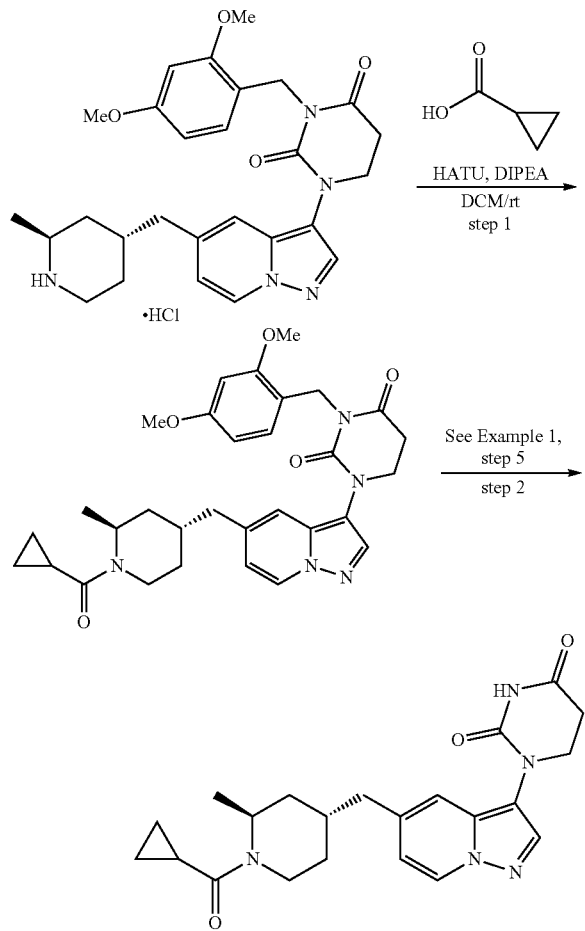

Step 1: 1-(5-(((2S,4R)-1-(cyclopropanecarbonyl)-2-methylpiperidin-4-yl)methyl)pyrazolo[1,5-a]pyridin-3-yl)-3-(2,4-dimethoxybenzyl)dihydropyrimidine-2,4(1H,3H)-dione HATU (43 mg, 0.11 mmol) and cyclopropanecarboxylic acid (6.5 mg, 0.076 mmol) were added to a solution of 3-(2,4-dimethoxybenzyl)-1-(5-(((2S,4R)-2-methylpiperidin-4-yl)methyl)pyrazolo[1,5-a]pyridin-3-yl)dihydropyrimidine-2,4(1H,3H)-dione hydrochloride (40 mg, 0.076 mmol) in DMF (1 mL) at rt. The mixture was stirred at rt for 5 min and then DIPEA (0.040 mL, 0.23 mmol) was added. The mixture was stirred at rt for 12 h and then diluted with ethyl acetate and washed sequentially with brine. The organic layer was dried over sodium sulfate, filtered and concentrated to give crude 1-(5-(((2S,4R)-1-(cyclopropanecarbonyl)-2-methylpiperidin-4-yl)methyl)pyrazolo[1,5-a]pyridin-3-yl)-3-(2,4-dimethoxybenzyl)dihydropyrimidine-2,4(1H,3H)-dione, which was used without further purification. LCMS [M+H]$^+$: 560.4.

Step 2: 1-(5-(((2S,4R)-1-(cyclopropanecarbonyl)-2-methylpiperidin-4-yl)methyl)pyrazolo[1,5-a]pyridin-3-yl)dihydropyrimidine-2,4(1H,3H)-dione (Example 287) was prepared from 1-(5-(((2S,4R)-1-(cyclopropanecarbonyl)-2-methylpiperidin-4-yl)methyl)pyrazolo[1,5-a]pyridin-3-yl)-3-(2,4-dimethoxybenzyl)dihydropyrimidine-2,4(1H,3H)-dione using the method of Example 1, step 5, wherein 1-(5-(((2S,4R)-1-(cyclopropanecarbonyl)-2-methylpiperidin-4-yl)methyl)pyrazolo[1,5-a]pyridin-3-yl)-3-(2,4-dimethoxybenzyl)dihydropyrimidine-2,4(1H,3H)-dione was used in place of 1-(5-((1-(cyclohexylmethyl)piperidin-4-yl)methyl)pyrazolo[1,5-a]pyridin-3-yl)-3-(2,4-dimethoxybenzyl)dihydropyrimidine-2,4(1H,3H)-dione. LCMS [M+H]$^+$: 410.2. $^1$H NMR (500 MHz, DMSO-d6) δ 10.43 (s, 1H), 8.56 (d, J=7.1 Hz, 1H), 7.99 (s, 1H), 7.36 (s, 1H), 6.81 (dd, J=7.2, 1.8 Hz, 1H), 4.85-4.48 (m, 1H), 4.19 (dd, J=89.0, 13.8 Hz, 1H), 3.77 (t, J=6.7 Hz, 2H), 3.22-3.04 (m, 1H), 2.79 (t, J=6.7 Hz, 2H), 2.67-2.54 (m, 2H), 2.09 (d, J=11.9 Hz, 1H), 1.93 (ddt, J=16.7, 13.1, 5.8 Hz, 1H), 1.71-1.47 (m, 2H), 1.43-0.92 (m, 5H), 0.82-0.58 (m, 4H).

The compounds in the following table were prepared by the method of Example 287, using the appropriate commercially available carboxylic acid in step 1.

| Example No. | Structure | Mass [M + H]$^+$ | $^1$H NMR |
|---|---|---|---|
| 288 | 1-(5-(((2S,4R)-1-isobutyryl-2-methylpiperidin-4-yl)methyl)pyrazolo[1,5-a]pyridin-3-yl)dihydropyrimidine-2,4(1H,3H)-dione | 412.2 | (500 MHz, DMSO-d6) δ 10.43 (s, 1H), 8.55 (d, J = 7.1 Hz, 1H), 7.99 (s, 1H), 7.35 (s, 1H), 6.81 (dd, J = 7.1, 1.8 Hz, 1H), 4.79-4.73 (m, 1H), 4.37-4.30 (m, 1H), 4.28 (t, J = 6.4 Hz, 1H), 3.77 (d, J = 6.7 Hz, 2H), 3.06 (td, J = 13.5, 2.7 Hz, 1H), 2.80 (dt, J = 10.8, 6.7 Hz, 3H), 2.71-2.54 (m, 1H), 2.08 (d, J = 5.6 Hz, 1H), 1.72-1.47 (m, 2H), 1.34-1.18 (m, 1H), 1.17 (d, J = 6.8 Hz, 1H), 1.10-0.92 (m, 9H). |

| Example No. | Structure | Mass [M + H]+ | 1H NMR |
|---|---|---|---|
| 289 | 1-(5-(((2S,4R)-1-(cyclobutanecarbonyl)-2-methylpiperidin-4-yl)methyl)pyrazolo[1,5-a]pyridin-3-yl)dihydropyrimidine-2,4(1H,3H)-dione | 424.4 | (500 MHz, DMSO-d6) δ 10.43 (s, 1H), 8.55 (d, J = 7.1 Hz, 1H), 7.99 (s, 1H), 7.34 (s, 1H), 6.80 (dd, J = 7.1, 1.8 Hz, 1H), 4.77-4.64 (m, 1H), 4.28 (d, J = 13.6 Hz, 1H), 4.07-3.98 (m, 1H), 3.76 (t, J = 6.7 Hz, 2H), 3.28 (dt, J = 18.1, 8.7 Hz, 1H), 2.78 (t, J = 6.7 Hz, 2H), 2.69-2.57 (m, 1H), 2.24-1.96 (m, 5H), 1.88 (dq, J = 10.8, 8.8 Hz, 1H), 1.79-1.66 (m, 1H), 1.60 (d, J = 12.9 Hz, 1H), 1.51 (d, J = 12.2 Hz, 1H), 1.22 (dtd, J = 18.4, 12.8, 5.4 Hz, 1H), 1.12 (d, J = 6.8 Hz, 2H), 1.06-0.87 (m, 3H). |
| 290 | 1-(5-(((2S,4R)-2-methyl-1-(1-methylpiperidin-4-carbonyl)piperidin-4-yl)methyl)pyrazolo[1,5-a]pyridin-3-yl)dihydropyrimidine-2,4(1H,3H)-dione | 467.1 | (500 MHz, DMSO-d6) δ 10.43 (s, 1H), 8.56 (d, J = 7.1 Hz, 1H), 8.00 (s, 1H), 7.34 (s, 1H), 6.80 (dt, J = 7.3, 1.9 Hz, 1H), 4.92-4.55 (m, 1H), 4.31 (d, J = 13.2 Hz, 1H), 3.77 (t, J = 6.7 Hz, 2H), 3.18-3.04 (m, 1H), 3.05-1.90 (m, 2H), 2.84 (dt, J = 8.0, 3.9 Hz, 1H), 2.79 (t, J = 6.7 Hz, 2H), 2.75 (d, J = 4.5 Hz, 3H), 2.71-2.57 (m, 1H), 2.08 (s, 1H), 1.97-1.49 (m, 6H), 1.38-1.17 (m, 2H), 1.16-0.86 (m, 3H). 3 missing protons attributed to overlap with solvent peak. |

Example 291. Preparation of 1-(5-(((2S,4R)-2-methyl-1-(pyrrolidin-1-ylsulfonyl)piperidin-4-yl)methyl)pyrazolo[1,5-a]pyridin-3-yl)dihydropyrimidine-2,4(1H,3H)-dione

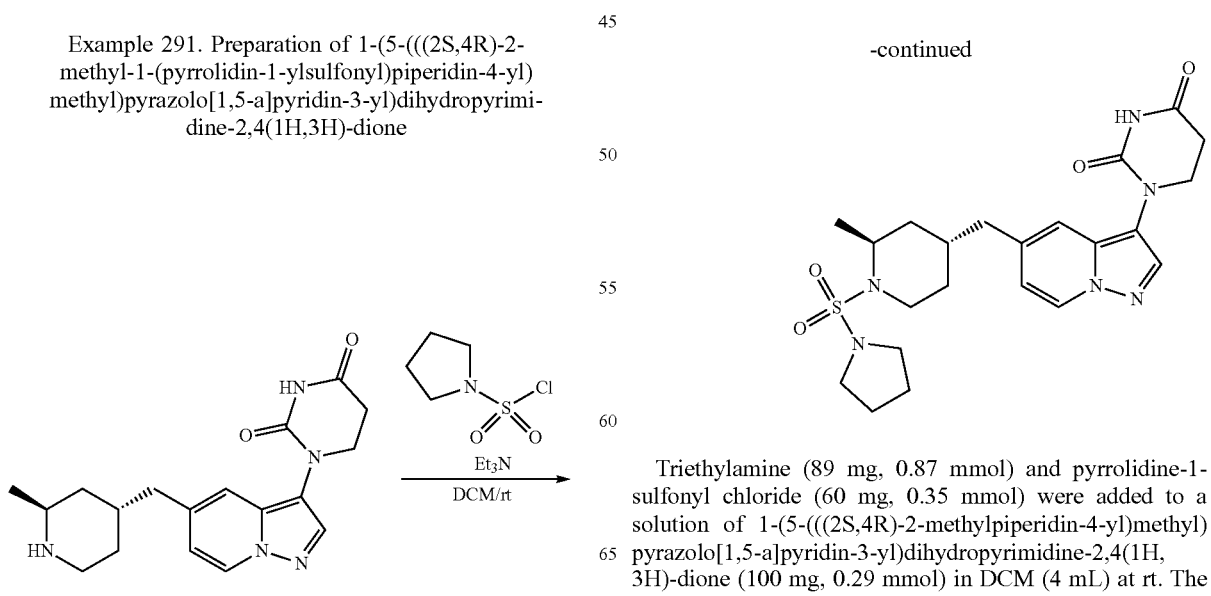

Triethylamine (89 mg, 0.87 mmol) and pyrrolidine-1-sulfonyl chloride (60 mg, 0.35 mmol) were added to a solution of 1-(5-(((2S,4R)-2-methylpiperidin-4-yl)methyl)pyrazolo[1,5-a]pyridin-3-yl)dihydropyrimidine-2,4(1H, 3H)-dione (100 mg, 0.29 mmol) in DCM (4 mL) at rt. The mixture was stirred at rt for 16 h, then diluted with saturated aqueous NaHCO₃ solution. The mixture was extracted with DCM and the organic layer was washed with brine. The organic layer was dried over sodium sulfate, filtered and concentrated. The crude material was purified by reverse phase HPLC using ACN/water/0.1% formic acid. The fractions containing the product were combined, frozen and lyophilized to afford 1-(5-(((2S,4R)-2-methyl-1-(pyrrolidin-1-ylsulfonyl)piperidin-4-yl)methyl)pyrazolo[1,5-a]pyridin-3-yl)dihydropyrimidine-2,4(1H,3H)-dione as white solid. LCMS [M+H]⁺: 475.2. ¹H NMR (400 MHz, MeOD) δ 8.41 (dd, J=7.2, 0.9 Hz, 1H), 7.98 (s, 1H), 7.37-7.32 (m, 1H), 6.83 (dd, J=7.2, 1.9 Hz, 1H), 4.10 (t, J=6.4 Hz, 1H), 3.88 (t, J=6.7 Hz, 2H), 3.52 (dt, J=13.2, 3.6 Hz, 1H), 3.24-3.18 (m, 4H), 3.05 (td, J=13.2, 2.7 Hz, 1H), 2.89 (t, J=6.8 Hz, 2H), 2.60 (d, J=7.1 Hz, 2H), 2.07 (ddd, J=11.9, 7.7, 4.0 Hz, 1H), 1.94-1.87 (m, 4H), 1.72-1.57 (m, 2H), 1.49 (td, J=12.7, 5.2 Hz, 1H), 1.23 (d, J=7.0 Hz, 4H). NH proton not observed due to solvent exchange.

The compounds in the following table were prepared by the method of Example 291, using the appropriate commercially available sulfamoyl chloride, carbamic chloride or isocyanate.

| Example No. | Structure | Mass [M + H]⁺ | ¹H NMR |
|---|---|---|---|
| 292 | (2S,4R)-4-((3-(2,4-dioxotetrahydropyrimidin-1(2H)-yl)pyrazolo[1,5-a]pyridin-5-yl)methyl)-N,N,2-trimethylpiperidine-1-sulfonamide | 449.1 | (400 MHz, MeOD) δ 8.41 (dd, J = 7.2, 0.9 Hz, 1H), 7.98 (s, 1H), 7.35 (dd, J = 1.9, 1.0 Hz, 1H), 6.83 (dd, J = 7.2, 1.9 Hz, 1H), 4.06 (t, J = 6.6 Hz, 1H), 3.88 (t, J = 6.8 Hz, 2H), 3.50 (d, J = 13.7 Hz, 1H), 3.06 (td, J = 13.2, 2.7 Hz, 1H), 2.89 (t, J = 6.8 Hz, 2H), 2.74 (s, 6H), 2.61 (d, J = 7.2 Hz, 2H), 2.13-2.00 (m, 1H), 1.72-1.45 (m, 3H), 1.27 (d, J = 4.6 Hz, 1H), 1.23 (d, J = 7.0 Hz, 3H). NH proton not observed due to solvent exchange. |
| 293 | (2S,4R)-N-cyclopentyl-4-((3-(2,4-dioxotetrahydropyrimidin-1(2H)-yl)pyrazolo[1,5-a]pyridin-5-yl)methyl)-2-methylpiperidine-1-sulfonamide | 489.4 | (400 MHz, MeOD) δ 8.41 (d, J = 7.2 Hz, 1H), 7.98 (s, 1H), 7.35 (s, 1H), 6.83 (dd, J = 7.2, 1.9 Hz, 1H), 4.10 (d, J = 6.4 Hz, 1H), 3.88 (t, J = 6.8 Hz, 2H), 3.55-3.46 (m, 2H), 3.05-2.95 (m, 1H), 2.89 (t, J = 6.8 Hz, 2H), 2.60 (d, J = 7.1 Hz, 2H), 2.06 (d, J = 17.9 Hz, 1H), 1.88 (t, J = 6.2 Hz, 2H), 1.74-1.47 (m, 9H), 1.27 (s, 1H), 1.23 (d, J = 6.9 Hz, 3H). Two NH protons not observed due to solvent exchange. |
| 294 | (2S,4R)-4-((3-(2,4-dioxotetrahydropyrimidin-1(2H)-yl)pyrazolo[1,5-a]pyridin-5-yl)methyl)-N,N,2-trimethylpiperidine-1-carboxamide | 413.3 | (400 MHz, MeOD) δ 8.41 (dd, J = 7.2, 0.9 Hz, 1H), 7.98 (s, 1H), 7.34 (dd, J = 1.9, 0.9 Hz, 1H), 6.83 (dd, J = 7.2, 1.9 Hz, 1H), 4.10-4.00 (m, 1H), 3.88 (t, J = 6.8 Hz, 2H), 3.44 (dt, J = 13.6, 3.7 Hz, 1H), 3.03 (td, J = 13.3, 2.7 Hz, 1H), 2.89 (t, J = 6.8 Hz, 2H), 2.80 (s, 6H), 2.59 (d, J = 7.1 Hz, 2H), 2.11 (dtd, J = 15.6, 8.1, 4.0 Hz, 1H), 1.66 (dt, J = 12.6, 3.1 Hz, 1H), 1.58 (ddt, J = 13.2, 4.0, 2.0 Hz, 1H), 1.43 (td, J = 12.8, 5.2 Hz, 1H), 1.28-1.20 (m, 1H), 1.18 (d, J = 7.0 Hz, 3H). NH proton not observed due to solvent exchange. |

| Example No. | Structure | Mass [M + H]⁺ | ¹H NMR |
|---|---|---|---|
| 295 | 1-(5-(((2S,4R)-2-methyl-1-(pyrrolidine-1-carbonyl)piperidin-4-yl)methyl)pyrazolo[1,5-a]pyridin-3-yl)dihydropyrimidine-2,4(1H,3H)-dione | 439.3 | (400 MHz, MeOD) δ 8.41 (dd, J = 7.2, 0.9 Hz, 1H), 7.98 (s, 1H), 7.34 (dd, J = 1.9, 1.0 Hz, 1H), 6.83 (dd, J = 7.2, 1.9 Hz, 1H), 4.17-4.09 (m, 1H), 3.88 (t, J = 6.8 Hz, 2H), 3.60-3.50 (m, 1H), 3.36-3.33 (m, 4H), 3.00 (td, J = 13.3, 2.7 Hz, 1H), 2.89 (t, J = 6.8 Hz, 2H), 2.59 (d, J = 7.2 Hz, 2H), 2.12 (ddd, J = 11.8, 7.9, 4.1 Hz, 1H), 1.84 (h, J = 3.4 Hz, 4H), 1.70-1.54 (m, 2H), 1.41 (td, J = 12.9, 5.3 Hz, 1H), 1.19 (d, J = 7.0 Hz, 4H). Missing NH due to solvent exchange. |
| 296 | (2S,4R)-N-cyclopentyl-4-((3-(2,4-dioxotetrahydropyrimidin-1(2H)-yl)pyrazolo[1,5-a]pyridin-5-yl)methyl)-2-methylpiperidine-1-carboxamide | 453.3 | (400 MHz, MeOD) δ 8.41 (dd, J = 7.2, 0.9 Hz, 1H), 7.98 (s, 1H), 7.40-7.25 (m, 1H), 6.83 (dd, J = 7.2, 1.9 Hz, 1H), 4.36 (t, J = 6.7 Hz, 1H), 4.01 (p, J = 7.2 Hz, 1H), 3.92-3.79 (m, 3H), 2.94-2.83 (m, 3H), 2.59 (d, J = 7.1 Hz, 2H), 2.15-2.03 (m, 1H), 1.90 (p, J = 6.3 Hz, 2H), 1.77-1.51 (m, 6H), 1.52-1.26 (m, 4H), 1.23-1.06 (m, 4H). Missing NH due to solvent exchange. |

Example 297. Preparation of 1-(5-((1-(pyrrolidin-1-ylsulfonyl)piperidin-4-yl)methyl)pyrazolo[1,5-a]pyridin-3-yl)dihydropyrimidine-2,4(1H,3H)-dione

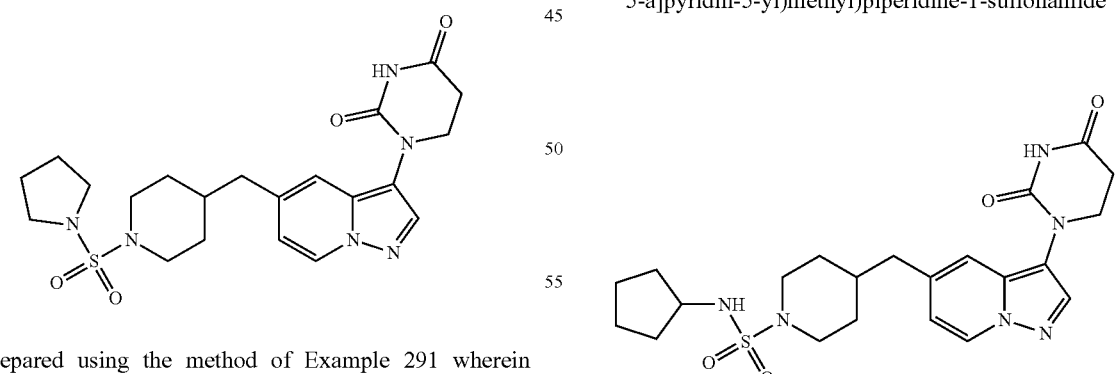

Prepared using the method of Example 291 wherein 1-(5-(piperidin-4-ylmethyl)pyrazolo[1,5-a]pyridin-3-yl)dihydropyrimidine-2,4(1H,3H)-dione was used in place of 1-(5-(((2S,4R)-2-methylpiperidin-4-yl)methyl)pyrazolo[1,5-a]pyridin-3-yl)dihydropyrimidine-2,4(1H,3H)-dione. LCMS [M+H]⁺: 461.3. ¹H NMR (400 MHz, MeOD) δ 8.40 (dd, J=7.2, 0.9 Hz, 1H), 7.98 (s, 1H), 7.36 (dd, J=1.9, 1.0 Hz, 1H), 6.82 (dd, J=7.2, 1.9 Hz, 1H), 3.88 (t, J=6.8 Hz, 2H), 3.66 (d, J 10=12.1 Hz, 2H), 3.29-3.24 (m, 3H), 2.89 (t, J=6.8 Hz, 2H), 2.77 (td, J=12.3, 2.4 Hz, 2H), 2.65 (d, J=7.0 Hz, 2H), 1.93-1.87 (m, 4H), 1.74 (d, J=13.9 Hz, 3H), 1.40-1.27 (m, 3H). NH proton not observed due to solvent exchange.

Example 298. Preparation of N-cyclopentyl-4-((3-(2,4-dioxotetrahydropyrimidin-1(2H)-yl)pyrazolo[1,5-a]pyridin-5-yl)methyl)piperidine-1-sulfonamide Prepared using the method of Example 291 wherein cyclopentylsulfamoyl chloride was used in place of pyrrolidine-1-sulfonyl chloride and 1-(5-(piperidin-4-ylmethyl)pyrazolo[1,5-a]pyridin-3-yl)dihydropyrimidine-2,4(1H, 3H)-dione was used in place of 1-(5-(((2S,4R)-2-methylpiperidin-4-yl)methyl)pyrazolo[1,5-a]pyridin-3-yl)dihydropyrimidine-2,4(1H,3H)-dione. LCMS [M+H]⁺:

475.3. ¹H NMR (400 MHz, MeOD) δ 8.41 (dd, J=7.1, 0.9 Hz, 1H), 7.99 (s, 1H), 7.39-7.31 (m, 1H), 6.83 (dd, J=7.2, 1.9 Hz, 1H), 3.88 (t, J=6.7 Hz, 2H), 3.67-3.56 (m, 3H), 2.89 (t, J=6.7 Hz, 2H), 2.71-2.61 (m, 3H), 1.90 (q, J=5.5 Hz, 2H), 1.78-1.66 (m, 4H), 1.61-1.46 (m, 5H), 1.32 (dd, J=18.1, 6.0 Hz, 4H). NH proton not observed due to solvent exchange.

Example 299. Preparation of (2S,4R)-4-((3-(2,4-dioxotetrahydropyrimidin-1(2H)-yl)pyrazolo[1,5-a]pyridin-5-yl)methyl)-N-ethyl-N,2-dimethylpiperidine-1-carboxamide

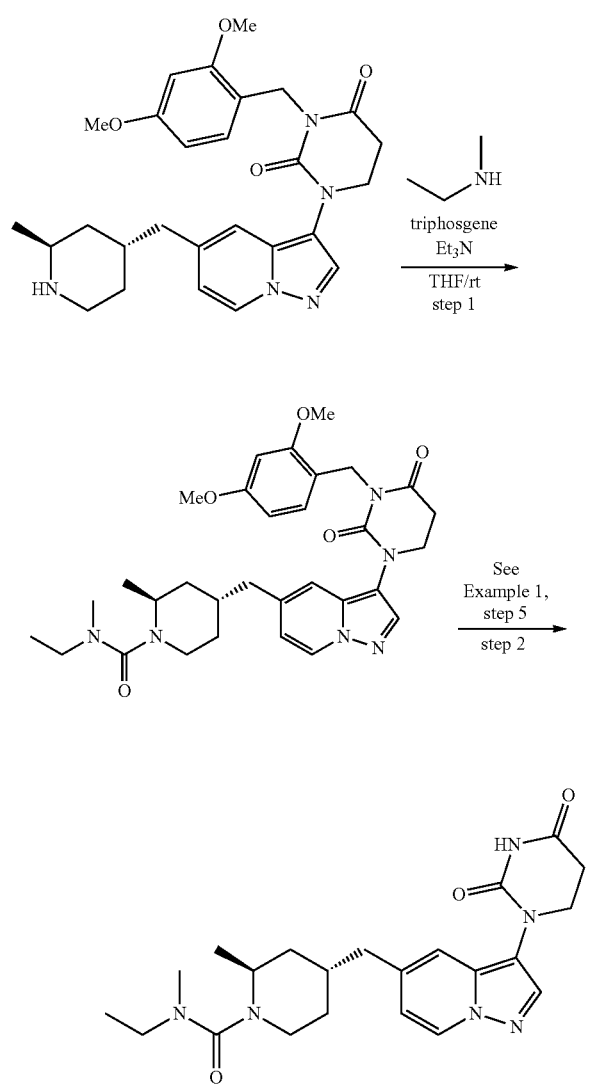

Step 1: (2S,4R)-4-((3-(3-(2,4-dimethoxybenzyl)-2,4-dioxotetrahydropyrimidin-1(2H)-yl)pyrazolo[1,5-a]pyridin-5-yl)methyl)-N-ethyl-N,2-dimethylpiperidine-1-carboxamide Triethylamine (74 mg, 0.73 mmol) and triphosgene (213 mg, 0.73 mmol) were added to a solution of 3-(2,4-dimethoxybenzyl)-1-(5-(((2S,4R)-2-methylpiperidin-4-yl)methyl)pyrazolo[1,5-a]pyridin-3-yl)dihydropyrimidine-2,4(1H,3H)-dione (120 mg, 0.24 mmol) in DCM (5 mL) at rt. The mixture was stirred at rt for 10 min, then N-methylethanamine (22 mg, 0.36 mmol) was added. The reaction was stirred at rt for 4h then diluted with water and extracted with EtOAc. The organic layer was dried over sodium sulfate, filtered and concentrated. The crude product was purified by flash silica gel chromatography (eluted with 6.5% MeOH/DCM) to give (2S,4R)-4-((3-(3-(2,4-dimethoxybenzyl)-2,4-dioxotetrahydropyrimidin-1(2H)-yl)pyrazolo[1,5-a]pyridin-5-yl)methyl)-N-ethyl-N,2-dimethylpiperidine-1-carboxamide (0.10 g, 0.17 mmol, 71% yield) as an off-white solid. LCMS [M+H]⁺: 576.9.

Step 2: (2S,4R)-4-((3-(2,4-dioxotetrahydropyrimidin-1(2H)-yl)pyrazolo[1,5-a]pyridin-5-yl)methyl)-N-ethyl-N,2-dimethylpiperidine-1-carboxamide (Example 299) was prepared from (2S,4R)-4-((3-(3-(2,4-dimethoxybenzyl)-2,4-dioxotetrahydropyrimidin-1(2H)-yl)pyrazolo[1,5-a]pyridin-5-yl)methyl)-N-ethyl-N,2-dimethylpiperidine-1-carboxamide by the method of Example 1, step 5, wherein (2S,4R)-4-((3-(3-(2,4-dimethoxybenzyl)-2,4-dioxotetrahydropyrimidin-1(2H)-yl)pyrazolo[1,5-a]pyridin-5-yl)methyl)-N-ethyl-N,2-dimethylpiperidine-1-carboxamide was used in place of 1-(5-((1-(cyclohexylmethyl)piperidin-4-yl)methyl)pyrazolo[1,5-a]pyridin-3-yl)-3-(2,4-dimethoxybenzyl)dihydropyrimidine-2,4(1H,3H)-dione. LCMS [M+H]⁺: 427.2. ¹H NMR (400 MHz, MeOD) δ 8.41 (dd, J=7.2, 0.9 Hz, 1H), 7.98 (s, 1H), 7.34 (d, J=1.6 Hz, 1H), 6.83 (dd, J=7.2, 1.9 Hz, 1H), 4.03 (t, J=6.5 Hz, 1H), 3.88 (t, J=6.8 Hz, 2H), 3.42 (d, J=13.8 Hz, 1H), 3.24-3.10 (m, 3H), 3.03 (td, J=13.2, 2.7 Hz, 1H), 2.89 (t, J=6.8 Hz, 2H), 2.79 (s, 3H), 2.59 (d, J=7.2 Hz, 2H), 2.11 (s, 1H), 1.62 (dd, J=29.5, 13.2 Hz, 2H), 1.49-1.39 (m, 1H), 1.17 (d, J=6.9 Hz, 3H), 1.13 (t, J=7.1 Hz, 3H). NH proton not observed due to solvent exchange.

Example 300. Preparation of 1-(5-((1-(((1s,3s)-3-methoxycyclobutyl)methyl)piperidin-4-yl)methyl)pyrazolo[1,5-a]pyridin-3-yl)dihydropyrimidine-2,4(1H,3H)-dione

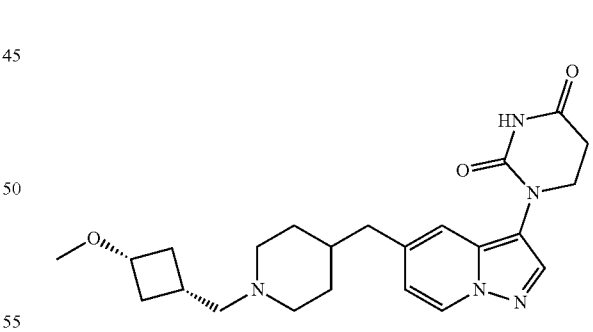

Prepared using the method of Example 112 wherein cis-3-methoxycyclobutane-1-carbaldehyde was used in place of 2-cyclohexyl-2,2-difluoroacetaldehyde in step 1. LCMS [M+H]⁺: 426.2. ¹H NMR (400 MHz, cd3od) δ 8.42 (d, J=7.2 Hz, 1H), 8.00 (s, 1H), 7.36 (s, 1H), 6.82 (dd, J=7.4, 1.8 Hz, 1H), 3.88 (t, J=6.8 Hz, 2H), 3.79 (p, J=7.3 Hz, 1H), 3.22 (d, J=4.2 Hz, 3H), 2.89 (t, J=6.8 Hz, 4H), 2.67 (d, J=6.7 Hz, 4H), 2.56-2.44 (m, 2H), 2.24-2.03 (m, 2H), 1.85 (d, J=14.0 Hz, 3H), 1.63 (dt, J=11.7, 9.2 Hz, 2H), 1.46 (d, J=13.0 Hz, 2H), 1.30 (s, 1H). NH proton not observed due to solvent exchange.

Example 301. Preparation of 1-(5-((1-(((1r,3R,4S)-3,4-difluorocyclopentyl)methyl)piperidin-4-yl)methyl)pyrazolo[1,5-a]pyridin-3-yl)dihydropyrimidine-2,4(1H,3H)-dione

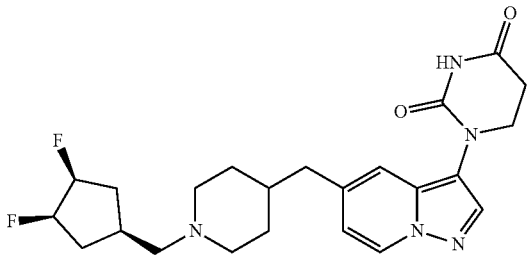

Prepared using the method of Example 112 wherein (1r,3R,4S)-3,4-difluorocyclopentane-1-carbaldehyde was used in place of 2-cyclohexyl-2,2-difluoroacetaldehyde in step 1. LCMS [M+H]+: 446.3. ¹H NMR (400 MHz, MeOD) δ 8.43 (dd, J=7.2, 0.9 Hz, 1H), 8.01 (s, 1H), 7.36 (dd, J=1.9, 0.9 Hz, 1H), 6.83 (dd, J=7.2, 1.9 Hz, 1H), 3.89 (t, J=6.8 Hz, 2H), 3.50-3.40 (m, 2H), 3.06 (d, J=7.2 Hz, 2H), 2.89 (t, J=6.8 Hz, 2H), 2.85-2.75 (m, 2H), 2.70 (d, J=6.8 Hz, 2H), 2.43 (dq, J=15.2, 7.9 Hz, 1H), 2.37-2.19 (m, 2H), 1.91 (d, J=14.4 Hz, 3H), 1.75 (ddq, J=26.1, 12.6, 6.0 Hz, 2H), 1.53 (q, J=13.1 Hz, 2H), 1.27 (d, J=24.2 Hz, 2H). NH proton not observed due to solvent exchange.

Example 302. Preparation of 1-(5-(((2S,4R)-1-(((1r,3S)-3-methoxycyclobutyl)methyl)-2-methylpiperidin-4-yl)methyl)pyrazolo[1,5-a]pyridin-3-yl)dihydropyrimidine-2,4(1H,3H)-dione

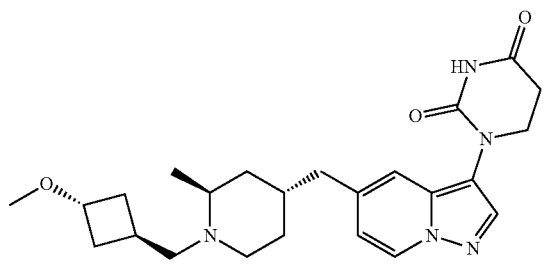

Prepared using the method of Example 141 wherein trans-3-methoxycyclobutane-1-carbaldehyde was used in place of 4,4-difluorocyclohexane-1-carbaldehyde in step 7. LCMS [M+H]+: 440.3. ¹H NMR (400 MHz, cd3od) δ 8.43 (d, J=7.3 Hz, 1H), 8.01 (d, J=1.8 Hz, 1H), 7.37 (d, J=7.3 Hz, 1H), 6.87-6.78 (m, 1H), 4.05-3.65 (m, 4H), 3.63-3.36 (m, 1H), 3.26-3.07 (m, 6H), 2.89 (t, J=6.7 Hz, 2H), 2.80-2.47 (m, 4H), 2.19 (d, J=8.3 Hz, 3H), 1.95-1.65 (m, 4H), 1.38 (ddd, J=34.9, 6.8, 4.2 Hz, 4H). Missing NH due to solvent exchange.

Example 303. Preparation of 1-(5-(((2S,4R)-1-(((1s,3R)-3-methoxycyclobutyl)methyl)-2-methylpiperidin-4-yl)methyl)pyrazolo[1,5-a]pyridin-3-yl)dihydropyrimidine-2,4(1H,3H)-dione

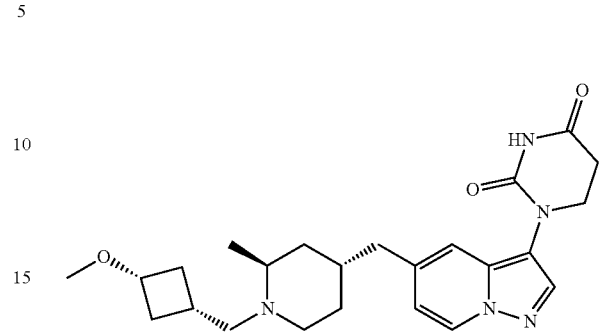

Prepared using the method of Example 141 wherein cis-3-methoxycyclobutane-1-carbaldehyde was used in place of 4,4-difluorocyclohexane-1-carbaldehyde in step 7. LCMS [M+H]+: 440.4.

¹H NMR (400 MHz, cd3od) δ 8.43 (dd, J=7.4, 1.8 Hz, 1H), 8.01 (d, J=1.6 Hz, 1H), 7.36 (s, 1H), 6.83 (dd, J=7.1, 1.9 Hz, 1H), 3.89 (td, J=6.8, 3.4 Hz, 2H), 3.75-3.67 (m, 1H), 3.26-3.21 (m, 4H), 3.19-3.06 (m, 3H), 2.89 (t, J=6.8 Hz, 2H), 2.66 (d, J=7.1 Hz, 2H), 2.60-2.47 (m, 2H), 2.30-2.12 (m, 3H), 1.87 (q, J=14.0 Hz, 2H), 1.70 (dddt, J=17.3, 12.0, 9.0, 3.6 Hz, 3H), 1.50 (dd, J=12.9, 5.0 Hz, 1H), 1.33 (dd, J=7.0, 3.5 Hz, 3H). NH proton not observed due to solvent exchange.

Example 304. Preparation of 1-(5-(((2S,4R)-1-(((1r,3R,4S)-3,4-difluorocyclopentyl)methyl)-2-methylpiperidin-4-yl)methyl)pyrazolo[1,5-a]pyridin-3-yl)dihydropyrimidine-2,4(1H,3H)-dione

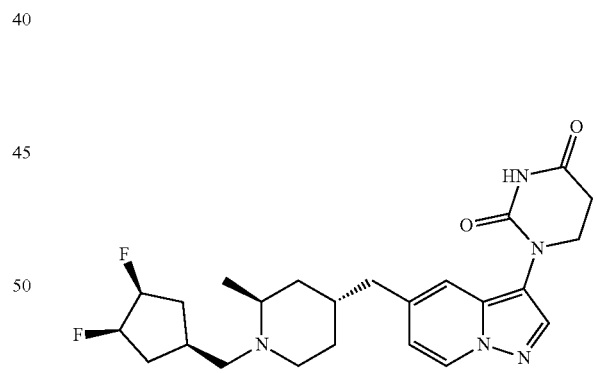

Prepared using the method of Example 141 wherein (1r,3R,4S)-3,4-difluorocyclopentane-1-carbaldehyde was used in place of 4,4-difluorocyclohexane-1-carbaldehyde in step 7. LCMS [M+H]+: 460.3. ¹H NMR (400 MHz, MeOD) δ 8.49 (s, 1H), 8.43 (dd, J=7.2, 0.9 Hz, 1H), 8.01 (s, 1H), 7.36 (dd, J=1.9, 0.9 Hz, 1H), 6.83 (dd, J=7.2, 1.9 Hz, 1H), 5.14-4.93 (m, 1H), 3.89 (t, J=6.8 Hz, 2H), 3.64 (s, 1H), 3.22-3.00 (m, 4H), 2.89 (t, J=6.8 Hz, 2H), 2.69 (d, J=7.2 Hz, 1H), 2.46-2.15 (m, 4H), 1.93-1.64 (m, 5H), 1.58 (s, 1H), 1.32 (q, J=6.3 Hz, 5H).

Example 305. Preparation of 1-(5-(((2S,4R)-2-methyl-1-(((1r,4S)-4-(trifluoromethyl)cyclohexyl)methyl)piperidin-4-yl)methyl)pyrazolo[1,5-a]pyridin-3-yl)dihydropyrimidine-2,4(1H,3H)-dione

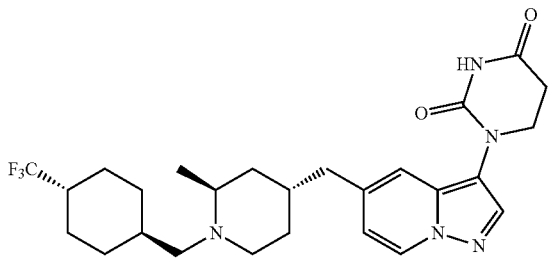

Prepared using the method of Example 141 wherein (1r,4r)-4-(trifluoromethyl)cyclohexane-1-carbaldehyde was used in place of 4,4-difluorocyclohexane-1-carbaldehyde in step 7. LCMS [M+H]+: 506.4. $^1$H NMR (300 MHz, cd3od) δ 8.44 (d, J=7.1 Hz, 1H), 8.02 (s, 1H), 7.37 (s, 1H), 6.84 (d, J=6.9 Hz, 1H), 3.89 (t, J=6.7 Hz, 2H), 3.74 (s, 1H), 2.98 (s, 2H), 2.89 (t, J=6.7 Hz, 2H), 2.70 (d, J=7.1 Hz, 2H), 2.25-2.13 (m, 2H), 2.05-1.75 (m, 8H), 1.49-1.26 (m, 8H), 1.14 (d, J=12.7 Hz, 2H). NH proton not observed due to solvent exchange.

Example 306. Preparation of 1-(5-(((2S,4R)-1-(((R)-3,3-difluorocyclopentyl)methyl)-2-methylpiperidin-4-yl)methyl)pyrazolo[1,5-a]pyridin-3-yl)dihydropyrimidine-2,4(1H,3H)-dione

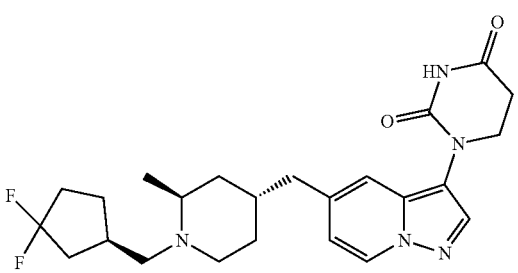

Prepared using the method of Example 141 wherein (R)-3,3-difluorocyclopentane-1-carbaldehyde was used in place of 4,4-difluorocyclohexane-1-carbaldehyde in step 7. LCMS [M+H]+: 460.3. $^1$H NMR (400 MHz, MeOD) δ 8.44 (d, J=7.1 Hz, 1H), 8.01 (s, 1H), 7.36 (d, J=2.3 Hz, 1H), 6.84 (ddd, J=7.1, 4.9, 1.9 Hz, 1H), 3.89 (td, J=6.8, 1.9 Hz, 2H), 3.82 (s, 1H), 3.69-3.40 (m, 1H), 3.23-3.06 (m, 2H), 2.89 (t, J=6.8 Hz, 2H), 2.72 (dd, J=42.6, 7.3 Hz, 2H), 2.63-2.35 (m, 2H), 2.34-2.03 (m, 4H), 2.01-1.50 (m, 6H), 1.40 (dd, J=41.6, 6.8 Hz, 4H). NH proton not observed due to solvent exchange.

Example 307. Preparation of 1-(5-(((2S,4R)-1-(((S)-3,3-difluorocyclopentyl)methyl)-2-methylpiperidin-4-yl)methyl)pyrazolo[1,5-a]pyridin-3-yl)dihydropyrimidine-2,4(1H,3H)-dione Prepared using the method of Example 141 wherein (S)-3,3-difluorocyclopentane-1-carbaldehyde was used in place of 4,4-difluorocyclohexane-1-carbaldehyde in step 7. LCMS [M+H]+: 460.3. $^1$H NMR (400 MHz, MeOD) δ 8.43 (d, J=7.2 Hz, 1H), 8.01 (s, 1H), 7.36 (d, J=2.1 Hz, 1H), 6.88-6.80 (m, 1H), 3.89 (td, J=6.8, 1.8 Hz, 2H), 3.82 (s, 1H), 3.23-3.05 (m, 2H), 2.89 (t, J=6.8 Hz, 2H), 2.67 (d, J=7.0 Hz, 2H), 2.62-2.37 (m, 2H), 2.31-2.05 (m, 4H), 1.98-1.52 (m, 6H), 1.47-1.22 (m, 5H). NH proton not observed due to solvent exchange.

Examples 308 and 309. Preparation of 1-(5-(((2S)-1-((4,4-difluorocyclohexyl)methyl)-4-fluoro-2-methylpiperidin-4-yl)methyl)pyrazolo[1,5-a]pyridin-3-yl)dihydropyrimidine-2,4(1H,3H)-dione

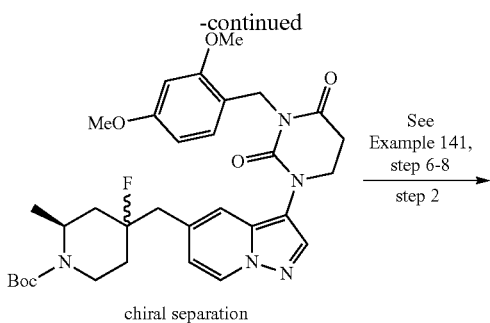

chiral separation

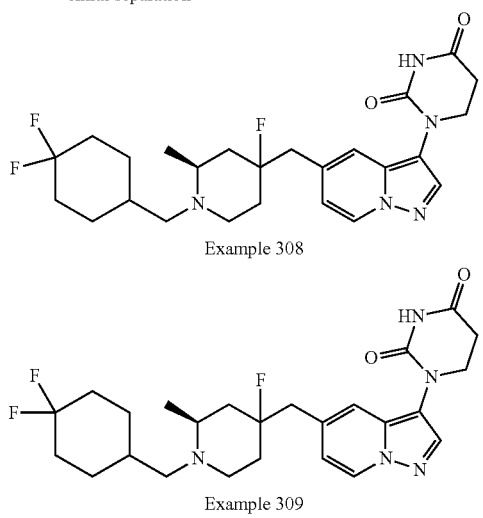

Example 308

Example 309

Step 1. tert-butyl (2S)-4-((3-(3-(2,4-dimethoxybenzyl)-2,4-dioxotetrahydropyrimidin-1(2H)-yl) pyrazolo[1,5-a]pyridin-5-yl)methyl)-4-fluoro-2-methylpiperidine-1-carboxylate To an oven-dried vial was added tert-butyl (2S)-4-(bromomethyl)-4-fluoro-2-methylpiperidine-1-carboxylate (0.270 g, 0.87 mmol), 1-(5-bromopyrazolo[1,5-a]pyridin-3-yl)-3-(2,4-dimethoxybenzyl)dihydropyrimidine-2,4(1H,3H)-dione (0.250 g, 0.544 mmol), NiCl$_2$(DME) (5 mg, 0.027 mmol), pyridine-2,6-bis(carboximidamide) dihydrochloride (6 mg, 0.027 mmol), NaI (0.020 g, 0.14 mmol) and Zn (0.070 g, 1.1 mmol). The vial was sealed with a septum cap, evacuated and refilled with nitrogen 3 times. DMA (3 mL) was added and the reaction was stirred at 70° C. for 17 h. The reaction was cooled to rt, diluted with EtOAc and filtered through a plug of silica gel, eluting with EtOAc. The eluent was concentrated and the residue was purified by silica gel column chromatography (eluted with 50-70% EtOAc in heptane) to give tert-butyl (2S)-4-((3-(3-(2,4-dimethoxybenzyl)-2,4-dioxotetrahydropyrimidin-1(2H)-yl) pyrazolo[1,5-a]pyridin-5-yl)methyl)-4-fluoro-2-methylpiperidine-1-carboxylate as a mixture of diastereomers. The diastereomers were separated by chiral HPLC purification: Column: Lux Cellulose-4 250×21.2 mm I.D., 5 μm Mobile phase: Phase A for n-hexane, and Phase B for 1:1 EtOH: MeOH (0.1% HCOOH); Isocratic elution: 50% (A):50% (B) Flow rate: 15 mL/min; Peak 1 (145 mg), LCMS [M+H-Boc]$^+$: 510.3, HPLC rt=17.04 min; Peak 2 (245 mg), LCMS [M+H-Boc]$^+$: 510.3, HPLC rt=17.64 min.

Step 2: 1-(5-(((2S)-1-((4,4-difluorocyclohexyl)methyl)-4-fluoro-2-methylpiperidin-4-yl)methyl)pyrazolo[1,5-a]pyridin-3-yl)dihydropyrimidine-2,4(1H,3H)-dione (Example 308) was prepared from tert-butyl (2S)-4-((3-(3-(2,4-dimethoxybenzyl)-2,4-dioxotetrahydropyrimidin-1(2H)-yl)pyrazolo[1,5-a]pyridin-5-yl)methyl)-4-fluoro-2-methylpiperidine-1-carboxylate (chiral peak 1) using the method of Example 141, steps 6-8 wherein tert-butyl (2S)-4-((3-(3-(2,4-dimethoxybenzyl)-2,4-dioxotetrahydropyrimidin-1(2H)-yl)pyrazolo[1,5-a]pyridin-5-yl)methyl)-4-fluoro-2-methylpiperidine-1-carboxylate (chiral peak 1) was used in place of tert-butyl (2S,4R)-4-((3-(3-(2,4-dimethoxybenzyl)-2,4-dioxotetrahydropyrimidin-1(2H)-yl)pyrazolo[1,5-a]pyridin-5-yl)methyl)-2-methylpiperidine-1-carboxylate in step 6. LCMS [M+H]$^+$: 492.1. $^1$H NMR (400 MHz, MeOD) δ 8.44 (dd, J=7.2, 0.9 Hz, 1H), 8.33 (s, 1H), 8.03 (s, 1H), 7.42 (s, 1H), 6.87 (d, J=7.2 Hz, 1H), 3.90 (t, J=6.8 Hz, 2H), 3.18-3.06 (m, 2H), 2.98 (s, 2H), 2.89 (t, J=6.8 Hz, 2H), 2.81 (s, 1H), 2.19-1.72 (m, 12H), 1.45-1.25 (m, 6H).

1-(5-(((2S)-1-((4,4-difluorocyclohexyl)methyl)-4-fluoro-2-methylpiperidin-4-yl)methyl)pyrazolo[1,5-a]pyridin-3-yl) dihydropyrimidine-2,4(1H,3H)-dione (Example 309) was prepared from tert-butyl (2S)-4-((3-(3-(2,4-dimethoxybenzyl)-2,4-dioxotetrahydropyrimidin-1(2H)-yl)pyrazolo[1,5-a]pyridin-5-yl)methyl)-4-fluoro-2-methylpiperidine-1-carboxylate (chiral peak 2) using the method of Example 141, steps 6-8 wherein tert-butyl (2S)-4-((3-(3-(2,4-dimethoxybenzyl)-2,4-dioxotetrahydropyrimidin-1(2H)-yl)pyrazolo[1,5-a]pyridin-5-yl)methyl)-4-fluoro-2-methylpiperidine-1-carboxylate (chiral peak 2) was used in place of tert-butyl (2S,4R)-4-((3-(3-(2,4-dimethoxybenzyl)-2,4-dioxotetrahydropyrimidin-1(2H)-yl)pyrazolo[1,5-a]pyridin-5-yl)methyl)-2-methylpiperidine-1-carboxylate in step 6. LCMS [M+H]$^+$: 492.1. $^1$H NMR (400 MHz, MeOD) δ 8.44 (d, J=7.2 Hz, 1H), 8.33 (s, 1H), 8.03 (s, 1H), 7.43 (s, 1H), 6.87 (d, J=7.2 Hz, 1H), 3.90 (t, J=6.7 Hz, 2H), 3.15-2.96 (m, 4H), 2.89 (t, J=6.8 Hz, 2H), 2.69 (s, 1H), 2.13-1.72 (m, 10H), 1.29 (t, J=5.0 Hz, 8H).

Example 310. Preparation of 1-(5-(((2S)-4-fluoro-2-methyl-1-(oxetan-3-yl)piperidin-4-yl)methyl)pyrazolo[1,5-a]pyridin-3-yl)dihydropyrimidine-2,4(1H, 3H)-dione

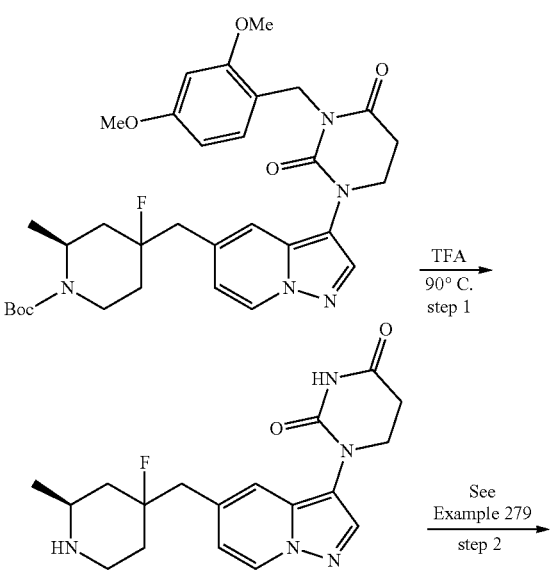

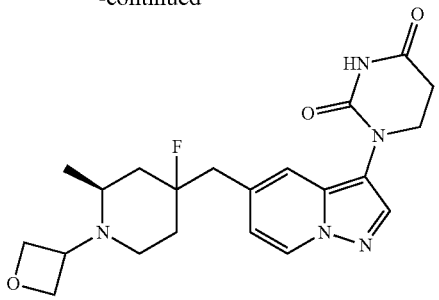

Step 1. 1-(5-(((2S)-4-fluoro-2-methylpiperidin-4-yl)methyl)pyrazolo[1,5-a]pyridin-3-yl)dihydropyrimidine-2,4(1H,3H)-dione TFA (2 mL) was added to tert-butyl (2S)-4-((3-(3-(2,4-dimethoxybenzyl)-2,4-dioxotetrahydropyrimidin-1(2H)-yl)pyrazolo[1,5-a]pyridin-5-yl)methyl)-4-fluoro-2-methylpiperidine-1-carboxylate (chiral peak 1 from Example 308, step 1) (350 mg, 0.574 mmol). The mixture was heated in a sealed vial for 24 h at 90° C. The mixture was then cooled to rt and, concentrated and azeotropically dried with toluene to provide crude 1-(5-(((2S)-4-fluoro-2-methylpiperidin-4-yl)methyl)pyrazolo[1,5-a]pyridin-3-yl)dihydropyrimidine-2,4(1H,3H)-dione which was used without further purification. LCMS [M+H]⁺: 360.0.

Step 2: 1-(5-(((2S)-4-fluoro-2-methyl-1-(oxetan-3-yl)piperidin-4-yl)methyl)pyrazolo[1,5-a]pyridin-3-yl)dihydropyrimidine-2,4(1H,3H)-dione (Example 310) was prepared from 1-(5-(((2S)-4-fluoro-2-methylpiperidin-4-yl)methyl)pyrazolo[1,5-a]pyridin-3-yl)dihydropyrimidine-2,4(1H,3H)-dione by the method of Example 279, wherein 1-(5-(((2S)-4-fluoro-2-methylpiperidin-4-yl)methyl)pyrazolo[1,5-a]pyridin-3-yl)dihydropyrimidine-2,4(1H,3H)-dione was used in place of 1-(5-(((2S,4R)-2-methylpiperidin-4-yl)methyl)pyrazolo[1,5-a]pyridin-3-yl)dihydropyrimidine-2,4(1H,3H)-dione hydrochloride. LCMS [M+H]⁺: 416.0. ¹H NMR (400 MHz, MeOD) δ 8.41 (dd, J=7.2, 0.9 Hz, 1H), 8.00 (s, 1H), 7.40 (d, J=1.7 Hz, 1H), 6.90-6.79 (m, 1H), 4.71-4.60 (m, 4H), 3.96 (q, J=7.0 Hz, 1H), 3.89 (t, J=6.8 Hz, 2H), 3.06 (d, J=24.6 Hz, 2H), 2.89 (t, J=6.8 Hz, 2H), 2.79 (ddt, J=17.7, 12.0, 5.9 Hz, 2H), 2.37 (dt, J=11.9, 5.7 Hz, 1H), 1.95-1.79 (m, 3H), 1.72 (td, J=13.1, 6.6 Hz, 1H), 0.98 (dd, J=6.7, 1.7 Hz, 3H). NH proton not observed due to solvent exchange.

Example 311. Preparation of 1-(5-(((2S)-4-fluoro-2-methyl-1-(oxetan-3-yl)piperidin-4-yl)methyl)pyrazolo[1,5-a]pyridin-3-yl)dihydropyrimidine-2,4(1H,3H)-dione

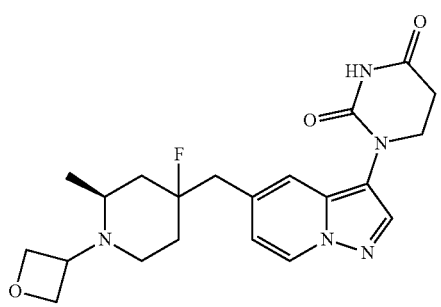

Prepared using the method of Example 310 wherein tert-butyl (2S)-4-((3-(3-(2,4-dimethoxybenzyl)-2,4-dioxotetrahydropyrimidin-1(2H)-yl)pyrazolo[1,5-a]pyridin-5-yl)methyl)-4-fluoro-2-methylpiperidine-1-carboxylate (chiral peak 2 from Example 308, step 1) was used in place of tert-butyl (2S)-4-((3-(3-(2,4-dimethoxybenzyl)-2,4-dioxotetrahydropyrimidin-1(2H)-yl)pyrazolo[1,5-a]pyridin-5-yl)methyl)-4-fluoro-2-methylpiperidine-1-carboxylate (chiral peak 1 from Example 308, step 1). LCMS [M+H]⁺: 416.0. ¹H NMR (400 MHz, MeOD) δ 8.41 (dd, J=7.2, 0.9 Hz, 1H), 8.00 (s, 1H), 7.42 (s, 1H), 6.87 (d, J=7.2 Hz, 1H), 4.71-4.54 (m, 4H), 3.89 (t, J=6.8 Hz, 2H), 2.99 (d, J=22.4 Hz, 2H), 2.89 (t, J=6.8 Hz, 2H), 2.58 (d, J=11.9 Hz, 1H), 2.40 (s, 1H), 2.20-2.10 (m, 1H), 1.85-1.65 (m, 3H), 1.64-1.37 (m, 2H), 0.87 (d, J=6.4 Hz, 3H). NH proton not observed due to solvent exchange.

Example 312. Preparation of (cis)-1-(5-((1-isobutyl-2-(trifluoromethyl)piperidin-4-yl)methyl)pyrazolo[1,5-a]pyridin-3-yl)dihydropyrimidine-2,4(1H,3H)-dione

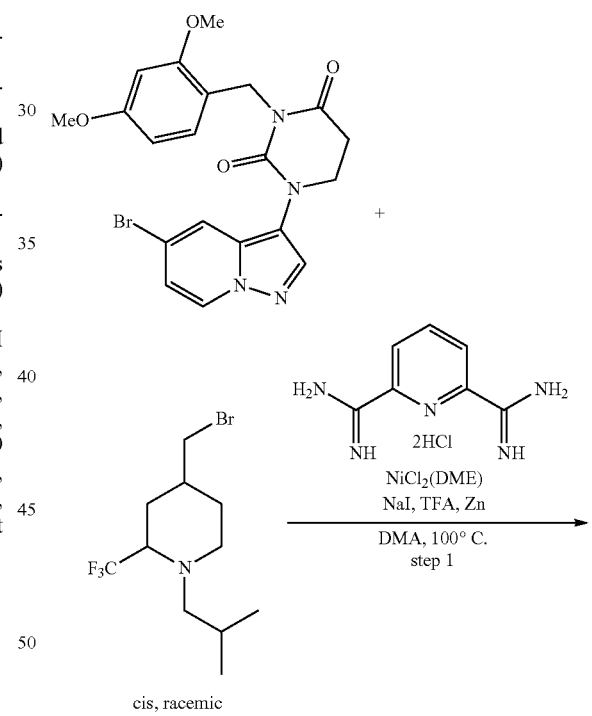

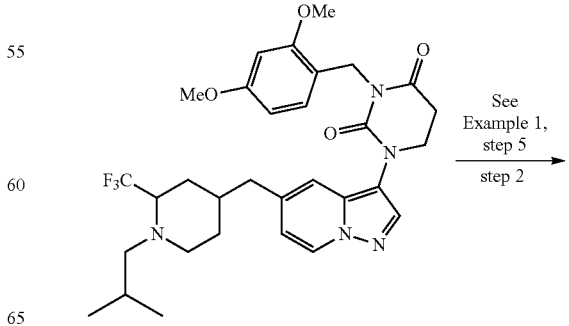

401
-continued

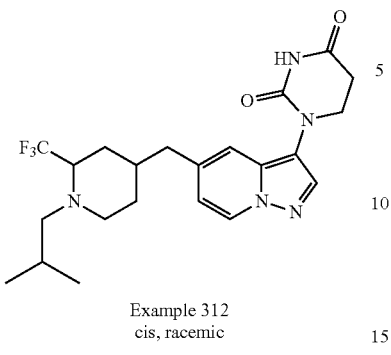

Example 312
cis, racemic

Step 1. (cis)-3-(2,4-dimethoxybenzyl)-1-(5-((1-isobutyl-2-(trifluoromethyl)piperidin-4-yl)methyl)pyrazolo[1,5-a]pyridin-3-yl)dihydropyrimidine-2,4(1H,3H)-dione To an oven-dried vial was added (cis)-4-(bromomethyl)-1-isobutyl-2-(trifluoromethyl)piperidine (14 mg, 0.049 mmol), 1-(5-bromopyrazolo[1,5-a]pyridin-3-yl)-3-(2,4-dimethoxybenzyl)dihydropyrimidine-2,4(1H,3H)-dione (17.5 mg, 0.038 mmol), NiCl$_2$(DME) (1 mg, 0.001 mmol), pyridine-2,6-bis(carboximidamide) dihydrochloride (1 mg, 0.001 mmol), NaI (1 mg, 0.009 mmol) and Zn (4 mg, 0.076 mmol). The vial was sealed with a septum cap, evacuated and refilled with nitrogen 3 times. DMA (2 mL) was added and the reaction was stirred at 100° C. for 17 h. The reaction was cooled to rt, diluted with EtOAc and filtered through a plug of silica gel, eluting with EtOAc. The eluent was concentrated to give crude (cis)-3-(2,4-dimethoxybenzyl)-1-(5-((1-isobutyl-2-(trifluoromethyl)piperidin-4-yl)methyl)pyrazolo[1,5-a]pyridin-3-yl)dihydropyrimidine-2,4(1H,3H)-dione which was used without further purification. LCMS [M+H]$^+$: 602.2.

Step 2: (cis)-1-(5-((1-isobutyl-2-(trifluoromethyl)piperidin-4-yl)methyl)pyrazolo[1,5-a]pyridin-3-yl)dihydropyrimidine-2,4(1H,3H)-dione (Example 312) was prepared from (cis)-3-(2,4-dimethoxybenzyl)-1-(5-((1-isobutyl-2-(trifluoromethyl)piperidin-4-yl)methyl)pyrazolo[1,5-a]pyridin-3-yl)dihydropyrimidine-2,4(1H,3H)-dione using the method of Example 1, step 5 wherein (cis)-3-(2,4-dimethoxybenzyl)-1-(5-((1-isobutyl-2-(trifluoromethyl)piperidin-4-yl)methyl)pyrazolo[1,5-a]pyridin-3-yl)dihydropyrimidine-2,4(1H,3H)-dione was used in place of 1-(5-((1-(cyclohexylmethyl)piperidin-4-yl)methyl)pyrazolo[1,5-a]pyridin-3-yl)-3-(2,4-dimethoxybenzyl)dihydropyrimidine-2,4(1H,3H)-dione. LCMS [M+H]$^+$: 452.4. $^1$H NMR (400 MHz, MeOD) δ 8.40 (dd, J=7.2, 0.9 Hz, 1H), 7.98 (s, 1H), 7.37 (dd, J=1.9, 1.0 Hz, 1H), 6.84 (dd, J=7.2, 1.9 Hz, 1H), 3.87 (t, J=6.8 Hz, 2H), 3.27 (d, J=8.1 Hz, 1H), 3.24-3.12 (m, 1H), 2.89 (t, J=6.8 Hz, 2H), 2.72 (dt, J=9.1, 6.4 Hz, 2H), 2.46 (t, J=7.4 Hz, 2H), 2.25 (dq, J=11.6, 5.6 Hz, 1H), 2.10-2.00 (m, 2H), 1.73 (dddd, J=13.3, 10.5, 7.9, 3.2 Hz, 4H), 0.91 (d, J=6.5 Hz, 3H), 0.86 (d, J=6.7 Hz, 3H).

Example 313. Preparation of (R)-1-(5-((octahydro-2H-pyrido[1,2-a]pyrazin-2-yl)methyl)pyrazolo[1,5-a]pyridin-3-yl)dihydropyrimidine-2,4(1H,3H)-dione

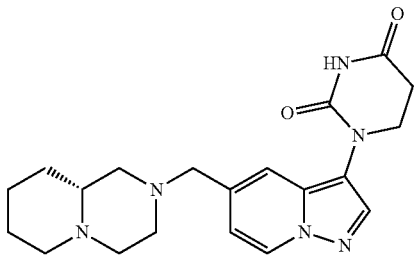

Prepared using the method of Example 156, steps 1 and 4, wherein potassium (R)-trifluoro((octahydro-2H-pyrido[1,2-a]pyrazin-2-yl)methyl)borate was used in place of potassium {[4-(tert-butoxycarbonyl)-1-piperazinyl]methyl}(trifluoro)borate. LCMS [M+H]$^+$: 383.0. $^1$H NMR (400 MHz, MeOD) δ 8.49 (d, J=7.1 Hz, 1H), 8.04 (s, 1H), 7.55 (s, 1H), 6.99 (dd, J=7.2, 1.8 Hz, 1H), 3.90 (t, J=6.7 Hz, 2H), 3.79 (s, 2H), 3.51-3.41 (m, 2H), 3.28-3.12 (m, 3H), 3.04 (td, J=12.9, 3.2 Hz, 1H), 2.89 (t, J=6.8 Hz, 2H), 2.63 (s, 1H), 2.37 (s, 1H), 1.94 (dd, J=30.0, 13.6 Hz, 3H), 1.77 (q, J=13.4 Hz, 1H), 1.69-1.43 (m, 2H), 1.37-1.27 (m, 1H). NH proton not observed due to solvent exchange.

Example 314. Preparation of (R)-1-(5-((4-oxohexahydropyrazino[2,1-c][1,4]oxazin-8(1H)-yl)methyl)pyrazolo[1,5-a]pyridin-3-yl)dihydropyrimidine-2,4(1H,3H)-dione

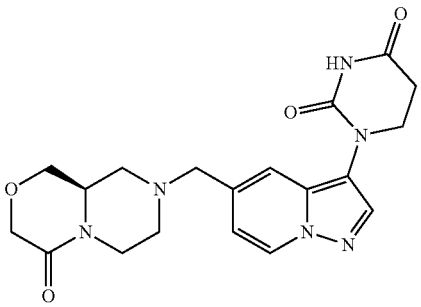

Prepared using the method of Example 156, steps 1 and 4, wherein potassium (R)-trifluoro((4-oxohexahydropyrazino[2,1-c][1,4]oxazin-8(1H)-yl)methyl)borate was used in place of potassium {[4-(tert-butoxycarbonyl)-1-piperazinyl]methyl}(trifluoro)borate. LCMS [M+H]$^+$: 399.0. $^1$H NMR (400 MHz, MeOD) δ 8.45 (dd, J=7.2, 0.9 Hz, 1H), 8.01 (s, 1H), 7.51 (dd, J=1.9, 1.0 Hz, 1H), 7.01 (dd, J=7.2, 1.8 Hz, 1H), 4.49 (ddd, J=13.3, 3.3, 1.8 Hz, 1H), 4.10 (d, J=1.7 Hz, 2H), 3.98 (dd, J=12.0, 4.6 Hz, 1H), 3.90 (t, J=6.8 Hz, 2H), 3.74-3.51 (m, 4H), 2.98-2.82 (m, 5H), 2.14 (td, J=11.6, 3.2 Hz, 1H), 2.06-1.94 (m, 1H). NH proton not observed due to solvent exchange.

Example 315. Preparation of (S)-1-(5-((1,1-dioxido-hexahydro-5H-isothiazolo[2,3-a]pyrazin-5-yl)methyl)pyrazolo[1,5-a]pyridin-3-yl)dihydropyrimidine-2,4(1H,3H)-dione

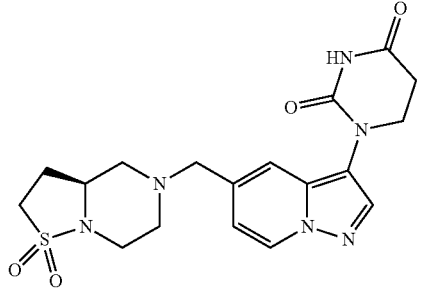

Prepared using the method of Example 156, steps 1 and 4, wherein potassium (S)-((1,1-dioxidohexahydro-5H-isothiazolo[2,3-a]pyrazin-5-yl)methyl)trifluoroborate was used in place of potassium {[4-(tert-butoxycarbonyl)-1-piperazinyl]methyl}(trifluoro)borate. LCMS [M+H]$^+$: 419.0. $^1$H NMR (400 MHz, MeOD) δ 8.45 (d, J=7.1 Hz, 1H), 8.01 (s, 1H), 7.50 (s, 1H), 7.00 (dd, J=7.2, 1.8 Hz, 1H), 3.89 (t, J=6.8 Hz, 2H), 3.65 (q, J=13.7 Hz, 2H), 3.26-3.10 (m, 3H), 3.04 (d, J=11.3 Hz, 1H), 2.96 (d, J=11.5 Hz, 1H), 2.92-2.86 (m, 3H), 2.40-2.14 (m, 2H), 2.09-1.90 (m, 3H). NH proton not observed due to solvent exchange.

Example 316. Preparation of 1-(5-(((S)-4-(((1r,3S)-3-methoxycyclobutyl)methyl)-3-methylpiperazin-1-yl)methyl)pyrazolo[1,5-a]pyridin-3-yl)dihydropyrimidine-2,4(1H,3H)-dione

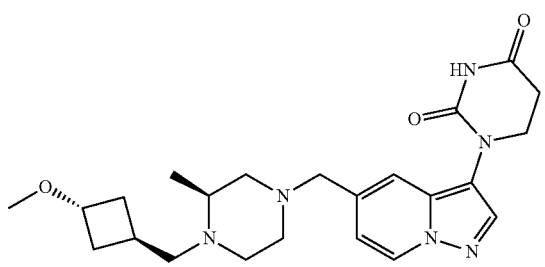

Prepared using the method of Example 192 wherein trans-3-methoxycyclobutane-1-carbaldehyde was used in place of cyclohexanecarbaldehyde in step 3. LCMS [M+H]$^+$: 441.1. $^1$H NMR (400 MHz, cd3od) δ 8.45 (d, J=7.2 Hz, 1H), 8.01 (s, 1H), 7.48 (s, 1H), 6.97 (dd, J=7.1, 1.9 Hz, 1H), 4.03-3.94 (m, 1H), 3.88 (t, J=6.8 Hz, 2H), 3.69-3.56 (m, 2H), 3.40 (d, J=12.6 Hz, 3H), 3.22 (d, J=4.3 Hz, 3H), 3.10 (d, J=11.6 Hz, 2H), 3.02 (s, 1H), 2.87 (t, J=6.7 Hz, 2H), 2.72 (d, J=8.3 Hz, 2H), 2.52 (s, 2H), 2.16 (ddt, J=36.3, 12.7, 7.4 Hz, 4H), 1.34 (d, J=6.6 Hz, 3H). NH proton not observed due to solvent exchange.

Example 317. Preparation of 1-(5-(((S)-4-(((1s,3R)-3-methoxycyclobutyl)methyl)-3-methylpiperazin-1-yl)methyl)pyrazolo[1,5-a]pyridin-3-yl)dihydropyrimidine-2,4(1H,3H)-dione

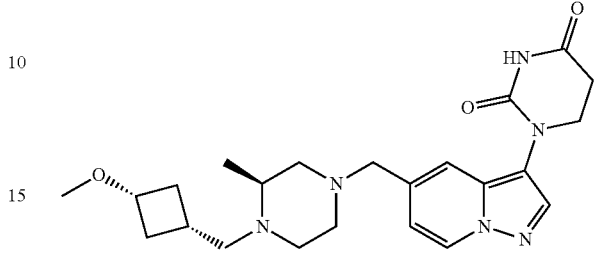

Prepared using the method of Example 192 wherein cis-3-methoxycyclobutane-1-carbaldehyde was used in place of cyclohexanecarbaldehyde in step 3. LCMS [M+H]$^+$: 441.3. $^1$H NMR (400 MHz, cd3od) δ 8.46 (d, J=7.2 Hz, 1H), 8.02 (s, 1H), 7.50 (s, 1H), 6.99 (dd, J=7.1, 1.9 Hz, 1H), 3.89 (t, J=6.8 Hz, 2H), 3.81 (p, J=7.2 Hz, 1H), 3.70-3.56 (m, 2H), 3.22 (s, 6H), 3.06-2.84 (m, 6H), 2.60-2.46 (m, 3H), 2.36 (s, 1H), 2.22 (qd, J=9.1, 6.6 Hz, 1H), 1.75-1.60 (m, 2H), 1.30 (d, J=6.3 Hz, 3H). NH proton not observed due to solvent exchange.

Example 318. Preparation of 1-(5-(((S)-4-(((1r,3R,4S)-3,4-difluorocyclopentyl)methyl)-3-methylpiperazin-1-yl)methyl)pyrazolo[1,5-a]pyridin-3-yl)dihydropyrimidine-2,4(1H,3H)-dione

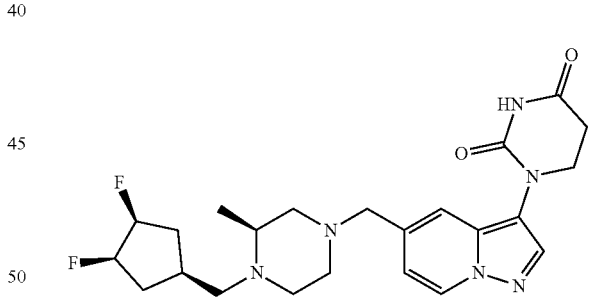

Prepared using the method of Example 192 wherein (1r,3R,4S)-3,4-difluorocyclopentane-1-carbaldehyde was used in place of cyclohexanecarbaldehyde in step 3. LCMS [M+H]$^+$: 461.4. $^1$H NMR (400 MHz, MeOD) δ 8.46 (dd, J=7.2, 0.9 Hz, 1H), 8.02 (s, 1H), 7.50 (d, J=1.8 Hz, 1H), 6.99 (dd, J=7.2, 1.8 Hz, 1H), 5.08-4.92 (m, 1H), 4.81 (s, 1H), 3.89 (t, J=6.8 Hz, 2H), 3.68-3.54 (m, 2H), 3.20-3.11 (m, 1H), 2.99 (t, J=11.1 Hz, 1H), 2.93-2.75 (m, 5H), 2.53 (d, J=75.2 Hz, 3H), 2.39-2.06 (m, 4H), 1.83-1.56 (m, 2H), 1.17 (d, J=6.1 Hz, 3H). NH proton not observed due to solvent exchange.

Example 319. Preparation of 1-(5-(((S)-4-(((R)-3,3-difluorocyclopentyl)methyl)-3-methylpiperazin-1-yl)methyl)pyrazolo[1,5-a]pyridin-3-yl)dihydropyrimidine-2,4(1H,3H)-dione

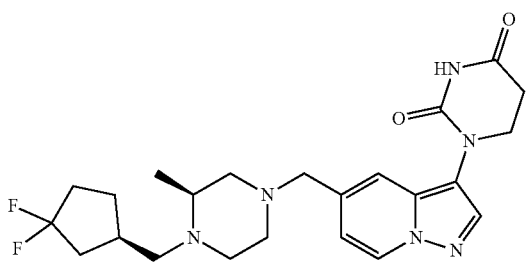

Prepared using the method of Example 192 wherein (R)-3,3-difluorocyclopentane-1-carbaldehyde was used in place of cyclohexanecarbaldehyde in step 3. LCMS [M+H]+: 461.2. ¹H NMR (300 MHz, CD₃OD) δ 8.45 (d, J=7.2 Hz, 1H), 8.01 (s, 1H), 7.50 (s, 1H), 7.05-6.94 (m, 1H), 3.89 (t, J=6.7 Hz, 2H), 3.56 (d, J=3.6 Hz, 2H), 2.89 (t, J=6.7 Hz, 3H), 2.74 (t, J=12.3 Hz, 3H), 2.61-1.91 (m, 11H), 1.38-1.25 (m, 2H), 1.06 (d, J=6.1 Hz, 2H). NH proton not observed due to solvent exchange.

Example 320. Preparation of 1-(5-(((S)-4-(((S)-3,3-difluorocyclopentyl)methyl)-3-methylpiperazin-1-yl)methyl)pyrazolo[1,5-a]pyridin-3-yl)dihydropyrimidine-2,4(1H,3H)-dione

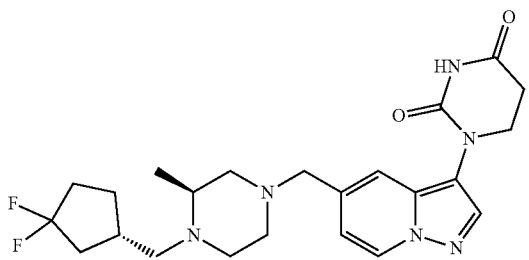

Prepared using the method of Example 192 wherein (S)-3,3-difluorocyclopentane-1-carbaldehyde was used in place of cyclohexanecarbaldehyde in step 3. LCMS [M+H]+: 461.1. ¹H NMR (400 MHz, MeOD) δ 8.44 (d, J=7.1 Hz, 1H), 8.01 (s, 1H), 7.49 (s, 1H), 6.99 (dd, J=7.2, 1.8 Hz, 1H), 3.89 (t, J=6.8 Hz, 2H), 3.54 (d, J=6.3 Hz, 1H), 2.89 (t, J=6.8 Hz, 3H), 2.79-2.63 (m, 3H), 2.50-1.90 (m, 12H), 1.32 (d, J=16.3 Hz, 1H), 1.04 (dd, J=6.1, 4.1 Hz, 3H). NH proton not observed due to solvent exchange.

Example 321. Preparation of (S)-1-(5-((4-(cyclopropylmethyl)-3-methylpiperazin-1-yl)methyl)pyrazolo[1,5-a]pyridin-3-yl)dihydropyrimidine-2,4(1H,3H)-dione

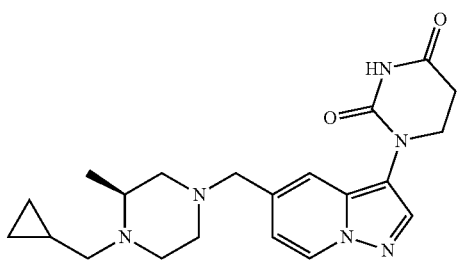

Prepared using the method of Example 192 wherein cyclopropanecarbaldehyde was used in place of cyclohexanecarbaldehyde in step 3. LCMS [M+H]+: 397.4. ¹H NMR (500 MHz, DMSO) δ 10.47 (s, 1H), 8.64 (d, J=7.2 Hz, 1H), 8.05 (s, 1H), 7.52 (s, 1H), 6.91 (dd, J=7.2, 1.8 Hz, 1H), 3.79 (t, J=6.7 Hz, 2H), 3.68 (s, 4H), 3.36 (s, 1H), 3.25-3.12 (m, 2H), 3.04 (d, J=14.6 Hz, 3H), 2.80 (t, J=6.7 Hz, 2H), 2.31 (d, J=11.9 Hz, 1H), 1.25 (d, J=6.4 Hz, 3H), 1.05 (s, 1H), 0.65 (s, 2H), 0.39 (d, J=29.5 Hz, 2H).

Example 322. Preparation of (S)-1-(5-((3-methyl-4-((1-methylcyclobutyl)methyl)piperazin-1-yl)methyl)pyrazolo[1,5-a]pyridin-3-yl)dihydropyrimidine-2,4(1H,3H)-dione

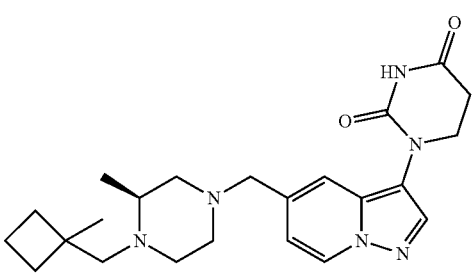

Prepared using the method of Example 192 wherein 1-methylcyclobutane-1-carbaldehyde was used in place of cyclohexanecarbaldehyde in step 3. LCMS [M+H]+: 425.2. ¹H NMR (500 MHz, DMSO) δ 10.47 (s, 1H), 8.64 (d, J=7.2 Hz, 1H), 8.05 (s, 1H), 7.51 (s, 1H), 6.91 (d, J=7.2 Hz, 1H), 3.79 (t, J=6.7 Hz, 6H), 2.96 (s, 6H), 2.80 (t, J=6.7 Hz, 3H), 2.10 (d, J=13.4 Hz, 1H), 2.01 (d, J=9.1 Hz, 1H), 1.88 (s, 1H), 1.84-1.71 (m, 2H), 1.67 (s, 1H), 1.27 (s, 6H).

Example 323. Preparation of 1-(5-(((S)-3-methyl-4-(((1 r,4S)-4-(trifluoromethyl)cyclohexyl)methyl)piperazin-1-yl)methyl)pyrazolo[1,5-a]pyridin-3-yl)dihydropyrimidine-2,4(1H,3H)-dione

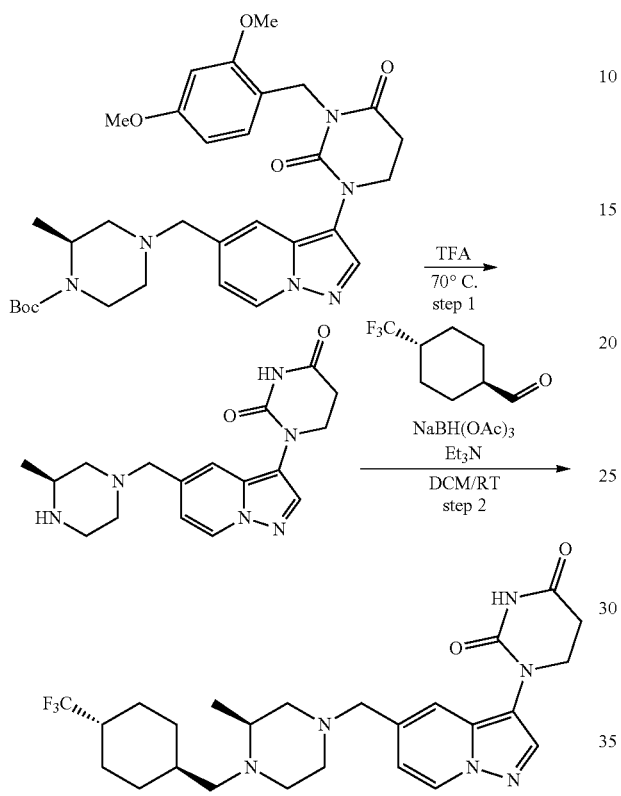

Step 1. (S)-1-(5-((3-methylpiperazin-1-yl)methyl)pyrazolo[1,5-a]pyridin-3-yl)dihydropyrimidine-2,4(1H,3H)-dione TFA (5 mL) was added to tert-butyl (S)-4-((3-(3-(2,4-dimethoxybenzyl)-2,4-dioxotetrahydropyrimidin-1(2H)-yl)pyrazolo[1,5-a]pyridin-5-yl)methyl)-2-methylpiperazine-1-carboxylate (0.24 g, 0.40 mmol). The mixture was heated in a sealed vial at 70° C. for 2 h. The mixture was then cooled to rt and, concentrated and azeotropically dried with toluene to provide crude product (0.3 g) which was used without further purification. LCMS [M+H]$^+$: 343.9.

Step 2. 1-(5-(((S)-3-methyl-4-(((1r,4S)-4-(trifluoromethyl)cyclohexyl)methyl)piperazin-1-yl)methyl)pyrazolo[1,5-a]pyridin-3-yl)dihydropyrimidine-2,4(1H,3H)-dione (1r,4r)-4-(trifluoromethyl)cyclohexane-1-carbaldehyde (0.126 g, 0.70 mmol) and triethylamine (0.14 mL, 1.05 mmol) were added to a solution of (S)-1-(5-((3-methylpiperazin-1-yl)methyl)pyrazolo[1,5-a]pyridin-3-yl)dihydropyrimidine-2,4(1H,3H)-dione (0.12 g, 0.35 mmol) in DCM (4 mL). The reaction mixture was stirred at rt for 90 min and then sodium triacetoxyborohydride (0.148 g, 0.70 mmol) was added. The reaction mixture was stirred at rt for 3 h and then quenched with a solution of saturated aqueous NaHCO$_3$ and extracted three times with DCM. The combined organic extracts were washed with brine, dried over Na$_2$SO$_4$, filtered and concentrated. The residue was dissolved in DMSO, filtered through a 1 micron filter and purified by reverse phase HPLC using ACN/Water/0.1% formic acid. The fractions containing the product were combined, frozen and lyophilized to afford a formate salt of 1-(5-(((S)-3-methyl-4-(((1 r,4S)-4-(trifluoromethyl)cyclohexyl)methyl)piperazin-1-yl)methyl)pyrazolo[1,5-a]pyridin-3-yl)dihydropyrimidine-2,4(1H,3H)-dione. LCMS [M+H]$^+$: 507.3. $^1$H NMR (400 MHz, cd3od) δ 8.46 (d, J=7.3 Hz, 1H), 8.03 (s, 1H), 7.51 (s, 1H), 6.99 (dd, J=7.1, 1.9 Hz, 1H), 3.90 (t, J=6.7 Hz, 2H), 3.70-3.59 (m, 2H), 3.38 (s, 1H), 3.21 (q, J=7.4 Hz, 2H), 3.04-2.95 (m, 1H), 2.89 (t, J=6.7 Hz, 3H), 2.60 (s, 2H), 2.37 (s, 1H), 2.15 (dd, J=23.1, 8.1 Hz, 1H), 1.98 (d, J=12.3 Hz, 2H), 1.86 (d, J=13.1 Hz, 1H), 1.72 (s, 1H), 1.43-1.23 (m, 7H), 1.10 (dt, J=21.2, 11.5 Hz, 2H). NH proton not observed due to solvent exchange.

Example 324. Preparation of 1-(5-(((3S)-3-methyl-4-(oxetan-2-ylmethyl)piperazin-1-yl)methyl)pyrazolo[1,5-a]pyridin-3-yl)dihydropyrimidine-2,4(1H,3H)-dione

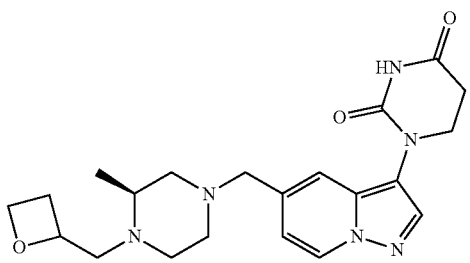

Prepared using the method of Example 323 wherein oxetane-2-carbaldehyde was used in place of (1r,4r)-4-(trifluoromethyl)cyclohexane-1-carbaldehyde in step 2. LCMS [M+H]$^+$: 413.0. $^1$H NMR (400 MHz, MeOD) δ 8.47 (dd, J=7.2, 0.9 Hz, 1H), 8.03 (s, 1H), 7.50 (s, 1H), 6.98 (dd, J=7.2, 1.9 Hz, 1H), 5.18 (q, J=9.2 Hz, 1H), 4.76-4.56 (m, 2H), 3.90 (t, J=6.8 Hz, 2H), 3.81-3.61 (m, 3H), 3.57-3.37 (m, 3H), 3.24-3.10 (m, 2H), 3.08-2.78 (m, 4H), 2.66-2.29 (m, 3H), 1.41-1.26 (m, 3H). NH proton not observed due to solvent exchange.

Example 325. Preparation of (S)-1-(5-((4-((2-oxaspiro[3.3]heptan-6-yl)methyl)-3-methylpiperazin-1-yl)methyl)pyrazolo[1,5-a]pyridin-3-yl)dihydropyrimidine-2,4(1H,3H)-dione

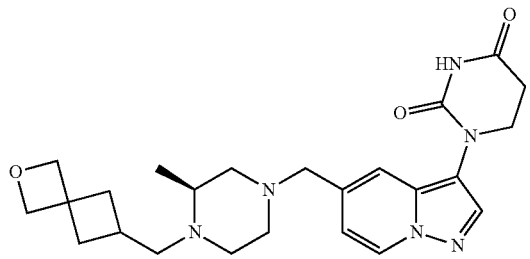

Prepared using the method of Example 323 wherein 2-oxaspiro[3.3]heptane-6-carbaldehyde was used in place of (1r,4r)-4-(trifluoromethyl)cyclohexane-1-carbaldehyde in step 2. LCMS [M+H]$^+$: 453.2. $^1$H NMR (300 MHz, cd3od) δ 8.47 (s, 1H), 8.45 (s, 1H), 8.03 (s, 1H), 7.49 (s, 1H), 6.98

(dd, J=7.2, 1.9 Hz, 1H), 4.75 (s, 2H), 4.57 (s, 2H), 3.89 (t, J=6.7 Hz, 2H), 3.67-3.56 (m, 2H), 3.21 (d, J=24.5 Hz, 2H), 2.89 (t, J=6.5 Hz, 6H), 2.56-2.41 (m, 4H), 2.38-2.21 (m, 1H), 2.04 (d, J=3.8 Hz, 2H), 1.76 (td, J=10.7, 5.4 Hz, 1H), 1.27 (d, J=6.5 Hz, 3H).

Example 326. Preparation of (S)-1-(5-((4-((6,6-difluorospiro[3.3]heptan-2-yl)methyl)-3-methylpiperazin-1-yl)methyl)pyrazolo[1,5-a]pyridin-3-yl)dihydropyrimidine-2,4(1H,3H)-dione

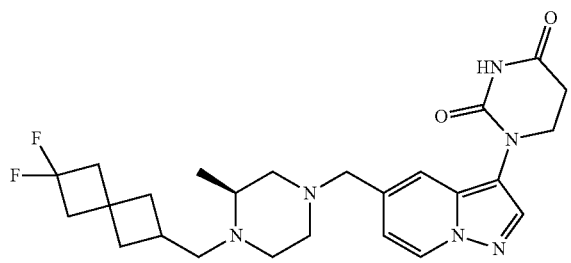

Prepared using the method of Example 323 wherein 6,6-difluorospiro[3.3]heptane-2-carbaldehyde was used in place of (1r,4r)-4-(trifluoromethyl)cyclohexane-1-carbaldehyde in step 2. LCMS [M+H]$^+$: 487.3. $^1$H NMR (400 MHz, MeOD) δ 8.45 (dd, J=7.2, 1.0 Hz, 1H), 8.02 (d, J=1.5 Hz, 1H), 7.49 (d, J=1.9 Hz, 1H), 6.98 (dt, J=7.3, 1.9 Hz, 1H), 3.89 (t, J=6.8 Hz, 2H), 3.68 (dd, J=5.5, 4.0 Hz, 1H), 3.63-3.52 (m, 2H), 3.22-3.11 (m, 2H), 2.93-2.75 (m, 6H), 2.75-2.55 (m, 3H), 2.55-2.37 (m, 3H), 2.35-1.93 (m, 5H), 1.33-1.17 (m, 3H). NH proton not observed due to solvent exchange.

Example 327. Preparation of (S)-1-(5-((4-(2,2-difluoroethyl)-3-methylpiperazin-1-yl)methyl)pyrazolo[1,5-a]pyridin-3-yl)dihydropyrimidine-2,4(1H,3H)-dione

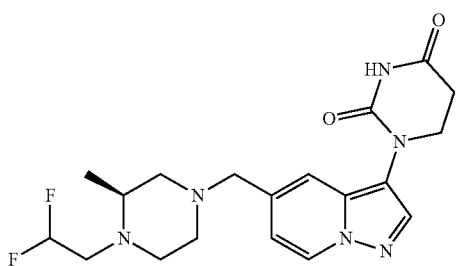

Prepared from (S)-3-(2,4-dimethoxybenzyl)-1-(5-((3-methylpiperazin-1-yl)methyl)pyrazolo[1,5-a]pyridin-3-yl)dihydropyrimidine-2,4(1H,3H)-dione trifluoroacetate by the method of Example 156, steps 3-4 using 2,2-difluoroethyl trifluoromethanesulfonate in step 3. LCMS [M+H]$^+$: 407.0. $^1$H NMR (400 MHz, MeOD) δ 8.47 (dd, J=7.2, 0.9 Hz, 1H), 8.02 (s, 1H), 7.53 (dd, J=1.9, 1.0 Hz, 1H), 7.00 (dd, J=7.2, 1.8 Hz, 1H), 5.93 (tt, J=56.0, 4.2 Hz, 1H), 3.90 (t, J=6.8 Hz, 2H), 3.72-3.62 (m, 2H), 3.15-2.95 (m, 2H), 2.89 (t, J=6.7 Hz, 2H), 2.82 (ddd, J=9.4, 6.8, 3.7 Hz, 2H), 2.76-2.58 (m, 3H), 2.44 (td, J=10.9, 2.8 Hz, 1H), 2.15 (dd, J=12.0, 8.8 Hz, 1H), 1.07 (d, J=6.2 Hz, 3H). NH proton not observed due to solvent exchange.

Example 328. Preparation of (S)-1-(5-((4-(2,2-difluoro-3-methoxypropyl)-3-methylpiperazin-1-yl)methyl)pyrazolo[1,5-a]pyridin-3-yl)dihydropyrimidine-2,4(1H,3H)-dione

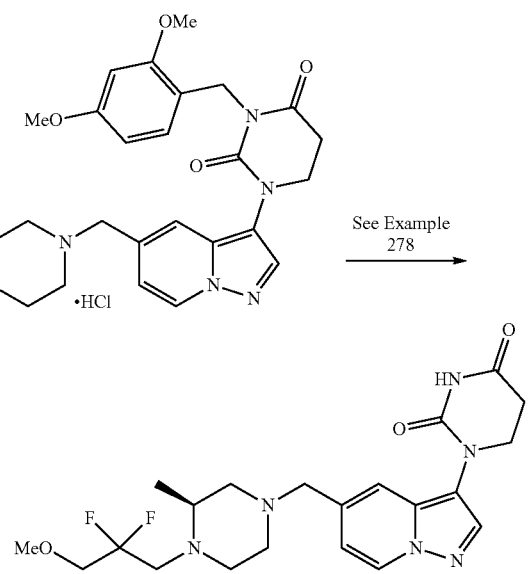

Prepared by the method of Example 278 wherein (S)-3-(2,4-dimethoxybenzyl)-1-(5-((3-methylpiperazin-1-yl)methyl)pyrazolo[1,5-a]pyridin-3-yl)dihydropyrimidine-2,4(1H,3H)-dione hydrochloride was used in place of 3-(2,4-dimethoxybenzyl)-1-(5-(((2S,4R)-2-methylpiperidin-4-yl)methyl)pyrazolo[1,5-a]pyridin-3-yl)dihydropyrimidine-2,4(1H,3H)-dione hydrochloride in step 1. LCMS [M+H]$^+$: 451.1. $^1$H NMR (300 MHz, METHANOL-d4) b ppm 8.46 (d, J=7.3 Hz, 1H), 8.01 (s, 1H), 7.51 (s, 1H), 6.99 (br d, J=6.9 Hz, 1H), 3.89 (t, J=6.8 Hz, 2H), 3.73-3.53 (m, 3H) 3.39 (s, 3H), 3.18-2.99 (m, 2H), 2.88 (t, J=6.76 Hz, 2H), 2.38-2.80 (m, 7H), 2.09-2.24 (m, 1H), 1.05 (d, J=6.3 Hz, 3H). NH proton not observed due to solvent exchange.

Example 329. Preparation of (S)-1-(5-((4-cyclobutyl-3-methylpiperazin-1-yl)methyl)pyrazolo[1,5-a]pyridin-3-yl)dihydropyrimidine-2,4(1H,3H)-dione

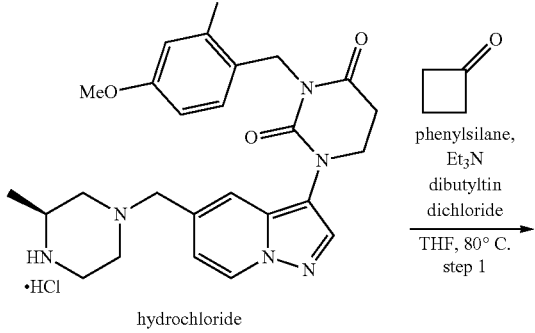

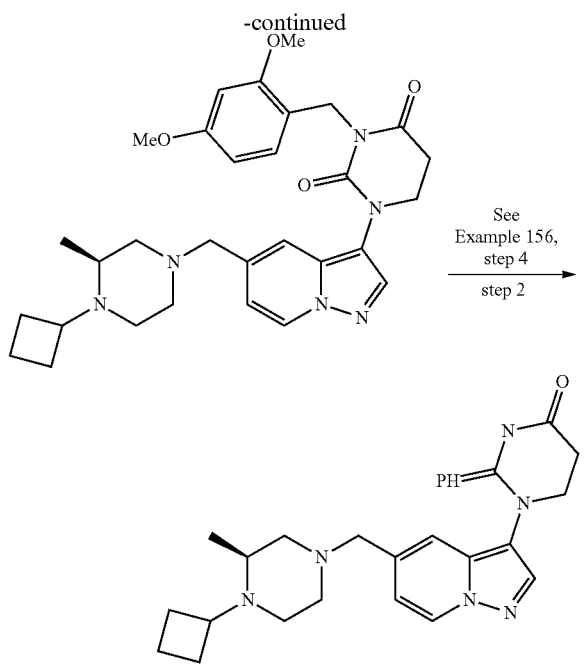

Step 1. (S)-1-(5-((4-cyclobutyl-3-methylpiperazin-1-yl)methyl)pyrazolo[1,5-a]pyridin-3-yl)-3-(2,4-dimethoxybenzyl)dihydropyrimidine-2,4(1H,3H)-dione To a solution of (S)-3-(2,4-dimethoxybenzyl)-1-(5-((3-methylpiperazin-1-yl)methyl)pyrazolo[1,5-a]pyridin-3-yl)dihydropyrimidine-2,4(1H,3H)-dione hydrochloride (50 mg, 0.094 mmol) in THF (2 mL) was added cyclobutanone (20 mg, 0.28 mmol), dibutyltin dichloride (86 mg, 0.28 mmol), and triethylamine (48 mg, 0.47 mmol). The mixture was stirred at rt for 1 h and then phenylsilane (20 mg, 0.19 mmol) was added. The reaction was stirred in a capped vial at 80° C. for 12 h. The reaction was cooled to rt, diluted with DCM and washed sequentially with water and brine. The organic layer was dried over Na$_2$SO$_4$, filtered and concentrated to give crude (S)-1-(5-((4-cyclobutyl-3-methylpiperazin-1-yl)methyl)pyrazolo[1,5-a]pyridin-3-yl)-3-(2,4-dimethoxybenzyl)dihydropyrimidine-2,4(1H,3H)-dione. The crude product was used in the next step without any other purification. LCMS [M+H]$^+$: 547.6.

Step 2: (S)-1-(5-((4-cyclobutyl-3-methylpiperazin-1-yl)methyl)pyrazolo[1,5-a]pyridin-3-yl)dihydropyrimidine-2,4(1H,3H)-dione (Example 329) was prepared using the method of Example 156, step 4, wherein (S)-1-(5-((4-cyclobutyl-3-methylpiperazin-1-yl)methyl)pyrazolo[1,5-a]pyridin-3-yl)-3-(2,4-dimethoxybenzyl)dihydropyrimidine-2,4(1H,3H)-dione was used in place of 1-(5-((4-(cyclohexylmethyl)piperazin-1-yl)methyl)pyrazolo[1,5-a]pyridin-3-yl)-3-(2,4-dimethoxybenzyl)dihydropyrimidine-2,4(1H,3H)-dione. LCMS [M+H]$^+$: 397.2. $^1$H NMR (500 MHz, DMSO) δ 10.47 (s, 1H), 8.64 (d, J=7.1 Hz, 1H), 8.05 (s, 1H), 7.50 (s, 1H), 6.90 (d, J=7.0 Hz, 1H), 3.79 (t, J=6.7 Hz, 6H), 3.12 (d, J=33.9 Hz, 4H), 3.03-2.85 (m, 2H), 2.79 (t, J=6.7 Hz, 2H), 2.17 (d, J=8.0 Hz, 4H), 1.83-1.63 (m, 2H), 1.26 (dd, J=31.8, 6.6 Hz, 3H).

The compounds in the following table were prepared by the method of Example 329, using the appropriate commercially available ketone in step 1.

| Example No. | Structure | Mass [M + H]$^+$ | $^1$H NMR |
|---|---|---|---|
| 330 | (S)-1-(5-((3-methyl-4-(tetrahydro-2H-pyran-4-yl)piperazin-1-yl)methyl)pyrazolo[1,5-a]pyridin-3-yl)dihydropyrimidine-2,4(1H,3H)-dione | 427.2 | (400 MHZ, MeOD) δ 8.46 (dd, J = 7.2, 0.9 Hz, 1H), 8.02 (s, 1H), 7.50 (dd, J = 1.9, 0.9 Hz, 1H), 6.99 (dd, J = 7.2, 1.8 Hz, 1H), 4.04 (d, J = 11.3 Hz, 2H), 3.90 (t, J = 6.8 Hz, 2H), 3.71 - 3.54 (m, 3H), 3.52-3.39 (m, 4H), 3.25-3.12 (m, 4H), 2.89 (t, J = 6.8 Hz, 2H), 2.81 (s, 1H), 2.03 (d, J = 6.1 Hz, 1H), 1.83 (d, J = 25.3 Hz, 2H), 1.71-1.58 (m, 1H), 1.36-1.27 (m, 3H). NH proton not observed due to solvent exchange. |
| 331 | 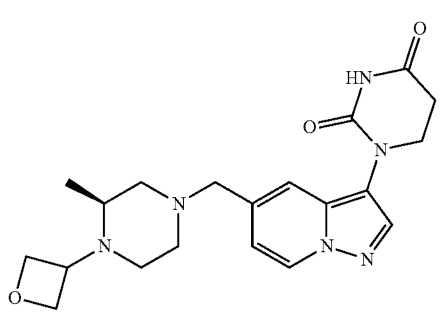 | 399.0 | (400 MHZ, MeOD) δ 8.45 (dd, J = 7.2, 1.0 Hz, 1H), 8.25 (s, 1H), 8.01 (s, 1H), 7.51 (dd, J = 1.9, 0.9 Hz, 1H), 6.99 (dd, J = 7.2, 1.8 Hz, 1H), 4.69 (dd, J = 12.8, 6.7 Hz, 3H), 4.61 (dd, J = 7.4, 6.3 Hz, 1H), 3.86 (dt, J = 21.3, 6.9 Hz, 3H), 3.68 - 3.56 (m, 2H), 2.89 (t, J = 6.8 Hz, 2H), 2.86-2.68 (m, 3H), 2.45 (dd, J = 25.5, 14.8 Hz, 2H), 2.32 - 2.12 (m, 2H), 0.92 (d, J = 6.5 Hz, 3H). |

| Example No. | Structure | Mass [M + H]⁺ | ¹H NMR |
|---|---|---|---|
| | (S)-1-(5-((3-methyl-4-(oxetan-3-yl)piperazin-1-yl)methyl)pyrazolo[1,5-a]pyridin-3-yl)dihydropyrimidine-2,4(1H,3H)-dione | | |
| 332 | (S)-1-(5-((3-methyl-4-(2-oxaspiro[3.3]heptan-6-yl)piperazin-1-yl)methyl)pyrazolo[1,5-a]pyridin 3-yl)dihydropyrimidine-2,4(1H,3H)-dione | 439.2 | (400 MHZ, MeOD) δ 8.48 (dd, J = 7.2, 0.9 Hz, 1H), 8.03 (s, 1H), 7.52 (s, 1H), 7.01 (dd, J = 7.2, 1.9 Hz, 1H), 3.90 (t, J = 6.8 Hz, 3H), 3.79-3.51 (m, 9H), 3.16-3.07 (m, 1H), 2.99 - 2.84 (m, 3H), 2.72-2.57 (m, 2H), 2.17-2.00 (m, 4H), 1.57 (d, J = 6.7 Hz, 3H). NH proton not observed due to solvent exchange. |
| 333 | (S)-1-(5-((4-cyclohexyl-3-methylpiperazin-1-yl)methyl)pyrazolo[1,5-a]pyridin-3-yl)dihydropyrimidine-2,4(1H,3H)-dione | 425.2 | (400 MHZ, MeOD) δ 8.46 (d, J = 7.1 Hz, 1H), 8.02 (s, 1H), 7.50 (d, J = 1.7 Hz, 1H), 6.99 (dd, J = 7.1, 1.8 Hz, 1H), 3.89 (t, J = 6.7 Hz, 2H), 3.68 - 3.57 (m, 2H), 3.45 (d, J = 25.8 Hz, 1H), 3.26 (s, 2H), 2.89 (t, J = 6.8 Hz, 4H), 2.41 (d, J = 60.0 Hz, 2H), 1.97 (dd, J = 42.9, 11.3 Hz, 4H), 1.72 (d, J = 13.1 Hz, 1H), 1.57 (d, J = 12.0 Hz, 1H), 1.49-1.12 (m, 8H). NH proton not observed due to solvent exchange. |
| 334 | (S)-1-(5-((4-(4,4-difluorocyclohexyl)-3-methylpiperazin-1-yl)methyl)pyrazolo[1,5-a]pyridin-3-yl)dihydropyrimidine-2,4(1H,3H)-dione | 461.2 | (500 MHZ, DMSO) δ 10.47 (s, 1H), 8.64 (d, J = 7.1 Hz, 1H), 8.05 (s, 1H), 7.50 (s, 1H), 6.91 (d, J = 7.3 Hz, 1H), 3.79 (t, J = 6.8 Hz, 3H), 3.62 (s, 4H), 3.03 (s, 4H), 2.80 (t, J = 6.7 Hz, 3H), 2.34 (s, 1H), 2.09 (t, J = 23.8 Hz, 5H), 1.77 (s, 1H), 1.63 (s, 1H), 1.38 (d, J = 6.6 Hz, 1H), 1.26 (s, 2H). |

| Example No. | Structure | Mass [M + H]+ | 1H NMR |
|---|---|---|---|
| 335 | 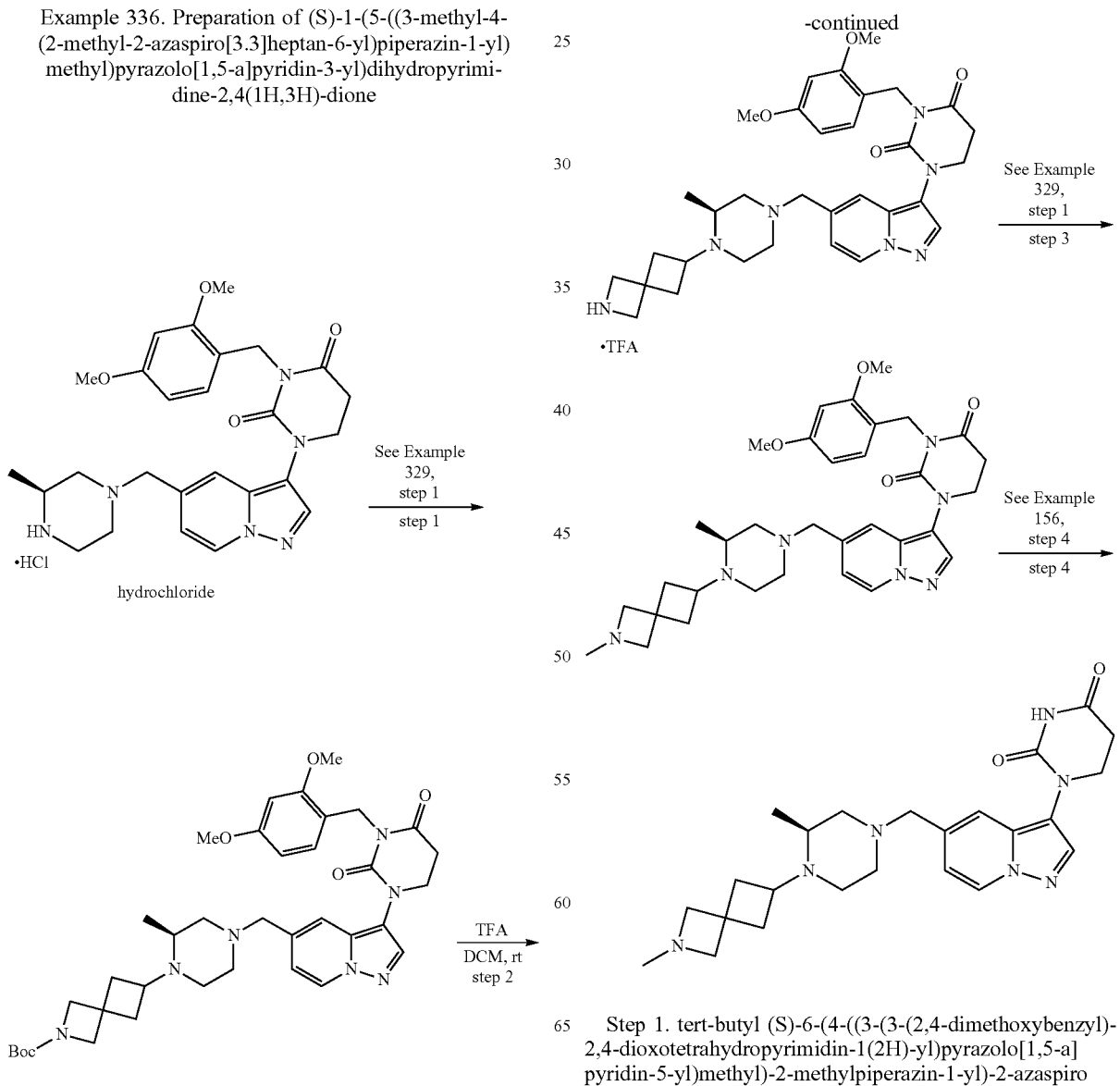

(S)-1-(5-((3-methyl-4-(spiro[3.3]heptan-2-yl)piperazin-1-yl)methyl)pyrazolo[1,5-a]pyridin-3-yl)dihydropyrimidine-2,4(1H,3H)-dione | 437.3 | (400 MHZ, MeOD) δ 8.47-8.44 (m, 1H), 8.02 (s, 1H), 7.49 (s, 1H), 6.98 (dd, J = 7.2, 1.9 Hz, 1H), 3.89 (t, J = 6.8 Hz, 2H), 3.70-3.54 (m, 3H), 3.25 (d, J = 9.0 Hz, 1H), 2.89 (t, J = 6.8 Hz, 5H), 2.41 (ddt, J = 27.4, 12.4, 6.0 Hz, 3H), 2.23 (t, J = 10.1 Hz, 1H), 2.12 (dd, J = 8.8, 6.0 Hz, 3H), 2.07-1.96 (m, 3H), 1.96-1.84 (m, 2H), 1.74-1.55 (m, 1H), 1.32 (d, J = 6.6 Hz, 3H). NH proton not observed due to solvent exchange. |

Example 336. Preparation of (S)-1-(5-((3-methyl-4-(2-methyl-2-azaspiro[3.3]heptan-6-yl)piperazin-1-yl)methyl)pyrazolo[1,5-a]pyridin-3-yl)dihydropyrimidine-2,4(1H,3H)-dione Step 1. tert-butyl (S)-6-(4-((3-(3-(2,4-dimethoxybenzyl)-2,4-dioxotetrahydropyrimidin-1(2H)-yl)pyrazolo[1,5-a]pyridin-5-yl)methyl)-2-methylpiperazin-1-yl)-2-azaspiro

[3.3]heptane-2-carboxylate was prepared using the method of Example 329, step 1, wherein tert-butyl 6-oxo-2-azaspiro[3.3]heptane-2-carboxylate was used in place of cyclobutanone. LCMS [M+H]+: 688.3.

Step 2. (S)-3-(2,4-dimethoxybenzyl)-1-(5-((3-methyl-4-(2-azaspiro[3.3]heptan-6-yl)piperazin-1-yl)methyl)pyrazolo[1,5-a]pyridin-3-yl)dihydropyrimidine-2,4(1H,3H)-dione trifluoroacetate TFA (4 mL) was added to a solution of tert-butyl (S)-6-(4-((3-(3-(2,4-dimethoxybenzyl)-2,4-dioxotetrahydropyrimidin-1(2H)-yl)pyrazolo[1,5-a]pyridin-5-yl)methyl)-2-methylpiperazin-1-yl)-2-azaspiro[3.3]heptane-2-carboxylate (300 mg, 0.43 mmol) in DCM (2 mL) at rt. The reaction was stirred at rt for 2 h and then concentrated. The residue was azeotropically dried with toluene to give crude (S)-3-(2,4-dimethoxybenzyl)-1-(5-((3-methyl-4-(2-azaspiro[3.3]heptan-6-yl)piperazin-1-yl)methyl)pyrazolo[1,5-a]pyridin-3-yl)dihydropyrimidine-2,4(1H,3H)-dione trifluoroacetate which was used without further purification.

Step 3. (S)-3-(2,4-dimethoxybenzyl)-1-(5-((3-methyl-4-(2-methyl-2-azaspiro[3.3]heptan-6-yl)piperazin-1-yl)methyl)pyrazolo[1,5-a]pyridin-3-yl)dihydropyrimidine-2,4(1H,3H)-dione was prepared using the method of Example 329, step 1, wherein paraformaldehyde was used in place of cyclobutanone and triethylamine was omitted. LCMS [M+H]+: 602.3.

Step 4. (S)-1-(5-(((3-methyl-4-(2-methyl-2-azaspiro[3.3]heptan-6-yl)piperazin-1-yl)methyl)pyrazolo[1,5-a]pyridin-3-yl)dihydropyrimidine-2,4(1H,3H)-dione was prepared from (S)-3-(2,4-dimethoxybenzyl)-1-(5-((3-methyl-4-(2-methyl-2-azaspiro[3.3]heptan-6-yl)piperazin-1-yl)methyl)pyrazolo[1,5-a]pyridin-3-yl)dihydropyrimidine-2,4(1H,3H)-dione by the method of Example 156, step 4. LCMS [M+H]+: 452.2. $^1$H NMR (400 MHz, MeOD) δ 8.44 (d, J=7.2 Hz, 1H), 8.01 (s, 1H), 7.48 (s, 1H), 6.98 (dd, J=7.1, 1.8 Hz, 1H), 4.16 (s, 2H), 4.03 (s, 2H), 3.89 (t, J=6.8 Hz, 2H), 3.16-3.09 (m, 1H), 2.93-2.79 (m, 5H), 2.70 (s, 2H), 2.60-2.17 (m, 7H), 2.00 (s, 1H), 1.68 (s, 1H), 1.48-1.37 (m, 2H), 1.09 (d, J=6.4 Hz, 3H). NH proton not observed due to solvent exchange.

Example 337. Preparation of (S)-1-(5-((3-methyl-4-(2-(methylsulfonyl)-2-azaspiro[3.3]heptan-6-yl)piperazin-1-yl)methyl)pyrazolo[1,5-a]pyridin-3-yl)dihydropyrimidine-2,4(1H,3H)-dione

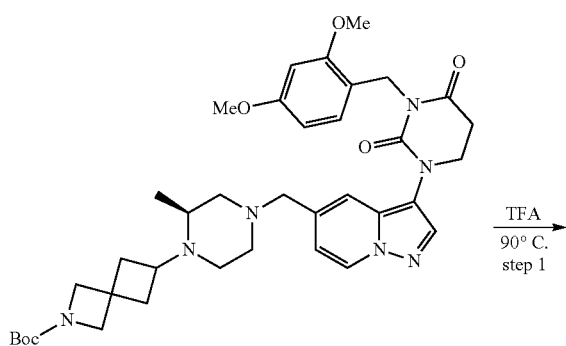

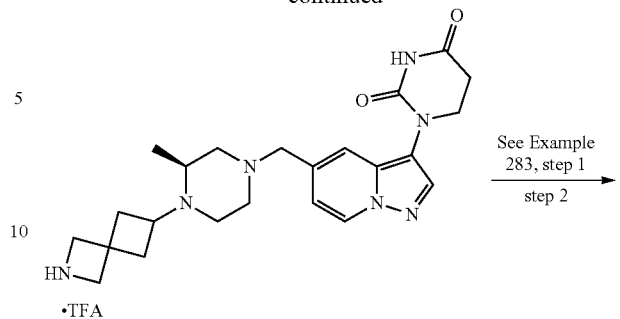

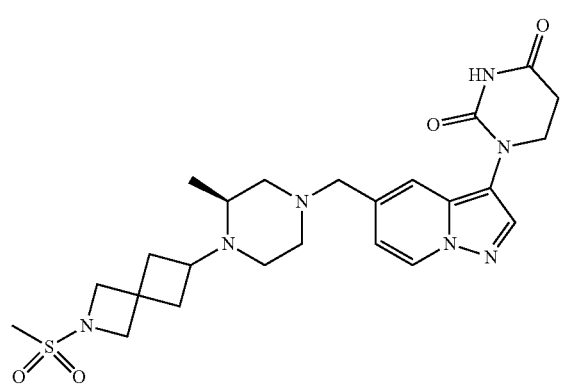

Step 1. (S)-1-(5-(((3-methyl-4-(2-azaspiro[3.3]heptan-6-yl)piperazin-1-yl)methyl)pyrazolo[1,5-a]pyridin-3-yl)dihydropyrimidine-2,4(1H,3H)-dione trifluoroacetate TFA (5 mL) was added to tert-butyl (S)-6-(4-((3-(3-(2,4-dimethoxybenzyl)-2,4-dioxotetrahydropyrimidin-1(2H)-yl)pyrazolo[1,5-a]pyridin-5-yl)methyl)-2-methylpiperazin-1-yl)-2-azaspiro[3.3]heptane-2-carboxylate (152 mg, 0.22 mmol). The reaction was stirred at 90° C. for 16 h and then concentrated. The residue was azeotropically dried with toluene to give crude (S)-1-(5-(((3-methyl-4-(2-azaspiro[3.3]heptan-6-yl)piperazin-1-yl)methyl)pyrazolo[1,5-a]pyridin-3-yl)dihydropyrimidine-2,4(1H,3H)-dione trifluoroacetate which was used without further purification.

Step 2: (S)-1-(5-(((3-methyl-4-(2-(methylsulfonyl)-2-azaspiro[3.3]heptan-6-yl)piperazin-1-yl)methyl)pyrazolo[1,5-a]pyridin-3-yl)dihydropyrimidine-2,4(1H,3H)-dione was prepared from (S)-1-(5-(((3-methyl-4-(2-azaspiro[3.3]heptan-6-yl)piperazin-1-yl)methyl)pyrazolo[1,5-a]pyridin-3-yl)dihydropyrimidine-2,4(1H,3H)-dione trifluoroacetate by the method of Example 283, step 1 wherein methanesulfonyl chloride was used in place of ethylsulfonyl chloride. LCMS [M+H]+: 516.3. $^1$H NMR (400 MHz, DMSO) δ 10.42 (s, 1H), 8.60-8.49 (m, 1H), 8.13 (s, 1H), 8.00 (s, 1H), 7.43 (s, 1H), 6.86 (dd, J=7.2, 1.8 Hz, 1H), 3.88 (s, 2H), 3.80-3.71 (m, 4H), 3.45 (q, J=13.7 Hz, 1H), 2.93 (s, 4H), 2.77 (t, J=6.7 Hz, 2H), 2.60 (s, 1H), 2.41 (s, 1H), 2.37-2.28 (m, 3H), 2.28-1.92 (m, 6H), 0.94 (d, J=6.3 Hz, 3H).

Example 338. Preparation of 1-(5-((4-cyclohexylpiperazin-1-yl)methyl)pyrazolo[1,5-a]pyridin-3-yl)dihydropyrimidine-2,4(1H,3H)-dione

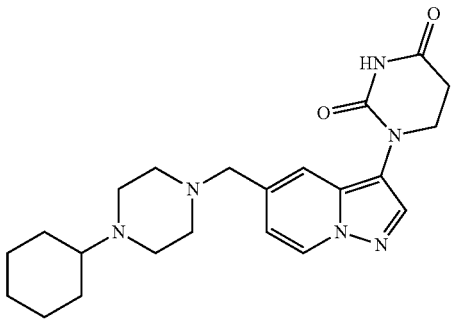

Prepared using the method of Example 329 wherein 3-(2,4-dimethoxybenzyl)-1-(5-(piperazin-1-ylmethyl)pyrazolo[1,5-a]pyridin-3-yl)dihydropyrimidine-2,4(1H,3H)-dione was used in place of (S)-3-(2,4-dimethoxybenzyl)-1-(5-((3-methylpiperazin-1-yl)methyl)pyrazolo[1,5-a]pyridin-3-yl)dihydropyrimidine-2,4(1H,3H)-dione and cyclohexanone was used in place of cyclobutanone in step 1. LCMS [M+H]$^+$: 411.2. $^1$H NMR (300 MHz, CD$_3$OD) δ 8.46 (d, J=7.1 Hz, 1H), 8.03 (s, 1H), 7.50 (s, 1H), 6.99 (dd, J=7.2, 1.8 Hz, 1H), 3.89 (t, J=6.8 Hz, 2H), 3.67 (s, 2H), 3.11 (s, 2H), 2.89 (t, J=6.8 Hz, 8H), 2.12 (d, J=9.2 Hz, 2H), 1.94 (d, J=10.7 Hz, 2H), 1.72 (d, J=12.7 Hz, 1H), 1.53-1.15 (m, 6H). NH proton not observed due to solvent exchange.

Example 339. Preparation of (S)-1-(5-((4-(ethylsulfonyl)-3-methylpiperazin-1-yl)methyl)pyrazolo[1,5-a]pyridin-3-yl)dihydropyrimidine-2,4(1H,3H)-dione

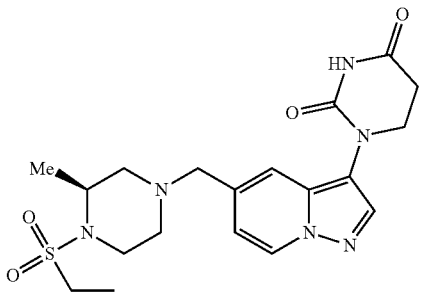

Prepared from (S)-3-(2,4-dimethoxybenzyl)-1-(5-((3-methylpiperazin-1-yl)methyl)pyrazolo[1,5-a]pyridin-3-yl)dihydropyrimidine-2,4(1H,3H)-dione by the method of Example 283. LCMS [M+H]$^+$: 435.1. $^1$H NMR (500 MHz, DMSO) δ 10.53 (s, 1H), 8.75 (d, J=7.2 Hz, 1H), 8.14 (s, 1H), 7.71 (s, 1H), 7.01 (d, J=7.2 Hz, 1H), 4.27 (d, J=76.7 Hz, 5H), 3.90-3.77 (m, 2H), 3.71 (s, 1H), 3.35 (s, 2H), 3.17 (tq, J=14.3, 7.1 Hz, 3H), 2.80 (dd, J=7.4, 6.1 Hz, 2H), 1.33 (d, J=7.0 Hz, 3H), 1.21 (t, J=7.3 Hz, 3H).

Example 340. Preparation of (S)-1-(5-((4-(cyclopropanecarbonyl)-3-methylpiperazin-1-yl)methyl)pyrazolo[1,5-a]pyridin-3-yl)dihydropyrimidine-2,4(1H,3H)-dione

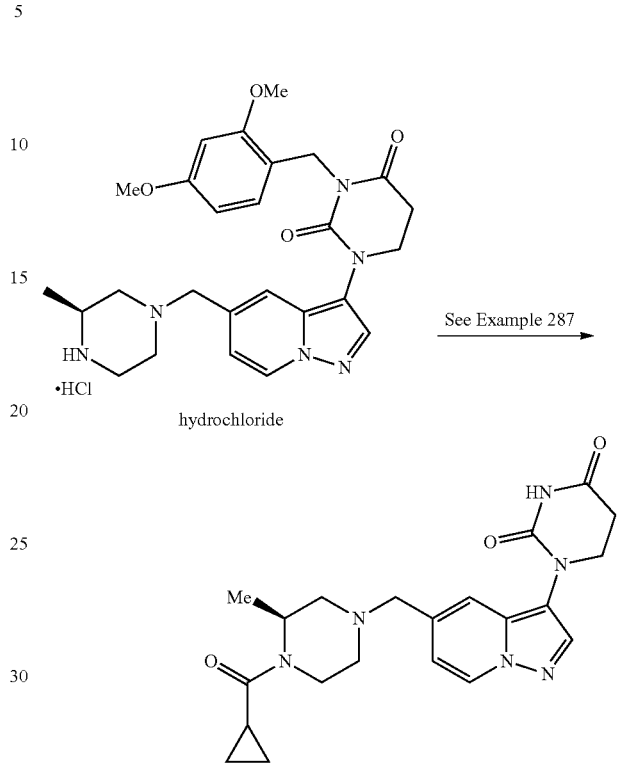

Prepared by the method of Example 287 wherein (S)-3-(2,4-dimethoxybenzyl)-1-(5-((3-methylpiperazin-1-yl)methyl)pyrazolo[1,5-a]pyridin-3-yl)dihydropyrimidine-2,4(1H,3H)-dione was used in place of 3-(2,4-dimethoxybenzyl)-1-(5-(((2S,4R)-2-methylpiperidin-4-yl)methyl)pyrazolo[1,5-a]pyridin-3-yl)dihydropyrimidine-2,4(1H,3H)-dione in step 1. LCMS [M+H]$^+$: 411.1. $^1$H NMR (500 MHz, DMSO) δ 10.54 (s, 1H), 8.77 (d, J=7.2 Hz, 1H), 8.15 (s, 1H), 7.73 (s, 1H), 7.10-6.93 (m, 1H), 4.80 (s, 1H), 4.37 (s, 2H), 3.84 (ddd, J=10.1, 8.3, 5.0 Hz, 4H), 3.37 (s, 2H), 3.01 (s, 1H), 2.80 (t, J=6.7 Hz, 2H), 1.97 (t, J=6.4 Hz, 1H), 1.35 (s, 1H), 1.19 (d, J=10.9 Hz, 2H), 0.75 (s, 5H).

Example 341. Preparation of (S)-1-(5-((4-isobutyryl-3-methylpiperazin-1-yl)methyl)pyrazolo[1,5-a]pyridin-3-yl)dihydropyrimidine-2,4(1H,3H)-dione

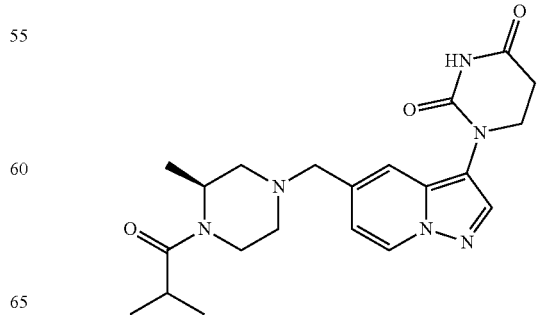

Prepared using the method of Example 340 wherein isobutyric acid was used in place of cyclopropanecarboxylic acid in step 1. LCMS [M+H]+: 413.2. 1H NMR (500 MHz, DMSO) δ 10.54 (s, 1H), 8.77 (d, J=7.2 Hz, 1H), 8.15 (s, 1H), 7.73 (s, 1H), 7.02 (d, J=7.3 Hz, 1H), 4.82 (s, 2H), 4.06 (s, 2H), 3.92-3.73 (m, 3H), 3.39 (d, J=41.9 Hz, 2H), 2.83 (dt, J=28.3, 6.7 Hz, 3H), 2.56 (s, 1H), 1.34 (d, J=6.9 Hz, 1H), 1.18 (d, J=7.1 Hz, 2H), 0.99 (dd, J=24.2, 6.9 Hz, 7H).

Example 342. Preparation of (S)-1-(5-((4-(cyclohexanecarbonyl)-3-methylpiperazin-1-yl)methyl)pyrazolo[1,5-a]pyridin-3-yl)dihydropyrimidine-2,4(1H,3H)-dione

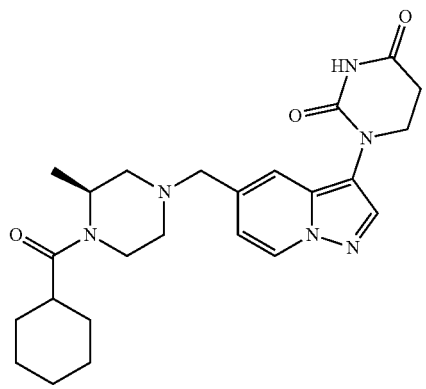

Prepared using the method of Example 340 wherein cyclohexanecarboxylic acid was used in place of cyclopropanecarboxylic acid in step 1. LCMS [M+H]+: 453.1. 1H NMR (500 MHz, DMSO) δ 10.54 (s, 1H), 8.77 (d, J=7.2 Hz, 1H), 8.15 (s, 1H), 7.72 (s, 1H), 7.02 (d, J=7.2 Hz, 1H), 4.81 (s, 1H), 4.41 (d, J=69.3 Hz, 3H), 3.82 (dd, J=7.0, 5.0 Hz, 4H), 3.40 (dd, J=35.2, 21.7 Hz, 3H), 2.94 (d, J=30.7 Hz, 2H), 2.80 (dd, J=7.3, 6.1 Hz, 2H), 1.71 (d, J=13.2 Hz, 2H), 1.64 (d, J=14.5 Hz, 2H), 1.31 (td, J=24.7, 14.1 Hz, 5H), 1.17 (d, J=7.3 Hz, 3H).

Example 343. Preparation of (S)-1-(5-((4-(cyclopentanecarbonyl)-3-methylpiperazin-1-yl)methyl)pyrazolo[1,5-a]pyridin-3-yl)dihydropyrimidine-2,4(1H,3H)-dione

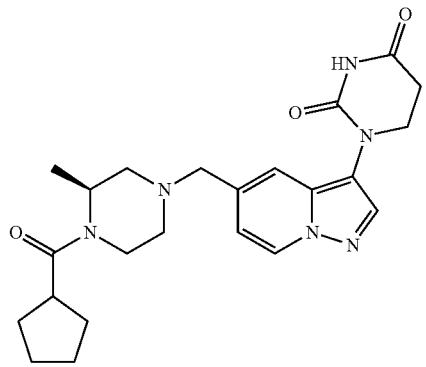

Prepared using the method of Example 340 wherein cyclopentanecarboxylic acid was used in place of cyclopropanecarboxylic acid in step 1. LCMS [M+H]+: 439.1. 1H NMR (500 MHz, DMSO) δ 10.54 (s, 1H), 8.77 (s, 1H), 8.15 (s, 1H), 7.72 (s, 1H), 7.02 (s, 1H), 4.81 (s, 1H), 4.37 (s, 4H), 3.87-3.58 (m, 2H), 3.39 (d, J=14.3 Hz, 3H), 3.09-2.86 (m, 2H), 2.80 (t, J=6.7 Hz, 2H), 1.75 (d, J=21.2 Hz, 3H), 1.56 (d, J=33.7 Hz, 5H), 1.33 (d, J=6.9 Hz, 1H), 1.18 (d, J=6.9 Hz, 2H).

Example 344. Preparation of (S)-1-(5-((4-(cyclobutanecarbonyl)-3-methylpiperazin-1-yl)methyl)pyrazolo[1,5-a]pyridin-3-yl)dihydropyrimidine-2,4(1H,3H)-dione

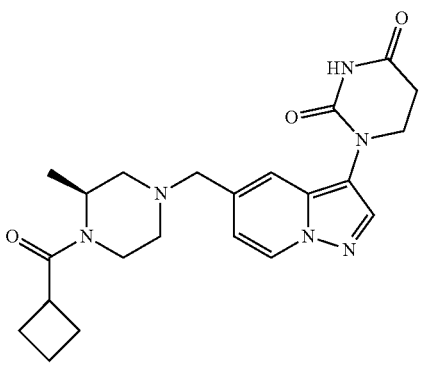

Prepared using the method of Example 340 wherein cyclobutanecarboxylic acid was used in place of cyclopropanecarboxylic acid in step 1. LCMS [M+H]+: 425.1. 1H NMR (500 MHz, DMSO) δ 10.53 (s, 1H), 8.76 (s, 1H), 8.14 (s, 1H), 7.71 (s, 1H), 7.00 (s, 1H), 4.58 (d, J=188.4 Hz, 5H), 3.90-3.72 (m, 3H), 3.50-3.17 (m, 3H), 2.97 (s, 1H), 2.80 (t, J=6.7 Hz, 2H), 2.27-2.01 (m, 4H), 1.91 (p, J=8.7 Hz, 1H), 1.76 (d, J=9.3 Hz, 1H), 1.29 (d, J=6.9 Hz, 1H), 1.18 (d, J=7.1 Hz, 2H).

Example 345. Preparation of 1-(5-(1-(4-isobutylpiperazin-1-yl)ethyl)pyrazolo[1,5-a]pyridin-3-yl)dihydropyrimidine-2,4(1H,3H)-dione

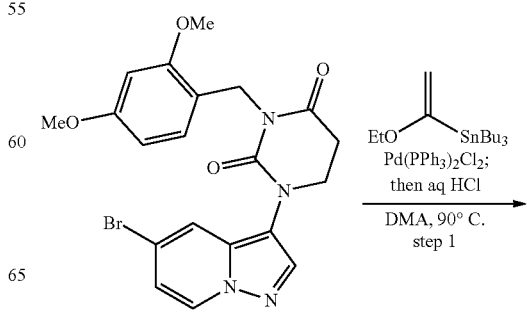

423

-continued

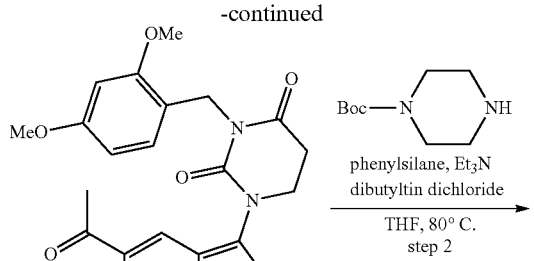

phenylsilane, Et₃N
dibutyltin dichloride
THF, 80° C.
step 2

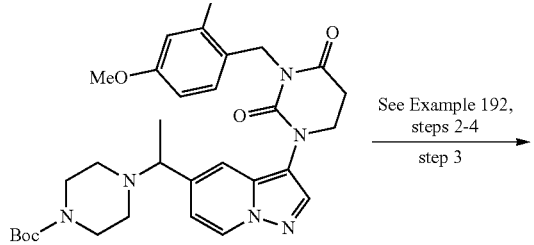

See Example 192,
steps 2-4
step 3

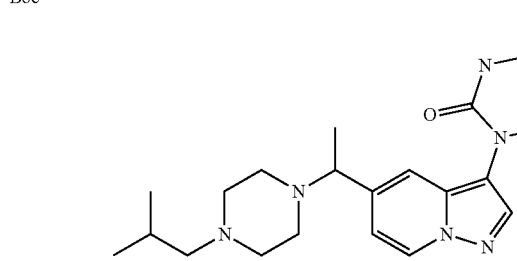

Step 1. 1-(5-acetylpyrazolo[1,5-a]pyridin-3-yl)-3-(2,4-dimethoxybenzyl)dihydropyrimidine-2,4(1H,3H)-dione Tributyl(1-ethoxyvinyl)stannane (757 mg, 2.09 mmol) and Pd(PPh₃)₂Cl₂ (122 mg, 0.174 mmol) were added to a solution of 1-(5-bromopyrazolo[1,5-a]pyridin-3-yl)-3-(2,4-dimethoxybenzyl)dihydropyrimidine-2,4(1H,3H)-dione (800 mg, 1.74 mmol) in DMF (8 mL) at rt. The mixture was stirred at 90° C. for 6 h, then cooled to rt and acidified with aqueous 1 N HCl solution. The mixture was partitioned between EtOAc and water. The organic layer was separated, washed with brine, dried over sodium sulfate, filtered and concentrated. The crude product was purified by flash silica gel chromatography (eluted with 45% EtOAc/hexane) to give 1-(5-acetylpyrazolo[1,5-a]pyridin-3-yl)-3-(2,4-dimethoxybenzyl)dihydropyrimidine-2,4(1H,3H)-dione as an orange solid. LCMS [M+H]⁺: 423.2.

Step 2. tert-butyl 4-(1-(3-(3-(2,4-dimethoxybenzyl)-2,4-dioxotetrahydropyrimidin-1(2H)-yl)pyrazolo[1,5-a]pyridin-5-yl)ethyl)piperazine-1-carboxylate To a solution of 1-(5-acetylpyrazolo[1,5-a]pyridin-3-yl)-3-(2,4-dimethoxybenzyl)dihydropyrimidine-2,4(1H,3H)-dione (170 mg, 0.402 mmol) and tert-butyl piperazine-1-carboxylate (89 mg, 0.48 mmol) in THF (5 mL) was added dibutyltin dichloride (244 mg, 0.804 mmol), and triethylamine (0.17 mL, 1.2 mmol). The mixture was stirred at 80° C. for 2 h and then phenylsilane (87 mg, 0.80 mmol) was added. The reaction was stirred in a capped vial at 80° C. for 12 h. The reaction was cooled to rt, diluted with EtOAc and washed with water. The organic layer was dried over

424

Na₂SO₄, filtered and concentrated to give crude tert-butyl 4-(1-(3-(3-(2,4-dimethoxybenzyl)-2,4-dioxotetrahydropyrimidin-1(2H)-yl)pyrazolo[1,5-a]pyridin-5-yl)ethyl)piperazine-1-carboxylate. The crude product was used in the next step without any other purification. LCMS [M+H]⁺: 593.0.

Step 3. 1-(5-(1-(4-isobutylpiperazin-1-yl)ethyl)pyrazolo[1,5-a]pyridin-3-yl)dihydropyrimidine-2,4(1H,3H)-dione was prepared by the method of Example 192, steps 2-4 wherein tert-butyl 4-(1-(3-(3-(2,4-dimethoxybenzyl)-2,4-dioxotetrahydropyrimidin-1(2H)-yl)pyrazolo[1,5-a]pyridin-5-yl)ethyl)piperazine-1-carboxylate was used in place of tert-butyl 4-((3-(3-(2,4-dimethoxybenzyl)-2,4-dioxotetrahydropyrimidin-1(2H)-yl)pyrazolo[1,5-a]pyridin-5-yl)methyl)piperazine-1-carboxylate in step 2 and isobutyraldehyde was used in place of cyclohexanecarbaldehyde in step 3. LCMS [M+H]⁺: 399.2. ¹H NMR (400 MHz, MeOD) δ 8.47 (d, J=7.3 Hz, 1H), 8.03 (s, 1H), 7.51-7.47 (m, 1H), 7.02 (dd, J=7.3, 1.9 Hz, 1H), 3.90 (t, J=6.8 Hz, 2H), 3.67 (q, J=6.6 Hz, 1H), 3.25-2.55 (m, 12H), 2.08 (dq, J=15.4, 7.6 Hz, 1H), 1.45 (d, J=6.7 Hz, 3H), 1.02 (d, J=6.6 Hz, 6H). NH proton not observed due to solvent exchange.

Example 346. Preparation of 1-(5-(((2S,4R)-1-isobutyl-2-methylpiperidin-4-yl)methyl)pyrazolo[1,5-a]pyridin-3-yl)pyrimidine-2,4(1H,3H)-dione

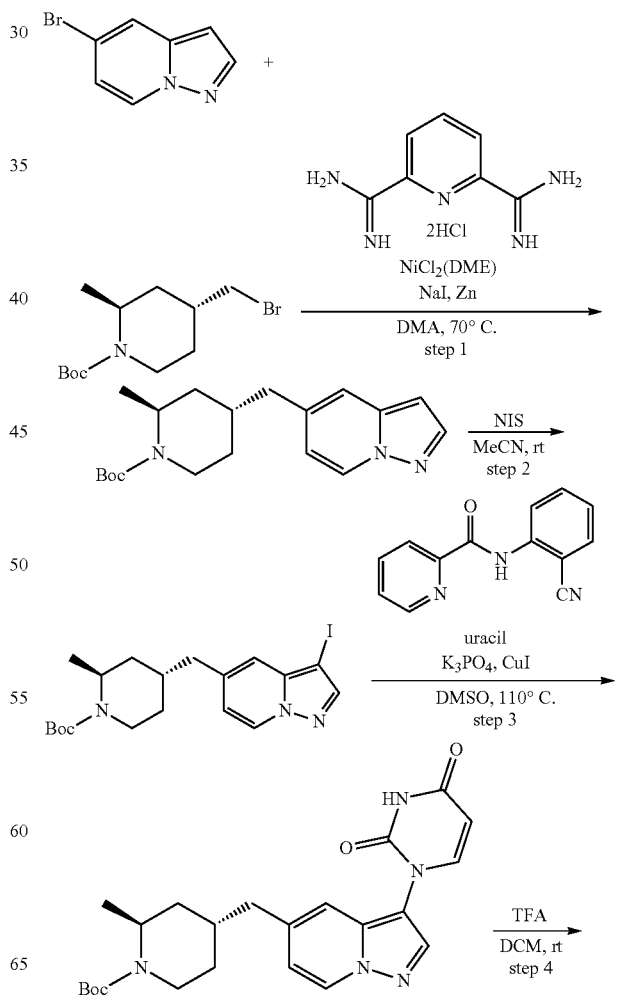

-continued

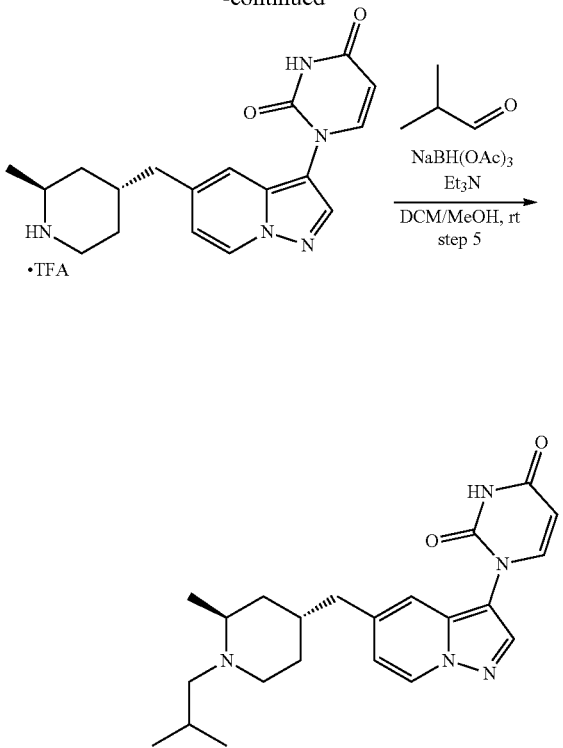

Step 1. tert-butyl (2S,4R)-2-methyl-4-(pyrazolo[1,5-a]pyridin-5-ylmethyl)piperidine-1-carboxylate To an oven-dried vial was added 5-bromopyrazolo[1,5-a]pyridine (100 mg, 507 μmol), nickel chloride, dimethoxyethane adduct (5.6 mg, 25 μmol), pyridine-2,6-bis(carboximidamide)-hydrochloride (6.0 mg, 25 μmol), activated zinc (83 mg, 1.3 mmol), tert-butyl (2S,4R)-4-(bromomethyl)-2-methylpiperidine-1-carboxylate (178 mg, 609 μmol) and sodium iodide (19 mg, 127 μmol). The reaction was sealed with a septa-top cap and purged with $N_2$ via needle. DMA (2 mL) was added, and the reaction was heated overnight at 70° C. The reaction was cooled to rt, diluted with EtOAc and filtered through a plug of silica gel, eluting with EtOAc. The eluent was concentrated and the residue was purified by silica gel column chromatography (eluted with 0-100% EtOAc in heptane) to give tert-butyl (2S,4R)-2-methyl-4-(pyrazolo[1,5-a]pyridin-5-ylmethyl)piperidine-1-carboxylate as a sticky solid. LCMS [M+H]$^+$: 330.3.

Step 2: tert-butyl (2S,4R)-4-((3-iodopyrazolo[1,5-a]pyridin-5-yl)methyl)-2-methylpiperidine-1-carboxylate To a solution of tert-butyl (2S,4R)-2-methyl-4-(pyrazolo[1,5-a] pyridin-5-ylmethyl) piperidine-1-carboxylate (220 mg, 668 μmol) in MeCN (5 mL) at 0° C. was added NIS (180 mg, 801 μmol). The reaction was then stirred at rt for 1 h. The reaction was quenched by addition of aqueous $Na_2S_2O_3$ solution and extracted with EtOAc. The organic layer was washed sequentially with water and brine, dried over $Na_2SO_4$, filtered and concentrated. Silica gel column chromatography (eluting with 0-100% EtOAc in heptane) provided tert-butyl (2S,4R)-4-((3-iodopyrazolo[1,5-a] pyridin-5-yl) methyl)-2-methylpiperidine-1-carboxylate as a transparent sticky solid. LCMS [M+H]$^+$: 456.1.

Step 3: tert-butyl (2S,4R)-4-((3-(2,4-dioxo-3,4-dihydropyrimidin-1(2H)-yl)pyrazolo[1,5-a]pyridin-5-yl) methyl)-2-methylpiperidine-1-carboxylate To an oven-dried vial was added a solution of tert-butyl (2S,4R)-4-((3-iodopyrazolo[1,5-a]pyridin-5-yl)methyl)-2-methylpiperidine-1-carboxylate (80 mg, 176 μmol) in DMSO (0.5 mL), pyrimidine-2,4(1H,3H)-dione (uracil) (26 mg, 228 μmol), potassium phosphate (78 mg, 369 μmol), N-(2-cyanophenyl) picolinamide (16 mg, 70 μmol) and copper(I) iodide (6.7 mg, 35 μmol). The vial was sealed with a septa-top cap and purged with $N_2$ via needle. The reaction was heated at 110° C. for 72 h. The reaction was quenched with aqueous 1M $KHSO_4$ and extracted with EtOAc. The organic layer was dried over $Na_2SO_4$, filtered and concentrated. Silica gel column chromatography (EtOAc/heptane) provided tert-butyl (2S,4R)-4-((3-(2,4-dioxo-3,4-dihydropyrimidin-1(2H)-yl)pyrazolo[1,5-a]pyridin-5-yl)methyl)-2-methylpiperidine-1-carboxylate. LCMS [M+H]$^+$: 440.2.

Step 4: 1-(5-(((2S,4R)-2-methylpiperidin-4-yl) methyl)pyrazolo[1,5-a]pyridin-3-yl)pyrimidine-2,4 (1H,3H)-dione trifluoroacetate To a solution of tert-butyl (2S,4R)-4-((3-(2,4-dioxo-3,4-dihydropyrimidin-1(2H)-yl)pyrazolo[1,5-a]pyridin-5-yl) methyl)-2-methylpiperidine-1-carboxylate (35 mg, 80 μmol) in DCM (2 mL) was added TFA (2 mL). The reaction was stirred at rt for 45 min. The reaction was concentrated and the crude material was azeotropically dried with toluene to give crude 1-(5-(((2S,4R)-2-methylpiperidin-4-yl)methyl) pyrazolo[1,5-a]pyridin-3-yl)pyrimidine-2,4(1H,3H)-dione trifluoroacetate which used without further purification. LCMS [M+H]$^+$: 340.2.

Step 5: 1-(5-(((2S,4R)-1-isobutyl-2-methylpiperidin-4-yl)methyl)pyrazolo[1,5-a]pyridin-3-yl)pyrimidine-2,4(1H,3H)-dione (Example 346)

To a solution of 1-(5-(((2S,4R)-2-methylpiperidin-4-yl) methyl)pyrazolo[1,5-a]pyridin-3-yl)pyrimidine-2,4(1H, 3H)-dione trifluoroacetate (36 mg, 79 μmol) in DCM (2 mL) and MeOH (500 μL) was added isobutyraldehyde (14 μL, 159 μmol) and triethylamine (10 μL, 71 μmol). The reaction was stirred at rt for 10 min and then sodium triacetoxyborohydride (84 mg, 397 μmol) was added. The reaction was stirred at rt overnight. The reaction was quenched with one drop of TFA and then concentrated. The crude material was dissolved in DMSO, filtered through a 1 micron filter and purified by reverse phase HPLC using ACN/Water/0.1% TFA to afford 1-(5-(((2S,4R)-1-isobutyl-2-methylpiperidin-4-yl)methyl)pyrazolo[1,5-a]pyridin-3-yl)pyrimidine-2,4 (1H,3H)-dione. LCMS [M+H]$^+$: 396.2. $^1$H NMR (500 MHz, DMSO) δ 11.51 (s, 1H), 8.67 (t, J=26.8 Hz, 1H), 8.14 (s, 1H), 7.71 (d, J=7.8 Hz, 1H), 7.36 (d, J=14.1 Hz, 1H), 6.87 (s, 1H), 5.71 (s, 1H), 3.59 (d, J=89.5 Hz, 1H), 3.23-2.69 (m, 2H), 2.59 (d, J=47.7 Hz, 1H), 2.36 (s, 1H), 2.23-1.81 (m, 2H), 1.78-1.14 (m, 7H), 0.89 (d, J=69.0 Hz, 8H).

Example 347. Preparation of 1-(5-(((2S,4R)-1-isobutyl-2-methylpiperidin-4-yl)methyl)pyrazolo[1,5-a]pyridin-3-yl)-5-methylpyrimidine-2,4(1H,3H)-dione

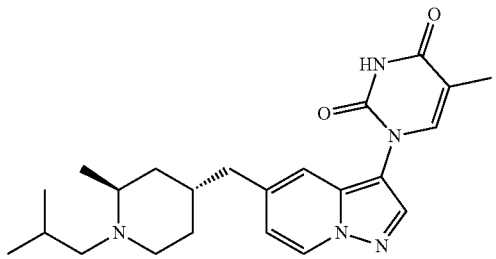

Prepared using the method of Example 346 wherein 5-methylpyrimidine-2,4(1H,3H)-dione was used in place of pyrimidine-2,4(1H,3H)-dione in step 3. LCMS [M+H]$^+$: 410.2. $^1$H NMR (500 MHz, DMSO) δ 11.53 (d, J=6.5 Hz, 1H), 8.73-8.54 (m, 1H), 8.15 (d, J=1.4 Hz, 1H), 7.62 (dd, J=8.8, 1.4 Hz, 1H), 7.42-7.23 (m, 1H), 6.89 (dd, J=7.2, 1.9 Hz, 1H), 3.69 (s, 1H), 3.24-2.90 (m, 3H), 2.89-2.69 (m, 2H), 2.60 (h, J=6.6 Hz, 1H), 2.23-1.88 (m, 2H), 1.83 (d, J=1.2 Hz, 3H), 1.77-1.61 (m, 3H), 1.61-1.43 (m, 1H), 1.34 (d, J=6.6 Hz, 1H), 1.22 (d, J=6.8 Hz, 2H), 1.03-0.88 (m, 6H).

Example 348. Preparation of 1-(5-(((2S,4R)-1-(cyclopropylmethyl)-2-methylpiperidin-4-yl)methyl)pyrazolo[1,5-a]pyridin-3-yl)-5-methylpyrimidine-2,4(1H,3H)-dione

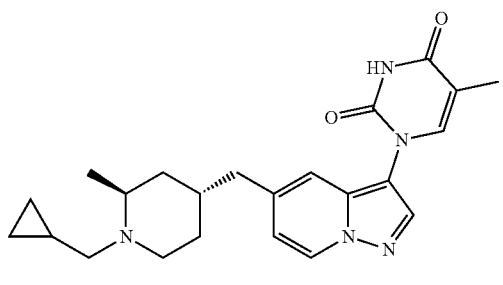

Prepared using the method of Example 346 wherein 5-methylpyrimidine-2,4(1H,3H)-dione was used in place of pyrimidine-2,4(1H,3H)-dione in step 3 and cyclopropanecarbaldehyde was used in place of isobutyraldehyde in step 5. LCMS [M+H]$^+$: 408.2. $^1$H NMR (500 MHz, DMSO) δ 11.53 (d, J=5.4 Hz, 1H), 8.69 (dt, J=7.2, 1.4 Hz, 1H), 8.16 (d, J=1.4 Hz, 1H), 7.63 (dd, J=9.4, 1.4 Hz, 1H), 7.37 (dd, J=14.6, 1.8 Hz, 1H), 6.90 (ddd, J=7.2, 3.6, 1.8 Hz, 1H), 3.65 (s, 1H), 3.44 (s, 1H), 3.37-2.93 (m, 3H), 2.75 (dd, J=14.9, 7.2 Hz, 1H), 2.69-2.56 (m, 1H), 2.26-2.03 (m, 1H), 1.83 (d, J=1.2 Hz, 3H), 1.80-1.53 (m, 3H), 1.51-1.37 (m, 1H), 1.32 (d, J=6.6 Hz, 1H), 1.23 (d, J=6.9 Hz, 2H), 1.05 (dt, J=27.2, 7.1 Hz, 1H), 0.73-0.53 (m, 2H), 0.49-0.22 (m, 2H).

Example 349. Preparation of 5-fluoro-1-(5-(((2S,4R)-1-isobutyl-2-methylpiperidin-4-yl)methyl)pyrazolo[1,5-a]pyridin-3-yl)pyrimidine-2,4(1H,3H)-dione Prepared using the method of Example 346 wherein 5-fluoropyrimidine-2,4(1H,3H)-dione was used in place of pyrimidine-2,4(1H,3H)-dione in step 3. LCMS [M+H]$^+$: 414.4. $^1$H NMR (500 MHz, DMSO) δ 12.04 (dd, J=8.4, 5.2 Hz, 1H), 8.69 (dd, J=7.3, 2.7 Hz, 1H), 8.29-8.06 (m, 2H), 7.51-7.37 (m, 1H), 6.97-6.82 (m, 1H), 3.38 (d, J=11.0 Hz, 1H), 2.97 (dt, J=12.7, 6.1 Hz, 3H), 2.90-2.70 (m, 2H), 2.61 (tt, J=13.0, 7.0 Hz, 1H), 2.29-1.91 (m, 2H), 1.68 (d, J=4.5 Hz, 3H), 1.62-1.44 (m, 1H), 1.35 (d, J=6.6 Hz, 1H), 1.23 (d, J=6.8 Hz, 2H), 1.08-0.83 (m, 6H).

Example 350. Preparation of 1-(5-(((2S,4R)-1-((4,4-difluorocyclohexyl)methyl)-2-methylpiperidin-4-yl)methyl)pyrazolo[1,5-a]pyridin-3-yl)-5-fluoropyrimidine-2,4(1H,3H)-dione

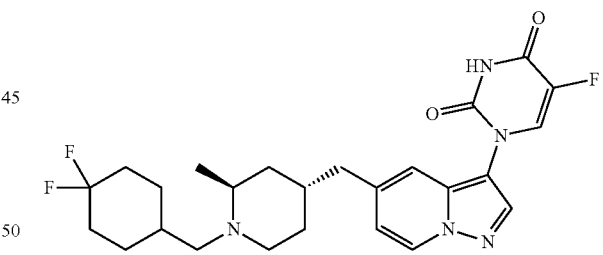

Prepared using the method of Example 346 wherein 5-fluoropyrimidine-2,4(1H,3H)-dione was used in place of pyrimidine-2,4(1H,3H)-dione in step 3 and 4,4-difluorocyclohexane-1-carbaldehyde was used in place of isobutyraldehyde in step 5. LCMS [M+H]$^+$: 490.4. $^1$H NMR (500 MHz, DMSO) δ 8.92 (s, 1H), 8.68 (dd, J=7.2, 3.2 Hz, 1H), 8.22 (dd, J=10.6, 6.5 Hz, 1H), 8.14 (d, J=2.0 Hz, 1H), 7.43 (d, J=17.7 Hz, 1H), 6.89 (d, J=7.2 Hz, 1H), 3.40-2.98 (m, 4H), 2.90 (t, J=6.2 Hz, 1H), 2.76-2.53 (m, 2H), 2.23-1.98 (m, 3H), 1.96-1.42 (m, 9H), 1.28 (dd, J=54.9, 6.8 Hz, 5H).

Example 351. Preparation of 1-(5-(((2S,4R)-1-((4,4-difluorocyclohexyl)methyl)-2-methylpiperidin-4-yl)methyl)pyrazolo[1,5-a]pyridin-3-yl)-5-methylpyrimidine-2,4(1H,3H)-dione

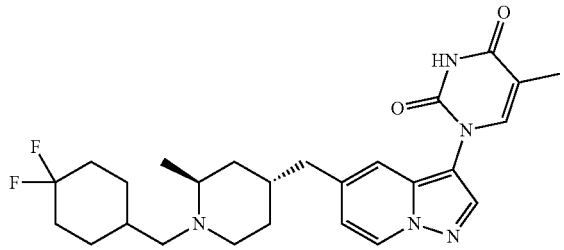

Prepared using the method of Example 346 wherein 5-methylpyrimidine-2,4(1H,3H)-dione was used in place of pyrimidine-2,4(1H,3H)-dione in step 3 and 4,4-difluorocyclohexane-1-carbaldehyde was used in place of isobutyraldehyde in step 5. LCMS [M+H]+: 486.4. ¹H NMR (500 MHz, DMSO) δ 8.89 (s, 1H), 8.67 (dd, J=7.2, 3.2 Hz, 1H), 8.14 (d, J=2.0 Hz, 1H), 7.61 (dd, J=9.8, 1.5 Hz, 1H), 7.34 (d, J=16.0 Hz, 1H), 6.87 (dd, J=7.2, 1.9 Hz, 1H), 3.73 (s, 1H), 3.53 (s, 1H), 3.28-2.97 (m, 2H), 2.89 (t, J=6.1 Hz, 1H), 2.75-2.53 (m, 2H), 2.10 (d, J=80.9 Hz, 3H), 1.93-1.42 (m, 12H), 1.27 (dd, J=53.7, 6.8 Hz, 5H).

Example 352. Preparation of 5-chloro-1-(5-(((2S,4R)-1-((4,4-difluorocyclohexyl)methyl)-2-methylpiperidin-4-yl)methyl)pyrazolo[1,5-a]pyridin-3-yl)pyrimidine-2,4(1H,3H)-dione

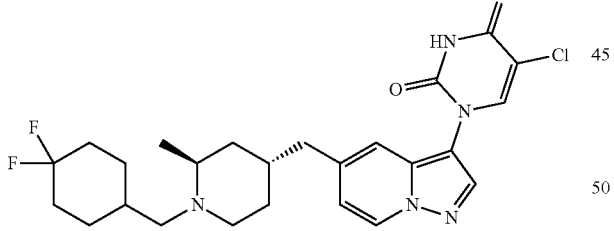

Prepared using the method of Example 346 wherein 5-chloropyrimidine-2,4(1H,3H)-dione was used in place of pyrimidine-2,4(1H,3H)-dione in step 3 and 4,4-difluorocyclohexane-1-carbaldehyde was used in place of isobutyraldehyde in step 5. LCMS [M+H]+: 506.4. ¹H NMR (500 MHz, DMSO) δ 8.86 (s, 1H), 8.68 (dd, J=7.2, 3.0 Hz, 1H), 8.24 (d, J=9.9 Hz, 1H), 8.16 (d, J=2.0 Hz, 1H), 7.43 (d, J=19.0 Hz, 1H), 6.91-6.85 (m, 1H), 3.41-2.99 (m, 4H), 2.90 (t, J=6.2 Hz, 1H), 2.75-2.54 (m, 2H), 2.24-1.95 (m, 3H), 1.95-1.41 (m, 9H), 1.27 (dd, J=54.4, 6.8 Hz, 5H).

Example 353. Preparation of 1-(5-(((2S,4R)-1-((4,4-difluorocyclohexyl)methyl)-2-methylpiperidin-4-yl)methyl)pyrazolo[1,5-a]pyridin-3-yl)-5-methoxypyrimidine-2,4(1H,3H)-dione

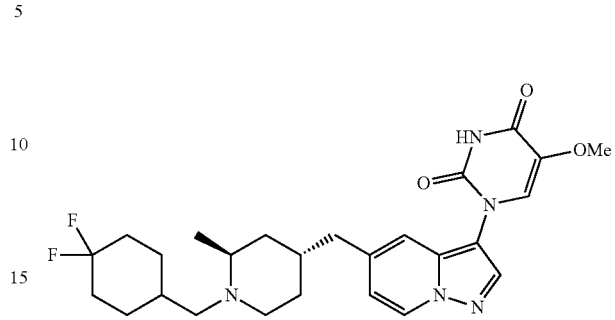

Prepared using the method of Example 346 wherein 5-methoxypyrimidine-2,4(1H,3H)-dione was used in place of pyrimidine-2,4(1H,3H)-dione in step 3 and 4,4-difluorocyclohexane-1-carbaldehyde was used in place of isobutyraldehyde in step 5. LCMS [M+H]+: 502.2. ¹H NMR (500 MHz, DMSO) δ 11.67 (s, 1H), 8.63 (d, J=7.1 Hz, 1H), 8.15 (s, 1H), 7.36 (d, J=4.2 Hz, 2H), 6.97-6.76 (m, 1H), 3.63 (s, 3H), 2.91 (s, 1H), 2.44-2.32 (m, 3H), 2.19 (s, 2H), 2.05-1.68 (m, 8H), 1.47 (d, J=52.8 Hz, 4H), 1.22 (d, J=25.8 Hz, 1H), 1.08 (d, J=12.7 Hz, 2H), 0.88 (s, 3H).

Example 354. Preparation of 5-cyclopropyl-1-(5-(((2S,4R)-1-isobutyl-2-methylpiperidin-4-yl)methyl)pyrazolo[1,5-a]pyridin-3-yl)pyrimidine-2,4(1H,3H)-dione

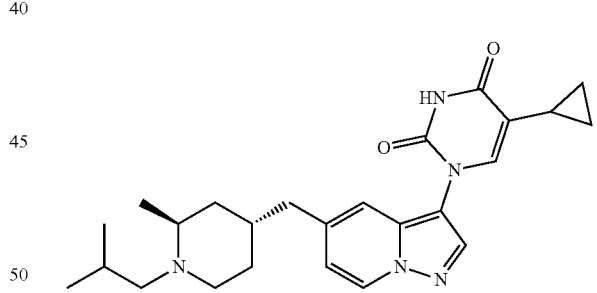

Prepared using the method of Example 346 wherein 5-cyclopropylpyrimidine-2,4(1H,3H)-dione was used in place of pyrimidine-2,4(1H,3H)-dione in step 3. LCMS [M+H]+: 436.2. ¹H NMR (500 MHz, DMSO) δ 11.52 (d, J=7.0 Hz, 1H), 8.68 (dd, J=7.2, 2.7 Hz, 1H), 8.15 (d, J=1.5 Hz, 1H), 7.44-7.24 (m, 2H), 6.88 (d, J=7.1 Hz, 1H), 3.70 (s, 2H), 3.24-2.90 (m, 2H), 2.90-2.70 (m, 2H), 2.69-2.56 (m, 3H), 2.30-1.92 (m, 1H), 1.85-1.42 (m, 4H), 1.34 (d, J=6.5 Hz, 1H), 1.22 (d, J=6.8 Hz, 2H), 1.09-0.87 (m, 6H), 0.71 (dt, J=8.8, 2.9 Hz, 2H), 0.68-0.57 (m, 2H).

Example 355. Preparation of 1-(5-(((2S,4R)-1-(cyclopropanecarbonyl)-2-methylpiperidin-4-yl)methyl)pyrazolo[1,5-a]pyridin-3-yl)pyrimidine-2,4(1H,3H)-dione

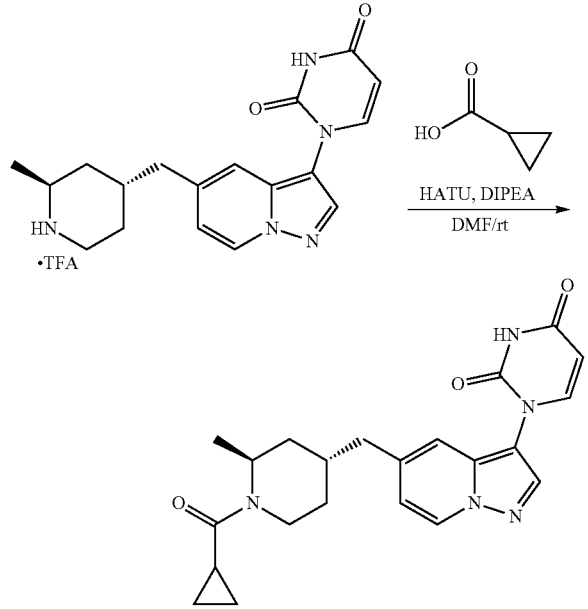

HATU (38 mg, 0.099 mmol) and cyclopropanecarboxylic acid (8.5 mg, 0.099 mmol) were added to a solution of 1-(5-(((2S,4R)-2-methylpiperidin-4-yl)methyl)pyrazolo[1,5-a]pyridin-3-yl)pyrimidine-2,4(1H,3H)-dione trifluoroacetate (30 mg, 0.066 mmol) in DMF (1.5 mL) at rt. The mixture was stirred at rt for 5 min and then DIPEA (0.035 mL, 0.19 mmol) was added. The mixture was stirred at rt overnight and then filtered through a 1 micron filter and purified by reverse phase HPLC using ACN/Water/0.1% TFA to afford 1-(5-(((2S,4R)-1-(cyclopropanecarbonyl)-2-methylpiperidin-4-yl)methyl)pyrazolo[1,5-a]pyridin-3-yl)pyrimidine-2,4(1H,3H)-dione. LCMS [M+H]$^+$: 408.2. $^1$H NMR (500 MHz, DMSO) δ 11.52 (d, J=2.3 Hz, 1H), 8.66 (dd, J=7.2, 0.9 Hz, 1H), 8.15 (s, 1H), 7.73 (d, J=7.8 Hz, 1H), 7.37 (d, J=1.6 Hz, 1H), 6.90 (dd, J=7.2, 1.9 Hz, 1H), 5.72 (dd, J=7.8, 2.3 Hz, 1H), 4.68 (d, J=66.7 Hz, 1H), 4.19 (dd, J=89.6, 13.7 Hz, 1H), 3.12 (t, J=13.1 Hz, 1H), 2.86-2.56 (m, 2H), 2.19-1.82 (m, 2H), 1.74-1.45 (m, 2H), 1.43-1.22 (m, 1H), 1.21-0.90 (m, 4H), 0.80-0.46 (m, 4H).

Example 356. Preparation of 1-(5-(((2S,4R)-1-(ethylsulfonyl)-2-methylpiperidin-4-yl)methyl)pyrazolo[1,5-a]pyridin-3-yl)pyrimidine-2,4(1H,3H)-dione

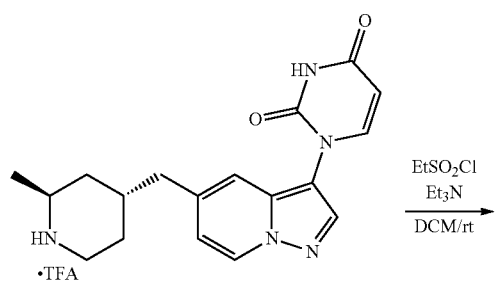

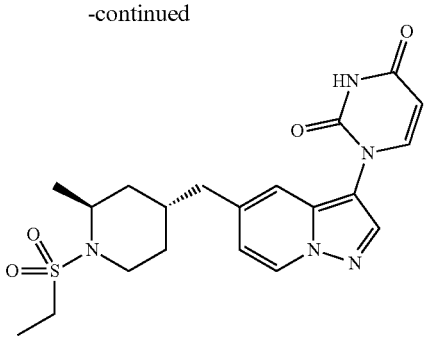

Triethylamine (0.046 mL, 0.33 mmol) and ethylsulfonyl chloride (0.019 mL, 0.19 mmol) were added to a solution of 1-(5-(((2S,4R)-2-methylpiperidin-4-yl)methyl)pyrazolo[1,5-a]pyridin-3-yl)pyrimidine-2,4(1H,3H)-dione trifluoroacetate (30 mg, 0.066 mmol) in DCM (2 mL) at 0° C. The mixture was stirred at rt overnight and then filtered through a 1 micron filter and purified by reverse phase HPLC using ACN/Water/0.1% TFA to afford 1-(5-(((2S,4R)-1-(ethylsulfonyl)-2-methylpiperidin-4-yl)methyl)pyrazolo[1,5-a]pyridin-3-yl)pyrimidine-2,4(1H,3H)-dione (8 mg, 14 μmol, 21% yield). LCMS [M+H]$^+$: 432.5. $^1$H NMR (500 MHz, DMSO) δ 11.52 (d, J=2.3 Hz, 1H), 8.66 (d, J=7.1 Hz, 1H), 8.15 (s, 1H), 7.73 (dd, J=7.8, 1.2 Hz, 1H), 7.37 (s, 1H), 6.89 (dd, J=7.2, 1.8 Hz, 1H), 5.72 (dd, J=7.8, 2.3 Hz, 1H), 4.05 (t, J=6.3 Hz, 1H), 3.49 (s, 1H), 3.14-2.86 (m, 3H), 2.59-2.54 (m, 2H), 2.03 (s, 1H), 1.55 (dd, J=32.4, 13.3 Hz, 2H), 1.37 (td, J=12.8, 5.3 Hz, 1H), 1.18 (t, J=7.3 Hz, 6H), 1.14-1.07 (m, 1H).

Example 357. Preparation of (S)-1-(5-((4-isobutyl-3-methylpiperazin-1-yl)methyl)pyrazolo[1,5-a]pyridin-3-yl)pyrimidine-2,4(1H,3H)-dione

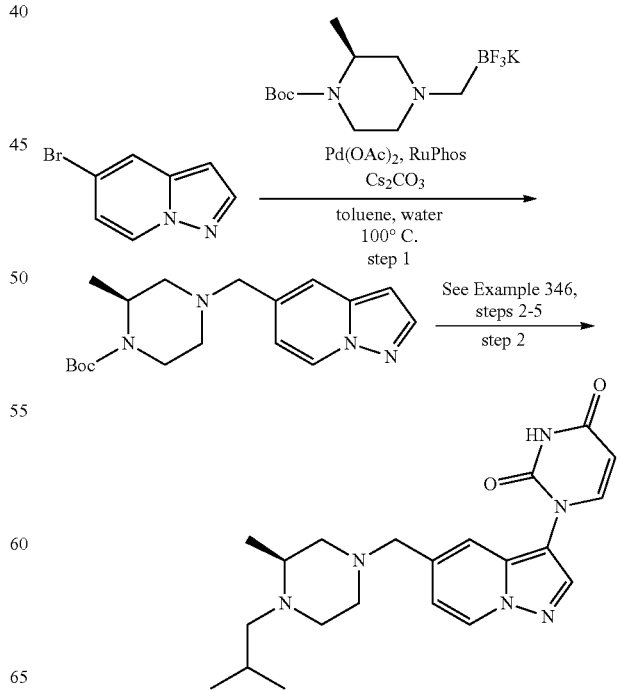

Step 1: tert-butyl (S)-2-methyl-4-(pyrazolo[1,5-a]pyridin-5-ylmethyl)piperazine-1-carboxylate To a suspension of 5-bromopyrazolo[1,5-a]pyridine (500 mg, 2.54 mmol) in toluene (10 mL) and water (1 mL) at room temperature was added Cs$_2$CO$_3$ (2.48 g, 7.61 mmol), tert-butyl (S)-2-methyl-4-((trifluoro-I4-boraneyl)methyl)piperazine-1-carboxylate, potassium salt (2.44 g, 7.61 mmol) and RuPhos (237 mg, 0.508 mmol), followed by Pd(OAc)$_2$ (57 mg, 0.25 μmol). The mixture was stirred at 100° C. overnight, then cooled to rt and partitioned between EtOAc and water. The organic layer was separated, washed with brine, dried over sodium sulfate, filtered and concentrated. Silica gel column chromatography (EtOAc/EtOH/heptane) provided tert-butyl (S)-2-methyl-4-(pyrazolo[1,5-a]pyridin-5-ylmethyl)piperazine-1-carboxylate (735 mg, 1.9 mmol, 75% yield). LCMS [M+H]$^+$: 331.4.

Step 2. (S)-1-(5-((4-isobutyl-3-methylpiperazin-1-yl)methyl)pyrazolo[1,5-a]pyridin-3-yl)pyrimidine-2,4(1H,3H)-dione was prepared by the method of Example 346, steps 2-5 wherein tert-butyl (S)-2-methyl-4-(pyrazolo[1,5-a]pyridin-5-ylmethyl)piperazine-1-carboxylate was used in place of tert-butyl (2S,4R)-2-methyl-4-(pyrazolo[1,5-a]pyridin-5-ylmethyl)piperidine-1-carboxylate in step 2. LCMS [M+H]$^+$: 397.2. $^1$H NMR (500 MHz, DMSO) δ 11.54 (s, 1H), 8.80-8.57 (m, 1H), 8.19 (s, 1H), 7.74 (d, J=7.8 Hz, 1H), 7.48 (d, J=22.7 Hz, 1H), 6.98 (d, J=7.1 Hz, 1H), 5.73 (d, J=8.2 Hz, 1H), 3.64 (d, J=14.1 Hz, 1H), 3.52 (t, J=15.9 Hz, 1H), 3.21-2.99 (m, 1H), 2.92 (d, J=13.0 Hz, 2H), 2.80-2.64 (m, 1H), 2.49-2.28 (m, 2H), 2.29-1.58 (m, 2H), 1.29 (d, J=6.4 Hz, 2H), 0.98 (dd, J=15.1, 6.6 Hz, 5H), 0.85 (s, 2H). Two missing protons attributed to overlap with solvent.

Example 358. Preparation of (S)-5-fluoro-1-(5-((4-isobutyl-3-methylpiperazin-1-yl)methyl)pyrazolo[1,5-a]pyridin-3-yl)pyrimidine-2,4(1H,3H)-dione

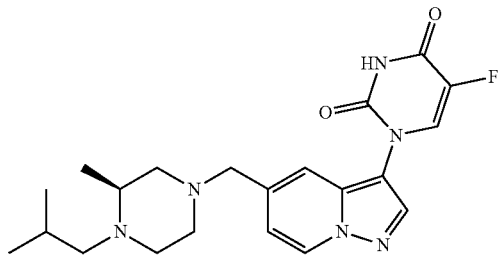

Prepared using the method of Example 357 wherein 5-fluoropyrimidine-2,4(1H,3H)-dione was used in place of pyrimidine-2,4(1H,3H)-dione in step 2. LCMS [M+H]$^+$: 415.2. $^1$H NMR (500 MHz, DMSO) δ 12.05 (d, J=5.3 Hz, 1H), 8.74 (d, J=7.2 Hz, 1H), 8.23 (d, J=6.4 Hz, 1H), 8.19 (s, 1H), 7.59 (s, 1H), 6.99 (dd, J=7.1, 1.8 Hz, 1H), 3.51 (s, 4H), 3.21-2.72 (m, 7H), 2.21-1.75 (m, 1H), 1.27 (s, 3H), 0.97 (t, J=6.7 Hz, 6H).

Example 359. Preparation of (S)-1-(5-((4-isobutyl-3-methylpiperazin-1-yl)methyl)pyrazolo[1,5-a]pyridin-3-yl)-5-methylpyrimidine-2,4(1H,3H)-dione

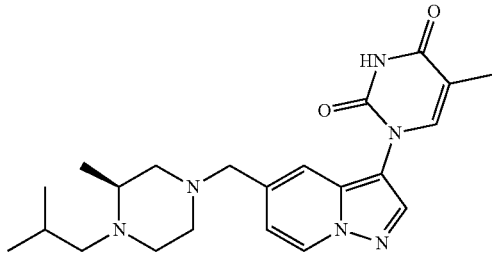

Prepared using the method of Example 357 wherein 5-methylpyrimidine-2,4(1H,3H)-dione was used in place of pyrimidine-2,4(1H,3H)-dione in step 2. LCMS [M+H]$^+$: 411.2. $^1$H NMR (500 MHz, DMSO) δ 11.52 (s, 1H), 8.71 (dd, J=7.1, 0.9 Hz, 1H), 8.17 (s, 1H), 7.61 (q, J=1.2 Hz, 1H), 7.50 (s, 1H), 6.97 (dd, J=7.2, 1.8 Hz, 1H), 3.72 (s, 5H), 3.05 (s, 4H), 2.75 (d, J=59.3 Hz, 2H), 2.01 (s, 1H), 1.81 (d, J=1.3 Hz, 3H), 1.26 (d, J=6.4 Hz, 3H), 0.94 (t, J=6.7 Hz, 6H).

Example 360. Preparation of (S)-1-(5-((4-isobutyl-3-methylpiperazin-1-yl)methyl)pyrazolo[1,5-a]pyridin-3-yl)-5-methoxypyrimidine-2,4(1H,3H)-dione

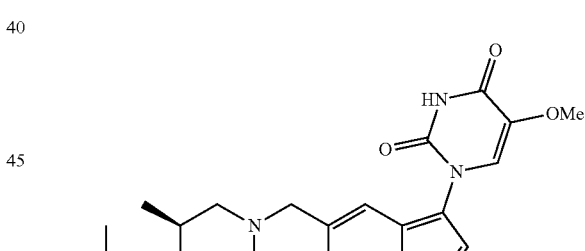

Prepared using the method of Example 357 wherein 5-methoxypyrimidine-2,4(1H,3H)-dione was used in place of pyrimidine-2,4(1H,3H)-dione in step 2. LCMS [M+H]$^+$: 427.2. $^1$H NMR (500 MHz, DMSO) δ 11.71 (s, 1H), 8.73 (d, J=7.2 Hz, 1H), 8.21 (s, 1H), 7.53 (s, 1H), 7.37 (s, 1H), 6.98 (d, J=7.2 Hz, 1H), 3.64 (s, 8H), 2.93 (d, J=47.3 Hz, 5H), 2.38 (s, 1H), 2.03 (s, 1H), 1.49-1.14 (m, 3H), 0.96 (t, J=6.3 Hz, 6H).

Example 361. Preparation of (S)-5-cyclopropyl-1-(5-((4-isobutyl-3-methylpiperazin-1-yl)methyl)pyrazolo[1,5-a]pyridin-3-yl)pyrimidine-2,4(1H,3H)-dione

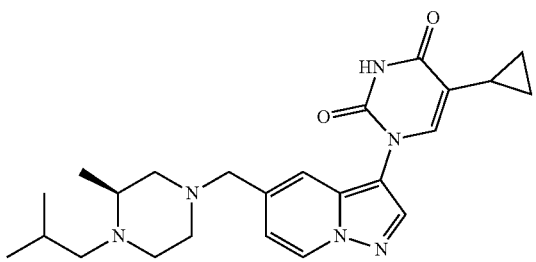

Prepared using the method of Example 357 wherein 5-cyclopropylpyrimidine-2,4(1H,3H)-dione was used in place of pyrimidine-2,4(1H,3H)-dione in step 2. LCMS [M+H]$^+$: 437.2. $^1$H NMR (500 MHz, DMSO) δ 11.53 (s, 1H), 8.72 (d, J=7.1 Hz, 1H), 8.19 (s, 1H), 7.49 (d, J=14.4 Hz, 1H), 7.35 (d, J=0.9 Hz, 1H), 6.97 (dd, J=7.2, 1.8 Hz, 1H), 3.52 (s, 5H), 2.94 (d, J=49.6 Hz, 5H), 2.38 (s, 1H), 2.03 (s, 1H), 1.65 (ddd, J=11.0, 8.6, 5.3 Hz, 1H), 1.39-1.16 (m, 3H), 0.96 (t, J=6.6 Hz, 6H), 0.81-0.67 (m, 2H), 0.65-0.47 (m, 2H).

Example 362. Preparation of (S)-1-(5-((4-(cyclopropylmethyl)-3-methylpiperazin-1-yl)methyl)pyrazolo[1,5-a]pyridin-3-yl)-5-methylpyrimidine-2,4(1H,3H)-dione

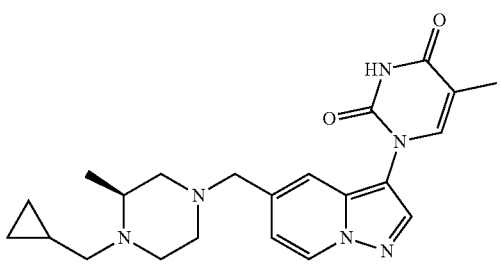

Prepared using the method of Example 357 wherein 5-methylpyrimidine-2,4(1H,3H)-dione was used in place of pyrimidine-2,4(1H,3H)-dione and cyclopropanecarbaldehyde was used in place of isobutyraldehyde in step 2. LCMS [M+H]$^+$: 409.2. $^1$H NMR (500 MHz, DMSO) δ 11.54 (s, 1H), 8.73 (d, J=7.3 Hz, 1H), 8.19 (s, 1H), 7.64 (d, J=1.4 Hz, 1H), 7.50 (s, 1H), 6.98 (dd, J=7.2, 1.8 Hz, 1H), 3.67 (d, J=13.9 Hz, 2H), 3.35 (s, 2H), 3.17 (d, J=11.8 Hz, 2H), 3.01 (t, J=13.6 Hz, 3H), 2.25 (t, J=11.8 Hz, 1H), 1.83 (d, J=1.3 Hz, 3H), 1.32 (d, J=6.6 Hz, 1H), 1.24 (d, J=6.4 Hz, 3H), 1.05 (s, 1H), 0.65 (d, J=13.3 Hz, 2H), 0.50-0.15 (m, 2H).

Example 363. Preparation of (S)-1-(5-((4-((4,4-difluorocyclohexyl)methyl)-3-methylpiperazin-1-yl)methyl)pyrazolo[1,5-a]pyridin-3-yl)pyrimidine-2,4(1H,3H)-dione

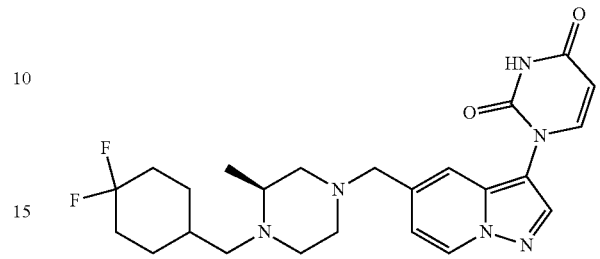

Prepared using the method of Example 357 wherein 4,4-difluorocyclohexane-1-carbaldehyde was used in place of isobutyraldehyde in step 2. LCMS [M+H]$^+$: 473.2. $^1$H NMR (500 MHz, DMSO) δ 11.56 (s, 1H), 8.74 (d, J=7.2 Hz, 1H), 8.21 (s, 1H), 7.74 (d, J=7.7 Hz, 1H), 7.52 (s, 1H), 7.14-6.62 (m, 1H), 5.82-5.52 (m, 1H), 4.19 (s, 2H), 3.68 (s, 3H), 3.29 (s, 2H), 2.99 (s, 3H), 2.36 (d, J=19.6 Hz, 1H), 2.04 (s, 2H), 1.96-1.59 (m, 5H), 1.26 (s, 5H).

Biological Data

Abbreviations

BSA bovine serum albumin
Cas9 CRISPR associated protein 9
CRISPR Clustered regularly interspaced short palindromic repeats
crRNA CRISPR RNA
DMEM Dulbecco's modified eagle media
DMSO Dimethyl sulfoxide
DTT Dithiothreitol
EDTA ethylenediaminetetraacetic acid
eGFP enhanced green fluorescent protein
FACS fluorescence-activated cell sorting
FBS fetal bovine serum
FITC fluorescein
Flt3L Fms-related tyrosine kinase 3 ligand, Flt3L
HbF Fetal hemoglobin
HEPES (4-(2-hydroxyethyl)-1-piperazineethanesulfonic acid)
IMDM Iscove's modified Dulbecco's medium
KCl potassium chloride
mPB mobilized peripheral blood
PBS phosphate buffered saline
rhEPO recombinant human erythropoietin
rhIL-3 recombinant human interleukin-3
rhIL-6 recombinant human interleukin-6
rhSCF recombinant human stem cell factor
rhTPO recominant human thrombopoietin
RNP ribonucleoprotein
shRNA short hairpin RNA
tracrRNA trans-activating crRNA
WIZ Widely-Interspaced Zinc Finger Containing Protein

Materials and Methods

Example 364: Quantification of WIZ Protein Levels in HiBit Tag Fusion Protein Assay The HiBit system from Promega was used to develop high-throughput and quantitative assays to measure changes in WIZ protein levels in response to compounds. The HiBit tag was derived from a split Nanoluciferase and has the following protein sequence: VSGWRLFKKIS (SEQ ID NO: 1). The complementary fragment of Nanoluciferase (known as LgBit, from Promega), was added to the HiBit tag to form an active Nanoluciferase enzyme whose activity can be precisely measured. In this way, the levels of a fusion protein with the HiBit tag can be quantified in cell lysates.

Lentiviral vectors, based on the Invitrogen™ pLenti6.2/V5 DEST backbone were constructed that places the HiBit tag upstream of WIZ and expressed the fusion protein from an HSVTK promotor.

To ensure moderate and consistent expression of the HiBit-WIZ fusion protein across all cells in the population, stable cell lines were constructed from cells harboring a single copy of the construct. Lentivirus packaged with the constructs were made using the ViraPower™ kit from Invitrogen™. 293T cells from ATCC (Catalog number: CRL-3216), were infected with the virus at low multiplicity of infection and selected by 5 µg/mL blasticidin in culture media for 2 weeks.

The levels of HiBit-WIZ tagged fusion proteins in compound-treated cell lines were measured as follows:

On day 1, cells were diluted to $1.0 \times 10^6$ cells/ml in normal growth medium. 20 µL of cell suspension were plated in each well of a solid white 384-well plate. Plates were incubated overnight in a 37° C. and 5% $CO_2$ humidified tissue culture incubator.

On day 2, serial dilutions of compounds were made in 384-well plates. Compound plates were set up with DMSO in columns 1, 2, 23, 24, and 10-point compound dilution series in column 3-12 and column 13-22. 10 mM stock solution of compound were placed into column 3 or 13 and a 1:5 serial dilution was carried out until there was a 10-point dilution series per compound. 50 nL of diluted compounds were transferred into the plated cells by Echo® (Labcyte) acoustic transfer. The highest concentration of compound was 25 µM. Plates were incubated overnight (about 18 hours) in a 37° C. and 5% $CO_2$ humidified tissue culture incubator.

On day 3, plates were removed from the incubator and allowed to equilibrate at room temperature for 60 minutes. HiBit substrate (Nano-Glo® HiBit Lytic Detection System, Promega Catalogue number: N3050) was added as described by the manufacturers protocols. Plates were incubated at room temperature for 30 minutes and luminescence was read using an EnVision® reader (PerkinElmer®). Data was analyzed and visualized using the Spotfire® software package. WIZ Degradation Activity of Compounds (Table 1)

Table 1 shows WIZ degradation activity of compounds of the disclosure in the WIZ HiBit assay in 293T cells. WIZ Amax reflects the DMSO-normalized, curve-fitted percentage of WIZ-HiBit remaining at 25 uM. It was calculated by normalizing DMSO controls to 100%, parametric curve fitting of the dose response data (10-point, 5-fold), followed by calculation of response at 25 uM using the fitted equation (nd=not determined).

TABLE 1

| Cmpd No. | WIZ $AC_{50}$ (µM) | WIZ Amax | % degradation of WIZ (100-Amax) |
| --- | --- | --- | --- |
| 1 | 0.020 | 9 | 91 |
| 2 | 0.023 | 9 | 91 |
| 3 | 0.020 | 10 | 90 |
| 4 | 0.005 | 10 | 90 |
| 5 | 0.204 | 11 | 89 |
| 6 | 0.013 | 11 | 89 |
| 7 | 0.023 | 14 | 86 |
| 8 | 0.008 | 14 | 86 |
| 9 | 0.031 | 16 | 84 |
| 10 | 0.004 | 16 | 84 |
| 11 | 0.055 | 16 | 84 |
| 12 | 0.051 | 16 | 84 |
| 13 | 0.019 | 16 | 84 |
| 14 | 0.028 | 16 | 84 |
| 15 | 0.523 | 29 | 71 |
| 16 | 0.018 | 16 | 84 |
| 17 | 0.048 | 18 | 82 |
| 18 | 0.034 | 18 | 82 |
| 19 | 0.020 | 19 | 81 |
| 20 | 0.022 | 21 | 79 |
| 21 | 0.025 | 22 | 78 |
| 22 | 0.071 | 23 | 77 |
| 23 | 0.144 | 23 | 77 |
| 24 | 1.075 | 23 | 77 |
| 25 | 0.040 | 24 | 76 |
| 26 | 0.297 | 24 | 76 |
| 27 | 0.046 | 24 | 76 |
| 28 | 0.105 | 25 | 75 |
| 29 | 0.232 | 26 | 74 |
| 30 | 0.201 | 20 | 80 |
| 31 | 0.027 | 26 | 74 |
| 32 | 0.023 | 18 | 82 |
| 33 | 0.031 | 27 | 73 |
| 34 | 0.945 | 27 | 73 |
| 35 | 3.138 | 27 | 73 |
| 36 | 0.068 | 28 | 72 |
| 37 | 0.446 | 28 | 72 |
| 38 | 0.112 | 29 | 71 |
| 39 | 0.083 | 29 | 71 |
| 39a | 0.087 | 32 | 68 |
| 40 | 0.052 | 30 | 70 |
| 41 | 0.027 | 30 | 70 |
| 42 | 0.026 | 30 | 70 |
| 43 | 0.034 | 30 | 70 |
| 44 | 0.043 | 30 | 70 |
| 45 | 0.023 | 30 | 70 |
| 46 | 0.058 | 31 | 69 |
| 47 | 0.157 | 31 | 69 |
| 48 | 0.061 | 32 | 68 |
| 49 | 2.787 | 34 | 66 |
| 50 | 0.113 | 34 | 66 |
| 51 | 0.039 | 34 | 66 |
| 52 | 0.987 | 41 | 59 |
| 53 | 0.037 | 35 | 65 |
| 54 | 0.044 | 36 | 64 |
| 55 | 0.103 | 36 | 64 |
| 56 | 0.204 | 37 | 63 |
| 57 | 0.107 | 37 | 63 |
| 58 | 0.033 | 37 | 63 |
| 59 | 0.098 | 42 | 58 |
| 60 | 0.034 | 39 | 61 |
| 61 | 1.739 | 38 | 62 |
| 62 | 0.049 | 27 | 73 |
| 63 | >25 | 64 | 36 |
| 64 | 0.043 | 6 | 94 |
| 65 | 0.032 | 6 | 94 |
| 66 | 0.195 | 28 | 72 |
| 67 | 0.561 | 39 | 61 |
| 68 | 0.384 | 43 | 57 |
| 69 | 0.350 | 65 | 35 |
| 70 | 0.021 | 17 | 83 |
| 71 | 0.007 | 15 | 85 |
| 72 | 0.006 | 13 | 87 |
| 73 | 0.003 | 11 | 89 |
| 74 | 0.003 | 10 | 90 |
| 75 | 0.098 | 19 | 81 |
| 76 | 0.036 | 19 | 81 |

TABLE 1-continued

| Cmpd No. | WIZ AC$_{50}$ (μM) | WIZ Amax | % degradation of WIZ (100-Amax) |
|---|---|---|---|
| 77 | 0.077 | 32 | 68 |
| 78 | 0.010 | 17 | 83 |
| 79 | 0.065 | 35 | 65 |
| 80 | 0.049 | 12 | 88 |
| 81 | 0.015 | 8 | 92 |
| 82 | 0.033 | 10 | 90 |
| 83 | 0.076 | 11 | 89 |
| 84 | 0.055 | 13 | 87 |
| 85 | 0.038 | 17 | 83 |
| 86 | 0.027 | 20 | 80 |
| 87 | 0.025 | 21 | 79 |
| 88 | 0.181 | 22 | 78 |
| 89 | 0.285 | 23 | 77 |
| 90 | 2.002 | 23 | 77 |
| 91 | 0.150 | 26 | 74 |
| 92 | 0.131 | 31 | 69 |
| 93 | 6.518 | 38 | 62 |
| 94 | 3.993 | 38 | 62 |
| 95 | >25 | 57 | 43 |
| 96 | >25 | 58 | 42 |
| 97 | 24.763 | 56 | 44 |
| 98 | 0.587 | 41 | 59 |
| 99 | 1.833 | 48 | 52 |
| 100 | 0.755 | 58 | 42 |
| 101 | >25 | 67 | 33 |
| 102 | 0.165 | 60 | 40 |
| 103 | 0.082 | 72 | 28 |
| 104 | 7.365 | 38 | 62 |
| 105 | 2.156 | 36 | 64 |
| 106 | 0.283 | 32 | 68 |
| 107 | 0.031 | 22 | 78 |
| 108 | 1.341 | 66 | 34 |
| 109 | 0.039 | 18 | 82 |
| 110 | 0.044 | 21 | 79 |
| 111 | 0.304 | 44 | 56 |
| 112 | 0.016 | 34 | 66 |
| 113 | 0.004 | 12 | 88 |
| 114 | 0.090 | 32 | 68 |
| 115 | 0.267 | 46 | 54 |
| 116 | 1.700 | 61 | 39 |
| 117 | 0.001 | 10 | 90 |
| 118 | 0.166 | 36 | 64 |
| 119 | 0.109 | 18 | 82 |
| 120 | 1.434 | 34 | 66 |
| 121 | >25 | 50 | 50 |
| 122 | 2.577 | 45 | 55 |
| 123 | 0.095 | 32 | 68 |
| 124 | 0.502 | 42 | 58 |
| 125 | 0.596 | 45 | 55 |
| 126 | 0.29 | 65 | 35 |
| 127 | 0.013 | 31 | 69 |
| 128 | 0.83 | 71 | 29 |
| 129 | 0.80 | 65 | 35 |
| 130 | 1.32 | 64 | 36 |
| 131 | 0.37 | 62 | 38 |
| 132 | 0.72 | 59 | 41 |
| 133 | 4.8 | 79 | 21 |
| 134 | 4.3 | 73 | 27 |
| 135 | 2.1 | 74 | 26 |
| 136 | 0.033 | 14 | 86 |
| 137 | 0.121 | 23 | 77 |
| 138 | 0.10 | 20 | 80 |
| 139 | 0.003 | 17 | 83 |
| 140 | 0.007 | 10 | 90 |
| 141 | 0.002 | 9 | 91 |
| 142 | 0.011 | 11 | 89 |
| 143 | 0.004 | 12 | 88 |
| 144 | 0.008 | 13 | 87 |
| 145 | 0.025 | 16 | 84 |
| 146 | 0.051 | 18 | 82 |
| 147 | 0.005 | 10 | 90 |
| 148 | 0.063 | 14 | 86 |
| 149 | 0.0004 | 10 | 90 |
| 150 | 0.0003 | 10 | 90 |
| 151 | 0.27 | 14 | 86 |
| 152 | 0.91 | 19 | 81 |
| 153 | 0.014 | 14 | 86 |
| 154 | 0.041 | 22 | 78 |
| 155 | 0.009 | 15 | 85 |
| 156 | 0.023 | 14 | 86 |
| 157 | 0.022 | 17 | 83 |
| 158 | 0.025 | 18 | 82 |
| 159 | 0.023 | 19 | 81 |
| 160 | 0.045 | 18 | 82 |
| 161 | 0.115 | 20 | 80 |
| 162 | 0.079 | 21 | 79 |
| 163 | 0.561 | 24 | 76 |
| 164 | 0.323 | 31 | 69 |
| 165 | 0.198 | 31 | 69 |
| 166 | 0.632 | 34 | 66 |
| 167 | 0.286 | 43 | 57 |
| 168 | 0.127 | 44 | 56 |
| 169 | 0.326 | 45 | 55 |
| 170 | 0.228 | 47 | 53 |
| 171 | 0.981 | 48 | 52 |
| 172 | 0.527 | 58 | 42 |
| 173 | 0.771 | 58 | 42 |
| 174 | 0.095 | 19 | 81 |
| 175 | 1.240 | 60 | 40 |
| 176 | 1.396 | 62 | 38 |
| 177 | 0.106 | 23 | 77 |
| 178 | 0.048 | 24 | 76 |
| 179 | 0.049 | 18 | 82 |
| 180 | 0.078 | 19 | 81 |
| 181 | 0.030 | 25 | 75 |
| 182 | 0.199 | 33 | 67 |
| 183 | 0.468 | 35 | 65 |
| 184 | 1.627 | 71 | 29 |
| 185 | 0.582 | 53 | 47 |
| 186 | 0.076 | 21 | 79 |
| 187 | 0.020 | 20 | 80 |
| 188 | 0.071 | 23 | 77 |
| 189 | 0.191 | 29 | 71 |
| 190 | 0.086 | 46 | 54 |
| 191 | 0.683 | 50 | 50 |
| 192 | 0.019 | 14 | 86 |
| 193 | 0.010 | 14 | 86 |
| 194 | 0.003 | 11 | 89 |
| 195 | 2.047 | 52 | 48 |
| 196 | 3.821 | 59 | 41 |
| 197 | 1.144 | 60 | 40 |
| 198 | 0.009 | 13 | 87 |
| 199 | 0.009 | 14 | 86 |
| 200 | 0.008 | 10 | 90 |
| 201 | 0.020 | 12 | 88 |
| 202 | 0.005 | 15 | 85 |
| 203 | 0.025 | 16 | 84 |
| 204 | 0.051 | 16 | 84 |
| 205 | 0.024 | 18 | 82 |
| 206 | 0.193 | 22 | 78 |
| 207 | 0.014 | 14 | 86 |
| 208 | 0.580 | 40 | 60 |
| 209 | 0.38 | 26 | 74 |
| 210 | 0.016 | 14 | 86 |
| 211 | 0.033 | 14 | 86 |
| 212 | 0.029 | 16 | 84 |
| 213 | 0.048 | 19 | 81 |
| 214 | 0.151 | 35 | 65 |
| 215 | 2.617 | 81 | 19 |
| 216 | 0.089 | 35 | 65 |
| 217 | 0.092 | 25 | 75 |
| 218 | 0.068 | 29 | 71 |
| 219 | 0.212 | 25 | 75 |
| 220 | 0.133 | 34 | 66 |
| 221 | 0.318 | 46 | 54 |
| 222 | 0.457 | 36 | 64 |
| 223 | 0.877 | 49 | 51 |
| 224 | 0.854 | 55 | 45 |
| 225 | 1.050 | 68 | 32 |
| 226 | 1.233 | 55 | 45 |

TABLE 1-continued

| Cmpd No. | WIZ AC$_{50}$ (μM) | WIZ Amax | % degradation of WIZ (100-Amax) |
|---|---|---|---|
| 227 | 0.956 | 40 | 60 |
| 228 | 0.704 | 45 | 55 |
| 229 | >25 | 100 | 0 |
| 230 | >25 | 100 | 0 |
| 231 | 0.15 | 47 | 53 |
| 232 | 0.206 | 52 | 48 |
| 233 | 0.589 | 60 | 40 |
| 234 | 0.942 | 58 | 42 |
| 235 | 3.277 | 65 | 35 |
| 236 | 3.198 | 95 | 5 |
| 237 | >25 | 94 | 6 |
| 238 | 0.754 | 81 | 19 |
| 239 | >25 | 100 | 0 |
| 240 | 0.025 | 20 | 80 |
| 241 | 0.351 | 56 | 44 |
| 242 | 1.604 | 93 | 7 |
| 243 | 3.065 | 87 | 13 |
| 244 | 1.179 | 47 | 53 |
| 245 | 0.351 | 48 | 52 |
| 246 | >25 | 100 | 0 |
| 247 | 1.371 | 85 | 15 |
| 248 | >25 | 100 | 0 |
| 249 | 0.30 | 59 | 41 |
| 250 | 1.35 | 59 | 41 |
| 251 | 0.165 | 82 | 18 |
| 252 | 0.277 | 58 | 42 |
| 253 | 0.531 | 77 | 23 |
| 254 | >25 | 100 | 0 |
| 255 | >25 | 100 | 0 |
| 256 | 0.186 | 22 | 78 |
| 257 | 0.101 | 26 | 74 |
| 258 | 0.148 | 31 | 69 |
| 259 | 0.258 | 39 | 61 |
| 260 | 0.796 | 32 | 68 |
| 261 | 0.417 | 37 | 63 |
| 262 | 0.583 | 32 | 68 |
| 263 | 0.88 | 45 | 55 |
| 264 | 0.26 | 36 | 64 |
| 266 | 0.044 | 19 | 81 |
| 267 | 0.10 | 14 | 86 |
| 268 | 0.024 | 11 | 89 |
| 269 | 1.02 | 51 | 49 |
| 270 | 0.099 | 43 | 57 |
| 271 | 0.702 | 37 | 63 |
| 272 | 0.025 | 31 | 69 |
| 273 | 0.040 | 22 | 78 |
| 274 | 0.032 | 23 | 77 |
| 275 | 0.020 | 21 | 79 |
| 276 | 0.009 | 15 | 84 |
| 277 | 0.203 | 24 | 76 |
| 278 | 0.066 | 28 | 72 |
| 279 | 0.026 | 9 | 91 |
| 280 | 0.008 | 12 | 88 |
| 281 | 0.004 | 17 | 83 |
| 282 | 0.001 | 19 | 81 |
| 283 | 0.029 | 19 | 80 |
| 284 | 0.018 | 20 | 80 |
| 285 | 0.003 | 18 | 82 |
| 286 | 0.031 | 20 | 79 |
| 287 | 0.015 | 19 | 81 |
| 288 | 0.008 | 20 | 80 |
| 289 | 0.033 | 21 | 79 |
| 290 | 1.70 | 46 | 54 |
| 291 | 0.015 | 17 | 83 |
| 292 | 0.011 | 17 | 83 |
| 293 | 0.065 | 24 | 76 |
| 294 | 0.018 | 19 | 81 |
| 295 | 0.024 | 20 | 80 |
| 296 | 0.010 | 23 | 77 |
| 297 | 0.029 | 32 | 68 |
| 298 | 0.242 | 49 | 51 |
| 299 | 0.009 | 18 | 82 |
| 300 | 0.003 | 18 | 82 |
| 301 | 0.002 | 14 | 86 |
| 302 | 0.042 | 16 | 84 |
| 303 | 0.046 | 20 | 80 |
| 304 | 0.002 | 13 | 87 |
| 305 | 0.002 | 15 | 85 |
| 306 | 0.008 | 16 | 84 |
| 307 | 0.006 | 16 | 84 |
| 308 | 0.044 | 23 | 77 |
| 309 | 0.056 | 38 | 62 |
| 310 | 0.15 | 27 | 73 |
| 311 | 0.31 | 22 | 78 |
| 312 | 0.37 | 56 | 44 |
| 313 | 0.085 | 30 | 70 |
| 314 | 2.56 | 66 | 34 |
| 315 | 1.02 | 47 | 53 |
| 316 | 0.061 | 17 | 83 |
| 317 | 0.031 | 20 | 80 |
| 318 | 0.010 | 13 | 87 |
| 319 | 0.004 | 21 | 78 |
| 320 | 0.018 | 21 | 78 |
| 321 | 0.067 | 22 | 78 |
| 322 | 0.031 | 14 | 86 |
| 323 | 0.004 | 17 | 83 |
| 324 | 0.108 | 28 | 72 |
| 325 | 0.047 | 18 | 82 |
| 326 | 0.049 | 13 | 87 |
| 327 | 0.653 | 46 | 54 |
| 328 | 0.338 | 48 | 52 |
| 329 | 0.166 | 17 | 83 |
| 330 | 0.041 | 18 | 82 |
| 331 | 0.073 | 24 | 76 |
| 332 | 22 | 51 | 49 |
| 333 | 0.068 | 13 | 87 |
| 334 | 0.032 | 15 | 85 |
| 335 | 0.006 | 12 | 88 |
| 336 | 12 | 24 | 76 |
| 337 | 0.399 | 17 | 83 |
| 338 | 0.033 | 17 | 83 |
| 339 | 0.715 | 65 | 35 |
| 340 | 0.862 | 68 | 32 |
| 341 | 0.799 | 70 | 30 |
| 342 | 0.916 | 63 | 37 |
| 343 | 0.495 | 54 | 46 |
| 344 | 1.07 | 65 | 35 |
| 345 | 0.191 | 27 | 73 |
| 346 | 0.108 | 13 | 87 |
| 347 | 0.378 | 11 | 89 |
| 348 | 0.400 | 14 | 86 |
| 349 | 0.118 | 14 | 86 |
| 350 | 0.028 | 10 | 90 |
| 351 | 0.047 | 9 | 91 |
| 352 | 0.192 | 10 | 90 |
| 353 | 9.1 | 30 | 70 |
| 354 | >25 | 100 | 0 |
| 355 | 0.183 | 18 | 82 |
| 356 | 0.162 | 17 | 83 |
| 357 | 0.124 | 15 | 85 |
| 358 | 0.128 | 14 | 86 |
| 359 | 0.365 | 11 | 89 |
| 360 | >25 | 76 | 24 |
| 361 | >25 | 100 | 0 |
| 362 | 0.765 | 16 | 84 |
| 363 | 0.109 | 15 | 85 |

Example 365: Small Molecule HbF Induction Assay

Cryopreserved primary human CD34$^+$ hematopoietic stem and progenitor cells were obtained from AllCells, LLC. The CD34$^+$ cells were isolated from the peripheral blood of healthy donors after mobilization by administration of granulocyte colony-stimulating factor. Cells were differentiated ex vivo toward the erythroid lineage using a 2-phase Culture method. In the first phase, cells were cultured in StemSpan™ Serum-Free Expansion Media (SFEM) (STEMCELL Technologies Inc.) supplemented with rhSCF (50 ng/mL, Peprotech®, Inc.), rhIL-6 (50 ng/mL, Peprotech®, Inc.), rhIL-3 (50 ng/mL, Peprotech®, Inc.), and rhFlt3L (50 ng/mL, Peprotech®, Inc.), and 1× antibiotic-antimycotic (Life Technologies, Thermo Fisher Scientific) for 6 days at 37° C. with 5% $CO_2$. During the second phase, cells were cultured in erythroid differentiation media at 5,000 cells/mL in the presence of compound for 7 days at 37° C. with 5% $CO_2$. Erythroid Differentiation Media is comprised of IMDM (Life Technologies) supplemented with insulin (10 µg/mL, Sigma Aldrich), heparin (2 U/mL Sigma Aldrich), holo-transferrin (330 µg/mL, Sigma Aldrich), human serum AB (5%, Sigma Aldrich), hydrocortisone (1 µM, STEMCELL Technologies), rhSCF (100 ng/mL, Peprotech®, Inc.), rhIL-3 (5 ng/mL, Peprotech®, Inc.), rhEPO (3 U/mL, Peprotech®, Inc.), and 1× antibiotic-antimycotic. All compounds were dissolved and diluted into dimethylsulfoxide (DMSO) and were added to culture media for a final concentration of 0.3% DMSO for testing in a 7-point, 1:3 dilution series starting at 30 uM.

Staining and Flow Cytometry

For viability analysis, samples were washed and resuspended in phosphate-buffered saline (PBS) and stained with LIVE/DEAD™ Fixable Violet Dead Cell Stain Kit (Life Technologies, L34963) for 20 minutes. Cells were then washed again with PBS and resuspended in PBS supplemented with 2% fetal bovine serum (FBS), and 2 mM EDTA to prepare for cell surface marker analysis. Cells were labeled with allophycocyanin-conjugated CD235a (1:100, BD Biosciences, 551336) and Brilliant Violet-conjugated CD71 (1:100, BD Biosciences, 563767) antibodies for 20 minutes. For analysis of cytoplasmic Fetal Hemoglobin (HbF), cells were fixed and permeabilized using the Fixation (BioLegend®, 420801) and Permeabilization Wash (BioLegend®, 421002) Buffers according to the manufacturer's protocol. During the permeabilization step, cells were stained with phycoerythrin-conjugated or FITC-conjugated HbF-specific antibody (1:10-1:25, Invitrogen™, MHFH04-4) for 30 minutes. Stained cells were washed with phosphate-buffered saline before analysis on the FACSCanto™ II flow cytometer or LSRFortessa™ (BD Biosciences). Data analysis was performed with FlowJo™ Software (BD Biosciences).

HbF Induction Activity of Compounds (Table 2)

mPB CD34+ cells were expanded for 6 days, then erythroid differentiated in the presence of compound for 7 days. Cells were fixed, stained and analyzed by flow cytometry. Table 2 shows HbF induction activity of the compounds. HbF Amax=the highest percentage of cells staining positive for HbF (% HbF+ cells) in the fitted dose-response curve. The baseline % HbF+ cells for DMSO-treated cells is approximately 30-40%.

TABLE 2

| Cmpd no. | HbF $EC_{50}$ (M) | HbF Amax |
|---|---|---|
| 17 | 0.266 | 80 |
| 109 | 0.129 | 77 |
| 141 | 0.006 | 90 |
| 142 | 0.038 | 89 |
| 145 | 0.030 | 76 |
| 156 | 0.012 | 81 |
| 160 | 0.999 | 84 |
| 179 | 0.074 | 79 |
| 203 | 0.045 | 82 |
| 207 | 0.089 | 85 |
| 210 | 0.064 | 86 |
| 283 | 0.127 | 61 |
| 287 | 0.060 | 63 |

Example 366: Cell Culture for shRNA and CRISPR Assays

HEK293T cells were maintained in DMEM high glucose complete media with sodium pyruvate, non-essential amino acids, 10% FBS, 2 mM L-glutamine, 100 U/mL pen/strep, 25 mM HEPES. Unless stated otherwise, all reagents for culturing HEK293T cells were obtained from Invitrogen™.

Mobilized peripheral blood (mPB) CD34+ cells (AllCells, LLC) were maintained in StemSpan™ serum-free expansion media (SFEM) (STEMCELL Technologies Inc.) supplemented with 50 ng/mL each of rhTPO, rhIL-6, rhFLT3L, rhSCF for 2-3 days prior to shRNA transduction or targeted ribonucleoprotein (RNP) electroporation targeting WIZ. All cytokines were obtained from Peprotech®, Inc. Cell cultures were maintained at 37° C. and 5% $CO_2$ in a humidified tissue culture incubator.

Generation of shRNA Lentiviral Clones Targeting WIZ

5'-phosphorylated sense and anti-sense complementary single-stranded DNA oligos of the respective shRNA against WIZ were synthesized by Integrated DNA Technologies, Inc. (IDT). Each DNA oligonucleotide was designed with PmeI/AscI restriction overhangs on 5'- and 3'-ends, respectively, for subsequent compatible ligation into the lentiviral vector backbone. Equimolar of each of the complementary oligonucleotides were annealed in NEB Buffer 2 (New England Biolabs® Inc.) by heating on a heating block at 98° C. for 5 minutes followed by cooling to room temperature on the bench top. Annealed double-stranded DNA oligonucleotides were ligated into pHAGE lentiviral backbone digested with PmeI/AscI using T4 DNA ligase kit (New England Biolabs). Ligation reactions were transformed into chemically competent Stbl3 cells (Invitrogen™) according to the manufacturer's protocol. Positive clones were verified using the sequencing primer (5'-ctacattttacatgatagg-3'; SEQ ID NO: 2) and plasmids were purified by Alta Biotech LLC.

Lentivirus particles for the respective shRNA constructs were generated by co-transfection of HEK293T cells with pCMV-dR8.91 and pCMV-VSV-G expressing envelope plasmid using Lipofectamine 3000 reagent in 150 mm tissue culture dish format as per manufacturer's instructions (Invitrogen™). Lentivirus supernatant was harvested 48 hours after co-transfection, filtered through a 0.45 µm filter (Millipore) and concentrated using Amicon Ultra 15 with Ultracel-100 membrane (Millipore). Infectious units of each of the lentivirus particle was determined by flow cytometry using eGFP expression as marker of transduction after serial dilution and infection of HEK293T cells.

The shRNA sequences are as follows:

```
shWIZ_#1
                                      (SEQ ID NO: 3)
5'-AGCCCACAATGCCACGGAAAT-3';

shWIZ_#2
                                      (SEQ ID NO: 4)
5'-GCAACATCTACACCCTCAAAT-3';
```

-continued

```
shWIZ_#4
                                  (SEQ ID NO: 5)
5'-TGACCGAGTGGTACGTCAATG-3';

shWIZ_#5
                                  (SEQ ID NO: 6)
5'-AGCGGCAGAACATCAACAAAT-3'.
```

Lentiviral shRNA Transduction and FACS of mPB CD34+ Cells mPB CD34+ transduction was performed on retronectin coated non-tissue culture treated 96 well-flat bottom plates (Corning, Inc.). Briefly, plates were coated with 100 µL of RetroNectin® (1 µg/mL) (TAKARABIO, Inc.), sealed and incubated at 4° C. overnight. RetroNectin® was then removed and plates were incubated with BSA (bovine serum albumin) (1%) in PBS for 30 minutes at room temperature. Subsequently, BSA (bovine serum albumin) was aspirated and replaced with 100 µL of lentiviral concentrate and centrifuged at 2000×g for 2 hours at room temperature. Next, residual supernatant was gently pipetted out and ready for transductions of mPB CD34+ cells. Ten thousand cells were plated in 150 µL of StemSpan™ Serum-free Expansion Medium (SFEM) supplemented with 50 ng/mL each of rhTPO, rhIL-6, rhFLT3L, rhSCF to initiate transduction. Cells were cultured for 72 hours prior to assessing transduction efficiencies using eGFP expression as a marker.

eGFP-positive cells were sorted on an FACSAria™ III (BD Biosciences). Briefly, the transduced mPB CD34+ cell population was washed and re-suspended with FACS buffer containing 1× Hank's buffered saline solution, EDTA (1 mM) and FBS (2%). Sorted eGFP-positive cells were used for the erythroid differentiation assay.

Targeting CRISPR Knockout of WIZ

Alt-R CRISPR-Cas9 crRNA and tracrRNA (5'-AG-CAUAGCAAGUUAAAAUAAGGCUAGUCCGUUAU-CAACUUGAAAAAGUGGCACCGAGUC GGUGCUUU-3'; SEQ ID NO: 7) were purchased from Integrated DNA Technologies, Inc. Equimolar tracrRNA was annealed with WIZ targeting crRNA (Table 3) in Tris buffer (10 mM, pH 7.5) by heating at 95° C. for 5 minutes using a polymerase chain reaction (PCR) machine (Bio-Rad) followed by cooling to room temperature on the benchtop. Subsequently, a ribonucleoprotein (RNP) complex was generated by mixing annealed tracrRNA:crRNA with 6 ug of Cas9 at 37° C. for 5 minutes in 1× buffer containing HEPES (100 mM), KCl (50 mM), $MgCl_2$ (2.5 mM), glycerol (0.03%), DTT (1 mM) and Tris pH 7.5 (2 mM).

Electroporation of the RNP complex was performed on a 4D-Nucleofector™ (Lonza) as per manufacturer's recommendation. Briefly, 50,000 mPB CD34+ cells resuspended in Primary Cell P3 Buffer with supplement (Lonza) were pre-mixed with 5 µL of RNP complex per well in nucleocuvettes and incubated for 5 minutes at room temperature. Subsequently, the mixture was electroporated using the CM-137 program. Cells were cultured for 72 hours post-RNP electroporation before initiating erythroid differentiation. The crRNA sequences are shown in Table 3 below.

TABLE 3

| Name | Sequence (5' to 3') | Target genomic region | Strand | SEQ ID NO |
|---|---|---|---|---|
| rg_0111 | ACGGAGGCTAAGCGTCGCAA | random guide, non-targeting | | 8 |
| WIZ_6 | AACATCTTTCGGGCCGTAGG | chr19:15427143-15427163 | (+) | 9 |
| WIZ_9 | GACATCCGCTGCGAGTTCTG | chr19:15427488-15427510 | (−) | 10 |
| WIZ_12 | TGCAGCGTCCCGGGCAGAGC | chr19:15425751-15425773 | (−) | 11 |
| WIZ_14 | CAAGCCGTGCCTCATCAAGA | chr19:15425571-15425593 | (−) | 12 |
| WIZ_15 | CGGGCACACCTGCGGCAGTT | chr19:15424942-15424964 | (−) | 13 |
| WIZ_18 | AGTGGGTGCGGCACTTACAG | chr19:15423169-15423191 | (−) | 14 |

Erythroid Differentiation of shRNA Transduced or RNP Electroporated mPB CD34+ Cells Erythroid differentiation was initiated by plating 8,000 RNP-electroporated or FACS sorted eGFP+ mPB 0034+ cells per well in 96-well tissue culture plate. Base differentiation media consists of IMDM (Iscove's Modified Dulbecco's Medium), human AB serum (5%), transferrin (330 µg/mL), Insulin (10 µg/mL) and Heparin (2 IU/mL). Differentiation media was supplemented with rhSCF (100 ng/mL), rhIL-3 (10 ng/mL), rhEPO (2.5 U/mL) and hydrocortisone (1 µM). After 4 days of differentiation, the cells were split (1:4) in fresh media to maintain optimal growth density. Cells were cultured for additional 3 days and utilized for assessment of fetal hemoglobin (HbF) expression.

Analysis of HbF Gene Expression by RNA-Seq

Two independent, targeted CRISPR/Cas9 knockout (KO) of WIZ was done using WIZ_6 and WIZ_18 gRNAs or a non-targeting scrambled gRNA negative control in mPB 0034+ HSCs. Cells from KO and negative control were then cultured for 7 days for erythroid differentiation and used for total RNA isolation (Zymo Research, catalogue #R1053). The quality of isolated RNA was determined before sequencing using Agilent RNA 6000 Pico Kit (Agilent, catalogue #5067-1513). RNA sequencing libraries were prepared using the Illumina TruSeq Stranded mRNA Sample Prep protocol and sequenced using the Illumina NovaSeq6000 platform (Illumina). Samples were sequenced to a length of 2×76 base-pairs. For each sample, salmon version 0.8.2 (Patro et al. 2017; doi: 10.1038/nmeth.4197) was used to map sequenced fragments to annotated transcripts in the human reference genome hg38 provided by the ENSEMBL database. Per-gene expression levels were obtained by summing the counts of transcript-level counts using tximport (Soneson et al. 2015; doi: 10.12688/f1000research.7563.1). DESeq2 was used to normalize for library size and transcript length differences, and to test for differential expression between samples treated with the gRNAs targeting WIZ and the samples treated with the scrambled gRNA controls (Love et al. 2014; doi: 10.1186/s13059-014-0550-8). Data were visualized using ggplot2 (Wickham H (2016). ggplot2: Elegant Graphics for Data Analysis. Springer-Verlag New York. ISBN 978-3-319-24277-4; https://ggplot2.tidyverse.org).

HbF Intracellular Staining

One hundred thousand cells were aliquoted into U-bottom 96-well plate and stained for 20 min in the dark with diluted LIVE/DEAD fixable violet viability dye as per manufacturer's recommendation (Invitrogen). Cells were washed with FACS staining buffer and subsequently stained with anti-CD71-BV711 (BD Biosciences) and anti-CD235a-APC (BD Biosciences) for 20 mins in the dark. After two rounds of washes with three volumes of 1×PBS, cells were fixed and permeabilized with 1×BD Cytofix/Cytoperm (BD Biosciences) for 30 minutes at room temperature in the dark. Subsequently, cells were washed twice with three volumes of 1× Perm/wash buffer (BD Biosciences). Anti-HbF-FITC (ThermoScientific) was diluted (1:25) in 1× perm/wash buffer, added to permeablized cells and incubated for 30 minutes at room temperature in the dark. Next, cells were washed twice with three volumes of 1× perm/wash buffer and analyzed by flow cytometry using LSR Fortessa (BD Biosciences). Data was analyzed with FlowJo software.

Results

WIZ KO Upregulates HBG1/2 Expression Upon Erythroid Differentiation

Targeted KO of WIZ using two independent gRNAs (WIZ_6 and WIZ_18) demonstrated upregulation of fetal hemoglobin genes (HBG1/2), as presented in FIG. 1A.

Figure 1B:
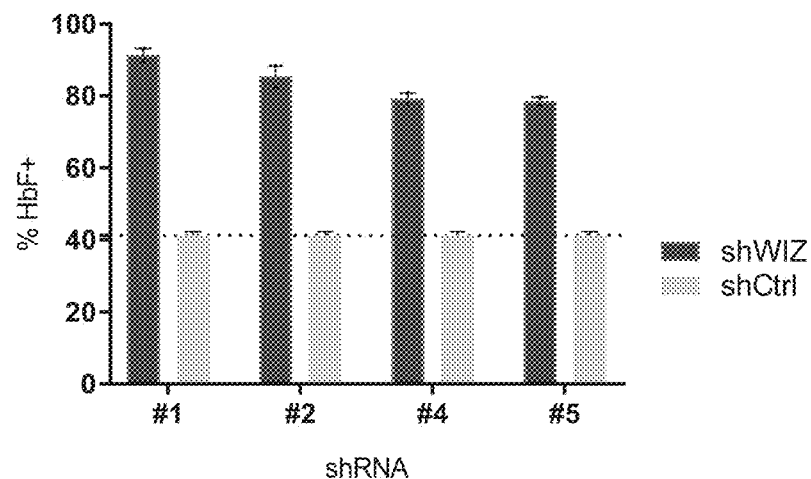
FIG. 1B depicts a bar graph showing the frequency of HbF+ cells due to shRNA-mediated loss of WIZ in human mobilized peripheral blood CD34+ derived erythroid cells.
Figure 1C:
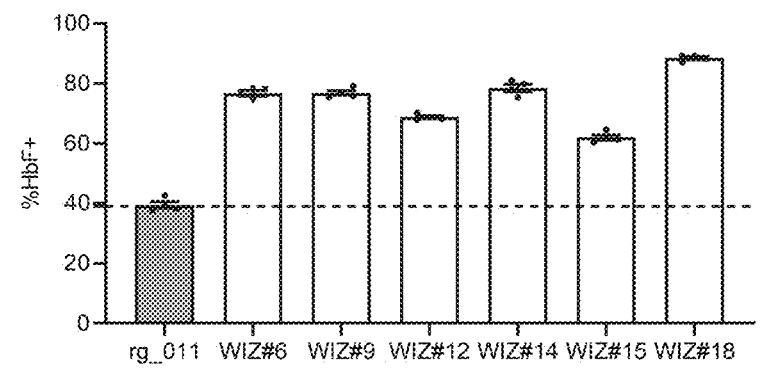
FIG. 1C depicts a bar graph showing the frequency of HbF+ cells due to CRISPR/Cas9-mediated loss of WIZ in human mobilized peripheral blood CD34+ derived erythroid cells.

Loss of WIZ Induces Fetal Hemoglobin Expression in mPB CD34+ Derived Erythroid Cells In order to validate whether WIZ is a negative regulator of HbF expression, shRNA and CRISPR-Cas9-mediated knockdown and knockout functional genetics approaches were employed. mPB CD34+ cells were treated with shRNA or CRISPR-Cas9 reagents and erythroid differentiated for 7 days prior to flow cytometry analysis. Targeted knockdown of WIZ transcript results in 78-91% HbF+ cells compared to 40% for the negative control scrambled shRNA. Error bars represent standard error of two biological replicates with three technical replicates each (FIG. 1B). CRISPR/Cas9-mediated targeted loss of WIZ results in 62-88% HbF+ cells compared to 39% for random guide crRNA. Error bars represent standard error of one biological sample with four technical replicates (FIG. 1C). To summarize, the results indicate that loss of WIZ induces HbF in human primary erythroid cells. As such, the zinc finger transcription factor Widely Interspaced Zinc Finger Motifs (WIZ) was identified as a novel target for HbF induction. These data provide genetic evidence that WIZ is a regulator of fetal hemoglobin expression and represents a novel target for the treatment of sickle cell disease and beta-thalassemia.

Having thus described several aspects of several embodiments, it is to be appreciated various alterations, modifications, and improvements will readily occur to those skilled in the art. Such alterations, modifications, and improvements are intended to be part of this disclosure, and are intended to be within the spirit and scope of the disclosure. Accordingly, the foregoing description and drawings are by way of example only.

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A method of treating or preventing a disorder that is affected by the reduction of WIZ protein levels in a subject in need thereof; inhibiting, reducing, or eliminating the activity of WIZ protein or WIZ protein expression in a subject in need thereof; inducing or promoting fetal hemoglobin in a subject in need thereof; reactivating fetal hemoglobin production or expression in a subject in need thereof; increasing fetal hemoglobin expression in a subject in need thereof; treating a hemoglobinopathy, a sickle cell disease, or beta-thalassemia in a subject in need thereof, the method comprising administering to the subject a therapeutically effective amount of a compound of Formula (I″) or a pharmaceutically acceptable salt thereof, wherein:

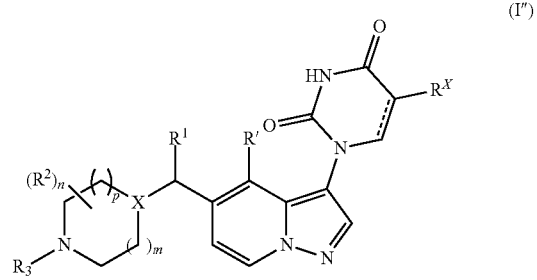

(I″)

═ is a single bond or a double bond;
X is selected from CH, CF, and N;
$R^x$ is selected from hydrogen, $C_1$-$C_6$alkyl, halo, $C_1$-$C_6$alkoxyl, and $C_3$-$C_8$cycloalkyl;
R' is selected from hydrogen and $C_1$-$C_6$alkyl;
$R^1$ is selected from hydrogen and $C_1$-$C_6$alkyl;
each $R^2$ is independently selected from $C_1$-$C_6$alkyl, $C_1$-$C_6$haloalkyl, halo, and oxo, wherein the $C_1$-$C_6$alkyl is substituted with 0-1 occurrence of $R^{2a}$; or 2 $R^2$ on non-adjacent carbon atoms together with the non-adjacent carbon atoms to which they are attached form a bridging ring;
$R^{2a}$ is selected from $C_1$-$C_6$alkoxyl and hydroxyl;
$R^3$ is selected from hydrogen, $C_1$-$C_8$alkyl, $C_2$-$C_6$alkenyl, —$SO_2R^4$, $C_1$-$C_6$haloalkyl, —C(═O)—O—($R^5$), —C(═O)—($R^6$), $C_3$-$C_{10}$cycloalkyl, and a 4- to 10-membered heterocyclyl comprising 1-2 heteroatoms independently selected from N, O and S, wherein the $C_1$-$C_8$alkyl and $C_1$-$C_6$haloalkyl are each independently substituted with 0-3 occurrences of $R^{3a}$, and wherein the $C_3$-$C_{10}$cycloalkyl and 4- to 10-membered heterocyclyl are each independently substituted with 0-3 occurrences of $R^{3b}$;
or
$R^3$ together with the nitrogen atom to which it is attached and $R^2$ together with the carbon atom to which it is attached form a 5- or 6-membered heterocyclyl comprising 0-1 additional heteroatom selected from N, O and S, which 5- or 6-membered heterocyclyl is substituted with 0-2 occurrences of an oxo group;
each $R^{3a}$ is independently selected from $C_3$-$C_{10}$cycloalkyl, a 4- to 10-membered heterocyclyl comprising 1-2 heteroatoms independently selected from N, O and S, a 5- to 10-membered heteroaryl comprising 1-4 heteroatoms independently selected from N, O, and S, $C_6$-$C_{10}$aryl, $C_1$-$C_6$alkoxyl, hydroxyl, and —C(═O)—$NR^7R^8$, wherein the $C_3$-$C_{10}$cycloalkyl, 4- to 6-membered heterocyclyl, 5- to 10-membered heteroaryl and $C_6$-$C_{10}$aryl are substituted with 0-4 occurrences of $R^{3b}$;
each $R^{3b}$ is independently selected from $C_1$-$C_6$alkoxyl, halo, $C_1$-$C_6$haloalkyl, $C_1$-$C_6$haloalkoxyl, $C_1$-$C_6$alkyl, —CN, —$SO_2NR^7R^8$, —$SO_2R^4$, and hydroxyl;
$R^4$ is selected from $C_3$-$C_8$cycloalkyl, $C_1$-$C_6$alkyl, a 4- to 6-membered heterocyclyl comprising 1-2 heteroatoms independently selected from N, O and S, $C_6$-$C_{10}$aryl, and —$NR^{4b}R^{4c}$, wherein the $C_1$-$C_6$alkyl is substituted with 0-1 occurrence of $R^{4a}$;
$R^{4a}$ is selected from $C_3$-$C_8$cycloalkyl, $C_6$-$C_{10}$aryl, and $C_1$-$C_6$alkoxyl;
$R^{4b}$ is selected from hydrogen, and $C_1$-$C_6$alkyl;
$R^{4c}$ is selected from hydrogen, $C_1$-$C_6$alkyl, and $C_3$-$C_8$cycloalkyl;
$R^5$ is selected from $C_1$-$C_6$alkyl, $C_3$-$C_8$cycloalkyl, and $C_6$-$C_{10}$aryl;
$R^6$ is selected from $C_1$-$C_6$alkyl, $C_3$-$C_8$cycloalkyl, $C_6$-$C_{10}$aryl, a 4- to 10-membered heterocyclyl comprising 1-2 heteroatoms independently selected from N, O and S, and —$NR^{4b}R^{4c}$ wherein the $C_1$-$C_6$alkyl is substituted with 0-1 occurrence of $R^{6a}$, the $C_3$-$C_8$cycloalkyl is substituted with 0-1 occurrence of $R^{6b}$ and the 4- to 10-membered heterocyclyl is substituted with 0-1 occurrence of $C_1$-$C_6$alkyl;
$R^{6a}$ is selected from $C_6$-$C_{10}$aryl and $C_3$-$C_8$cycloalkyl;
$R^{6b}$ is selected from halo, $C_1$-$C_6$haloalkyl, $C_1$-$C_6$haloalkoxyl, and $C_1$-$C_6$alkyl;
$R^7$ is selected from hydrogen and $C_1$-$C_6$alkyl;

$R^8$ is selected from hydrogen and $C_1$-$C_6$alkyl;
or
$R^7$ and $R^8$ together with the nitrogen atom to which they are attached form a 5- or 6-membered heterocyclyl comprising 0-1 additional heteroatom selected from N, O, and S;
n is 0, 1, 2, 3 or 4;
m is 0, 1 or 2; and
p is 0 or 1.

2. The method of claim 1, wherein the compound of Formula (I'') is a compound of Formula (I') or a pharmaceutically acceptable salt thereof, wherein the compound of Formula (I') is:

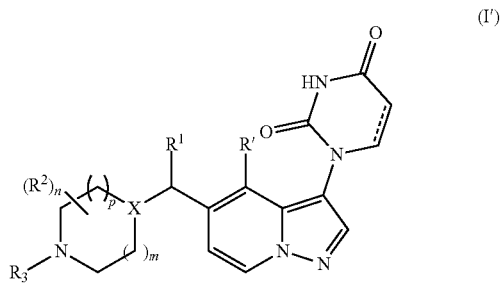

(I')

wherein
═ is a single bond or a double bond;
X is selected from CH, CF, and N;
R' is selected from hydrogen and $C_1$-$C_6$alkyl;
$R^1$ is selected from hydrogen and $C_1$-$C_6$alkyl;
each $R^2$ is independently selected from $C_1$-$C_6$alkyl, $C_1$-$C_6$haloalkyl, halo, and oxo, wherein the $C_1$-$C_6$alkyl is substituted with 0-1 occurrence of $R^{2a}$; or 2 $R^2$ on non-adjacent carbon atoms together with the non-adjacent carbon atoms to which they are attached form a bridging ring;
$R^{2a}$ is selected from $C_1$-$C_6$alkoxyl and hydroxyl;
$R^3$ is selected from hydrogen, $C_1$-$C_8$alkyl, $C_2$-$C_6$alkenyl, —$SO_2R^4$, $C_1$-$C_6$haloalkyl, —C(═O)—O—($R^5$) and —C(═O)—($R^6$), wherein the $C_1$-$C_8$alkyl and $C_1$-$C_6$haloalkyl are independently substituted with 0-3 occurrences of $R^{3a}$;
or
$R^3$ together with the nitrogen atom to which it is attached and $R^2$ together with the carbon atom to which it is attached form a 5- or 6-membered heterocyclyl comprising 0-1 additional heteroatom selected from N, O and S;
each $R^{3a}$ is independently selected from $C_3$-$C_{10}$cycloalkyl, a 4- to 6-membered heterocyclyl comprising 1-2 heteroatoms independently selected from N, O and S, a 5- to 10-membered heteroaryl comprising 1-4 heteroatoms independently selected from N, O, and S, $C_6$-$C_{10}$aryl, $C_1$-$C_6$alkoxyl, hydroxyl, and —C(═O)—$NR^7R^8$, wherein the $C_3$-$C_{10}$cycloalkyl, 4- to 6-membered heterocyclyl, 5- to 10-membered heteroaryl and $C_6$-$C_{10}$aryl are substituted with 0-4 occurrences of $R^{3b}$;
each $R^{3b}$ is independently selected from $C_1$-$C_6$alkoxyl, halo, $C_1$-$C_6$haloalkyl, $C_1$-$C_6$haloalkoxyl, $C_1$-$C_6$alkyl, —CN, —$SO_2NR^7R^8$, —$SO_2R^4$, and hydroxyl;
$R^4$ is selected from $C_3$-$C_8$cycloalkyl, $C_1$-$C_6$alkyl, a 4- to 6-membered heterocyclyl comprising 1-2 heteroatoms independently selected from N, O and S, and C$_6$-C$_{10}$aryl, wherein the C$_1$-C$_6$alkyl is substituted with 0-1 occurrence of R$^{4a}$;

R$^{4a}$ is selected from C$_3$-C$_8$cycloalkyl, C$_6$-C$_{10}$aryl, and C$_1$-C$_6$alkoxyl;

R$^5$ is selected from C$_1$-C$_6$alkyl C$_3$-C$_8$cycloalkyl, and C$_6$-C$_{10}$aryl;

R$^6$ is selected from C$_1$-C$_6$alkyl, C$_3$-C$_8$cycloalkyl, and C$_6$-C$_{10}$aryl, wherein the C$_1$-C$_6$alkyl is substituted with 0-1 occurrence of R$^{6a}$ and the C$_3$-C$_8$cycloalkyl is substituted with 0-1 occurrence of R$^{6b}$;

R$^{6a}$ is selected from C$_6$-C$_{10}$aryl and C$_3$-C$_8$cycloalkyl;

R$^{6b}$ is selected from halo, C$_1$-C$_6$haloalkyl, C$_1$-C$_6$haloalkoxyl, and C$_1$-C$_6$alkyl;

R$^7$ is selected from hydrogen and C$_1$-C$_6$alkyl;

R$^8$ is selected from hydrogen and C$_1$-C$_6$alkyl;

or

R$^7$ and R$^8$ together with the nitrogen atom to which they are attached form a 5- or 6-membered heterocyclyl comprising 0-1 additional heteroatom selected from N, O, and S;

n is 0, 1, 2, 3 or 4;

m is 0, 1 or 2; and p is 0 or 1.

3. The method of claim 1, wherein the compound of Formula (I″) is a compound of Formula (I) or a pharmaceutically acceptable salt thereof, wherein the compound of Formula (I) is:

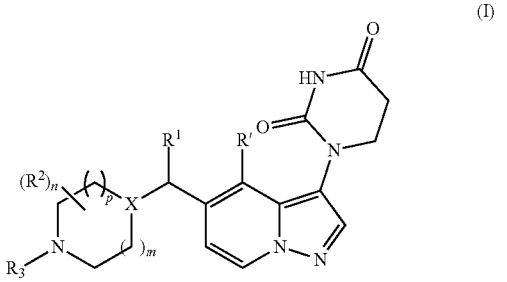

(I)

wherein

X is selected from CH, CF, and N;

R' is selected from hydrogen and C$_1$-C$_6$alkyl;

R$^1$ is selected from hydrogen and C$_1$-C$_6$alkyl;

each R$^2$ is independently selected from C$_1$-C$_6$alkyl, C$_1$-C$_6$haloalkyl, halo, and oxo, wherein the C$_1$-C$_6$alkyl is substituted with 0-1 occurrence of R$^{2a}$; or 2 R$^2$ on non-adjacent carbon atoms together with the non-adjacent carbon atoms to which they are attached form a bridging ring;

R$^{2a}$ is selected from C$_1$-C$_6$alkoxyl and hydroxyl;

R$^3$ is selected from hydrogen, C$_1$-C$_8$alkyl, C$_2$-C$_6$alkenyl, —SO$_2$R$^4$, C$_1$-C$_6$haloalkyl, —C(=O)—O—(R$^5$) and —C(=O)—(R$^6$), wherein the C$_1$-C$_8$alkyl and C$_1$-C$_6$haloalkyl are independently substituted with 0-3 occurrences of R$^{3a}$;

or

R$^3$ together with the nitrogen atom to which it is attached and R$^2$ together with the carbon atom to which it is attached form a 5- or 6-membered heterocyclyl comprising 0-1 additional heteroatom selected from N, O and S;

each R$^{3a}$ is independently selected from C$_3$-C$_{10}$cycloalkyl, a 4- to 6-membered heterocyclyl comprising 1-2 heteroatoms independently selected from N, O and S, a 5- to 10-membered heteroaryl comprising 1-4 heteroatoms independently selected from N, O, and S, C$_6$-C$_{10}$aryl, C$_1$-C$_6$alkoxyl, hydroxyl, and —C(=O)—NR$^7$R$^8$, wherein the C$_3$-C$_{10}$cycloalkyl, 4- to 6-membered heterocyclyl, 5- to 10-membered heteroaryl and C$_6$-C$_{10}$aryl are substituted with 0-4 occurrences of R$^{3b}$;

each R$^{3b}$ is independently selected from C$_1$-C$_6$alkoxyl, halo, C$_1$-C$_6$haloalkyl, C$_1$-C$_6$haloalkoxyl, C$_1$-C$_6$alkyl, —CN, —SO$_2$NR$^7$R$^8$, —SO$_2$R$^4$, and hydroxyl;

R$^4$ is selected from C$_3$-C$_8$cycloalkyl, C$_1$-C$_6$alkyl, a 4- to 6-membered heterocyclyl comprising 1-2 heteroatoms independently selected from N, O and S, and C$_6$-C$_{10}$aryl, wherein the C$_1$-C$_6$alkyl is substituted with 0-1 occurrence of R$^{4a}$;

R$^{4a}$ is selected from C$_3$-C$_8$cycloalkyl, C$_6$-C$_{10}$aryl, and C$_1$-C$_6$alkoxyl;

R$^5$ is selected from C$_1$-C$_6$alkyl C$_3$-C$_8$cycloalkyl, and C$_6$-C$_{10}$aryl;

R$^6$ is selected from C$_1$-C$_6$alkyl, C$_3$-C$_8$cycloalkyl, and C$_6$-C$_{10}$aryl, wherein the C$_1$-C$_6$alkyl is substituted with 0-1 occurrence of R$^{6a}$ and the C$_3$-C$_8$cycloalkyl is substituted with 0-1 occurrence of R$^{6b}$;

R$^{6a}$ is selected from C$_6$-C$_{10}$aryl and C$_3$-C$_8$cycloalkyl;

R$^{6b}$ is selected from halo, C$_1$-C$_6$haloalkyl, C$_1$-C$_6$haloalkoxyl, and C$_1$-C$_6$alkyl;

R$^7$ is selected from hydrogen and C$_1$-C$_6$alkyl;

R$^8$ is selected from hydrogen and C$_1$-C$_6$alkyl;

or

R$^7$ and R$^8$ together with the nitrogen atom to which they are attached form a 5- or 6-membered heterocyclyl comprising 0-1 additional heteroatom selected from N, O, and S;

n is 0, 1, 2, 3 or 4;

m is 0, 1 or 2; and p is 0 or 1.

4. The method of claim 1, wherein

X is selected from CH, CF, and N;

R' is selected from hydrogen and C$_1$-C$_3$alkyl;

R$^1$ is selected from hydrogen and C$_1$-C$_3$alkyl;

each R$^2$ is independently selected from unsubstituted C$_1$-C$_6$alkyl, C$_1$-C$_6$haloalkyl and halo; or 2 R$^2$ on non-adjacent carbon atoms together with the non-adjacent carbon atoms to which they are attached form a bridging ring;

R$^3$ is selected from hydrogen, C$_1$-C$_8$alkyl, C$_2$-C$_6$alkenyl, —SO$_2$R$^4$, C$_1$-C$_6$haloalkyl, —C(=O)—O—(R$^5$) and —C(=O)—(R$^6$), wherein the C$_1$-C$_8$alkyl and C$_1$-C$_6$haloalkyl are independently substituted with 0-3 occurrences of R$^{3a}$;

or

R$^3$ together with the nitrogen atom to which it is attached and R$^2$ together with the carbon atom to which it is attached form a 5- or 6-membered heterocyclyl comprising 0-1 additional heteroatom selected from N and O;

each R$^{3a}$ is independently selected from C$_3$-C$_{10}$cycloalkyl, a 4- to 6-membered heterocyclyl comprising 1-2 heteroatoms independently selected from N, O and S, a 5- to 10-membered heteroaryl comprising 1-4 heteroatoms independently selected from N, O, and S, C$_6$-C$_{10}$aryl, C$_1$-C$_6$alkoxyl, hydroxyl, and —C(=O)—NR$^7$R$^8$, wherein the C$_3$-C$_{10}$cycloalkyl, 4- to 6-membered heterocyclyl, 5- to 10-membered heteroaryl and C$_6$-C$_{10}$aryl are substituted with 0-4 occurrences of R$^{3b}$;

each $R^{3b}$ is independently selected from $C_1$-$C_6$alkoxyl, halo, $C_1$-$C_6$haloalkyl, $C_1$-$C_6$haloalkoxyl, $C_1$-$C_6$alkyl, —CN, —$SO_2NR^7R^8$, —$SO_2R^4$, and hydroxyl;

$R^4$ is selected from $C_3$-$C_8$cycloalkyl, $C_1$-$C_6$alkyl, a 4- to 6-membered heterocyclyl comprising 1-2 heteroatoms independently selected from N, O and S, and $C_6$-$C_{10}$aryl, wherein the $C_1$-$C_6$alkyl is substituted with 0-1 occurrence of $R^{4a}$;

$R^{4a}$ is selected from $C_3$-$C_8$cycloalkyl, $C_6$-$C_{10}$aryl, and $C_1$-$C_6$alkoxyl;

$R^5$ is selected from $C_1$-$C_6$alkyl $C_3$-$C_8$cycloalkyl, and $C_6$-$C_{10}$aryl;

$R^6$ is selected from $C_1$-$C_6$alkyl, $C_3$-$C_8$cycloalkyl, and $C_6$-$C_{10}$aryl, wherein the $C_1$-$C_6$alkyl is substituted with 0-1 occurrence of $R^{6a}$ and the $C_3$-$C_8$cycloalkyl is substituted with 0-1 occurrence of $R^{6b}$;

$R^{6a}$ is selected from $C_6$-$C_{10}$aryl and $C_3$-$C_8$cycloalkyl;

$R^{6b}$ is selected from chloro, fluoro, $C_1$-$C_6$haloalkyl, $C_1$-$C_6$haloalkoxyl, and $C_1$-$C_6$alkyl;

$R^7$ is selected from hydrogen and $C_1$-$C_6$alkyl;

$R^8$ is selected from hydrogen and $C_1$-$C_6$alkyl;

or $R^7$ and $R^8$ together with the nitrogen atom to which they are attached form a 5- or 6-membered heterocyclyl comprising 0-1 additional heteroatom selected from N, O, and S;

n is 0, 1, 2 or 3;

m is 0, 1 or 2; and p is 0 or 1.

5. The method of claim 1, wherein

X is selected from CH and N;

R' is selected from hydrogen and methyl;

$R^1$ is selected from hydrogen and methyl;

each $R^2$ is independently selected from unsubstituted $C_1$-$C_6$alkyl and halo; or 2 $R^2$ on non-adjacent carbon atoms together with the non-adjacent carbon atoms to which they are attached form a $C_1$-$C_3$alkylene bridging ring;

$R^3$ is selected from hydrogen, $C_1$-$C_8$alkyl, $C_2$-$C_6$alkenyl, —$SO_2R^4$, $C_1$-$C_6$haloalkyl, —C(=O)—O—($R^5$) and —C(=O)—($R^6$), wherein the $C_1$-$C_8$alkyl and $C_1$-$C_6$haloalkyl are independently substituted with 0-3 occurrences of $R^{3a}$;

or $R^3$ together with the nitrogen atom to which it is attached and $R^2$ together with the carbon atom to which it is attached form a 5- or 6-membered heterocyclyl comprising 0-1 additional O heteroatom;

each $R^{3a}$ is independently selected from $C_3$-$C_{10}$cycloalkyl, a 4- to 6-membered heterocyclyl comprising 1-2 heteroatoms independently selected from N, O and S, a 5- to 10-membered heteroaryl comprising 1-4 heteroatoms independently selected from N, O, and S and phenyl, wherein the $C_3$-$C_{10}$cycloalkyl, 4- to 6-membered heterocyclyl, 5- to 10-membered heteroaryl and phenyl are substituted with 0-4 occurrences of $R^{3b}$;

each $R^{3b}$ is independently selected from $C_1$-$C_6$alkoxyl, halo, $C_1$-$C_6$haloalkyl, $C_1$-$C_6$haloalkoxyl, $C_1$-$C_6$alkyl, —CN, —$SO_2NR^7R^8$, —$SO_2R^4$, and hydroxyl;

$R^4$ is selected from $C_3$-$C_8$cycloalkyl, $C_1$-$C_6$alkyl, a 4- to 6-membered heterocyclyl comprising 1-2 heteroatoms independently selected from N, O and S, and $C_6$-$C_{10}$aryl, wherein the $C_1$-$C_6$alkyl is substituted with 1 occurrence of $R^{4a}$;

$R^{4a}$ is selected from $C_3$-$C_8$cycloalkyl, $C_6$-$C_{10}$aryl, and $C_1$-$C_6$alkoxyl;

$R^5$ is selected from $C_1$-$C_6$alkyl $C_3$-$C_6$cycloalkyl, and $C_6$-$C_{10}$aryl;

$R^6$ is selected from $C_1$-$C_6$alkyl, $C_3$-$C_8$cycloalkyl, and $C_6$-$C_{10}$aryl, wherein the $C_1$-$C_6$alkyl is substituted with 0-1 occurrence of $R^{6a}$ and the $C_3$-$C_8$cycloalkyl is substituted with 0-1 occurrence of $R^{6b}$;

$R^{6a}$ is selected from $C_6$-$C_{10}$aryl and $C_3$-$C_8$cycloalkyl;

$R^{6b}$ is selected from chloro, fluoro, $C_1$-$C_6$haloalkyl, $C_1$-$C_6$haloalkoxyl, and $C_1$-$C_6$alkyl;

$R^7$ is selected from hydrogen and $C_1$-$C_6$alkyl;

$R^8$ is selected from hydrogen and $C_1$-$C_6$alkyl;

or $R^7$ and $R^8$ together with the nitrogen atom to which they are attached form a 5- or 6-membered heterocyclyl comprising 0-1 additional heteroatom selected from N, O, and S;

n is 0, 1, 2 or 3;

m is 0, 1 or 2; and p is 0 or 1.

6. The method of claim 1, wherein

X is selected from CH and N;

R' is hydrogen;

$R^1$ is hydrogen;

each $R^2$ is independently selected from unsubstituted $C_1$-$C_3$alkyl;

$R^3$ is selected from $C_1$-$C_6$alkyl, $C_2$-$C_6$alkenyl, —$SO_2R^4$ and unsubstituted $C_1$-$C_6$haloalkyl, wherein the $C_1$-$C_6$alkyl is substituted with 0-2 occurrences of $R^{3a}$;

each $R^{3a}$ is independently selected from $C_3$-$C_{10}$cycloalkyl, a 4- to 6-membered heterocyclyl comprising 1 O heteroatom, a 6-membered heteroaryl comprising 1-2 N heteroatoms and phenyl, wherein the $C_3$-$C_{10}$cycloalkyl, 4- to 6-membered heterocyclyl, 6-membered heteroaryl and phenyl are substituted with 0-2 occurrences of $R^{3b}$;

each $R^{3b}$ is independently selected from chloro, fluoro, $C_1$-$C_6$haloalkyl, $C_1$-$C_6$haloalkoxyl and $C_1$-$C_6$alkyl;

$R^4$ is selected from $C_3$-$C_8$cycloalkyl, $C_1$-$C_6$alkyl, a 4- to 6-membered heterocyclyl comprising 1 O heteroatom and phenyl, wherein the $C_1$-$C_6$alkyl is substituted with 1 occurrence of $R^{4a}$;

$R^{4a}$ is selected from $C_3$-$C_8$cycloalkyl and phenyl;

n is 0, 1 or 2;

m is 1 or 2; and p is 1.

7. The method of claim 1, wherein the compound is of Formula (Ia):

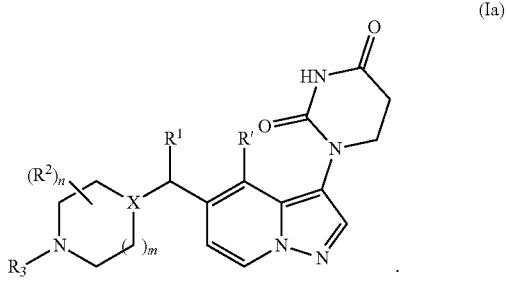

(Ia)

8. The method of claim 1, wherein $R^3$ is selected from methyl, ethyl, n-propyl, i-propyl, 2-propanyl, butyl, i-butyl, 2-butyl, 3-methyl-2-butyl, i-pentyl, 3-pentanyl, neopentyl, 2,4-dimethylpentanyl, and —$CH_2$—$(CH_2)_{0-1}$—$R^{3a}$.

9. The method of claim 1, wherein $R^{3a}$ is $C_3$-$C_{10}$cycloalkyl, wherein the $C_3$-$C_{10}$cycloalkyl is substituted with 0-4 occurrences of $R^{3b}$, wherein each $R^{3b}$ is independently selected from $C_1$-$C_6$alkoxyl, chloro, fluoro, $C_1$-$C_6$haloalkyl, $C_1$-$C_6$haloalkoxyl and $C_1$-$C_6$alkyl.

10. The method of claim 1, wherein $R^{3a}$ is selected from cyclopropyl, cyclobutyl, cyclopentyl, cyclohexyl, cycloheptyl, adamantanyl

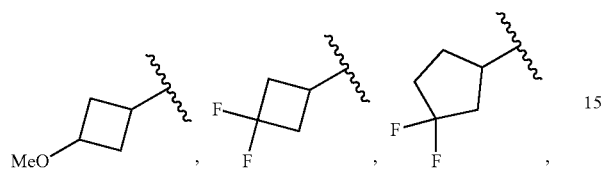

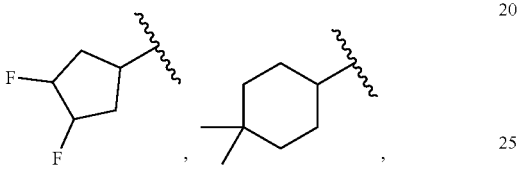

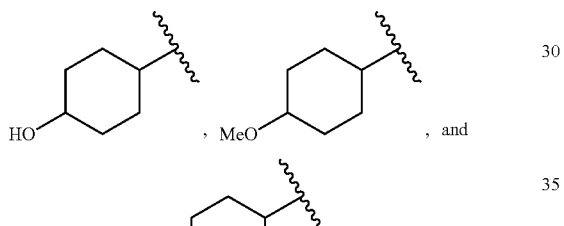

, and

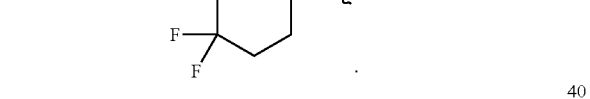

.

11. The method of claim 1, wherein === is a single bond.

12. The method of claim 1, wherein the compound is:

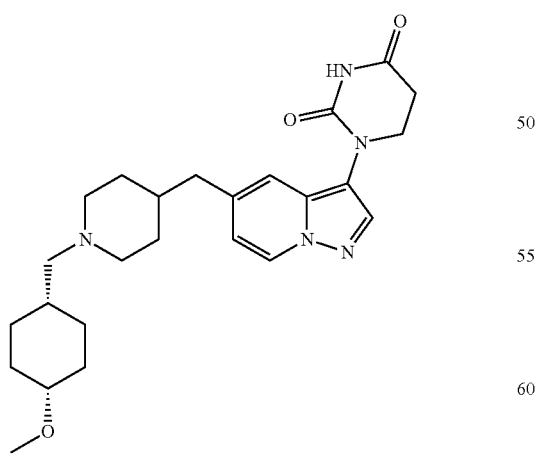

1-(5-((1-(((1s,4s)-4-methoxycyclohexyl)methyl)piperazin-4-yl)methyl)pyrazolo[1,5-a]pyridin-3-yl)dihydropyrimidine-2,4(1H,3H)-dione

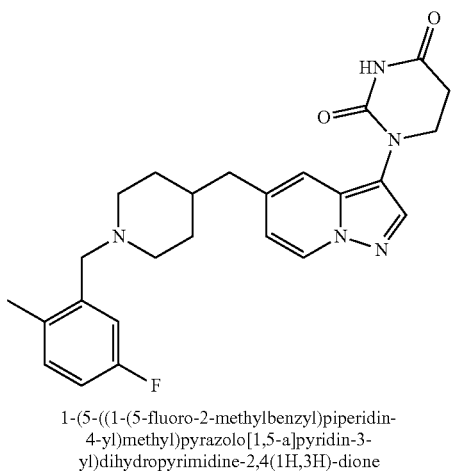

1-(5-((1-(5-fluoro-2-methylbenzyl)piperidin-4-yl)methyl)pyrazolo[1,5-a]pyridin-3-yl)dihydropyrimidine-2,4(1H,3H)-dione

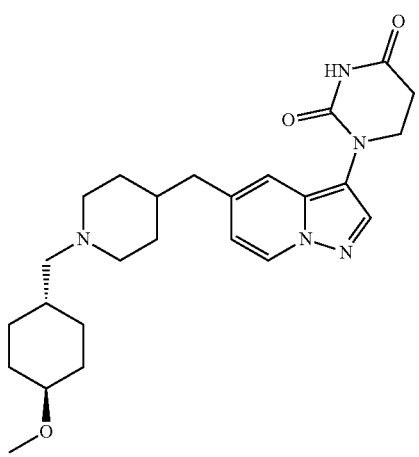

1-(5-((1-(((1r,4r)-4-methoxycyclohexyl)methyl)piperidin-4-yl)methyl)pyrazolo[1,5-a]pyridin-3-yl)dihydropyrimidine-2,4(1H,3H)-dione

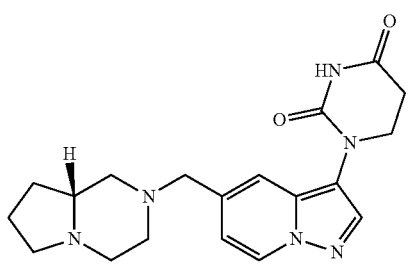

(R)-1-(5-((hexahydropyrrolo[1,2-a]pyrazin-2(1H)-yl)methyl)pyrazolo[1,5-a]pyridin-3-yl)dihydropyrimidine-2,4(1H,3H)-dione -continued

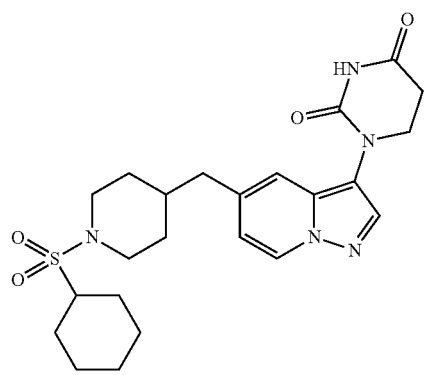

1-(5-((1-(cyclohexylsulfonyl)piperidin-4-
yl)methyl)pyrazolo[1,5-a]pyridin-3-
yl)dihydropyrimidine-2,4(1H,3H)-dione

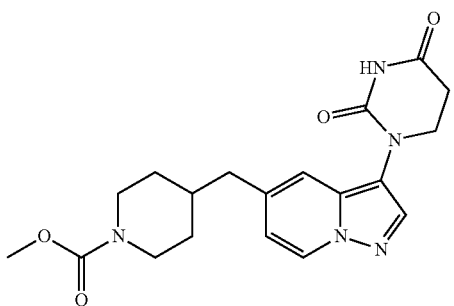

methyl 4-((3-(2,4-dioxotetrahydropyrimidin-
1(2H)-yl)pyrazolo[1,5-a]pyridin-5-
yl)methyl)piperidine-1-carboxylate

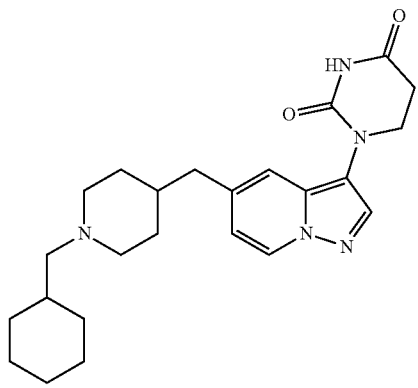

1-(5-((1-(cyclohexylmethyl)piperidin-4-
yl)methyl)pyrazolo[1,5-a]pyridin-3-
yl)dihydropyrimidine-2,4(1H,3H)-dione

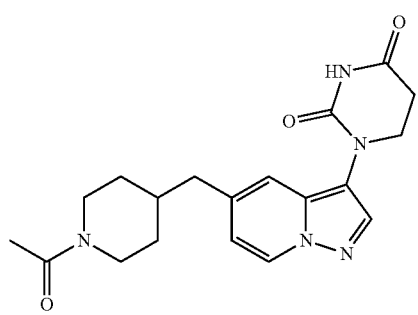

1-(5-((1-acetylpiperidin-4-
yl)methyl)pyrazolo[1,5-a]pyridin-3-
yl)dihydropyrimidine-2,4(1H,3H)-dione -continued

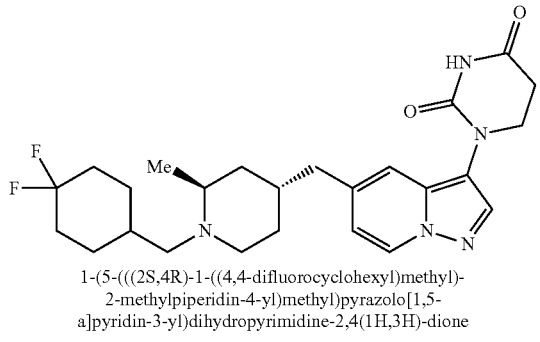

1-(5-((((2S,4R)-1-((4,4-difluorocyclohexyl)methyl)-
2-methylpiperidin-4-yl)methyl)pyrazolo[1,5-
a]pyridin-3-yl)dihydropyrimidine-2,4(1H,3H)-dione

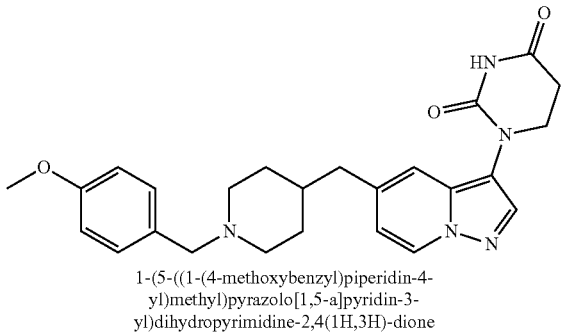

1-(5-((1-(4-methoxybenzyl)piperidin-4-
yl)methyl)pyrazolo[1,5-a]pyridin-3-
yl)dihydropyrimidine-2,4(1H,3H)-dione

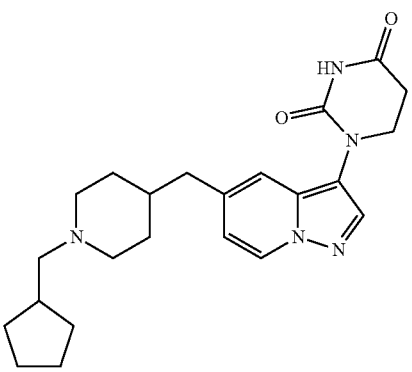

1-(5-((1-(cyclopentylmethyl)piperidin-4-
yl)methyl)pyrazolo[1,5-a]pyridin-3-
yl)dihydropyrimidine-2,4(1H,3H)-dione

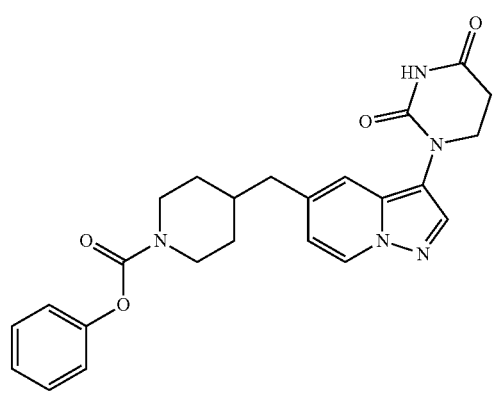

phenyl 4-((3-(2,4-dioxotetrahydropyrimidin-
1(2H)-yl)pyrazolo[1,5-a]pyridin-5-
yl)methyl)piperidine-1-carboxylate

463

-continued

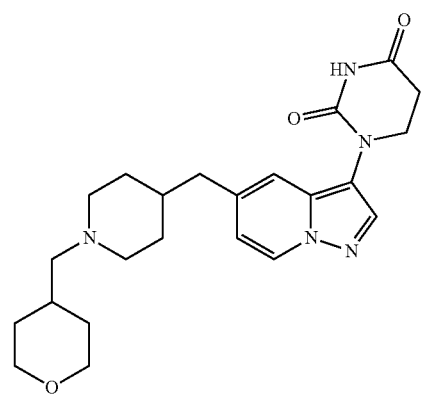

1-(5-((1-((tetrahydro-2H-pyran-4-
yl)methyl)piperidin-4-
yl)methyl)pyrazolo[1,5-a]pyridin-3-
yl)dihydropyrimidine-2,4(1H,3H)-dione

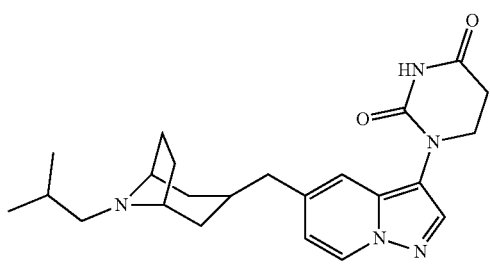

1-(5-(((1R,5S)-8-isobutyl-8-
azabicyclo[3.2.1]octan-3-
yl)methyl)pyrazolo[1,5-a]pyridin-3-
yl)dihydropyrimidine-2,4(1H,3H)-dione

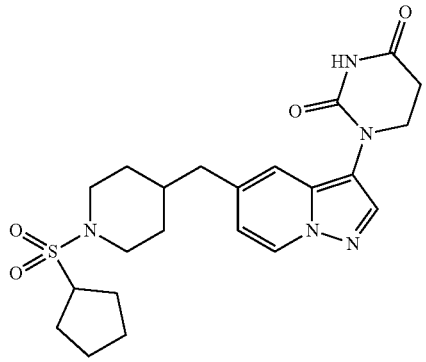

1-(5-((1-(cyclopentylsulfonyl)piperidin-4-
yl)methyl)pyrazolo[1,5-a]pyridin-3-
yl)dihydropyrimidine-2,4(1H,3H)-dione

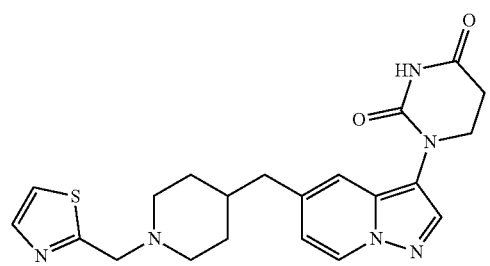

1-(5-((1-(thiazol-2-ylmethyl)piperidin-4-
yl)methyl)pyrazolo[1,5-a]pyridin-3-
yl)dihydropyrimidine-2,4(1H,3H)-dione

464

-continued

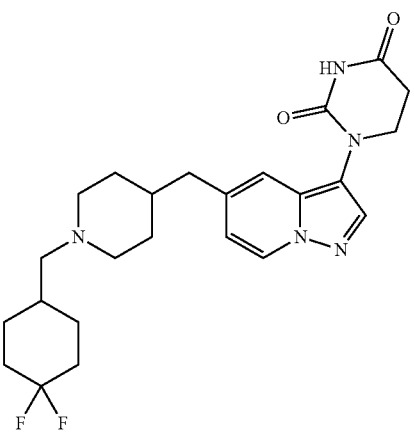

1-(5-((1-((4,4-
difluorocyclohexyl)methyl)piperidin-4-
yl)methyl)pyrazolo[1,5-a]pyridin-3-
yl)dihydropyrimidine-2,4(1H,3H)-dione

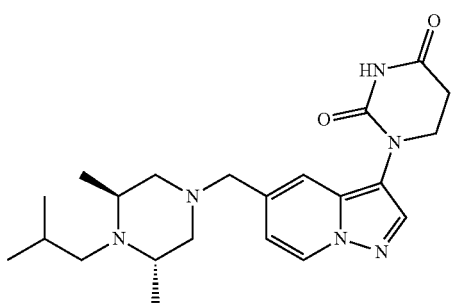

1-(5-(((3S,5S)-4-isobutyl-3,5-
dimethylpiperazin-1-yl)methyl)pyrazolo[1,5-
a]pyridin-3-yl)dihydropyrimidine-
2,4(1H,3H)-dione

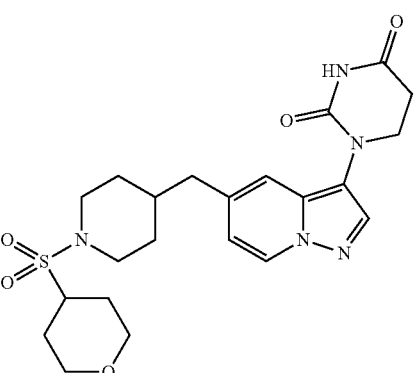

1-(5-((1-((tetrahydro-2H-pyran-4-
yl)sulfonyl)piperidin-4-
yl)methyl)pyrazolo[1,5-a]pyridin-3-
yl)dihydropyrimidine-2,4(1H,3H)-dione -continued

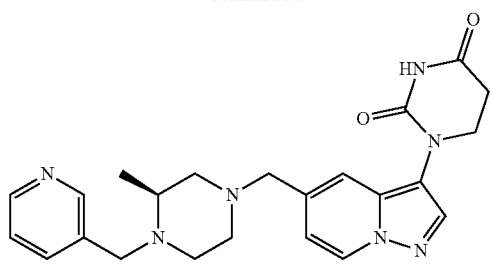

(S)-1-(5-((3-methyl-4-(pyridin-3-ylmethyl)piperazin-1-yl)methyl)pyrazolo[1,5-a]pyridin-3-yl)dihydropyrimidine-2,4(1H,3H)-dione

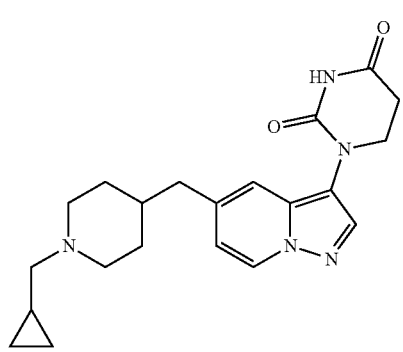

1-(5-((1-(cyclopropylmethyl)piperidin-4-yl)methyl)pyrazolo[1,5-a]pyridin-3-yl)dihydropyrimidine-2,4(1H,3H)-dione

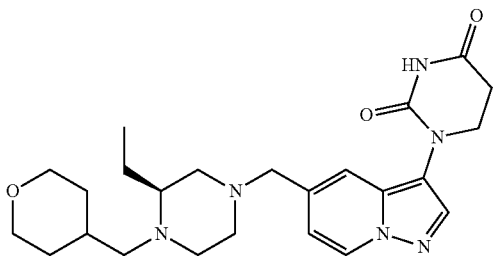

(S)-1-(5-(((3-ethyl-4-((tetrahydro-2H-pyran-4-yl)methyl)piperazin-1-yl)methyl)pyrazolo[1,5-a]pyridin-3-yl)dihydropyrimidine-2,4(1H,3H)-dione

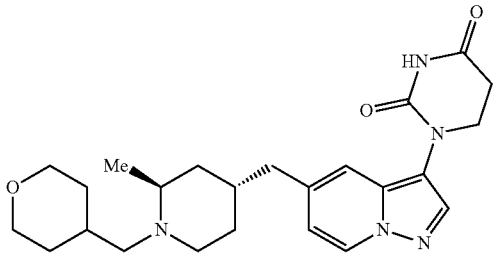

1-(5-(((2S,4R)-2-methyl-1-((tetrahydro-2H-pyran-4-yl)methyl)piperidin-4-yl)methyl)pyrazolo[1,5-a]pyridin-3-yl)dihydropyrimidine-2,4(1H,3H)-dione -continued

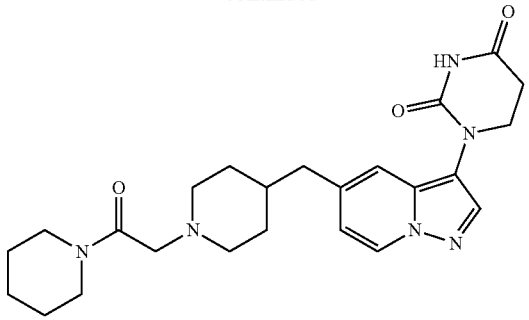

1-(5-((1-(2-oxo-2-(piperidin-1-yl)ethyl)piperidin-4-yl)methyl)pyrazolo[1,5-a]pyridin-3-yl)dihydropyrimidine-2,4(1H,3H)-dione

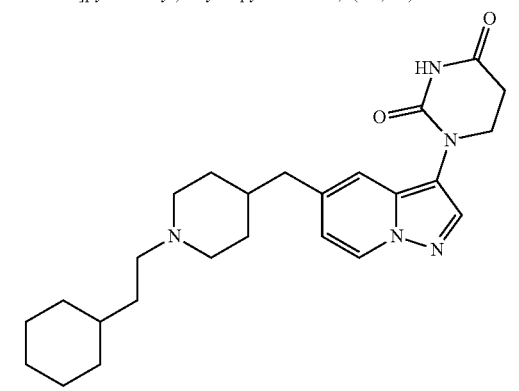

1-(5-((1-(2-cyclohexylethyl)piperidin-4-yl)methyl)pyrazolo[1,5-a]pyridin-3-yl)dihydropyrimidine-2,4(1H,3H)-dione

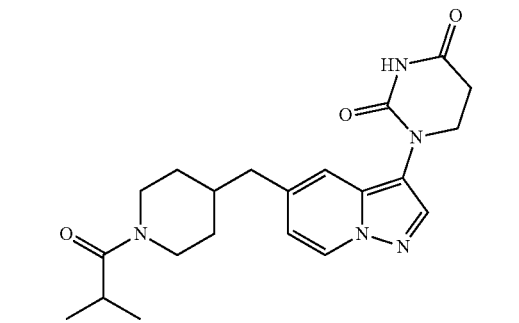

1-(5-((1-isobutyrylpiperidin-4-yl)methyl)pyrazolo[1,5-a]pyridin-3-yl)dihydropyrimidine-2,4(1H,3H)-dione

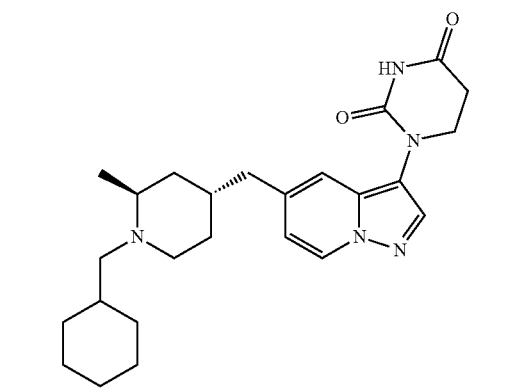

1-(5-(((2S,4R)-1-(cyclohexylmethyl)-2-methylpiperidin-4-yl)methyl)pyrazolo[1,5-a]pyridin-3-yl)dihydropyrimidine-2,4(1H,3H)-dione 467
-continued

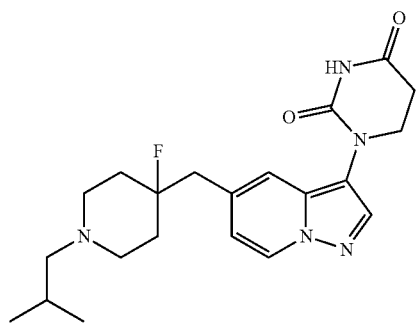

1-(5-((4-fluoro-1-isobutylpiperidin-4-yl)methyl)pyrazolo[1,5-a]pyridin-3-yl)dihydropyrimidine-2,4(1H,3H)-dione

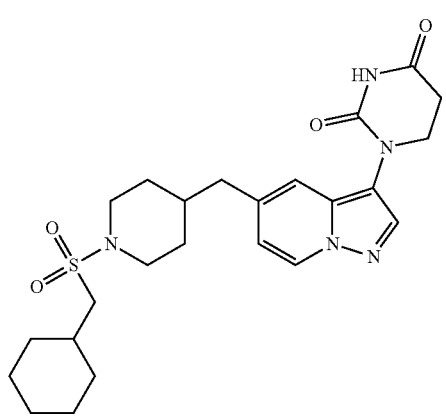

1-(5-((1-((cyclohexylmethyl)sulfonyl)piperidin-4-yl)methyl)pyrazolo[1,5-a]pyridin-3-yl)dihydropyrimidine-2,4(1H,3H)-dione

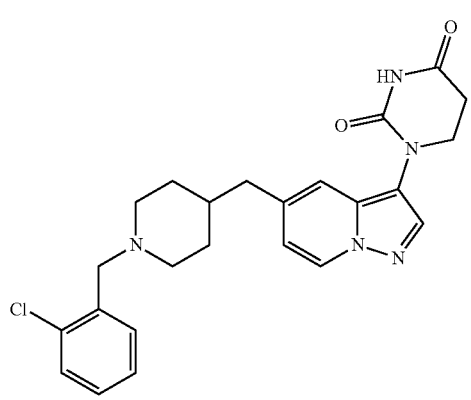

1-(5-((1-(2-chlorobenzyl)piperidin-4-yl)methyl)pyrazolo[1,5-a]pyridin-3-yl)dihydropyrimidine-2,4(1H,3H)-dione 468
-continued

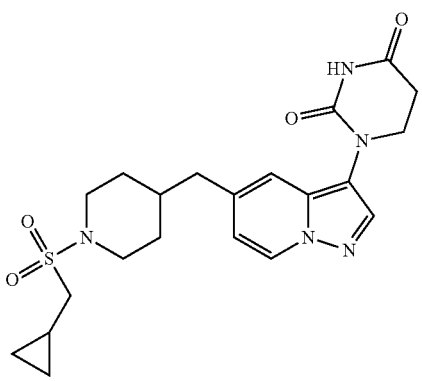

1-(5-((1-((cyclopropylmethyl)sulfonyl)piperidin-4-yl)methyl)pyrazolo[1,5-a]pyridin-3-yl)dihydropyrimidine-2,4(1H,3H)-dione

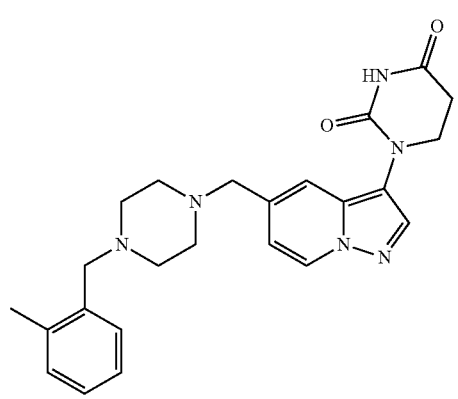

1-(5-((4-(2-methylbenzyl)piperidin-1-yl)methyl)pyrazolo[1,5-a]pyridin-3-yl)dihydropyrimidine-2,4(1H,3H)-dione

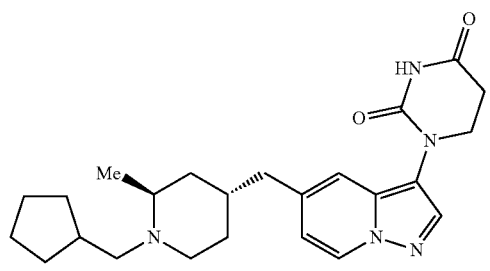

1-(5(((2S,4R)-1-(cyclopentylmethyl)-2-methylpiperidin-4-yl)methyl)pyrazolo[1,5-a]pyridin-3-yl)dihydropyrimidine-2,4(1H,3H)-dione

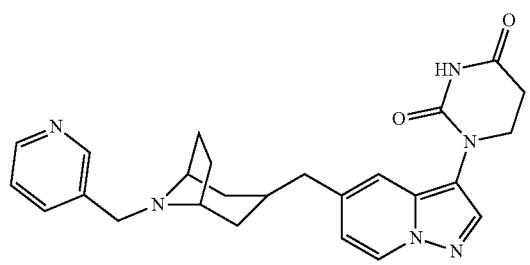

1-(5-(((1R,5S)-8(pyridin-3-ylmethyl)-8-azabicyclo[3.2.1]octan-3-yl)methyl)pyrazolo[1,5-a]pyridin-3-yl)dihydropyrimidine-2,4(1H,3H)-dione

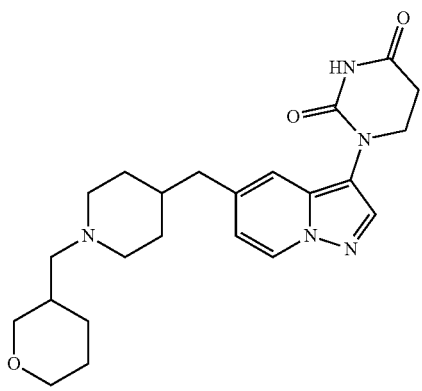

1-(5-((1-((tetrahydro-2H-pyran-3-yl)methyl)piperidin-4-yl)methyl)pyrazolo[1,5-a]pyridin-3-yl)dihydropyrimidine-2,4(1H,3H)-dione

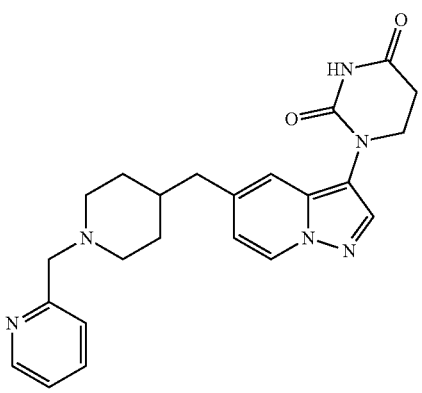

1-(5-((1-(pyridin-2-ylmethyl)piperidin-4-yl)methyl)pyrazolo[1,5-a]pyridin-3-yl)dihydropyrimidine-2,4(1H,3H)-dione

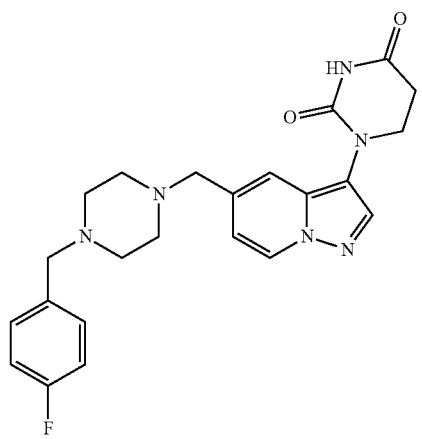

1-(5-((4-(4-fluorobenzyl)piperazin-1-yl)methyl)pyrazolo[1,5-a]pyridin-3-yl)dihydropyrimidine-2,4(1H,3H)-dione

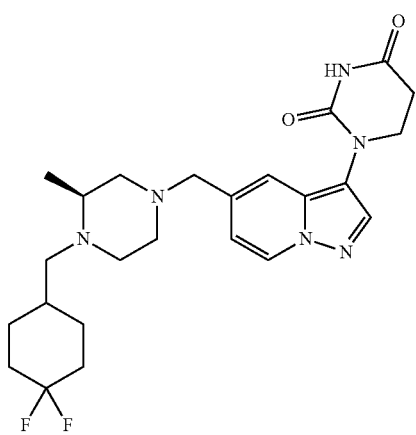

(S)-1-(5-((4-((4,4-difluorocyclohexyl)methyl)-3-methylpiperazin-1-yl)methyl)pyrazolo[1,5-a]pyridin-3-yl)dihydropyrimidine-2,4(1H,3H)-dione

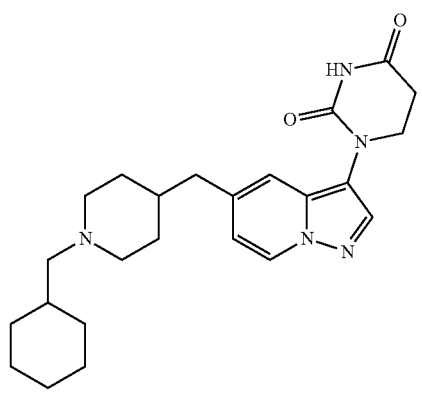

1-(5-((4-(cyclohexylmethyl)piperazin-1-yl)methyl)pyrazolo[1,5-a]pyridin-3-yl)dihydropyrimidine-2,4(1H,3H)-dione

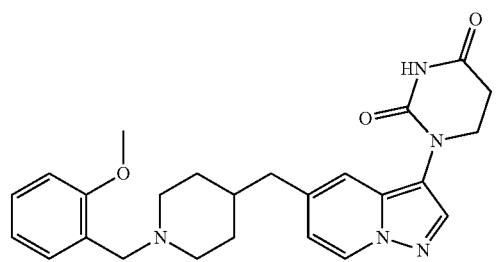

1-(5-((1-(2-methoxybenzyl)piperidin-4-yl)methyl)pyrazolo[1,5-a]pyridin-3-yl)dihydropyrimidine-2,4(1H,3H)-dione

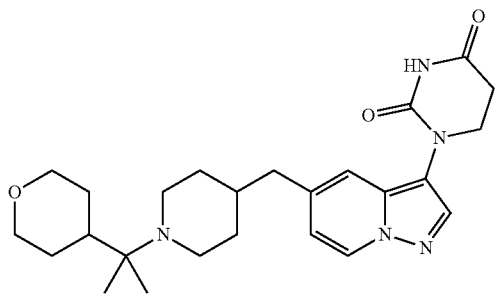

1-(5-((1-(2-(tetrahydro-2H-pyran-4-yl)propan-2-yl)piperidin-4-yl)methyl)pyrazolo[1,5-a]pyridin-3-yl)dihydropyrimidine-2,4(1H,3H)-dione

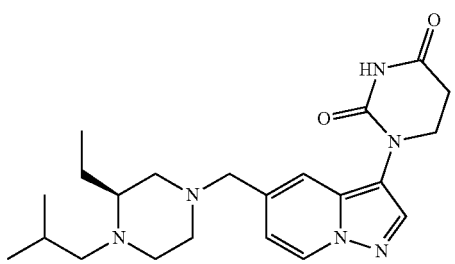

(S)-1-(5-(((3-ethyl-4-isobutylpiperazin-1-yl)methyl)pyrazolo[1,5-a]pyridin-3-yl)dihydropyrimidine-2,4(1H,3H)-dione

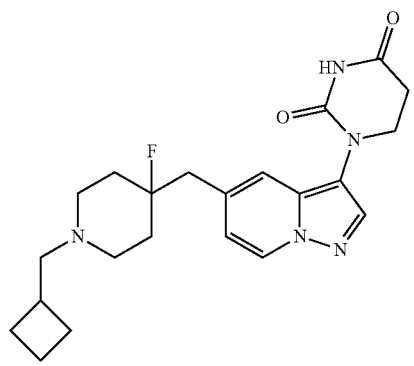

1-(5-((1-(cyclobutylmethyl)-4-fluoropiperidin-4-yl)methyl)pyrazolo[1,5-a]pyridin-3-yl)dihydropyrimidine-2,4(1H,3H)-dione

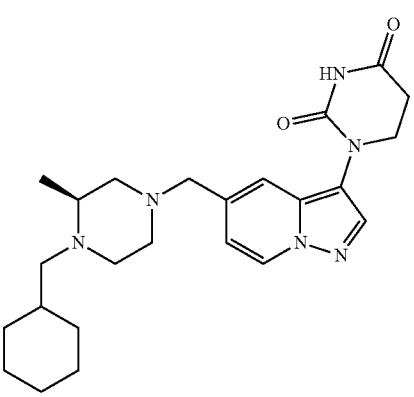

(S)-1-(5-((4-(cyclohexylmethyl)-3-methylpiperazin-1-yl)methyl)pyrazolo[1,5-a]pyridin-3-yl)dihydropyrimidine-2,4(1H,3H)-dione

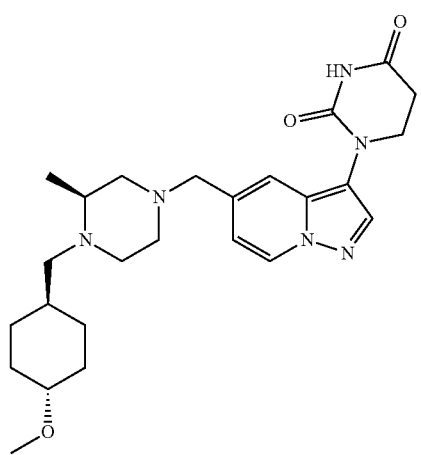

(1-(5-(((S)-4-(((1r,4S)-4-methoxycyclohexyl)methyl)-3-methylpiperazin-1-yl)methyl)pyrazolo[1,5-a]pyridin-3-yl)dihydropyrimidine-2,4(1H,3H)-dione

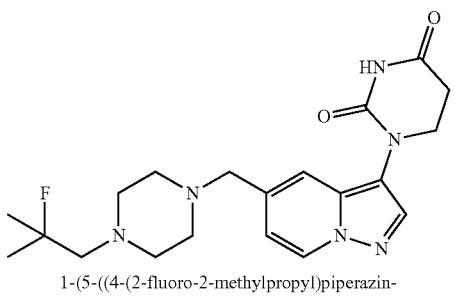

1-(5-((4-(2-fluoro-2-methylpropyl)piperazin-1-yl)methyl)pyrazolo[1,5-a]pyridin-3-yl)dihydropyrimidine-2,4(1H,3H)-dione

473

-continued

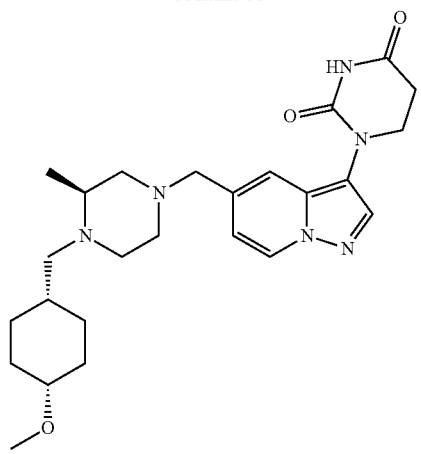

(1-(5-(((S)-4-(((1s,4R)-4-
methoxycyclohexyl)methyl)-3-
methylpiperazin-1-yl)methyl)pyrazolo[1,5-
a]pyridin-3-yl)dihydropyrimidine-
2,4(1H,3H)-dione

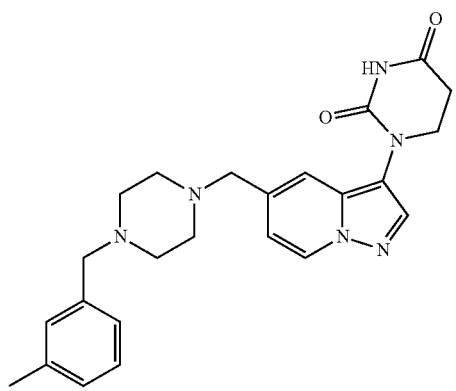

1-(5-((4-(3-methylbenzyl)piperazin-1-
yl)methyl)pyrazolo[1,5-a]pyridin-3-
yl)dihydropyrimidine-2,4(1H,3H)-dione

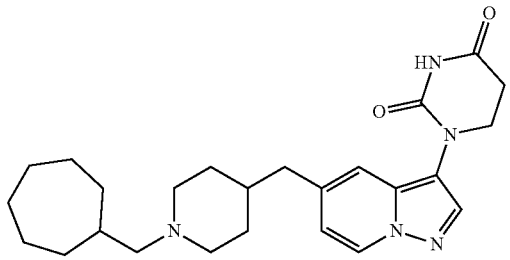

1-(5-((1-(cycloheptylmethyl)piperidin-4-
yl)methyl)pyrazolo[1,5-a]pyridin-3-
yl)dihydropyrimidine-2,4(1H,3H)-dione

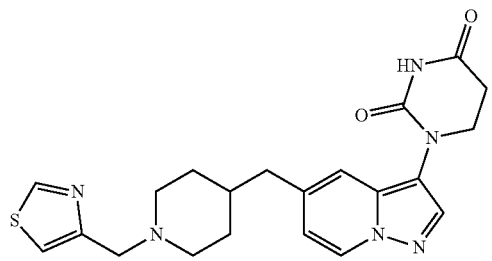

1-(5-((1-(thiazol-4-ylmethyl)piperidin-4-
yl)methyl)pyrazolo[1,5-a]pyridin-3-
yl)dihydropyrimidine-2,4(1H,3H)-dione

474

-continued

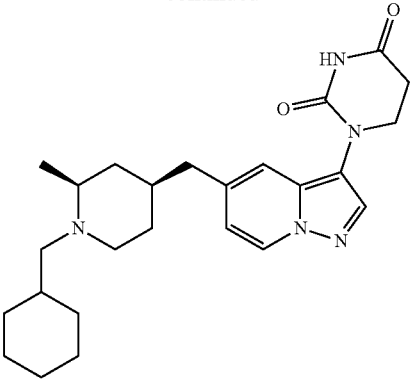

1-(5-(((2S,4S)-1-(cyclohexylmethyl)-2-
methylpiperidin-4-yl)methyl)pyrazolo[1,5-
a]pyridin-3-yl)dihydropyrimidine-2,4(1H,3H)-dione

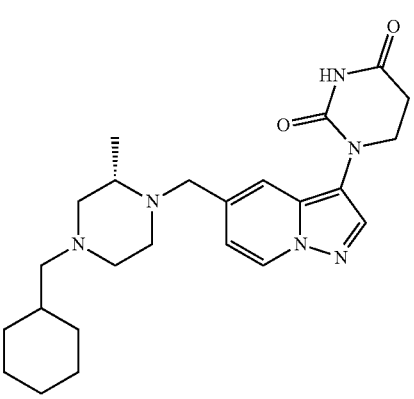

(S)-1-(5-((4-(cyclohexylmethyl)-2-
methylpiperazin-1-yl)methyl)pyrazolo[1,5-
a]pyridin-3-yl)dihydropyrimidine-2,4(1H,3H)-dione

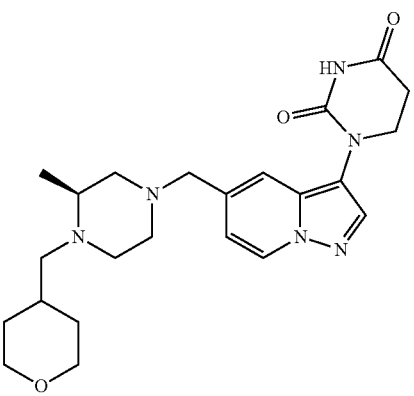

(S)-1-(5-((3-methyl-4-((tetrahydro-2H-pyran-
4-yl)methyl)piperazin-1-yl)methyl)pyrazolo[1,5-
a]pyridin-3-yl)dihydropyrimidine-2,4(1H,3H)-dione 475
-continued

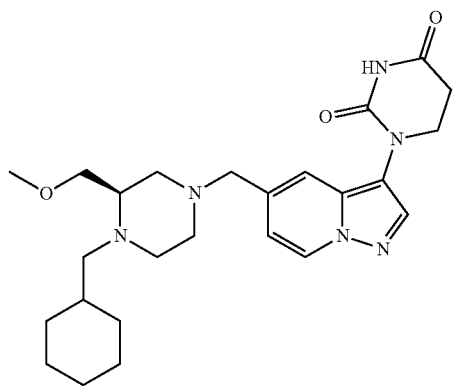

(R)-1-(5-((4-(cyclohexylmethyl)-3-
(methoxymethyl)piperazin-1-yl)methyl)pyrazolo[1,5-
a]pyridin-3-yl)dihydropyrimidine-2,4(1H,3H)-dione

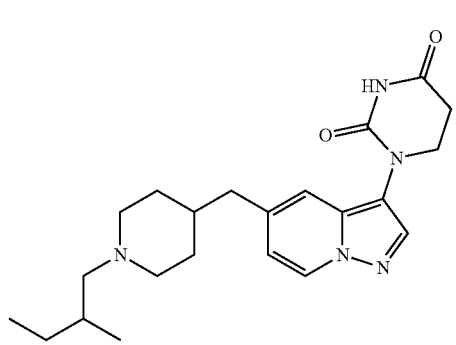

(1-(5-((1-(2-methylbutyl)piperidin-4-
yl)methyl)pyrazolo[1,5-a]pyridin-3-
yl)dihydropyrimidine-2,4(1H,3H)-dione

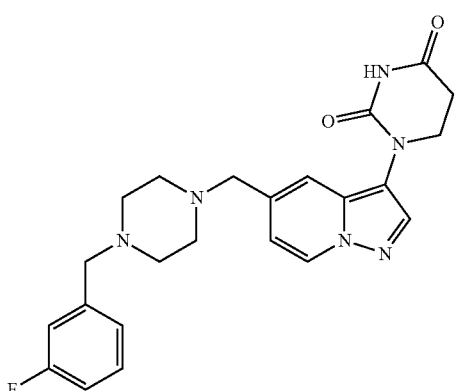

(1-(5-((4-(3-fluorobenzyl)piperazin-1-
yl)methyl)pyrazolo[1,5-a]pyridin-3-
yl)dihydropyrimidine-2,4(1H,3H)-dione 476
-continued

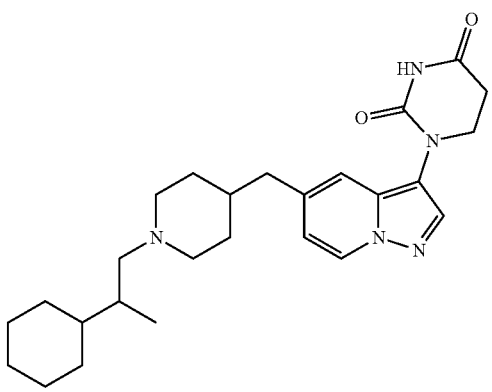

(1-(5-((1-(2-cyclohexylpropyl)piperidin-4-
yl)methyl)pyrazolo[1,5-a]pyridin-3-
yl)dihydropyrimidine-2,4(1H,3H)-dione

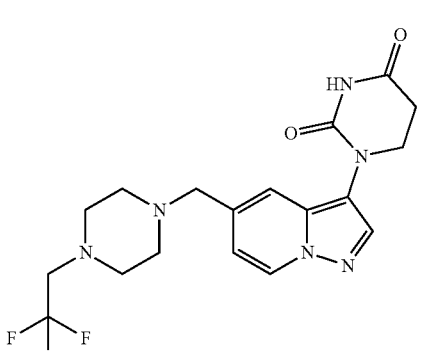

(1-(5-((4-(2,2,2-trifluoroethyl)piperazin-1-
yl)methyl)pyrazolo[1,5-a]pyridin-3-
yl)dihydropyrimidine-2,4(1H,3H)-dione

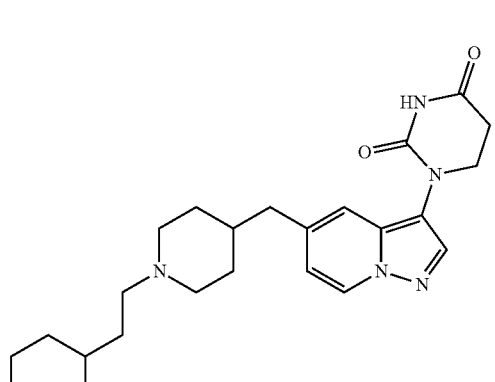

(1-(5-((1-(2-(tetrahydro-2H-pyran-4-
yl)ethyl)piperidin-4-yl)methyl)pyrazolo[1,5-
a]pyridin-3-yl)dihydropyrimidine-2,4(1H,3H)-dione

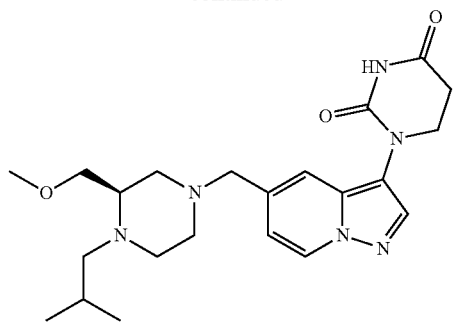

(R)-1-(5-((4-isobutyl-3-
(methoxymethyl)piperazin-1-
yl)methyl)pyrazolo[1,5-a]pyridin-3-
yl)dihydropyrimidine-2,4(1H,3H)-dione

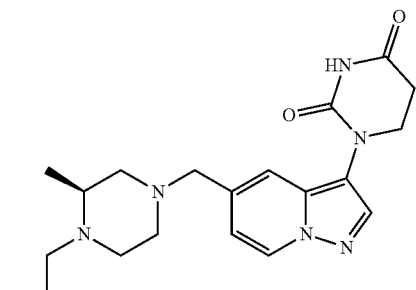

(S)-1-(5-((4-isobutyl-3-methylpiperazin-1-
yl)methyl)pyrazolo[1,5-a]pyridin-3-
yl)dihydropyrimidine-2,4(1H,3H)-dione

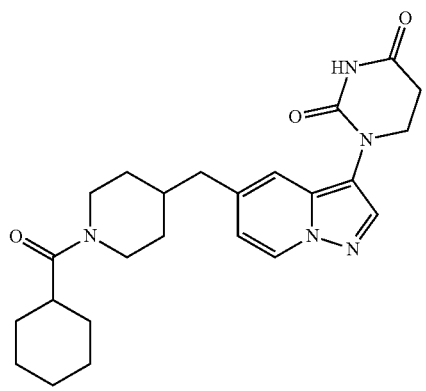

1-(5-((1-(cyclohexanecarbonyl)piperidin-4-
yl)methyl)pyrazolo[1,5-a]pyridin-3-
yl)dihydropyrimidine-2,4(1H,3H)-dione

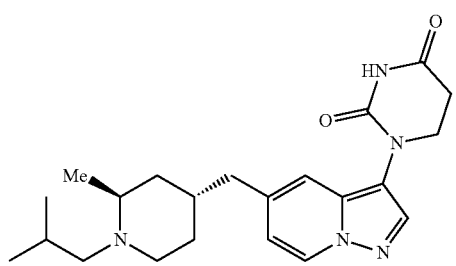

1-(5-(((2S,4R)-1-isobutyl-2-methylpiperidin-
4-yl)methyl)pyrazolo[1,5-a]pyridin-3-
yl)dihydropyrimidine-2,4(1H,3H)-dione

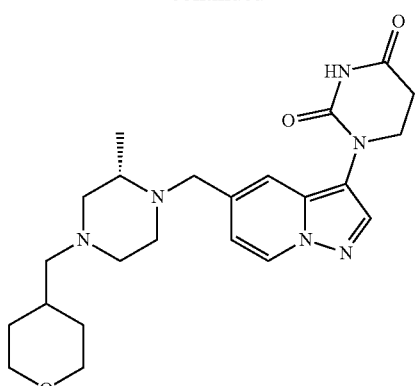

(S)-1-(5-((2-methyl-4-((tetrahydro-2H-pyran-
4-yl)methyl)piperazin-1-
yl)methyl)pyrazolo[1,5-a]pyridin-3-
yl)dihydropyrimidine-2,4(1H,3H)-dione

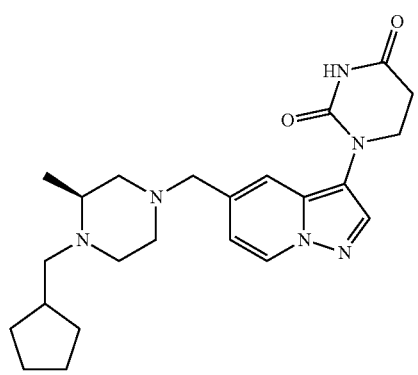

(S)-1-(5-((4-(cyclopentylmethyl)-3-
methylpiperazin-1-yl)methyl)pyrazolo[1,5-
a]pyridin-3-yl)dihydropyrimidine-2,4(1H,3H)-dione

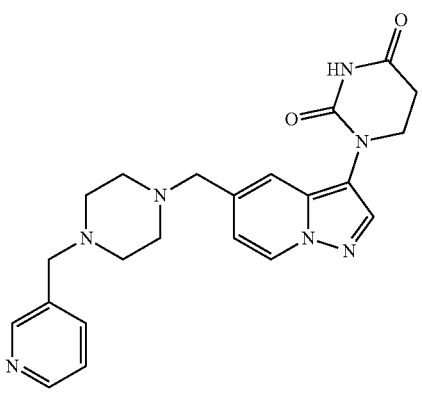

1-(5-((4-(pyridin-3-ylmethyl)piperazin-1-
yl)methyl)pyrazolo[1,5-a]pyridin-3-
yl)dihydropyrimidine-2,4(1H,3H)-dione 479
-continued

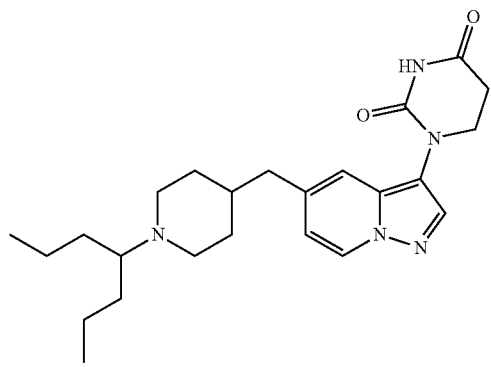

1-(5-((1-heptan-4-yl)piperidin-4-yl)methyl)pyrazolo[1,5-a]pyridin-3-yl)dihydropyrimidine-2,4(1H,3H)-dione

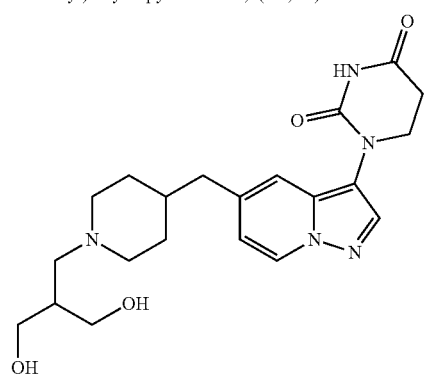

1-(5-((1-(3-hydroxy-2-(hydroxymethyl)propyl)piperidin-4-yl)methyl)pyrazolo[1,5-a]pyridin-3-yl)dihydropyrimidine-2,4(1H,3H)-dione

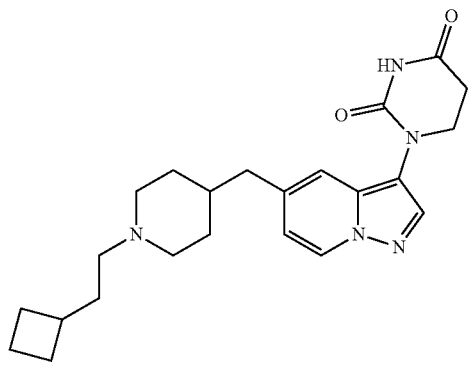

1-(5-((1-(2-cyclobutylethyl)piperidin-4-yl)methyl)pyrazolo[1,5-a]pyridin-3-yl)dihydropyrimidine-2,4(1H,3H)-dione

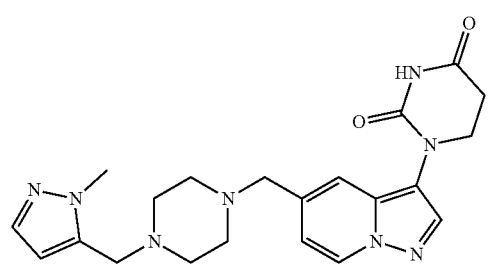

1-(5-((4-((1-methyl-1H-pyrazol-5-yl)methyl)piperazin-1-yl)methyl)pyrazolo[1,5-a]pyridin-3-yl)dihydropyrimidine-2,4(1H,3H)-dione 480
-continued

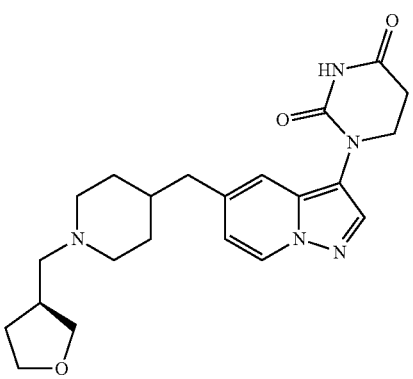

(S)-1-(5-((1-((tetrahydrofuran)-3-yl)methyl)piperidin-4-yl)methyl)pyrazolo[1,5-a]pyridin-3-yl)dihydropyrimidine-2,4(1H,3H)-dione

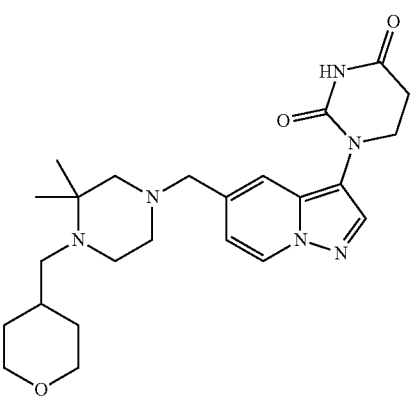

1-(5-((3,3-dimethyl-4-((tetrahydro-2H-pyran-4-yl)methyl)piperazin-1-yl)methyl)pyrazolo[1,5-a]pyridin-3-yl)dihydropyrimidine-2,4(1H,3H)-dione

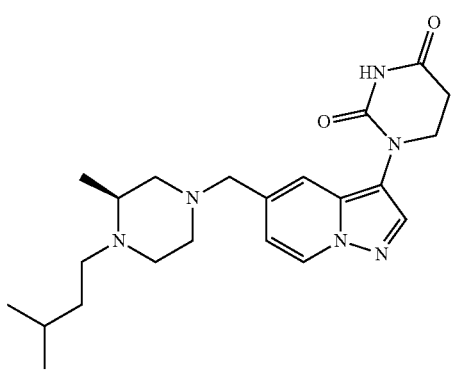

(S)-1-(5-((4-isopentyl-3-methylpiperazin-1-yl)methyl)pyrazolo[1,5-a]pyridin-3-yl)dihydropyrimidine-2,4(1H,3H)-dione 481
-continued

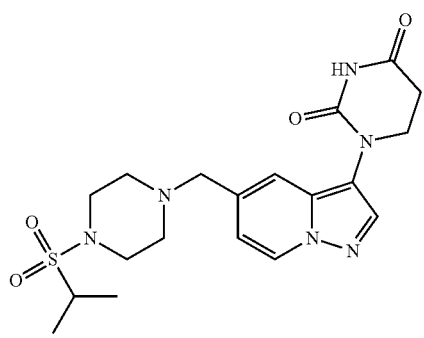

1-(5-((4-(isopropylsulfonyl)piperazin-1-yl)methyl)pyrazolo[1,5-a]pyridin-3-yl)dihydropyrimidine-2,4(1H,3H)-dione

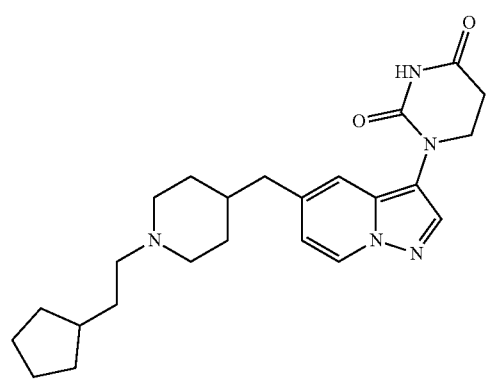

1-(5-((1-(2-cyclopentylethyl)piperidin-4-yl)methyl)pyrazolo[1,5-a]pyridin-3-yl)dihydropyrimidine-2,4(1H,3H)-dione

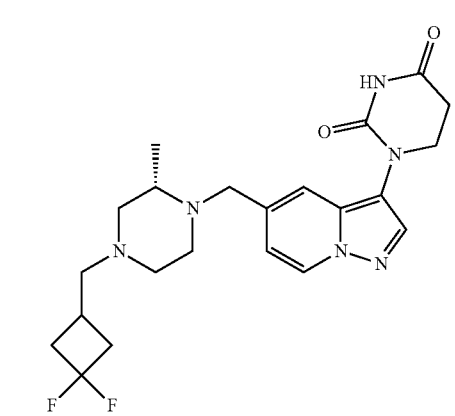

(S)-1-(5-((4-((3,3-difluorocyclobutyl)methyl)-2-methylpiperazin-1-yl)methyl)pyrazolo[1,5-a]pyridin-3-yl)dihydropyrimidine-2,4(1H,3H)-dione 482
-continued

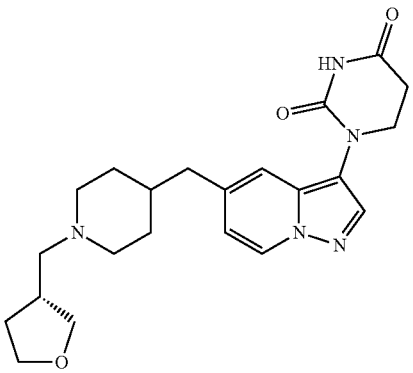

(R)-1-(5-((1-((tetrahydrofuran)-3-yl)methyl)piperidin-4-yl)methyl)pyrazolo[1,5-a]pyridin-3-yl)dihydropyrimidine-2,4(1H,3H)-dione

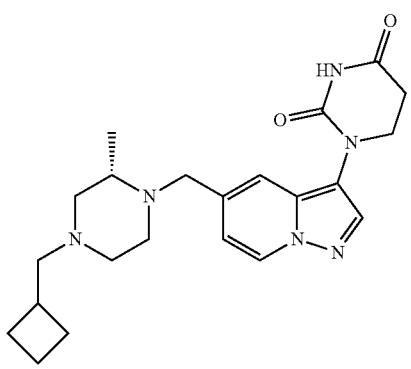

(S)-1-(5-((4-(cyclobutylmethyl)-2-methylpiperazin-1-yl)methyl)pyrazolo[1,5-a]pyridin-3-yl)dihydropyrimidine-2,4(1H,3H)-dione

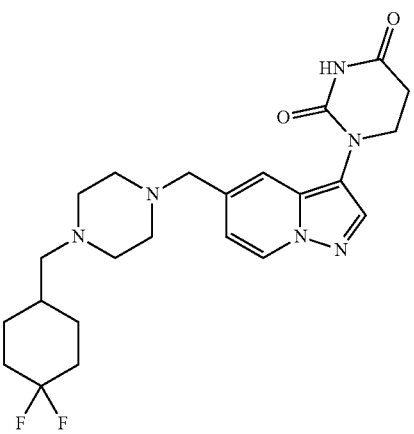

1-(5-((4-((4,4-difluorocyclohexyl)methyl)piperazin-1-yl)methyl)pyrazolo[1,5-a]pyridin-3-yl)dihydropyrimidine-2,4(1H,3H)-dione -continued

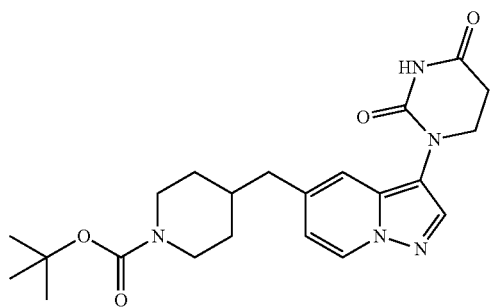

tert-butyl 4-((3-(2,4-
dioxotetrahydropyrimidin-1(2H)-
yl)pyrazolo[1,5-a]pyridin-5-
yl)methyl)piperidine-1-carboxylate

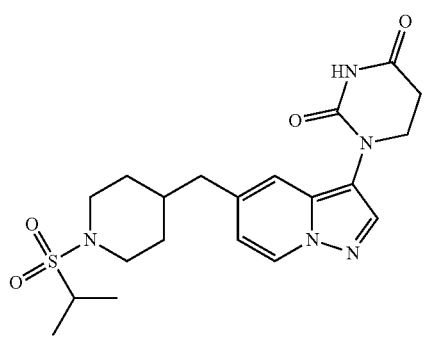

1-(5-((1-(isopropylsulfonyl)piperidin-4-
yl)methyl)pyrazolo[1,5-a]pyridin-3-
yl)dihydropyrimidine-2,4(1H,3H)-dione

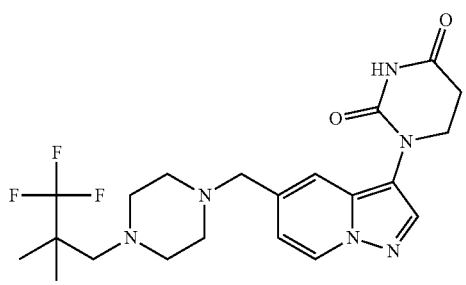

1-(5-((4-(3,3,3-trifluoro-2,2-
dimethylpropyl)piperazin-1-
yl)methyl)pyrazolo[1,5-a]pyridin-3-
yl)dihydropyrimidine-2,4(1H,3H)-dione

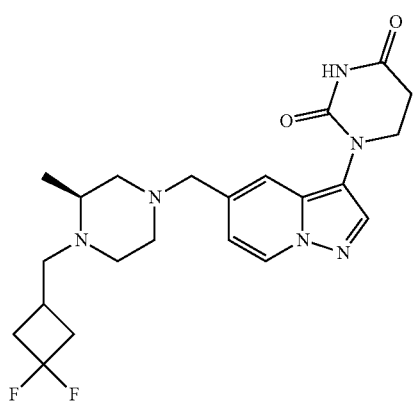

(S)-1-(5-((4-((3,3-difluorocyclobutyl)methyl)-
3-methylpiperazin-1-yl)methyl)pyrazolo[1,5-
a]pyridin-3-yl)dihydropyrimidine-2,4(1H,3H)-dione -continued

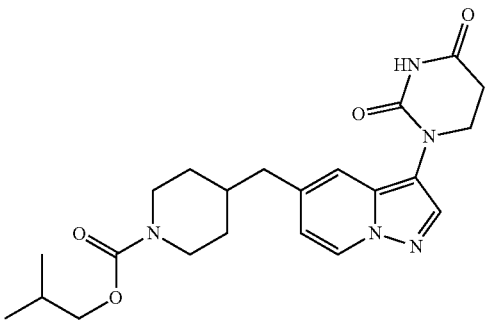

isobutyl 4-((3-(2,4-dioxotetrahydropyrimidin-
1(2H)-yl)pyrazolo[1,5-a]pyridin-5-
yl)methyl)piperidine-1-carboxylate

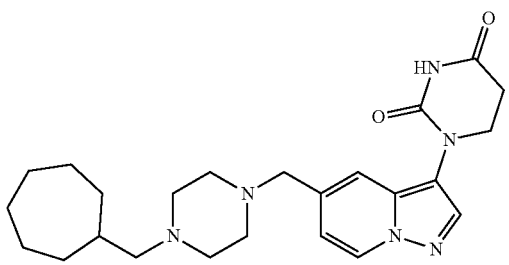

1-(5-((4-(cycloheptylmethyl)piperazin-1-
yl)methyl)pyrazolo[1,5-a]pyridin-3-
yl)dihydropyrimidine-2,4(1H,3H)-dione

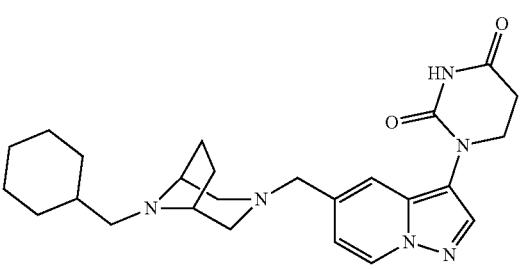

1-(5-(((1R,5S)-8-(cyclohexylmethyl)-3,8-
diazabicyclo[3.2.1]octan-3-
yl)methyl)pyrazolo[1,5-a]pyridin-3-
yl)dihydropyrimidine-2,4(1H,3H)-dione

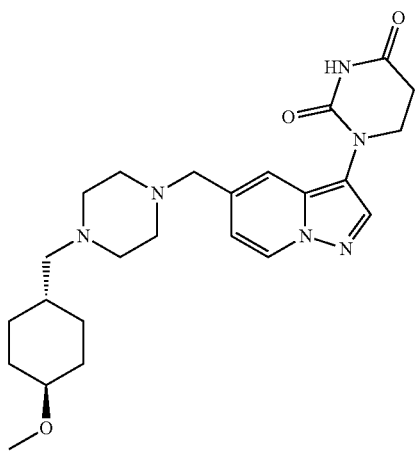

1-(5-((4-(((1r,4r)-4-
methoxycyclohexyl)methyl)piperazin-1-
yl)methyl)pyrazolo[1,5-a]pyridin-3-
yl)dihydropyrimidine-2,4(1H,3H)-dione -continued

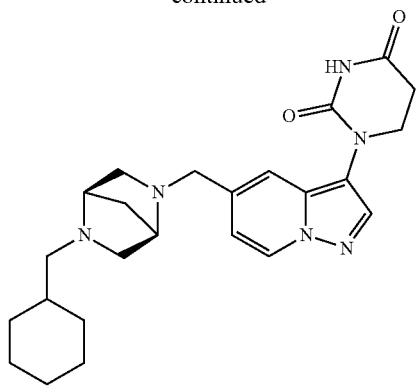

1-(5-((((1R,4R)-5-(cyclohexylmethyl)-2,5-diazabicyclo[2.2.1]heptan-2-yl)methyl)pyrazolo[1,5-a]pyridin-3-yl)dihydropyrimidine-2,4(1H,3H)-dione

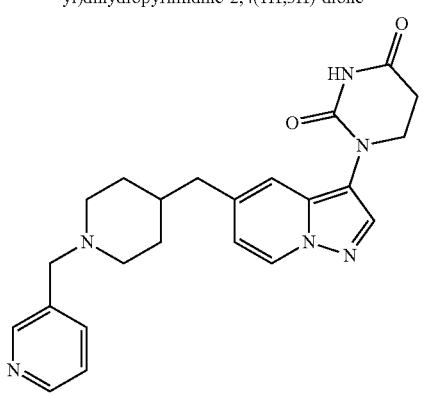

1-(5-((1-(pyridin-3-ylmethyl)piperidin-4-yl)methyl)pyrazolo[1,5-a]pyridin-3-yl)dihydropyrimidine-2,4(1H,3H)-dione

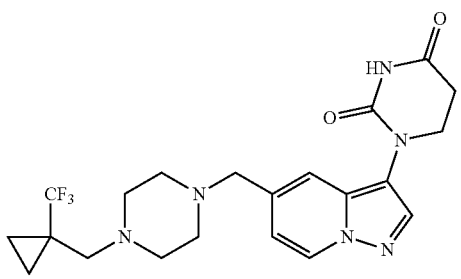

1-(5-((4-((1-(trifluoromethyl)cyclopropyl)methyl)piperazin-1-yl)methyl)pyrazolo[1,5-a]pyridin-3-yl)dihydropyrimidine-2,4(1H,3H)-dione

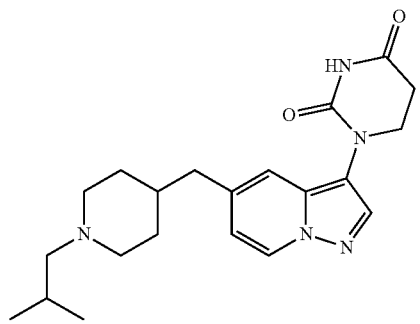

1-(5-((1-isobutylpiperidin-4-yl)methyl)pyrazolo[1,5-a]pyridin-3-yl)dihydropyrimidine-2,4(1H,3H)-dione -continued

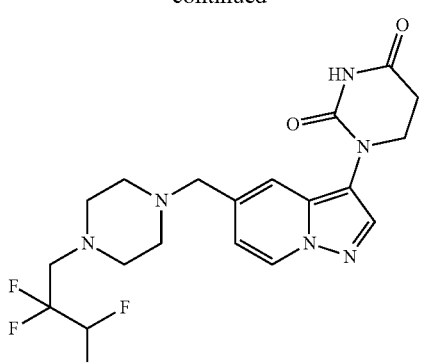

1-(5-((4-(2,2,3,3-tetrafluoropropyl)piperazin-1-yl)methyl)pyrazolo[1,5-a]pyridin-3-yl)dihydropyrimidine-2,4(1H,3H)-dione

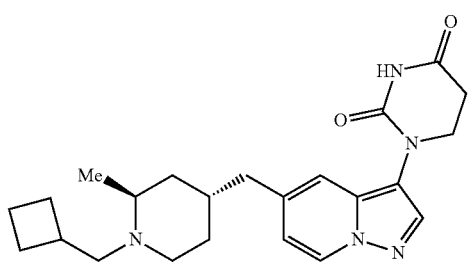

1-(5-(((2S,4R)-1-(cyclobutylmethyl)-2-methylpiperidin-4-yl)methyl)pyrazolo[1,5-a]pyridin-3-yl)dihydropyrimidine-2,4(1H,3H)-dione

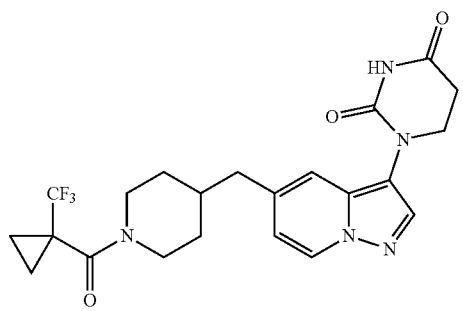

1-(5-((1-(1-(trifluoromethyl)cyclopropane-1-carbonyl)piperidin-4-yl)methyl)pyrazolo[1,5-a]pyridin-3-yl)dihydropyrimidine-2,4(1H,3H)-dione

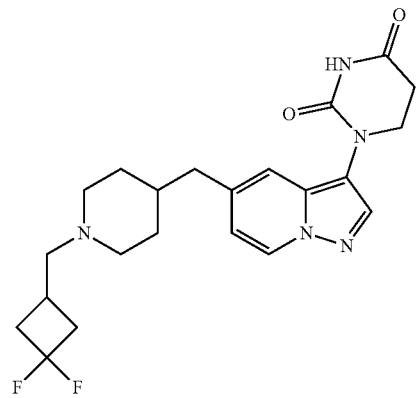

1-(5-((1-((3,3-difluorocyclobytyl)methyl)piperidin-4-yl)methyl)pyrazolo[1,5-a]pyridin-3-yl)dihydropyrimidine-2,4(1H,3H)-dione -continued

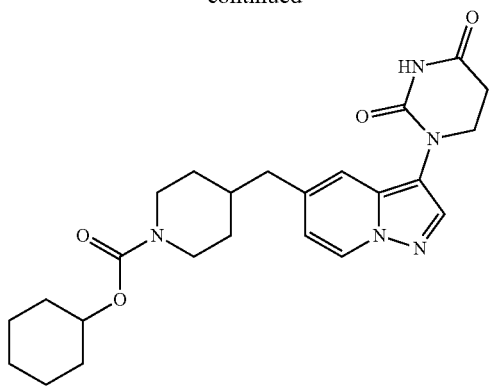

cyclohexyl 4-((3-(2,4-dioxotetrahydropyrimidin-1(2H)-yl)pyrazolo[1,5-a]pyridin-5-yl)methyl)piperidine-1-carboxylate

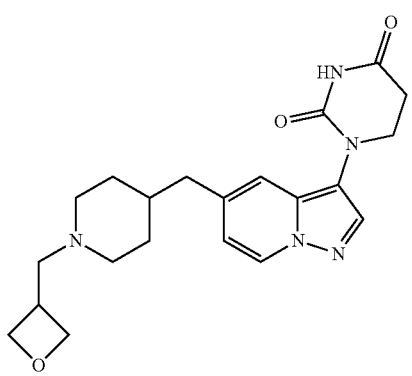

1-(5-((1-(oxetan-3-ylmethyl)piperidin-4-yl)methyl)pyrazolo[1,5-a]pyridin-3-yl)dihydropyrimidine-2,4(1H,3H)-dione

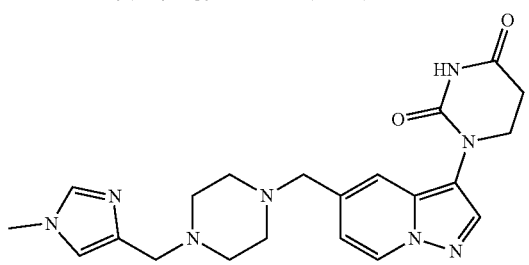

1-(5-((4-((1-methyl-1H-imidazol-4-yl)methyl)piperazin-1-yl)methyl)pyrazolo[1,5-a]pyridin-3-yl)dihydropyrimidine-2,4(1H,3H)-dione

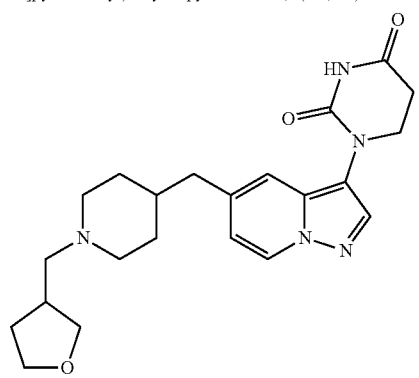

1-(5-((1-((tetrahydrofuran-3-yl)methyl)piperidin-4-yl)methyl)pyrazolo[1,5-a]pyridin-3-yl)dihydropyrimidine-2,4(1H,3H)-dione -continued

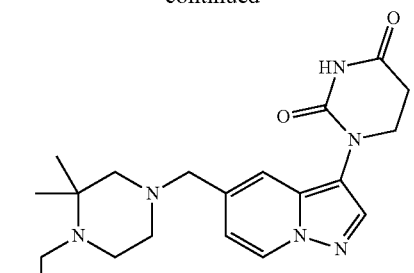

1-(5-((4-isobutyl-3,3-dimethylpiperazin-1-yl)methyl)pyrazolo[1,5-a]pyridin-3-yl)dihydropyrimidine-2,4(1H,3H)-dione

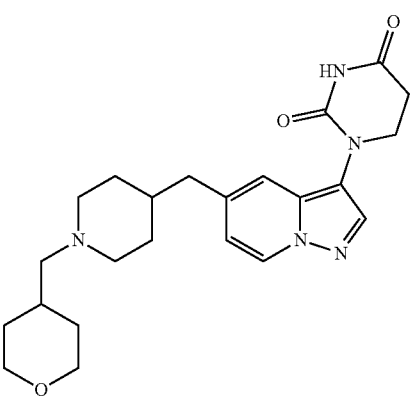

1-(5-((4-((tetrahydro-2H-pyran-4-yl)methyl)piperazin-1-yl)methyl)pyrazolo[1,5-a]pyridin-3-yl)dihydropyrimidine-2,4(1H,3H)-dione

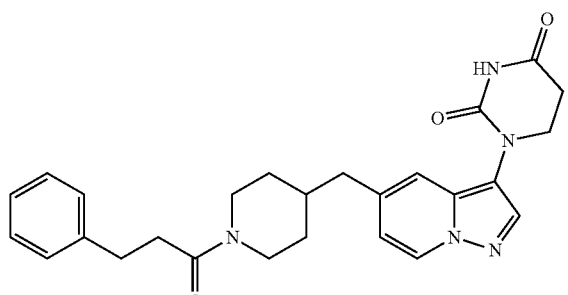

1-(5-((1-(3-phenylpropanoyl)piperidin-4-yl)methyl)pyrazolo[1,5-a]pyridin-3-yl)dihydropyrimidine-2,4(1H,3H)-dione

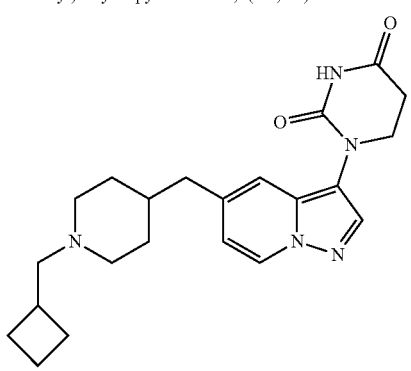

1-(5-((1-(cyclobutylmethyl)piperidin-4-yl)methyl)pyrazolo[1,5-a]pyridin-3-yl)dihydropyrimidine-2,4(1H,3H)-dione

489

-continued

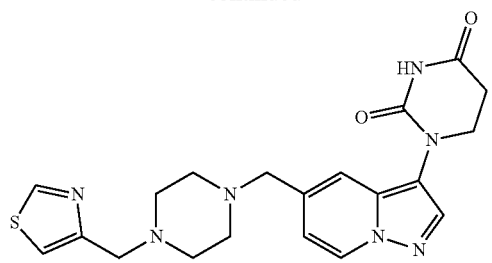

1-(5-((4-(thiazol-4-ylmethyl)piperazin-1-
yl)methyl)pyrazolo[1,5-a]pyridin-3-
yl)dihydropyrimidine-2,4(1H,3H)-dione

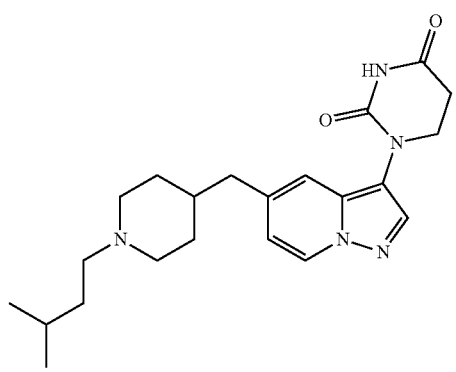

1-(5-((1-isopentylpiperidin-4-
yl)methyl)pyrazolo[1,5-a]pyridin-3-
yl)dihydropyrimidine-2,4(1H,3H)-dione

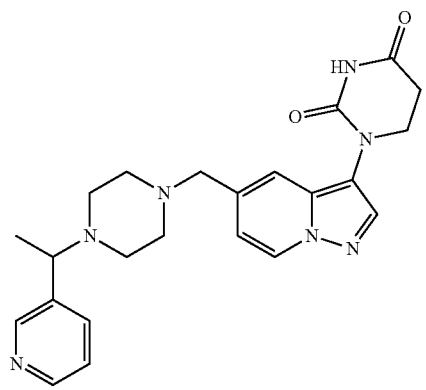

1-(5-((4-(1-(pyridin-3-yl)ethyl)piperazin-1-
yl)methyl)pyrazolo[1,5-a]pyridin-3-
yl)dihydropyrimidine-2,4(1H,3H)-dione

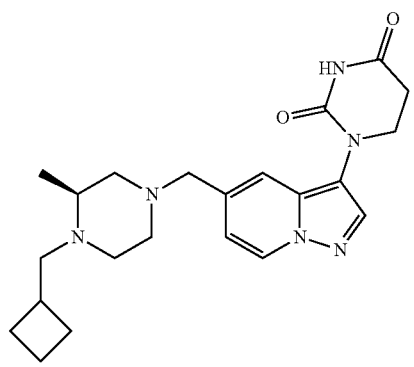

(S)-1-(5-((4-(cyclobutylmethyl)-3-
methylpiperazin-1-yl)methyl)pyrazolo[1,5-
a]pyridin-3-yl)dihydropyrimidine-2,4(1H,3H)-dione

490

-continued

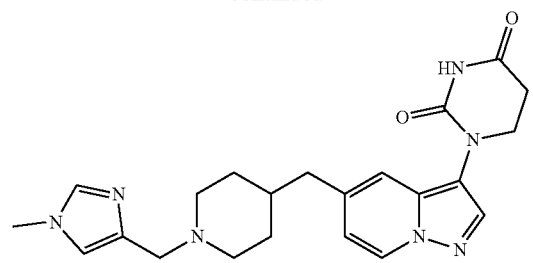

1-(5-((1-((1-methyl-1H-imidazol-4-
yl)methyl)piperidin-4-yl)methyl)pyrazolo[1,5-
a]pyridin-3-yl)dihydropyrimidine-2,4(1H,3H)-dione

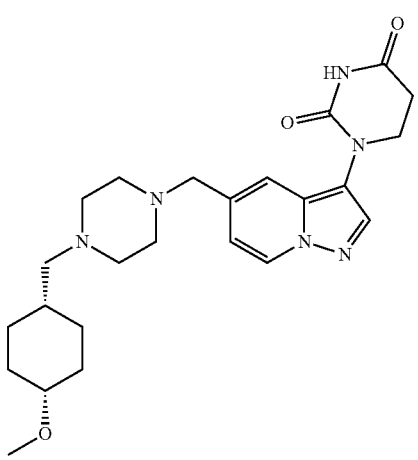

1-(5-((4-(((1s,4s)-4-
methoxycyclohexyl)methyl)piperazin-1-
yl)methyl)pyrazolo[1,5-a]pyridin-3-
yl)dihydropyrimidine-2,4(1H,3H)-dione

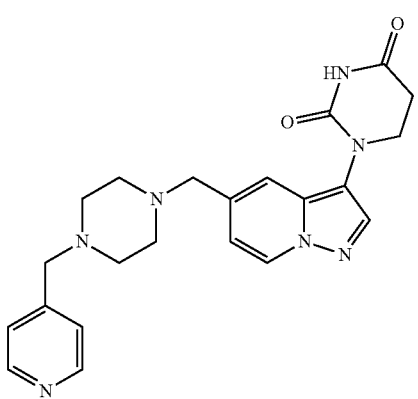

1-(5-((4-(pyridin-4-ylmethyl)piperazin-1-
yl)methyl)pyrazolo[1,5-a]pyridin-3-
yl)dihydropyrimidine-2,4(1H,3H)-dione

491

-continued

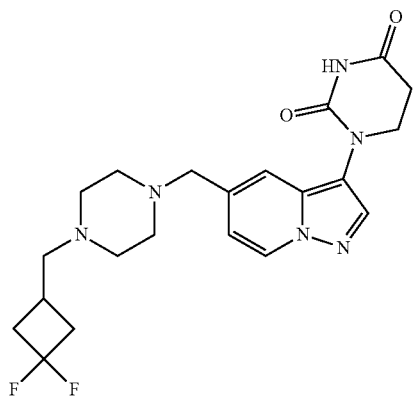

1-(5-((4-((3,3-difluorocyclobutyl)methyl)piperazin-1-yl)methyl)pyrazolo[1,5-a]pyridin-3-yl)dihydropyrimidine-2,4(1H,3H)-dione

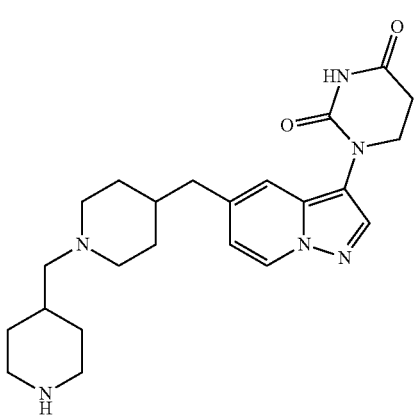

1-(5-((1-(piperidin-4-ylmethyl)piperidin-4-yl)methyl)pyrazolo[1,5-a]pyridin-3-yl)dihydropyrimidine-2,4(1H,3H)-dione

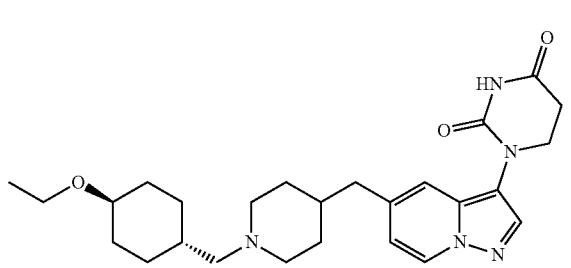

1-(5-((1-(((1r,4r)-4-ethoxycyclohexyl)methyl)piperidin-4-yl)methyl)pyrazolo[1,5-a]pyridin-3-yl)dihydropyrimidine-2,4(1H,3H)-dione

492

-continued

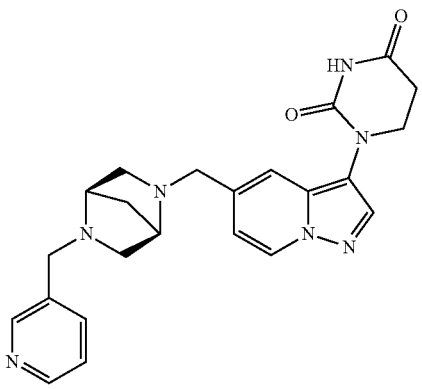

1-(5-(((1R,4R)-5-(pyridin-3-ylmethyl)-2,5-diazabicyclo[2.2.1]heptan-2-yl)methyl)pyrazolo[1,5-a]pyridin-3-yl)dihydropyrimidine-2,4(1H,3H)-dione

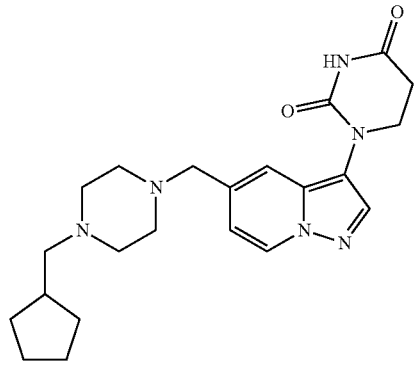

1-(5-((4-(cyclopentylmethyl)piperazin-1-yl)methyl)pyrazolo[1,5-a]pyridin-3-yl)dihydropyrimidine-2,4(1H,3H)-dione

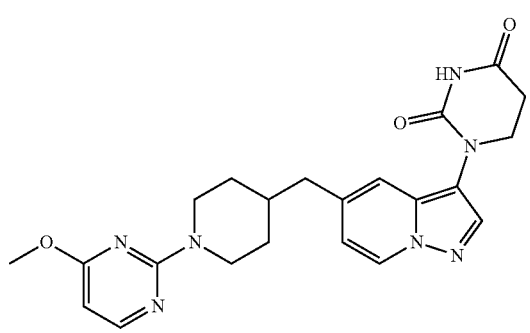

1-(5-((1-(4-methoxypyrimidin-2-yl)piperidin-4-yl)methyl)pyrazolo[1,5-a]pyridin-3-yl)dihydropyrimidine-2,4(1H,3H)-dione

493

-continued

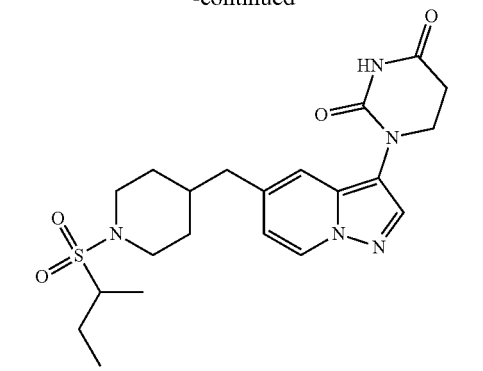

1-(5-((1-(sec-butylsulfonyl)piperidin-4-
yl)methyl)pyrazolo[1,5-a]pyridin-3-
yl)dihydropyrimidine-2,4(1H,3H)-dione

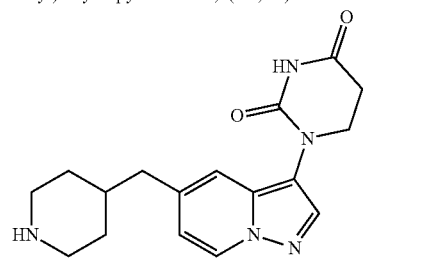

1-(5-(piperidin-4-ylmethyl)pyrazolo[1,5-
a]pyridin-3-yl)dihydropyrimidine-
2,4(1H,3H)-dione

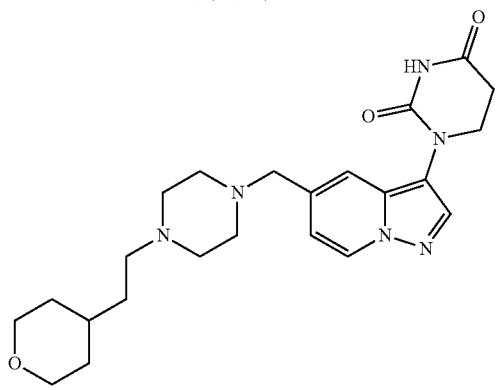

1-(5-((4-(2-(tetrahydro-2H-pyran-4-
yl)ethyl)piperazin-1-yl)methyl)pyrazolo[1,5-
a]pyridin-3-yl)dihydropyrimidine-
2,4(1H,3H)-dione

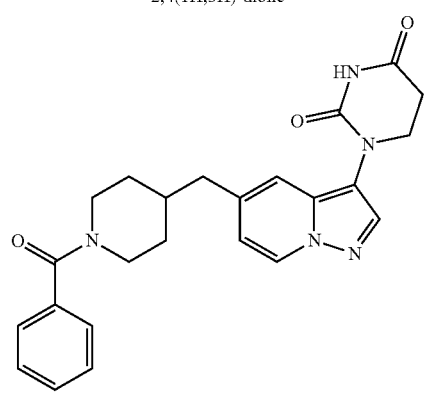

1-(5-((1-benzoylpiperidin-4-
yl)methyl)pyrazolo[1,5-a]pyridin-3-
yl)dihydropyrimidine-2,4(1H,3H)-dione

494

-continued

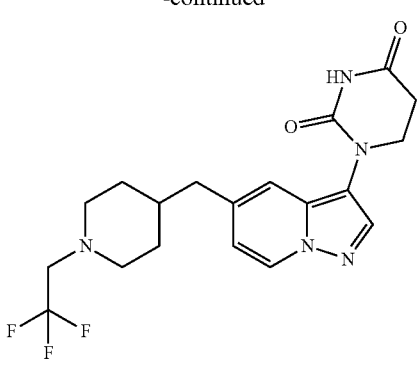

1-(5-((1-(2,2,2-trifluoroethyl)piperidin-4-
yl)methyl)pyrazolo[1,5-a]pyridin-3-
yl)dihydropyrimidine-2,4(1H,3H)-dione

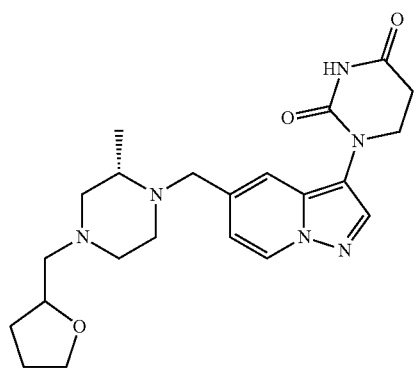

1-(5-(((2S)-2-methyl-4-((tetrahydrofuran-2-
yl)methyl)piperazin-1-
yl)methyl)pyrazolo[1,5-a]pyridin-3-
yl)dihydropyrimidine-2,4(1H,3H)-dione

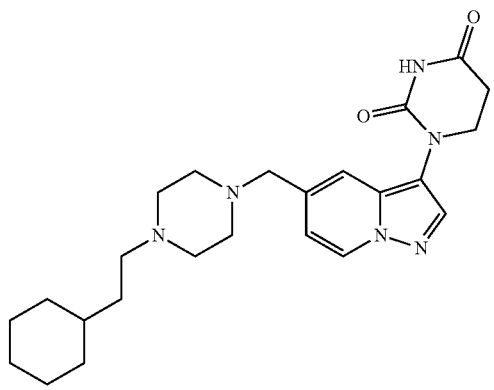

1-(5-((4-(2-cyclohexylethyl)piperazin-1-
yl)methyl)pyrazolo[1,5-a]pyridin-3-
yl)dihydropyrimidine-2,4(1H,3H)-dione 495
-continued

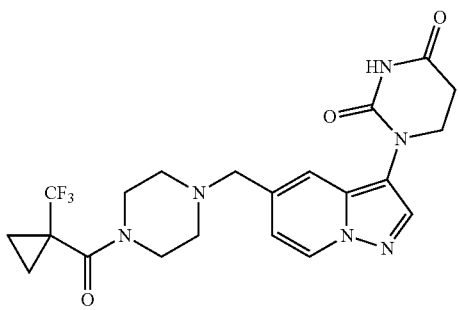
1-(5-((4-(1-(trifluoromethyl)cyclopropane-1-carbonyl)piperazin-1-yl)methyl)pyrazolo[1,5-a]pyridin-3-yl)dihydropyrimidine-2,4(1H,3H)-dione

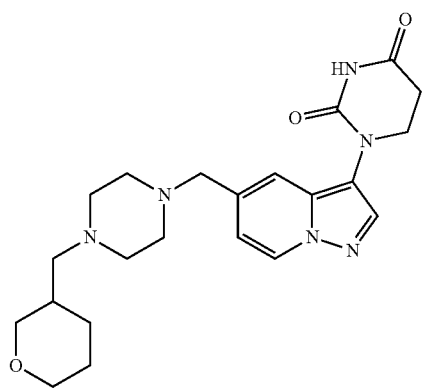
1-(5-((4-((tetrahydro-2H-pyran-3-yl)methyl)piperazin-1-yl)methyl)pyrazolo[1,5-a]pyridin-3-yl)dihydropyrimidine-2,4(1H,3H)-dione

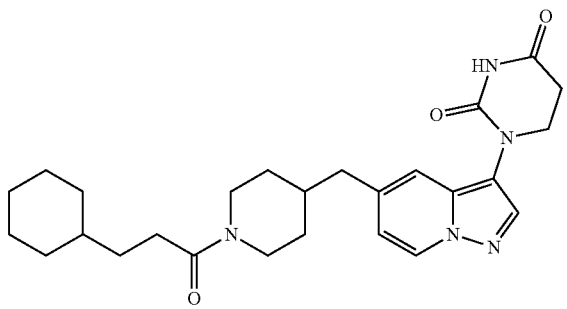
1-(5-((1-(3-cyclohexylpropanoyl)piperidin-4-yl)methyl)pyrazolo[1,5-a]pyridin-3-yl)dihydropyrimidine-2,4(1H,3H)-dione

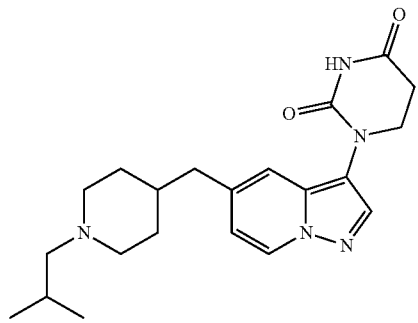
1-(5-((4-isobutylpiperazin-1-yl)methyl)pyrazolo[1,5-a]pyridin-3-yl)dihydropyrimidine-2,4(1H,3H)-dione 496
-continued

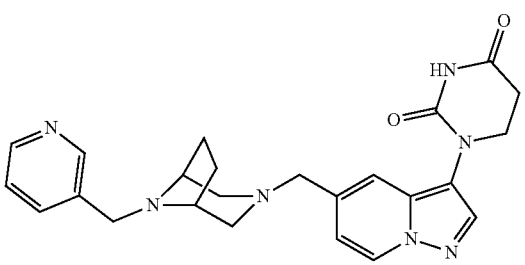
1-(5-(((1R,5S)-8-(pyridin-3-ylmethyl)-3,8-diazabicyclo[3.2.1]octan-3-yl)methyl)pyrazolo[1,5-a]pyridin-3-yl)dihydropyrimidine-2,4(1H,3H)-dione

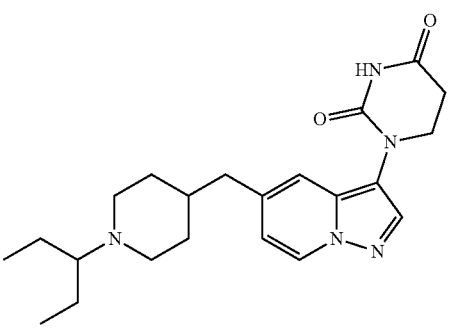
1-(5-((1-(pentan-3-yl)piperidin-4-yl)methyl)pyrazolo[1,5-a]pyridin-3-yl)dihydropyrimidine-2,4(1H,3H)-dione

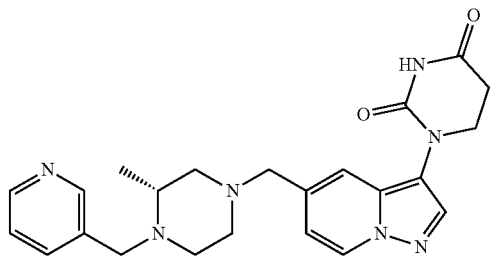
(R)-1-(5-((3-methyl-4-(pyridin-3-ylmethyl)piperazin-1-yl)methyl)pyrazolo[1,5-a]pyridin-3-yl)dihydropyrimidine-2,4(1H,3H)-dione

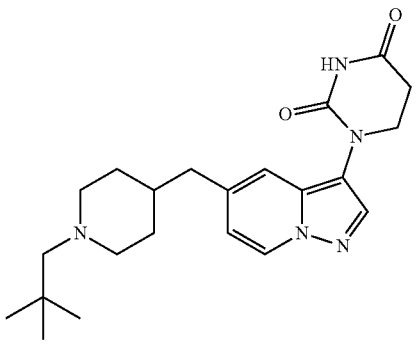
1-(5-((1-neopentylpiperidin-4-yl)methyl)pyrazolo[1,5-a]pyridin-3-yl)dihydropyrimidine-2,4(1H,3H)-dione

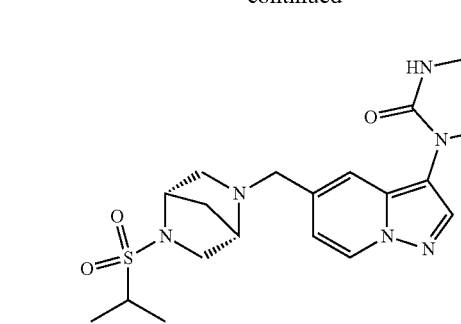

1-(5-(((1S,4S)-5-(isopropylsulfonyl)-2,5-
diazabicyclo[2.2.1]heptan-2-
yl)methyl)pyrazolo[1,5-a]pyridin-3-
yl)dihydropyrimidine-2,4(1H,3H)-dione

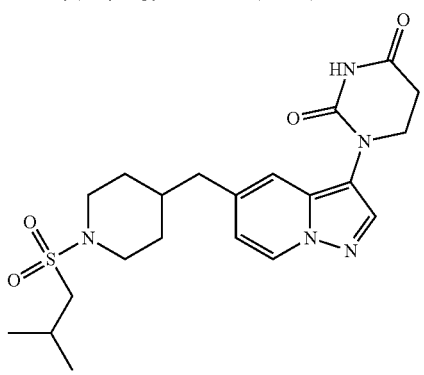

1-(5-((1-isobutylsulfonyl)piperidin-4-
yl)methyl)pyrazolo[1,5-a]pyridin-3-
yl)dihydropyrimidine-2,4(1H,3H)-dione

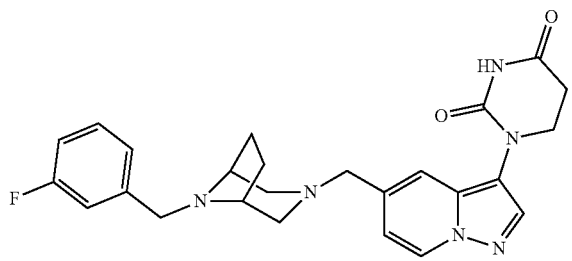

1-(5-(((1R,5S)-8-(3-fluorobenzyl)-3,8-
diazabicyclo[3.2.1]octan-3-
yl)methyl)pyrazolo[1,5-a]pyridin-3-
yl)dihydropyrimidine-2,4(1H,3H)-dione

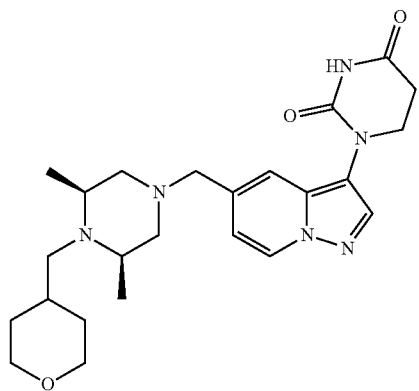

1-(5-(((3S,5R)-3,5-dimethyl-4-((tetrahydro-
2H-pyran-4-yl)methyl)piperazin-1-
yl)methyl)pyrazolo[1,5-a]pyridin-3-
yl)dihydropyrimidine-2,4(1H,3H)-dione

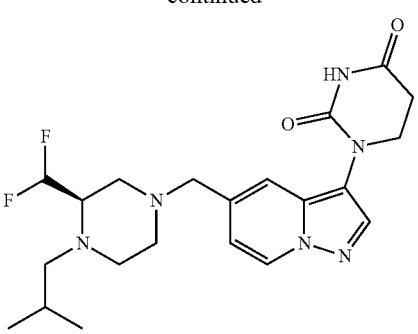

(R)-1-(5-((3-(difluoromethyl)-4-
isobutylpiperazin-1-yl)methyl)pyrazolo[1,5-
a]pyridin-3-yl)dihydropyrimidine-2,4(1H,3H)-dione

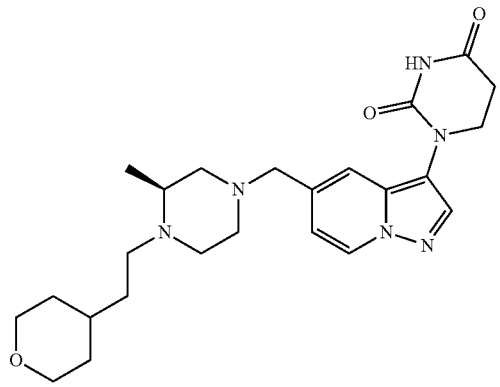

(S)-1-(5-((3-methyl-4-(2-(tetrahydro-2H-
pyran-4-yl)ethyl)piperazin-1-yl)methyl)pyrazolo[1,5-
a]pyridin-3-yl)dihydropyrimidine-2,4(1H,3H)-dione

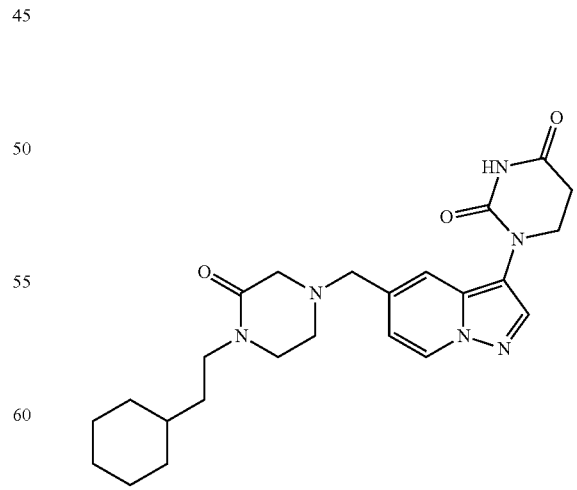

1-(5-((4-(2-cyclohexylethyl)-3-oxopiperazin-
1-yl)methyl)pyrazolo[1,5-a]pyridin-3-
yl)dihydropyrimidine-2,4(1H,3H)-dione

499

-continued

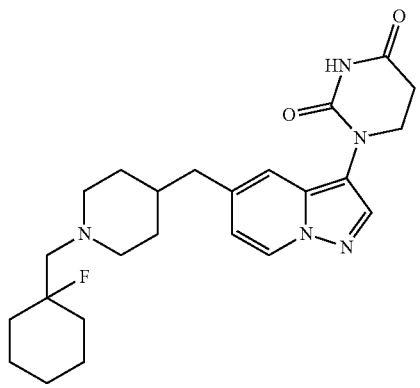

1-(5-((1-((1-
fluorocyclohexyl)methyl)piperidin-4-
yl)methyl)pyrazolo[1,5-a]pyridin-3-
yl)dihydropyrimidine-2,4(1H,3H)-dione

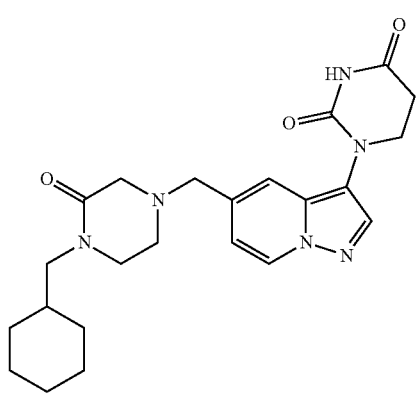

1-(5-((4-(cyclohexylmethyl)-3-oxopiperazin-
1-yl)methyl)pyrazolo[1,5-a]pyridin-3-
yl)dihydropyrimidine-2,4(1H,3H)-dione

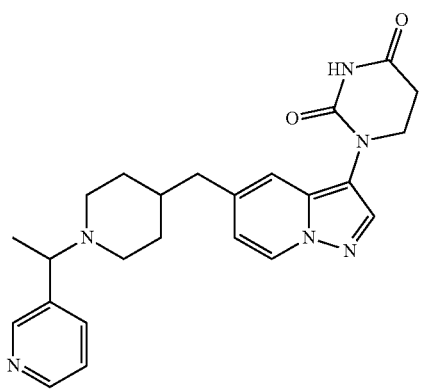

1-(5-((1-(1-(pyridin-3-yl)ethyl)piperidin-4-
yl)methyl)pyrazolo[1,5-a]pyridin-3-
yl)dihydropyrimidine-2,4(1H,3H)-dione

500

-continued

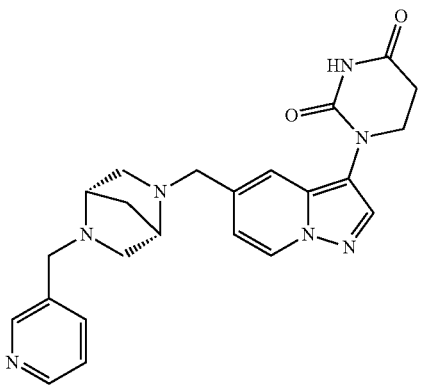

1-(5-(((1S,4S)-5-(pyridin-3-ylmethyl)-2,5-
diazabicyclo[2.2.1]heptan-2-yl)methyl)pyrazolo[1,5-
a]pyridin-3-yl)dihydropyrimidine-2,4(1H,3H)-dione

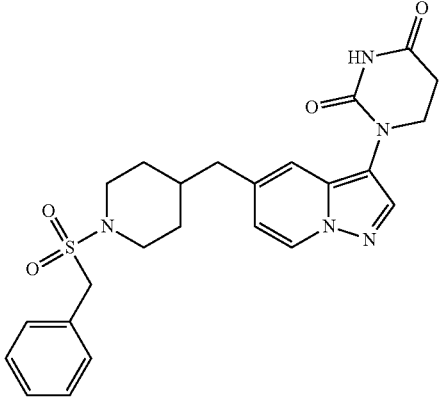

1-(5-((1-(benzylsulfonyl)piperidin-4-
yl)methyl)pyrazolo[1,5-a]pyridin-3-
yl)dihydropyrimidine-2,4(1H,3H)-dione

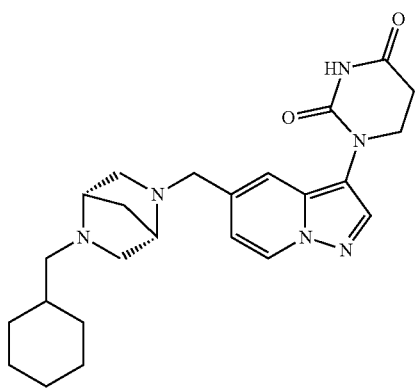

1-(5-(((1S,4S)-5-(cyclohexylmethyl)-2,5-
diazabicyclo[2.2.1]heptan-2-yl)methyl)pyrazolo[1,5-
a]pyridin-3-yl)dihydropyrimidine-2,4(1H,3H)-dione 501
-continued

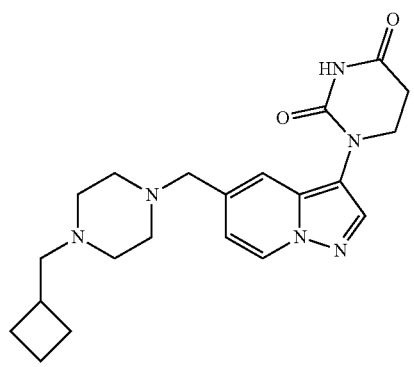

1-(5-((4-(cyclobutylmethyl)piperazin-1-
yl)methyl)pyrazolo[1,5-a]pyridin-3-
yl)dihydropyrimidine-2,4(1H,3H)-dione

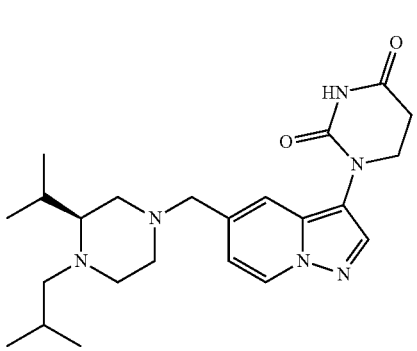

(S)-1-(5-((4-isobutyl-3-isopropylpiperazin-1-
yl)methyl)pyrazolo[1,5-a]pyridin-3-
yl)dihydropyrimidine-2,4(1H,3H)-dione

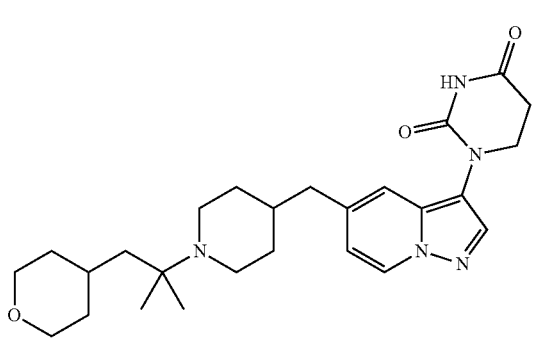

1-(5-((1-(2-methyl-1-(tetrahydro-2H-pyran-4-
yl)propan-2-yl)piperidin-4-
yl)methyl)pyrazolo[1,5-a]pyridin-3-
yl)dihydropyrimidine-2,4(1H,3H)-dione 502
-continued

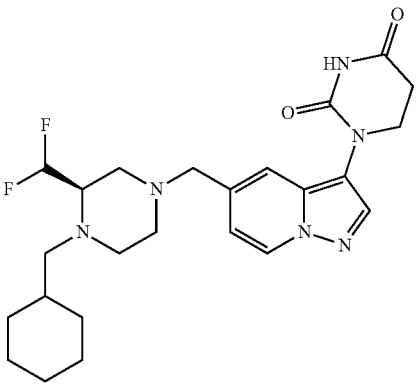

(R)-1-(5-((4-(cyclohexylmethyl)-3-
(difluoromethyl)piperazin-1-
yl)methyl)pyrazolo[1,5-a]pyridin-3-
yl)dihydropyrimidine-2,4(1H,3H)-dione

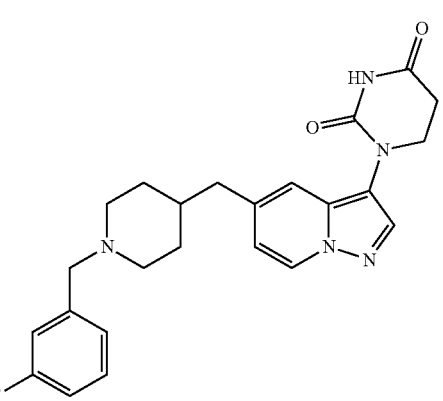

1-(5-((1-(3-fluorobenzyl)piperidin-4-
yl)methyl)pyrazolo[1,5-a]pyridin-3-
yl)dihydropyrimidine-2,4(1H,3H)-dione

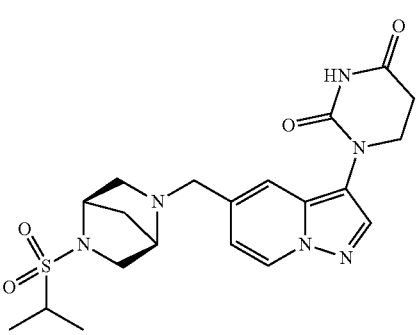

1-(5-(((1R,4R)-5-(isopropylsulfonyl)-2,5-
diazabicyclo[2.2.1]heptan-2-yl)methyl)pyrazolo[1,5-
a]pyridin-3-yl)dihydropyrimidine-2,4(1H,3H)-dione

503

-continued

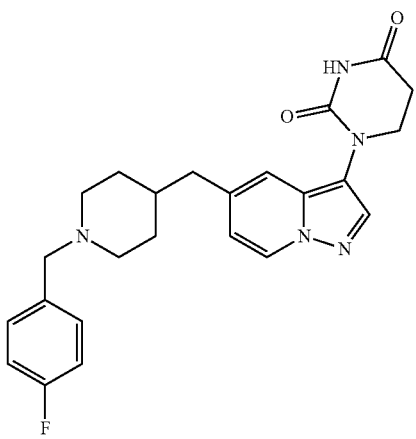

1-(5-((1-(4-fluorobenzyl)piperidin-4-
yl)methyl)pyrazolo[1,5-a]pyridin-3-
yl)dihydropyrimidine-2,4(1H,3H)-dione

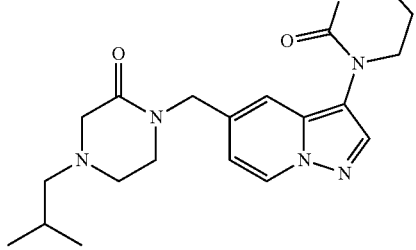

1-(5-((4-isobutyl-2-oxopiperazin-1-
yl)methyl)pyrazolo[1,5-a]pyridin-3-
yl)dihydropyrimidine-2,4(1H,3H)-dione

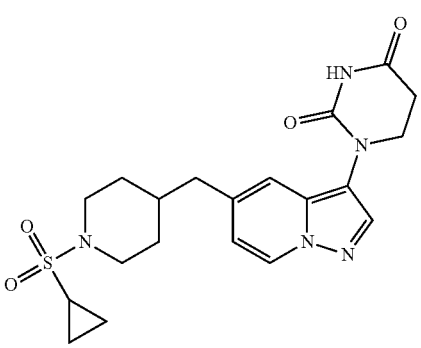

1-(5-((1-(cyclopropylsulfonyl)piperidin-4-
yl)methyl)pyrazolo[1,5-a]pyridin-3-
yl)dihydropyrimidine-2,4(1H,3H)-dione

504

-continued

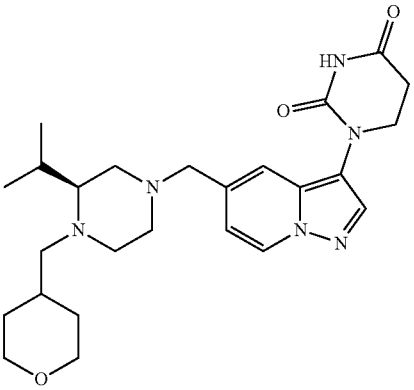

(S)-1-(5-((3-isopropyl-4-((tetrahydro-2H-
pyran-4-yl)methyl)piperazin-1-
yl)methyl)pyrazolo[1,5-a]pyridin-3-
yl)dihydropyrimidine-2,4(1H,3H)-dione

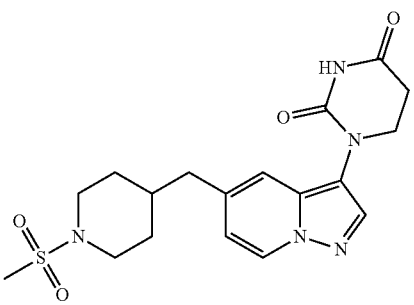

1-(5-((1-(methylsulfonyl)piperidin-4-
yl)methyl)pyrazolo[1,5-a]pyridin-3-
yl)dihydropyrimidine-2,4(1H,3H)-dione

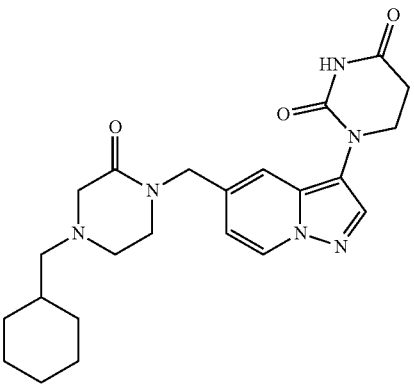

1-(5-((4-(cyclohexylmethyl)-2-oxopiperazin-
1-yl)methyl)pyrazolo[1,5-a]pyridin-3-
yl)dihydropyrimidine-2,4(1H,3H)-dione

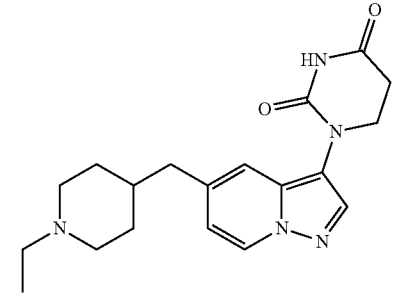

1-(5-((1-ethylpiperidin-4-
yl)methyl)pyrazolo[1,5-a]pyridin-3-
yl)dihydropyrimidine-2,4(1H,3H)-dione

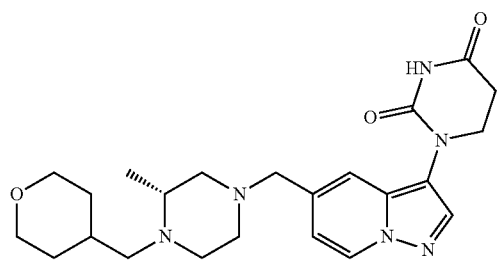

(R)-1-(5-((3-methyl-4-((tetrahydro-2H-
pyran-4-yl)methyl)piperazin-1-
yl)methyl)pyrazolo[1,5-a]pyridin-3-
yl)dihydropyrimidine-2,4(1H,3H)-dione

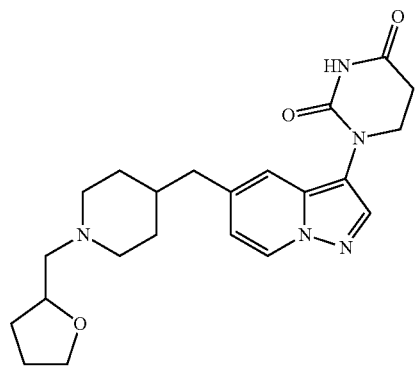

1-(5-((4-((tetrahydrofuran-3-
yl)methyl)piperazin-1-
yl)methyl)pyrazolo[1,5-a]pyridin-3-
yl)dihydropyrimidine-2,4(1H,3H)-dione

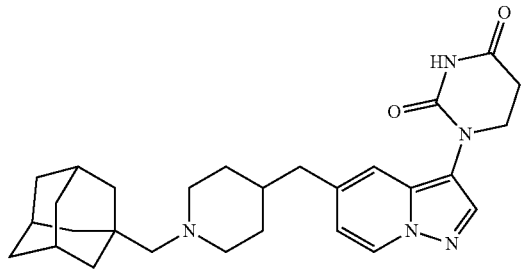

1-(5-((1-(((3r,5r,7r)-adamantan-1-
yl)methyl)piperidin-4-yl)methyl)pyrazolo[1,5-
a]pyridin-3-yl)dihydropyrimidine-2,4(1H,3H)-dione

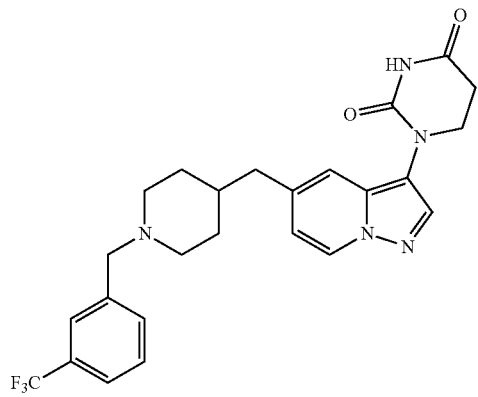

1-(5-((1-(3-trifluoromethyl)benzyl)piperazin-
4-yl)methyl)pyrazolo[1,5-a]pyridin-3-
yl)dihydropyrimidine-2,4(1H,3H)-dione

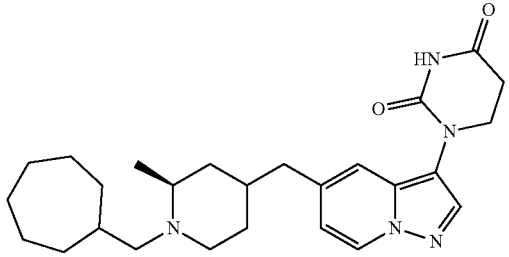

(S)-1-(5-((4-(cycloheptylmethyl)-3-
methylpiperazin-1-yl)methyl)pyrazolo[1,5-
a]pyridin-3-yl)dihydropyrimidine-2,4(1H,3H)-dione

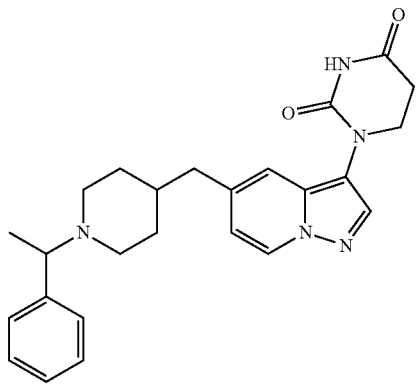

1-(5-((1-(1-phenylethyl)piperidin-4-
yl)methyl)pyrazolo[1,5-a]pyridin-3-
yl)dihydropyrimidine-2,4(1H,3H)-dione

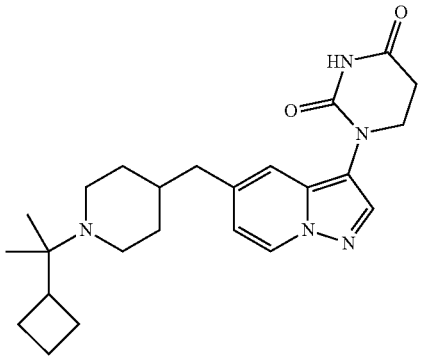

1-(5-((1-(2-cyclobutylpropan-2-yl)piperidin-
4-yl)methyl)pyrazolo[1,5-a]pyridin-3-
yl)dihydropyrimidine-2,4(1H,3H)-dione

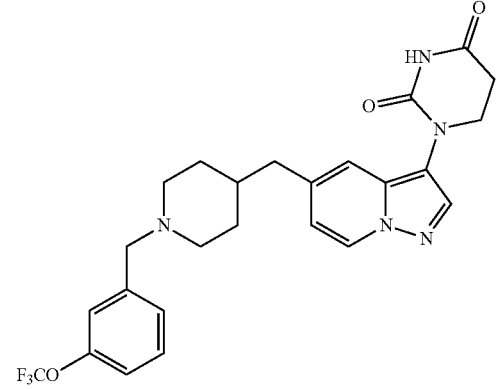

1-(5-((1-(3-trifluoromethoxy)benzyl)piperidin-
4-yl)methyl)pyrazolo[1,5-a]pyridin-3-
yl)dihydropyrimidine-2,4(1H,3H)-dione

507

-continued

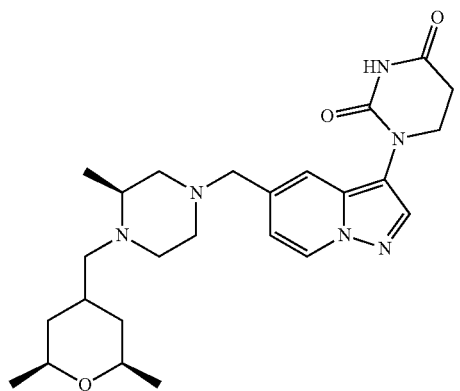

1-(5-(((3S)-4-(((2R,6S)-2,6-
dimethyltetrahydro-2H-pyran-4-yl)methyl)-3-
methylpiperazin-1-yl)methyl)pyrazolo[1,5-
a]pyridin-3-yl)dihydropyrimidine-2,4(1H,3H)-dione

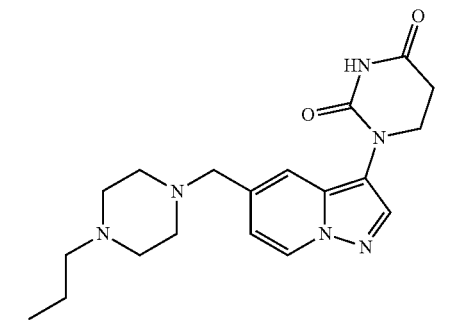

1-(5-((4-propylpiperazin-1-
yl)methyl)pyrazolo[1,5-a]pyridin-3-
yl)dihydropyrimidine-2,4(1H,3H)-dione

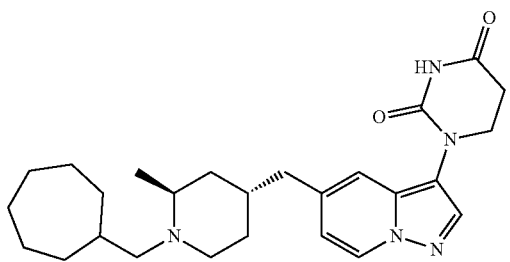

1-(5-(((2S,4R)-1-(cycloheptylmethyl)-2-
methylpiperidin-4-yl)methyl)pyrazolo[1,5-
a]pyridin-3-yl)dihydropyrimidine-2,4(1H,3H)-dione

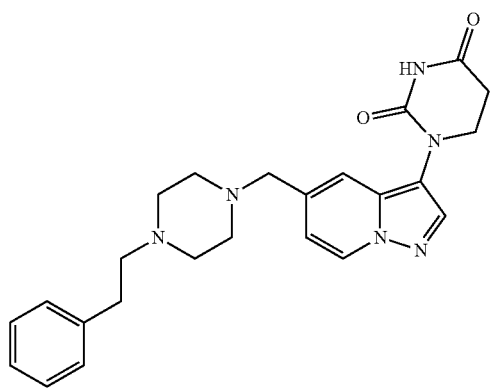

1-(5-((4-phenethylpiperazin-1-
yl)methyl)pyrazolo[1,5-a]pyridin-3-
yl)dihydropyrimidine-2,4(1H,3H)-dione

508

-continued

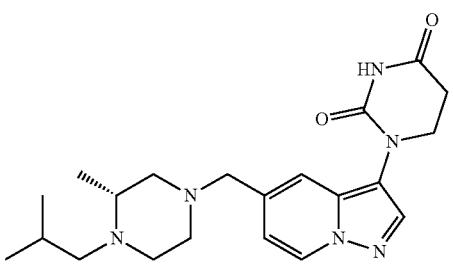

(R)-1-(5-((4-isobutyl-3-methylpiperazin-1-
yl)methyl)pyrazolo[1,5-a]pyridin-3-
yl)dihydropyrimidine-2,4(1H,3H)-dione

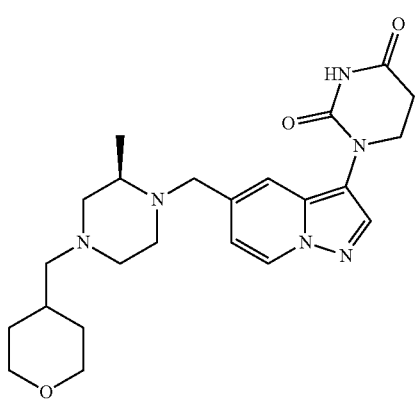

(R)-1-(5-((2-methyl-4-((tetrahydro-2H-pyran-
4-yl)methyl)piperazin-1-yl)methyl)pyrazolo[1,5-a]
pyridin-3-yl)dihydropyrimidine-2,4(1H,3H)-dione

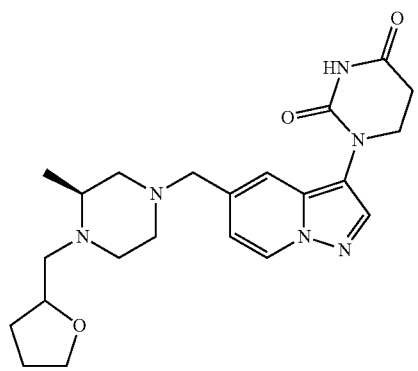

1-(5-(((3S)-3-methyl-4-((tetrahydrofuran-2-yl)
methyl)piperazin-1-yl)methyl)pyrazolo[1,5-a]
pyridin-3-yl)dihydropyrimidine-2,4(1H,3H)-dione

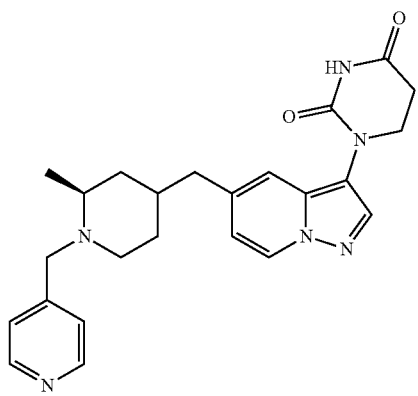

1-(5-((1-(pyridin-4-ylmethyl)piperidin-4-yl)
methyl)pyrazolo[1,5-a]pyridin-3-yl)
dihydropyrimidine-2,4(1H,3H)-dione

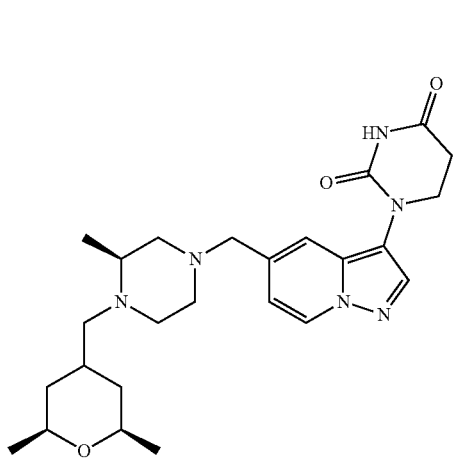

1-(5-((4-(((2R,6S)-2,6-dimethyltetrahydro-2H-pyran-
4-yl)methyl)piperazin-1-yl)methyl)pyrazolo[1,5-a]
pyridin-3-yl)dihydropyrimidine-2,4(1H,3H)-dione

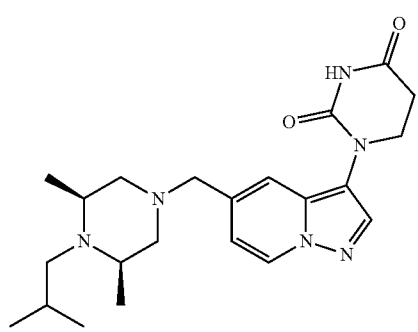

1-(5-(((3S,5R)-4-isobutyl-3,5-dimethylpiperazin-1-yl)
methyl)pyrazolo[1,5-a]pyridin-3-yl)
dihydropyrimidine-2,4(1H,3H)-dione

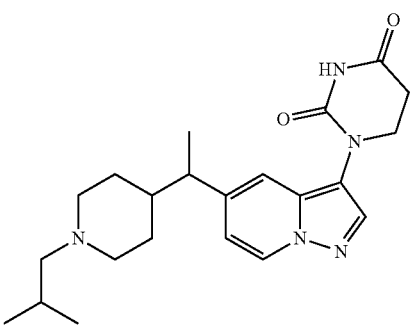

1-(5-(1-(1-isobutylpiperidin-4-yl)
ethyl)pyrazolo[1,5-a]pyridin-3-yl)
dihydropyrimidine-2,4(1H,3H)-dione

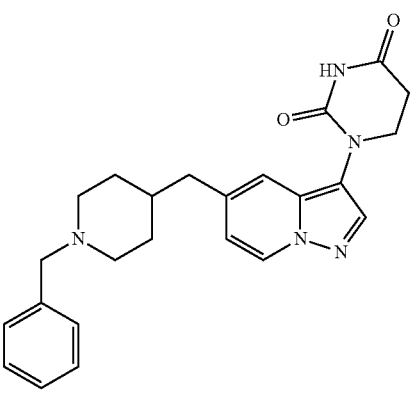

1-(5-((1-benzylpiperidin-4-yl)
methyl)pyrazolo[1,5-a]pyridin-3-yl)
dihydropyrimidine-2,4(1H,3H)-dione

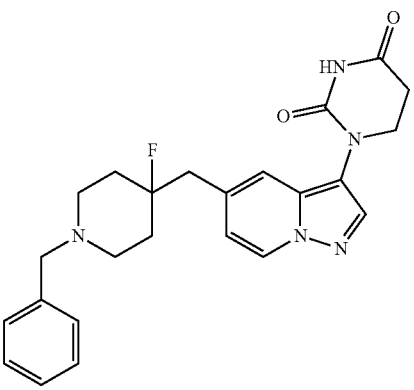

1-(5-((1-benzyl-4-fluoropiperidin-4-yl)
methyl)pyrazolo[1,5-a]pyridin-3-yl)
dihydropyrimidine-2,4(1H,3H)-dione 511
-continued

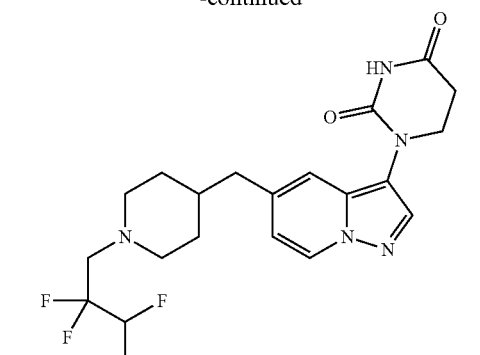

1-(5-((1-(2,2,3,3-tetrafluoropropyl)piperidin-
4-yl)methyl)pyrazolo[1,5-a]pyridin-3-yl)
dihydropyrimidine-2,4(1H,3H)-dione

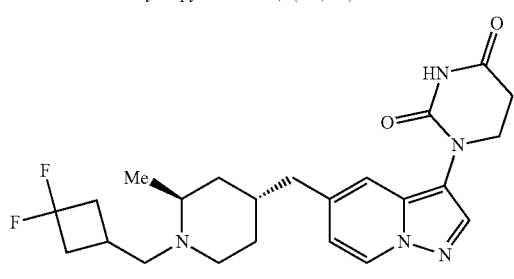

1-(5-(((2S,4R)-1-((3,3-difluorocyclobutyl)-2-
methylpiperidin-4-yl)methyl)
pyrazolo[1,5-a]pyridin-3-yl)
dihydropyrimidine-2,4(1H,3H)-dione

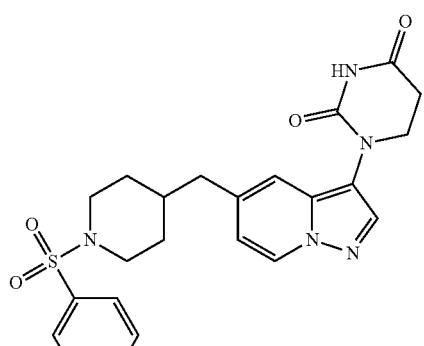

1-(5-((1-(phenylsulfonyl)piperidin-4-yl)
methyl)pyrazolo[1,5-a]pyridin-3-yl)
dihydropyrimidine-2,4(1H,3H)-dione

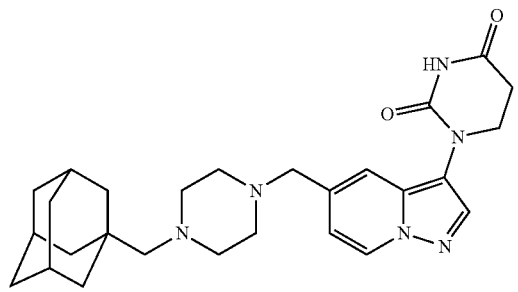

1-(5-((4-(((3r,5r,7r)-adamantan-1-yl)
methyl)piperazin-1-yl)methyl)pyrazolo
[1,5-a]pyridin-3-yl)
dihydropyrimidine-2,4(1H,3H)-dione 512
-continued

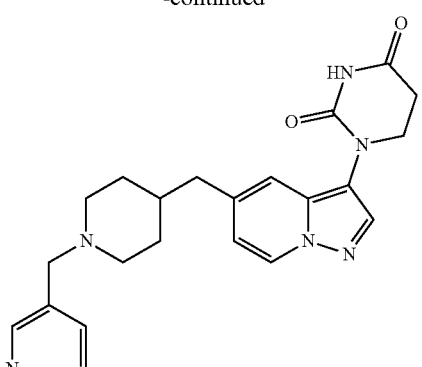

1-(5-((1-((5-fluoropyridin-3-yl)methyl)piperidin-4-yl)
methyl)pyrazolo[1,5-a]pyridin-3-yl)
dihydropyrimidine-2,4(1H,3H)-dione

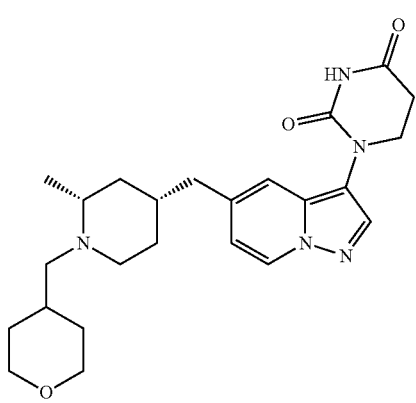

1-(5-(((2R,4R)-2-methyl-1-((tetrahydro-2H-pyran-4-yl)
methyl)piperidin-4-yl)methyl)pyrazolo
[1,5-a]pyridin-3-yl)dihydropyrimidine-2,4(1H,3H)-dione

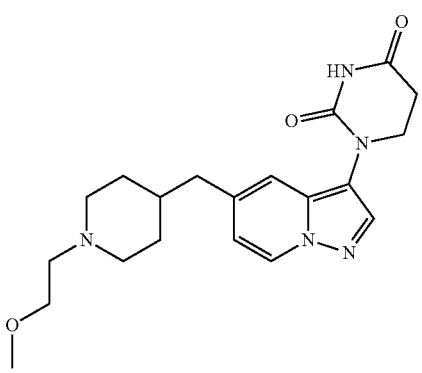

1-(5-((1-(2-methoxyethyl)piperidin-4-yl)
methyl)pyrazolo[1,5-a]pyridin-3-yl)
dihydropyrimidine-2,4(1H,3H)-dione

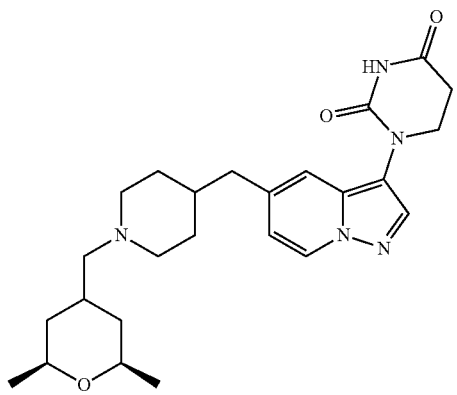

1-(5-((1-(((2R,6S)-2,6-dimethyltetrahydro-
2H-pyran-4-yl)methyl)piperidin-4-yl)methyl)
pyrazolo[1,5-a]pyridin-3-yl)
dihydropyrimidine-2,4(1H,3H)-dione

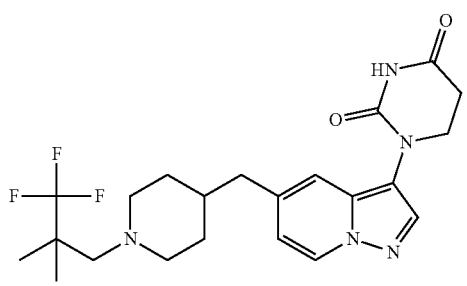

1-(5-((1-(3,3,3-trifluoro-2,2-dimethylpropyl)
piperidin-4-yl)methyl)pyrazolo[1,5-a]pyridin-3-yl)
dihydropyrimidine-2,4(1H,3H)-dione

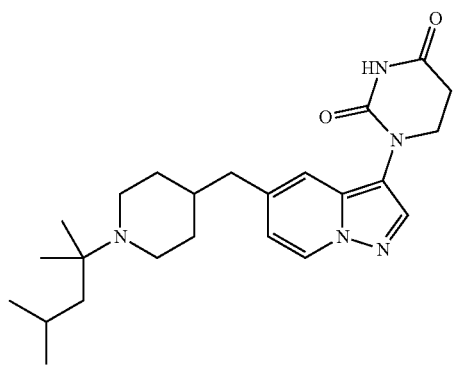

1-(5-((1-(2,4-dimethylpentan-2-yl)piperidin-4-yl)
methyl)pyrazolo[1,5-a]pyridin-3-yl)
dihydropyrimidine-2,4(1H,3H)-dione

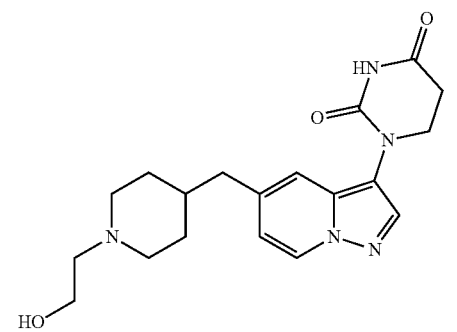

1-(5-((1-(2-hydroxyethyl)piperidin-4-yl)
methyl)pyrazolo[1,5-a]pyridin-3-yl)
dihydropyrimidine-2,4(1H,3H)-dione

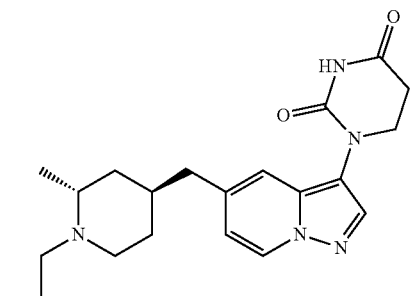

1-(5-(((2R,4S)-1-isobutyl-2-methylpiperidin--4-yl)
methyl)pyrazolo[1,5-a]pyridin-3-yl)
dihydropyrimidine-2,4(1H,3H)-dione

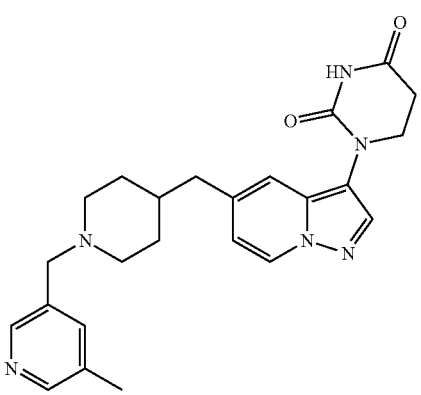

1-(5-(((1-((5-methylpyridin-3-yl)methyl)
piperidin-4-yl)methyl)pyrazolo[1,5-a]
pyridin-3-yl)dihydropyrimidine-2,4(1H,3H)-dione

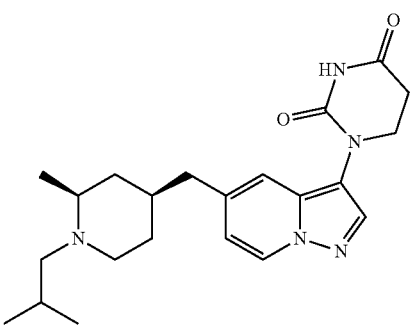

1-(5-(((2S,4S)-1-isobutyl-2-methylpiperidin-4-yl)
methyl)pyrazolo[1,5-a]pyridin-3-yl)
dihydropyrimidine-2,4(1H,3H)-dione

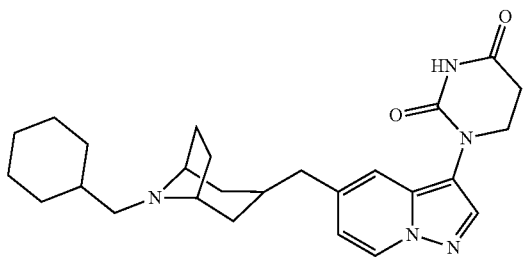

1-(5-(((1R,5S)-8-(cyclohexylmethyl)-8-azabicyclo
[3.2.1]octan-3-yl)methyl)pyrazolo[1,5-a]
pyridin-3-yl)dihydropyrimidine-2,4(1H,3H)-dione

515

-continued

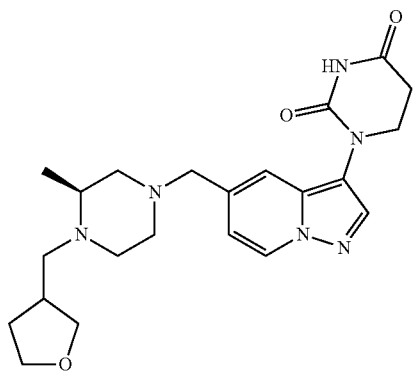

1-(5-(((3S)-3-methyl-4-((tetrahydrofuran-2-yl)
methyl)piperazin-1-yl)methyl)
pyrazolo[1,5-a]pyridin-3-yl)
dihydropyrimidine-2,4(1H,3H)-dione

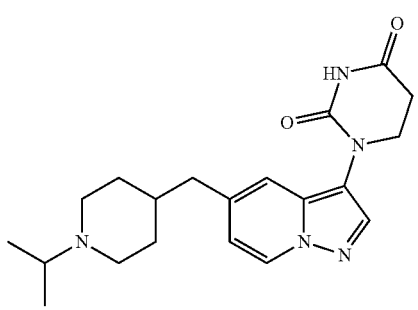

1-(5-((1-isopropylpiperidin-4-yl)
methyl)pyrazolo[1,5-a]pyridin-3-yl)
dihydropyrimidine-2,4(1H,3H)-dione

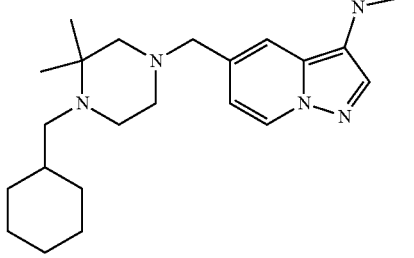

1-(5-(((4-(cyclohexylmethyl)-3,3-dimethylpiperazin-1-yl)
methyl)pyrazolo[1,5-a]pyridin-3-yl)
dihydropyrimidine-2,4(1H,3H)-dione

516

-continued

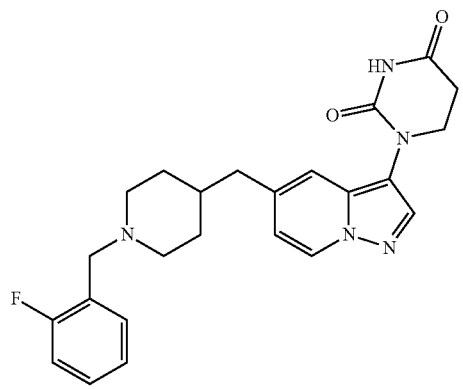

1-(5-((1-(2-fluorobenzyl)piperidin-
4-yl)methyl)pyrazolo[1,5-a]pyridin-3-yl)
dihydropyrimidine-2,4(1H,3H)-dione

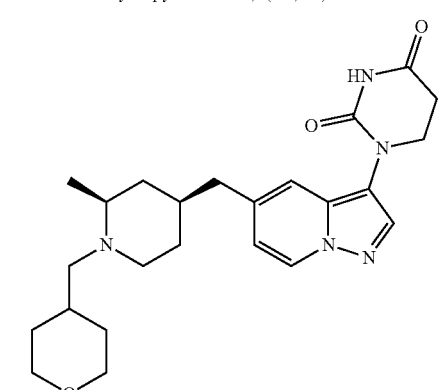

1-(5-(((2S,4S)-2-methyl-1-((tetrahydro-2H-pyran-4-yl)
methyl)piperidin-4-yl)methyl)pyrazolo[1,5-a]
pyridin-3-yl)dihydropyrimidine-2,4(1H,3H)-dione

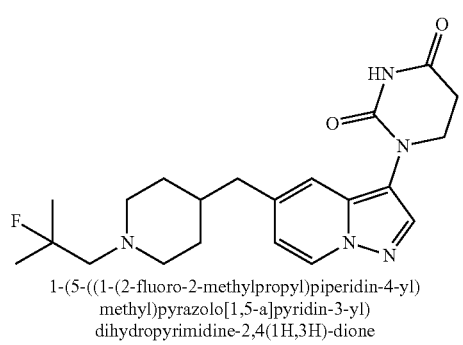

1-(5-((1-(2-fluoro-2-methylpropyl)piperidin-4-yl)
methyl)pyrazolo[1,5-a]pyridin-3-yl)
dihydropyrimidine-2,4(1H,3H)-dione

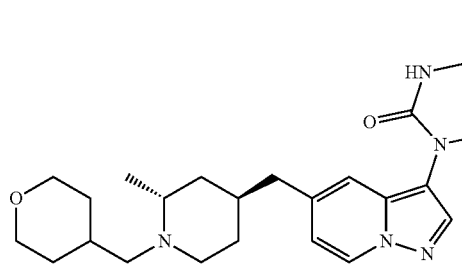

1-(5-(((2R,4S)-2-methyl-1-((tetrahydro-2H-pyran-
4-yl)methyl)piperidin-4-yl)methyl)pyrazolo[1,5-a]
pyridin-3-yl)dihydropyrimidine-2,4(1H,3H)-dione 517
-continued

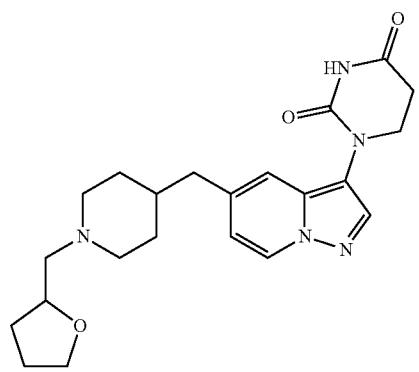

1-(5-((1-((tetrahydrofuran-2-yl)methyl)piperidin-
4-yl)methyl)pyrazolo[1,5-a]pyridin-3-yl)
dihydropyrimidine-2,4(1H,3H)-dione

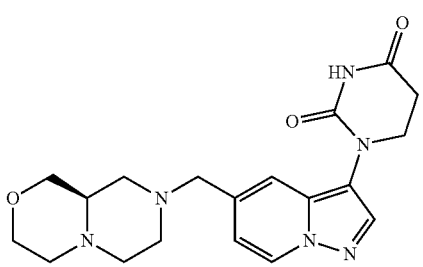

(R)-1-(5-((hexahydropyrazino[2,1-c][1,4]oxazin-8
(1H)-yl)methyl)pyrazolo[1,5-a]pyridin-3-yl)
dihydropyrimidine-2,4(1H,3H)-dione

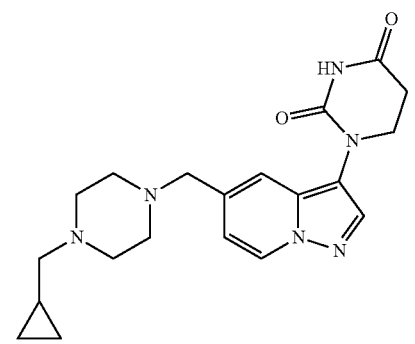

1-(5-((4-(cyclopropylmethyl)piperazin-1-yl)methyl)
pyrazolo[1,5-a]pyridin-3-yl)
dihydropyrimidine-2,4(1H,3H)-dione

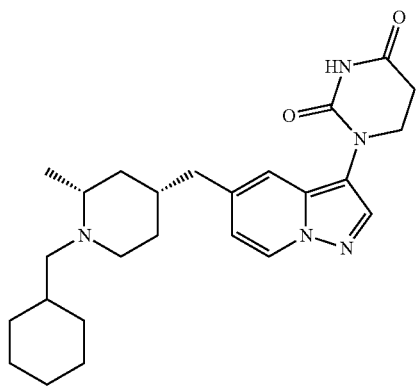

1-(5-(((2R,4R)-1-(cyclohexylmethyl)-2-
methylpiperidin-4-yl)methyl)pyrazolo
[1,5-a]pyridin-3-yl)dihydropyrimidine-2,4(1H,3H)-dione 518
-continued

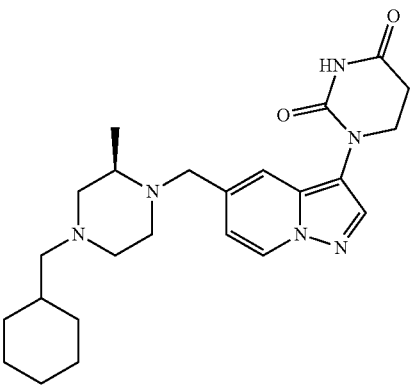

(R)-1-(5-((4-(cyclohexylmethyl)-2-
methylpiperazin-1-yl)methyl)pyrazolo
[1,5-a]pyridin-3-yl)dihydropyrimidine-2,4(1H,3H)-dione

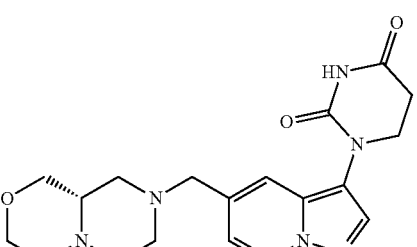

(S)-1-(5-((hexahydropyrazino[2,1-c][1,4]
oxazin-8(1H)-yl)methyl)pyrazolo[1,5-a]
pyridin-3-yl)dihydropyrimidine-2,4(1H,3H)-dione

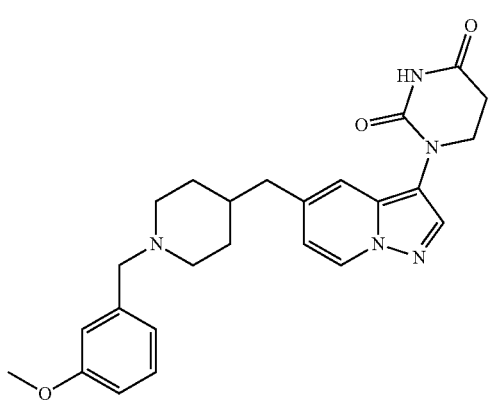

1-(5-((1-(3-methoxybenzyl)piperidin-4-yl)
methyl)pyrazolo[1,5-a]pyridin-3-yl)
dihydropyrimidine-2,4(1H,3H)-dione

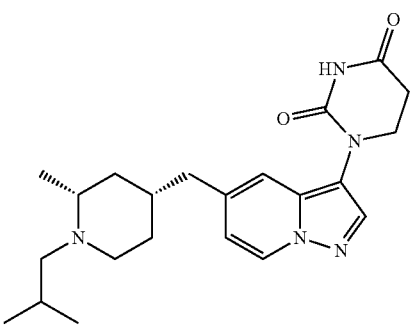

1-(5-(((2R,4R)-1-isobutyl-2-
methylpiperidin-4-yl)methyl)pyrazolo[1,5-a]
pyridin-3-yl)dihydropyrimidine-2,4(1H,3H)-dione

519

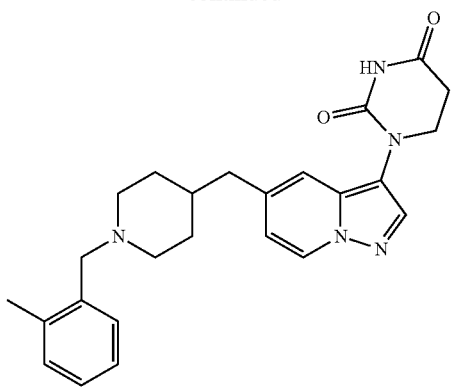

1-(5-((1-(2-(methylbenzyl)piperidin-4-yl)
methyl)pyrazolo[1,5-a]pyridin-3-yl)
dihydropyrimidine-2,4(1H,3H)-dione

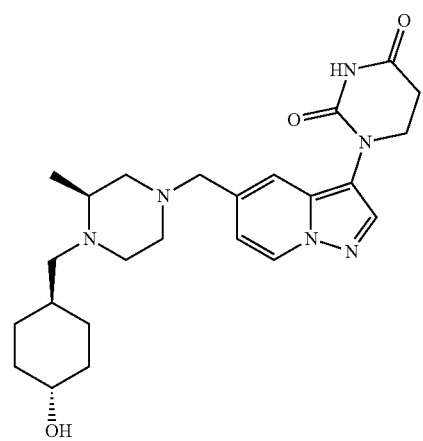

1-(5-(((S)-4-(((1r,4S)-4-hydroxycyclohexyl)methyl)-3-
methylpiperazin-1-yl)methyl)pyrazolo[1,5-a]
pyridin-3-yl)dihydropyrimidine-2,4(1H,3H)-dione

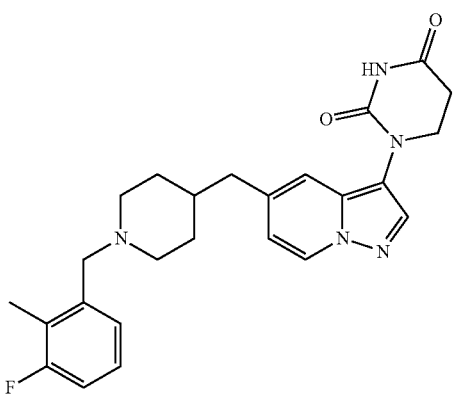

1-(5-((1-(3-fluoro-2-methylbenzyl))piperidin-
4-yl)methyl)pyrazolo[1,5-a]pyridin-3-yl)
dihydropyrimidine-2,4(1H,3H)-dione

520

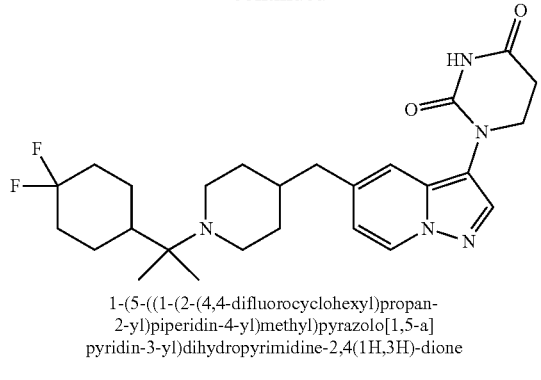

1-(5-((1-(2-(4,4-difluorocyclohexyl)propan-
2-yl)piperidin-4-yl)methyl)pyrazolo[1,5-a]
pyridin-3-yl)dihydropyrimidine-2,4(1H,3H)-dione

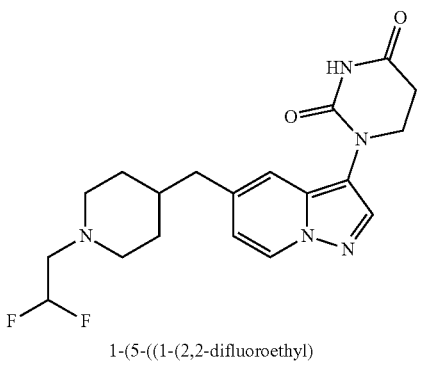

1-(5-((1-(2,2-difluoroethyl)
piperidin-4-yl)methyl)pyrazolo[1,5-a]
pyridin-3-yl)dihydropyrimidine-2,4(1H,3H)-dione

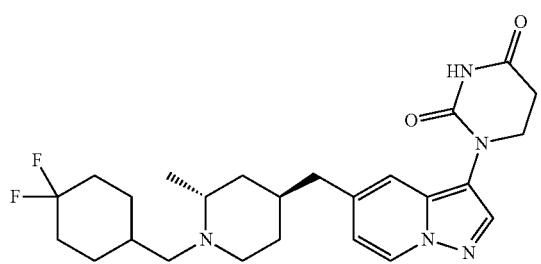

1-(5-(((2R,4S)-1-((4,4-difluorocyclohexyl)methyl)-2-
methylpiperidin-4-yl)methyl)pyrazolo[1,5-a]
pyridin-3-yl)dihydropyrimidine-2,4(1H,3H)-dione

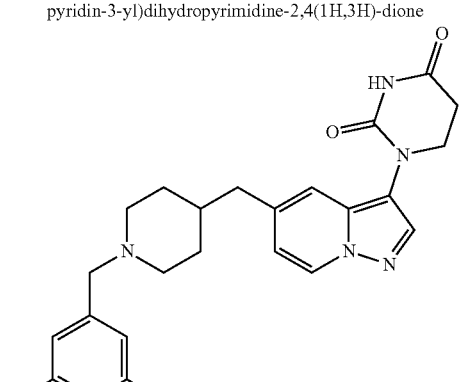

1-(5-((1-(3,5-difluorobenzyl)piperidin-4-yl)
methyl)pyrazolo[1,5-a]pyridin-3-yl)
dihydropyrimidine-2,4(1H,3H)-dione -continued

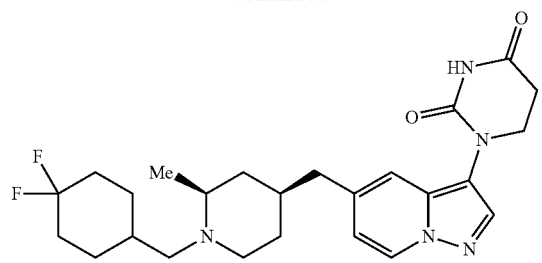

1-(5-(((2S,4S)-1-((4,4-difluorocyclohexyl)methyl)-2-methylpiperidin-4-yl)methyl)pyrazolo[1,5-a]pyridin-3-yl)dihydropyrimidine-2,4(1H,3H)-dione

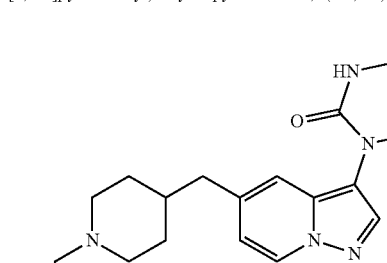

1-(5-((1-(3,4-difluorobenzyl)piperidin-4-yl)methyl)pyrazolo[1,5-a]pyridin-3-yl)dihydropyrimidine-2,4(1H,3H)-dione

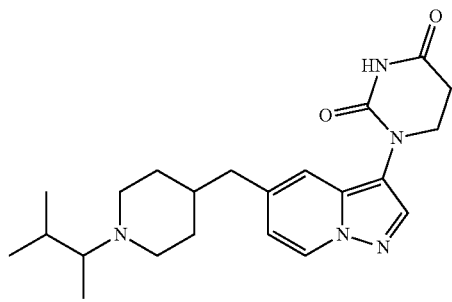

1-(5-((1-(3-methylbutan-2-yl)piperidin-4-yl)methyl)pyrazolo[1,5-a]pyridin-3-yl)dihydropyrimidine-2,4(1H,3H)-dione

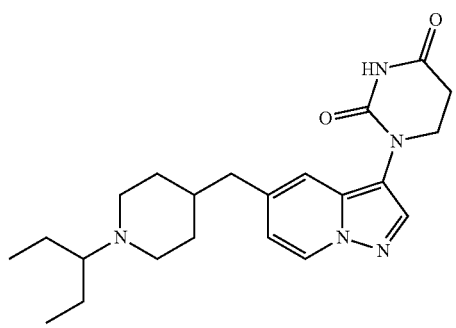

1-(5-((4-(pentan-3-yl)piperazin-1-yl)methyl)pyrazolo[1,5-a]pyridin-3-yl)dihydropyrimidine-2,4(1H,3H)-dione -continued

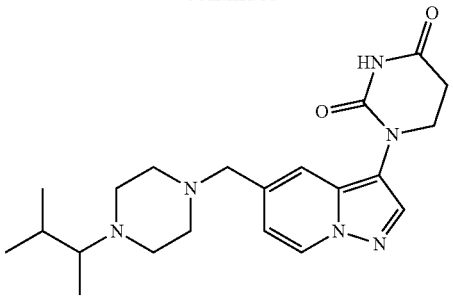

1-(5-((4-(3-methylbutan-2-yl)piperazin-1-yl)methyl)pyrazolo[1,5-a]pyridin-3-yl)dihydropyrimidine-2,4(1H,3H)-dione

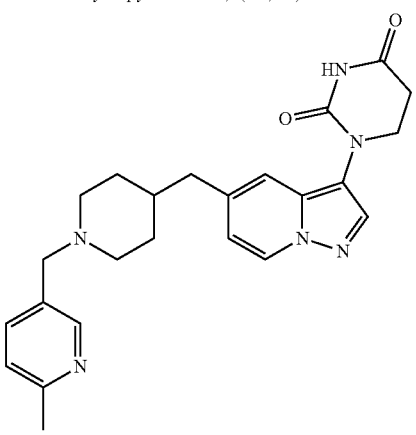

1-(5((1-((6-methylpyridin-3-yl)methyl)piperidin-4-yl)methyl)pyrazolo[1,5-a]pyridin-3-yl)dihydropyrimidine-2,4(1H,3H)-dione

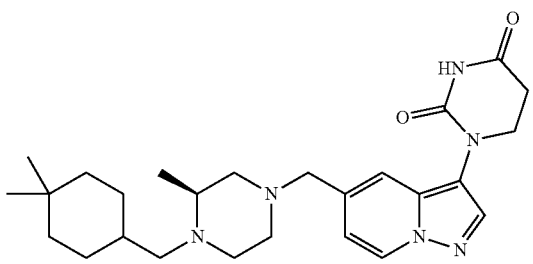

(S)-1-(5-((4-((4,4-dimethylcyclohexyl)methyl)-3-methylpiperazin-1-yl)methyl)pyrazolo[1,5-a]pyridin-3-yl)dihydropyrimidine-2,4(1H,3H)-dione

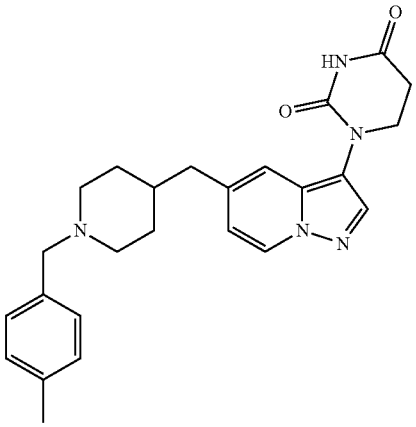

1-(5-((1-(4-methylbenzyl(piperidin-4-yl)methyl)pyrazolo[1,5-a]pyridin-3-yl)dihydropyrimidine-2,4(1H,3H)-dione -continued

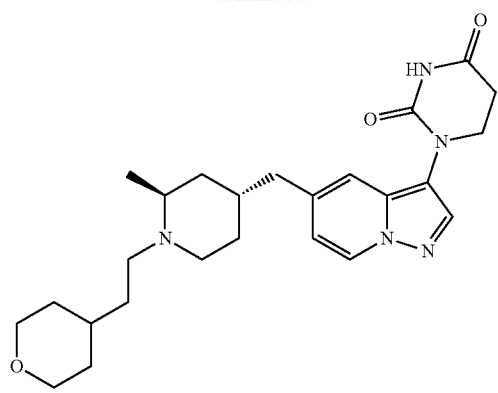

1-(5-(((2S,4R)-2-methyl-1-(2-(tetrahydro-2H-pyran-4-yl)ethyl)piperidin-4-yl)methyl)pyrazolo[1,5-a]pyridin-3-yl)dihydropyrimidine-2,4(1H,3H)-dione

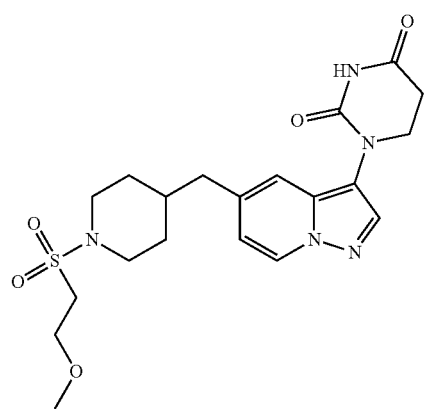

1-(5-((1-((2-methoxyethyl)sulfonyl)piperidin-4-yl)methyl)pyrazolo[1,5-a]pyridin-3-yl)dihydropyrimidine-2,4(1H,3H)-dione

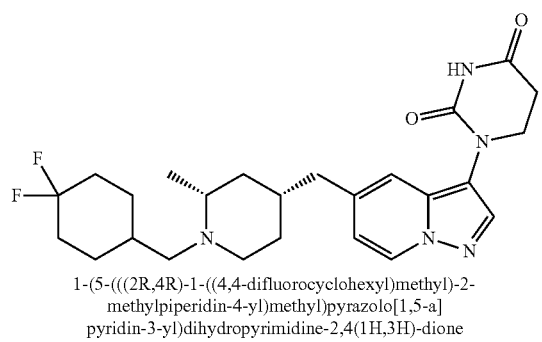

1-(5-(((2R,4R)-1-((4,4-difluorocyclohexyl)methyl)-2-methylpiperidin-4-yl)methyl)pyrazolo[1,5-a]pyridin-3-yl)dihydropyrimidine-2,4(1H,3H)-dione

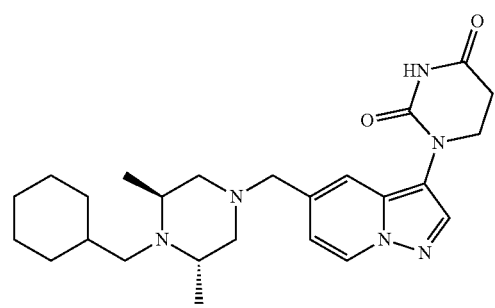

1-(5-(((3S,5S)-4-(cyclohexylmethyl)-3,5-dimethylpiperazin-1-yl)methyl)pyrazolo[1,5-a]pyridin-3-yl)dihydropyrimidine-2,4(1H,3H)-dione -continued

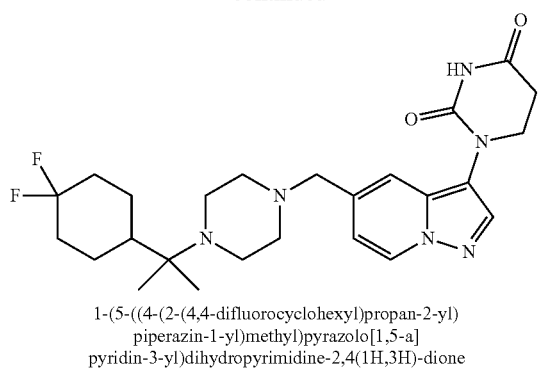

1-(5-((4-(2-(4,4-difluorocyclohexyl)propan-2-yl)piperazin-1-yl)methyl)pyrazolo[1,5-a]pyridin-3-yl)dihydropyrimidine-2,4(1H,3H)-dione

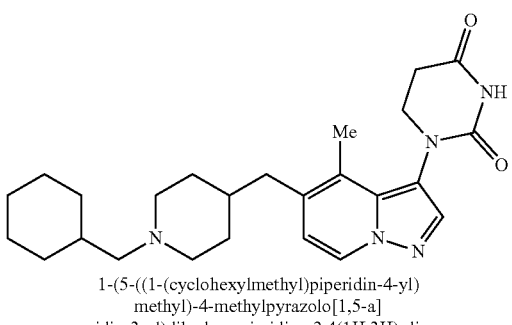

1-(5-((1-(cyclohexylmethyl)piperidin-4-yl)methyl)-4-methylpyrazolo[1,5-a]pyridin-3-yl)dihydropyrimidine-2,4(1H,3H)-dione

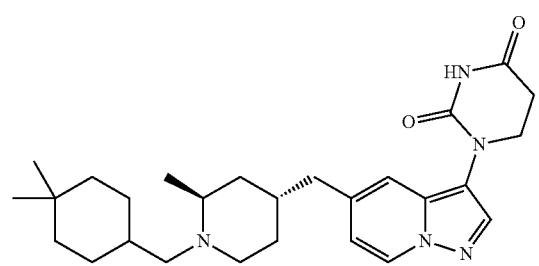

1-(5-(((2S,4R)-1-((4,4-dimethylcyclohexyl)-2-methylpiperidin-4-yl)methyl)pyrazolo[1,5-a]pyridin-3-yl)dihydropyrimidine-2,4(1H,3H)-dione

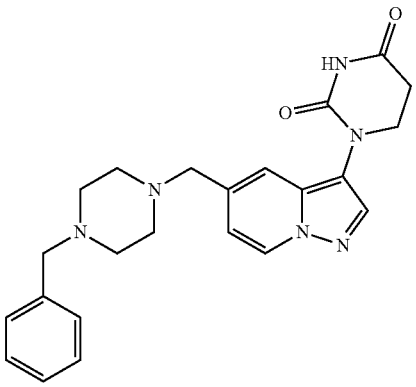

1-(5-((4-benzylpiperazin-1-yl)methyl)pyrazolo[1,5-a]pyridin-3-yl)dihydropyrimidine-2,4(1H,3H)-dione

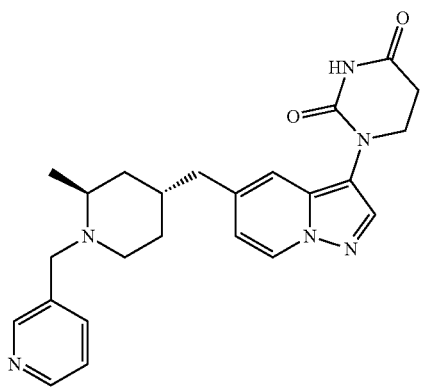

1-(5-(((2S,4R)-2-methyl-1-(pyridin-3-ylmethyl)
piperidin-4-yl)methyl)pyrazolo[1,5-a]
pyridin-3-yl)dihydropyrimidine-2,4(1H,3H)-dione

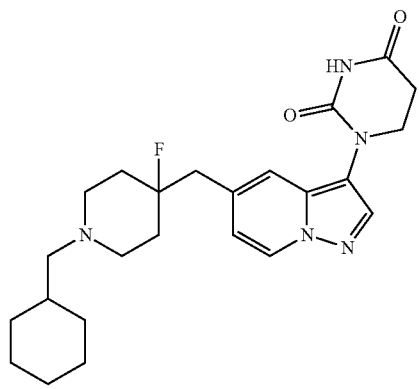

1-(5-((1-cyclohexylmethyl)-4-fluoropiperidin-
4-yl)methyl)pyrazolo[1,5-a]pyridin-3-yl)
dihydropyrimidine-2,4(1H,3H)-dione

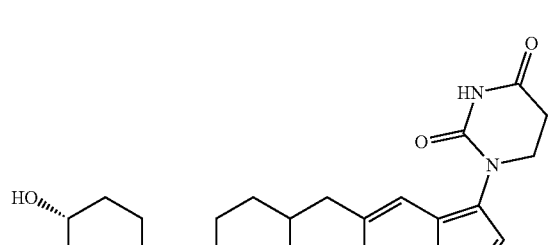

1-(5-((1-(((1r,4r)-4-hydroxycyclohexyl)methyl)
piperidin-4-yl)methyl)pyrazolo[1,5-a]
pyridin-3-yl)dihydropyrimidine-2,4(1H,3H)-dione

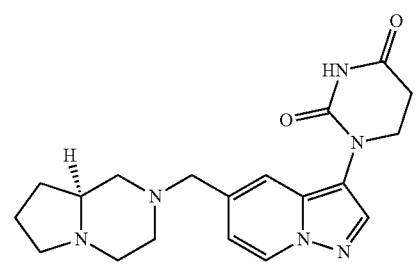

(S)-1-(5-((hexahydropyrrolo[1,2-a]pyrazin-
2(1H)-yl)methyl)pyrazolo[1,5-a]
pyridin-3-yl)dihydropyrimidine-2,4(1H,3H)-dione

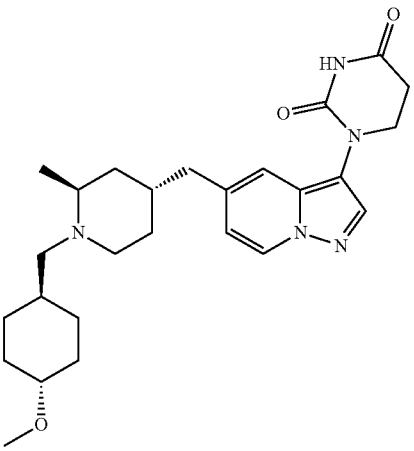

1-(5-(((2S,4R)-1-(((1r,4S)-4-methoxycyclohexyl)
methyl)-2-methylpiperidin-4-yl)methyl)pyrazolo
[1,5-a]pyridin-3-yl)dihydropyrimidine-2,4(1H,3H)-dione

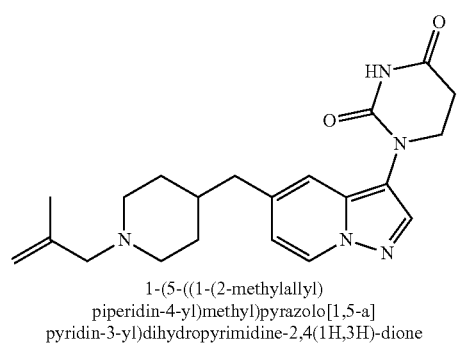

1-(5-((1-(2-methylallyl)
piperidin-4-yl)methyl)pyrazolo[1,5-a]
pyridin-3-yl)dihydropyrimidine-2,4(1H,3H)-dione

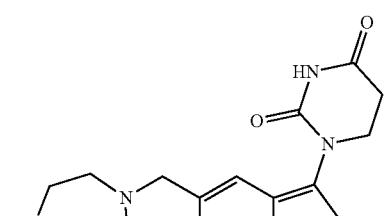

1-(5-((1,4-diazepan-1-yl)
methyl)pyrazolo[1,5-a]pyridin-3-yl)
dihydropyrimidine-2,4(1H,3H)-dione

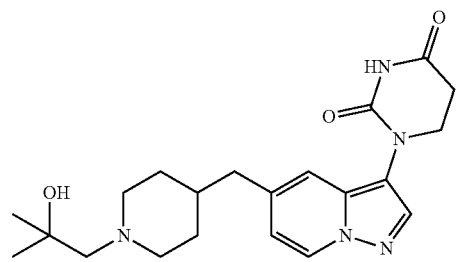

1-(5-((1-(2-hydroxy-2-methylpropyl)piperidin-4-yl)
methyl)pyrazolo[1,5-a]pyridin-3-yl)
dihydropyrimidine-2,4(1H,3H)-dione -continued

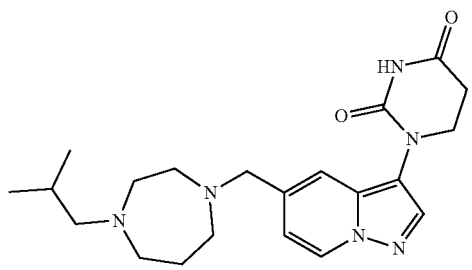

1-(5-((4-isobutyl-1,4-diazepan-1-yl)
methyl)pyrazolo[1,5-a]pyridin-3-yl)
dihydropyrimidine-2,4(1H,3H)-dione

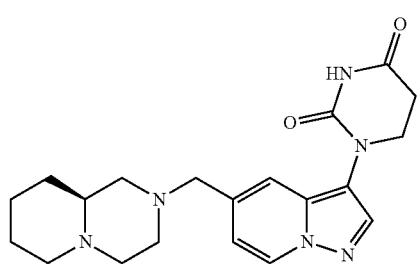

(S)-1-(5-((octahydro-2H-pyridol[1,2-a]
pyrazin-2-yl)methyl)pyrazolo[1,5-a]
pyridin-3-yl)dihydropyrimidine-2,4(1H,3H)-dione

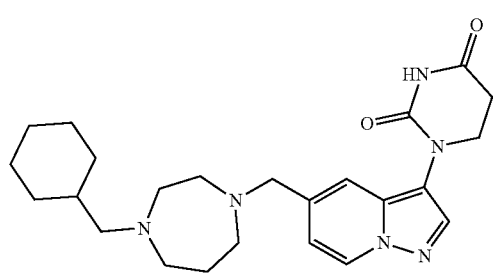

1-(5-((4-(cyclohexylmethyl)-1,4-diazepan-1-yl)
methyl)pyrazolo[1,5-a]pyridin-3-yl)
dihydropyrimidine-2,4(1H,3H)-dione

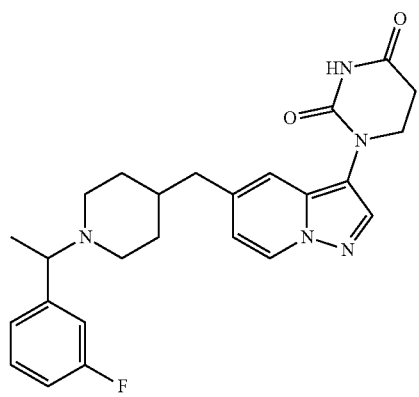

1-(5-((1-(1-(3-fluorophenyl)ethyl)
piperidin-4-yl)methyl)pyrazolo[1,5-a]
pyridin-3-yl)dihydropyrimidine-2,4(1H,3H)-dione -continued

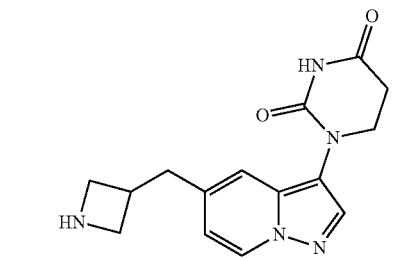

1-(5-(azetidin-3-ylmethyl)
pyrazolo[1,5-a]pyridin-3-yl)
dihydropyrimidine-2,4(1H,3H)-dione

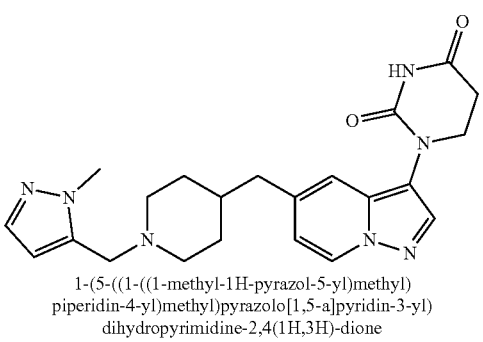

1-(5-((1-((1-methyl-1H-pyrazol-5-yl)methyl)
piperidin-4-yl)methyl)pyrazolo[1,5-a]pyridin-3-yl)
dihydropyrimidine-2,4(1H,3H)-dione

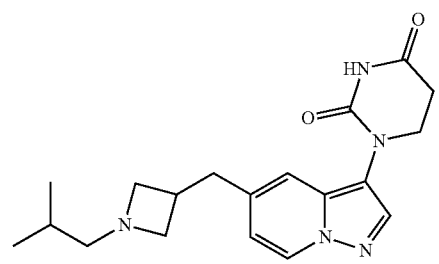

1-(5-((1-isobutylazetidin-3-yl)
methyl)pyrazolo[1,5-a]pyridin-3-yl)
dihydropyrimidine-2,4(1H,3H)-dione

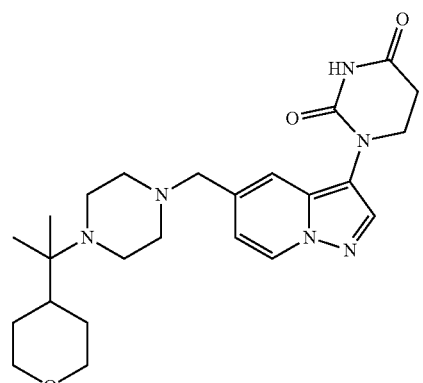

1-(5-((4-(2-(tetrahydro-2H-pyran-4-)propan-2-yl)
piperazin-1-yl)methyl)pyrazolo[1,5-a]pyridin-3-yl)
dihydropyrimidine-2,4(1H,3H)-dione 529
-continued

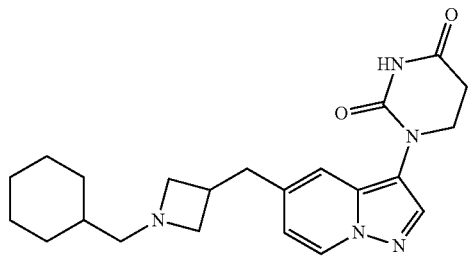

1-(5-((1-(cyclohexylmethyl)azetidin-3-yl)
methyl)pyrazolo[1,5-a]pyridin-3-yl)
dihydropyrimidine-2,4(1H,3H)-dione

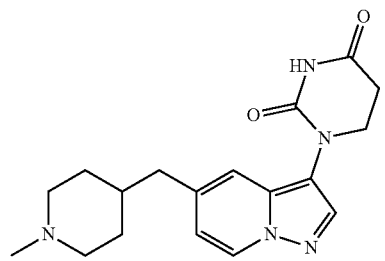

1-(5-((1-methylpiperidin-4-yl)methyl)
pyrazolo[1,5-a]pyridin-3-yl)
dihydropyrimidine-2,4(1H,3H)-dione

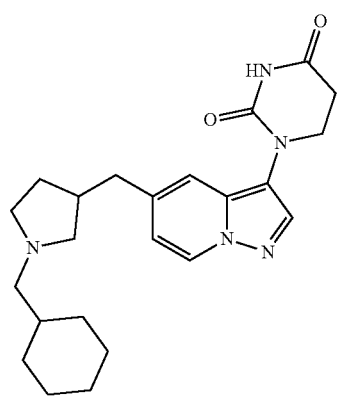

1-(5-((1-(cyclohexylmethyl)pyrrolidin-3-yl)
methyl)pyrazolo[1,5-a]pyridin-3-yl)
dihydropyrimidine-2,4(1H,3H)-dione

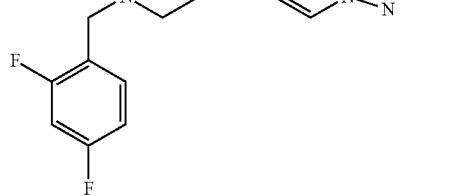

1-(5-((1-(2,4-difluorobenzyl)
piperidin-4-yl)methyl)pyrazolo[1,5-a]
pyridin-3-yl)dihydropyrimidine-2,4(1H,3H)-dione 530
-continued

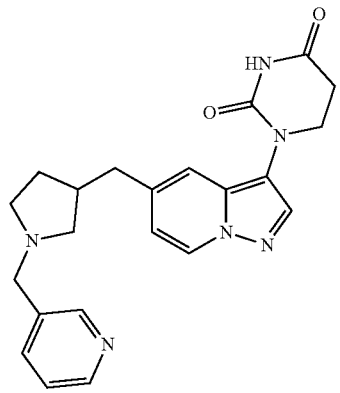

1-(5-((1-(pyridin-3-ylmethyl)pyrrolidin-3-
yl)methyl)pyrazolo[1,5-a]pyridin-3-yl)
dihydropyrimidine-2,4(1H,3H)-dione

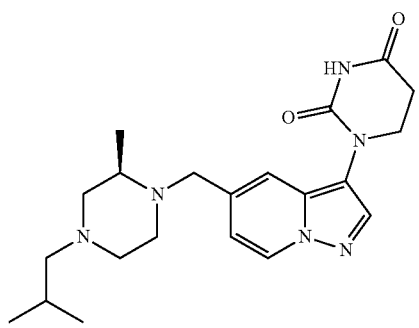

(R)-1-(5-((4-isobutyl-2-methylpiperazin-1-yl)
methyl)pyrazolo[1,5-a]pyridin-3-yl)
dihydropyrimidine-2,4(1H,3H)-dione

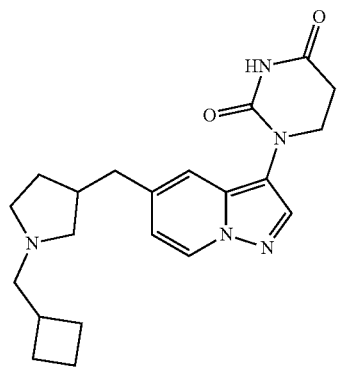

1-(5-((1-(cyclobutylmethyl)pyrrolidin-3-
yl)methyl)pyrazolo[1,5-a]pyridin-3-yl)
dihydropyrimidine-2,4(1H,3H)-dione 531
-continued

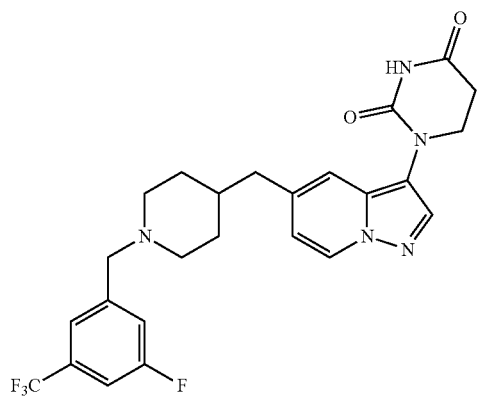

1-(5-((1-(3-fluoro-5-(trifluoromethyl)benzyl)
piperidin-4-yl)methyl)pyrazolo[1,5-a]pyridin-3-yl)
dihydropyrimidine-2,4(1H,3H)-dione

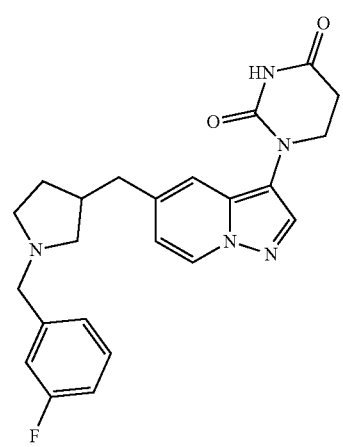

1-(5-((1-(3-fluorobenzyl)pyrrolidin-3-
yl)methyl)pyrazolo[1,5-a]pyridin-3-yl)
dihydropyrimidine-2,4(1H,3H)-dione

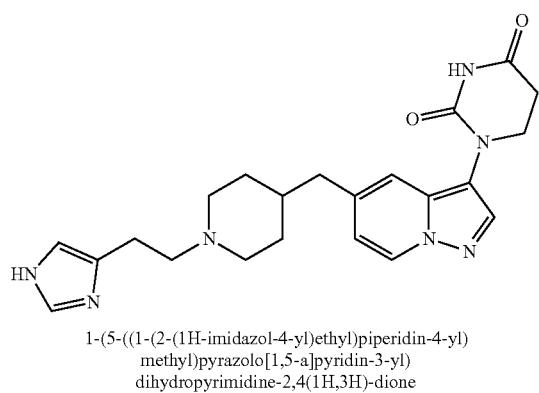

1-(5-((1-(2-(1H-imidazol-4-yl)ethyl)piperidin-4-yl)
methyl)pyrazolo[1,5-a]pyridin-3-yl)
dihydropyrimidine-2,4(1H,3H)-dione 532
-continued

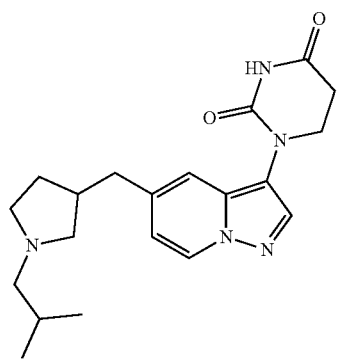

1-(5-((1-isobutylpyrrolidin-3-yl)
methyl)pyrazolo[1,5-a]pyridin-3-yl)
dihydropyrimidine-2,4(1H,3H)-dione

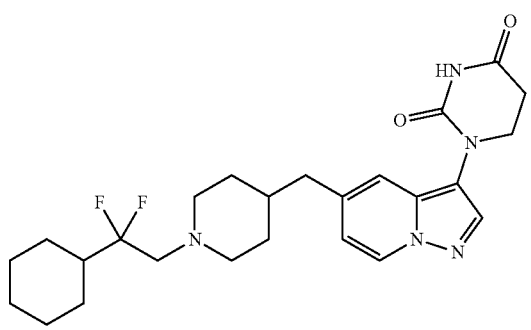

1-(5-((1-(2-cyclohexyl-2,2-difluoroethyl)piperidin-4-
yl)methyl)pyrazolo[1,5-a]pyridin-3-yl)
dihydropyrimidine-2,4(1H,3H)-dione

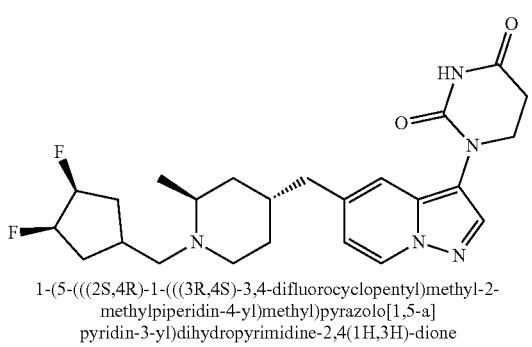

1-(5-(((2S,4R)-1-(((3R,4S)-3,4-difluorocyclopentyl)methyl-2-
methylpiperidin-4-yl)methyl)pyrazolo[1,5-a]
pyridin-3-yl)dihydropyrimidine-2,4(1H,3H)-dione

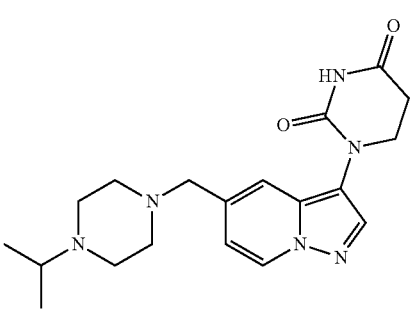

1-(5-((4-isopropylpiperazin-1-yl)
methyl)pyrazolo[1,5-a]pyridin-3-yl)
dihydropyrimidine-2,4(1H,3H)-dione 533
-continued

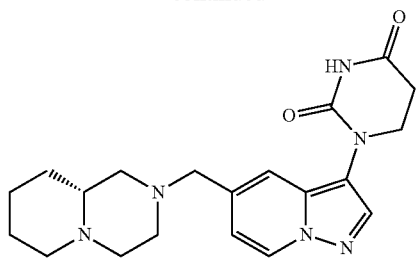

(R)-1-(5-((octahydro-2H-pyrido[1,2-a]
pyrazin-2-yl)methyl)pyrazolo[1,5-a]
pyridin-3-yl)dihydropyrimidine-2,4(1H,3H)-dione

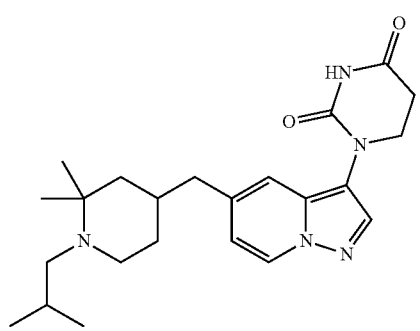

1-(5-((1-isobutyl-2,2-dimethylpiperidin-4-
yl)methyl)pyrazolo[1,5-a]pyridin-3-yl)
dihydropyrimidine-2,4(1H,3H)-dione

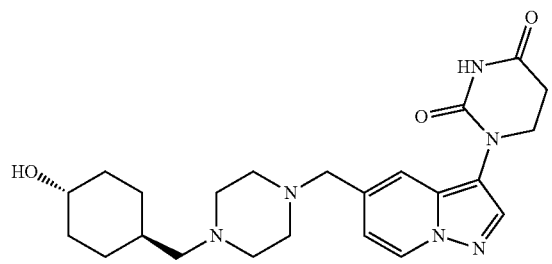

1-(5-((4-(((1r,4r)-4-hydroxycyclohexyl)methyl)
piperazin-1-yl)methyl)pyrazolo[1,5-a]
pyridin-3-yl)dihydropyrimidine-2,4(1H,3H)-dione

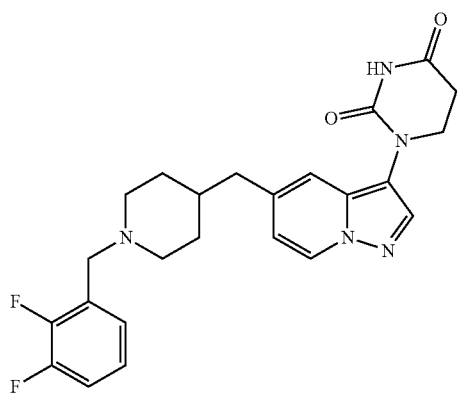

1-(5-((1-(2,3-difluorobenzyl)piperidin-4-
yl)methyl)pyrazolo[1,5-a]pyridin-3-yl)
dihydropyrimidine-2,4(1H,3H)-dione 534
-continued

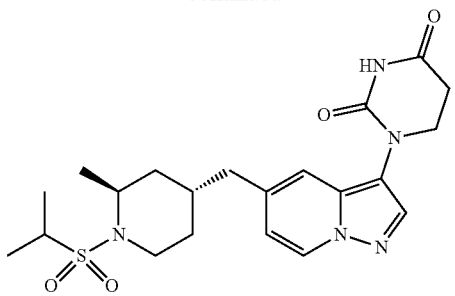

1-(5-(((2S,4R)-1-(isopropylsulfonyl)-2-
methylpiperidin-4-yl)methyl)pyrazolo[1,5-a]
pyridin-3-yl)dihydropyrimidine-2,4(1H,3H)-dione

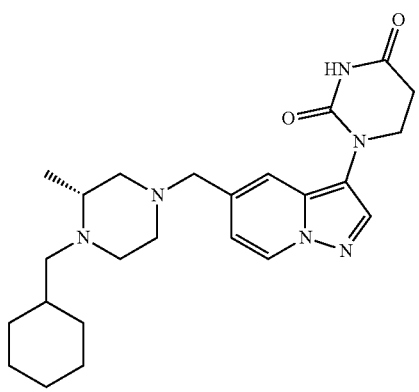

(R)-1-(5-((4-(cyclohexylmethyl)-3-
methylpiperazin-1-yl)methyl)pyrazolo[1,5-a]
pyridin-3-yl)dihydropyrimidine-2,4(1H,3H)-dione

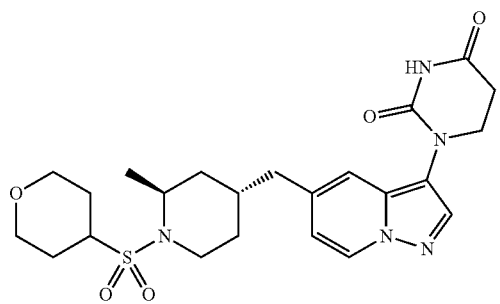

1-(5-(((2S,4R)-2-methyl-1-((tetrahydro-2H-pyran-4-yl)
sulfonyl)piperidin-4-yl)methyl)pyrazolo
[1,5-a]pyridin-3-yl)dihydropyrimidine-2,4(1H,3H)-dione

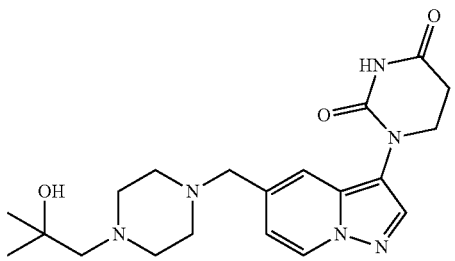

1-(5-((4-(2-hydroxy-2-methylpropyl)piperazin-1-
yl)methyl)pyrazolo[1,5-a]pyridin-3-yl)
dihydropyrimidine-2,4(1H,3H)-dione

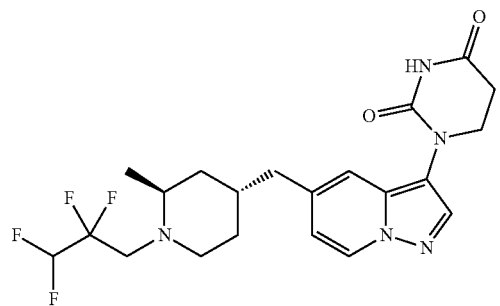

1-(5-(((2S,4R)-2-methyl-1-(2,2,3,3-tetrafluoropropyl)
piperidin-4-yl)methyl)pyrazolo[1,5-a]
pyridin-3-yl)dihydropyrimidine-2,4(1H,3H)-dione

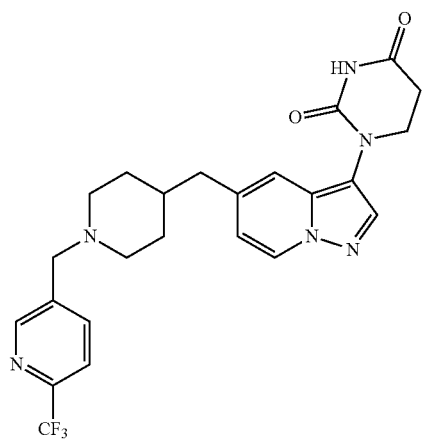

1-(5-((1-((6-(trifluoromethyl)pyridin-3-yl)methyl)
piperidin-4-yl)methyl)pyrazolo[1,5-a]pyridin-3-yl)
dihydropyrimidine-2,4(1H,3H)-dione

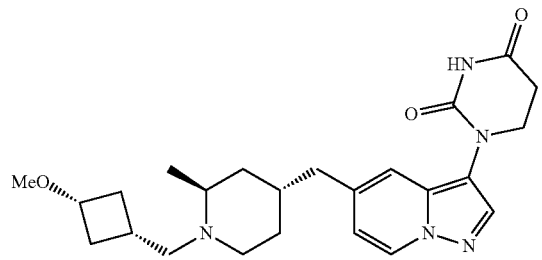

1-(5-(((2S,4R)-1-(((1s,3R)-3-methoxycyclobutyl)methyl)-2-
methylpiperidin-4-yl)methyl)pyrazolo[1,5-a]
pyridin-3-yl)dihydropyrimidine-2,4(1H,3H)-dione

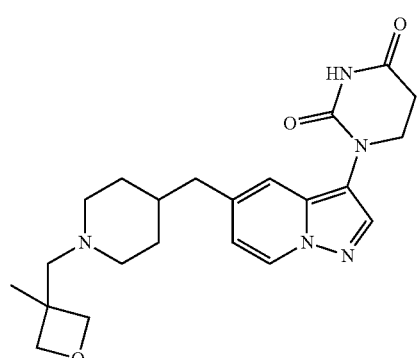

1-(5-((1-((3-methyloxetan-3-yl)methyl)
piperidin-4-yl)methyl)pyrazolo[1,5-a]
pyridin-3-yl)dihydropyrimidine-2,4(1H,3H)-dione

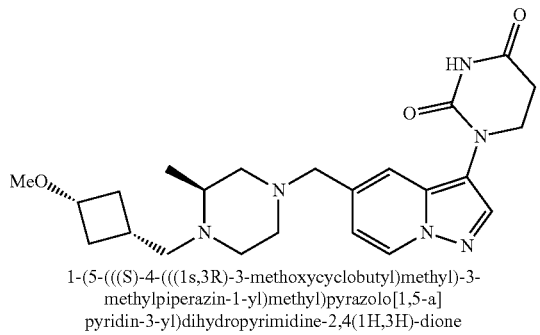

1-(5-(((S)-4-(((1s,3R)-3-methoxycyclobutyl)methyl)-3-
methylpiperazin-1-yl)methyl)pyrazolo[1,5-a]
pyridin-3-yl)dihydropyrimidine-2,4(1H,3H)-dione

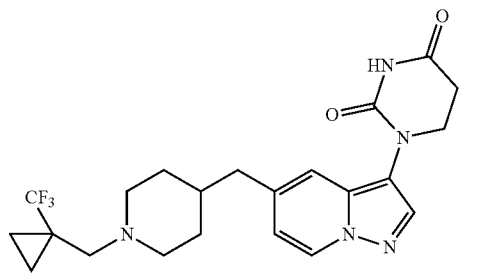

1-(5-((1-((1-(trifluoromethyl)cyclopropyl)methyl)
piperidin-4-yl)methyl)pyrazolo[1,5-a]
pyridin-3-yl)dihydropyrimidine-2,4(1H,3H)-dione

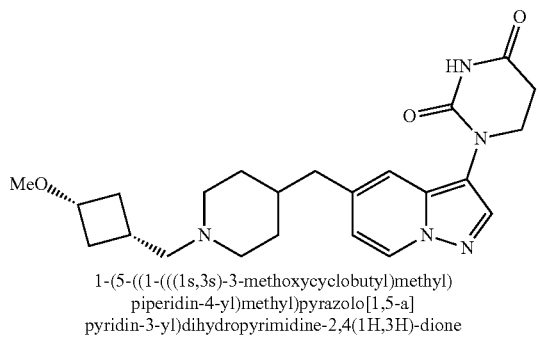

1-(5-((1-(((1s,3s)-3-methoxycyclobutyl)methyl)
piperidin-4-yl)methyl)pyrazolo[1,5-a]
pyridin-3-yl)dihydropyrimidine-2,4(1H,3H)-dione

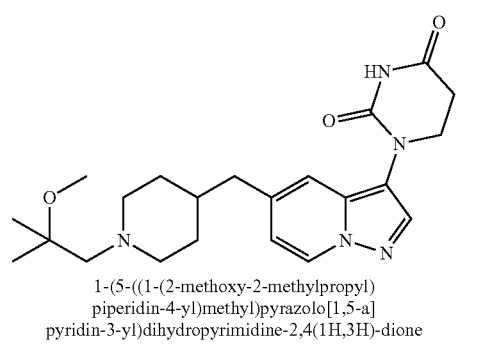

1-(5-((1-(2-methoxy-2-methylpropyl)
piperidin-4-yl)methyl)pyrazolo[1,5-a]
pyridin-3-yl)dihydropyrimidine-2,4(1H,3H)-dione

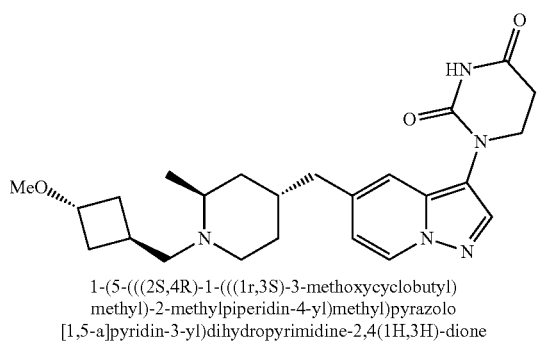

1-(5-(((2S,4R)-1-(((1r,3S)-3-methoxycyclobutyl)
methyl)-2-methylpiperidin-4-yl)methyl)pyrazolo
[1,5-a]pyridin-3-yl)dihydropyrimidine-2,4(1H,3H)-dione 537
-continued

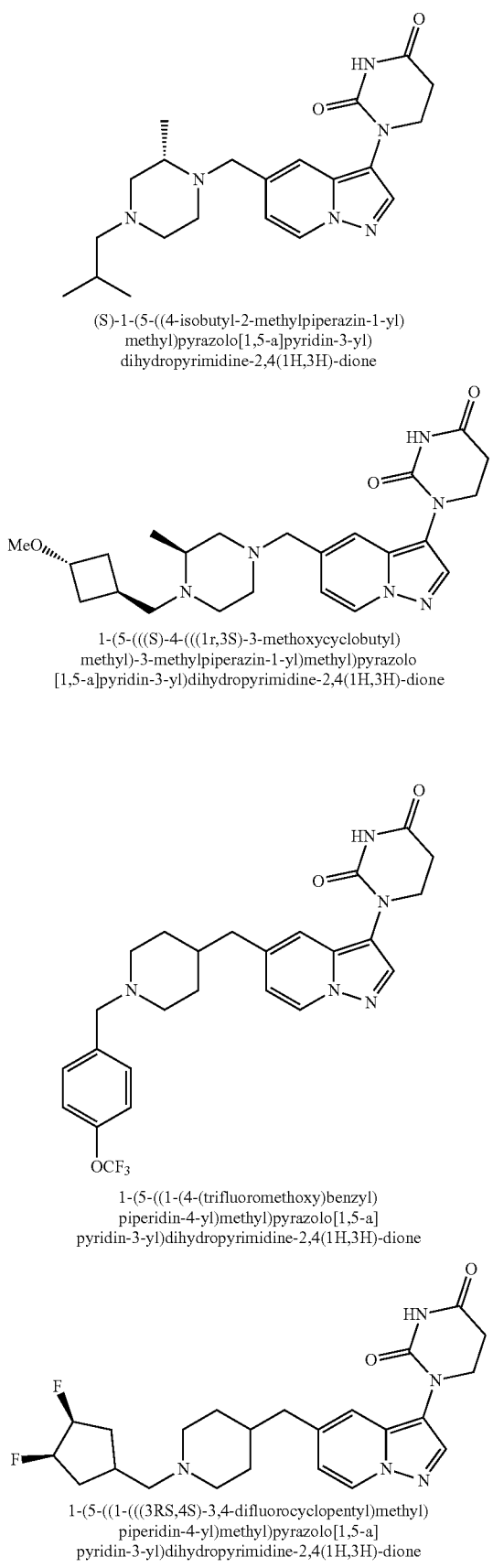

(S)-1-(5-((4-isobutyl-2-methylpiperazin-1-yl)
methyl)pyrazolo[1,5-a]pyridin-3-yl)
dihydropyrimidine-2,4(1H,3H)-dione 1-(5-(((S)-4-(((1r,3S)-3-methoxycyclobutyl)
methyl)-3-methylpiperazin-1-yl)methyl)pyrazolo
[1,5-a]pyridin-3-yl)dihydropyrimidine-2,4(1H,3H)-dione 1-(5-((1-(4-(trifluoromethoxy)benzyl)
piperidin-4-yl)methyl)pyrazolo[1,5-a]
pyridin-3-yl)dihydropyrimidine-2,4(1H,3H)-dione 1-(5-((1-(((3RS,4S)-3,4-difluorocyclopentyl)methyl)
piperidin-4-yl)methyl)pyrazolo[1,5-a]
pyridin-3-yl)dihydropyrimidine-2,4(1H,3H)-dione 538
-continued

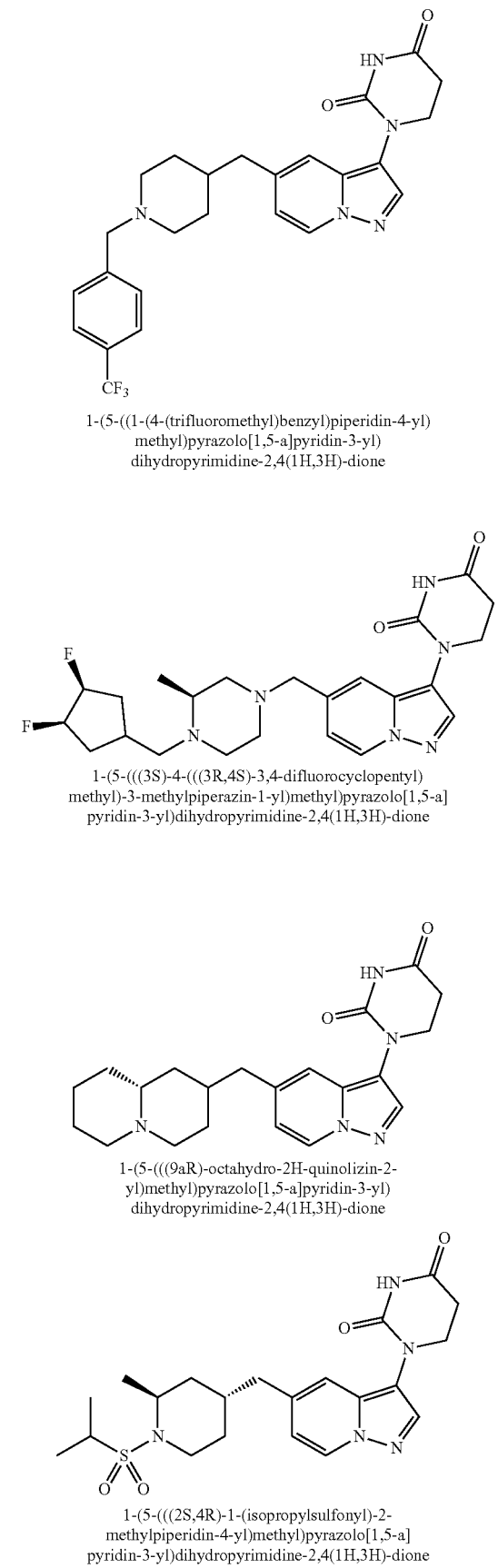

1-(5-((1-(4-(trifluoromethyl)benzyl)piperidin-4-yl)
methyl)pyrazolo[1,5-a]pyridin-3-yl)
dihydropyrimidine-2,4(1H,3H)-dione 1-(5-(((3S)-4-(((3R,4S)-3,4-difluorocyclopentyl)
methyl)-3-methylpiperazin-1-yl)methyl)pyrazolo[1,5-a]
pyridin-3-yl)dihydropyrimidine-2,4(1H,3H)-dione 1-(5-(((9aR)-octahydro-2H-quinolizin-2-
yl)methyl)pyrazolo[1,5-a]pyridin-3-yl)
dihydropyrimidine-2,4(1H,3H)-dione 1-(5-(((2S,4R)-1-(isopropylsulfonyl)-2-
methylpiperidin-4-yl)methyl)pyrazolo[1,5-a]
pyridin-3-yl)dihydropyrimidine-2,4(1H,3H)-dione

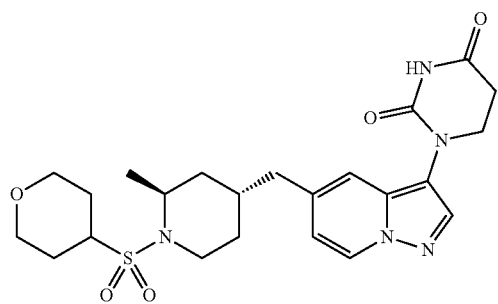

1-(5-(((2S,4R)-2-methyl-1-((tetrahydro-2H-pyran-4-yl)
sulfonyl)piperidin-4-yl)methyl)pyrazolo[1,5-a]
pyridin-3-yl)dihydropyrimidine-2,4(1H,3H)-dione

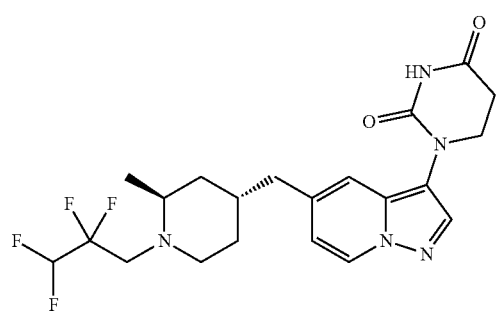

1-(5-(((2S,4R)-2-methyl-1-(2,2,3,3-tetrafluoropropyl)
piperidin-4-yl)methyl)pyrazolo[1,5-a]
pyridin-3-yl)dihydropyrimidine-2,4(1H,3H)-dione

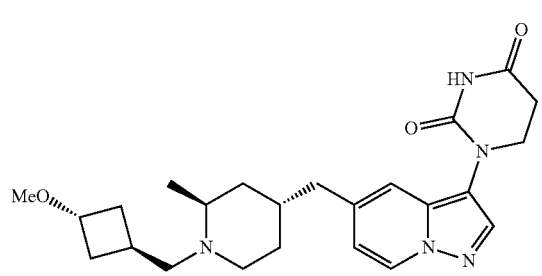

1-(5-(((2S,4R)-1-(((1r,3S)-3-methoxycyclobutyl)methyl)-2-
methylpiperidin-4-yl)methyl)pyrazolo[1,5-a]
pyridin-3-yl)dihydropyrimidine-2,4(1H,3H)-dione

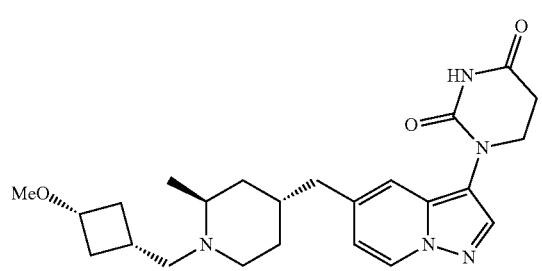

1-(5-(((2S,4R)-1-(((1s,3R)-3-methoxycyclobutyl)methyl)-2-
methylpiperidin-4-yl)methyl)pyrazolo[1,5-a]
pyridin-3-yl)dihydropyrimidine-2,4(1H,3H)-dione

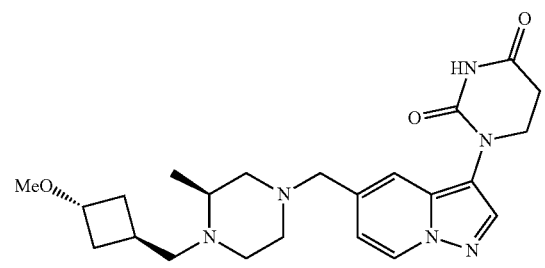

1-(5-(((S)-4-(((1r,3S)-3-methoxycyclobutyl)methyl)-3-
methylpiperazin-1-yl)methyl)pyrazolo[1,5-a]
pyridin-3-yl)dihydropyrimidine-2,4(1H,3H)-dione

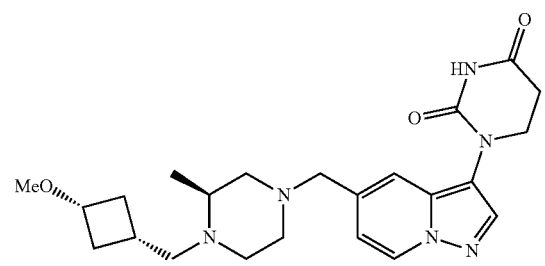

1-(5-(((S)-4-(((1s,3R)-3-methoxycyclobutyl)methyl)-3-
methylpiperazin-1-yl)methyl)pyrazolo[1,5-a]
pyridin-3-yl)dihydropyrimidine-2,4(1H,3H)-dione

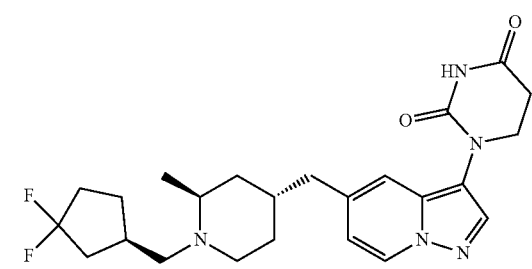

1-(5-(((2S,4R)-1-(((R)-3,3-difluorocyclopentyl)methyl)-2-
methylpiperidin-4-yl)methyl)pyrazolo[1,5-a]
pyridin-3-yl)dihydropyrimidine-2,4(1H,3H)-dione

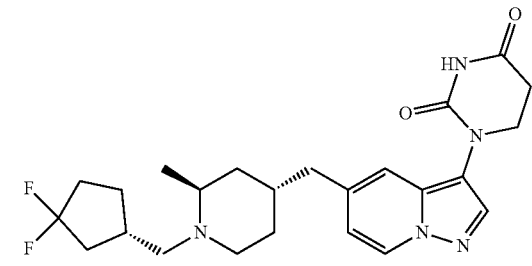

1-(5-(((2S,4R)-1-(((S)-3,3-difluorocyclopentyl)methyl)-2-
methylpiperidin-4-yl)methyl)pyrazolo[1,5-a]
pyridin-3-yl)dihydropyrimidine-2,4(1H,3H)-dione

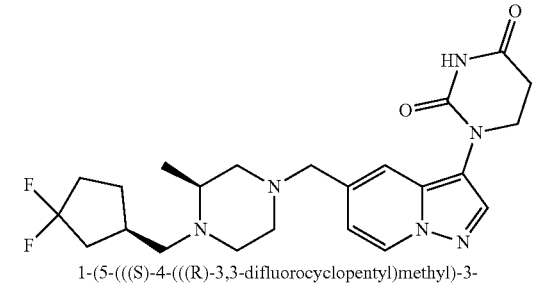

1-(5-(((S)-4-(((R)-3,3-difluorocyclopentyl)methyl)-3-
methylpiperazin-1-yl)methyl)pyrazolo[1,5-a]
pyridin-3-yl)dihydropyrimidine-2,4(1H,3H)-dione

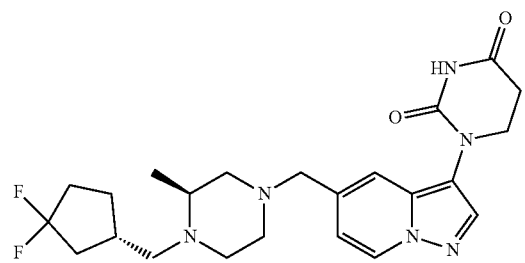

1-(5-(((S)-4-(((S)-3,3-difluorocyclopentyl)methyl)-3-
methylpiperazin-1-yl)methyl)pyrazolo[1,5-a]
pyridin-3-yl)dihydropyrimidine-2,4(1H,3H)-dione

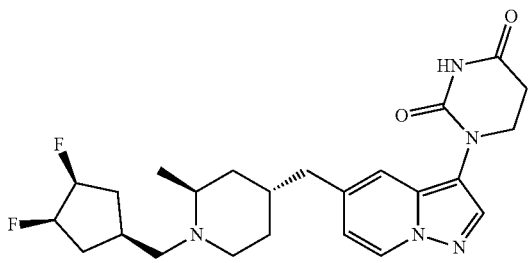

1-(5-(((2S,4R)-1-(((1r,3R,4S)-3,4-difluorocyclopentyl)
methyl)-2-methylpiperidin-4-yl)methyl)pyrazolo
[1,5-a]pyridin-3-yl)dihydropyrimidine-2,4(1H,3H)-dione

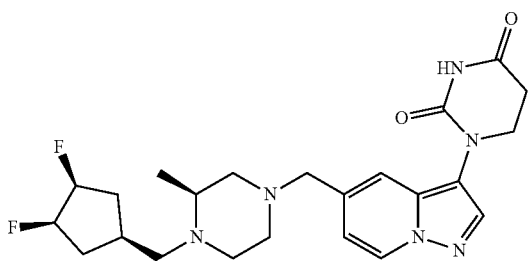

1-(5-(((S)-4-(((1r,3R,4S)-3,4-difluorocyclopentyl)
methyl)-3-methylpiperazin-1-yl)methyl)pyrazolo
[1,5-a]pyridin-3-yl)dihydropyrimidine-2,4(1H,3H)-dione

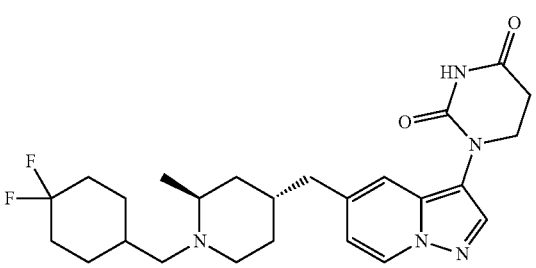

1-(5-(((2S,4R)-1-((4,4-difluorocyclohexyl)methyl)-2-
methylpiperidin-4-yl)methyl)pyrazolo[1,5-a]
pyridin-3-yl)pyrimidine-2,4(1H,3H)-dione

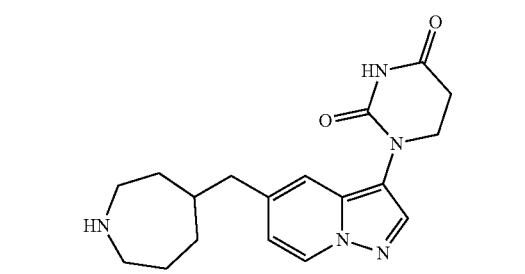

1-(5-(azepan-4-ylmethyl)pyrazolo[1,5-a]
pyridin-3-yl)dihydropyrimidine-2,4(1H,3H)-dione

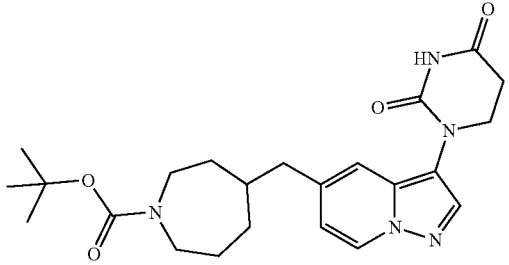

tert-butyl 4-((3-(2,4-dioxotetrahydropyrimidin-1(2H)-yl)
pyrazolo[1,5-a]pyridin-5-yl)methyl)azepane-1-carboxylate

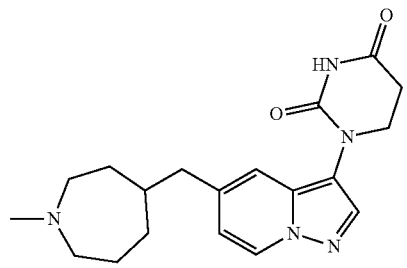

1-(5-((1-((1-methylazepan-4-yl)
methyl)pyrazolo[1,5-a]pyridin-3-yl)
dihydropyrimidine-2,4(1H,3H)-dione

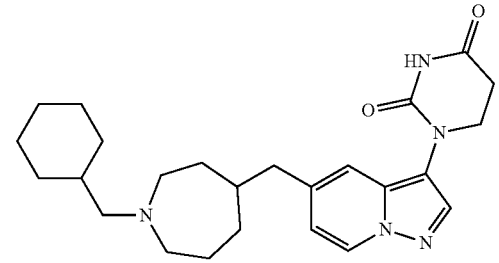

1-(5-((1-(cyclohexylmethyl)azepan-4-yl)
methyl)pyrazolo[1,5-a]pyridin-3-yl)
dihydropyrimidine-2,4(1H,3H)-dione

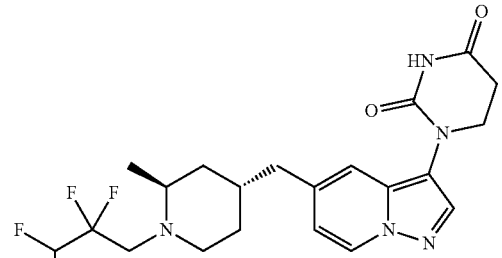

1-(5-(((2S,4R)-2-methyl-1-(2,2,3,3-tetrafluoropropyl)
piperidin-4-yl)methyl)pyrazolo[1,5-a]
pyridin-3-yl)dihydropyrimidine-2,4(1H,3H)-dione

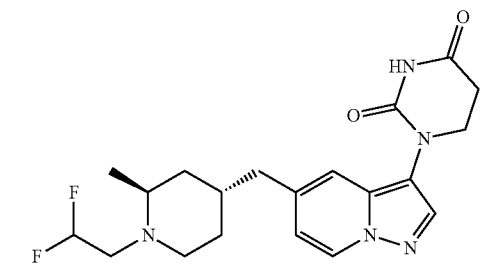

1-(5-(((2S,4R)-1-(2,2-difluoroethyl)-2-
methylpiperidin-4-yl)methyl)pyrazolo[1,5-a]
pyridin-3-yl)dihydropyrimidine-2,4(1H,3H)-dione

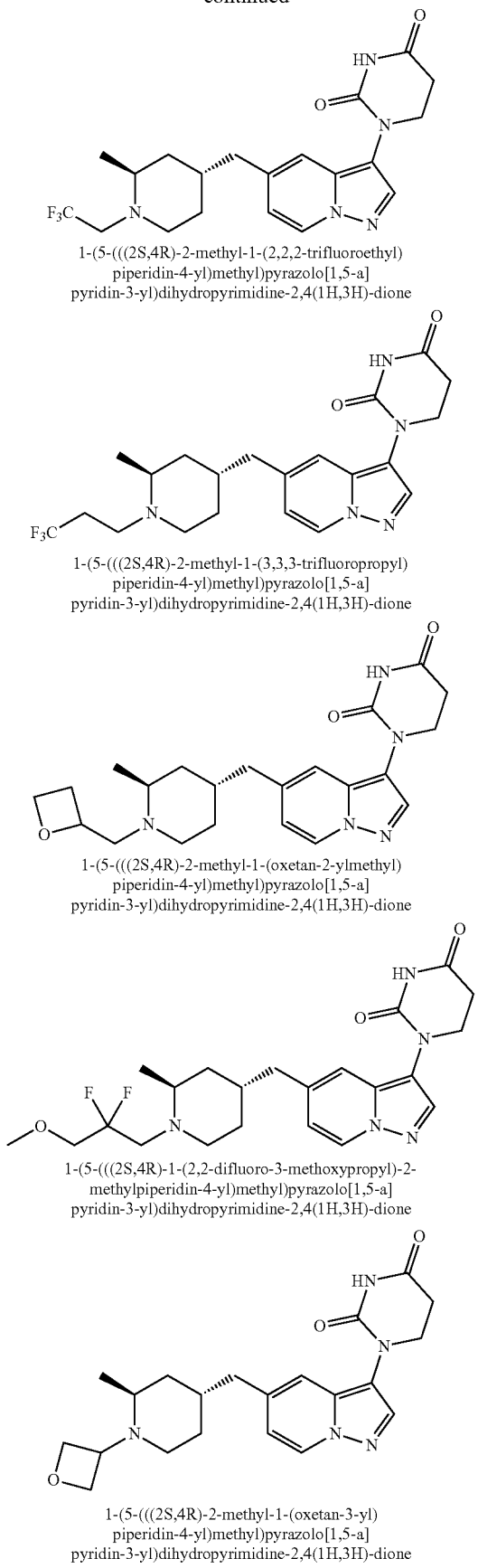

1-(5-(((2S,4R)-2-methyl-1-(2,2,2-trifluoroethyl)
piperidin-4-yl)methyl)pyrazolo[1,5-a]
pyridin-3-yl)dihydropyrimidine-2,4(1H,3H)-dione 1-(5-(((2S,4R)-2-methyl-1-(3,3,3-trifluoropropyl)
piperidin-4-yl)methyl)pyrazolo[1,5-a]
pyridin-3-yl)dihydropyrimidine-2,4(1H,3H)-dione 1-(5-(((2S,4R)-2-methyl-1-(oxetan-2-ylmethyl)
piperidin-4-yl)methyl)pyrazolo[1,5-a]
pyridin-3-yl)dihydropyrimidine-2,4(1H,3H)-dione 1-(5-(((2S,4R)-1-(2,2-difluoro-3-methoxypropyl)-2-
methylpiperidin-4-yl)methyl)pyrazolo[1,5-a]
pyridin-3-yl)dihydropyrimidine-2,4(1H,3H)-dione 1-(5-(((2S,4R)-2-methyl-1-(oxetan-3-yl)
piperidin-4-yl)methyl)pyrazolo[1,5-a]
pyridin-3-yl)dihydropyrimidine-2,4(1H,3H)-dione

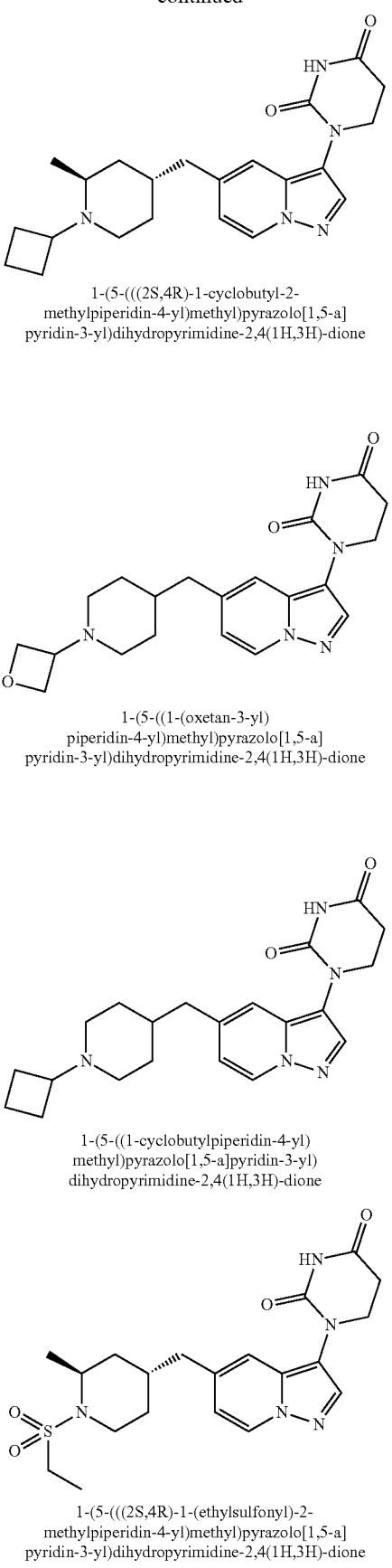

1-(5-(((2S,4R)-1-cyclobutyl-2-
methylpiperidin-4-yl)methyl)pyrazolo[1,5-a]
pyridin-3-yl)dihydropyrimidine-2,4(1H,3H)-dione 1-(5-((1-(oxetan-3-yl)
piperidin-4-yl)methyl)pyrazolo[1,5-a]
pyridin-3-yl)dihydropyrimidine-2,4(1H,3H)-dione 1-(5-((1-cyclobutylpiperidin-4-yl)
methyl)pyrazolo[1,5-a]pyridin-3-yl)
dihydropyrimidine-2,4(1H,3H)-dione 1-(5-(((2S,4R)-1-(ethylsulfonyl)-2-
methylpiperidin-4-yl)methyl)pyrazolo[1,5-a]
pyridin-3-yl)dihydropyrimidine-2,4(1H,3H)-dione

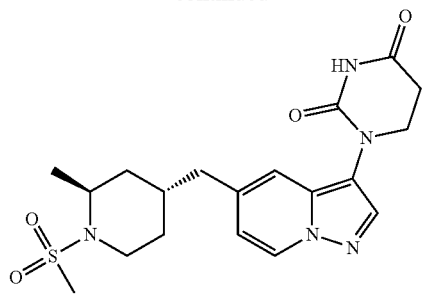 [SMILES: C[C@H]1C[C@H](Cc2ccn3ncc(N4CCC(=O)NC4=O)c3c2)CCN1S(C)(=O)=O]

1-(5-(((2S,4R)-2-methyl-1-(methylsulfonyl)
piperidin-4-yl)methyl)pyrazolo[1,5-a]
pyridin-3-yl)dihydropyrimidine-2,4(1H,3H)-dione

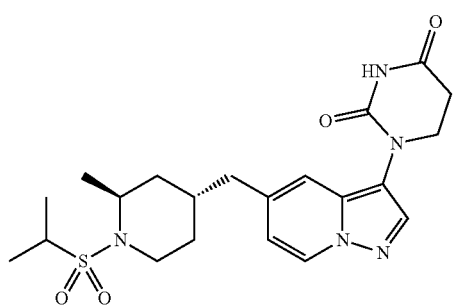

1-(5-(((2S,4R)-1-(isopropylsulfonyl)-2-
methylpiperidin-4-yl)methyl)pyrazolo[1,5-a]
pyridin-3-yl)dihydropyrimidine-2,4(1H,3H)-dione

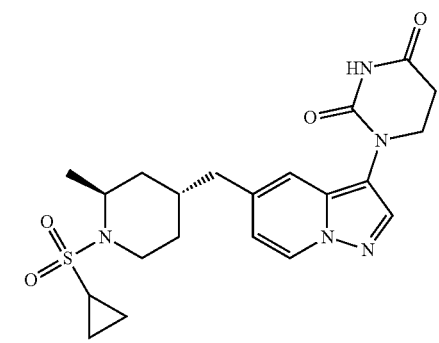 [SMILES: C[C@H]1C[C@H](Cc2ccn3ncc(N4CCC(=O)NC4=O)c3c2)CCN1S(=O)(=O)C1CC1]

1-(5-(((2S,4R)-1-(cyclopropylsulfonyl)-2-
methylpiperidin-4-yl)methyl)pyrazolo[1,5-a]
pyridin-3-yl)dihydropyrimidine-2,4(1H,3H)-dione

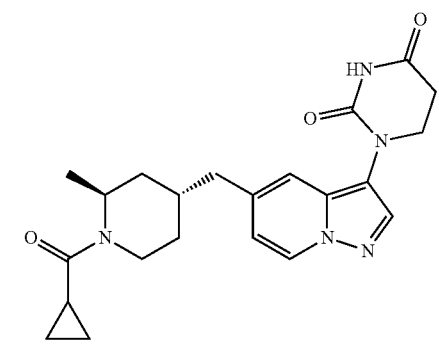

1-(5-(((2S,4R)-1-(cyclopropanecarbonyl)-2-
methylpiperidin-4-yl)methyl)pyrazolo[1,5-a]
pyridin-3-yl)dihydropyrimidine-2,4(1H,3H)-dione

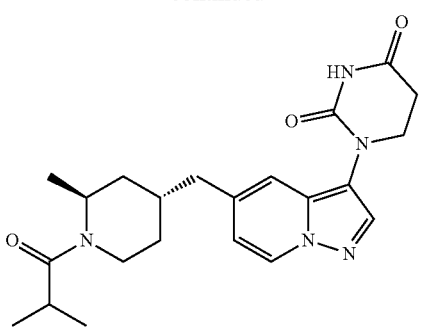 [SMILES: CC(C)C(=O)N1CC[C@@H](Cc2ccn3ncc(N4CCC(=O)NC4=O)c3c2)C[C@@H]1C]

1-(5-(((2S,4R)-1-isobutyryl-2-
methylpiperidin-4-yl)methyl)pyrazolo[1,5-a]
pyridin-3-yl)dihydropyrimidine-2,4(1H,3H)-dione

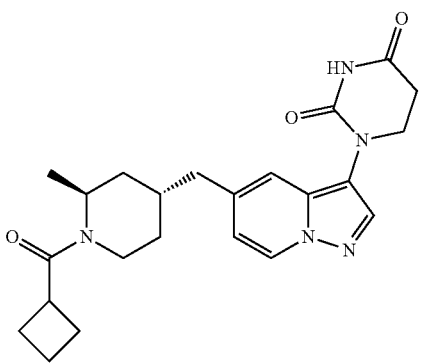 [SMILES: C[C@H]1C[C@H](Cc2ccn3ncc(N4CCC(=O)NC4=O)c3c2)CCN1C(=O)C1CCC1]

1-(5-(((2S,4R)-1-(cyclobutanecarbonyl)-2-
methylpiperidin-4-yl)methyl)pyrazolo[1,5-a]
pyridin-3-yl)dihydropyrimidine-2,4(1H,3H)-dione

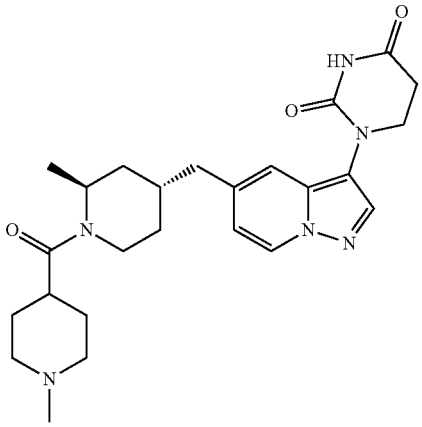 [SMILES: C[C@H]1C[C@H](Cc2ccn3ncc(N4CCC(=O)NC4=O)c3c2)CCN1C(=O)C1CCN(C)CC1]

1-(5-(((2S,4R)-2-methyl-1-(1-methylpiperidine-4-
carbonyl)piperidin-4-yl)methyl)pyrazolo[1,5-a]
pyridin-3-yl)dihydropyrimidine-2,4(1H,3H)-dione

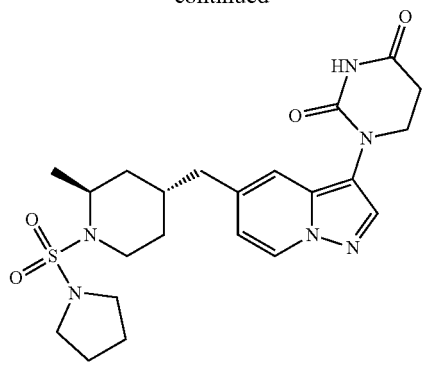

1-(5-(((2S,4R)-2-methyl-1-(pyrrolidin-1-ylsulfonyl)
piperidin-4-yl)methyl)pyrazolo[1,5-a]
pyridin-3-yl)dihydropyrimidine-2,4(1H,3H)-dione

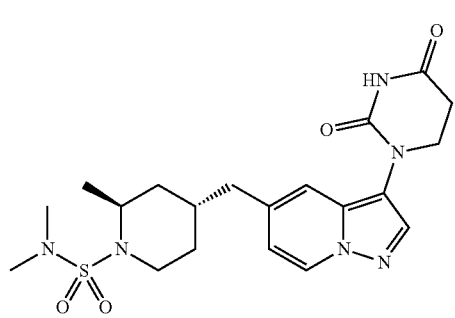

(2S,4R)-4-((3-(2,4-dioxotetrahydropyrimidin-
1(2H)-yl)pyrazolo[1,5-a]pyridin-5-yl)
methyl)-N,N,2-trimethylpiperidine-1-sulfonamide

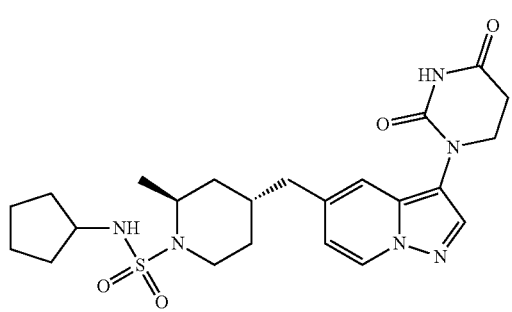 [SMILES: C[C@H]1C[C@H](Cc2ccn3ncc(N4CCC(=O)NC4=O)c3c2)CCN1S(=O)(=O)NC1CCCC1]

(2S,4R)-N-cyclopentyl-4-((3-(2,4-dioxotetrahydropyrimidin-
1(2H)-yl)pyrazolo[1,5-a]pyridin-5-yl)
methyl)-2-methylpiperidine-1-sulfonamide

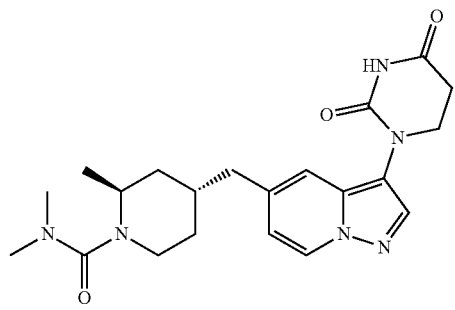 [SMILES: C[C@H]1C[C@H](Cc2ccn3ncc(N4CCC(=O)NC4=O)c3c2)CCN1C(=O)N(C)C]

(2S,4R)-4-((3-(2,4-dioxotetrahydropyrimidin-
1(2H)-yl)pyrazolo[1,5-a]pyridin-5-yl)
methyl)-N,N,2-trimethylpiperidine-1-carboxamide

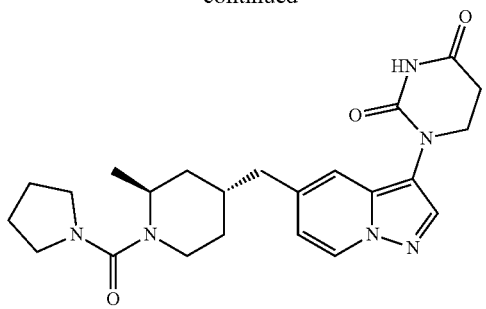

1-(5-(((2S,4R)-2-methyl-1-(pyrrolidine-1-carbonyl)
piperidin-4-yl)methyl)pyrazolo[1,5-a]
pyridin-3-yl)dihydropyrimidine-2,4(1H,3H)-dione

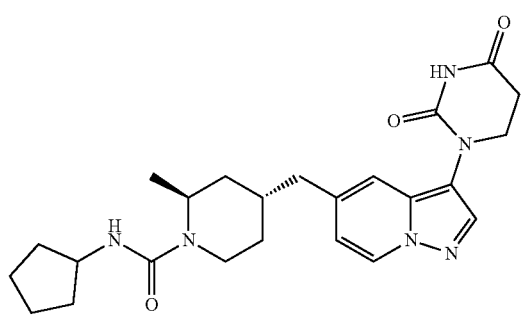 [SMILES: C[C@H]1C[C@H](Cc2ccn3ncc(N4CCC(=O)NC4=O)c3c2)CCN1C(=O)NC1CCCC1]

(2S,4R)-N-cyclopentyl-4-((3-(2,4-dioxotetrahydropyrimidin-
1(2H)-yl)pyrazolo[1,5-a]pyridin-5-yl)
methyl)-2-methylpiperidine-1-carboxamide

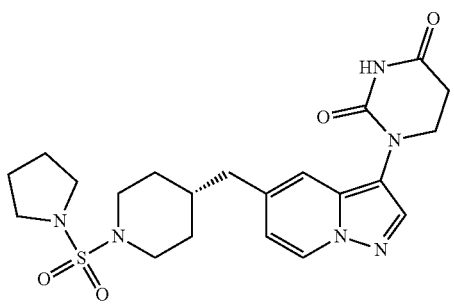 [SMILES: O=C1CCN(c2cnn3ccc(CC4CCN(S(=O)(=O)N5CCCC5)CC4)cc23)C(=O)N1]

1-(5-((1-(pyrrolidin-1-ylsulfonyl)
piperidin-4-yl)methyl)pyrazolo[1,5-a]
pyridin-3-yl)dihydropyrimidine-2,4(1H,3H)-dione

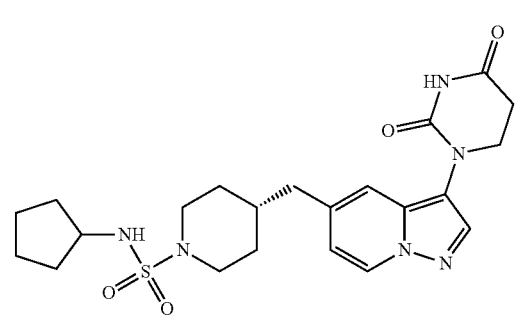 [SMILES: O=C1CCN(c2cnn3ccc(CC4CCN(S(=O)(=O)NC5CCCC5)CC4)cc23)C(=O)N1]

N-cyclopentyl-4-((3-(2,4-dioxotetrahydropyrimidin-
1(2H)-yl)pyrazolo[1,5-a]pyridin-5-yl)
methyl)piperidine-1-sulfonamide

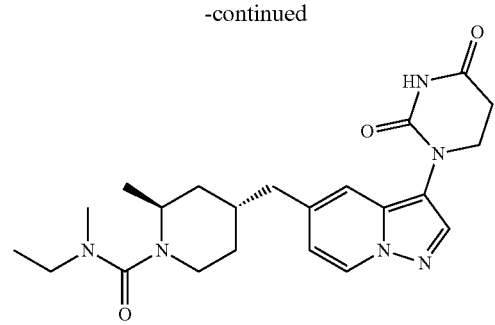

(2S,4R)-4-((3-(2,4-dioxotetrahydropyrimidin-1(2H)-yl)pyrazolo[1,5-a]pyridin-5-yl)methyl)-N-ethyl-N,2-dimethylpiperidine-1-carboxamide

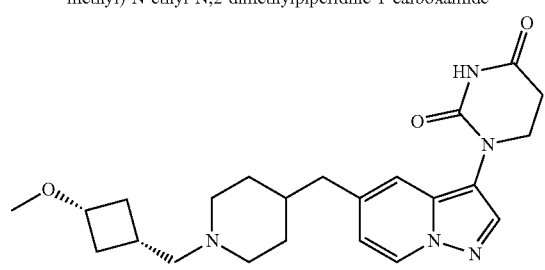

1-(5-((1-(((1s,3s)-3-methoxycyclobutyl)methyl)piperidin-4-yl)methyl)pyrazolo[1,5-a]pyridin-3-yl)dihydropyrimidine-2,4(1H,3H)-dione

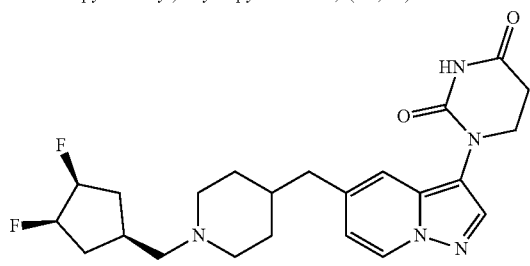

1-(5-((1-(((1r,3R,4S)-3,4-difluorocyclopentyl)methyl)piperidin-4-yl)methyl)pyrazolo[1,5-a]pyridin-3-yl)dihydropyrimidine-2,4(1H,3H)-dione

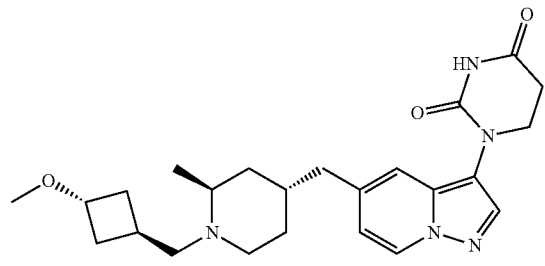 [SMILES: CO[C@H]1C[C@H](CN2CC[C@@H](Cc3ccn4ncc(N5CCC(=O)NC5=O)c4c3)C[C@@H]2C)C1]

1-(5-(((2S,4R)-1-(((1r,3S)-3-methoxycyclobutyl)methyl)-2-methylpiperidin-4-yl)methyl)pyrazolo[1,5-a]pyridin-3-yl)dihydropyrimidine-2,4(1H,3H)-dione

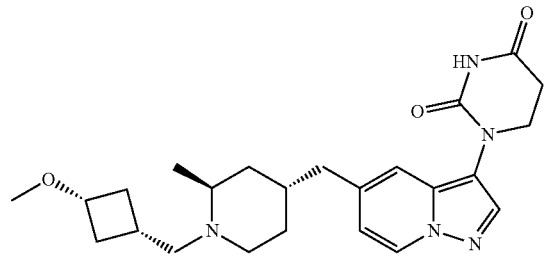

1-(5-(((2S,4R)-1-(((1s,3R)-3-methoxycyclobutyl)methyl)-2-methylpiperidin-4-yl)methyl)pyrazolo[1,5-a]pyridin-3-yl)dihydropyrimidine-2,4(1H,3H)-dione

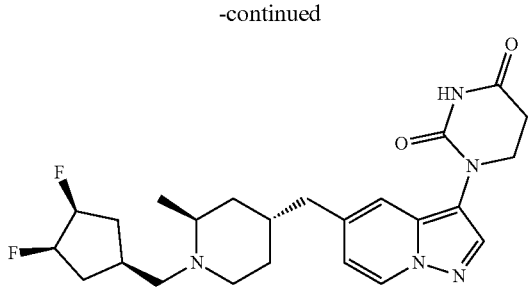

1-(5-(((2S,4R)-1-(((1r-3R,4S)-3,4-difluorocyclopentyl)methyl)-2-methylpiperidin-4-yl)methyl)pyrazolo[1,5-a]pyridin-3-yl)dihydropyrimidine-2,4(1H,3H)-dione

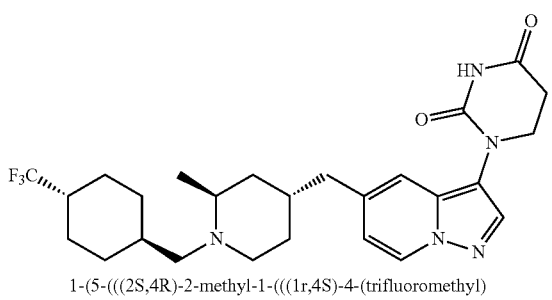

1-(5-(((2S,4R)-2-methyl-1-(((1r,4S)-4-(trifluoromethyl)cyclohexyl)methyl)piperidin-4-yl)methyl)pyrazolo[1,5-a]pyridin-3-yl)dihydropyrimidine-2,4(1H,3H)-dione

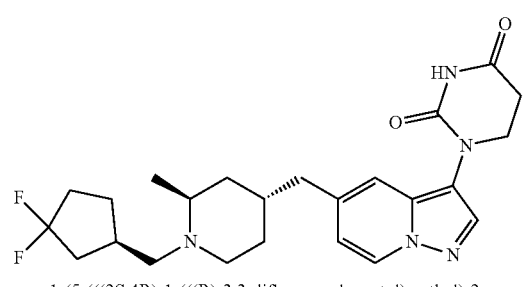

1-(5-(((2S,4R)-1-(((R)-3,3-difluorocyclopentyl)methyl)-2-methylpiperidin-4-yl)methyl)pyrazolo[1,5-a]pyridin-3-yl)dihydropyrimidine-2,4(1H,3H)-dione

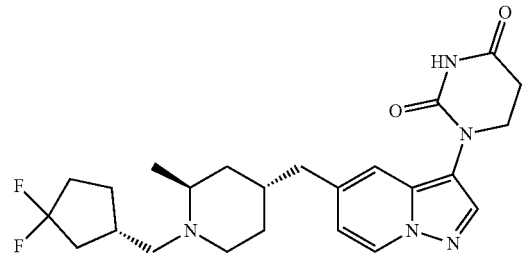

1-(5-(((2S,4R)-1-(((S)-3,3-difluorocyclopentyl)methyl)-2-methylpiperidin-4-yl)methyl)pyrazolo[1,5-a]pyridin-3-yl)dihydropyrimidine-2,4(1H,3H)-dione

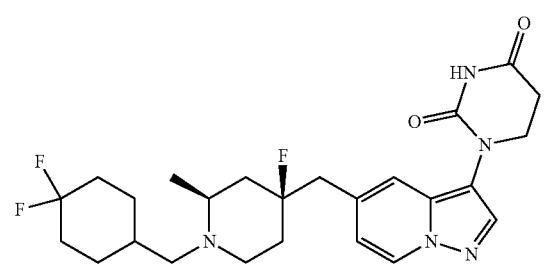

1-(5-(((2S,4S)-1-((4,4-difluorocyclohexyl)methyl)-4-fluoro-2-methylpiperidin-4-yl)methyl)pyrazolo[1,5-a]pyridin-3-yl)dihydropyrimidine-2,4(1H,3H)-dione

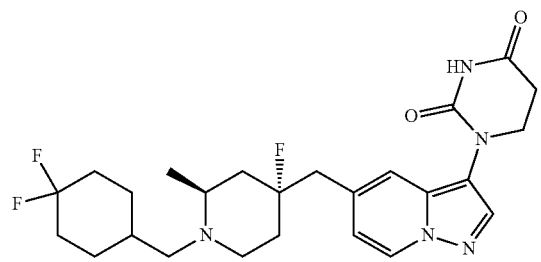

1-(5-(((2S,4R)-1-((4,4-difluorocyclohexyl)methyl)-4-
fluoro-2-methylpiperidin-4-yl)methyl)pyrazolo[1,5-a]
pyridin-3-yl)dihydropyrimidine-2,4(1H,3H)-dione

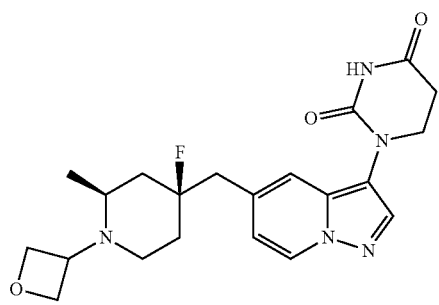

1-(5-(((2S,4S)-4-fluoro-2-methyl-1-(oxetan-3-yl)
piperidin-4-yl)methyl)pyrazolo[1,5-a]
pyridin-3-yl)dihydropyrimidine-2,4(1H,3H)-dione

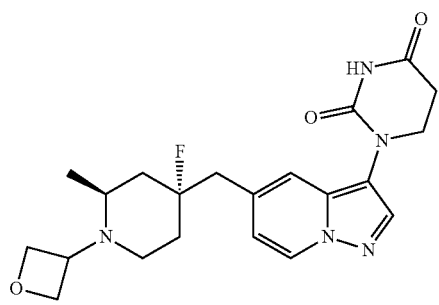 [SMILES: C[C@H]1CC(F)(Cc2ccn3ncc(N4CCC(=O)NC4=O)c3c2)CCN1C1COC1]

1-(5-(((2S,4R)-4-fluoro-2-methyl-1-(oxetan-3-yl)
piperidin-4-yl)methyl)pyrazolo[1,5-a]
pyridin-3-yl)dihydropyrimidine-2,4(1H,3H)-dione

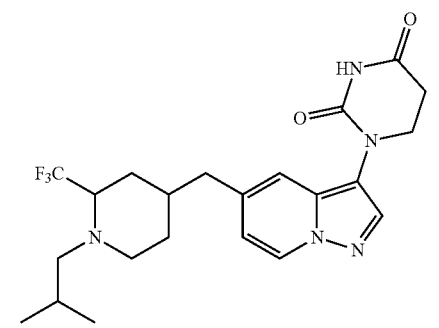

1-(5-((1-isobutyl-2-(trifluoromethyl)
piperidin-4-yl)methyl)pyrazolo[1,5-a]
pyridin-3-yl)dihydropyrimidine-2,4(1H,3H)-dione

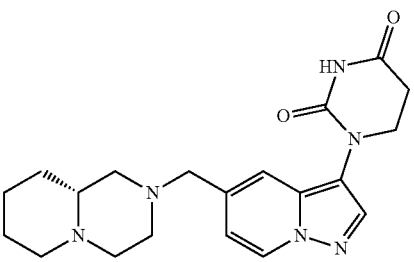 [SMILES: O=C1CCN(c2cnn3ccc(CN4CCN5CCCC[C@@H]5C4)cc23)C(=O)N1]

(R)-1-(5-((octahydro-2H-pyrido[1,2-a]
pyrazin-2-yl)methyl)pyrazolo[1,5-a]
pyridin-3-yl)dihydropyrimidine-2,4(1H,3H)-dione

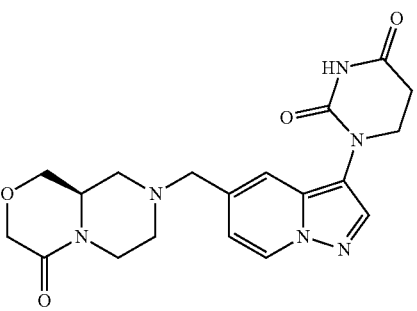 [SMILES: O=C1CCN(c2cnn3ccc(CN4CCN5C(=O)COC[C@H]5C4)cc23)C(=O)N1]

(R)-1-(5-((4-oxohexahydropyrazino[2,1-c][1,4]
oxazin-8(1H)-yl)methyl)pyrazolo[1,5-a]
pyridin-3-yl)dihydropyrimidine-2,4(1H,3H)-dione

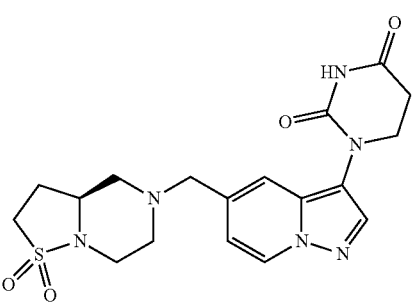

(S)-1-(5-((1,1-dioxidohexahydro-5H-isothiazolo[2,3-a]
pyrazin-5-yl)methyl)pyrazolo[1,5-a]
pyridin-3-yl)dihydropyrimidine-2,4(1H,3H)-dione

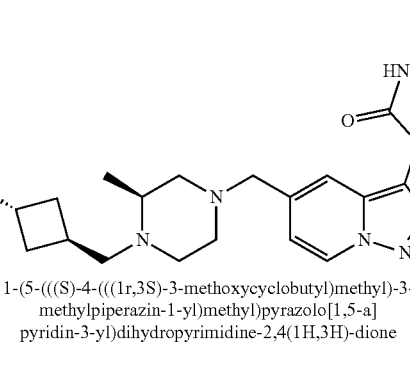

1-(5-(((S)-4-(((1r,3S)-3-methoxycyclobutyl)methyl)-3-
methylpiperazin-1-yl)methyl)pyrazolo[1,5-a]
pyridin-3-yl)dihydropyrimidine-2,4(1H,3H)-dione

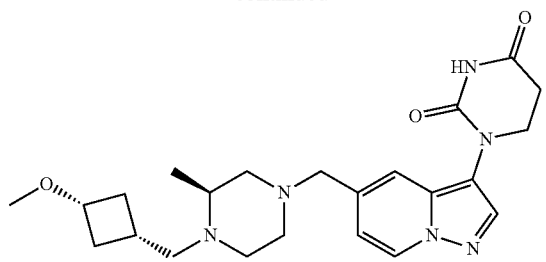 [SMILES: CO[C@H]1C[C@@H](CN2CCN(Cc3ccn4ncc(N5CCC(=O)NC5=O)c4c3)C[C@@H]2C)C1]

1-(5-(((S)-4-(((1r,3R)-3-methoxycyclobutyl)methyl)-3-methylpiperazin-1-yl)methyl)pyrazolo[1,5-a]pyridin-3-yl)dihydropyrimidine-2,4(1H,3H)-dione

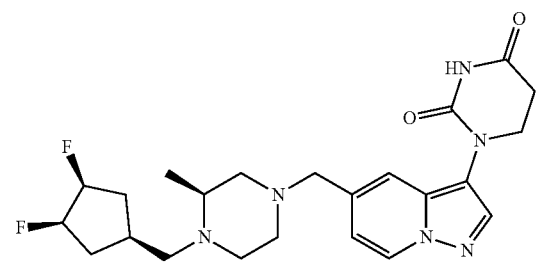 [SMILES: C[C@H]1CN(Cc2ccn3ncc(N4CCC(=O)NC4=O)c3c2)CCN1C[C@H]1C[C@@H](F)[C@@H](F)C1]

1-(5-(((S)-4-(((1r,3R,4S)-3,4-difluorocyclopentyl)methyl)-3-methylpiperazin-1-yl)methyl)pyrazolo[1,5-a]pyridin-3-yl)dihydropyrimidine-2,4(1H,3H)-dione

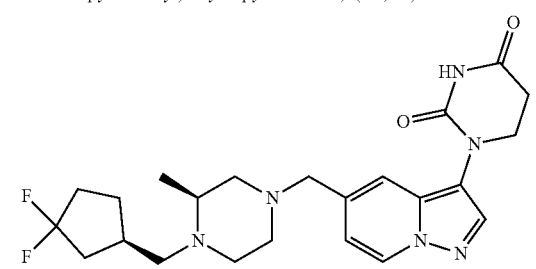

1-(5-(((S)-4-(((R)-3,3-difluorocyclopentyl)methyl)-3-methylpiperazin-1-yl)methyl)pyrazolo[1,5-a]pyridin-3-yl)dihydropyrimidine-2,4(1H,3H)-dione

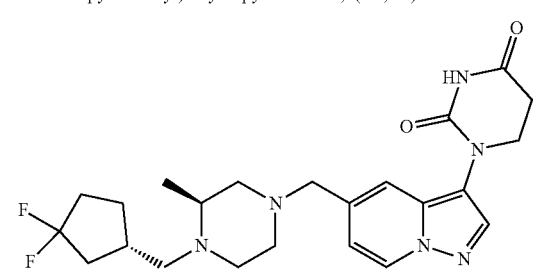

1-(5-(((S)-4-(((S)-3,3-difluorocyclopentyl)methyl)-3-methylpiperazin-1-yl)methyl)pyrazolo[1,5-a]pyridin-3-yl)dihydropyrimidine-2,4(1H,3H)-dione

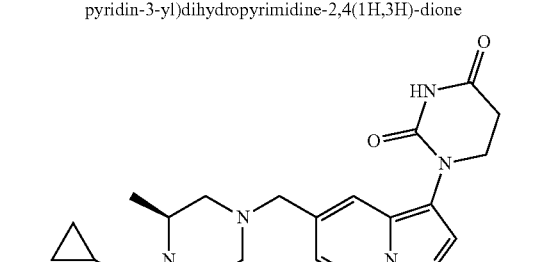

(S)-1-(5-((4-(cyclopropylmethyl)-3-methylpiperazin-1-yl)methyl)pyrazolo[1,5-a]pyridin-3-yl)dihydropyrimidine-2,4(1H,3H)-dione

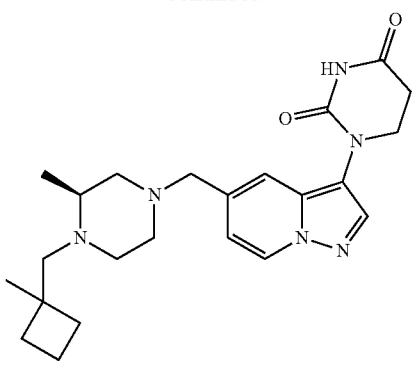

(S)-1-(5-((3-methyl-4-((1-methylcyclobutyl)methyl)piperazin-1-yl)methyl)pyrazolo[1,5-a]pyridin-3-yl)dihydropyrimidine-2,4(1H,3H)-dione

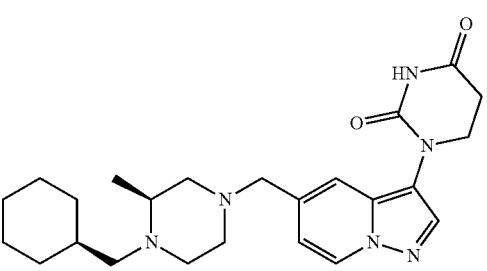

1-(5-(((S)-3-methyl-4-(((1r,4S)-4-(trifluoromethyl)cyclohexyl)methyl)piperazin-1-yl)methyl)pyrazolo[1,5-a]pyridin-3-yl)dihydropyrimidine-2,4(1H,3H)-dione

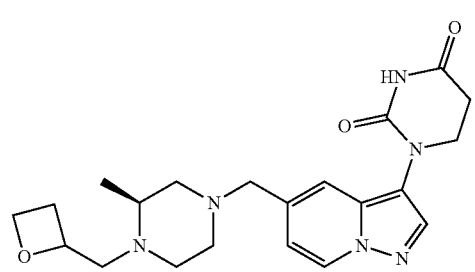 [SMILES: C[C@H]1CN(Cc2ccn3ncc(N4CCC(=O)NC4=O)c3c2)CCN1CC1CCO1]

1-(5-(((3S)-3-methyl-4-(oxetan-2-ylmethyl)piperazin-1-yl)methyl)pyrazolo[1,5-a]pyridin-3-yl)dihydropyrimidine-2,4(1H,3H)-dione

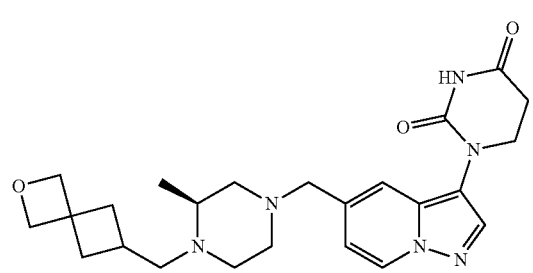 [SMILES: C[C@H]1CN(Cc2ccn3ncc(N4CCC(=O)NC4=O)c3c2)CCN1CC1CC2(COC2)C1]

(S)-1-(5-((4-((2-oxaspiro[3.3]heptan-6-yl)methyl)-3-methylpiperazin-1-yl)methyl)pyrazolo[1,5-a]pyridin-3-yl)dihydropyrimidine-2,4(1H,3H)-dione 555
-continued

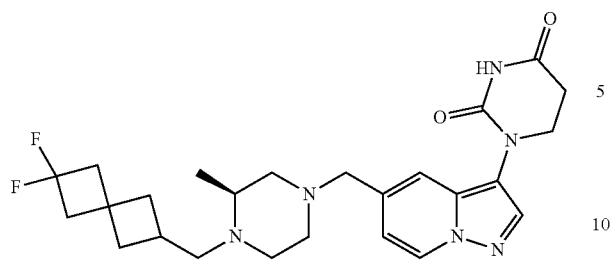

(S)-1-(5-((4-((6,6-difluorospiro[3.3]heptan-2-yl)
methyl)-3-methylpiperazin-1-yl)methyl)pyrazolo[1,5-a]
pyridin-3-yl)dihydropyrimidine-2,4(1H,3H)-dione

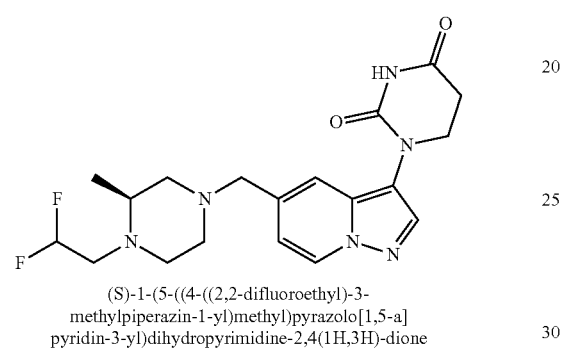

(S)-1-(5-((4-((2,2-difluoroethyl)-3-
methylpiperazin-1-yl)methyl)pyrazolo[1,5-a]
pyridin-3-yl)dihydropyrimidine-2,4(1H,3H)-dione

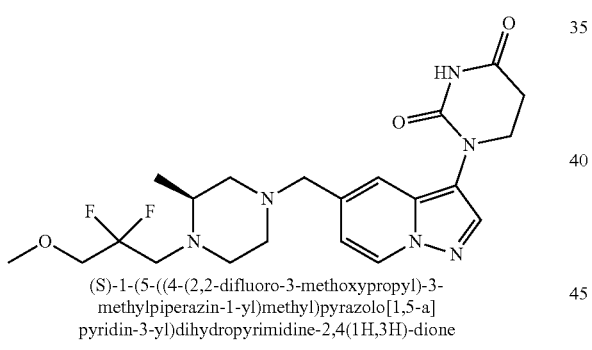

(S)-1-(5-((4-(2,2-difluoro-3-methoxypropyl)-3-
methylpiperazin-1-yl)methyl)pyrazolo[1,5-a]
pyridin-3-yl)dihydropyrimidine-2,4(1H,3H)-dione

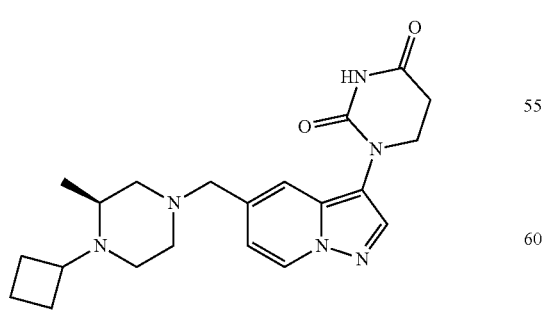

(S)-1-(5-((4-cyclobutyl-3-
methylpiperazin-1-yl)methyl)pyrazolo[1,5-a]
pyridin-3-yl)dihydropyrimidine-2,4(1H,3H)-dione 556
-continued

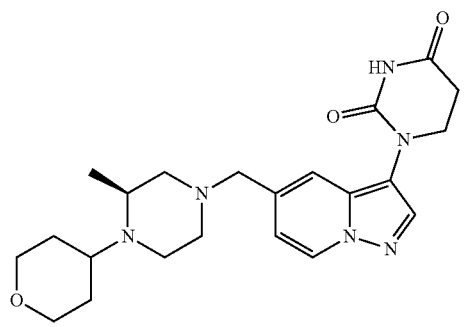 [SMILES: C[C@H]1CN(Cc2ccn3ncc(N4CCC(=O)NC4=O)c3c2)CCN1C1CCOCC1]

(S)-1-(5-((3-methyl-4-(tetrahydro-2H-pyran-4-yl)
piperazin-1-yl)methyl)pyrazolo[1,5-a]
pyridin-3-yl)dihydropyrimidine-2,4(1H,3H)-dione

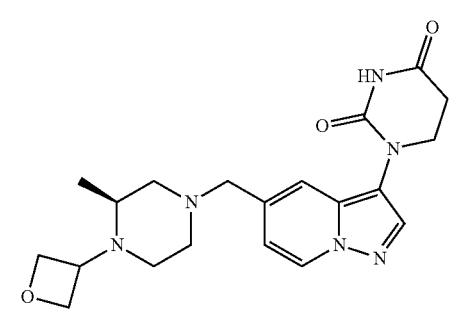

(S)-1-(5-((3-methyl-4-(oxetan-3-yl)
piperazin-1-yl)methyl)pyrazolo[1,5-a]
pyridin-3-yl)dihydropyrimidine-2,4(1H,3H)-dione

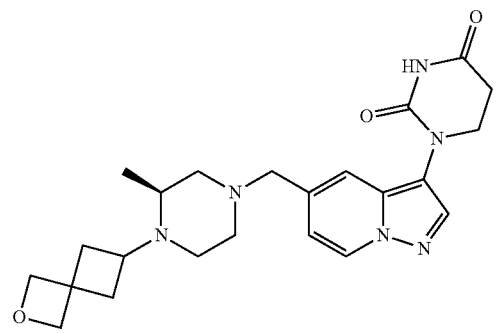 [SMILES: C[C@H]1CN(Cc2ccn3ncc(N4CCC(=O)NC4=O)c3c2)CCN1C1CC2(COC2)C1]

(S)-1-(5-((3-methyl-4-(oxaspiro[3.3]heptan-6-yl)
piperazin-1-yl)methyl)pyrazolo[1,5-a]
pyridin-3-yl)dihydropyrimidine-2,4(1H,3H)-dione

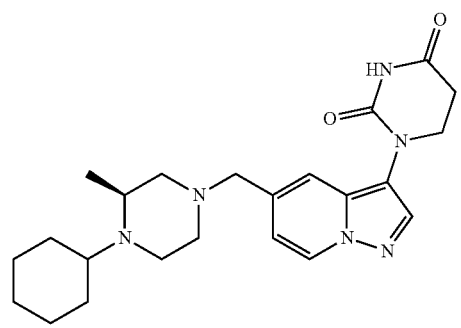 [SMILES: C[C@H]1CN(Cc2ccn3ncc(N4CCC(=O)NC4=O)c3c2)CCN1C1CCCCC1]

(S)-1-(5-((4-cyclohexyl-3-
methylpiperazin-1-yl)methyl)pyrazolo[1,5-a]
pyridin-3-yl)dihydropyrimidine-2,4(1H,3H)-dione -continued

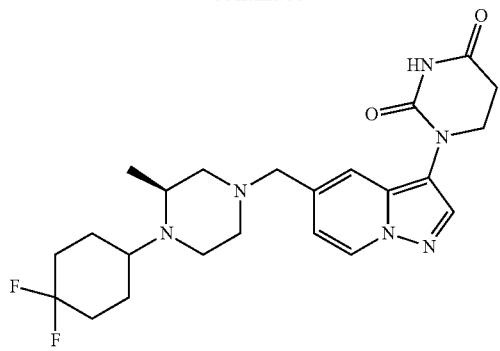

(S)-1-(5-((4-(4,4-difluorocyclohexyl)-3-methylpiperazin-1-yl)methyl)pyrazolo[1,5-a]pyridin-3-yl)dihydropyrimidine-2,4(1H,3H)-dione

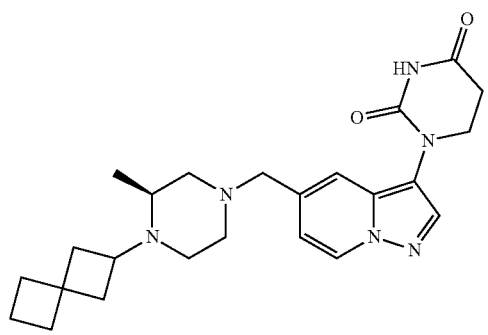 [SMILES: C[C@H]1CN(Cc2ccn3ncc(N4CCC(=O)NC4=O)c3c2)CCN1C1CC2(CCC2)C1]

(S)-1-(5-((3-methyl-4-(spiro[3.3]heptan-2-yl)piperazin-1-yl)methyl)pyrazolo[1,5-a]pyridin-3-yl)dihydropyrimidine-2,4(1H,3H)-dione

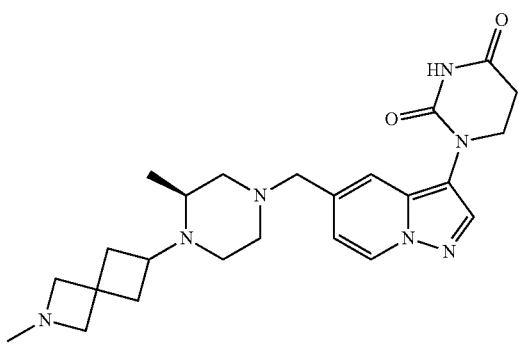

(S)-1-(5-((3-methyl-4-(2-methyl-2-azaspiro[3.3]heptan-6-yl)piperazin-1-yl)methyl)pyrazolo[1,5-a]pyridin-3-yl)dihydropyrimidine-2,4(1H,3H)-dione

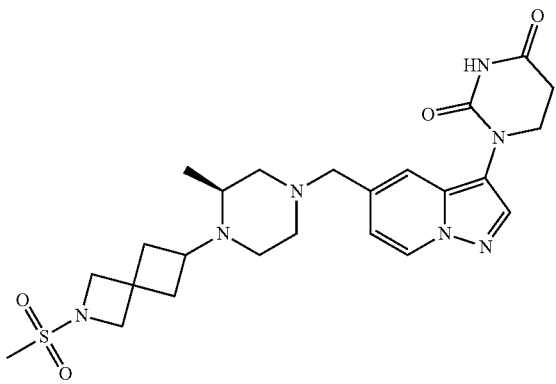

(S)-1-(5-((3-methyl-4-(2-(methylsulfonyl)-2-azaspiro[3.3]heptan-6-yl)piperazin-1-yl)methyl)pyrazolo[1,5-a]pyridin-3-yl)dihydropyrimidine-2,4(1H,3H)-dione -continued

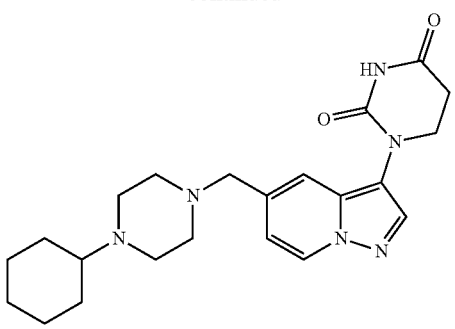 [SMILES: O=C1CCN(c2cnn3ccc(CN4CCN(C5CCCCC5)CC4)cc23)C(=O)N1]

1-(5-((4-cyclohexylpiperazin-1-yl)methyl)pyrazolo[1,5-a]pyridin-3-yl)dihydropyrimidine-2,4(1H,3H)-dione

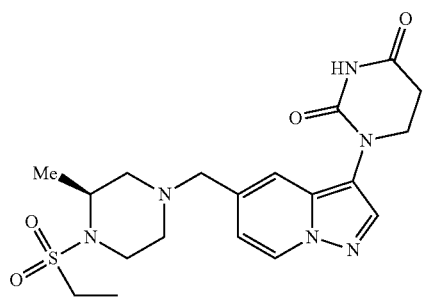 [SMILES: CCS(=O)(=O)N1CCN(Cc2ccn3ncc(N4CCC(=O)NC4=O)c3c2)C[C@@H]1C]

(S)-1-(5-((4-(ethylsulfonyl)-3-methylpiperazin-1-yl)methyl)pyrazolo[1,5-a]pyridin-3-yl)dihydropyrimidine-2,4(1H,3H)-dione

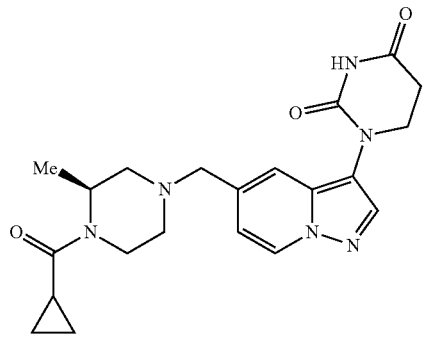

(S)-1-(5-((4-(cyclopropanecarbonyl)-3-methylpiperazin-1-yl)methyl)pyrazolo[1,5-a]pyridin-3-yl)dihydropyrimidine-2,4(1H,3H)-dione

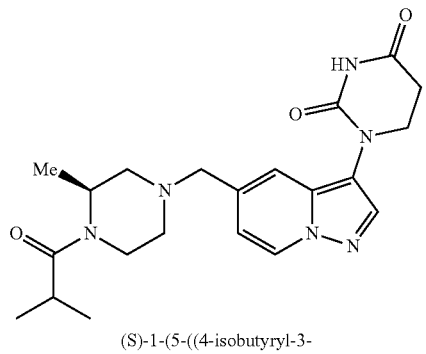

(S)-1-(5-((4-isobutyryl-3-methylpiperazin-1-yl)methyl)pyrazolo[1,5-a]pyridin-3-yl)dihydropyrimidine-2,4(1H,3H)-dione 559
-continued

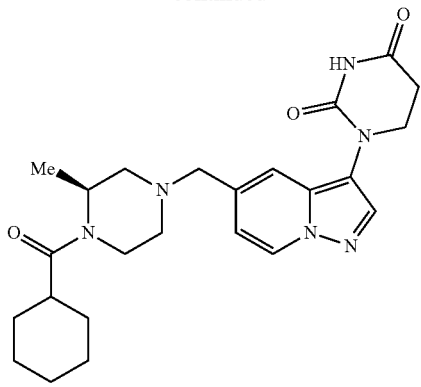 [SMILES: C[C@H]1CN(Cc2ccn3ncc(N4CCC(=O)NC4=O)c3c2)CCN1C(=O)C1CCCCC1]

(S)-1-(5-((4-(cyclohexanecarbonyl)-3-
methylpiperazin-1-yl)methyl)pyrazolo[1,5-a]
pyridin-3-yl)dihydropyrimidine-2,4(1H,3H)-dione

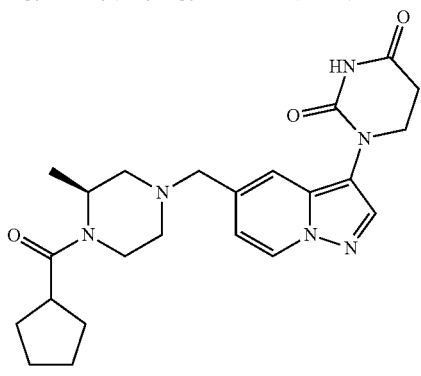 [SMILES: C[C@H]1CN(Cc2ccn3ncc(N4CCC(=O)NC4=O)c3c2)CCN1C(=O)C1CCCC1]

(S)-1-(5-((4-(cyclopentanecarbonyl)-3-
methylpiperazin-1-yl)methyl)pyrazolo[1,5-a]
pyridin-3-yl)dihydropyrimidine-2,4(1H,3H)-dione

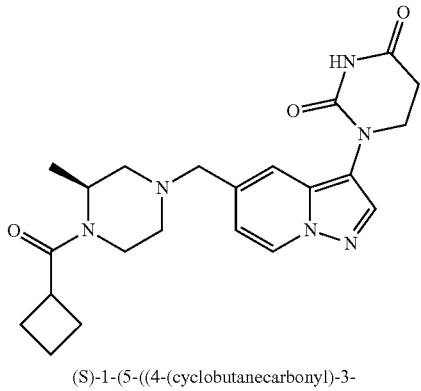

(S)-1-(5-((4-(cyclobutanecarbonyl)-3-
methylpiperazin-1-yl)methyl)pyrazolo[1,5-a]
pyridin-3-yl)dihydropyrimidine-2,4(1H,3H)-dione

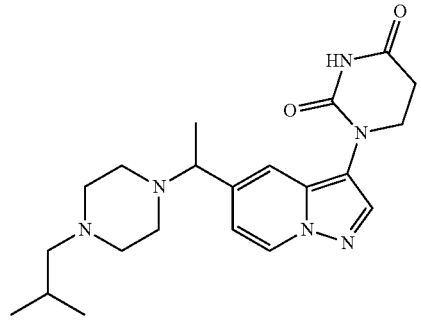

1-(5-(1-(4-isobutylpiperazin-1-yl)ethyl)pyrazolo[1,5-a]
pyridin-3-yl)dihydropyrimidine-2,4(1H,3H)-dione 560
-continued

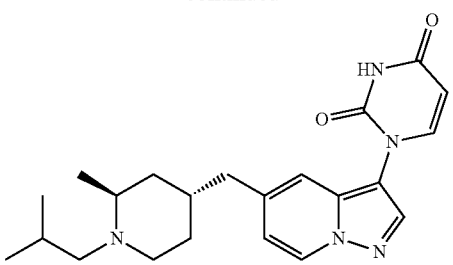

1-(5-(((2S,4R)-1-isobutyl-2-
methylpiperidin-4-yl)methyl)pyrazolo[1,5-a]
pyridin-3-yl)pyrimidine-2,4(1H,3H)-dione

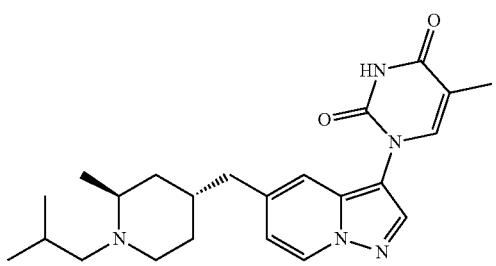 [SMILES: Cc1cn(-c2cnn3ccc(C[C@@H]4CCN(CC(C)C)[C@@H](C)C4)cc23)c(=O)[nH]c1=O]

1-(5-(((2S,4R)-1-isobutyl-2-
methylpiperidin-4-yl)methyl)pyrazolo[1,5-a]
pyridin-3-yl)-5-methylpyrimidine-2,4(1H,3H)-dione

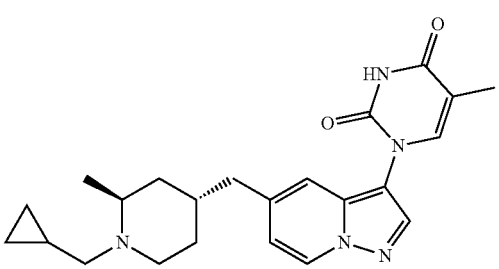 [SMILES: Cc1cn(-c2cnn3ccc(C[C@@H]4CCN(CC5CC5)[C@@H](C)C4)cc23)c(=O)[nH]c1=O]

1-(5-(((2S,4R)-1-(cyclopropylmethyl)-2-
methylpiperidin-4-yl)methyl)pyrazolo[1,5-a]
pyridin-3-yl)-5-methylpyrimidine-2,4(1H,3H)-dione

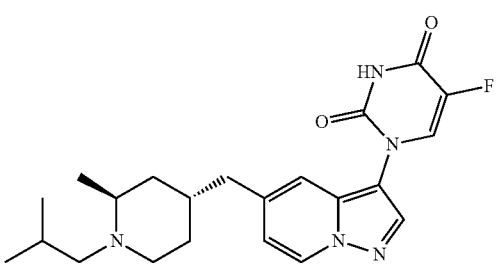 [SMILES: CC(C)CN1CCN(Cc2ccn3ncc(-n4cc(F)c(=O)[nH]c4=O)c3c2)C[C@@H]1C]

5-fluoro-1-(5-(((2S,4R)-1-isobutyl-2-
methylpiperidin-4-yl)methyl)pyrazolo[1,5-a]
pyridin-3-yl)-5-pyrimidine-2,4(1H,3H)-dione

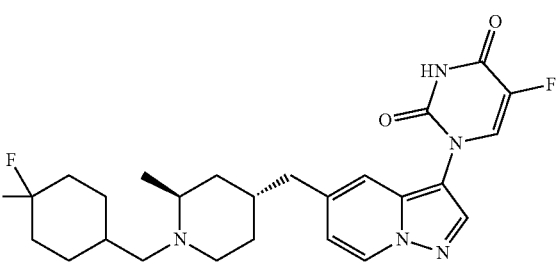

1-(5-(((2S,4R)-1-((4,4-difluorocyclohexyl)methyl)-2-
methylpiperidin-4-yl)methyl)pyrazolo[1,5-a]
pyridin-3-yl)-5-fluoropyrimidine-2,4(1H,3H)-dione

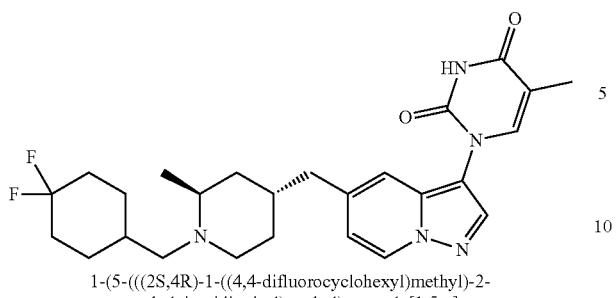

1-(5-(((2S,4R)-1-((4,4-difluorocyclohexyl)methyl)-2-
methylpiperidin-4-yl)methyl)pyrazolo[1,5-a]
pyridin-3-yl)-5-methylpyrimidine-2,4(1H,3H)-dione

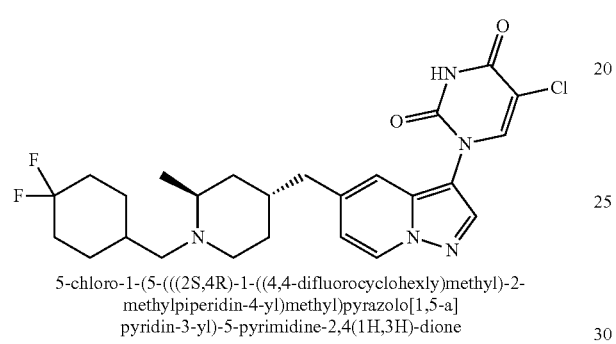

5-chloro-1-(5-(((2S,4R)-1-((4,4-difluorocyclohexly)methyl)-2-
methylpiperidin-4-yl)methyl)pyrazolo[1,5-a]
pyridin-3-yl)-5-pyrimidine-2,4(1H,3H)-dione

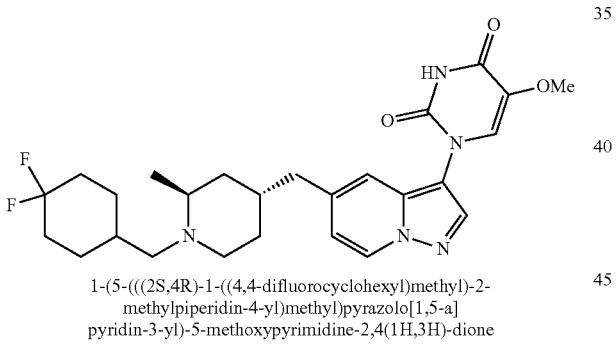

1-(5-(((2S,4R)-1-((4,4-difluorocyclohexyl)methyl)-2-
methylpiperidin-4-yl)methyl)pyrazolo[1,5-a]
pyridin-3-yl)-5-methoxypyrimidine-2,4(1H,3H)-dione

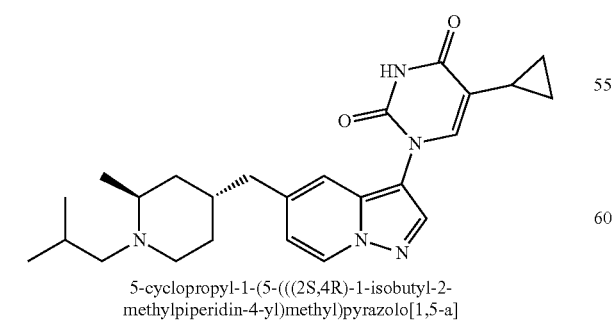

5-cyclopropyl-1-(5-(((2S,4R)-1-isobutyl-2-
methylpiperidin-4-yl)methyl)pyrazolo[1,5-a]
pyridin-3-yl)pyrimidine-2,4(1H,3H)-dione

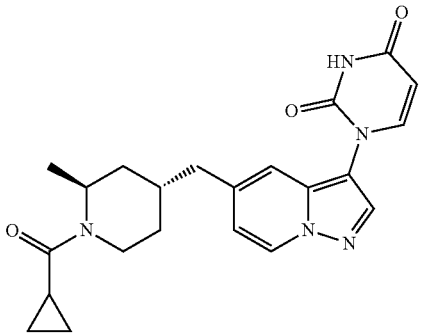

1-(5-(((2S,4R)-1-(cyclopropanecarbonyl)-2-
methylpiperidin-4-yl)methyl)pyrazolo[1,5-a]
pyridin-3-yl)pyrimidine-2,4(1H,3H)-dione

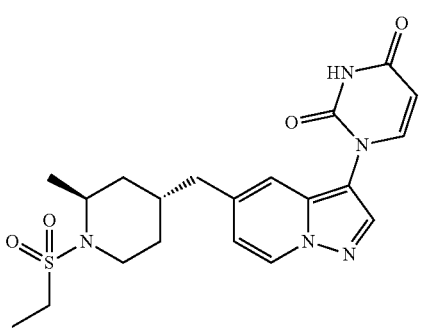

1-(5-(((2S,4R)-1-(ethylsulfonyl)-2-
methylpiperidin-4-yl)methyl)pyrazolo[1,5-a]
pyridin-3-yl)pyrimidine-2,4(1H,3H)-dione

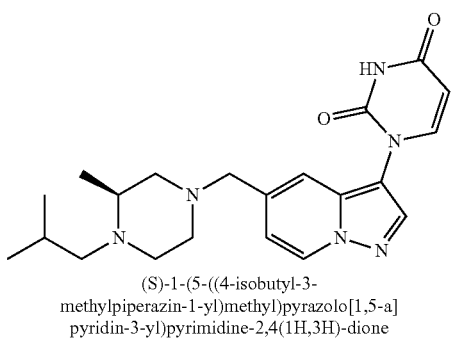

(S)-1-(5-((4-isobutyl-3-
methylpiperazin-1-yl)methyl)pyrazolo[1,5-a]
pyridin-3-yl)pyrimidine-2,4(1H,3H)-dione

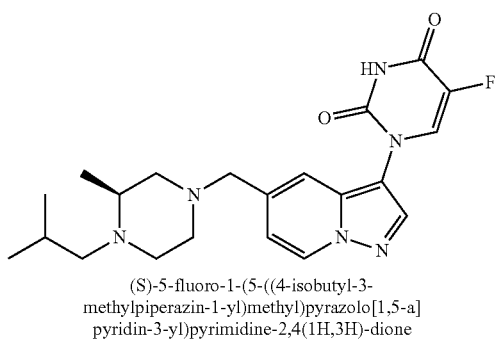

(S)-5-fluoro-1-(5-((4-isobutyl-3-
methylpiperazin-1-yl)methyl)pyrazolo[1,5-a]
pyridin-3-yl)pyrimidine-2,4(1H,3H)-dione

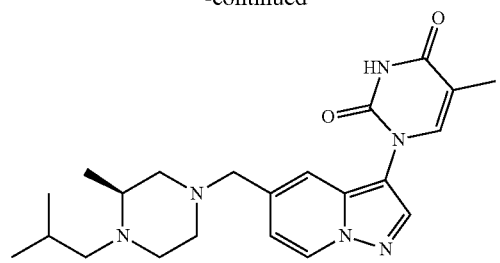

(S)-1-(5-((4-isobutyl-3-methylpiperazin-1-yl)methyl)pyrazolo[1,5-a]pyridin-3-yl)-5-methylpyrimidine-2,4(1H,3H)-dione

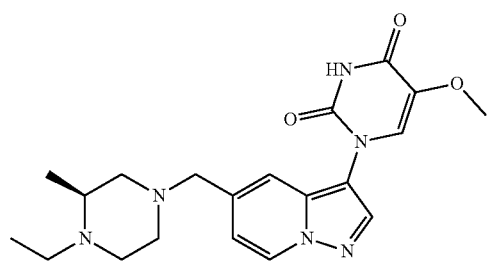

(S)-1-(5-((4-isobutyl-3-methylpiperazin-1-yl)methyl)pyrazolo[1,5-a]pyridin-3-yl)-5-methoxypyrimidine-2,4(1H,3H)-dione

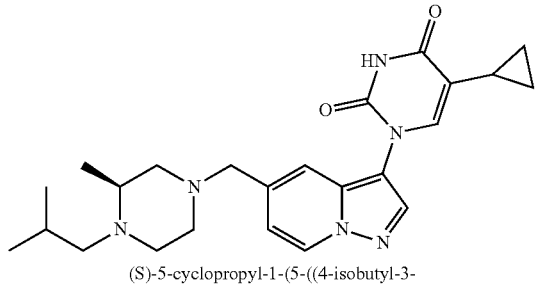

(S)-5-cyclopropyl-1-(5-((4-isobutyl-3-methylpiperazin-1-yl)methyl)pyrazolo[1,5-a]pyridin-3-yl)pyrimidine-2,4(1H,3H)-dione

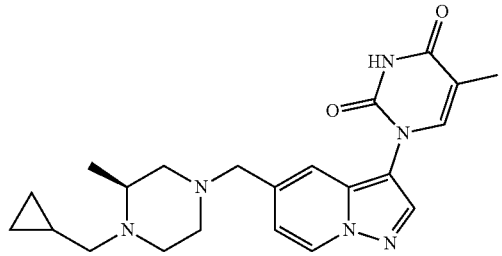 [SMILES: Cc1cn(-c2cnn3ccc(CN4CCN(CC5CC5)[C@@H](C)C4)cc23)c(=O)[nH]c1=O]

(S)-1-(5-((4-cyclopropylmethyl)-3-methylpiperazin-1-yl)methyl)pyrazolo[1,5-a]pyridin-3-yl)-5-methylpyrimidine-2,4(1H,3H)-dione

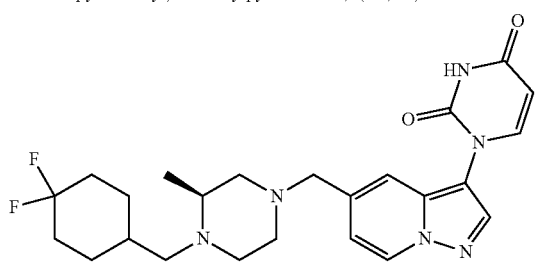

(S)-1-(5-((4-((4,4-difluorocyclohexyl)methyl-3-methylpiperazin-1-yl)methyl)pyrazolo[1,5-a]pyridin-3-yl)pyrimidine-2,4(1H,3H)-dione or a pharmaceutically acceptable salt thereof.

13. The method of claim 1, wherein the method is of treating or preventing a disorder that is affected by the reduction of WIZ protein levels in a subject in need thereof.

14. The method of claim 1, wherein the method is of inhibiting, reducing, or eliminating the activity of WIZ protein or WIZ protein expression.

15. The method of claim 1, wherein the method is of inducing or promoting fetal hemoglobin in a subject in need thereof.

16. The method of claim 1, wherein the method is of reactivating fetal hemoglobin production or expression in a subject in need thereof.

17. The method of claim 1, wherein the method is of increasing fetal hemoglobin expression in a subject in need thereof.

18. The method of claim 1, wherein the method is of treating a hemoglobinopathy in a subject in need thereof.

19. The method of claim 1, wherein the method is of treating a sickle cell disease in a subject in need thereof.

20. The method of claim 1, wherein the method is of treating beta-thalassemia in a subject in need thereof.

21. The method of claim 1, wherein the compound is selected from the group consisting of

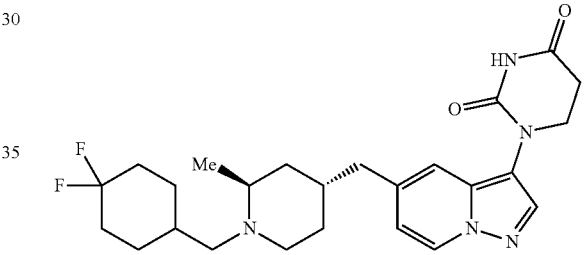

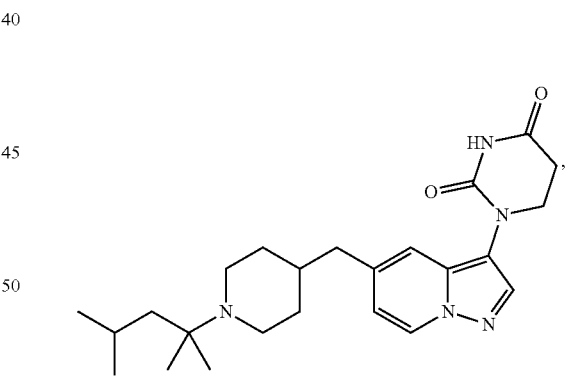

-continued

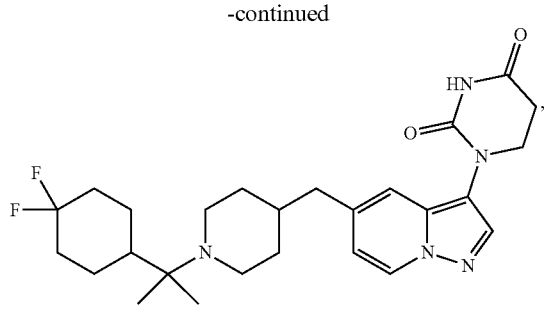

,

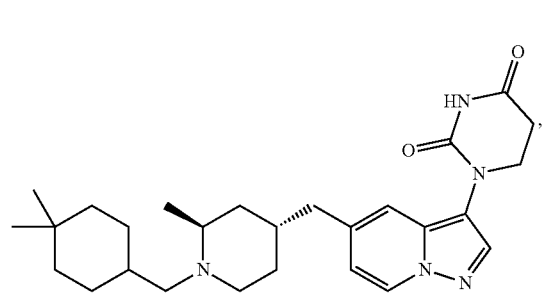

,

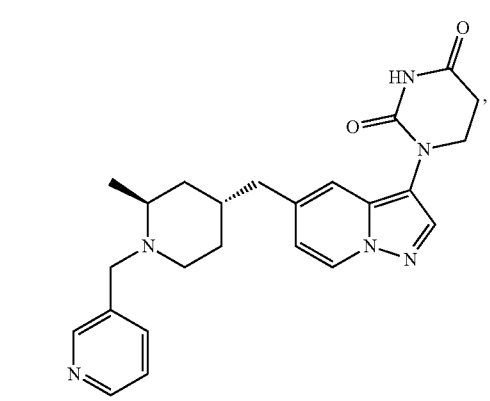 [SMILES: C[C@H]1C[C@H](Cc2ccn3ncc(N4CCC(=O)NC4=O)c3c2)CCN1Cc1cccnc1]

, and pharmaceutically acceptable salts thereof.

22. The method of claim 21, wherein the compound is:

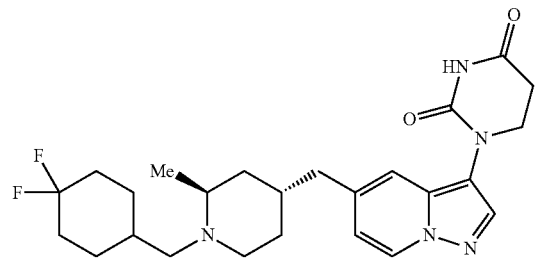 [SMILES: C[C@H]1C[C@H](Cc2ccn3ncc(N4CCC(=O)NC4=O)c3c2)CCN1CC1CCC(F)(F)CC1]

or a pharmaceutically acceptable salt thereof.

23. The method of claim 21, wherein the compound is:

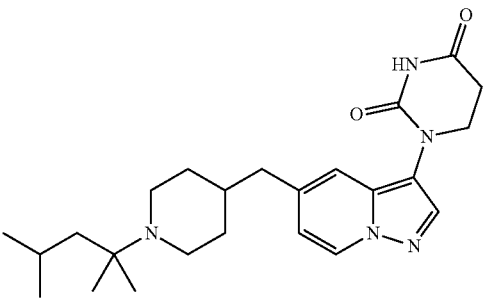 [SMILES: CC(C)CC(C)(C)N1CCC(Cc2ccn3ncc(N4CCC(=O)NC4=O)c3c2)CC1]

or a pharmaceutically acceptable salt thereof.

24. The method of claim 21, wherein the compound is:

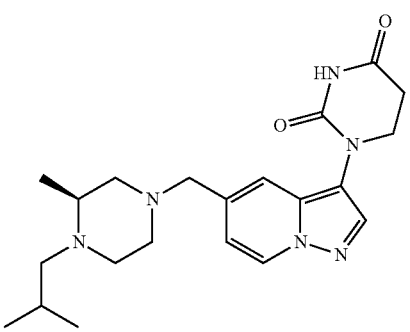 [SMILES: CC(C)CN1CCN(Cc2ccn3ncc(N4CCC(=O)NC4=O)c3c2)C[C@@H]1C]

or a pharmaceutically acceptable salt thereof.

25. The method of claim 21, wherein the compound is:

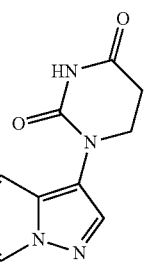

or a pharmaceutically acceptable salt thereof.

26. The method of claim 19, wherein the compound is selected from the group consisting of

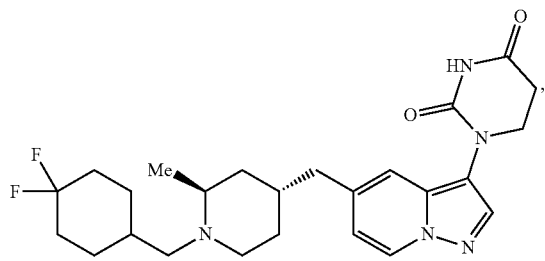

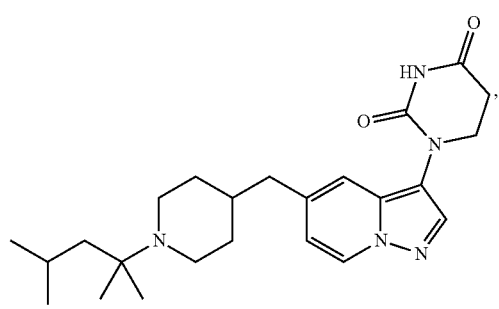

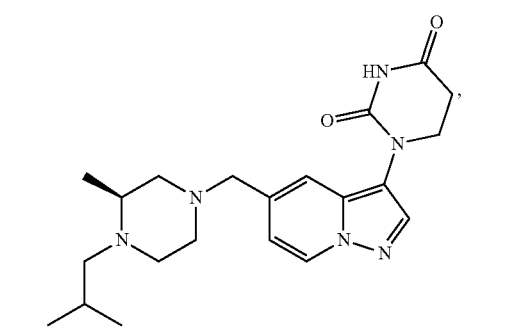

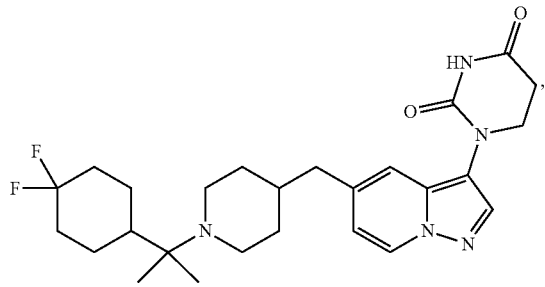

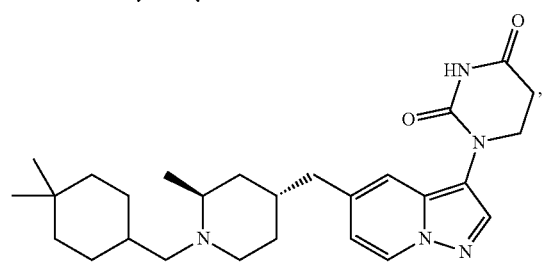

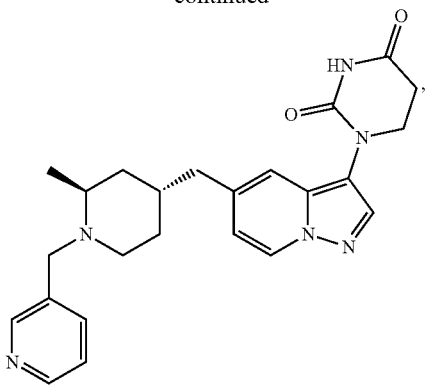

and pharmaceutically acceptable salts thereof.

27. The method of claim 26, wherein the compound is:

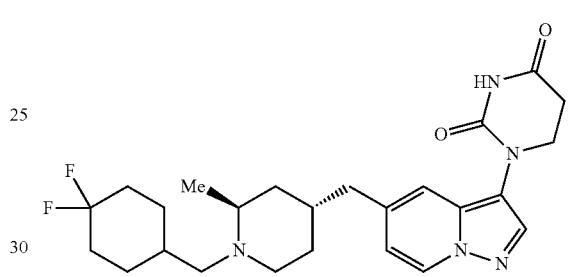

or a pharmaceutically acceptable salt thereof.

28. The method of claim 26, wherein the compound is:

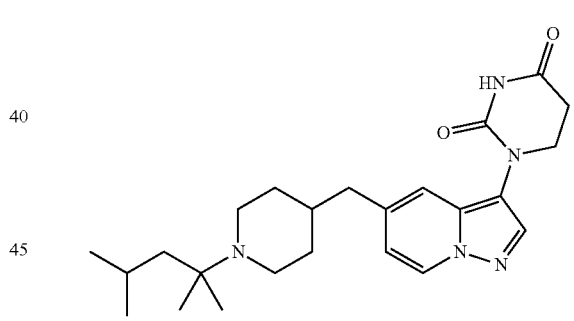

or a pharmaceutically acceptable salt thereof.

29. The method of claim 26, wherein the compound is:

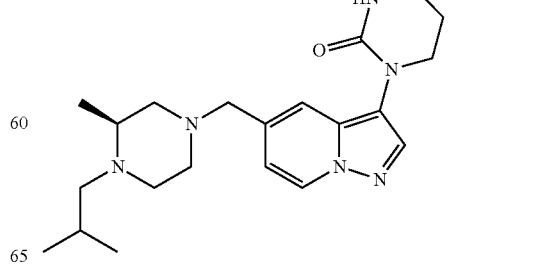

or a pharmaceutically acceptable salt thereof.

30. The method of claim 26, wherein the compound is:
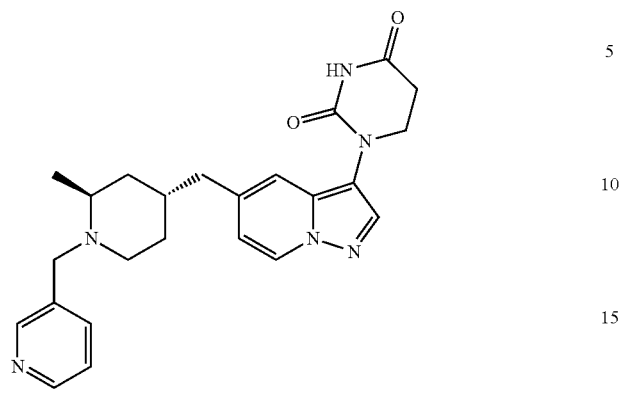
or a pharmaceutically acceptable salt thereof.
* * * * *

SEQUENCE LISTING

```
Sequence total quantity: 14
SEQ ID NO: 1            moltype = AA  length = 11
FEATURE                 Location/Qualifiers
REGION                  1..11
                        note = source = /note="Description of Artificial Sequence:
                         Synthetic peptide"
source                  1..11
                        mol_type = protein
                        organism = synthetic construct
SEQUENCE: 1
VSGWRLFKKI S                                                              11

SEQ ID NO: 2            moltype = DNA  length = 19
FEATURE                 Location/Qualifiers
misc_feature            1..19
                        note = source = /note="Description of Artificial Sequence:
                         Synthetic primer"
source                  1..19
                        mol_type = other DNA
                        organism = synthetic construct
SEQUENCE: 2
ctacatttta catgatagg                                                      19
```

```
SEQ ID NO: 3               moltype = DNA  length = 21
FEATURE                    Location/Qualifiers
misc_feature               1..21
                           note = source = /note="Description of Artificial Sequence:
                           Synthetic oligonucleotide"
source                     1..21
                           mol_type = other DNA
                           organism = synthetic construct
SEQUENCE: 3
agcccacaat gccacggaaa t                                                   21

SEQ ID NO: 4               moltype = DNA  length = 21
FEATURE                    Location/Qualifiers
misc_feature               1..21
                           note = source = /note="Description of Artificial Sequence:
                           Synthetic oligonucleotide"
source                     1..21
                           mol_type = other DNA
                           organism = synthetic construct
SEQUENCE: 4
gcaacatcta caccctcaaa t                                                   21

SEQ ID NO: 5               moltype = DNA  length = 21
FEATURE                    Location/Qualifiers
misc_feature               1..21
                           note = source = /note="Description of Artificial Sequence:
                           Synthetic oligonucleotide"
source                     1..21
                           mol_type = other DNA
                           organism = synthetic construct
SEQUENCE: 5
tgaccgagtg gtacgtcaat g                                                   21

SEQ ID NO: 6               moltype = DNA  length = 21
FEATURE                    Location/Qualifiers
misc_feature               1..21
                           note = source = /note="Description of Artificial Sequence:
                           Synthetic oligonucleotide"
source                     1..21
                           mol_type = other DNA
                           organism = synthetic construct
SEQUENCE: 6
agcggcagaa catcaacaaa t                                                   21

SEQ ID NO: 7               moltype = RNA  length = 67
FEATURE                    Location/Qualifiers
misc_feature               1..67
                           note = source = /note="Description of Artificial Sequence:
                           Synthetic oligonucleotide"
source                     1..67
                           mol_type = other RNA
                           organism = synthetic construct
SEQUENCE: 7
agcatagcaa gttaaaataa ggctagtccg ttatcaactt gaaaaagtgg caccgagtcg         60
gtgcttt                                                                   67

SEQ ID NO: 8               moltype = DNA  length = 20
FEATURE                    Location/Qualifiers
misc_feature               1..20
                           note = source = /note="Description of Artificial Sequence:
                           Synthetic oligonucleotide"
source                     1..20
                           mol_type = other DNA
                           organism = synthetic construct
SEQUENCE: 8
acggaggcta agcgtcgcaa                                                     20

SEQ ID NO: 9               moltype = DNA  length = 20
FEATURE                    Location/Qualifiers
misc_feature               1..20
                           note = source = /note="Description of Artificial Sequence:
                           Synthetic oligonucleotide"
```

-continued

```
source                   1..20
                         mol_type = other DNA
                         organism = synthetic construct
SEQUENCE: 9
aacatctttc gggccgtagg                                               20

SEQ ID NO: 10            moltype = DNA  length = 20
FEATURE                  Location/Qualifiers
misc_feature             1..20
                         note = source = /note="Description of Artificial Sequence:
                         Synthetic oligonucleotide"
source                   1..20
                         mol_type = other DNA
                         organism = synthetic construct
SEQUENCE: 10
gacatccgct gcgagttctg                                               20

SEQ ID NO: 11            moltype = DNA  length = 20
FEATURE                  Location/Qualifiers
misc_feature             1..20
                         note = source = /note="Description of Artificial Sequence:
                         Synthetic oligonucleotide"
source                   1..20
                         mol_type = other DNA
                         organism = synthetic construct
SEQUENCE: 11
tgcagcgtcc cgggcagagc                                               20

SEQ ID NO: 12            moltype = DNA  length = 20
FEATURE                  Location/Qualifiers
misc_feature             1..20
                         note = source = /note="Description of Artificial Sequence:
                         Synthetic oligonucleotide"
source                   1..20
                         mol_type = other DNA
                         organism = synthetic construct
SEQUENCE: 12
caagccgtgc ctcatcaaga                                               20

SEQ ID NO: 13            moltype = DNA  length = 20
FEATURE                  Location/Qualifiers
misc_feature             1..20
                         note = source = /note="Description of Artificial Sequence:
                         Synthetic oligonucleotide"
source                   1..20
                         mol_type = other DNA
                         organism = synthetic construct
SEQUENCE: 13
cgggcacacc tgcggcagtt                                               20

SEQ ID NO: 14            moltype = DNA  length = 20
FEATURE                  Location/Qualifiers
misc_feature             1..20
                         note = source = /note="Description of Artificial Sequence:
                         Synthetic oligonucleotide"
source                   1..20
                         mol_type = other DNA
                         organism = synthetic construct
SEQUENCE: 14
agtgggtgcg gcacttacag                                               20
```